United States Patent
Zhang et al.

(10) Patent No.: US 11,666,577 B2
(45) Date of Patent: *Jun. 6, 2023

(54) MLKL INHIBITORS

(71) Applicant: National Institute of Biological Sciences, Beijing, Beijing (CN)

(72) Inventors: Zhiyuan Zhang, Beijing (CN); Xiaodong Wang, Beijing (CN); Shaoqiang Huang, Beijing (CN); Bo Yan, Beijing (CN); Lei Liu, Beijing (CN); Huayi Wang, Beijing (CN); Jianguang Han, Beijing (CN); Zhi Huang, Beijing (CN); Weiye Cao, Beijing (CN)

(73) Assignee: National Institute of Biological Sciences, Beijing, Beijing (CN)

( * ) Notice: Subject to any disclaimer, the term of this patent is extended or adjusted under 35 U.S.C. 154(b) by 563 days.

This patent is subject to a terminal disclaimer.

(21) Appl. No.: 16/550,316

(22) Filed: Aug. 26, 2019

(65) Prior Publication Data
US 2019/0381052 A1    Dec. 19, 2019

Related U.S. Application Data

(63) Continuation of application No. PCT/CN2018/077464, filed on Feb. 27, 2018.

(51) Int. Cl.
*A61K 31/522* (2006.01)
*A61P 25/00* (2006.01)
*A61K 31/5377* (2006.01)

(52) U.S. Cl.
CPC ........ *A61K 31/522* (2013.01); *A61K 31/5377* (2013.01)

(58) Field of Classification Search
CPC .............................. A61K 31/522; A61P 29/00
See application file for complete search history.

(56) References Cited

U.S. PATENT DOCUMENTS 9,359,359 B2 * 6/2016 Chenard .............. C07D 473/04

* cited by examiner

*Primary Examiner* — Samira J Jean-Louis
(74) *Attorney, Agent, or Firm* — Richard Aron Osman

(57) ABSTRACT

The invention provides compounds that inhibit human MLKL, and pharmaceutically acceptable salts, hydrates and stereoisomers thereof. The compounds are employed in pharmaceutical compositions, and methods of making and use, including treating a person in need thereof with an effective amount of the compound or composition.

20 Claims, No Drawings

MLKL INHIBITORS

We disclose here the development of novel Mixed Lineage Kinase Domain-Like protein (MLKL) inhibitors with single nanomolar potency. Using the converting biochemistry to chemistry activity-based protein profiling (BTC-ABPP) method, we were able to determine that the inhibitors covalently bind to Cysteine86 (Cys-86) of MLKL. This is the first example of the use of LC-MS/MS to identify the binding site of an MLKL inhibitor.

Necroptosis is a type of programmed necrotic cell death involved in organ development, tissue homeostasis, inflammation, and disease pathogenesis.[1] After necroptosis induction, receptor interacting protein kinase 1 (RIP1),[2] RIP3,[3] and MLKL[4] are activated sequentially. MLKL, as the executor of necroptosis, can then form oligomers and translocate to cellular membranes, where it mediates ion influx and/or causes the disruption of cell structures.[5] Recent studies have established that MLKL is involved in multiple human inflammatory diseases, including acute pancreatitis, multiple sclerosis, inflammatory bowel disease, and allergic colitis.[6] In this context, MLKL is viewed as a potential therapeutic target for drug discovery.

There are only two known MLKL inhibitors: necrosulfonamide (NSA)[4] and GW806742X.[7] The moderate potency and a narrow structure-activity-relationship (SAR) profile of NSA has limited its development as a drug.[1a, 8] GW806742X which targets the pseudo-kinase domain of MLKL has been found to have off-target activity against other kinases, including VEGFR2[9]. We also disclose that GW806742X also has off-target activities against RIP1 and RIP3, so it is not possible to conclude that the prevention of necroptosis as mediated by GW806742X relies solely on the targeting of MLKL. Given the deficiencies of the MLKL inhibitors reported to date, the development of novel, highly potent MLKL inhibitors is a pressing need.

SUMMARY OF THE INVENTION

The invention provides methods and compositions for treating an MLKL-mediated disorder, disease or condition. In an aspect the invention provides methods comprising treating a person in need thereof with an MLKL-inhibitor compound of formula I:

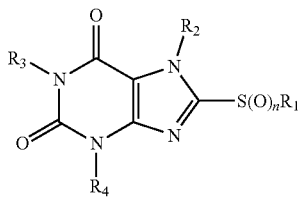

wherein:
each of R1-R4 is independently H, or optionally substituted, optionally hetero-, optionally cyclic C1-C18 hydrocarbyl, or optionally substituted heteroatom, and R1 and R2 are optionally joined to form a ring;
n is 0, 1 or 2; and
or a pharmaceutically acceptable salt, hydrate or stereoisomer the compound.

In embodiments:
(a) one of R1-R4 is alkylcarbocylic, such as methylcyclopropyl;
(b) one of R1-R4 comprises a fluoroalkyl, such as CF3;
(c) R4 is alkylcyano or alkylCR, such as CH$_2$CR wherein R is H, or optionally substituted, optionally hetero-, optionally cyclic C1-C18 hydrocarbyl; and/or
(d) R1 and R2 are joined to form a ring, such as R1/R2 are Me/Me or Me/Et joined to form a ring.

In embodiments:
one, two or three of R1-R4 is Me;
n is 2;
one of R1-R4 is alkylcyano or alkylCR, such as CH$_2$CR wherein R is H, or optionally substituted, optionally hetero-, optionally cyclic C1-C18 hydrocarbyl; and/or In embodiments:
each of R1, R2 and R3 is Me;
n is 2; and
R4 is alkylcyano or alkylCR, such as CH$_2$CR, wherein R is H, or optionally substituted, optionally hetero-, optionally cyclic C1-C18 hydrocarbyl, In embodiments: R1 and R2 are joined to form a ring, such as R1/R2 are Me/Me or Me/Et joined to form a ring.

In embodiments: the optionally substituted, optionally hetero-, optionally cyclic C1-C18 hydrocarbyl is optionally-substituted, optionally hetero-, optionally cyclic alkyl, alkenyl or alkynyl, or optionally-substituted, optionally heteroaryl; and/or the optionally substituted heteroatom is halogen, optionally substituted hydroxyl (such as alkoxy, aryloxy), optionally substituted acyl (such as formyl, alkanoyl, carbamoyl, carboxyl, amido), optionally substituted amino such as (such as amino, alkylamino, dialkylamino, amido, sulfamidyl), optionally substituted thiol (such as mercapto, alkylthiol, aryl thiol), optionally substituted sulfinyl or sulfonyl (such as alkylsulfinyl, arylsulfinyl, alkyl sulfonyl, arylsulfonyl), nitro, or cyano.

In embodiments: the compound comprises a formula of Table 1.

In embodiments: the MLKL-mediated disorder is a pathology associated with cell death, such as ischemia-reperfusion damage, neurodegeneration, and inflammation, including inflammatory diseases such as acute pancreatitis, multiple sclerosis, inflammatory bowel disease, and allergic colitis.

In embodiments the methods further comprise the antecedent step of diagnosing the disorder, disease or condition, or the subsequent step of detecting a resultant amelioration of the associated disorder, disease or condition.

In another aspect the invention provides a composition comprising a medicament for treating a pathology associated with necroptosis or cell death, such as ischemia-reperfusion damage, neurodegeneration, and inflammation, such as an anti-inflammatory drug, and a second, different MLKL-inhibitor compound of formula I:

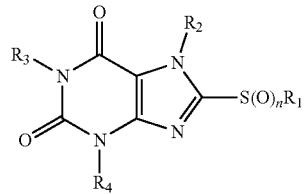

wherein:
each of R1-R4 is independently H, or optionally substituted, optionally hetero-, optionally cyclic C1-C18 hydrocarbyl, or optionally substituted heteroatom, and R1 and R2 are optionally joined to form a ring;
n is 0, 1 or 2; and
or a pharmaceutically acceptable salt, hydride or stereoisomer the compound.

In embodiments the compositions share the embodiments of the methods.

In another aspect the invention provides an MLKL-inhibitor compound of formula I:

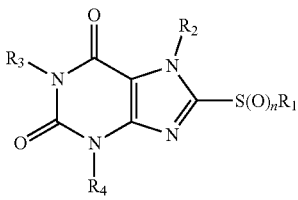

wherein:

each of R1-R4 is independently H, or optionally substituted, optionally hetero-, optionally cyclic C1-C18 hydrocarbyl, or optionally substituted heteroatom, and R1 and R2 are optionally joined to form a ring; and n is 0, 1 or 2; and (a) one of R1-R4 is alkylcarbocylic, such as methylcyclopropyl;

(b) one of R1-R4 comprises a fluoroalkyl, such as CF3;

(c) R4 is alkylcyano or alkylCR, such as $CH_2CR$ wherein R is H, or optionally substituted, optionally hetero-, optionally cyclic C1-C18 hydrocarbyl; and/or (d) R1 and R2 are joined to form a ring, such as R1/R2 are Me/Me or Me/Et joined to form a ring;

or a pharmaceutically acceptable salt, hydrate or stereoisomer the compound.

In embodiments: one, two or three of R1-R4 is Me; and/or n is 2.

In embodiments: the optionally substituted, optionally hetero-, optionally cyclic C1-C18 hydrocarbyl is optionally-substituted, optionally hetero-, optionally cyclic alkyl, alkenyl or alkynyl, or optionally-substituted, optionally heteroaryl; and/or the optionally substituted heteroatom is halogen, optionally substituted hydroxyl (such as alkoxy, aryloxy), optionally substituted acyl (such as formyl, alkanoyl, carbamoyl, carboxyl, amido), optionally substituted amino (such as amino, alkylamino, dialkylamino, amido, sulfamidyl), optionally substituted thiol (such as mercapto, alkylthiol, aryl thiol), optionally substituted sulfinyl or sulfonyl (such as alkylsulfinyl, arylsulfinyl, alkyl sulfonyl, arylsulfonyl), nitro, or cyano.

In embodiments the compound comprises a formula of a novel compound of Table 1.

In embodiments the subject compound or composition is in unit dosage form.

The invention encompasses all combinations of the particular embodiments recited herein.

DESCRIPTION OF PARTICULAR EMBODIMENTS OF THE INVENTION

The following descriptions of particular embodiments and examples are provided by way of illustration and not by way of limitation. Those skilled in the art will readily recognize a variety of noncritical parameters that could be changed or modified to yield essentially similar results. The invention provides myriad embodiments.

Unless contraindicated or noted otherwise, in these descriptions and throughout this specification, the terms "a" and "an" mean one or more, the term "or" means and/or and polynucleotide sequences are understood to encompass opposite strands as well as alternative backbones described herein. Furthermore, genuses are recited as shorthand for a recitation of all members of the genus; for example, the recitation of (C1-C3) alkyl is shorthand for a recitation of all C1-C3 alkyls: methyl, ethyl and propyl, including isomers thereof.

The term "heteroatom" as used herein generally means any atom other than carbon or hydrogen. Preferred heteroatoms include oxygen (O), phosphorus (P), sulfur (S), nitrogen (N), and halogens, and preferred heteroatom functional groups are haloformyl, hydroxyl, aldehyde, amine, azo, carboxyl, cyanyl, thocyanyl, carbonyl, halo, hydroperoxyl, imine, aldimine, isocyanide, iscyante, nitrate, nitrile, nitrite, nitro, nitroso, phosphate, phosphono, sulfide, sulfonyl, sulfo, and sulfhydryl.

The term "alkyl," by itself or as part of another substituent, means, unless otherwise stated, a straight or branched chain, or cyclic hydrocarbon radical, or combination thereof, which is fully saturated, having the number of carbon atoms designated (i.e. C1-C8 means one to eight carbons). Examples of alkyl groups include methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl and the like. Preferred alkyls are C1-C8, C3-C18 if cyclic.

The term "alkenyl", by itself or as part of another substituent, means a straight or branched chain, or cyclic hydrocarbon radical, or combination thereof, which may be mono- or polyunsaturated, having the number of carbon atoms designated (i.e. C2-C8 means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl) and higher homologs and isomers thereof. Preferred alkenyls are C1-C8, C3-C18 if cyclic.

The term "alkynyl", by itself or as part of another substituent, means a straight or branched chain hydrocarbon radical, or combination thereof, which may be mono- or polyunsaturated, having the number of carbon atoms designated (i.e. C2-C8 means two to eight carbons) and one or more triple bonds. Examples of alkynyl groups include ethynyl, 1- and 3-propynyl, 3-butynyl and higher homologs and isomers thereof. Preferred alkynyls are C1-C8, C3-C18 if cyclic.

The term "alkylene" by itself or as part of another substituent means a divalent radical derived from alkyl, as exemplified by —$CH_2$—$CH_2$—$CH_2$—$CH_2$—. Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, P, Si and S, wherein the nitrogen, sulfur, and phosphorous atoms may optionally be oxidized and the nitrogen heteroatom may optionally be quaternized. The heteroatom(s) O, N, P and S may be placed at any interior position of the heteroalkyl group. The heteroatom Si may be placed at any position of the heteroalkyl group, including the position at which the alkyl group is attached to the remainder of the molecule. Examples include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH3)-CH$_3$. Up to two heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent means a divalent radical derived from heteroalkyl, as exemplified by —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Accordingly, a cycloalkyl group has the number of carbon atoms designated (i.e., C3-C8 means three to eight carbons) and may also have one or two double bonds. A heterocycloalkyl group consists of the number of carbon atoms designated and from one to three heteroatoms selected from the group consisting of O, N, Si and S, and wherein the nitrogen and sulfur atoms may optionally be oxidized and the nitrogen heteroatom may optionally be quaternized. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyrid-yl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" and "halogen," by themselves or as part of another substituent, mean, unless otherwise stated, a fluorine, chlorine, bromine, or iodine atom. Additionally, terms such as "haloalkyl," are meant to include alkyl substituted with halogen atoms, which can be the same or different, in a number ranging from one to (2m'+1), where m' is the total number of carbon atoms in the alkyl group. For example, the term "halo(C1-C4)alkyl" is mean to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). The term "perhaloalkyl" means, unless otherwise stated, alkyl substituted with (2m'+1) halogen atoms, where m' is the total number of carbon atoms in the alkyl group. For example the term "perhalo(C1-C4)alkyl" is meant to include trifluoromethyl, pentachloroethyl, 1,1,1-trifluoro-2-bromo-2-chloroethyl and the like.

The term "acyl" refers to those groups derived from an organic acid by removal of the hydroxy portion of the acid. Accordingly, unsubstituted acyl is meant to include, for example, acetyl, propionyl, butyryl, decanoyl, pivaloyl, benzoyl and the like.

The term "aryl" means, unless otherwise stated, a polyunsaturated, typically aromatic, hydrocarbon substituent which can be a single ring or multiple rings (up to three rings) which are fused together or linked covalently. Non-limiting examples of aryl groups include phenyl, 1-naphthyl, 2-naphthyl, 4-biphenyl and 1,2,3,4-tetrahydronaphthalene. Preferred aryls are C5-C18.

The term heteroaryl," refers to aryl groups (or rings) that contain from zero to four heteroatoms selected from N, O, and S, wherein the nitrogen and sulfur atoms are optionally oxidized and the nitrogen heteroatom are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O, =NR', =N—OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR'—SO$_2$NR'", —NR"CO$_2$R', —NH—C(NH$_2$)=NH, —NR'C(NH$_2$)=NH, —NH—C(NH$_2$)=NR', —S(O)R', —SO$_2$R', —SO$_2$NR'R", —NR"SO$_2$R, —CN and —NO$_2$, in a number ranging from zero to three, with those groups having zero, one or two substituents being particularly preferred. R', R" and R'" each independently refer to hydrogen, unsubstituted (C1-C8) alkyl and heteroalkyl, unsubstituted aryl, aryl substituted with one to three halogens, unsubstituted alkyl, alkoxy or thioalkoxy groups, or aryl-(C1-C4)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. Typically, an alkyl or heteroalkyl group will have from zero to three substituents, with those groups having two or fewer substituents being preferred in the invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —CF$_3$ and —CH$_2$CF$_3$).

Preferred substituents for the alkyl and heteroalkyl radicals are selected from: —OR', =O, —NR'R", —SR', halogen, —SiR'R"R'", —OC(O)R', —C(O)R', —CO₂R', —CONR'R", —OC(O)NR'R", —NR"C(O)R', —NR"CO₂R', —NR'—SO₂NR"R'", —S(O)R', —SO₂R', —SO₂NR'R", —NR"SO₂R, —CN and —NO₂, where R' and R" are as defined above. Further preferred substituents are selected from: —OR', =O, —NR'R", halogen, —OC(O)R', —CO₂R', —CONR'R", —OC(O)NR'R", —NR"C(O)R', —NR"CO₂R', —NR'—SO₂NR"R'", —SO₂R', —SO₂NR'R", —NR"SO₂R, —CN and —NO₂.

Similarly, substituents for the aryl and heteroaryl groups are varied and selected from: halogen, —OR', —OC(O)R', —NR'R", —SR', —R', —CN, —NO₂, —CO₂R', —CONR'R", —C(O)R', —OC(O)NR'R", —NR"C(O)R', —NR"CO2R', —NR'—C(O)NR"R'", —NR'—SO₂NR"R'", —NH—C(NH2)=NH, —NR'C(NH₂)=NH, —NH—C(NH₂)=NR', —S(O)R', —SO₂R', —SO₂NR'R", —NR"SO₂R, —N₃, —CH(Ph)₂, perfluoro(C1-C4)alkoxy and perfluoro(C1-C4)alkyl, in a number ranging from zero to the total number of open valences on the aromatic ring system; and where R', R" and R'" are independently selected from hydrogen, (C1-C8)alkyl and heteroalkyl, unsubstituted aryl and heteroaryl, (unsubstituted aryl)-(C1-C4)alkyl and (unsubstituted aryl)oxy-(C1-C4)alkyl. When the aryl group is 1,2,3,4-tetrahydronaphthalene, it may be substituted with a substituted or unsubstituted (C3-C7)spirocycloalkyl group. The (C3-C7)spirocycloalkyl group may be substituted in the same manner as defined herein for "cycloalkyl". Typically, an aryl or heteroaryl group will have from zero to three substituents, with those groups having two or fewer substituents being preferred in the invention. In one embodiment of the invention, an aryl or heteroaryl group will be unsubstituted or monosubstituted. In another embodiment, an aryl or heteroaryl group will be unsubstituted.

Preferred substituents for aryl and heteroaryl groups are selected from: halogen, —OR', —OC(O)R', —NR'R", —SR', —R', —CN, —NO₂, —CO₂R', —CONR'R", —C(O)R', —OC(O)NR'R", —NR"C(O)R', —S(O)R', —SO₂R', —SO₂NR'R", —NR"SO₂R, —N₃, —CH(Ph)₂, perfluoro(C1-C4)alkoxy and perfluoro(C1-C4)alkyl, where R' and R" are as defined above. Further preferred substituents are selected from: halogen, —OR', —OC(O)R', —NR'R", —R', —CN, —NO₂, —CO₂R', —CONR'R", —NR"C(O)R', —SO₂R', —SO₂NR'R", —NR"SO₂R, perfluoro(C1-C4) alkoxy and perfluoro(C1-C4)alkyl.

The substituent —CO₂H, as used herein, includes bio-isosteric replacements therefor; see, e.g., The Practice of Medicinal Chemistry; Wermuth, C. G., Ed.; Academic Press: New York, 1996; p. 203.

Two of the substituents on adjacent atoms of the aryl or heteroaryl ring may optionally be replaced with a substituent of the formula -T-C(O)—(CH₂)q-U—, wherein T and U are independently —NH—, —O—, —CH₂— or a single bond, and q is an integer of from 0 to 2. Alternatively, two of the substituents on adjacent atoms of the aryl or heteroaryl ring may optionally be replaced with a substituent of the formula -A-(CH2)r-B—, wherein A and B are independently —CH₂—, —O—, —NH—, —S—, —S(O)—, —S(O)₂—, —S(O)₂NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH₂)s-X—(CH₂)t-, where s and t are independently integers of from 0 to 3, and X is —O—, —NR'—, —S—, —S(O)—, —S(O)₂—, or —S(O)₂NR'—.

The substituent R' in —NR'— and —S(O)₂NR'— is selected from hydrogen or unsubstituted (C1-C6)alkyl.

In embodiments substituents, particularly for R1-R4, are selected from:

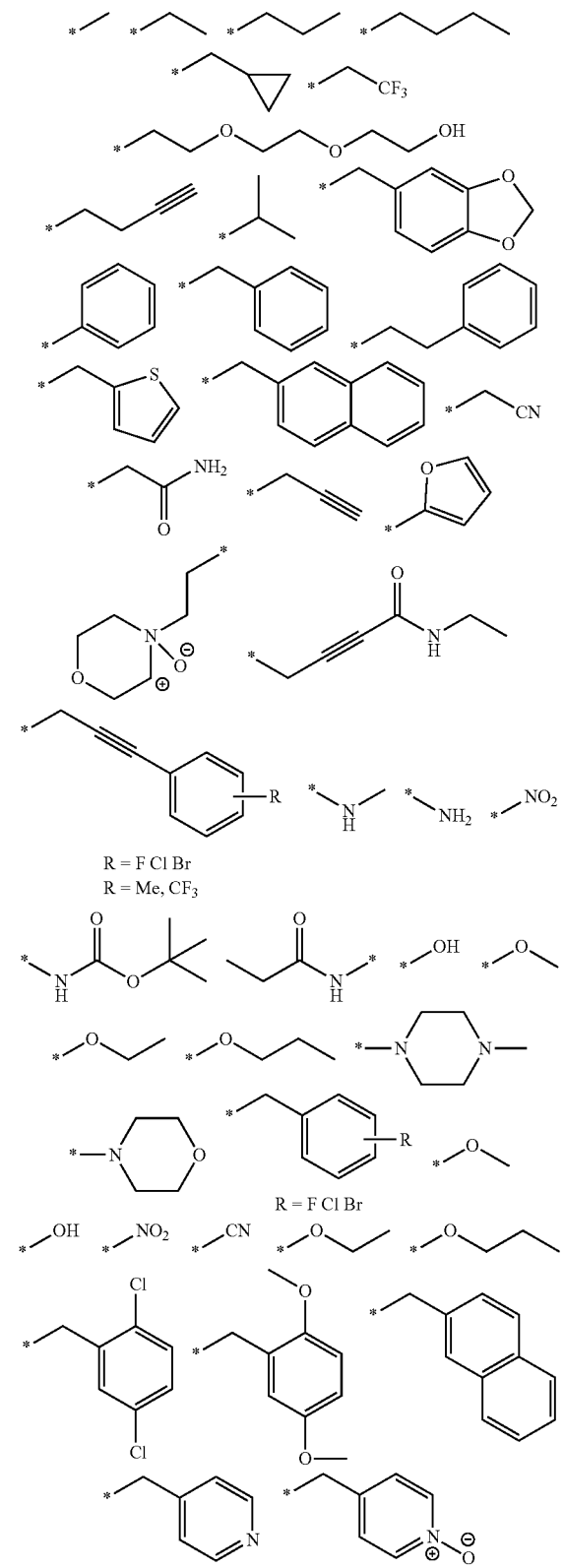

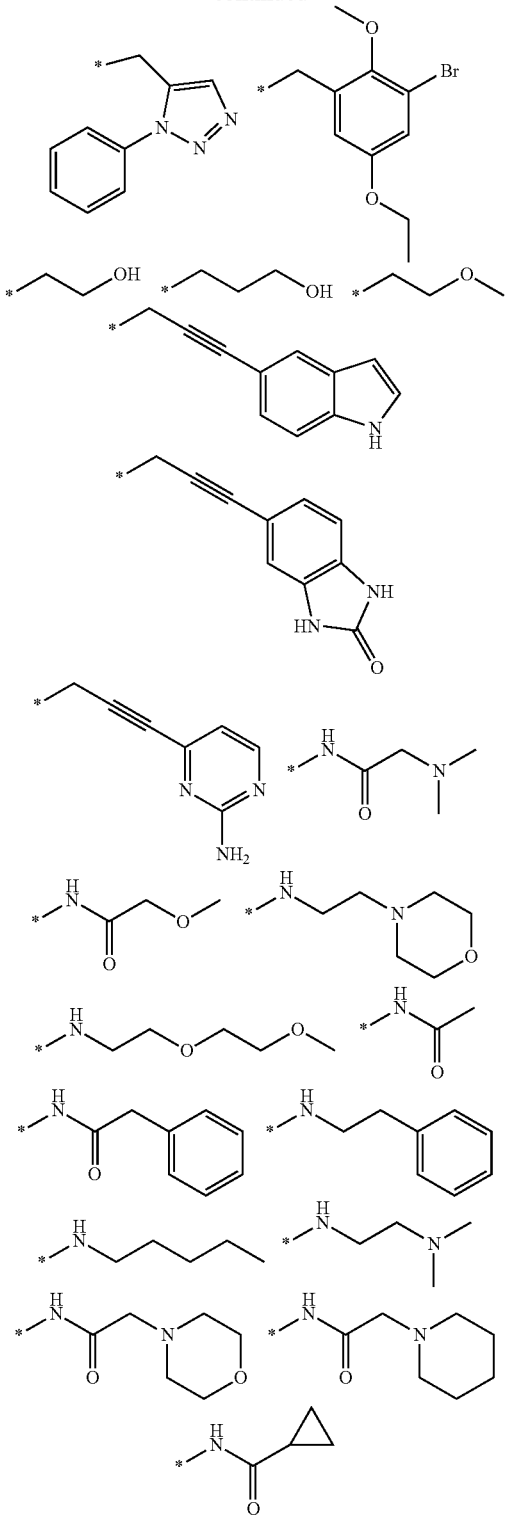

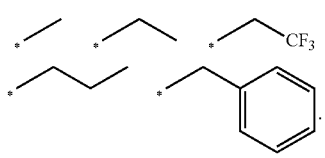

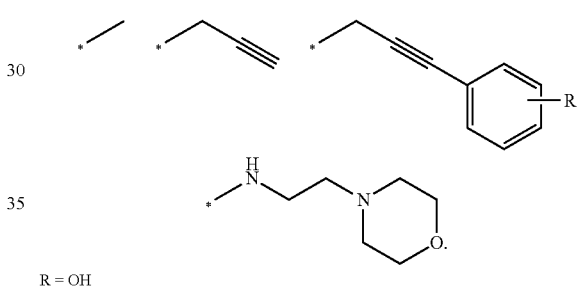

R = OH

In embodiments R1 is —NR5R6, wherein R5 and R6 are independently H, or optionally substituted, optionally hetero-, optionally cyclic C1-C18 hydrocarbyl, or optionally substituted heteroatom. In embodiments: the optionally substituted, optionally hetero-, optionally cyclic C1-C18 hydrocarbyl is optionally-substituted, optionally hetero-, optionally cyclic alkyl, alkenyl or alkynyl, or optionally-substituted, optionally hetero-aryl; and/or the optionally substituted heteroatom is halogen, optionally substituted hydroxyl (such as alkoxy, aryloxy), optionally substituted acyl (such as formyl, alkanoyl, carbamoyl, carboxyl, amido), optionally substituted amino such as (such as amino, alkylamino, dialkylamino, amido, sulfamidyl), optionally substituted thiol (such as mercapto, alkylthiol, aryl thiol), optionally substituted sulfinyl or sulfonyl (such as alkylsulfinyl, arylsulfinyl, alkyl sulfonyl, arylsulfonyl), nitro, or cyano.

In embodiments, R2, R3 and R4 are methyl and/or R5 is H or methyl, and/or R6 is a substituent selected from:

In embodiments R1 and R2 are joined to form a ring, such as R1/R2 are Me/Me or Me/Et joined to form a 5- or 6-membered ring, particularly wherein R3 is methyl and/or R4 is a substituent selected from:

Preferred substituents are disclosed herein and exemplified in the tables, structures, examples, and claims, and may be applied across different compounds of the invention, i.e. substituents of any given compound may be combinatorially used with other compounds.

In particular embodiments applicable substituents are independently substituted or unsubstituted heteroatom, substituted or unsubstituted, 0-3 heteroatom C1-C6 alkyl, substituted or unsubstituted, 0-3 heteroatom C2-C6 alkenyl, substituted or unsubstituted, 0-3 heteroatom C2-C6 alkynyl, or substituted or unsubstituted, 0-3 heteroatom C6-C14 aryl, wherein each heteroatom is independently oxygen, phosphorus, sulfur or nitrogen.

In more particular embodiments, applicable substituents are independently aldehyde, aldimine, alkanoyloxy, alkoxy, alkoxycarbonyl, alkyloxy, alkyl, amine, azo, halogens, carbamoyl, carbonyl, carboxamido, carboxyl, cyanyl, ester, halo, haloformyl, hydroperoxyl, hydroxyl, imine, isocyanide, iscyante, N-tert-butoxycarbonyl, nitrate, nitrile, nitrite, nitro, nitroso, phosphate, phosphono, sulfide, sulfonyl, sulfo, sulfhydryl, thiol, thiocyanyl, trifluoromethyl or trifluromethyl ether (OCF3).

The term "pharmaceutically acceptable salts" is meant to include salts of the active compounds which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug is a compound of the invention which is administered as an ester (the "prodrug"), but then is metabolically hydrolyzed to the carboxylic acid, the active entity. Additional examples include peptidyl derivatives of a compound of the invention.

Certain compounds of the invention can exist in unsolvated forms as well as solvated forms, including hydrated forms. In general, the solvated forms are equivalent to unsolvated forms and are intended to be encompassed within the scope of the invention. Certain compounds of the invention may exist in multiple crystalline or amorphous forms. In general, all physical forms are equivalent for the uses contemplated by the invention and are intended to be within the scope of the invention.

Certain compounds of the invention possess asymmetric carbon atoms (optical centers) or double bonds; the racemates, diastereomers, geometric isomers and individual isomers are all intended to be encompassed within the scope of the invention.

The compounds of the invention may also contain unnatural proportions of atomic isotopes at one or more of the constituent atoms, such as deuterium, e.g. —$CD_3$, $CD_2H$ or $CDH_2$ in place of methyl. For example, the compounds may be radiolabeled with radioactive isotopes, such as for example tritium ($^3H$), iodine-125 ($^{125}I$) or carbon-14 ($^{14}C$). All isotopic variations of the compounds of the invention, whether radioactive or not, are intended to be encompassed within the scope of the invention.

The term "therapeutically effective amount" refers to the amount of the subject compound that will elicit, to some significant extent, the biological or medical response of a tissue, system, animal or human that is being sought by the researcher, veterinarian, medical doctor or other clinician, such as when administered, is sufficient to prevent development of, or alleviate to some extent, one or more of the symptoms of the condition or disorder being treated.

The therapeutically effective amount will vary depending on the compound, the disease and its severity and the age, weight, etc., of the mammal to be treated.

The invention also provides pharmaceutical compositions comprising the subject compounds and a pharmaceutically acceptable excipient, particularly such compositions comprising a unit dosage of the subject compounds, particularly such compositions copackaged with instructions describing use of the composition to treat an applicable disease or condition (herein).

The compositions for administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, losenges or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Suitable excipients or carriers and methods for preparing administrable compositions are known or apparent to those skilled in the art and are described in more detail in such publications as Remington's Pharmaceutical Science, Mack Publishing Co, NJ (1991). In addition, the compounds may be advantageously used in conjunction with other therapeutic agents as described herein or otherwise known in the art, particularly other anti-necrosis agents. Hence the compositions may be administered separately, jointly, or combined in a single dosage unit.

The amount administered depends on the compound formulation, route of administration, etc. and is generally empirically determined in routine trials, and variations will necessarily occur depending on the target, the host, and the route of administration, etc.

Generally, the quantity of active compound in a unit dose of preparation may be varied or adjusted from about 1, 3, 10 or 30 to about 30, 100, 300 or 1000 mg, according to the particular application. In a particular embodiment, unit dosage forms are packaged in a multipack adapted for sequential use, such as blisterpack, comprising sheets of at least 6, 9 or 12 unit dosage forms.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The compounds can be administered by a variety of methods including, but not limited to, parenteral, topical, oral, or local administration, such as by aerosol or transdermally, for prophylactic and/or therapeutic treatment. Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

The therapeutics of the invention can be administered in a therapeutically effective dosage and amount, in the process of a therapeutically effective protocol for treatment of the patient. For more potent compounds, microgram (ug) amounts per kilogram of patient may be sufficient, for example, in the range of about 1, 10 or 100 ug/kg to about 0.01, 0.1, 1, 10, or 100 mg/kg of patient weight though optimal dosages are compound specific, and generally empirically determined for each compound.

In general, routine experimentation in clinical trials will determine specific ranges for optimal therapeutic effect, for each therapeutic, each administrative protocol, and administration to specific patients will also be adjusted to within effective and safe ranges depending on the patient condition and responsiveness to initial administrations. However, the ultimate administration protocol will be regulated according to the judgment of the attending clinician considering such factors as age, condition and size of the patient as well as compounds potency, severity of the disease being treated. For example, a dosage regimen of the compounds can be oral administration of from 10 mg to 2000 mg/day, preferably 10 to 1000 mg/day, more preferably 50 to 600 mg/day, in two to four (preferably two) divided doses. Intermittent therapy (e.g., one week out of three weeks or three out of four weeks) may also be used.

The compounds of the invention may be particularly useful for the treatment of diseases/disorders which are likely to be regulated at least in part by programmed necrosis, apoptosis or the production of inflammatory cytokines, particularly inflammatory bowel disease (including Crohn's disease and ulcerative colitis), psoriasis, retinal detachment, retinitis pigmentosa, macular degeneration, pancreatitis, atopic dermatitis, arthritis (including rheumatoid arthritis, spondyloarthritis, gout, systemic onset juvenile idiopathic arthritis (SoJIA), psoriatic arthritis), systemic lupus erythematosus (SLE), Sjogren's syndrome, systemic scleroderma, anti-phospholipid syndrome (APS), vasculitis, osteoarthritis, liver damage/diseases (non-alcohol steatohepatitis, alcohol steatohepatitis, autoimmune hepatitis, autoimmune hepatobiliary diseases, primary sclerosing cholangitis (PSC), acetaminophen toxicity, hepatotoxicity), kidney damage/injury (nephritis, renal transplant, surgery, administration of nephrotoxic drugs e.g. cisplatin, acute kidney injury (AKI)) Celiac disease, autoimmune idiopathic thrombocytopenic purpura (autoimmune ITP), transplant rejection, ischemia reperfusion injury of solid organs, sepsis, systemic inflammatory response syndrome (SIRS), cerebrovascular accident (CVA, stroke), myocardial infarction (MI), atherosclerosis, Huntington's disease, Alzheimer's disease, Parkinson's disease, Amyotrophic lateral sclerosis (ALS), allergic diseases (including asthma and atopic dermatitis), multiple sclerosis, type I diabetes, Wegener's granulomatosis, pulmonary sarcoidosis, Behcet's disease, interleukin-1 converting enzyme (ICE, also known as caspase-1) associated fever syndrome, chronic obstructive pulmonary disease (COPD), tumor necrosis factor receptor-associated periodic syndrome (TRAPS), peridontitis, EMO-deficiency syndrome (F-kappa-B essential modulator gene (also known as IKK gamma or IKKG) deficiency syndrome), HOIL-1 deficiency ((also known as RBCK1) heme-oxidized IRP2 ubiquitin ligase-1 deficiency), linear ubiquitin chain assembly complex (LUBAC) deficiency syndrome, hematological and solid organ malignancies, bacterial infections and viral infections (such as tuberculosis and influenza), and Lysosomal storage diseases (particularly, Gaucher Disease, and including GM2 Gangliosidosis, Alpha-mannosidosis, Aspartylglucosaminuria, Cholesteryl Ester storage disease, Chronic Hexosaminidase A Deficiency, Cystinosis, Danon disease, Fabry disease, Farber disease, Fucosidosis, Galactosialidosis, GM1 gangliosidosis, Mucolipidosis, Infantile Free Sialic Acid Storage Disease, Juvenile Hexosaminidase A Deficiency, Krabbe disease, Lysosomal acid lipase deficiency, Metachromatic Leukodystrophy, Mucopolysaccharidoses disorders, Multiple sulfatase deficiency, Niemann-Pick Disease, Neuronal Ceroid Lipofuscinoses, Pompe disease, Pycnodysostosis, Sandhoff disease, Schindler disease, Sialic Acid Storage Disease, Tay-Sachs and Wolman disease). The treatment of the above-noted diseases/disorders may concern, more specifically, the amelioration of organ injury or damage sustained as a result of the noted diseases. For example, the compounds of this invention may be particularly useful for amelioration of brain tissue injury or damage following ischemic brain injury or traumatic brain injury, or for amelioration of heart tissue injury or damage following myocardial infarction, or for amelioration of brain tissue injury or damage associated with Huntington's disease, Alzheimer's disease or Parkinson's disease, or for amelioration of liver tissue injury or damage associated with non-alcohol steatohepatitis, alcohol steatohepatitis, autoimmune hepatitis autoimmune hepatobiliary diseases, or primary sclerosing cholangitis. In addition, the treatment of diseases/disorders selected from those described herein may concern, more specifically, the amelioration of liver tissue injury or damage associated with overdose of acetaminophen, or for amelioration of kidney tissue injury or damage following renal transplant or the administration of nephrotoxic drugs or substances e.g. cisplatin.

The subject compounds may be particularly useful for the treatment of inflammatory bowel disease (including Crohn's disease and ulcerative colitis), psoriasis, retinal detachment, retinitis pigmentosa, arthritis (including rheumatoid arthritis, spondyloarthritis, gout, and systemic onset juvenile idiopathic arthritis (SoJIA)), transplant rejection, and/or ischemia reperfusion injury of solid organs. The compounds may also be useful for treatment of burn injuries.

Treatment of MLKL-mediated disease conditions, or more broadly, treatment of immune mediated disease, may be achieved using the compounds as a monotherapy, or in dual or multiple combination therapy, particularly for the treatment of refractory cases, such as in combination with other anti-inflammatory and/or anti-TNF agents, which may be administered in therapeutically effective amounts as is known in the art.

The subject compounds may be employed alone or in combination with other therapeutic agents. Combination therapies thus comprise the administration of at least one pharmaceutically acceptable crystalline form of the compounds and at least one other therapeutically active agent. The subject compounds and the other therapeutically active agent(s) may be administered together in a single pharmaceutical composition or separately and, when administered separately this may occur simultaneously or sequentially in any order. The amounts of the subject compounds and the other therapeutically active agent(s) and the relative timings of administration will be selected in order to achieve the desired combined therapeutic effect. Thus in a further aspect, there is provided a combination comprising a pharmaceutically acceptable crystalline form of the compounds together with one or more other therapeutically active agents.

Thus in one aspect of this invention, a pharmaceutically acceptable crystalline form of a subject compound, or a pharmaceutical composition comprising a pharmaceutically acceptable crystalline form of a subject compound may be used in combination with or include one or more other therapeutic agents, for example an antiinflammatory agent and/or an anti-TNF agent. For example, a subject compound may be administered in combination with other antiinflammatory agents for any of the indications above, including oral or topical corticosteroids (such as prednisone (Deltasone®) and bundesonide), anti-TNF agents (including anti-TNF biologic agents), 5-aminosalicyclic acid and mesalamine preparations, hydroxycloroquine, thiopurines (azathioprin, mercaptopurin), methotrexate, cyclophosphamide, cyclosporine, calcineurin inhibitors (cyclosporine, pimecrolimus, tacrolimus), mycophenolic acid (CellCept®), mTOR inhibitors (temsirolimus, everolimus), JAK inhibitors (tofacitinib), (Xeljan®)), Syk inhibitors (fostamatinib), anti-IL6 biologies, anti-IL1 (anakinra (Kineret®), canakinumab (Ilaris®), rilonacept (Arcalyst®)), anti-IL12 and IL23 biologies (ustekinumab (Stelara®)), anti-IL17 biologies (secukinumab), anti-CD22 (epratuzumab), anti-integrin agents (natalizumab (Tysabri®)), vedolizumab (Entyvio®)), anti-IFNa (sifalimumab), anti-CD20 or CD4 biologies and other cytokine inhibitors or biologies to T-cell or B-cell receptors or interleukins.

Examples of suitable anti-inflammatory biologic agents include Actemra® (anti-IL6R mAb), anti-CD20 mAbs (rituximab (Rituxan®) and ofatumumab (Arzerra®)), abatacept (Orencia®), anakinra (Kineret®), ustekinumab (Stelara®), and belimumab (Benlysta®).

Examples of other suitable anti-inflammatory biologic agents include Canakinumab (Ilaris®), rilonacept (Arcalyst®), secukinumab, epratuzumab, sifalimumab, and ustekinumab (Stelara®).

Examples of suitable anti-TNF agents biologic agents include etanecerpt (Enbrel®), adalimumab (Humira®), infliximab (Remicade®), certolizumab (Cimzia®), and golimumab (Simponi®).

A therapeutically "effective amount" is intended to mean that amount of compound that, when administered to a patient in need of such treatment, is sufficient to effect treatment, as defined herein, e.g., when administered to a human in need thereof is sufficient to modulate and/or inhibit the activity of MLKL such that a disease condition which is mediated by MLKL is reduced, alleviated or prevented.

"Treating" or "treatment" is intended to mean at least the mitigation of a disease or disorder in a patient. The methods of treatment for mitigation of a disease or disorder include the use of the compounds in this invention in any conventionally acceptable manner, for example for prevention, retardation, prophylaxis, therapy or cure of a MLKL-mediated disease or disorder, as described hereinabove.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the disease or disorder being treated, the severity of the disease or disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change. Total daily dosages range from 1 mg to 2000 mg.

For use in therapy, the compounds of the invention will be normally, but not necessarily, formulated into a pharmaceutical composition, or administration unit, prior to administration to a patient. Accordingly, the invention also is directed to a pharmaceutical composition comprising a compound of the invention and one or more pharmaceutically acceptable excipients. The invention also is directed to an administration unit comprising a compound of the invention and one or more pharmaceutically acceptable excipients.

The pharmaceutical compositions or administration units of the invention may be prepared and packaged in bulk form wherein an effective amount of a compound of the invention can be extracted and then given to the patient such as with powders, syrups, and solutions for injection. Alternatively, the pharmaceutical compositions or administration units of the invention may be prepared and packaged in unit dosage form. For oral application, for example, one or more tablets or capsules may be administered. A dose of the pharmaceutical composition contains at least a therapeutically effective amount of a compound of the invention. When prepared in unit dosage form, the pharmaceutical compositions or administration units may contain from 1 mg to 1000 mg of a subject compound.

As provided herein, unit dosage forms (pharmaceutical compositions or administration units) containing from 1 mg to 1000 mg of compound may be administered one, two, three, or four times per day, preferably one, two, or three times per day, and more preferably, one or two times per day, to effect treatment of a MLKL-mediated disease or disorder.

As used herein, "pharmaceutically acceptable excipient" means a material, composition or vehicle involved in giving form or consistency to the composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically acceptable.

The compounds of the invention and the pharmaceutically acceptable excipient or excipients will typically be formulated into a dosage form adapted for administration to the patient by the desired route of administration. Conventional dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound or compounds of the invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation. Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The pharmaceutical compositions of the invention are prepared using techniques and methods known to those skilled in the art. Some of the methods commonly used in the art are described in Remington's Pharmaceutical Sciences (supra). Accordingly, another embodiment of this invention is a method of preparing a pharmaceutical composition or administration unit comprising the step of admixing a pharmaceutically acceptable crystalline form of a subject compound with one or more pharmaceutically acceptable excipients.

In one aspect, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

Exemplary Compounds

In embodiments the compounds are selected from Table 1.

TABLE 1

Series 1: black plain numbered compounds are novel; disclosed compositions
and uses of bold red numbered compounds (1, 2, 4, 5, 7, 8, 10, 18, 20, 21, 72, 73, 75, 87) are novel.

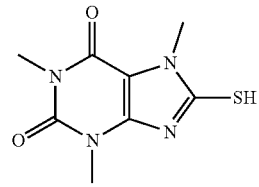

1

TABLE 1-continued
Series 1: black plain numbered compounds are novel; disclosed compositions
and uses of bold red numbered compounds (1, 2, 4, 5, 7, 8, 10, 18, 20, 21, 72, 73, 75, 87) are novel.
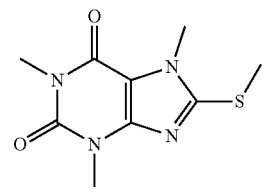
2
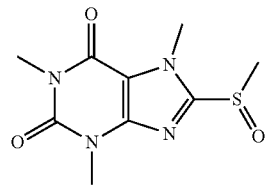 [SMILES: Cn1c(=O)c2c(nc(S(C)=O)n2C)n(C)c1=O]
3
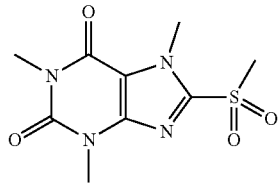 [SMILES: Cn1c(=O)c2c(nc(S(C)(=O)=O)n2C)n(C)c1=O]
4
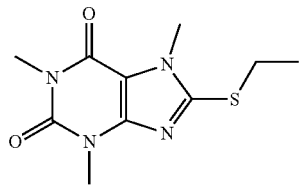 [SMILES: CCSc1nc2c(c(=O)n(C)c(=O)n2C)n1C]
5
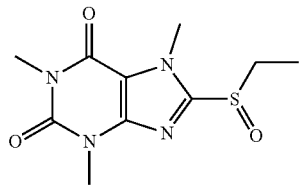 [SMILES: CCS(=O)c1nc2c(c(=O)n(C)c(=O)n2C)n1C]
6
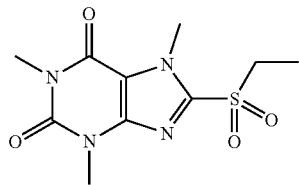 [SMILES: CCS(=O)(=O)c1nc2c(c(=O)n(C)c(=O)n2C)n1C]
7
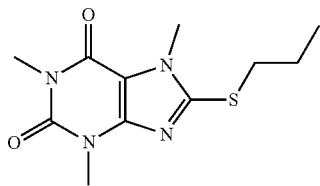 [SMILES: CCCSc1nc2c(c(=O)n(C)c(=O)n2C)n1C]
8
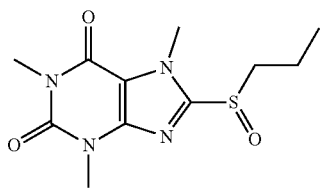 [SMILES: CCCS(=O)c1nc2c(c(=O)n(C)c(=O)n2C)n1C]
9

TABLE 1-continued
Series 1: black plain numbered compounds are novel; disclosed compositions
and uses of bold red numbered compounds (1, 2, 4, 5, 7, 8, 10, 18, 20, 21, 72, 73, 75, 87) are novel.
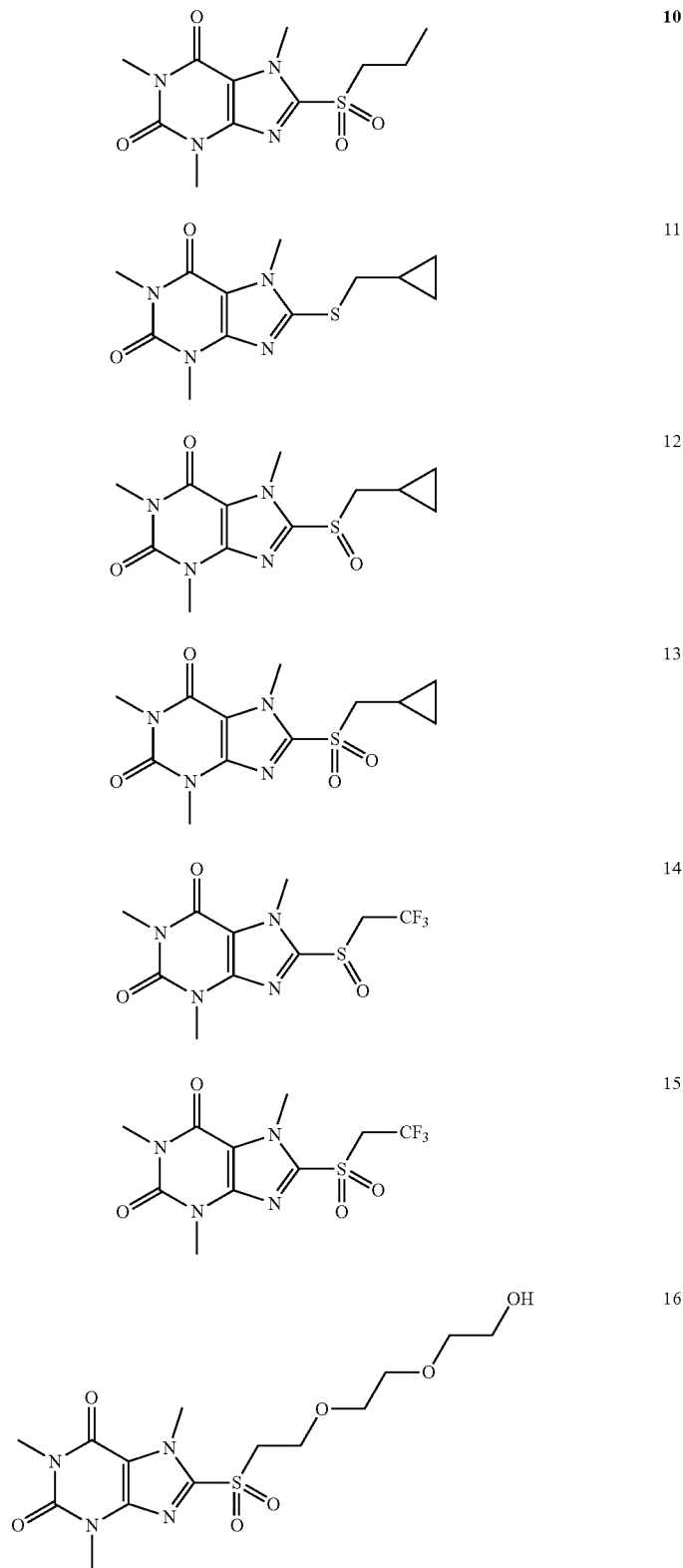
10
11
12
13
14
15
16

TABLE 1-continued
Series 1: black plain numbered compounds are novel; disclosed compositions
and uses of bold red numbered compounds (1, 2, 4, 5, 7, 8, 10, 18, 20, 21, 72, 73, 75, 87) are novel.
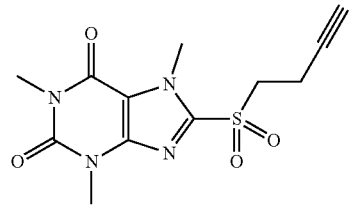 [SMILES: C#CCCS(=O)(=O)c1nc2c(c(=O)n(C)c(=O)n2C)n1C]
17
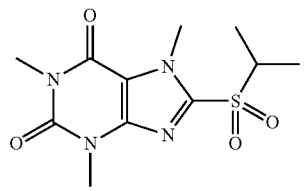 [SMILES: CC(C)S(=O)(=O)c1nc2c(c(=O)n(C)c(=O)n2C)n1C]
18
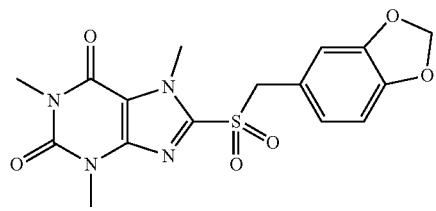 [SMILES: Cn1c(=O)c2c(nc(S(=O)(=O)Cc3ccc4c(c3)OCO4)n2C)n(C)c1=O]
19
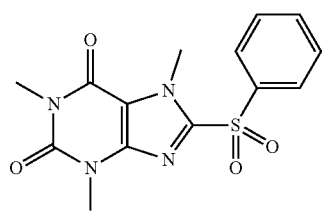 [SMILES: Cn1c(=O)c2c(nc(S(=O)(=O)c3ccccc3)n2C)n(C)c1=O]
20
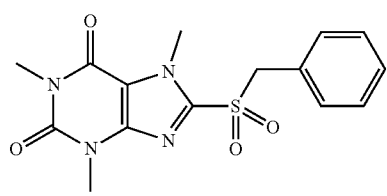 [SMILES: Cn1c(=O)c2c(nc(S(=O)(=O)Cc3ccccc3)n2C)n(C)c1=O]
21
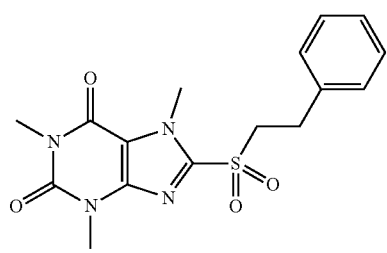 [SMILES: Cn1c(=O)c2c(nc(S(=O)(=O)CCc3ccccc3)n2C)n(C)c1=O]
22
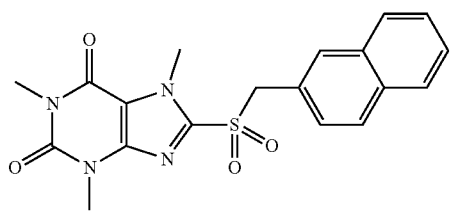 [SMILES: Cn1c(=O)c2c(nc(S(=O)(=O)Cc3ccc4ccccc4c3)n2C)n(C)c1=O]
23

TABLE 1-continued
Series 1: black plain numbered compounds are novel; disclosed compositions and uses of bold red numbered compounds (1, 2, 4, 5, 7, 8, 10, 18, 20, 21, 72, 73, 75, 87) are novel.
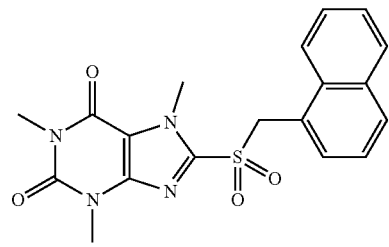 [SMILES: Cn1c(=O)c2c(nc(S(=O)(=O)Cc3cccc4ccccc34)n2C)n(C)c1=O]
24
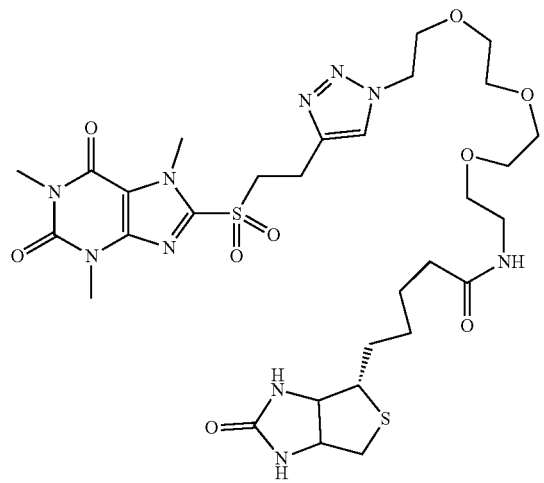 [SMILES: Cn1c(=O)c2c(nc(S(=O)(=O)CCc3cn(CCOCCOCCOCCNC(=O)CCCC[C@@H]4SCC5NC(=O)NC54)nn3)n2C)n(C)c1=O]
25
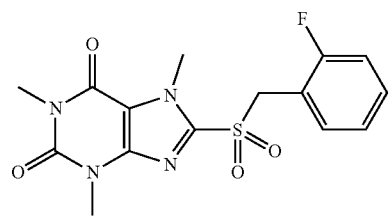 [SMILES: Cn1c(=O)c2c(nc(S(=O)(=O)Cc3ccccc3F)n2C)n(C)c1=O]
26
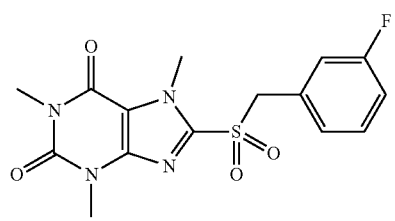 [SMILES: Cn1c(=O)c2c(nc(S(=O)(=O)Cc3cccc(F)c3)n2C)n(C)c1=O]
27
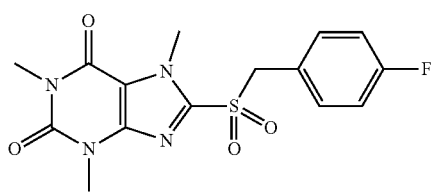 [SMILES: Cn1c(=O)c2c(nc(S(=O)(=O)Cc3ccc(F)cc3)n2C)n(C)c1=O]
28
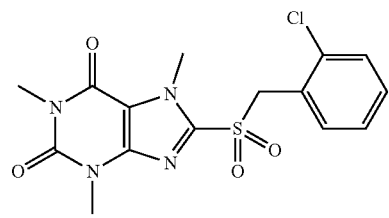 [SMILES: Cn1c(=O)c2c(nc(S(=O)(=O)Cc3ccccc3Cl)n2C)n(C)c1=O]
29

TABLE 1-continued
Series 1: black plain numbered compounds are novel; disclosed compositions and uses of bold red numbered compounds (1, 2, 4, 5, 7, 8, 10, 18, 20, 21, 72, 73, 75, 87) are novel.
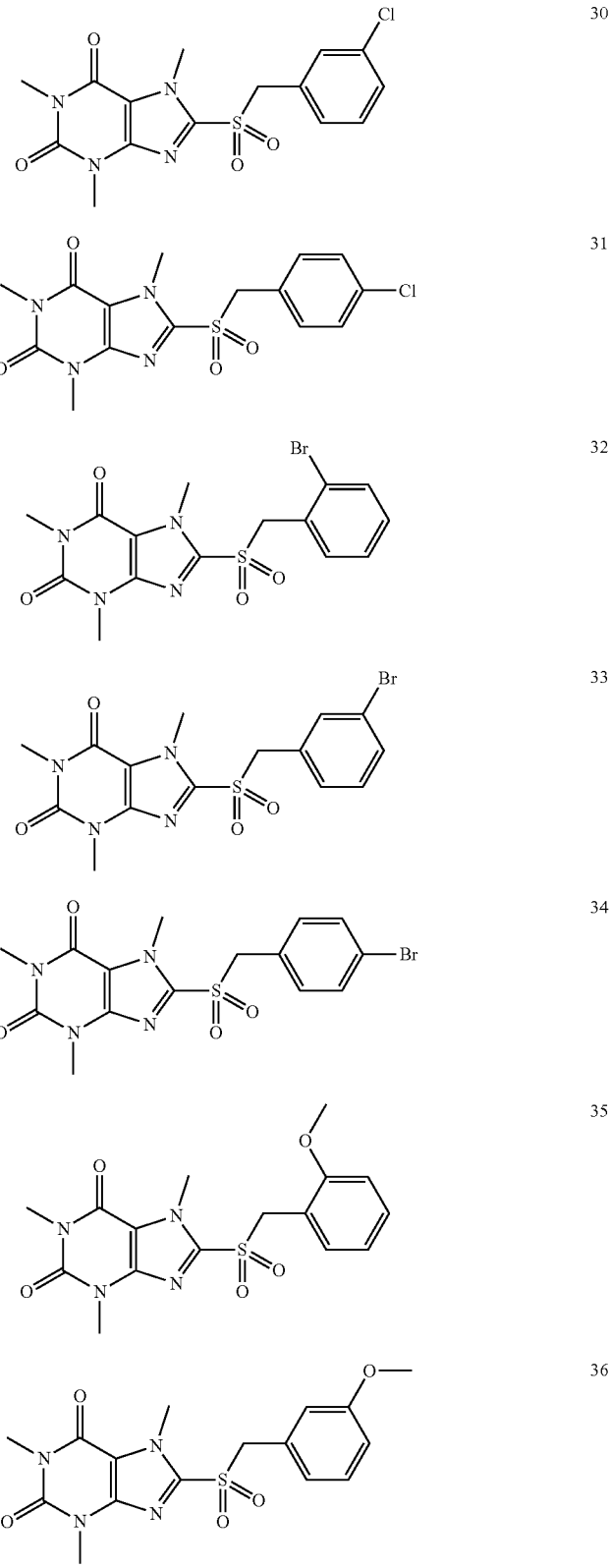

TABLE 1-continued
Series 1: black plain numbered compounds are novel; disclosed compositions
and uses of bold red numbered compounds (1, 2, 4, 5, 7, 8, 10, 18, 20, 21, 72, 73, 75, 87) are novel.
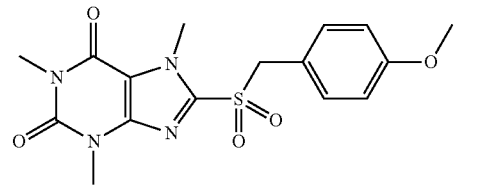
37
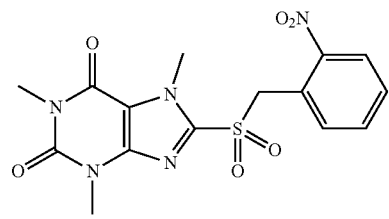 [SMILES: Cn1c(=O)c2c(nc(S(=O)(=O)Cc3ccccc3[N+](=O)[O-])n2C)n(C)c1=O]
38
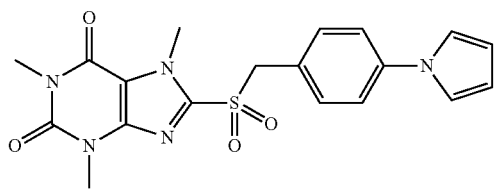 [SMILES: Cn1c(=O)c2c(nc(S(=O)(=O)Cc3ccc(-n4cccc4)cc3)n2C)n(C)c1=O]
39
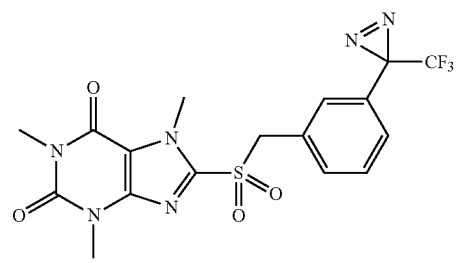 [SMILES: Cn1c(=O)c2c(nc(S(=O)(=O)Cc3cccc(C4(C(F)(F)F)N=N4)c3)n2C)n(C)c1=O]
40
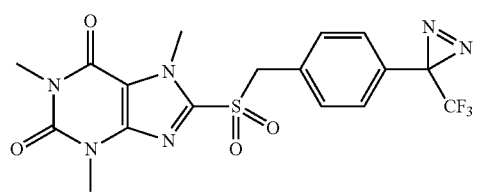 [SMILES: Cn1c(=O)c2c(nc(S(=O)(=O)Cc3ccc(C4(C(F)(F)F)N=N4)cc3)n2C)n(C)c1=O]
41
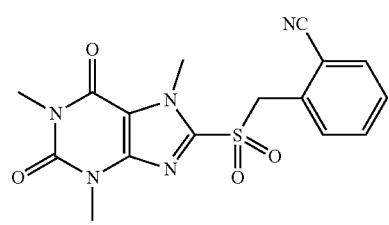 [SMILES: Cn1c(=O)c2c(nc(S(=O)(=O)Cc3ccccc3C#N)n2C)n(C)c1=O]
42
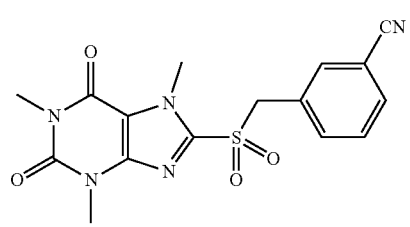 [SMILES: Cn1c(=O)c2c(nc(S(=O)(=O)Cc3cccc(C#N)c3)n2C)n(C)c1=O]
43

TABLE 1-continued
Series 1: black plain numbered compounds are novel; disclosed compositions and uses of bold red numbered compounds (1, 2, 4, 5, 7, 8, 10, 18, 20, 21, 72, 73, 75, 87) are novel.
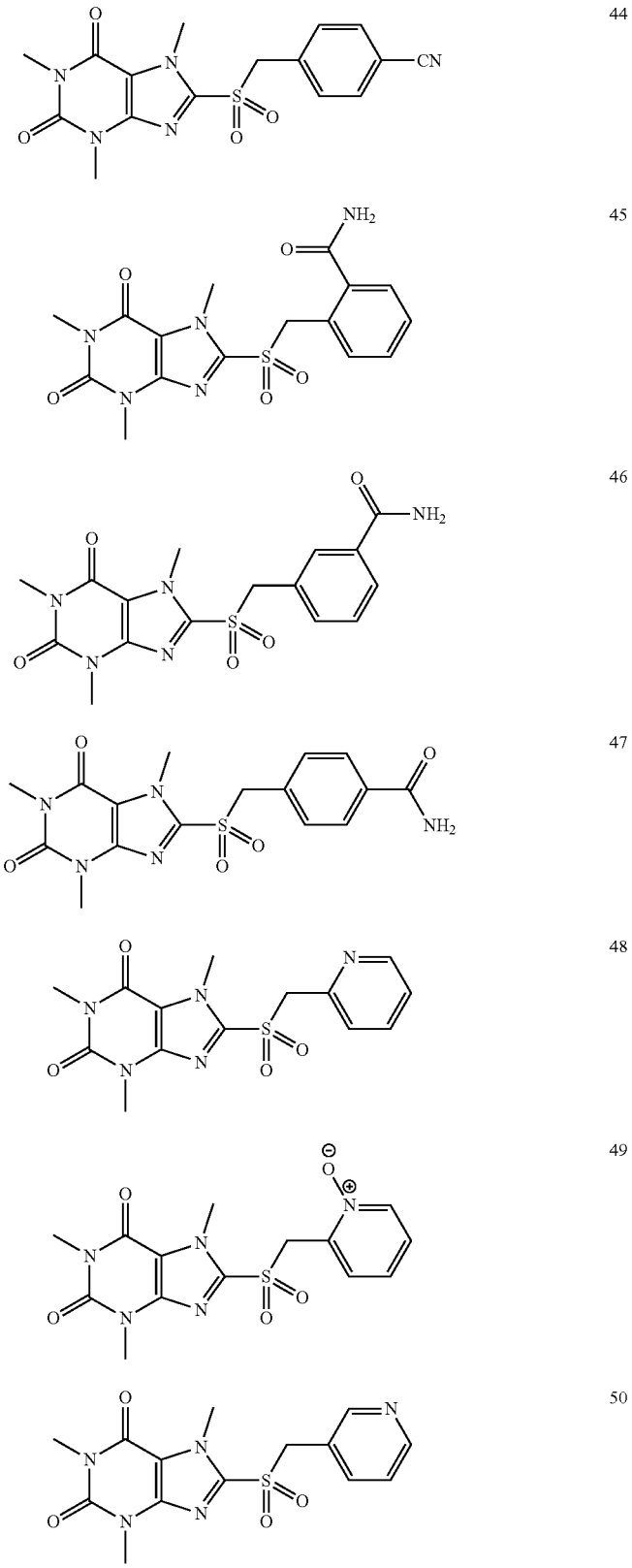

TABLE 1-continued
Series 1: black plain numbered compounds are novel; disclosed compositions and uses of bold red numbered compounds (1, 2, 4, 5, 7, 8, 10, 18, 20, 21, 72, 73, 75, 87) are novel.
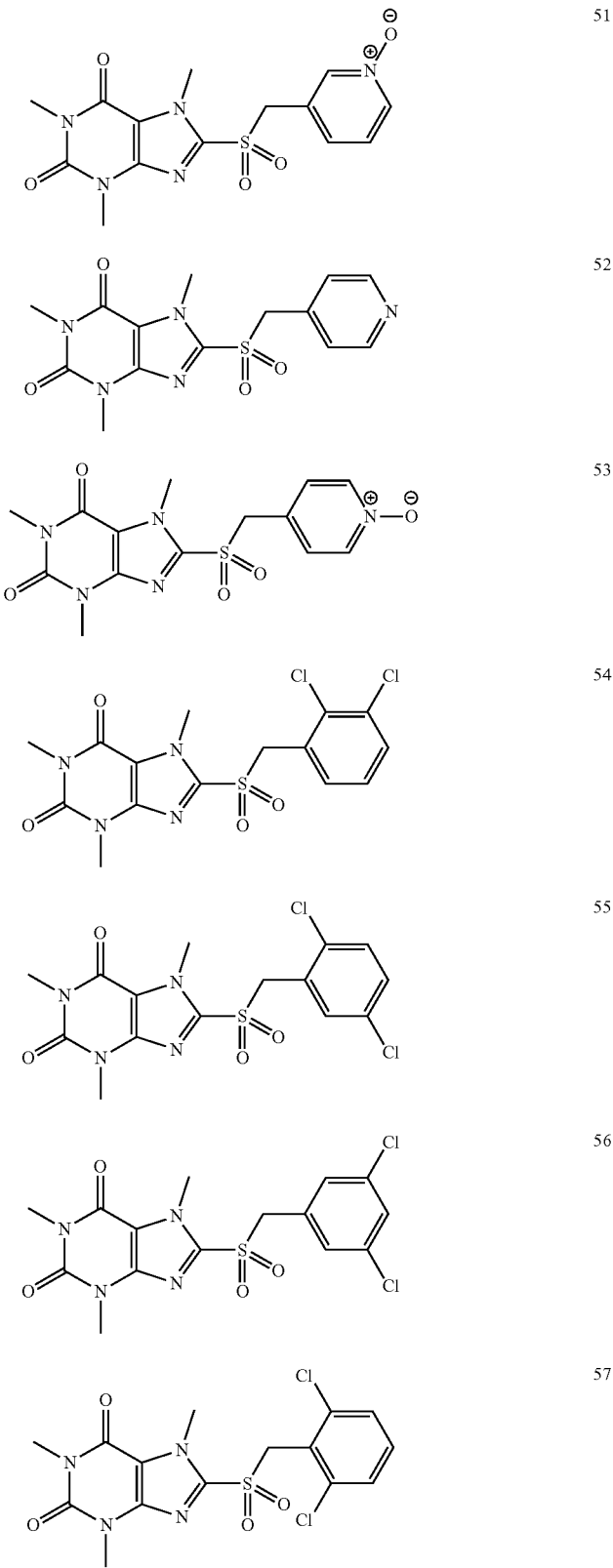

TABLE 1-continued
Series 1: black plain numbered compounds are novel; disclosed compositions
and uses of bold red numbered compounds (1, 2, 4, 5, 7, 8, 10, 18, 20, 21, 72, 73, 75, 87) are novel.
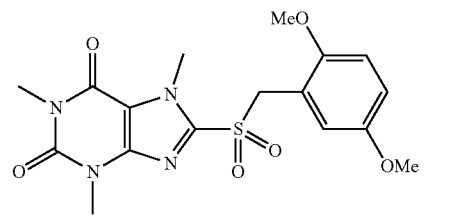
58
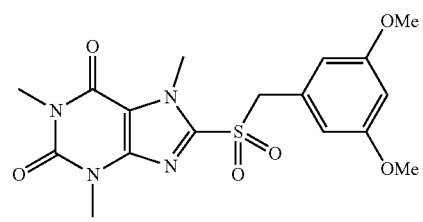 [SMILES: COc1cc(CS(=O)(=O)c2nc3c(c(=O)n(C)c(=O)n3C)n2C)cc(OC)c1]
59
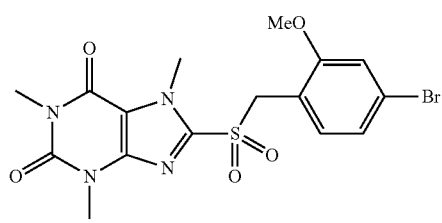 [SMILES: COc1cc(Br)ccc1CS(=O)(=O)c1nc2c(c(=O)n(C)c(=O)n2C)n1C]
60
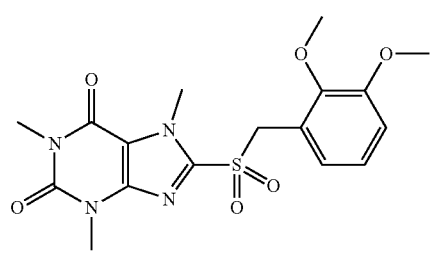
61
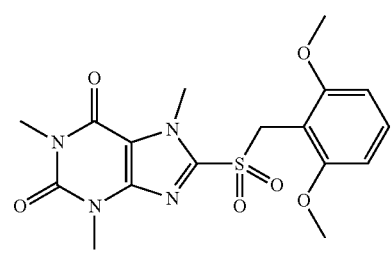 [SMILES: COc1cccc(OC)c1CS(=O)(=O)c1nc2c(c(=O)n(C)c(=O)n2C)n1C]
62
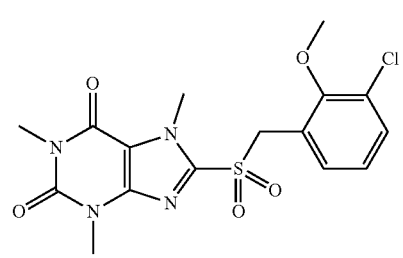 [SMILES: COc1c(Cl)cccc1CS(=O)(=O)c1nc2c(c(=O)n(C)c(=O)n2C)n1C]
63

TABLE 1-continued
Series 1: black plain numbered compounds are novel; disclosed compositions and uses of bold red numbered compounds (1, 2, 4, 5, 7, 8, 10, 18, 20, 21, 72, 73, 75, 87) are novel.
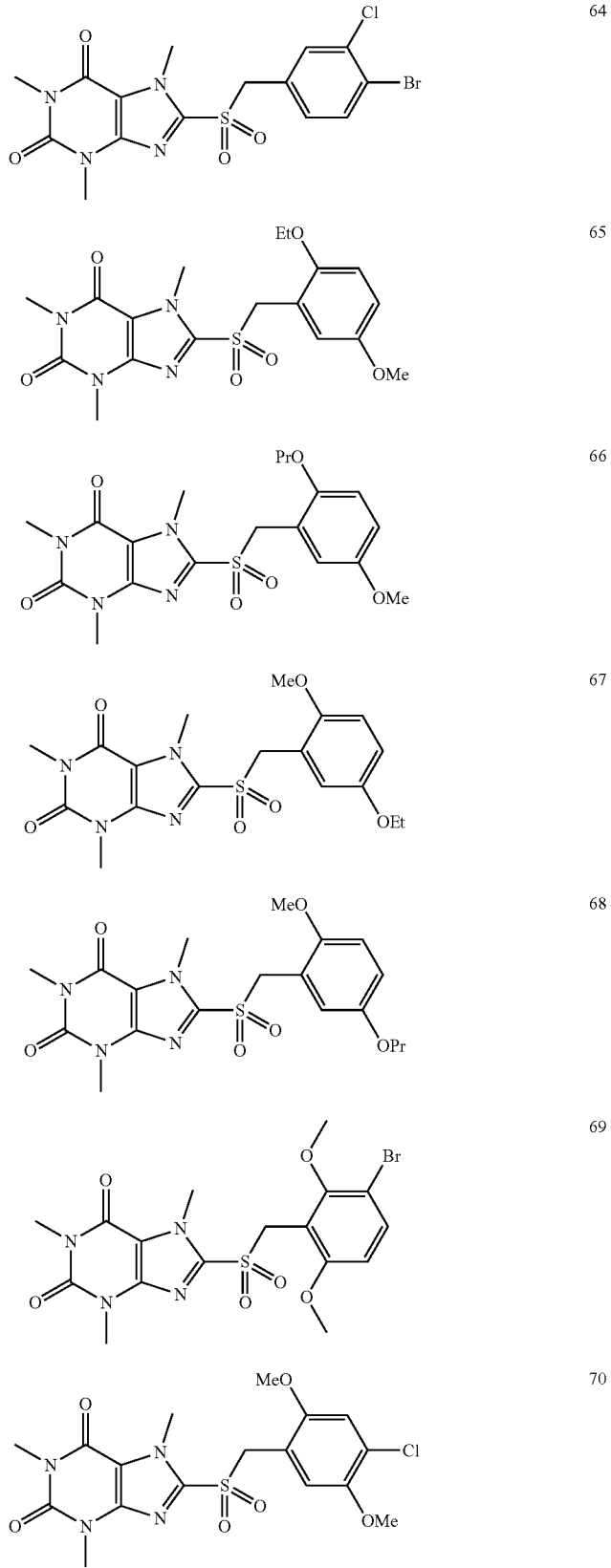

TABLE 1-continued
Series 1: black plain numbered compounds are novel; disclosed compositions and uses of bold red numbered compounds (1, 2, 4, 5, 7, 8, 10, 18, 20, 21, 72, 73, 75, 87) are novel.
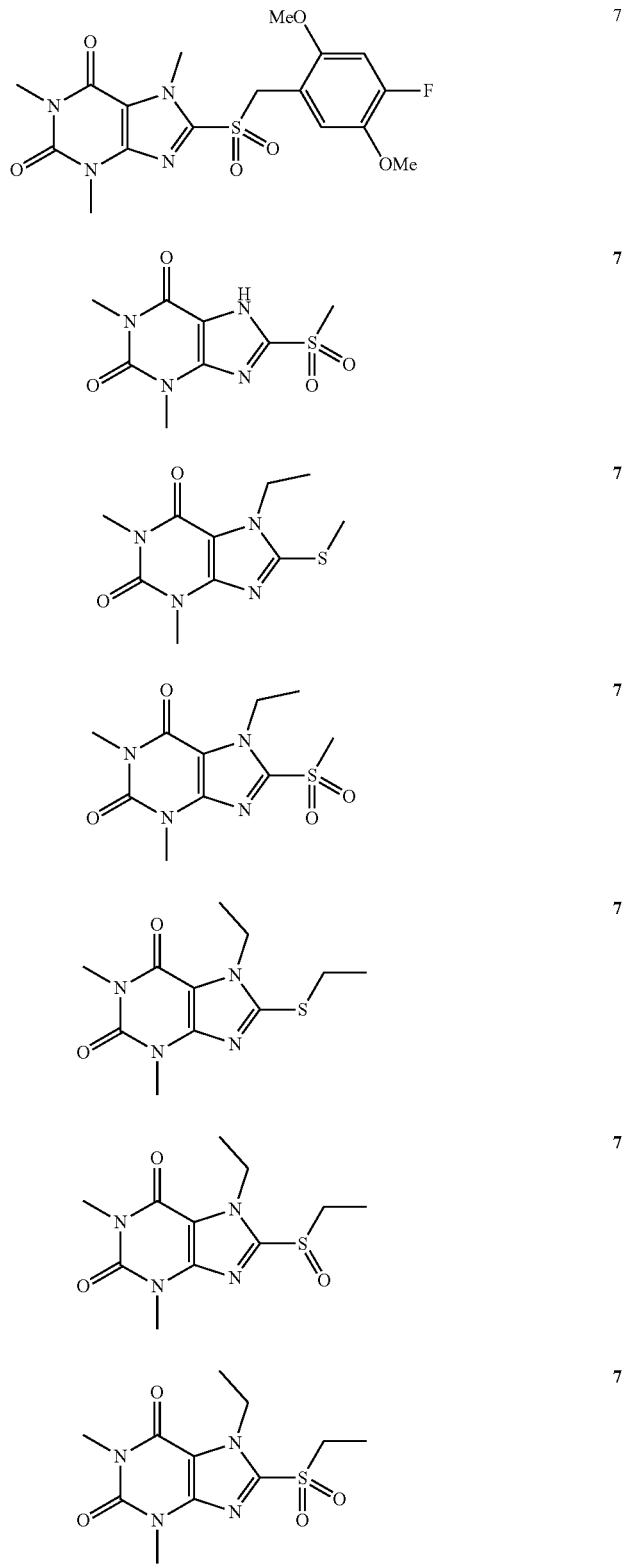

TABLE 1-continued
Series 1: black plain numbered compounds are novel; disclosed compositions
and uses of bold red numbered compounds (1, 2, 4, 5, 7, 8, 10, 18, 20, 21, 72, 73, 75, 87) are novel.
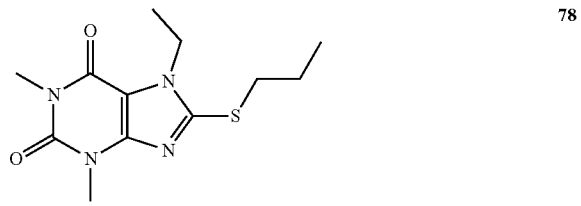
78
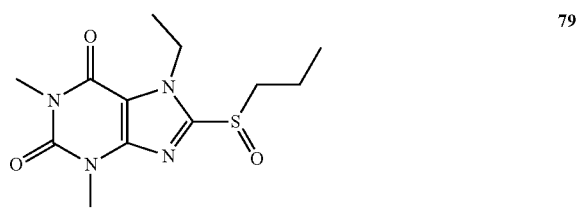
79
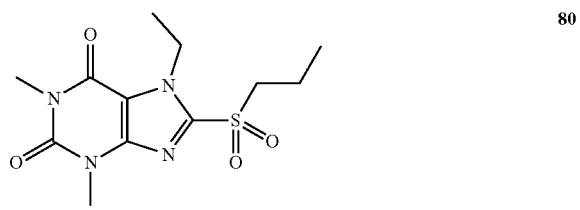
80
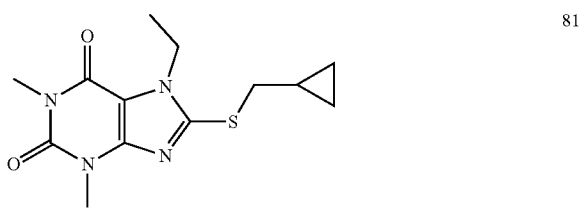
81
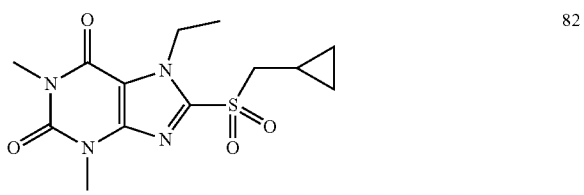
82
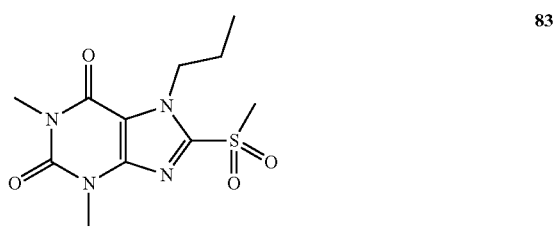
83
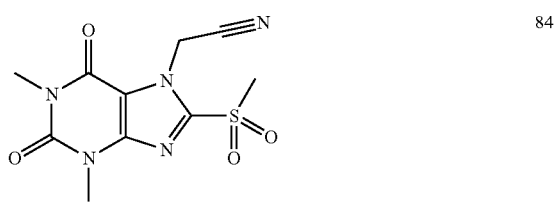
84

TABLE 1-continued
Series 1: black plain numbered compounds are novel; disclosed compositions
and uses of bold red numbered compounds (1, 2, 4, 5, 7, 8, 10, 18, 20, 21, 72, 73, 75, 87) are novel.
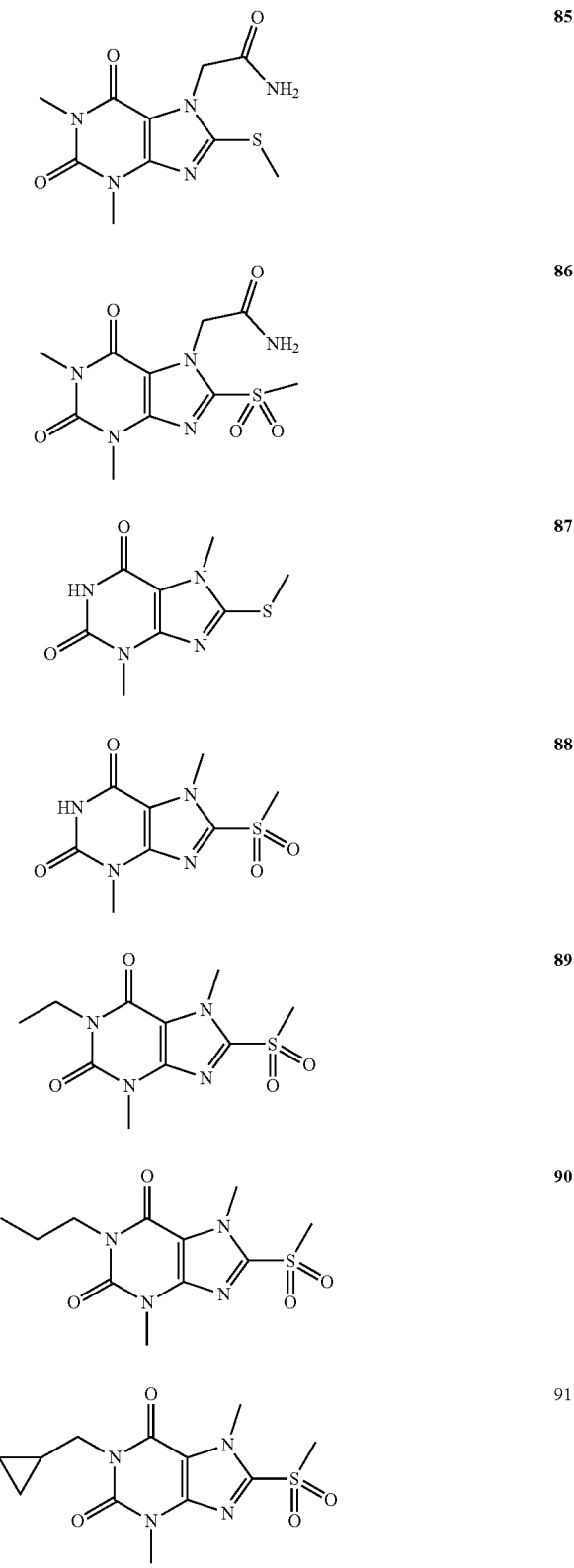
85
86
87
88
89
90
91

TABLE 1-continued
Series 1: black plain numbered compounds are novel; disclosed compositions and uses of bold red numbered compounds (1, 2, 4, 5, 7, 8, 10, 18, 20, 21, 72, 73, 75, 87) are novel.
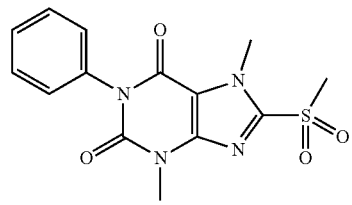 [SMILES: Cn1c(S(C)(=O)=O)nc2c1c(=O)n(-c1ccccc1)c(=O)n2C]  92
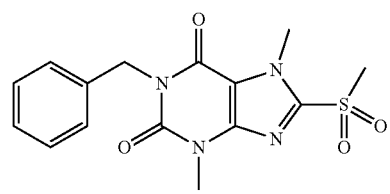 [SMILES: Cn1c(S(C)(=O)=O)nc2c1c(=O)n(Cc1ccccc1)c(=O)n2C]  93
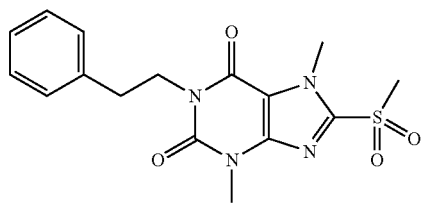 [SMILES: Cn1c(S(C)(=O)=O)nc2c1c(=O)n(CCc1ccccc1)c(=O)n2C]  94
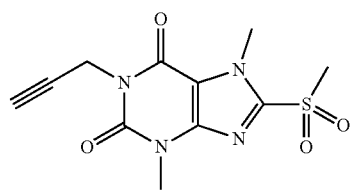 [SMILES: C#CCn1c(=O)c2c(nc(S(C)(=O)=O)n2C)n(C)c1=O]  95
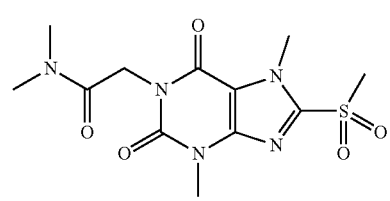 [SMILES: CN(C)C(=O)Cn1c(=O)c2c(nc(S(C)(=O)=O)n2C)n(C)c1=O]  96
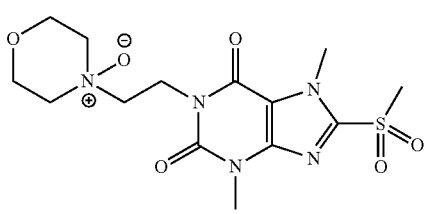 [SMILES: Cn1c(S(C)(=O)=O)nc2c1c(=O)n(CC[N+]1([O-])CCOCC1)c(=O)n2C]  97
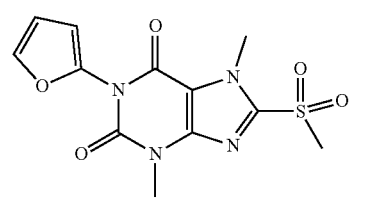 [SMILES: Cn1c(S(C)(=O)=O)nc2c1c(=O)n(-c1ccco1)c(=O)n2C]  98

TABLE 1-continued
Series 1: black plain numbered compounds are novel; disclosed compositions
and uses of bold red numbered compounds (1, 2, 4, 5, 7, 8, 10, 18, 20, 21, 72, 73, 75, 87) are novel.
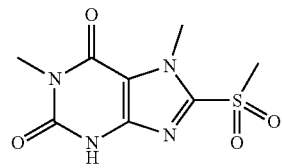 [SMILES: Cn1c(=O)[nH]c2nc(S(C)(=O)=O)n(C)c2c1=O] 99
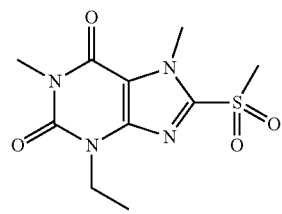 [SMILES: CCn1c(=O)n(C)c(=O)c2c1nc(S(C)(=O)=O)n2C] 100
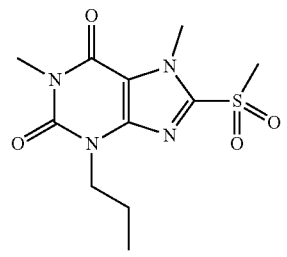 [SMILES: CCCn1c(=O)n(C)c(=O)c2c1nc(S(C)(=O)=O)n2C] 101
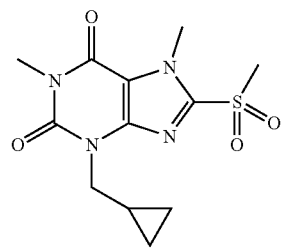 [SMILES: Cn1c(=O)c2c(nc(S(C)(=O)=O)n2C)n(CC2CC2)c1=O] 102
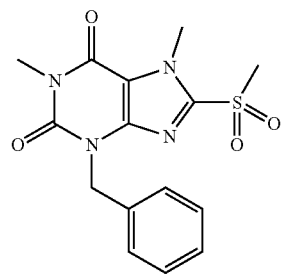 [SMILES: Cn1c(=O)c2c(nc(S(C)(=O)=O)n2C)n(Cc2ccccc2)c1=O] 103
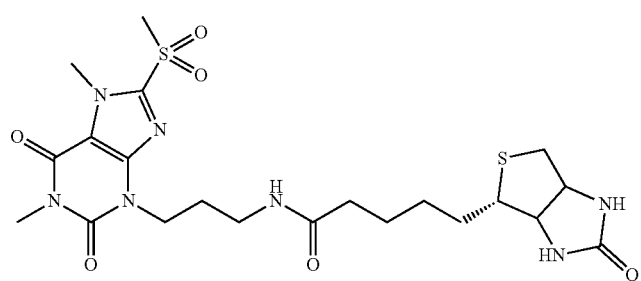 [SMILES: Cn1c(=O)c2c(nc(S(C)(=O)=O)n2C)n(CCCNC(=O)CCCC[C@@H]2SCC3NC(=O)NC32)c1=O] 104

TABLE 1-continued
Series 1: black plain numbered compounds are novel; disclosed compositions and uses of bold red numbered compounds (1, 2, 4, 5, 7, 8, 10, 18, 20, 21, 72, 73, 75, 87) are novel.
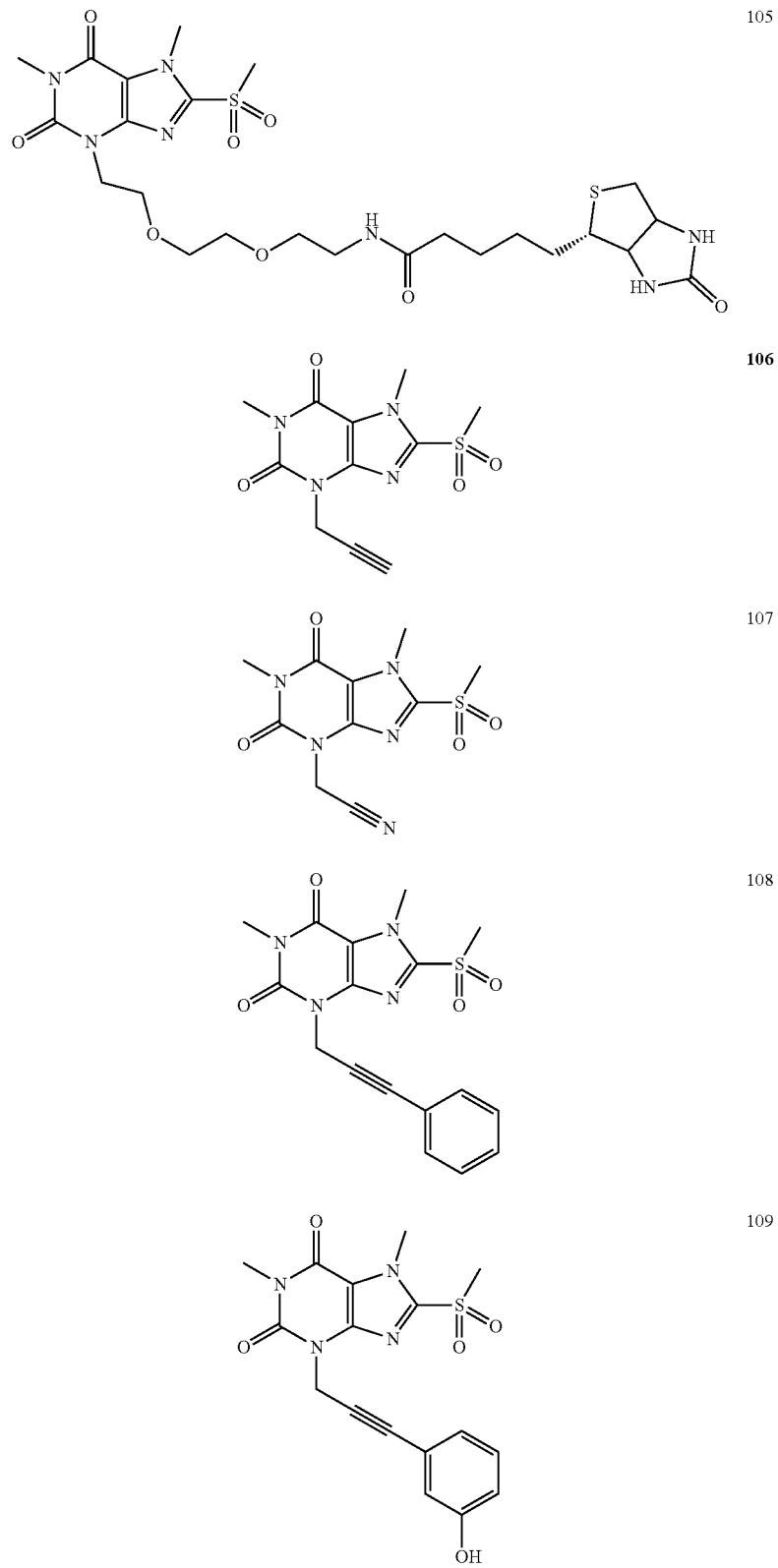
105
106
107
108
109

TABLE 1-continued
Series 1: black plain numbered compounds are novel; disclosed compositions
and uses of bold red numbered compounds (1, 2, 4, 5, 7, 8, 10, 18, 20, 21, 72, 73, 75, 87) are novel.
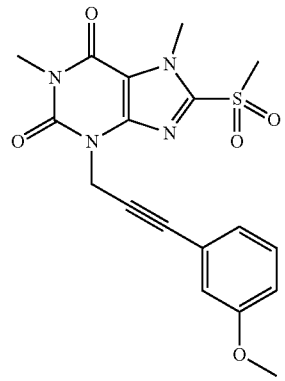 [SMILES: COc1cccc(C#CCn2c(=O)n(C)c(=O)c3c2nc(S(C)(=O)=O)n3C)c1]
110
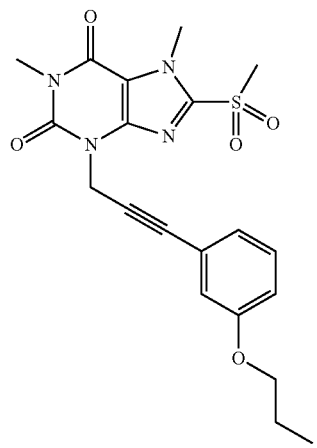 [SMILES: CCCOc1cccc(C#CCn2c(=O)n(C)c(=O)c3c2nc(S(C)(=O)=O)n3C)c1]
111
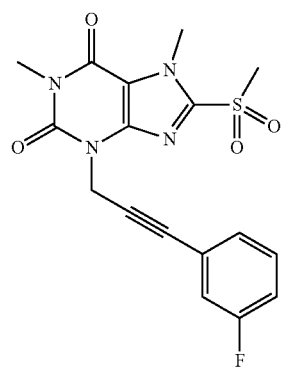 [SMILES: Cn1c(=O)c2c(nc(S(C)(=O)=O)n2C)n(CC#Cc2cccc(F)c2)c1=O]
112
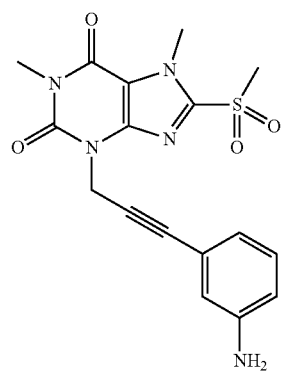 [SMILES: Cn1c(=O)c2c(nc(S(C)(=O)=O)n2C)n(CC#Cc2cccc(N)c2)c1=O]
113

TABLE 1-continued
Series 1: black plain numbered compounds are novel; disclosed compositions
and uses of bold red numbered compounds (1, 2, 4, 5, 7, 8, 10, 18, 20, 21, 72, 73, 75, 87) are novel.
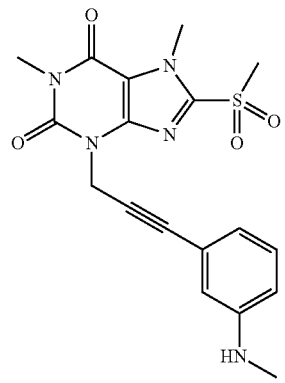 [SMILES: CNc1cccc(C#CCn2c(=O)n(C)c(=O)c3c2nc(S(C)(=O)=O)n3C)c1]
114
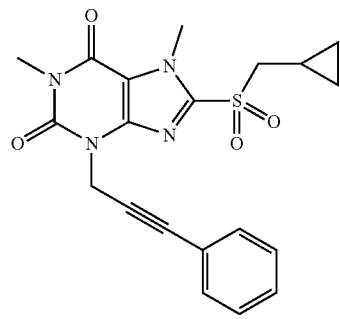 [SMILES: Cn1c(=O)c2c(nc(S(=O)(=O)CC3CC3)n2C)n(CC#Cc2ccccc2)c1=O]
115
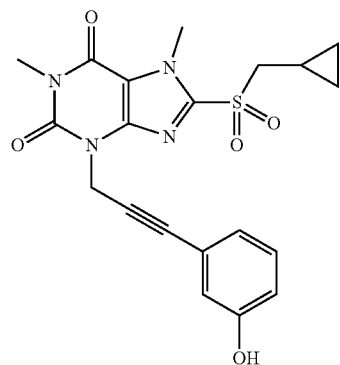 [SMILES: Cn1c(=O)c2c(nc(S(=O)(=O)CC3CC3)n2C)n(CC#Cc2cccc(O)c2)c1=O]
116
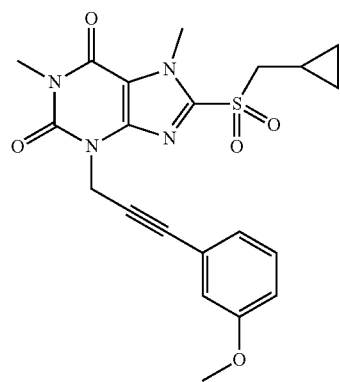 [SMILES: COc1cccc(C#CCn2c(=O)n(C)c(=O)c3c2nc(S(=O)(=O)CC2CC2)n3C)c1]
117

TABLE 1-continued
Series 1: black plain numbered compounds are novel; disclosed compositions
and uses of bold red numbered compounds (1, 2, 4, 5, 7, 8, 10, 18, 20, 21, 72, 73, 75, 87) are novel.
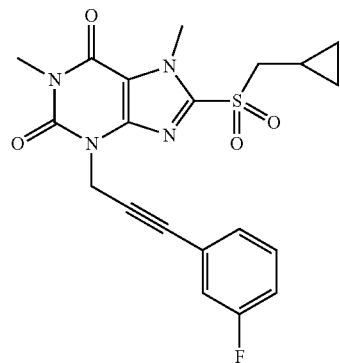 [SMILES: Cn1c(=O)c2c(nc(S(=O)(=O)CC3CC3)n2C)n(CC#Cc2cccc(F)c2)c1=O]
118
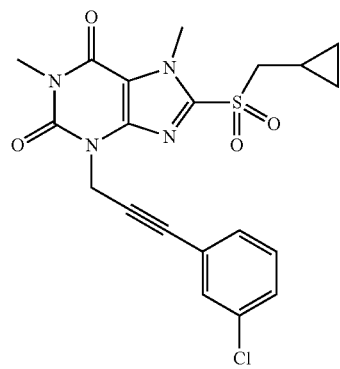 [SMILES: Cn1c(=O)c2c(nc(S(=O)(=O)CC3CC3)n2C)n(CC#Cc2cccc(Cl)c2)c1=O]
119
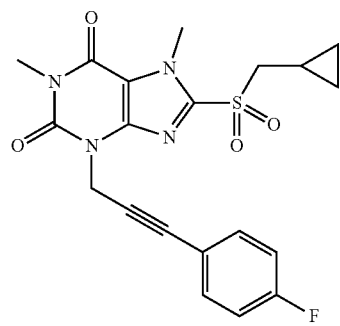 [SMILES: Cn1c(=O)c2c(nc(S(=O)(=O)CC3CC3)n2C)n(CC#Cc2ccc(F)cc2)c1=O]
120
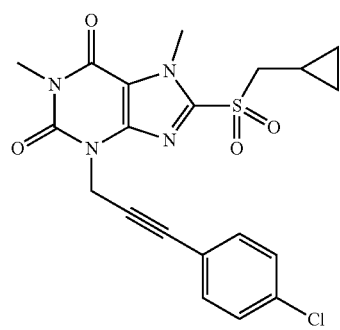
121

TABLE 1-continued
Series 1: black plain numbered compounds are novel; disclosed compositions
and uses of bold red numbered compounds (1, 2, 4, 5, 7, 8, 10, 18, 20, 21, 72, 73, 75, 87) are novel.
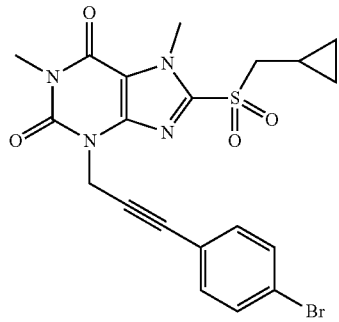 [SMILES: Cn1c(=O)c2c(nc(S(=O)(=O)CC3CC3)n2C)n(CC#Cc2ccc(Br)cc2)c1=O]
122
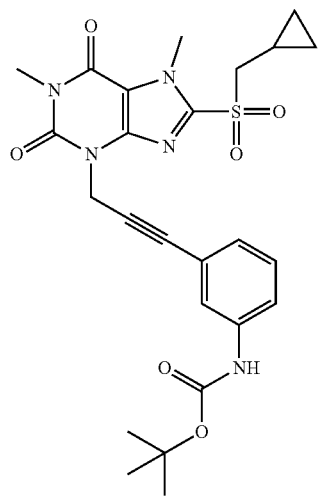 [SMILES: Cn1c(=O)c2c(nc(S(=O)(=O)CC3CC3)n2C)n(CC#Cc2cccc(NC(=O)OC(C)(C)C)c2)c1=O]
123
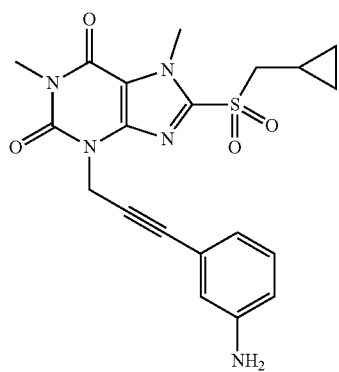 [SMILES: Cn1c(=O)c2c(nc(S(=O)(=O)CC3CC3)n2C)n(CC#Cc2cccc(N)c2)c1=O]
124
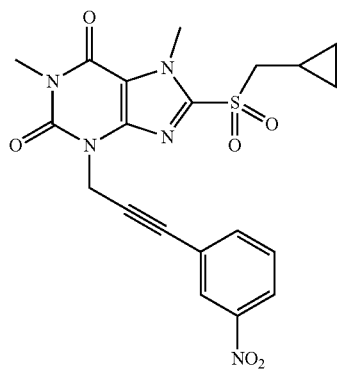 [SMILES: Cn1c(=O)c2c(nc(S(=O)(=O)CC3CC3)n2C)n(CC#Cc2cccc([N+](=O)[O-])c2)c1=O]
125

TABLE 1-continued
Series 1: black plain numbered compounds are novel; disclosed compositions and uses of bold red numbered compounds (1, 2, 4, 5, 7, 8, 10, 18, 20, 21, 72, 73, 75, 87) are novel.
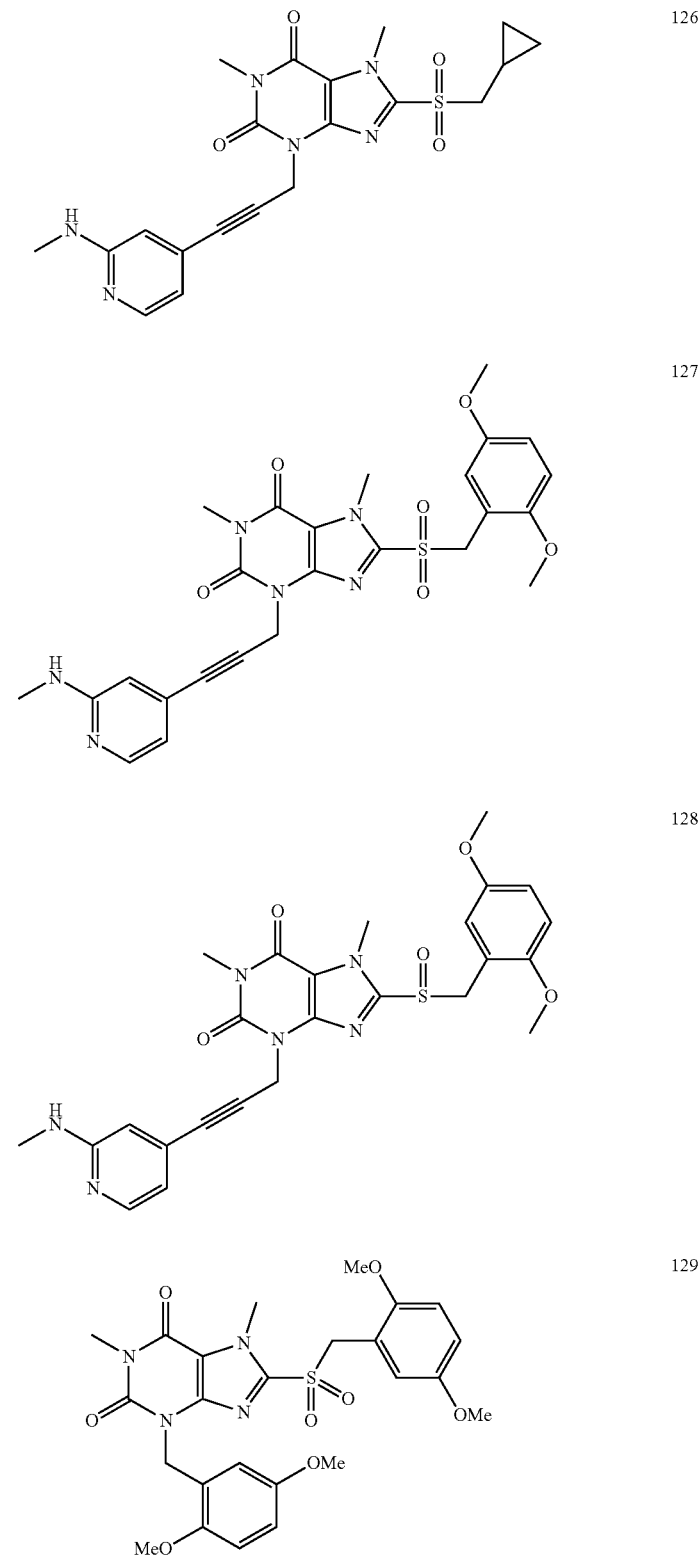

TABLE 1-continued
Series 1: black plain numbered compounds are novel; disclosed compositions
and uses of bold red numbered compounds (1, 2, 4, 5, 7, 8, 10, 18, 20, 21, 72, 73, 75, 87) are novel.
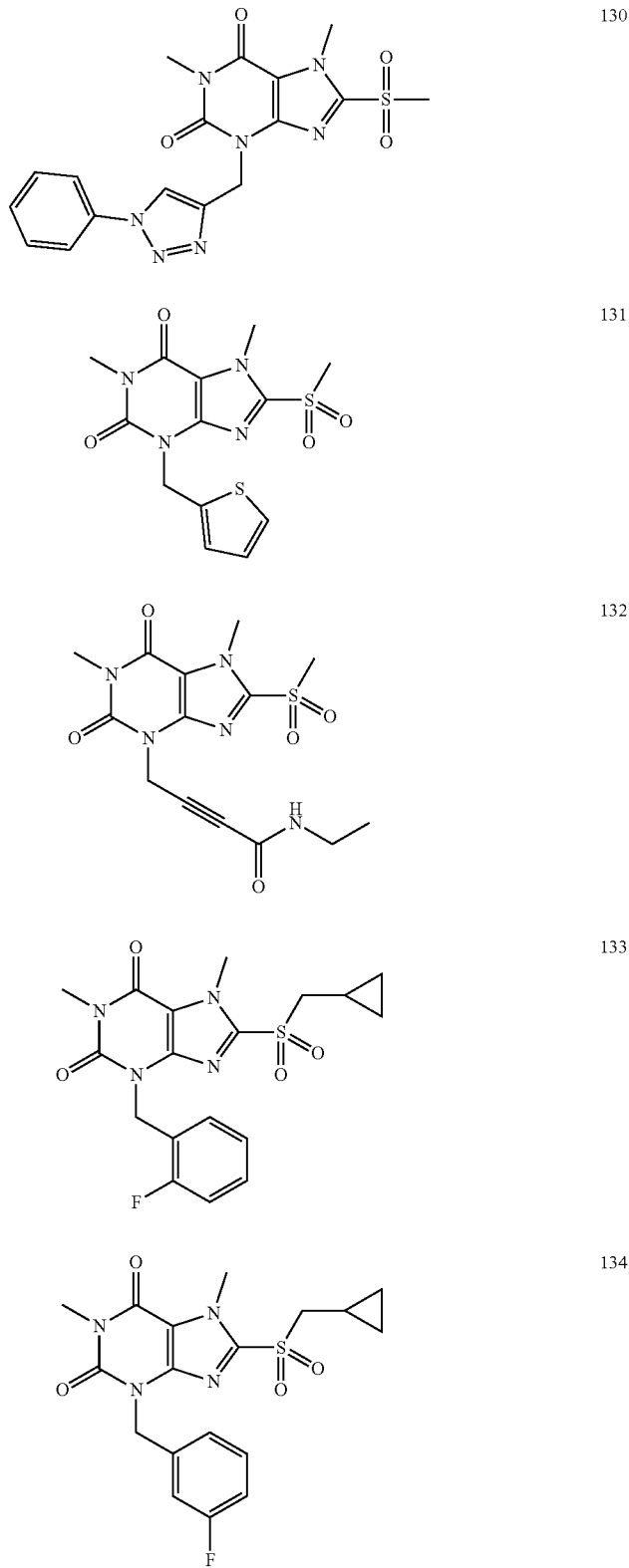
130
131
132
133
134

TABLE 1-continued
Series 1: black plain numbered compounds are novel; disclosed compositions
and uses of bold red numbered compounds (1, 2, 4, 5, 7, 8, 10, 18, 20, 21, 72, 73, 75, 87) are novel.
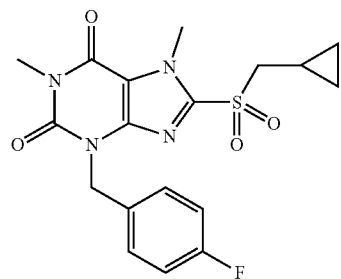 [SMILES: Cn1c(=O)c2c(nc(S(=O)(=O)CC3CC3)n2C)n(Cc2ccc(F)cc2)c1=O]
135
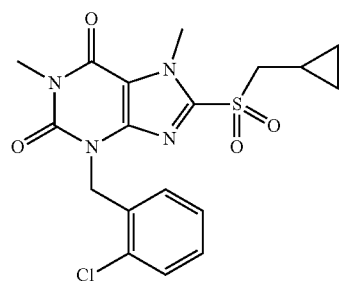 [SMILES: Cn1c(=O)c2c(nc(S(=O)(=O)CC3CC3)n2C)n(Cc2ccccc2Cl)c1=O]
136
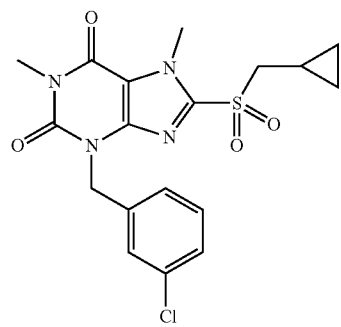 [SMILES: Cn1c(=O)c2c(nc(S(=O)(=O)CC3CC3)n2C)n(Cc2cccc(Cl)c2)c1=O]
137
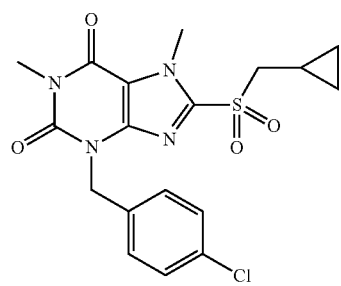 [SMILES: Cn1c(=O)c2c(nc(S(=O)(=O)CC3CC3)n2C)n(Cc2ccc(Cl)cc2)c1=O]
138
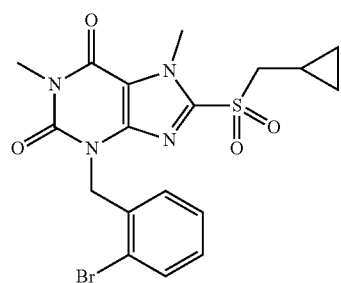 [SMILES: Cn1c(=O)c2c(nc(S(=O)(=O)CC3CC3)n2C)n(Cc2ccccc2Br)c1=O]
139

TABLE 1-continued
Series 1: black plain numbered compounds are novel; disclosed compositions
and uses of bold red numbered compounds (1, 2, 4, 5, 7, 8, 10, 18, 20, 21, 72, 73, 75, 87) are novel.
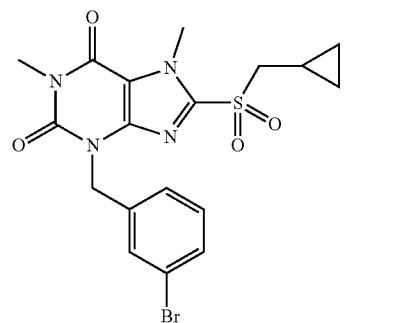 [SMILES: Cn1c(=O)c2c(nc(S(=O)(=O)CC3CC3)n2C)n(Cc2cccc(Br)c2)c1=O]
140
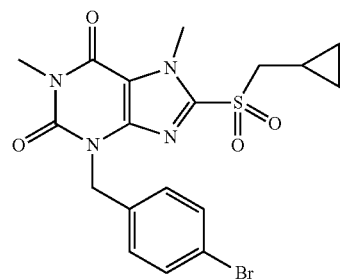 [SMILES: Cn1c(=O)c2c(nc(S(=O)(=O)CC3CC3)n2C)n(Cc2ccc(Br)cc2)c1=O]
141
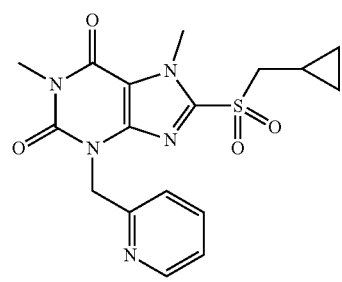 [SMILES: Cn1c(=O)c2c(nc(S(=O)(=O)CC3CC3)n2C)n(Cc2ccccn2)c1=O]
142
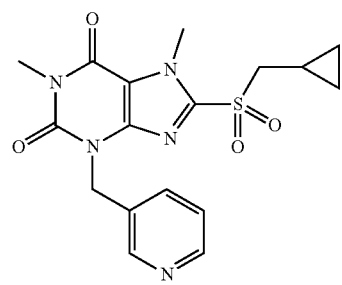 [SMILES: Cn1c(=O)c2c(nc(S(=O)(=O)CC3CC3)n2C)n(Cc2cccnc2)c1=O]
143
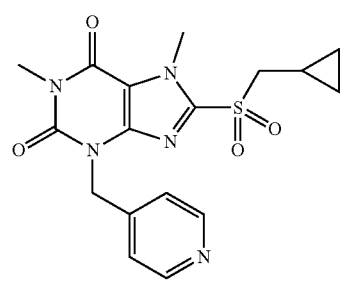 [SMILES: Cn1c(=O)c2c(nc(S(=O)(=O)CC3CC3)n2C)n(Cc2ccncc2)c1=O]
144

TABLE 1-continued
Series 1: black plain numbered compounds are novel; disclosed compositions
and uses of bold red numbered compounds (1, 2, 4, 5, 7, 8, 10, 18, 20, 21, 72, 73, 75, 87) are novel.
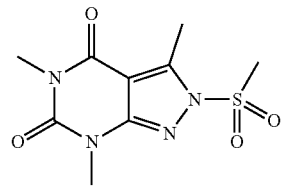 [SMILES: Cc1c2c(=O)n(C)c(=O)n(C)c2nn1S(C)(=O)=O]
145
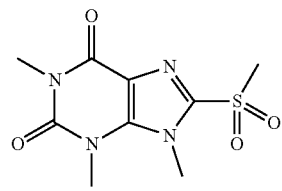 [SMILES: Cn1c(=O)c2nc(S(C)(=O)=O)n(C)c2n(C)c1=O]
146
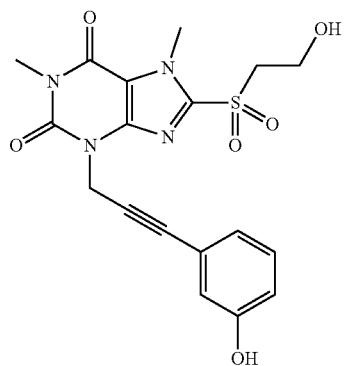 [SMILES: Cn1c(=O)c2c(nc(S(=O)(=O)CCO)n2C)n(CC#Cc2cccc(O)c2)c1=O]
147
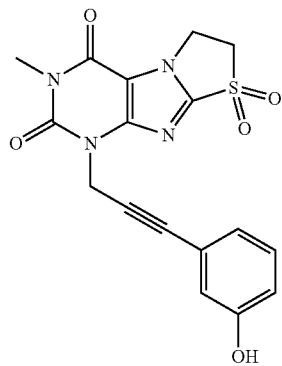 [SMILES: Cn1c(=O)c2c(nc3n2CCS3(=O)=O)n(CC#Cc2cccc(O)c2)c1=O]
148
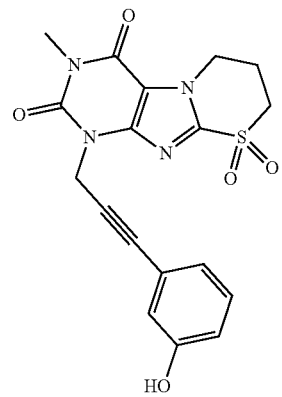 [SMILES: Cn1c(=O)c2c(nc3n2CCCS3(=O)=O)n(CC#Cc2cccc(O)c2)c1=O]
149

TABLE 1-continued
Series 1: black plain numbered compounds are novel; disclosed compositions
and uses of bold red numbered compounds (1, 2, 4, 5, 7, 8, 10, 18, 20, 21, 72, 73, 75, 87) are novel.
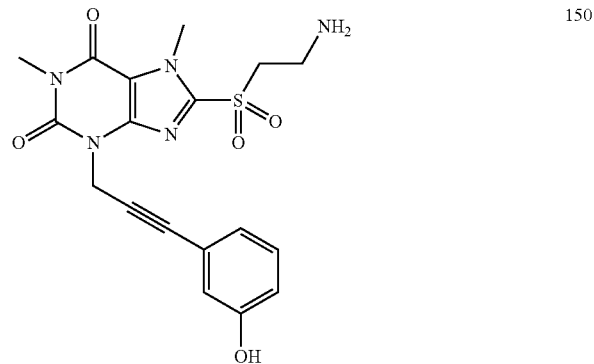
150
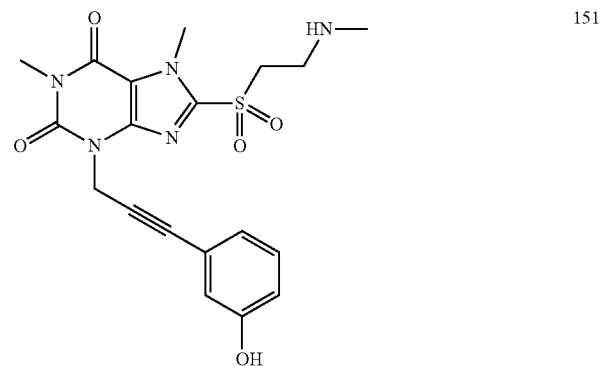
151
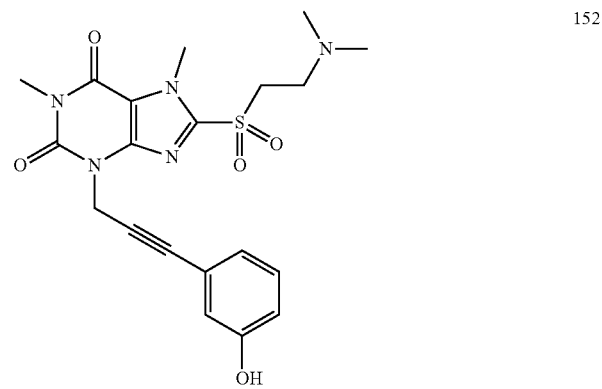
152
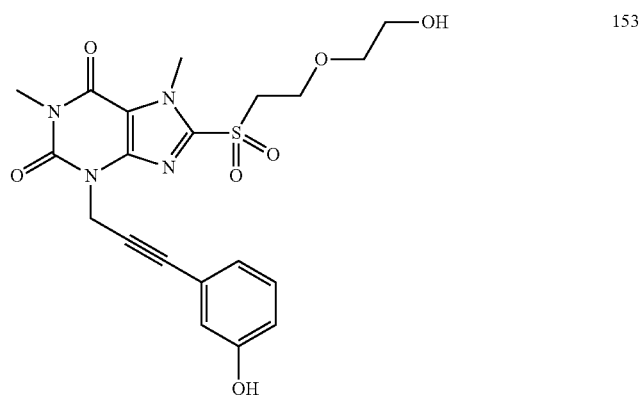
153

TABLE 1-continued
Series 1: black plain numbered compounds are novel; disclosed compositions
and uses of bold red numbered compounds (1, 2, 4, 5, 7, 8, 10, 18, 20, 21, 72, 73, 75, 87) are novel.
154
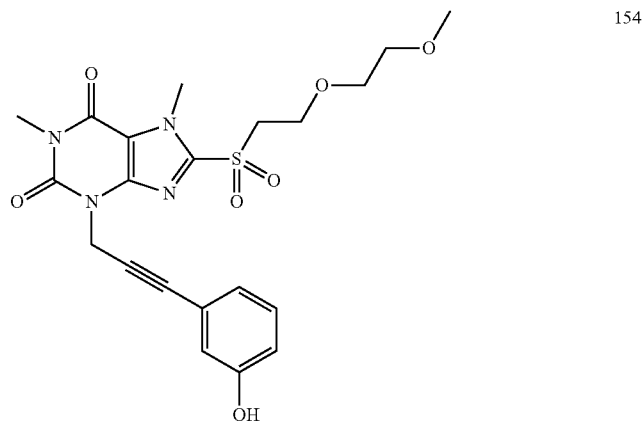
155
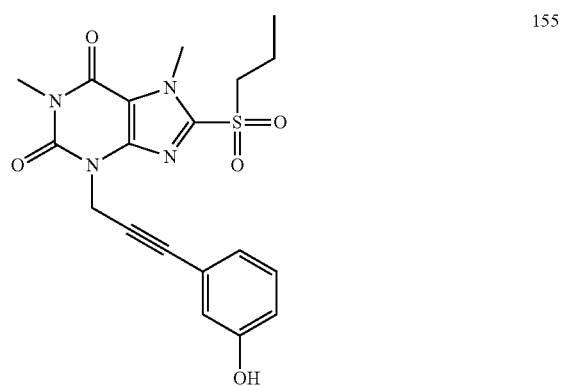
156
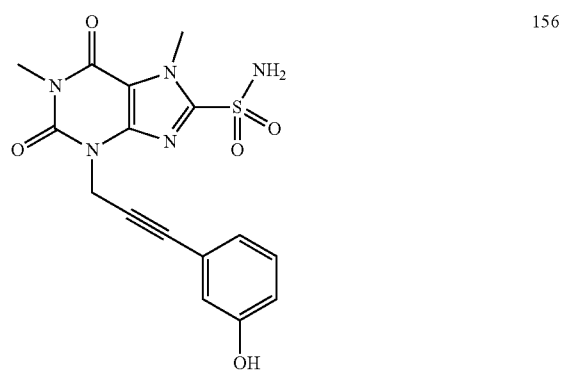
157
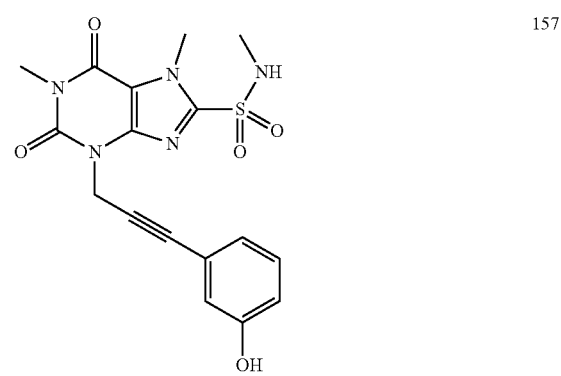

TABLE 1-continued
Series 1: black plain numbered compounds are novel; disclosed compositions and uses of bold red numbered compounds (1, 2, 4, 5, 7, 8, 10, 18, 20, 21, 72, 73, 75, 87) are novel.
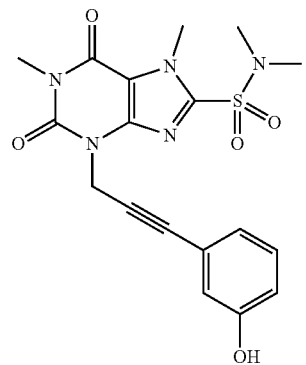 [SMILES: CN(C)S(=O)(=O)c1nc2c(c(=O)n(C)c(=O)n2CC#Cc2cccc(O)c2)n1C]
158
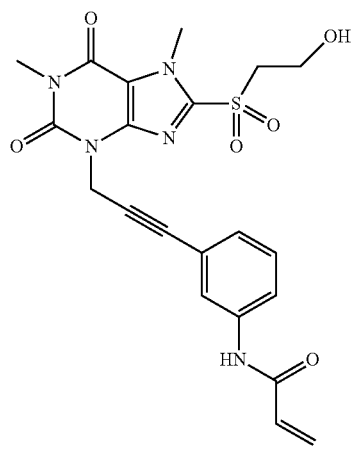 [SMILES: C=CC(=O)Nc1cccc(C#CCn2c(=O)n(C)c(=O)c3c2nc(S(=O)(=O)CCO)n3C)c1]
159
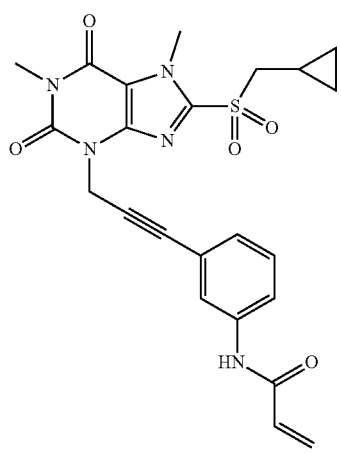 [SMILES: C=CC(=O)Nc1cccc(C#CCn2c(=O)n(C)c(=O)c3c2nc(S(=O)(=O)CC2CC2)n3C)c1]
160

TABLE 1-continued
Series 1: black plain numbered compounds are novel; disclosed compositions and uses of bold red numbered compounds (1, 2, 4, 5, 7, 8, 10, 18, 20, 21, 72, 73, 75, 87) are novel.
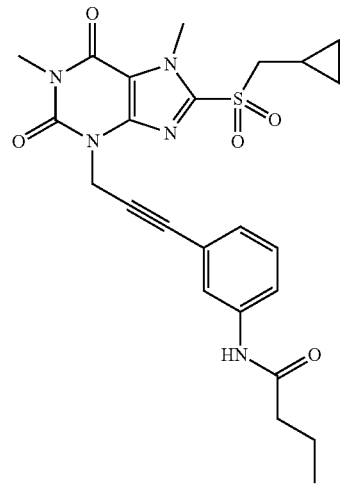 [SMILES: CCCC(=O)Nc1cccc(C#CCn2c(=O)n(C)c(=O)c3c2nc(S(=O)(=O)CC2CC2)n3C)c1]
161
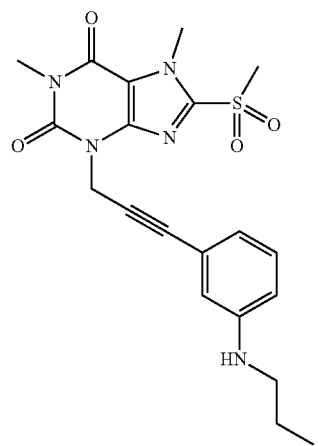 [SMILES: CCCNc1cccc(C#CCn2c(=O)n(C)c(=O)c3c2nc(S(C)(=O)=O)n3C)c1]
162
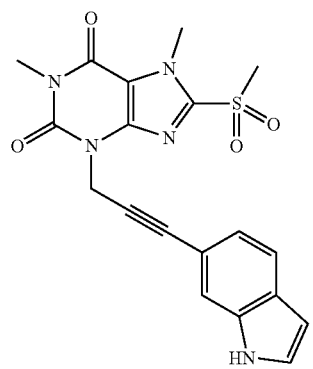 [SMILES: Cn1c(=O)c2c(nc(S(C)(=O)=O)n2C)n(CC#Cc2ccc3cc[nH]c3c2)c1=O]
163

TABLE 1-continued
Series 1: black plain numbered compounds are novel; disclosed compositions and uses of bold red numbered compounds (1, 2, 4, 5, 7, 8, 10, 18, 20, 21, 72, 73, 75, 87) are novel.
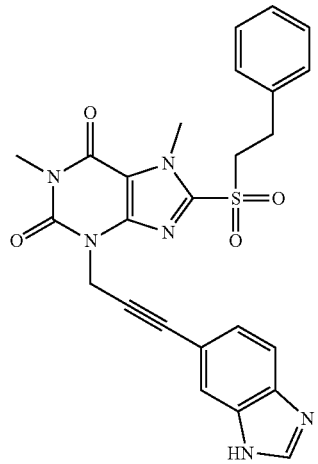 [SMILES: Cn1c(=O)c2c(nc(S(=O)(=O)CCc3ccccc3)n2C)n(CC#Cc2ccc3nc[nH]c3c2)c1=O]
164
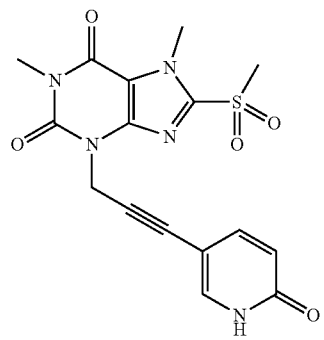 [SMILES: Cn1c(=O)c2c(nc(S(C)(=O)=O)n2C)n(CC#Cc2ccc(=O)[nH]c2)c1=O]
165
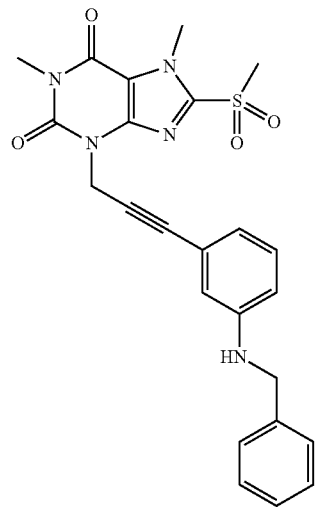 [SMILES: Cn1c(=O)c2c(nc(S(C)(=O)=O)n2C)n(CC#Cc2cccc(NCc3ccccc3)c2)c1=O]
166

TABLE 1-continued
Series 1: black plain numbered compounds are novel; disclosed compositions and uses of bold red numbered compounds (1, 2, 4, 5, 7, 8, 10, 18, 20, 21, 72, 73, 75, 87) are novel.
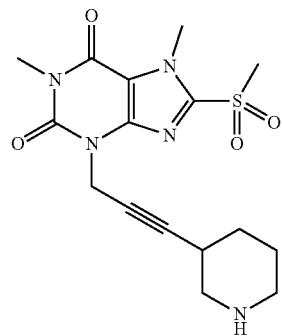 [SMILES: Cn1c(=O)c2c(nc(S(C)(=O)=O)n2C)n(CC#CC2CCCNC2)c1=O]
167
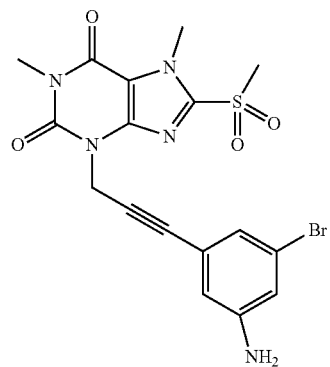 [SMILES: Cn1c(=O)c2c(nc(S(C)(=O)=O)n2C)n(CC#Cc2cc(N)cc(Br)c2)c1=O]
168
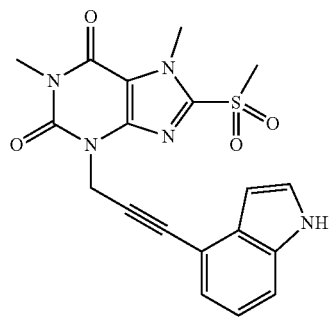 [SMILES: Cn1c(=O)c2c(nc(S(C)(=O)=O)n2C)n(CC#Cc2cccc3[nH]ccc23)c1=O]
169
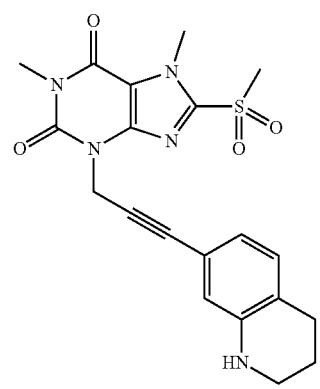 [SMILES: Cn1c(=O)c2c(nc(S(C)(=O)=O)n2C)n(CC#Cc2ccc3c(c2)NCCC3)c1=O]
170

TABLE 1-continued
Series 1: black plain numbered compounds are novel; disclosed compositions and uses of bold red numbered compounds (1, 2, 4, 5, 7, 8, 10, 18, 20, 21, 72, 73, 75, 87) are novel.
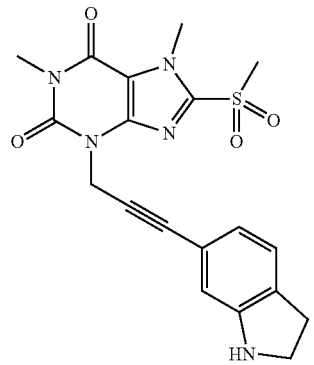 [SMILES: Cn1c(=O)c2c(nc(S(C)(=O)=O)n2C)n(CC#Cc2ccc3c(c2)NCC3)c1=O]
171
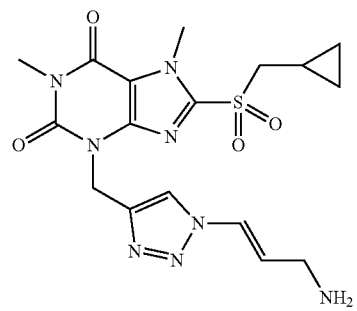 [SMILES: Cn1c(=O)c2c(nc(S(=O)(=O)CC3CC3)n2C)n(Cc2cn(/C=C/CN)nn2)c1=O]
172
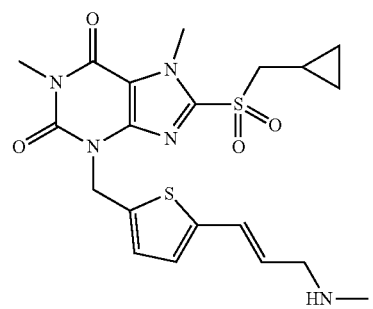 [SMILES: CNC/C=C/c1ccc(Cn2c(=O)n(C)c(=O)c3c2nc(S(=O)(=O)CC2CC2)n3C)s1]
173
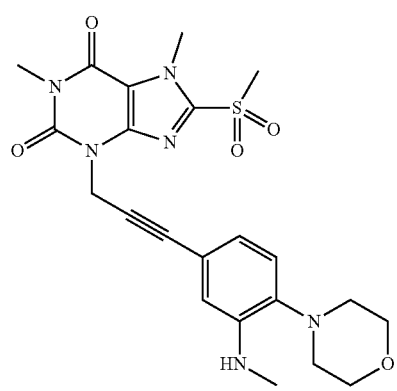 [SMILES: CNc1cc(C#CCn2c(=O)n(C)c(=O)c3c2nc(S(C)(=O)=O)n3C)ccc1N1CCOCC1]
174

TABLE 1-continued

Series 1: black plain numbered compounds are novel; disclosed compositions and uses of bold red numbered compounds (1, 2, 4, 5, 7, 8, 10, 18, 20, 21, 72, 73, 75, 87) are novel.

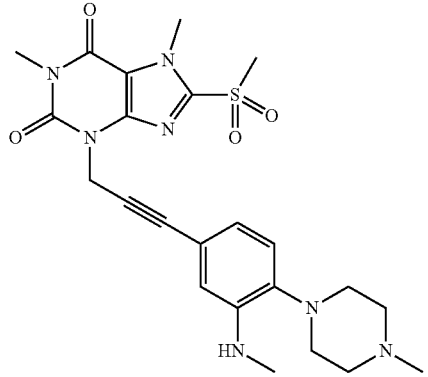 [SMILES: CNc1cc(C#CCn2c(=O)n(C)c(=O)c3c2nc(S(C)(=O)=O)n3C)ccc1N1CCN(C)CC1]

175

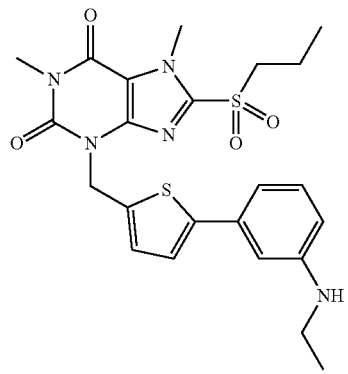 [SMILES: CCCS(=O)(=O)c1nc2c(c(=O)n(C)c(=O)n2Cc2ccc(-c3cccc(NCC)c3)s2)n1C]

176

Synthesis

Compound of 1: 8-chloro-1,3,7-trimethyl-1H-purine-2,6(3H,7H)-dione

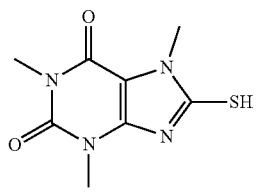

(I) Synthesis of 8-chloro-1,3,7-trimethyl-1H-purine-2,6(3H,7H)-dione

To a solution of 8-chloro-1,3-dimethyl-1H-purine-2,6 (3H,7H)-dione (200.0 mg, 0.93 mmol) and $K_2CO_3$ (154.8 mg, 1.12 mmol) in anhydrous DMF (2 mL) was added iodomethane (159.1 mg, 1.12 mmol) and stirred under nitrogen at RT for 4 h. The reaction mixture was poured into water and extracted with dichloromethane (3*5 mL) and the organic layer was separated, dried over $Na_2SO_4$, filtered, concentrated and purified by chromatography on silica gel (PE:EA=2:1) to give a white solid (151.0 mg, 70.4%). $^1$H-NMR (400 MHz, $CDCl_3$): δ 3.95 (s, 3H), 3.55 (s, 3H), 3.40 (s, 3H). Mass (m/z): 229.04[M+H]+.

(II) Synthesis of 8-mercapto-1,3,7-trimethyl-1H-purine-2,6(3H,7H)-dione

To a solution of 8-chloro-1,3,7-trimethyl-1H-purine-2,6 (3H,7H)-dione (151.0 mg, 0.66 mmol) in anhydrous DMF (2 mL) was added NaHS (111.3 mg, 1.98 mmol) and heated to 105° C. for 7 h. Then the mixture was cooled to RT and acidified to PH=3. The mixture was poured into water and extracted with dichloromethane (3*5 mL) and the organic layer was separated, dried over $Na_2SO_4$, filtered, concentrated and purified by chromatography on silica gel (PE:EA=1:4) to give a white solid (128.0 mg, 86.7%). $^1$H-NMR (400 MHz, DMSO-$d_6$): δ 13.68 (s, 1H), 3.68 (s, 3H), 3.37 (s, 3H), 3.19 (s, 3H). Mass (m/z): 227.05 [M+H]+.

Compound 2: 1,3,7-trimethyl-8-(methylthio)-1H-purine-2,6(3H,7H)-dione

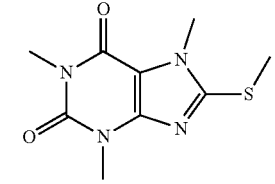

To a solution of compound 1 (20.0 mg, 0.09 mmol) and $K_2CO_3$ (14.7 mg, 0.11 mmol) in anhydrous DMF (2 mL) was added iodomethane (15.1 mg, 0.11 mmol) and stirred under nitrogen at RT for 2 h. The reaction mixture was poured into water and extracted with dichloromethane (3*5 mL) and the organic layer was separated, dried over Na$_2$SO$_4$, filtered, concentrated and purified by prep. TLC to give a white solid (19.2 mg, 95.05%). $^1$H-NMR (400 MHz, CDCl$_3$): δ 3.84 (s, 3H), 3.57 (s, 3H), 3.39 (s, 3H), 2.72 (s, 3H). Mass (m/z): 241.07 [M+H]+.

Compound 3: 1,3,7-trimethyl-8-(methylsulfinyl)-1H-purine-2,6(3H,7H)-dione

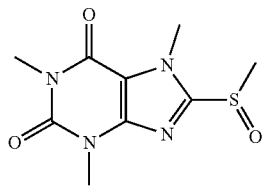 [SMILES: Cn1c(=O)c2c(nc(S(C)=O)n2C)n(C)c1=O]

Compound 4: 1,3,7-trimethyl-8-(methylsulfonyl)-1H-purine-2,6(3H,7H)-dione

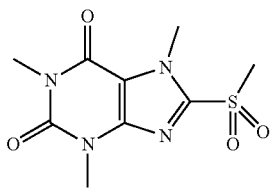 [SMILES: Cn1c(=O)c2c(nc(S(C)(=O)=O)n2C)n(C)c1=O]

To a solution of compound 2 (18.0 mg, 0.07 mmol) in MeOH (2 mL) was added oxone (69.2 mg, 0.1 mmol) in H$_2$O (2 mL). Then the mixture was stirred at RT for 5 h. Then the solvent was removed and extracted with dichloromethane (3*5 mL) and the organic layer was separated, dried over Na$_2$SO$_4$, filtered, concentrated and purified by prep. TLC to obtain compound 3 as a white solid (3.4 mg, 20.5%). $^1$H-NMR (400 MHz, CDCl$_3$): δ 4.28 (s, 3H), 3.58 (s, 3H), 3.41 (s, 3H), 3.18 (s, 3H). Mass (m/z): 257.06 [M+H]+.

To obtain compound 46.3 mg (30.8%) as a white solid. $^1$H-NMR (400 MHz, CDCl$_3$): δ 4.32 (s, 3H), 3.57 (s, 3H), 3.43 (s, 3H), 3.42 (s, 3H). Mass (m/z): 273.06 [M+H]+.

Compound 5: 8-(ethylthio)-1,3,7-trimethyl-1H-purine-2,6(3H,7H)-dione

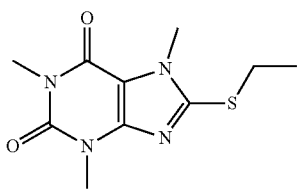 [SMILES: CCSc1nc2c(c(=O)n(C)c(=O)n2C)n1C]

To a solution of compound 1 (30 mg) and K$_2$CO$_3$ (21.98 mg) in anhydrous DMF (2 mL) was added iodoethane (24.8 mg) and stirred under nitrogen at RT for 3 h. The reaction mixture was poured into water and extracted with ethyl acetate (3*5 mL) and the organic layer was separated, dried over Na$_2$SO$_4$, filtered, concentrated and purified by prep. TLC (PE:EA 1:1) to obtain 25.2 mg (74.8%) as a white solid. $^1$H-NMR (400 MHz, CDCl$_3$): δ 3.85 (s, 3H), 3.57 (s, 3H), 3.39 (s, 3H), 3.28 (q, J=7.6 Hz, 2H), 1.43 (t, J=7.6 Hz, 3H). Mass (m/z): 255.08 [M+H]+.

Compound 6: 8-(ethylsulfinyl)-1,3,7-trimethyl-1H-purine-2,6(3H,7H)-dione

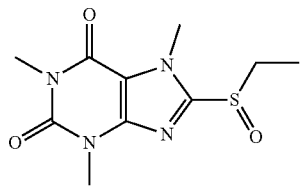 [SMILES: CCS(=O)c1nc2c(c(=O)n(C)c(=O)n2C)n1C]

Compound 7: 8-(ethylsulfonyl)-1,3,7-trimethyl-1H-purine-2,6(3H,7H)-dione

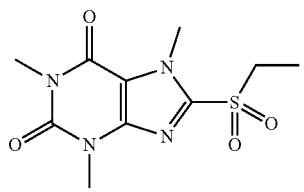 [SMILES: CCS(=O)(=O)c1nc2c(c(=O)n(C)c(=O)n2C)n1C]

To a solution of compound 6 (20 mg) in MeOH (2 mL) was added oxone (72.61 mg) in H$_2$O (2 mL). Then the mixture was stirred at RT for 2 h. Then the solvent was removed and extracted with dichloromethane (3*5 mL) and the organic layer was separated, dried over Na$_2$SO$_4$, filtered, concentrated and purified by prep. TLC to obtain compound 6 5.7 mg (34.5%) as a white solid. $^1$H-NMR (400 MHz, CDCl$_3$): δ 4.28 (s, 3H), 3.57 (s, 3H), 3.42 (s, 3H), 3.41 (q, J=7.6 Hz, 2H), 1.39 (t, J=7.6 Hz, 3H). Mass (m/z): 271.08 [M+H]+.

To obtain compound 712.3 mg (42.7%) as a white solid. $^1$H-NMR (400 MHz, CDCl$_3$): δ 4.33 (s, 3H), 3.59 (s, 3H), 3.55 (q, J=7.6 Hz, 2H), 3.42 (s, 3H), 1.46 (t, J=7.6 Hz, 3H). Mass (m/z): 287.07 [M+H]+.

Compound 8: 1,3,7-trimethyl-8-(propylthio)-1H-purine-2,6(3H,7H)-dione

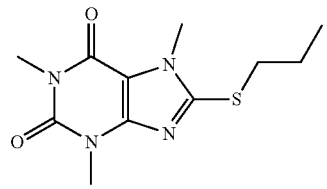 [SMILES: CCCSc1nc2c(c(=O)n(C)c(=O)n2C)n1C]

To a solution of compound 1 (30 mg) and K$_2$CO$_3$ (21.98 mg) in anhydrous DMF (2 mL) was added 1-iodopropane (27.07 mg) and stirred under nitrogen at RT for 3 h. The reaction mixture was poured into water and extracted with ethyl acetate (3*5 mL) and the organic layer was separated, dried over Na₂SO₄, filtered, concentrated and purified by prep. TLC (PE:EA 1:1) to obtain 30.2 mg (84.2%) as a white solid. ¹H-NMR (400 MHz, CDCl₃): δ 3.85 (s, 3H), 3.56 (s, 3H), 3.39 (s, 3H), 3.25 (q, J=2.8 Hz, 2H), 1.83-1.74 (m, 2H), 1.05 (t, J=7.2 Hz, 3H). Mass (m/z): 269.10 [M+H]+.

Compound 9: 1,3,7-trimethyl-8-(propylsulfinyl)-1H-purine-2,6(3H,7H)-dione

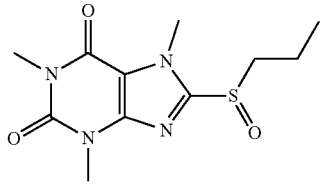 [SMILES: CCCS(=O)c1nc2c(c(=O)n(C)c(=O)n2C)n1C]

Compound 10: 1,3,7-trimethyl-8-(propylsulfonyl)-1H-purine-2,6(3H,7H)-dione

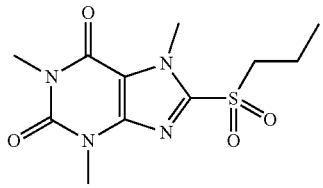 [SMILES: CCCS(=O)(=O)c1nc2c(c(=O)n(C)c(=O)n2C)n1C]

To a solution of compound 8 (25 mg) in MeOH (2 mL) was added oxone (86.01 mg) in H₂O (2 mL). Then the mixture was stirred at RT for 3 h. Then the solvent was removed and extracted with dichloromethane (3*10 mL) and the organic layer was separated, dried over Na₂SO₄, filtered, concentrated and purified by prep. TLC to obtain compound 9 7.9 mg (30.1%) as a white solid. ¹H-NMR (400 MHz, CDCl₃): δ 4.26 (s, 3H), 3.56 (s, 3H), 3.47 (q, J=6.8 Hz, 2H), 3.41 (s, 3H), 1.89-1.67 (m, 2H), 1.37 (t, J=7.2 Hz, 3H). Mass (m/z): 285.09 [M+H]+.

To obtain compound 10 15.2 mg (39.1%) as a white solid. ¹H-NMR (400 MHz, CDCl₃): δ 4.32 (s, 3H), 3.56 (s, 3H), 3.49 (q, J=5.6 Hz, 2H), 3.41 (s, 3H), 1.95-1.89 (m, 2H), 1.10 (t, J=7.6 Hz, 3H). Mass (m/z): 301.09 [M+H]+.

Compound 11: 8-(cyclopropylmethylthio)-1,3,7-trimethyl-1H-purine-2,6(3H,7H)-dione

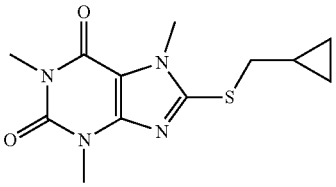 [SMILES: Cn1c(=O)c2c(nc(SCC3CC3)n2C)n(C)c1=O]

To a solution of compound 1 (30 mg) and K₂CO₃ (21.98 mg) in anhydrous DMF (2 mL) was added (bromomethyl) cyclopropane (21.34 mg) and stirred under nitrogen at RT for 2.5 h. The reaction mixture was poured into water and extracted with ethyl acetate (3*5 mL) and the organic layer was separated, dried over Na₂SO₄, filtered, concentrated and purified by prep. TLC (PE:EA 1:1) to obtain 36.5 mg (97.3%) as a white solid. ¹H-NMR (400 MHz, CDCl₃): δ 3.87 (s, 3H), 3.56 (s, 3H), 3.39 (s, 3H), 3.21 (d, J=7.6 Hz, 2H), 1.21-1.17 (m, 1H), 0.66-0.62 (m, 2H), 0.35-0.33 (m, 2H). Mass (m/z): 281.10 [M+H]+.

Compound 12: 8-(cyclopropylmethylsulfinyl)-1,3,7-trimethyl-1H-purine-2,6(3H,7H)-dione

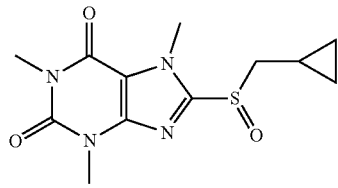 [SMILES: Cn1c(=O)c2c(nc(S(=O)CC3CC3)n2C)n(C)c1=O]

Compound 13: 8-(cyclopropylmethylsulfonyl)-1,3,7-trimethyl-1H-purine-2,6(3H,7H)-dione

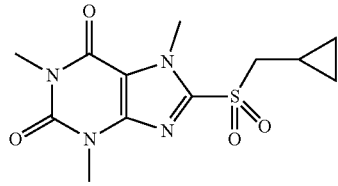 [SMILES: Cn1c(=O)c2c(nc(S(=O)(=O)CC3CC3)n2C)n(C)c1=O]

To a solution of compound 11 (23 mg) in MeOH (2 mL) was added oxone (75.7 mg) in H₂O (2 mL). Then the mixture was stirred at RT for 2 h. Then the solvent was removed and extracted with dichloromethane (3*10 mL) and the organic layer was separated, dried over Na₂SO₄, filtered, concentrated and purified by prep. TLC to obtain compound 12 7.7 mg (29.5%) as a white solid. ¹H-NMR (400 MHz, CDCl₃): δ 4.26 (s, 3H), 3.56 (s, 3H), 3.40 (s, 3H), 3.33 (d, J=7.6 Hz, 2H), 1.15-1.05 (m, 1H), 0.72-0.68 (m, 2H), 0.42-0.36 (m, 2H). Mass (m/z): 297.09 [M+H]+.

To obtain compound 13 13.4 mg (49.7%) as a white solid. ¹H-NMR (400 MHz, CDCl₃): δ 4.36 (s, 3H), 3.57 (s, 3H), 3.43 (s, 3H), 3.41 (d, J=4.0 Hz, 2H), 1.19-1.11 (m, 1H), 0.71-0.66 (m, 2H), 0.34-0.30 (m, 2H). Mass (m/z): 313.09 [M+H]+.

Compound 14: 1,3,7-trimethyl-8-(2,2,2-trifluoroethylsulfinyl)-1H-purine-2,6(3H,7H)-dione

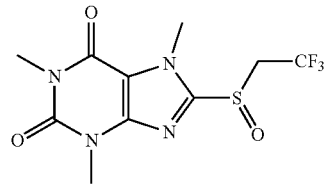 [SMILES: Cn1c(=O)c2c(nc(S(=O)CC(F)(F)F)n2C)n(C)c1=O]

Compound 15: 1,3,7-trimethyl-8-(2,2,2-trifluoroethylsulfonyl)-1H-purine-2,6(3H,7H)-dione

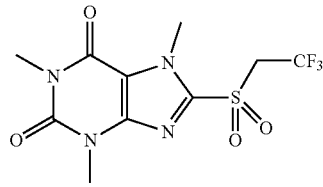 [SMILES: Cn1c(=O)c2c(nc(S(=O)(=O)CC(F)(F)F)n2C)n(C)c1=O]

(I) Synthesis of 1,3,7-trimethyl-8-(2,2,2-trifluoroethylthio)-1H-purine-2,6(3H,7H)-dione To a solution of compound 1 (30.0 mg, 0.13 mmol) and K$_2$CO$_3$ (21.4 mg, 0.15 mmol) in anhydrous DMF (5 mL) was added 2-bromo-1,1,1-trifluoroethane (25.9 mg, 0.15 mmol) and stirred under nitrogen at RT for overnight. Then the reaction mixture was poured into water and extracted with EA (3*10 mL) and the organic layer was separated, dried over Na$_2$SO$_4$, filtered, concentrated and purified by prep. TLC to give a white solid (14.1 mg). Mass (m/z): 309.06 [M+H]+.

(II) Synthesis of 1,3,7-trimethyl-8-(2,2,2-trifluoroethylsulfonyl)-1H-purine-2,6(3H,7H)-dione and 1,3,7-trimethyl-8-(2,2,2-trifluoroethylsulfinyl)-1H-purine-2,6(3H,7H)-dione To a solution of 1,3,7-trimethyl-8-(2,2,2-trifluoroethylthio)-1H-purine-2,6(3H,7H)-dione (10 mg, 0.03 mmol) in DCM (2 mL) was added m-CPBA (11.2 mg, 0.06 mmol). Then the mixture was stirred at RT for 2 h. Then the solvent was removed and extracted with dichloromethane (3*5 mL) and the organic layer was separated, dried over Na$_2$SO$_4$, filtered, concentrated and purified by prep. TLC to obtain compound 14 as a white solid (3.1 mg, 28.8%). $^1$H-NMR (400 MHz, CDCl3): δ 4.38 (m, 2H), 4.35 (s, 3H), 3.58 (s, 3H), 3.42 (s, 3H). Mass (m/z): 341.05 [M+H]+.

To obtain compound 15 4.3 mg (30.4%) as a white solid. $^1$H-NMR (400 MHz, CDCl$_3$): δ 4.55-4.46 (m, 1H), 4.28 (s, 3H), 4.11-4.05 (m, 1H), 3.58 (s, 3H), 3.42 (s, 3H). Mass (m/z): 325.05 [M+H]+.

Compound 16: 8-(2-(2-(2-hydroxyethoxy)ethoxy)ethylsulfonyl)-1,3,7-trimethyl-1H-purine-2,6(3H,7H)-dione

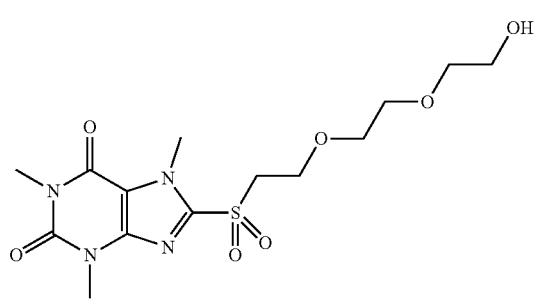 [SMILES: Cn1c(=O)c2c(nc(S(=O)(=O)CCOCCOCCO)n2C)n(C)c1=O]

(I) Synthesis of 8-(2-(2-(2-hydroxyethoxy)ethoxy)ethylthio)-1,3,7-trimethyl-1H-purine-2,6(3H,7H)-dione To a solution of compound 1 (100 mg, 0.44 mmol) and Cs$_2$CO$_3$ (172.9 mg, 0.53 mmol) in anhydrous DMF (4 mL) was added 2-(2-(2-chloroethoxy) ethoxy)ethanol (89.4 mg, 0.53 mmol) and reacted in the microwave on a Biotage Smith Synthesis at 130° C. for 1 h. Then the mixture was cooled to RT and acidified to PH=3 extracted with dichloromethane (3*10 mL) and the organic layer was separated, dried over Na$_2$SO$_4$, filtered, concentrated to give a white solid (28.4 mg). Mass (m/z): 359.13 [M+H]+.

(II) Synthesis of 8-(2-(2-(2-hydroxyethoxy)ethoxy)ethylsulfonyl)-1,3,7-trimethyl-1H-purine-2,6(3H,7H)-dione To a solution of 8-(2-(2-(2-hydroxyethoxy)ethoxy)ethylthio)-1,3,7-trimethyl-1H-purine-2,6(3H,7H)-dione (25.0 mg, 0.07 mmol) in MeOH (2 mL) was added oxone (171.7 mg, 0.28 mmol) in H2O (2 mL). Then the mixture was stirred at RT for 5 h. Then the solvent was removed and extracted with dichloromethane (3*10 mL) and the organic layer was separated, dried over Na2SO4, filtered, concentrated and purified by prep. TLC to give a white solid (2.3 mg, 8.43%). 1H-NMR (400 MHz, CDCl3): δ 4.32 (s, 3H), 4.00-3.92 (m, 2H), 3.94-3.90 (m, 4H), 3.77-3.66 (m, 2H), 3.58 (s, 3H), 3.57-3.42 (m, 4H), 3.41 (s, 3H). Mass (m/z): 391.12 [M+H]+.

Compound 17: 8-(but-3-ynylsulfonyl)-1,3,7-trimethyl-1H-purine-2,6(3H,7H)-dione

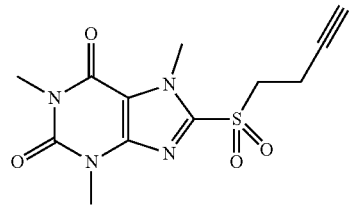 [SMILES: C#CCCS(=O)(=O)c1nc2c(c(=O)n(C)c(=O)n2C)n1C]

(I) Synthesis of 8-(but-3-ynylthio)-1,3,7-trimethyl-1H-purine-2,6(3H,7H)-dione

To a solution of compound 1 (50.0 mg, 0.22 mmol) and K$_2$CO$_3$ (36.6 mg, 0.26 mmol) in anhydrous DMF (2 mL) was added 4-bromobut-1-yne (35.3 mg, 0.26 mmol) and stirred under nitrogen at RT for overnight. Then the reaction mixture was poured into water and extracted with dichloromethane (3*10 mL) and the organic layer was separated, dried over Na$_2$SO$_4$, filtered, concentrated to give a white solid (52.3 mg). Mass (m/z): 279.08 [M+H]+.

(II) Synthesis of 8-(but-3-ynylsulfonyl)-1,3,7-trimethyl-1H-purine-2,6(3H,7H)-dione To a solution of 8-(but-3-ynylthio)-1,3,7-trimethyl-1H-purine-2,6(3H,7H)-dione (25.0 mg, 0.09 mmol) in MeOH (2 mL) was added oxone (221.1 mg, 0.36 mmol) in H$_2$O (2 mL). Then the mixture was stirred at RT for 5 h. Then the solvent was removed and extracted with dichloromethane (3*5 mL) and the organic layer was separated, dried over Na₂SO₄, filtered, concentrated and purified by prep. TLC to give a white solid (20.1 mg, 72.3%). ¹H-NMR (400 MHz, CDCl₃): δ 4.32 (s, 3H), 3.72 (t, J=7.2 Hz, 2H), 3.57 (s, 3H), 3.41 (s, 3H), 2.86-2.81 (m, 2H), 1.98 (t, J=2.8 Hz, 1H). Mass (m/z): 311.07 [M+H]+.

Compound 18: 8-(isopropylsulfonyl)-1,3,7-trimethyl-1H-purine-2,6(3H,7H)-dione

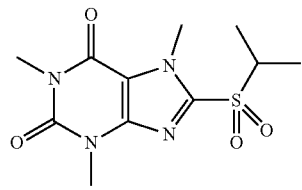 [SMILES: CC(C)S(=O)(=O)c1nc2c(c(=O)n(C)c(=O)n2C)n1C]

(I) Synthesis of 8-(isopropylthio)-1,3,7-trimethyl-1H-purine-2,6(3H,7H)-dione

To a solution of compound 1 (50.0 mg, 0.22 mmol) and K₂CO₃ (36.6 mg, 0.26 mmol) in anhydrous DMF (5 mL) was added 2-iodopropane (45.1 mg, 0.26 mmol) and stirred under nitrogen at RT for overnight. Then the reaction mixture was poured into water and extracted with dichloromethane (3*10 mL) and the organic layer was separated, dried over Na₂SO₄, filtered, concentrated and purified by prep. TLC (PE:EA) to give a white solid (34.7 mg, 58.6%).

(II) Synthesis of 8-(isopropylsulfonyl)-1,3,7-trimethyl-1H-purine-2,6(3H,7H)-dione To a solution of 8-(isopropylthio)-1,3,7-trimethyl-1H-purine-2,6(3H,7H)-dione (30.0 mg) in MeOH (2 mL) was added oxone (275.3 mg) in H₂O (2 mL). Then the mixture was stirred at RT for 5 h. Then the solvent was removed and extracted with dichloromethane (3*5 mL) and the organic layer was separated, dried over Na₂SO₄, filtered, concentrated and purified by prep. TLC (PE:EA 1:1) to give 31.5 mg (93.75%) as a white solid. ¹H-NMR (400 MHz, CDCl3): δ 4.34 (s, 3H), 3.77-0.372 (m, 1H), 3.57 (s, 3H), 3.42 (s, 3H), 1.43 (d, J=7.2 Hz, 6H). Mass (m/z): 301.09 [M+H]+.

Compound 19: 8-(benzo[d][1,3]dioxol-5-ylmethylsulfonyl)-1,3,7-trimethyl-1H-purine-2,6(3H,7H)-dione

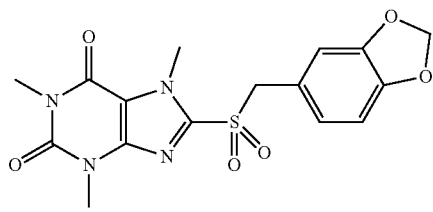 [SMILES: Cn1c(=O)c2c(nc(S(=O)(=O)Cc3ccc4c(c3)OCO4)n2C)n(C)c1=O]

(I) Synthesis of 5-(bromomethyl)benzo[d][1,3]dioxole

To a solution of benzo[d][1,3]dioxol-5-ylmethanol (1 g) in DCM was slowly added tribromophosphine (2.65 g) at 0° C. Then the mixture was stirred at RT overnight. The solvent was removed and extracted with dichloromethane (3*15 mL) and concentrated to give a yellow solid (1.2 g, 84.51%).

(II) Synthesis of 8-((benzo[d][1,3]dioxol-5-ylmethyl)thio)-1,3,7-trimethyl-1H-purine-2,6(3H,7H)-dione To a solution of compound 1 (50.0 mg, 0.22 mmol) and K₂CO₃ (36.6 mg, 0.26 mmol) in anhydrous DMF (5 mL) was added 5-(bromomethyl)benzo[d][1,3]dioxole (57.1 mg, 0.26 mmol) and stirred under nitrogen at RT for overnight. Then the reaction mixture was poured into water and extracted with dichloromethane (3*10 mL) and the organic layer was separated, dried over Na₂SO₄, filtered, concentrated and purified by prep. TLC (PE:EA 1:1) to give a white solid (23.4 mg, 29.4%).

(III) Synthesis of 8-((benzo[d][1,3]dioxol-5-ylmethyl)sulfonyl)-1,3,7-trimethyl-1H-purine-2,6(3H,7H)-dione To a solution of 8-((benzo[d][1,3]dioxol-5-ylmethyl)thio)-1,3,7-trimethyl-1H-purine-2,6(3H,7H)-dione (50.0 mg) in DCM (5 mL) was added m-CPBA (47.9 mg) Then the mixture was stirred at RT for 2 h. Then the solvent was removed and extracted with dichloromethane (3*5 mL) and the organic layer was separated, dried over Na₂SO₄, filtered, concentrated and purified by prep. TLC (1:1) to give 20.3 mg (38.4%) as a white solid. ¹H-NMR (400 MHz, CDCl3): δ 6.74-6.71 (m, 2H), 6.59 (s, 1H), 5.98 (s, 2H), 4.58 (s, 2H), 3.91 (s, 3H), 3.62 (s, 3H), 3.40 (s, 3H). Mass (m/z): 393.08 [M+H]+.

Compound 20: 1,3,7-trimethyl-8-(phenylsulfonyl)-1H-purine-2,6(3H,7H)-dione

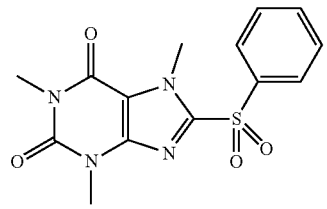 [SMILES: Cn1c(=O)c2c(nc(S(=O)(=O)c3ccccc3)n2C)n(C)c1=O]

(I) Synthesis of 1,3,7-trimethyl-8-(phenylthio)-1H-purine-2,6(3H,7H)-dione

To a solution of 8-chloro-1,3,7-trimethyl-1H-purine-2,6 (3H,7H)-dione (100.0 mg, 0.44 mmol) and Cs₂CO₃ (354.5 mg, 1.09 mmol) in anhydrous DMF (5 mL) was added benzenethiol (57.9 mg, 0.53 mmol) and stirred under nitrogen at RT for overnight. Then the reaction mixture was poured into water and extracted with EA (3*10 mL) and the organic layer was separated, dried over Na₂SO₄, filtered, concentrated and purified by prep. TLC to give a white solid (54.7 mg, 41.3%). ¹H-NMR (400 MHz, CDCl₃): δ 7.45-7.31 (m, 5H), 3.93 (s, 3H), 3.57 (s, 3H), 3.40 (s, 3H). Mass (m/z): 303.08 [M+H]+.

(II) Synthesis of 1,3,7-trimethyl-8-(phenylsulfonyl)-1H-purine-2,6(3H,7H)-dione

To a solution of 1,3,7-trimethyl-8-(phenylthio)-1H-purine-2,6(3H,7H)-dione (28.0 mg, 0.09 mmol) in MeOH (5 mL) was added oxone (227.9 mg, 0.37 mmol) in H$_2$O (5 mL). Then the mixture was stirred at RT for 5 h. Then the solvent was removed and extracted with dichloromethane (3*10 mL) and the organic layer was separated, dried over Na$_2$SO$_4$, filtered, concentrated and purified by prep. TLC to give a white solid (14.3 mg, 46.2%). $^1$H-NMR (400 MHz, CDCl$_3$): δ 8.08-8.05 (m, 2H), 7.73-7.70 (m, 1H), 7.63-7.59 (m, 2H), 4.32 (s, 3H), 3.52 (s, 3H), 3.38 (s, 3H). Mass (m/z): 335.07 [M+H]+.

Compound 21:8-(benzylsulfonyl)-1,3,7-trimethyl-1H-purine-2,6(3H,7H)-dione

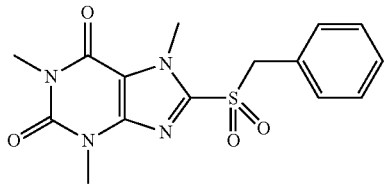 [SMILES: Cn1c(=O)c2c(nc(S(=O)(=O)Cc3ccccc3)n2C)n(C)c1=O]

(I) Synthesis of 8-(benzylthio)-1,3,7-trimethyl-1H-purine-2,6(3H,7H)-dione

To a solution of compound 1 (70.0 mg) and K$_2$CO$_3$ (52.1 mg) in anhydrous DMF (5 mL) was added (bromomethyl) benzene (63.5 mg) and stirred under nitrogen at RT overnight. Then the reaction mixture was poured into water and extracted with EA (3*10 mL) and the organic layer was separated, dried over Na$_2$SO$_4$, filtered, concentrated to give a white solid.

(II) Synthesis of 8-(benzylsulfonyl)-1,3,7-trimethyl-1H-purine-2,6(3H,7H)-dione

To a solution of 8-(benzylthio)-1,3,7-trimethyl-1H-purine-2,6(3H,7H)-dione (50.0 mg) in MeOH (2 mL) was added oxone (388.96 mg) in H$_2$O (2 mL). Then the mixture was stirred at RT for 5 h. Then the solvent was removed and extracted with dichloromethane (3*5 mL) and the organic layer was separated, dried over Na$_2$SO$_4$, filtered, concentrated and purified by prep. TLC (PE:EA 1:1) to give 28.4 mg (51.6%) as a white solid. $^1$H-NMR (400 MHz, CDCl3): δ 7.40-7.32 (m, 3H), 7.17-7.15 (m, 2H), 4.65 (s, 2H), 3.70 (s, 3H), 3.63 (s, 3H), 3.40 (s, 3H). Mass (m/z): 349.09 [M+H]+.

Compound 22: 1,3,7-trimethyl-8-(phenethylsulfonyl)-1H-purine-2,6(3H,7H)-dione

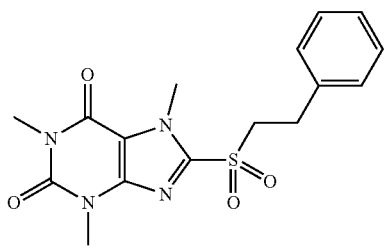 [SMILES: Cn1c(=O)c2c(nc(S(=O)(=O)CCc3ccccc3)n2C)n(C)c1=O]

(I) Synthesis of 1,3,7-trimethyl-8-(phenethylthio)-1H-purine-2,6(3H,7H)-dione

To a solution of compound 1 (70.0 mg) and K$_2$CO$_3$ (52.8 mg) in anhydrous DMF (5 mL) was added (2-bromoethyl) benzene (68.95 mg) and stirred under nitrogen at RT overnight. Then the reaction mixture was poured into water and extracted with EA (3*10 mL) and the organic layer was separated, dried over Na$_2$SO$_4$, filtered, concentrated to give a yellow oil.

(II) Synthesis of 1,3,7-trimethyl-8-(phenethylsulfonyl)-1H-purine-2,6(3H,7H)-dione To a solution of 1,3,7-trimethyl-8-(phenethylthio)-1H-purine-2,6(3H,7H)-dione (20 mg) in MeOH (1 mL) was added oxone (149.1 mg) in H$_2$O (1 mL). Then the mixture was stirred at RT for 5 h. Then the solvent was removed and extracted with dichloromethane (3*5 mL) and the organic layer was separated, dried over Na$_2$SO$_4$, filtered, concentrated and purified by prep. TLC (PE:EA 1:1) to give 6.3 mg (28.77%) as a white solid. $^1$H-NMR (400 MHz, CDCl3): δ 7.29-7.17 (m, 5H), 4.29 (s, 3H), 3.83 (t, J=8.0 Hz, 2H), 3.54 (s, 3H), 3.41 (s, 3H), 3.21 (t, J=8.0 Hz, 2H). Mass (m/z): 363.10 [M+H]+.

Compound 23: 1,3,7-trimethyl-8-(naphthalen-2-ylmethylsulfonyl)-1H-purine-2,6(3H,7H)-dione

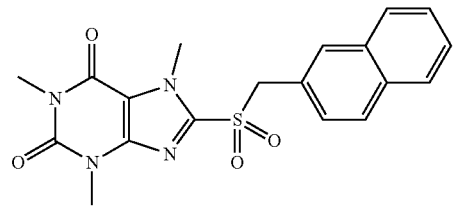 [SMILES: Cn1c(=O)c2c(nc(S(=O)(=O)Cc3ccc4ccccc4c3)n2C)n(C)c1=O]

(I) Synthesis of 1,3,7-trimethyl-8-((naphthalen-2-ylmethyl)thio)-1H-purine-2,6(3H,7H)-dione To a solution of compound 1 (50 mg) and K$_2$CO$_3$ (36.6 mg) in anhydrous DMF (5 mL) was added 2-(bromomethyl) naphthalene (58.7 mg) and stirred under nitrogen at RT overnight.

Then the reaction mixture was poured into water and extracted with EA (3*5 mL) and the organic layer was separated, dried over Na$_2$SO$_4$, filtered, concentrated and purified by prep. TLC (PE:EA 1:1) to give 20.4 mg (25.2%) as a white solid.

(II) Synthesis of 1,3,7-trimethyl-8-((naphthalen-2-ylmethyl)sulfonyl)-1H-purine-2,6(3H,7H)-dione To a solution of 1,3,7-trimethyl-8-((naphthalen-2-ylmethyl)thio)-1H-purine-2,6(3H,7H)-dione (10 mg) in MeOH (1 mL) was added oxone (67.2 mg) in H$_2$O (1 mL). Then the mixture was stirred at RT overnight. Then the solvent was removed and extracted with dichloromethane (3*5 mL) and the organic layer was separated, dried over Na$_2$SO$_4$, filtered, concentrated and purified by prep. TLC (PE:EA 1:2) to give 8.2 mg (75.5%) as a white solid. $^1$H-NMR (400 MHz, CDCl3): δ 7.85-7.75 (m, 4H), 7.54-7.52 (m, 2H), 7.24-7.20 (m, 1H), 4.85 (s, 2H), 3.72 (s, 3H), 3.65 (s, 3H), 3.38 (s, 3H). Mass (m/z): 399.10 [M+H]+.

Compound 24: 1,3,7-trimethyl-8-(naphthalen-1-ylmethylsulfonyl)-1H-purine-2,6(3H,7H)-dione

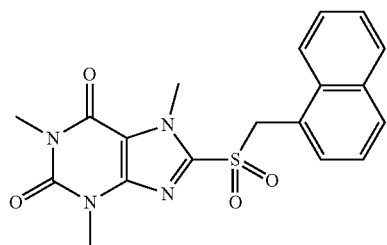 [SMILES: Cn1c(=O)c2c(nc(S(=O)(=O)Cc3cccc4ccccc34)n2C)n(C)c1=O]

(I) Synthesis of 1,3,7-trimethyl-8-((naphthalen-1-ylmethyl)thio)-1H-purine-2,6(3H,7H)-dione To a solution of compound 1 (50 mg) and K$_2$CO$_3$ (36.6 mg) in anhydrous DMF (5 mL) was added 1-(bromomethyl)naphthalene (58.7 mg) and stirred under nitrogen at RT overnight. Then the reaction mixture was poured into water and extracted with EA (3*5 mL) and the organic layer was separated, dried over Na$_2$SO$_4$, filtered, concentrated and purified by prep. TLC (PE:EA 1:1) to give 18.5 mg (22.85%) as a white solid.

(II) Synthesis of 1,3,7-trimethyl-8-((naphthalen-1-ylmethyl)sulfonyl)-1H-purine-2,6(3H,7H)-dione To a solution of 1,3,7-trimethyl-8-((naphthalen-1-ylmethyl)thio)-1H-purine-2,6(3H,7H)-dione (10 mg) in MeOH (1 mL) was added oxone (67.2 mg) in H$_2$O (1 mL). Then the mixture was stirred at RT overnight. Then the solvent was removed and extracted with dichloromethane (3*5 mL) and the organic layer was separated, dried over Na$_2$SO$_4$, filtered, concentrated and purified by prep. TLC (PE:EA 1:2) to give 5.2 mg (48.2%) as a white solid. $^1$H-NMR (400 MHz, CDCl3): δ 7.95-7.85 (m, 3H), 7.49-7.43 (m, 3H), 7.41-7.35 (m, 1H), 5.16 (s, 2H), 3.64 (s, 3H), 3.41 (s, 3H), 3.36 (s, 3H). Mass (m/z): 399.10 [M+H]+.

Compound 25: 5-((4S)-2-oxohexahydro-1H-thieno[3,4-d]imidazol-4-yl)-N-(2-(2-(2-(2-(4-(2-(1,3,7-trimethyl-2,6-dioxo-2,3,6,7-tetrahydro-1H-purin-8-ylsulfonyl)ethyl)-1H-1,2,3-triazol-1-yl)ethoxy)ethoxy)ethoxy)ethyl)pentanamide

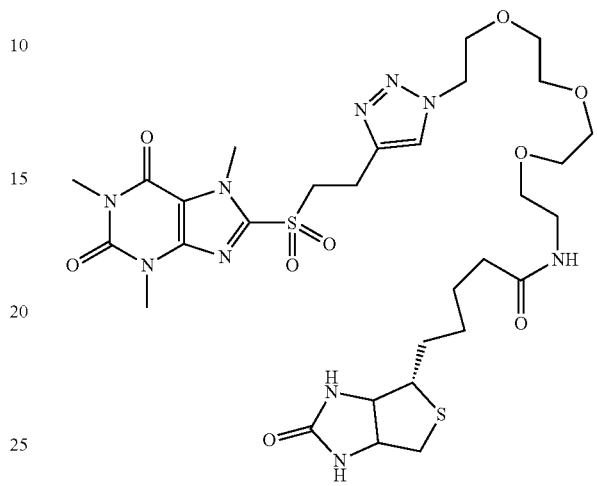

To a solution of compound 17 (10.0 mg, 0.03 mmol), N-(2-(2-(2-(2-azidoethoxy)ethoxy)ethoxy)ethyl)-5-((4S)-2-oxohexahydro-1H-thieno[3,4-d]imidazol-4-yl)pentanamide (17.2 mg, 0.04 mmol) and CuI (0.31 mg, 0.002 mmol) in anhydrous THF (1 mL) was added TEA (6.6 mg, 0.06 mmol) and stirred under nitrogen at RT for 4 h. Then the reaction mixture was poured into water and extracted with dichloromethane (3*3 mL) and the organic layer was separated, dried over Na$_2$SO$_4$, filtered, concentrated and purified by pre-HPLC to give a white solid (4.3 mg, 14.7%). $^1$H-NMR (400 MHz, DMSO-d$_6$): δ 7.91 (s, 1H), 7.81 (t, J=5.6 Hz, 1H), 6.43 (br, 1H), 4.40 (t, J=5.2 Hz, 2H), 4.31-4.28 (m, 1H), 4.18 (s, 3H), 4.13-4.10 (m, 1H), 3.98 (t, J=7.6 Hz, 2H), 3.73 (t, J=5.2 Hz, 2H), 3.49-3.47 (m, 6H), 3.47 (s, 3H), 3.37 (t, J=6.0 Hz, 2H), 3.25 (s, 3H), 3.16-3.09 (m, 6H), 2.83-2.79 (m, 1H), 2.58-2.53 (m, 1H), 2.04 (t, J=7.2 Hz, 2H), 1.60-1.57 (m, 1H), 1.49-1.43 (m, 4H), 1.23-1.13 (m, 3H). Mass (m/z): 755.29 [M+H]+.

Compound 26: 8-(2-fluorobenzylsulfonyl)-1,3,7-trimethyl-1H-purine-2,6(3H,7H)-dione

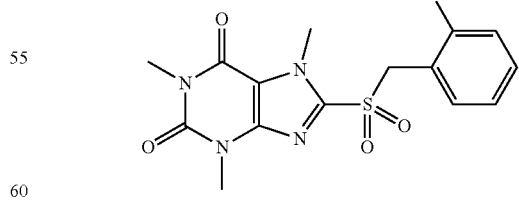

(I) Synthesis of 8-((2-fluorobenzyl)thio)-1,3,7-trimethyl-1H-purine-2,6(3H,7H)-dione To a solution of compound 1 (50 mg) and K$_2$CO$_3$ (36.6 mg) in anhydrous DMF (5 mL) was added 1-(bromomethyl)-2-fluorobenzene (50.2 mg) and stirred under nitrogen at RT overnight. Then the reaction mixture was poured into water and extracted with dichloromethane (3*10 mL) and the organic layer was separated, dried over Na₂SO₄, filtered, concentrated and purified by prep. TLC (PE:EA 1:1) to give a white solid (24.8 mg, 33.6%).

(II) Synthesis of 8-((2-fluorobenzyl)sulfonyl)-1,3,7-trimethyl-1H-purine-2,6(3H,7H)-dione To a solution of 8-((2-fluorobenzyl)thio)-1,3,7-trimethyl-1H-purine-2,6(3H,7H)-dione (10.0 mg) in MeOH (3 mL) was added oxone (73.6 mg) in H₂O (3 mL). Then the mixture was stirred at RT for 5 h. Then the solvent was removed and extracted with dichloromethane (3*5 mL) and the organic layer was separated, dried over Na₂SO₄, filtered, concentrated and purified by prep. TLC to give 6.3 mg (57.5%) as a white solid. ¹H-NMR (400 MHz, CDCl3): δ 7.43-7.05 (m, 4H), 4.75 (s, 2H), 3.89 (s, 3H), 3.60 (s, 3H), 3.41 (s, 3H). Mass (m/z): 367.08 [M+H]+.

Compound 27: 8-(3-fluorobenzylsulfonyl)-1,3,7-trimethyl-1H-purine-2,6(3H,7H)-dione

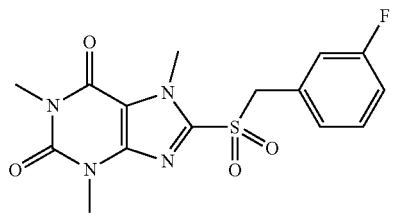 [SMILES: Cn1c(=O)c2c(nc(S(=O)(=O)Cc3cccc(F)c3)n2C)n(C)c1=O]

(I) Synthesis of 8-((3-fluorobenzyl)thio)-1,3,7-trimethyl-1H-purine-2,6(3H,7H)-dione To a solution of compound 1 (50 mg) and K₂CO₃ (36.6 mg) in anhydrous DMF (5 mL) was added 1-(bromomethyl)-3-fluorobenzene (50.2 mg) and stirred under nitrogen at RT overnight. Then the reaction mixture was poured into water and extracted with dichloromethane (3*10 mL) and the organic layer was separated, dried over Na₂SO₄, filtered, concentrated and purified by prep. TLC (PE:EA 1:1) to give a white solid (27.4 mg, 37.1%).

(II) Synthesis of 8-((3-fluorobenzyl)sulfonyl)-1,3,7-trimethyl-1H-purine-2,6(3H,7H)-dione To a solution of 8-((3-fluorobenzyl)thio)-1,3,7-trimethyl-1H-purine-2,6(3H,7H)-dione (10.0 mg) in MeOH (3 mL) was added oxone (73.6 mg) in H₂O (3 mL). Then the mixture was stirred at RT for 5 h. Then the solvent was removed and extracted with dichloromethane (3*5 mL) and the organic layer was separated, dried over Na₂SO₄, filtered, concentrated and purified by prep. TLC to give 7.1 mg (64.78%) as a white solid. ¹H-NMR (400 MHz, CDCl3): δ 7.35-6.97 (m, 4H), 4.69 (s, 2H), 3.91 (s, 3H), 3.62 (s, 3H), 3.40 (s, 3H). Mass (m/z): 367.08 [M+H]+.

Compound 28: 8-(4-fluorobenzylsulfonyl)-1,3,7-trimethyl-1H-purine-2,6(3H,7H)-dione

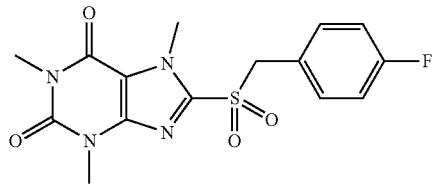 [SMILES: Cn1c(=O)c2c(nc(S(=O)(=O)Cc3ccc(F)cc3)n2C)n(C)c1=O]

(I) Synthesis of 8-((4-fluorobenzyl)thio)-1,3,7-trimethyl-1H-purine-2,6(3H,7H)-dione To a solution of compound 1 (50 mg) and K₂CO₃ (36.6 mg) in anhydrous DMF (5 mL) was added 1-(bromomethyl)-4-fluorobenzene (50.2 mg) and stirred under nitrogen at RT overnight. Then the reaction mixture was poured into water and extracted with dichloromethane (3*10 mL) and the organic layer was separated, dried over Na₂SO₄, filtered, concentrated and purified by prep. TLC (PE:EA 1:1) to give a white solid (29.3 mg, 39.65%).

(II) Synthesis of 8-((4-fluorobenzyl)sulfonyl)-1,3,7-trimethyl-1H-purine-2,6(3H,7H)-dione To a solution of 8-((4-fluorobenzyl)thio)-1,3,7-trimethyl-1H-purine-2,6(3H,7H)-dione (10.0 mg) in MeOH (3 mL) was added oxone (73.6 mg) in H₂O (3 mL). Then the mixture was stirred at RT for 5 h. Then the solvent was removed and extracted with dichloromethane (3*5 mL) and the organic layer was separated, dried over Na₂SO₄, filtered, concentrated and purified by prep. TLC to give 8.4 mg (76.64%) as a white solid. ¹H-NMR (400 MHz, CDCl3): δ 7.22 (q, J=8.8 Hz, 2H), 7.12 (t, J=8.4 Hz, 2H), 4.67 (s, 2H), 3.89 (s, 3H), 3.62 (s, 3H), 3.41 (s, 3H). Mass (m/z): 367.08 [M+H]+.

Compound 29: 8-(2-chlorobenzylsulfonyl)-1,3,7-trimethyl-1H-purine-2,6(3H,7H)-dione

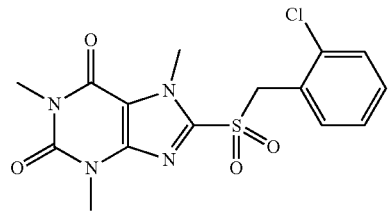

(I) Synthesis of 8-(2-chlorobenzylthio)-1,3,7-trimethyl-1H-purine-2,6(3H,7H)-dione To a solution of compound 1 (40.0 mg, 0.17 mmol) and K₂CO₃ (29.3 mg, 0.21 mmol) in anhydrous DMF (2 mL) was added 1-(bromomethyl)-2-chlorobenzene (43.6 mg, 0.21 mmol) and stirred under nitrogen at RT for overnight. Then the reaction mixture was poured into water and extracted with dichloromethane (3*10 mL) and the organic layer was separated, dried over Na₂SO₄, filtered, concentrated and purified by prep. TLC to give a white solid (18.4 mg, 30.2%). $^1$H-NMR (400 MHz, CDCl3): δ 7.40-7.38 (m, 2H), 7.23-7.19 (m, 1H), 7.19-7.15 (m, 1H), 4.56 (s, 2H), 3.72 (s, 3H), 3.61 (s, 3H), 3.38 (s, 3H). Mass (m/z): 351.06 [M+H]+.

(II) Synthesis of 8-(2-chlorobenzylsulfonyl)-1,3,7-trimethyl-1H-purine-2,6(3H,7H)-dione To a solution of 8-(2-chlorobenzylthio)-1,3,7-trimethyl-1H-purine-2,6(3H,7H)-dione (15.0 mg, 0.04 mmol) in MeOH (3 mL) was added oxone (105.2 mg, 0.17 mmol) in H$_2$O (3 mL). Then the mixture was stirred at RT for 5 h. Then the solvent was removed and extracted with dichloromethane (3*5 mL) and the organic layer was separated, dried over Na$_2$SO$_4$, filtered, concentrated and purified by prep. TLC to give a white solid (11.2 mg, 68.3%). $^1$H-NMR (400 MHz, CDCl3): δ 7.41-7.39 (m, 4H), 4.88 (s, 2H), 3.84 (s, 3H), 3.58 (s, 3H), 3.41 (s, 3H). Mass (m/z): 383.05 [M+H]+.

Compound 30: 8-(3-chlorobenzylsulfonyl)-1,3,7-trimethyl-1H-purine-2,6(3H,7H)-dione

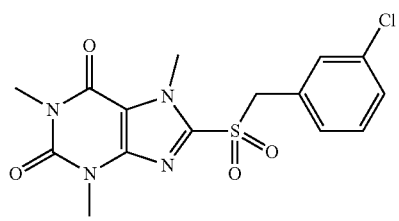

(I) Synthesis of 8-((3-chlorobenzyl)thio)-1,3,7-trimethyl-1H-purine-2,6(3H,7H)-dione To a solution of compound 1 (40.0 mg, 0.17 mmol) and K$_2$CO$_3$ (29.3 mg, 0.21 mmol) in anhydrous DMF (2 mL) was added 1-(bromomethyl)-3-chlorobenzene (43.6 mg, 0.21 mmol) and stirred under nitrogen at RT for overnight. Then the reaction mixture was poured into water and extracted with dichloromethane (3*10 mL) and the organic layer was separated, dried over Na$_2$SO$_4$, filtered, concentrated and purified by prep. TLC (PE:EA 1:1) to give a white solid (29.3 mg, 48.1%). Mass (m/z): 351.06 [M+H]+.

(II) Synthesis of 8-((3-chlorobenzyl)sulfonyl)-1,3,7-trimethyl-1H-purine-2,6(3H,7H)-dione To a solution of 8-((3-chlorobenzyl)thio)-1,3,7-trimethyl-1H-purine-2,6(3H,7H)-dione (15.0 mg, 0.04 mmol) in MeOH (5 mL) was added oxone (140.2 mg) in H$_2$O (5 mL). Then the mixture was stirred at RT for 5 h. Then the solvent was removed and extracted with dichloromethane (3*5 mL) and the organic layer was separated, dried over Na$_2$SO$_4$, filtered, concentrated and purified by prep. TLC to give 15.4 mg (70.65%) as a white solid. $^1$H-NMR (400 MHz, CDCl3): δ 7.39-7.26 (m, 3H), 7.12-7.10 (m, 1H), 4.67 (s, 2H), 3.91 (s, 3H), 3.63 (s, 3H), 3.40 (s, 3H). Mass (m/z): 383.05 [M+H]+.

Compound 31: 8-(4-chlorobenzylsulfonyl)-1,3,7-trimethyl-1H-purine-2,6(3H,7H)-dione

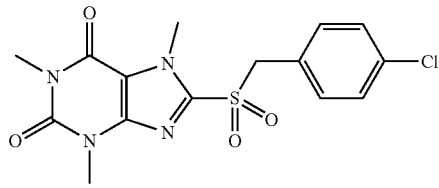 [SMILES: Cn1c(=O)c2c(nc(S(=O)(=O)Cc3ccc(Cl)cc3)n2C)n(C)c1=O]

(I) Synthesis of 8-((4-chlorobenzyl)thio)-1,3,7-trimethyl-1H-purine-2,6(3H,7H)-dione To a solution of compound 1 (40.0 mg, 0.17 mmol) and K$_2$CO$_3$ (29.3 mg, 0.21 mmol) in anhydrous DMF (2 mL) was added 1-(bromomethyl)-4-chlorobenzene (43.6 mg, 0.21 mmol) and stirred under nitrogen at RT for overnight. Then the reaction mixture was poured into water and extracted with dichloromethane (3*10 mL) and the organic layer was separated, dried over Na$_2$SO$_4$, filtered, concentrated and purified by prep. TLC (PE:EA 1:1) to give a white solid (28.3 mg, 46.3%). Mass (m/z): 351.06 [M+H]+.

(II) Synthesis of 8-((4-chlorobenzyl)sulfonyl)-1,3,7-trimethyl-1H-purine-2,6(3H,7H)-dione To a solution of 8-((4-chlorobenzyl)thio)-1,3,7-trimethyl-1H-purine-2,6(3H,7H)-dione (20.0 mg, 0.04 mmol) in MeOH (5 mL) was added oxone (140.2 mg) in H$_2$O (5 mL). Then the mixture was stirred at RT for 5 h. Then the solvent was removed and extracted with dichloromethane (3*5 mL) and the organic layer was separated, dried over Na$_2$SO$_4$, filtered, concentrated and purified by prep. TLC to give 16.1 mg (73.85%) as a white solid. $^1$H-NMR (400 MHz, CDCl3): δ 7.35 (d, J=1.6 Hz, 1H), 7.33 (d, J=1.6 Hz, 1H), 7.19 (d, J=2.0 Hz, 1H), 7.17 (d, J=2.0 Hz, 1H), 4.67 (s, 2H), 3.91 (s, 3H), 3.62 (s, 3H), 3.40 (s, 3H). Mass (m/z): 383.05 [M+H]+.

Compound 32: 8-(2-bromobenzylsulfonyl)-1,3,7-trimethyl-1H-purine-2,6(3H,7H)-dione

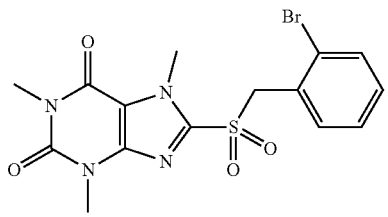

(I) Synthesis of 8-((2-bromobenzyl)thio)-1,3,7-trimethyl-1H-purine-2,6(3H,7H)-dione To a solution of compound 1 (50 mg) and K$_2$CO$_3$ (36.6 mg) in anhydrous DMF (5 mL) was added 1-bromo-2-(bromomethyl)benzene (66.1 mg) and stirred under nitrogen at RT for overnight. Then the reaction mixture was poured into water and extracted with dichloromethane (3*10 mL) and the organic layer was separated, dried over Na$_2$SO$_4$, filtered, concentrated and purified by prep. TLC (PE:EA 1:1) to give a white solid (30.1 mg, 34.4%). Mass (m/z): 351.06 [M+H]+.

(II) Synthesis of 8-((2-bromobenzyl)sulfonyl)-1,3,7-trimethyl-1H-purine-2,6(3H,7H)-dione To a solution of 8-((2-bromobenzyl)thio)-1,3,7-trimethyl-1H-purine-2,6(3H,7H)-dione (10.0 mg) in MeOH (3 mL) was added oxone (62.2 mg) in H$_2$O (3 mL). Then the mixture was stirred at RT for 5 h. Then the solvent was removed and extracted with dichloromethane (3*5 mL) and the organic layer was separated, dried over Na$_2$SO$_4$, filtered, concentrated and purified by prep. TLC to give 8.3 mg (76.85%) as a white solid. $^1$H-NMR (400 MHz, CDCl3): δ 7.59-7.27 (m, 4H), 4.91 (s, 2H), 3.84 (s, 3H), 3.58 (s, 3H), 3.41 (s, 3H). Mass (m/z): 427.00[M+H]+.

Compound 33: 8-(3-bromobenzylsulfonyl)-1,3,7-trimethyl-1H-purine-2,6(3H,7H)-dione

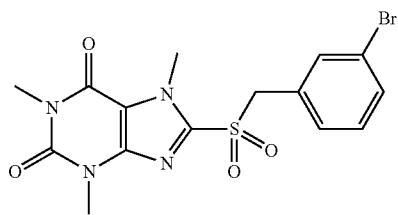 [SMILES: Cn1c(=O)c2c(nc(S(=O)(=O)Cc3cccc(Br)c3)n2C)n(C)c1=O]

(I) Synthesis of 8-((3-bromobenzyl)thio)-1,3,7-trimethyl-1H-purine-2,6(3H,7H)-dione To a solution of compound 1 (50 mg) and K$_2$CO$_3$ (36.6 mg) in anhydrous DMF (5 mL) was added 1-bromo-3-(bromomethyl)benzene (66.1 mg) and stirred under nitrogen at RT for overnight. Then the reaction mixture was poured into water and extracted with dichloromethane (3*10 mL) and the organic layer was separated, dried over Na$_2$SO$_4$, filtered, concentrated and purified by prep. TLC (PE:EA 1:1) to give a white solid (34.5 mg, 39.5%).

(II) Synthesis of 8-((3-bromobenzyl)sulfonyl)-1,3,7-trimethyl-1H-purine-2,6(3H,7H)-dione To a solution of 8-((3-bromobenzyl)thio)-1,3,7-trimethyl-1H-purine-2,6(3H,7H)-dione (10.0 mg) in MeOH (3 mL) was added oxone (62.2 mg) in H$_2$O (3 mL). Then the mixture was stirred at RT for 5 h. Then the solvent was removed and extracted with dichloromethane (3*5 mL) and the organic layer was separated, dried over Na$_2$SO$_4$, filtered, concentrated and purified by prep. TLC to give 5.6 mg (51.99%) as a white solid. $^1$H-NMR (400 MHz, CDCl$_3$): δ 7.53-7.51 (m, 1H), 7.41 (s, 1H), 7.23-7.16 (m, 2H), 4.66 (s, 2H), 3.91 (s, 3H), 3.63 (s, 3H), 3.41 (s, 3H). Mass (m/z): 427.00 [M+H]+.

Compound 34: 8-(4-bromobenzylsulfonyl)-1,3,7-trimethyl-1H-purine-2,6(3H,7H)-dione

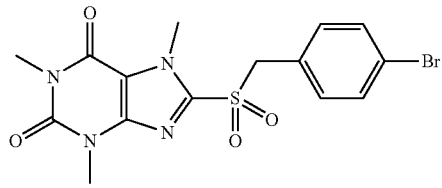 [SMILES: Cn1c(=O)c2c(nc(S(=O)(=O)Cc3ccc(Br)cc3)n2C)n(C)c1=O]

(I) Synthesis of 8-((4-bromobenzyl)thio)-1,3,7-trimethyl-1H-purine-2,6(3H,7H)-dione To a solution of compound 1 (50 mg) and K$_2$CO$_3$ (36.6 mg) in anhydrous DMF (5 mL) was added 1-bromo-4-(bromomethyl)benzene (66.1 mg) and stirred under nitrogen at RT for overnight. Then the reaction mixture was poured into water and extracted with dichloromethane (3*10 mL) and the organic layer was separated, dried over Na$_2$SO$_4$, filtered, concentrated and purified by prep. TLC (PE:EA 1:1) to give a white solid (30.1 mg, 34.4%).

(II) Synthesis of 8-((4-bromobenzyl)sulfonyl)-1,3,7-trimethyl-1H-purine-2,6(3H,7H)-dione To a solution of 8-((4-bromobenzyl)thio)-1,3,7-trimethyl-1H-purine-2,6(3H,7H)-dione (10.0 mg) in MeOH (3 mL) was added oxone (62.2 mg) in H$_2$O (3 mL). Then the mixture was stirred at RT for 5 h. Then the solvent was removed and extracted with dichloromethane (3*5 mL) and the organic layer was separated, dried over Na$_2$SO$_4$, filtered, concentrated and purified by prep. TLC to give 7.2 mg (66.7%) as a white solid. $^1$H-NMR (400 MHz, CDCl3): δ 7.49 (d, J=8.4 Hz, 2H), 7.12 (d, J=8.4 Hz, 2H), 4.66 (s, 2H), 3.92 (s, 3H), 3.62 (s, 3H), 3.40 (s, 3H). Mass (m/z): 427.00 [M+H]+.

Compound 35: 8-(2-methoxybenzylsulfonyl)-1,3,7-trimethyl-1H-purine-2,6(3H,7H)-dione

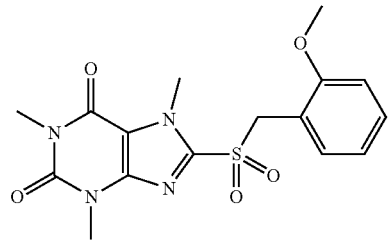 [SMILES: COc1ccccc1CS(=O)(=O)c1nc2c(c(=O)n(C)c(=O)n2C)n1C]

(I) Synthesis of 8-((2-methoxybenzyl)thio)-1,3,7-trimethyl-1H-purine-2,6(3H,7H)-dione To a solution of compound 1 (50 mg) and K$_2$CO$_3$ (36.6 mg) in anhydrous DMF (5 mL) was added 1-(chloromethyl)-2-methoxybenzene (41.6 mg) and stirred under nitrogen at RT overnight. Then the reaction mixture was poured into water and extracted with dichloromethane (3*10 mL) and the organic layer was separated, dried over Na$_2$SO$_4$, filtered, concentrated and purified by prep. TLC (PE:EA 1:1) to give a white solid (30.1 mg, 39.2%).

(II) Synthesis of 8-((2-methoxybenzyl)sulfonyl)-1,3,7-trimethyl-1H-purine-2,6(3H,7H)-dione To a solution of 8-((2-methoxybenzyl)thio)-1,3,7-trimethyl-1H-purine-2,6(3H,7H)-dione (30 mg) in MeOH (2 mL) was added oxone (212.6 mg) in H$_2$O (2 mL). Then the mixture was stirred at RT for 5 h. Then the solvent was removed and extracted with dichloromethane (3*5 mL) and the organic layer was separated, dried over Na$_2$SO$_4$, filtered, concentrated and purified by prep. TLC to give 18.2 mg (56.87%) as a white solid. $^1$H-NMR (400 MHz, CDCl3): δ 7.36 (t, J=7.6 Hz, 1H), 7.16 (d, J=7.2 Hz, 1H), 6.94 (t, J=7.2 Hz, 1H), 6.82 (d, J=8.0 Hz, 1H), 4.74 (s, 2H), 3.74 (s, 3H), 3.61 (s, 6H), 3.40 (s, 3H). Mass (m/z): 379.10 [M+H]+.

Compound 36: 8-(3-methoxybenzylsulfonyl)-1,3,7-trimethyl-1H-purine-2,6(3H,7H)-dione

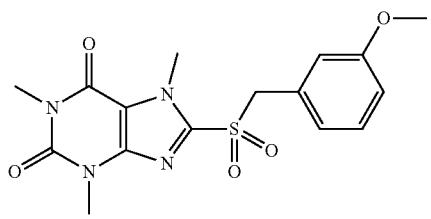

(I) Synthesis of 8-((3-methoxybenzyl)thio)-1,3,7-trimethyl-1H-purine-2,6(3H,7H)-dione To a solution of compound 1 (50 mg) and K$_2$CO$_3$ (36.6 mg) in anhydrous DMF (5 mL) was added 1-(bromomethyl)-2-methoxybenzene (53.4 mg) and stirred under nitrogen at RT overnight. Then the reaction mixture was poured into water and extracted with dichloromethane (3*10 mL) and the organic layer was separated, dried over Na$_2$SO$_4$, filtered, concentrated and purified by prep. TLC (PE:EA 1:1) to give a white solid (40.4 mg, 52.6%).

(II) Synthesis of 8-((3-methoxybenzyl)sulfonyl)-1,3,7-trimethyl-1H-purine-2,6(3H,7H)-dione To a solution of 8-((3-methoxybenzyl)thio)-1,3,7-trimethyl-1H-purine-2,6(3H,7H)-dione (40 mg) in MeOH (3 mL) was added oxone (283.5 mg) in H$_2$O (3 mL). Then the mixture was stirred at RT for 5 h. Then the solvent was removed and extracted with dichloromethane (3*5 mL) and the organic layer was separated, dried over Na$_2$SO$_4$, filtered, concentrated and purified by prep. TLC to give 20.4 mg (46.68%) as a white solid. $^1$H-NMR (400 MHz, CDCl3): δ 7.22 (d, J=8.0 Hz, 1H), 6.94 (q, J=8.4 Hz, 1H), 6.76 (s, 1H), 6.67 (d, J=7.6 Hz, 1H), 4.62 (s, 2H), 3.78 (s, 3H), 3.76 (s, 3H), 3.63 (s, 3H), 3.40 (s, 3H). Mass (m/z): 379.10 [M+H]+.

Compound 37: 8-(4-methoxybenzylsulfonyl)-1,3,7-trimethyl-1H-purine-2,6(3H,7H)-dione

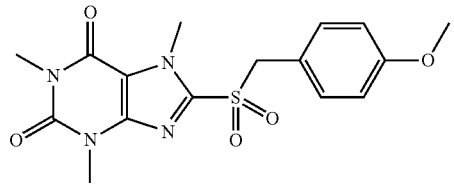 [SMILES: COc1ccc(CS(=O)(=O)c2nc3c(c(=O)n(C)c(=O)n3C)n2C)cc1]

(I) Synthesis of 8-((4-methoxybenzyl)thio)-1,3,7-trimethyl-1H-purine-2,6(3H,7H)-dione To a solution of compound 1 (50 mg) and K$_2$CO$_3$ (36.6 mg) in anhydrous DMF (5 mL) was added 1-(chloromethyl)-4-methoxybenzene (41.6 mg) and stirred under nitrogen at RT overnight. Then the reaction mixture was poured into water and extracted with dichloromethane (3*10 mL) and the organic layer was separated, dried over Na$_2$SO$_4$, filtered, concentrated and purified by prep. TLC (PE:EA 1:1) to give a white solid (23.4 mg, 30.5%).

(II) Synthesis of 8-((4-methoxybenzyl)sulfonyl)-1,3,7-trimethyl-1H-purine-2,6(3H,7H)-dione To a solution of 8-((4-methoxybenzyl)thio)-1,3,7-trimethyl-1H-purine-2,6(3H,7H)-dione (20 mg) in MeOH (2 mL) was added oxone (141.7 mg) in H$_2$O (2 mL). Then the mixture was stirred at RT for 5 h. Then the solvent was removed and extracted with dichloromethane (3*5 mL) and the organic layer was separated, dried over Na$_2$SO$_4$, filtered, concentrated and purified by prep. TLC to give 14.1 mg (64.7%) as a white solid. $^1$H-NMR (400 MHz, CDCl3): δ 7.08 (d, J=7.6 Hz, 2H), 6.84 (d, J=7.2 Hz, 2H), 4.59 (s, 2H), 3.79 (s, 3H), 3.77 (s, 3H), 3.63 (s, 3H), 3.40 (s, 3H). Mass (m/z): 379.10 [M+H]+

Compound 38: 1,3,7-trimethyl-8-(2-nitrobenzylsulfonyl)-1H-purine-2,6(3H,7H)-dione

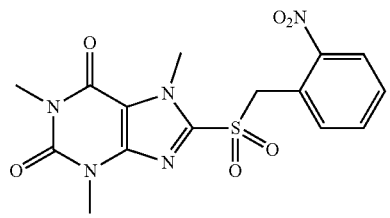

(I) Synthesis of 1,3,7-trimethyl-8-((2-nitrobenzyl)thio)-1H-purine-2,6(3H,7H)-dione To a solution of compound 1 (30 mg) and K$_2$CO$_3$ (21.4 mg) in anhydrous DMF (5 mL) was added 1-(bromomethyl)-2-nitrobenzene (34.3 mg) and stirred under nitrogen at RT overnight. Then the reaction mixture was poured into water and extracted with dichloromethane (3*10 mL) and the organic layer was separated, dried over Na$_2$SO$_4$, filtered, concentrated and purified by prep. TLC (PE:EA 1:1) to give a white solid (16.8 mg, 35%).

(II) Synthesis of 1,3,7-trimethyl-8-((2-nitrobenzyl)sulfonyl)-1H-purine-2,6(3H,7H)-dione To a solution of 1,3,7-trimethyl-8-((2-nitrobenzyl)thio)-1H-purine-2,6(3H,7H)-dione (15 mg) in MeOH (3 mL) was added oxone (102.1 mg) in H$_2$O (3 mL). Then the mixture was stirred at RT for 5 h. Then the solvent was removed and extracted with dichloromethane (3*5 mL) and the organic layer was separated, dried over Na$_2$SO$_4$, filtered, concentrated and purified by prep. TLC to give 8.3 mg (50.92%) as a white solid. $^1$H-NMR (400 MHz, CDCl3): δ 8.03 (t, J=6.8 Hz, 1H), 7.68-7.58 (m, 3H), 5.29 (s, 2H), 4.08 (s, 3H), 3.55 (s, 3H), 3.41 (s, 3H). Mass (m/z): 394.07 [M+H]+

Compound 39: 8-(4-(1H-pyrrol-1-yl)benzylsulfonyl)-1,3,7-trimethyl-1H-purine-2,6(3H,7H)-dione

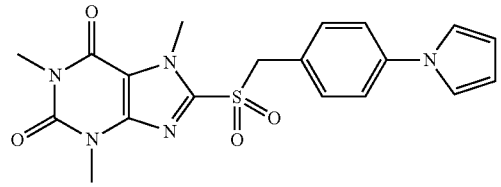 [SMILES: Cn1c(=O)c2c(nc(S(=O)(=O)Cc3ccc(-n4cccc4)cc3)n2C)n(C)c1=O]

(I) Synthesis of 1-(4-(bromomethyl)phenyl)-1H-pyrrole

To a solution of (4-(1H-pyrrol-1-yl)phenyl)methanol (100 mg) in DCM was slowly added tribromophosphine (232 mg) at 0° C. Then the mixture was stirred at RT overnight. The solvent was removed and extracted with dichloromethane (3*5 mL) and concentrated to give a yellow solid (63 mg, 46.5%).

(II) Synthesis of 8-((4-(1H-pyrrol-1-yl)benzyl)thio)-1,3,7-trimethyl-1H-purine-2,6(3H,7H)-dione To a solution of compound 1 (50.0 mg, 0.22 mmol) and K$_2$CO$_3$ (36.6 mg, 0.26 mmol) in anhydrous DMF (5 mL) was added 1-(4-(bromomethyl)phenyl)-1H-pyrrole (62.6 mg, 0.26 mmol) and stirred under nitrogen at RT for overnight. Then the reaction mixture was poured into water and extracted with dichloromethane (3*10 mL) and the organic layer was separated, dried over Na$_2$SO$_4$, filtered, concentrated and purified by prep. TLC (PE:EA 1:1) to give a white solid (10.8 mg, 12.81%).

(III) Synthesis of 8-((4-(1H-pyrrol-1-yl)benzyl)sulfonyl)-1,3,7-trimethyl-1H-purine-2,6(3H,7H)-dione To a solution of 8-((4-(1H-pyrrol-1-yl)benzyl)thio)-1,3,7-trimethyl-1H-purine-2,6(3H,7H)-dione (10 mg) in MeOH (3 mL) was added oxone (64.5 mg) in H$_2$O (3 mL). Then the mixture was stirred at RT for 5 h. Then the solvent was removed and extracted with dichloromethane (3*5 mL) and the organic layer was separated, dried over Na$_2$SO$_4$, filtered, concentrated and purified by prep. TLC (PE:EA 1:1) to give 3.8 mg (32.5%) as a white solid. $^1$H-NMR (400 MHz, CDCl3): δ 8.24 (d, J=8.4 Hz, 2H), 7.55 (d, J=8.4 Hz, 2H), 7.26-7.25 (m, 4H), 4.87 (s, 2H), 4.08 (s, 3H), 3.62 (s, 3H), 3.41 (s, 3H). Mass (m/z): 414.12 [M+H]+

Compound 40: 1,3,7-trimethyl-8-(3-(3-(trifluoromethyl)-3H-diazirin-3-yl)benzylsulfonyl)-1H-purine-2,6(3H,7H)-dione

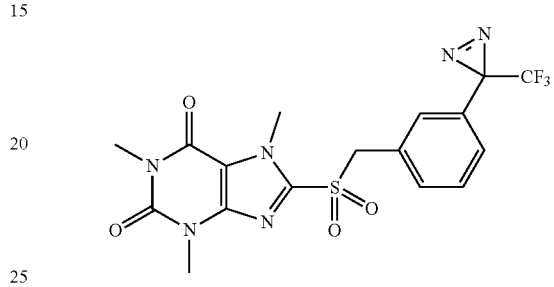

(I) Synthesis of 1,3,7-trimethyl-8-(3-(3-(trifluoromethyl)-3H-diazirin-3-yl) benzylthio)-1H-purine-2,6(3H,7H)-dione To a solution of compound 1 (50.0 mg, 0.22 mmol) and K$_2$CO$_3$ (37.8 mg, 0.27 mmol) in anhydrous DMF (3 mL) was added 3-(3-(bromomethyl)phenyl)-3-(trifluoromethyl)-3H-diazirine (73.8 mg, 0.27 mmol) and stirred which was protected from light under nitrogen at RT for overnight. Then the reaction mixture was poured into water and extracted with dichloromethane (3*10 mL) and the organic layer was separated, dried over Na$_2$SO$_4$, filtered, concentrated and purified by chromatography on silica gel (PE:EA=4:1 to DCM:MeOH=10:1) to give a white solid (12.3 mg, 13.1%). $^1$H-NMR (400 MHz, CDCl3): δ 7.43 (d, J=6.4 Hz, 1H), 7.34 (t, J=8.0 Hz, 1H), 7.21 (s, 1H), 7.11 (d, J=8.0 Hz, 1H), 4.43 (s, 2H), 3.74 (s, 3H), 3.61 (s, 3H), 3.38 (s, 3H). Mass (m/z): 425.09 [M+H]+.

(II) Synthesis of 1,3,7-trimethyl-8-(3-(3-(trifluoromethyl)-3H-diazirin-3-yl)benzylsulfonyl)-1H-purine-2,6(3H,7H)-dione To a solution of 1,3,7-trimethyl-8-(3-(3-(trifluoromethyl)-3H-diazirin-3-yl) benzylthio)-1H-purine-2,6(3H,7H)-dione (10 mg, 0.02 mmol) in DCM (3 mL) was added m-CPBA (6.2 mg, 0.03 mmol). Then the mixture was stirred which was protected from light at RT for 2 h. Then the solvent was removed and extracted with dichloromethane (3*10 mL) and the organic layer was separated, dried over Na$_2$SO$_4$, filtered, concentrated and purified by prep. TLC to give a white solid (5.7 mg, 53.4%). $^1$H-NMR (400 MHz, CDCl3): δ 7.45-7.39 (m, 2H), 7.23 (t, J=7.2 Hz, 1H), 6.94 (s, 1H), 4.70 (s, 2H), 3.87 (s, 3H), 3.64 (s, 3H), 3.40 (s, 3H). Mass (m/z): 457.08 [M+H]+.

Compound 41: 1,3,7-trimethyl-8-(4-(3-(trifluoromethyl)-3H-diazirin-3-yl)benzylsulfonyl)-1H-purine-2,6(3H,7H)-dione

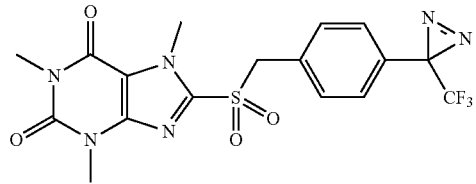 [SMILES: Cn1c(=O)c2c(nc(S(=O)(=O)Cc3ccc(C4(C(F)(F)F)N=N4)cc3)n2C)n(C)c1=O]

The compound was synthesized in a manner that similar to compound 40 to get 8.4 mg (77.7%) as a white solid. ¹H-NMR (400 MHz, CDCl3): δ 7.34 (d, J=8.4 Hz, 2H), 7.19 (d, J=8.0 Hz, 2H), 4.74 (s, 2H), 3.97 (s, 3H), 3.61 (s, 3H), 3.41 (s, 3H). Mass (m/z): 457.08 [M+H]+.

Compound 42: 2-((1,3,7-trimethyl-2,6-dioxo-2,3,6,7-tetrahydro-1H-purin-8-ylsulfonyl)methyl)benzonitrile

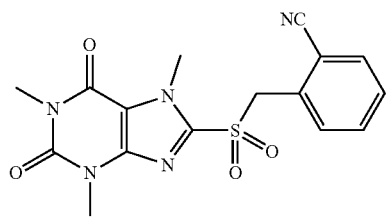

(I) Synthesis of 2-((1,3,7-trimethyl-2,6-dioxo-2,3,6,7-tetrahydro-1H-purin-8-ylthio)methyl)benzonitrile To a solution of compound 1 (100.0 mg, 0.44 mmol) and K₂CO₃ (73.2 mg, 0.53 mmol) in anhydrous DMF (5 mL) was added 2-(bromo methyl)benzonitrile (103.1 mg, 0.53 mmol) and stirred under nitrogen at RT for overnight. Then the reaction mixture was poured into water and extracted with EA (3*10 mL) and the organic layer was separated, dried over Na₂SO₄, filtered, concentrated and purified by prep. TLC to give a white solid (80.9 mg, 53.62%). ¹H-NMR (400 MHz, CDCl3): δ 7.65-7.35 (m, 4H), 4.62 (s, 2H), 3.75 (s, 3H), 3.57 (s, 3H), 3.35 (s, 3H). Mass (m/z): 342.09 [M+H]+.

(II) Synthesis of 2-((1,3,7-trimethyl-2,6-dioxo-2,3,6,7-tetrahydro-1H-purin-8-ylsulfonyl)methyl)benzonitrile To a solution of 2-((1,3,7-trimethyl-2,6-dioxo-2,3,6,7-tetrahydro-1H-purin-8-ylthio)methyl)benzonitrile (15.0 mg, 0.04 mmol) in MeOH (2 mL) was added oxone (108.2 mg, 0.17 mmol) in H2O (5 mL). Then the mixture was stirred at RT for 5 h. Then the solvent was removed and extracted with dichloromethane (3*5 mL) and the organic layer was separated, dried over Na2SO4, filtered, concentrated and purified by prep. TLC to give a white solid (7.2 mg, 43.91%). 1H-NMR (400 MHz, CDCl3): δ 7.71-7.53 (m, 4H), 4.94 (s, 2H), 4.01 (s, 3H), 3.58 (s, 3H), 3.41 (s, 3H). Mass (m/z): 374.08 [M+H]+.

Compound 43: 3-((1,3,7-trimethyl-2,6-dioxo-2,3,6,7-tetrahydro-1H-purin-8-ylsulfonyl)methyl)benzonitrile

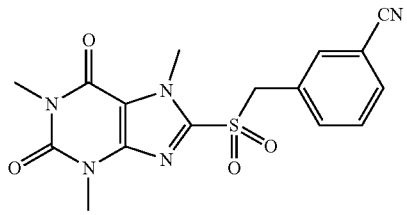 [SMILES: Cn1c(=O)c2c(nc(S(=O)(=O)Cc3cccc(C#N)c3)n2C)n(C)c1=O]

(I) Synthesis of 3-((1,3,7-trimethyl-2,6-dioxo-2,3,6,7-tetrahydro-1H-purin-8-ylthio)methyl)benzonitrile To a solution of compound 1 (100.0 mg, 0.44 mmol) and K₂CO₃ (73.2 mg, 0.53 mmol) in anhydrous DMF (5 mL) was added 3-(bromo methyl)benzonitrile (103.1 mg, 0.53 mmol) and stirred under nitrogen at RT for overnight. Then the reaction mixture was poured into water and extracted with EA (3*10 mL) and the organic layer was separated, dried over Na₂SO₄, filtered, concentrated and purified by prep. TLC to give a white solid (68.3 mg, 45.3%).

(II) Synthesis of 3-((1,3,7-trimethyl-2,6-dioxo-2,3,6,7-tetrahydro-1H-purin-8-ylsulfonyl)methyl)benzonitrile To a solution of 3-((1,3,7-trimethyl-2,6-dioxo-2,3,6,7-tetrahydro-1H-purin-8-ylthio)methyl)benzonitrile (15.0 mg, 0.04 mmol) in MeOH (2 mL) was added oxone (108.2 mg, 0.17 mmol) in H₂O (5 mL). Then the mixture was stirred at RT for 5 h. Then the solvent was removed and extracted with dichloromethane (3*5 mL) and the organic layer was separated, dried over Na₂SO₄, filtered, concentrated and purified by prep. TLC to give 10.7 mg (65.3%) as a white solid. ¹H-NMR (400 MHz, CDCl3): δ 7.71-7.51 (m, 4H), 4.79 (s, 2H), 4.06 (s, 3H), 3.62 (s, 3H), 3.41 (s, 3H). Mass (m/z): 374.08 [M+H]+.

Compound 44: 4-((1,3,7-trimethyl-2,6-dioxo-2,3,6,7-tetrahydro-1H-purin-8-ylsulfonyl)methyl)benzonitrile

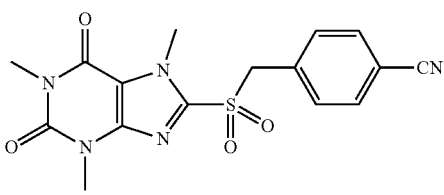 [SMILES: Cn1c(=O)c2c(nc(S(=O)(=O)Cc3ccc(C#N)cc3)n2C)n(C)c1=O]

(I) Synthesis of 4-((1,3,7-trimethyl-2,6-dioxo-2,3,6,7-tetrahydro-1H-purin-8-ylthio)methyl)benzonitrile To a solution of compound 1 (50 mg, 0.22 mmol) and K₂CO₃ (37.8 mg) in anhydrous DMF (2 mL) was added 4-(bromo methyl)benzonitrile (51.2 mg) and stirred under nitrogen at RT for overnight. Then the reaction mixture was poured into water and extracted with EA (3*10 mL) and the organic layer was separated, dried over Na₂SO₄, filtered, concentrated and purified by prep. TLC (PE:EA 1:1) to give a white solid (23 mg, 30.5%).

(II) Synthesis of 4-((1,3,7-trimethyl-2,6-dioxo-2,3,6,7-tetrahydro-1H-purin-8-ylsulfonyl)methyl)benzonitrile To a solution of 4-((1,3,7-trimethyl-2,6-dioxo-2,3,6,7-tetrahydro-1H-purin-8-ylthio)methyl)benzonitrile (15.0 mg, 0.04 mmol) in MeOH (2 mL) was added oxone (108.4 mg, 0.17 mmol) in H2O (5 mL). Then the mixture was stirred at RT for 5 h. Then the solvent was removed and extracted with dichloromethane (3*5 mL) and the organic layer was separated, dried over Na2SO4, filtered, concentrated and purified by prep. TLC (PE:EA 1:2) to give 11.0 mg (67.1%) as a white solid. 1H-NMR (400 MHz, CDCl3): δ 7.68 (d, J=8.0 Hz, 2H), 7.46 (d, J=8.0 Hz, 2H), 4.81 (s, 2H), 4.04 (s, 3H), 3.61 (s, 3H), 3.41 (s, 3H). Mass (m/z): 374.08 [M+H]+

Compound 45: 2-((1,3,7-trimethyl-2,6-dioxo-2,3,6,7-tetrahydro-1H-purin-8-ylsulfonyl)methyl)benzamide

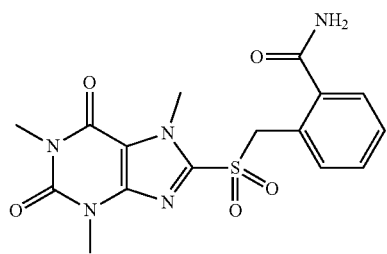 [SMILES: Cn1c(=O)c2c(nc(S(=O)(=O)Cc3ccccc3C(N)=O)n2C)n(C)c1=O]

The compound 2-((1,3,7-trimethyl-2,6-dioxo-2,3,6,7-tetrahydro-1H-purin-8-ylthio)methyl)benzonitrile was synthesized in a manner that described in compound 42.

(I) Synthesis of 2-((1,3,7-trimethyl-2,6-dioxo-2,3,6,7-tetrahydro-1H-purin-8-ylthio)methyl)benzamide To a solution of 2-((1,3,7-trimethyl-2,6-dioxo-2,3,6,7-tetrahydro-1H-purin-8-ylthio)methyl)benzonitrile (15.0 mg, 0.04 mmol) and K₂CO₃ (0.85 mg, 0.006 mmol) in DMSO (2 mL) was slowly added H₂O₂ (2.3 mg, 0.06 mmol) and stirred under nitrogen at RT for overnight. Then the reaction mixture was poured into water and extracted with dichloromethane (3*5 mL) and the organic layer was separated, dried over Na₂SO₄, filtered, concentrated to give a white solid (15.1 mg). Mass (m/z): 360.11 [M+H]+.

(II) Synthesis of 2-((1,3,7-trimethyl-2,6-dioxo-2,3,6,7-tetrahydro-1H-purin-8-ylsulfonyl)methyl)benzamide To a solution of 2-((1,3,7-trimethyl-2,6-dioxo-2,3,6,7-tetrahydro-1H-purin-8-ylthio)methyl)benzamide (10.0 mg, 0.03 mmol) in MeOH (2 mL) was added oxone (68.5 mg, 0.1 mmol) in H₂O (2 mL). Then the mixture was stirred at RT for 5 h. Then the solvent was removed and extracted with dichloromethane (3*5 mL) and the organic layer was separated, dried over Na₂SO₄, filtered, concentrated and purified by prep. TLC to give a white solid (8.7 mg, 80.55%). ¹H-NMR (400 MHz, DMSO-d₆): δ 7.77-7.37 (m, 4H), 7.36 (br, 2H), 5.38 (s, 2H), 3.75 (s, 3H), 3.38 (s, 3H), 3.25 (s, 3H). Mass (m/z): 392.10 [M+H]+.

Compound 46: 3-((1,3,7-trimethyl-2,6-dioxo-2,3,6,7-tetrahydro-1H-purin-8-ylsulfonyl)methyl)benzamide

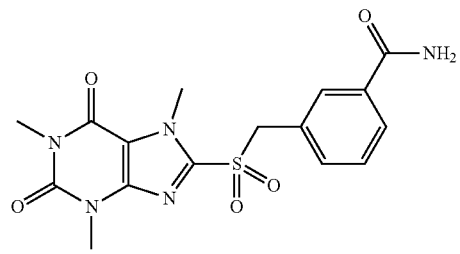 [SMILES: Cn1c(=O)c2c(nc(S(=O)(=O)Cc3cccc(C(N)=O)c3)n2C)n(C)c1=O]

The compound was synthesized in a manner that similar to compound 45 to finally get 7.3 mg (67.6%) as a white solid. ¹H-NMR (400 MHz, CDCl₃): δ 7.78-7.76 (m, 2H), 7.46-7.45 (m, 2H), 4.76 (s, 2H), 3.91 (s, 3H), 3.64 (s, 3H), 3.40 (s, 3H). Mass (m/z): 392.10 [M+H]+.

Compound 47: 4-((1,3,7-trimethyl-2,6-dioxo-2,3,6,7-tetrahydro-1H-purin-8-ylsulfonyl)methyl)benzamide

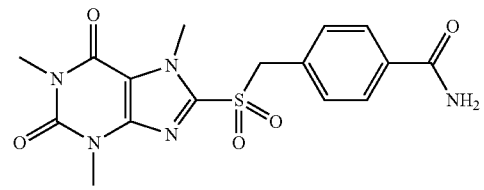 [SMILES: Cn1c(=O)c2c(nc(S(=O)(=O)Cc3ccc(C(N)=O)cc3)n2C)n(C)c1=O]

The compound was synthesized in a manner that similar to compound 45 to finally get 10.3 mg (95.4%) as a white solid. ¹H-NMR (400 MHz, CDCl₃): δ 7.80 (d, J=8.0 Hz, 2H), 7.37 (d, J=8.4 Hz, 2H), 4.77 (s, 2H), 3.93 (s, 3H), 3.62 (s, 3H), 3.41 (s, 3H). Mass (m/z): 392.10 [M+H]+.

Compound 48: 1,3,7-trimethyl-8-(pyridin-2-ylmethylsulfonyl)-1H-purine-2,6(3H,7H)-dione

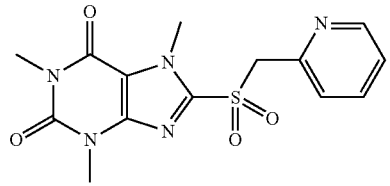 [SMILES: Cn1c(=O)c2c(nc(S(=O)(=O)Cc3ccccn3)n2C)n(C)c1=O]

Compound 49: 2-((1,3,7-trimethyl-2,6-dioxo-2,3,6,7-tetrahydro-1H-purin-8-ylsulfonyl)methyl)pyridine 1-oxide

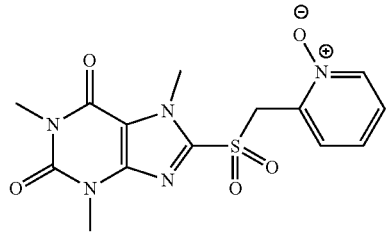 [SMILES: Cn1c(=O)c2c(nc(S(=O)(=O)Cc3cccc[n+]3[O-])n2C)n(C)c1=O]

(I) Synthesis of 1,3,7-trimethyl-8-(pyridin-2-ylmethylthio)-1H-purine-2,6(3H,7H)-dione To a solution of compound 1 (500.0 mg, 2.21 mmol) and $K_2CO_3$ (366.4 mg, 2.65 mmol) in anhydrous DMF (25 mL) was added 2-(bromomethyl) pyridine (674.1 mg, 2.66 mmol) and stirred under nitrogen at RT for overnight. Then the reaction mixture was poured into water and extracted with EA (3*50 mL) and the organic layer was separated, dried over $Na_2SO_4$, filtered, concentrated and recrystallization from EA:PE=1:5 to give a white solid (307.4 mg). Mass (m/z): 318.09 [M+H]+.

(II) Synthesis of 1,3,7-trimethyl-8-(pyridin-2-ylmethylsulfonyl)-1H-purine-2,6(3H,7H)-dione and 2-((1,3,7-trimethyl-2,6-dioxo-2,3,6,7-tetrahydro-1H-purin-8-ylsulfonyl)methyl)pyridine 1-oxide To a solution of 1,3,7-trimethyl-8-(pyridin-2-ylmethylthio)-1H-purine-2,6(3H,7H)-dione (50.0 mg, 0.16 mmol) in MeOH (3 mL) was added oxone (387.9 mg, 0.64 mmol) in $H_2O$ (3 mL). Then the mixture was stirred at RT for 30 min. Then the solvent was removed and extracted with dichloromethane (3*5 mL) and the organic layer was separated, dried over $Na_2SO_4$, filtered, concentrated and purified by prep. TLC to obtain compound 48 as a white solid (14.2 mg, 25.5%). $^1$H-NMR (400 MHz, $CDCl_3$): δ 8.50-8.48 (m, 1H), 7.79-7.76 (m, 1H), 7.51-7.33 (m, 2H), 4.85 (s, 2H), 3.88 (s, 3H), 3.58 (s, 3H), 3.41 (s, 3H). Mass (m/z): 350.08 [M+H]+.

To obtain Compound 49 8.3 mg (75.4%) as a white solid. $^1$H-NMR (400 MHz, $CDCl_3$): δ 8.11-8.10 (m, 1H), 7.61-7.60 (m, 1H), 7.34-7.33 (m, 2H), 5.09 (s, 2H), 4.26 (s, 3H), 3.47 (s, 3H), 3.41 (s, 3H). Mass (m/z): 366.08 [M+H]+.

Compound 50: 1,3,7-trimethyl-8-(pyridin-3-ylmethylsulfonyl)-1H-purine-2,6(3H,7H)-dione

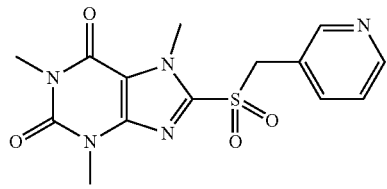

Compound 51: 3-((1,3,7-trimethyl-2,6-dioxo-2,3,6,7-tetrahydro-1H-purin-8-ylsulfonyl)methyl)pyridine 1-oxide

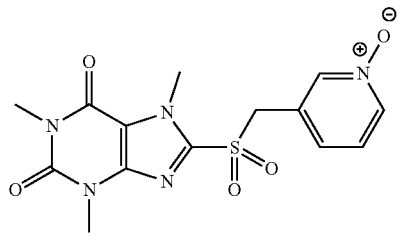 [SMILES: Cn1c(=O)c2c(nc(S(=O)(=O)Cc3ccc[n+]([O-])c3)n2C)n(C)c1=O]

(I) Synthesis of 1,3,7-trimethyl-8-(pyridin-3-ylmethylthio)-1H-purine-2,6(3H,7H)-dione To a solution of compound 1 (30 mg) and $K_2CO_3$ (21.4 mg) in anhydrous DMF (25 mL) was added 3-(bromomethyl) pyridine (40.3 mg) and stirred under nitrogen at RT for overnight.

Then the reaction mixture was poured into water and extracted with EA (3*50 mL) and the organic layer was separated, dried over $Na_2SO_4$, filtered, concentrated and purified by prep. TLC (DCM:MeOH 10:1) to give a white solid (16.2 mg, 38.6%). Mass (m/z): 318.09 [M+H]+.

(II) Synthesis of 1,3,7-trimethyl-8-(pyridin-3-ylmethylsulfonyl)-1H-purine-2,6(3H,7H)-dione and 3-((1,3,7-trimethyl-2,6-dioxo-2,3,6,7-tetrahydro-1H-purin-8-ylsulfonyl)methyl) pyridine 1-oxide To a solution of 1,3,7-trimethyl-8-(pyridin-3-ylmethylthio)-1H-purine-2,6(3H,7H)-dione (10 mg) in MeOH (2 mL) was added oxone (77.6 mg) in $H_2O$ (2 mL). Then the mixture was stirred at RT for 30 min. Then the solvent was removed and extracted with dichloromethane (3*5 mL) and the organic layer was separated, dried over $Na_2SO_4$, filtered, concentrated and purified by prep. TLC (DCM:MeOH 10:1) to obtain compound 504.3 mg (37.3%) as a white solid. $^1$H-NMR (400 MHz, $CDCl_3$): δ 8.63 (s, 1H), 8.46-8.45 (m, 1H), 7.73-7.71 (m, 1H), 7.34-7.33 (m, 1H), 4.77 (s, 2H), 3.97 (s, 3H), 3.60 (s, 3H), 3.39 (s, 3H). Mass (m/z): 350.08 [M+H]+.

To obtain compound 51 3.7 mg (35.7%) as a white solid. $^1$H-NMR (400 MHz, $CDCl_3$): δ 8.26 (s, 1H), 8.21-8.20 (m, 1H), 7.33-7.32 (m, 2H), 4.75 (s, 2H), 4.18 (s, 3H), 3.60 (s, 3H), 3.40 (s, 3H). Mass (m/z): 366.08 [M+H]+.

Compound 52: 1,3,7-trimethyl-8-(pyridin-4-ylmethylsulfonyl)-1H-purine-2,6(3H,7H)-dione

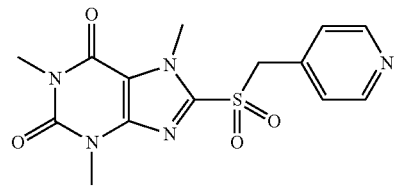 [SMILES: Cn1c(=O)c2c(nc(S(=O)(=O)Cc3ccncc3)n2C)n(C)c1=O]

Compound 53: 4-((1,3,7-trimethyl-2,6-dioxo-2,3,6,7-tetrahydro-1H-purin-8-ylsulfonyl)methyl)pyridine 1-oxide

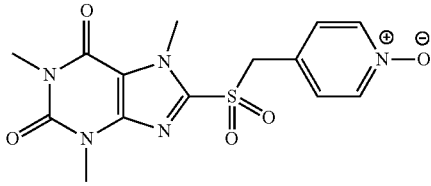 [SMILES: Cn1c(=O)c2c(nc(S(=O)(=O)Cc3cc[n+]([O-])cc3)n2C)n(C)c1=O]

(I) Synthesis of 1,3,7-trimethyl-8-(pyridin-4-ylmethylthionyl)-1H-purine-2,6(3H,7H)-dione To a solution of compound (30 mg) and K$_2$CO$_3$ (21.4 mg) in anhydrous DMF (25 mL) was added 3-(bromomethyl) pyridine (40.3 dg) and stirred under nitrogen at RT for overnight. Then the reaction mixture was poured into water and extracted with EA (3*50 mL) and the organic layer was separated, dried over Na$_2$SO$_4$, filtered, concentrated and purified by prep. TLC (DCM:MeOH 10:1) to give a white solid (15 mg, 35.7%). Mass (m/z): 318.09 [M+H]+.

(II) Synthesis of 1,3,7-trimethyl-8-(pyridin-4-ylmethylsulfonyl)-1H-purine-2,6(3H,7H)-dione and 4-((1,3,7-trimethyl-2,6-dioxo-2,3,6,7-tetrahydro-1H-purin-8-ylsulfonyl)methyl) pyridine 1-oxide To a solution of 1,3,7-trimethyl-8-(pyridin-3-ylmethylthio)-1H-purine-2,6(3H,7H)-dione (10 mg) in MeOH (2 mL) was added oxone (77.6 mg) in H$_2$O (2 mL). Then the mixture was stirred at RT for 30 min. Then the solvent was removed and extracted with dichloromethane (3*5 mL) and the organic layer was separated, dried over Na$_2$SO$_4$, filtered, concentrated and purified by prep. TLC (DCM:MeOH 10:1) to obtain compound 524.2 mg (35.2%) as a white solid. 1H-NMR (400 MHz, CDCl3): δ 8.65 (d, J=4.8 Hz, 2H), 7.27 (d, J=5.2 Hz, 2H), 4.74 (s, 2H), 4.02 (s, 3H), 3.61 (s, 3H), 3.40 (s, 3H). Mass (m/z): 350.08 [M+H]+.
To obtain compound 53 3.2 mg (30.4%) as a white solid. 1H-NMR (400 MHz, CDCl3): δ 8.20 (d, J=6.8 Hz, 2H), 7.31 (d, J=6.8 Hz, 2H), 4.76 (s, 2H), 4.19 (s, 3H), 3.59 (s, 3H), 3.41 (s, 3H). Mass (m/z): 366.08 [M+H]+.

Compound 54: 8-(2,3-dichlorobenzylsulfonyl)-1,3,7-trimethyl-1H-purine-2,6(3H,7H)-dione

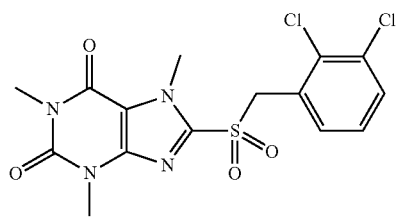 [SMILES: Cn1c(=O)c2c(nc(S(=O)(=O)Cc3cccc(Cl)c3Cl)n2C)n(C)c1=O]

(I) Synthesis of 8-(2,3-dichlorobenzylthio)-1,3,7-trimethyl-1H-purine-2,6(3H,7H)-dione To a solution of compound 1 (50.0 mg, 0.22 mmol) and K$_2$CO$_3$ (36.6 mg, 0.26 mmol) in anhydrous DMF (5 mL) was added 1-(bromomethyl)-2,3-dichlorobenzene (63.7 mg, 0.26 mmol) and stirred under nitrogen at RT for overnight. Then the reaction mixture was poured into water and extracted with dichloromethane (3*10 mL) and the organic layer was separated, dried over Na$_2$SO$_4$, filtered, concentrated and purified by prep. TLC to give a white solid (14.3 mg). Mass (m/z): 385.02 [M+H]+.

(II) Synthesis of 8-(2,3-dichlorobenzylsulfonyl)-1,3,7-trimethyl-1H-purine-2,6(3H,7H)-dione To a solution of 8-(2,3-dichlorobenzylthio)-1,3,7-trimethyl-1H-purine-2,6(3H,7H)-dione (10.0 mg, 0.03 mmol) in MeOH (3 mL) was added oxone (63.9 mg, 0.10 mmol) in H$_2$O (3 mL). Then the mixture was stirred at RT for 5 h. Then the solvent was removed and extracted with dichloromethane (3*5 mL) and the organic layer was separated, dried over Na$_2$SO$_4$, filtered, concentrated and purified by prep. TLC to give a white solid (4.2 mg, 38.9%). $^1$H-NMR (400 MHz, CDCl$_3$): δ 7.54-7.27 (m, 3H), 4.97 (s, 2H), 4.02 (s, 3H), 3.57 (s, 3H), 3.42 (s, 3H). Mass (m/z): 417.01[M+H]+.

Compound 55: 8-(2,5-dichlorobenzylsulfonyl)-1,3,7-trimethyl-1H-purine-2,6(3H,7H)-dione

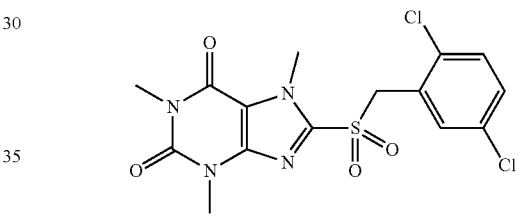

(I) Synthesis of 8-(2,5-dichlorobenzylthio)-1,3,7-trimethyl-1H-purine-2,6(3H,7H)-dione To a solution of compound 1 (50.0 mg, 0.22 mmol) and K$_2$CO$_3$ (36.6 mg, 0.26 mmol) in anhydrous DMF (5 mL) was added 1-(bromomethyl)-2,5-dichlorobenzene (63.7 mg, 0.26 mmol) and stirred under nitrogen at RT for overnight. Then the reaction mixture was poured into water and extracted with dichloromethane (3*10 mL) and the organic layer was separated, dried over Na$_2$SO$_4$, filtered, concentrated and purified by prep. TLC (PE:EA 1:1) to give a white solid (20.1 mg, 23.6%). Mass (m/z): 385.02 [M+H]+.

(II) Synthesis of 8-(2,5-dichlorobenzylsulfonyl)-1,3,7-trimethyl-1H-purine-2,6(3H,7H)-dione To a solution of 8-(2,5-dichlorobenzylthio)-1,3,7-trimethyl-1H-purine-2,6(3H,7H)-dione (10.0 mg, 0.03 mmol) in MeOH (3 mL) was added oxone (63.9 mg, 0.10 mmol) in H$_2$O (3 mL). Then the solvent was removed and extracted with dichloromethane (3*5 mL) and the organic layer was separated, dried over Na$_2$SO$_4$, filtered, concentrated and purified by prep. TLC (PE:EA 1:1) to give 8.3 mg (76.85%) as a white solid. $^1$H-NMR (400 MHz, CDCl$_3$): δ 7.48 (s, 1H), 7.35-7.34 (m, 2H), 4.88 (s, 2H), 4.03 (s, 3H), 3.58 (s, 3H), 3.42 (s, 3H). Mass (m/z): 417.01 [M+H]+.

Compound 56: 8-(3,5-dichlorobenzylsulfonyl)-1,3,7-trimethyl-1H-purine-2,6(3H,7H)-dione

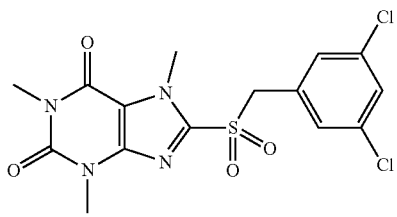 [SMILES: Cn1c(=O)c2c(nc(S(=O)(=O)Cc3cc(Cl)cc(Cl)c3)n2C)n(C)c1=O]

(I) Synthesis of 8-(3,5-dichlorobenzylthio)-1,3,7-trimethyl-1H-purine-2,6(3H,7H)-dione To a solution of compound 1 (50.0 mg, 0.22 mmol) and K₂CO₃ (36.6 mg, 0.26 mmol) in anhydrous DMF (5 mL) was added 1,3-dichloro-5-(chloromethyl)benzene (51.8 mg, 0.26 mmol) and stirred under nitrogen at RT for overnight. Then the reaction mixture was poured into water and extracted with dichloromethane (3*10 mL) and the organic layer was separated, dried over Na₂SO₄, filtered, concentrated and purified by prep. TLC (PE:EA 1:1) to give a white solid (25.3 mg, 29.7%). Mass (m/z): 385.02 [M+H]+.

(II) Synthesis of 8-(3,5-dichlorobenzylsulfonyl)-1,3,7-trimethyl-1H-purine-2,6(3H,7H)-dione To a solution of 8-(3,5-dichlorobenzylthio)-1,3,7-trimethyl-1H-purine-2,6(3H,7H)-dione (20 mg) in MeOH (5 mL) was added oxone (127.7 mg) in H₂O (5 mL). Then the mixture was stirred at RT for 5 h. Then the solvent was removed and extracted with dichloromethane (3*5 mL) and the organic layer was separated, dried over Na₂SO₄, filtered, concentrated and purified by prep. TLC (PE:EA 1:1) to give 11.3 mg (52.3%) as a white solid. ¹H-NMR (400 MHz, CDCl₃): δ 7.39 (s, 1H), 7.24 (s, 2H), 4.68 (s, 2H), 4.08 (s, 3H), 3.62 (s, 3H), 3.41 (s, 3H). Mass (m/z): 417.01 [M+H]+.

Compound 57: 8-(2,6-dichlorobenzylsulfonyl)-1,3,7-trimethyl-1H-purine-2,6(3H,7H)-dione

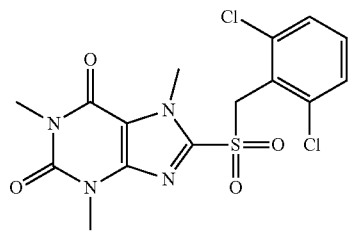 [SMILES: Cn1c(=O)c2c(nc(S(=O)(=O)Cc3c(Cl)cccc3Cl)n2C)n(C)c1=O]

(I) Synthesis of 8-(2,6-dichlorobenzylthio)-1,3,7-trimethyl-1H-purine-2,6(3H,7H)-dione To a solution of compound 1 (50.0 mg, 0.22 mmol) and K₂CO₃ (36.6 mg, 0.26 mmol) in anhydrous DMF (5 mL) was added 2-(bromomethyl)-1,3-dichlorobenzene (63.7 mg, 0.26 mmol) and stirred under nitrogen at RT for overnight. Then the reaction mixture was poured into water and extracted with dichloromethane (3*10 mL) and the organic layer was separated, dried over Na₂SO₄, filtered, concentrated and purified by prep. TLC (PE:EA 1:1) to give a white solid (20.1 mg, 23.6%). Mass (m/z): 385.02 [M+H]+.

(II) Synthesis of 8-(2,6-dichlorobenzylsulfonyl)-1,3,7-trimethyl-1H-purine-2,6(3H,7H)-dione To a solution of 8-(2,6-dichlorobenzylthio)-1,3,7-trimethyl-1H-purine-2,6(3H,7H)-dione (10 mg) in MeOH (3 mL) was added oxone (63.9 mg) in H₂O (3 mL). Then the mixture was stirred at RT for 5 h. Then the solvent was removed and extracted with dichloromethane (3*5 mL) and the organic layer was separated, dried over Na₂SO₄, filtered, concentrated and purified by prep. TLC (PE:EA 1:1) to give 7.9 mg (73.1%) as a white solid. ¹H-NMR (400 MHz, CDCl₃): δ7.40-7.25 (m, 3H), 5.16 (s, 2H), 3.99 (s, 3H), 3.57 (s, 3H), 3.43 (s, 3H). Mass (m/z): 417.01 [M+H]+.

Compound 58: 8-(2,5-dimethoxybenzylsulfonyl)-1,3,7-trimethyl-1H-purine-2,6(3H,7H)-dione

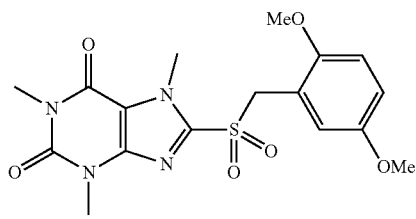 [SMILES: COc1ccc(OC)c(CS(=O)(=O)c2nc3c(c(=O)n(C)c(=O)n3C)n2C)c1]

(I) Synthesis of 8-((2,5-dimethoxybenzyl)thio)-1,3,7-trimethyl-1H-purine-2,6(3H,7H)-dione To a solution of compound 1 (50.0 mg) and K₂CO₃ (36.6 mg) in anhydrous DMF (5 mL) was added 2-(bromomethyl)-1,4-dimethoxybenzene (61.4 mg) and stirred under nitrogen at RT for overnight. Then the reaction mixture was poured into water and extracted with dichloromethane (3*10 mL) and the organic layer was separated, dried over Na₂SO₄, filtered, concentrated and purified by prep. TLC (PE:EA 1:1) to give a white solid (26.4 mg, 31.8%).

(II) Synthesis of 8-((2,5-dimethoxybenzyl)sulfonyl)-1,3,7-trimethyl-1H-purine-2,6(3H,7H)-dione To a solution of 8-(2,6-dichlorobenzylthio)-1,3,7-trimethyl-1H-purine-2,6(3H,7H)-dione (10 mg) in MeOH (5 mL) was added oxone (65.4 mg) in H₂O (5 mL). Then the mixture was stirred at RT for 5 h. Then the solvent was removed and extracted with dichloromethane (3*5 mL) and the organic layer was separated, dried over Na₂SO₄, filtered, concentrated and purified by prep. TLC (PE:EA 1:1) to give 8.1 mg (75%) as a white solid. ¹H-NMR (400 MHz, CDCl₃): δ6.87-6.75 (m, 3H), 4.70 (s, 2H), 3.82 (s, 3H), 3.72 (s, 3H), 3.59 (s, 3H), 3.54 (s, 3H), 3.39 (s, 3H). Mass (m/z): 409.11 [M+H]+.

Compound 59: 8-(3,5-dimethoxybenzylsulfonyl)-1,3,7-trimethyl-1H-purine-2,6(3H,7H)-dione

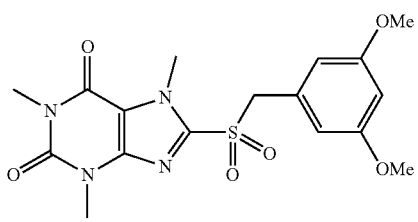 [SMILES: COc1cc(CS(=O)(=O)c2nc3c(c(=O)n(C)c(=O)n3C)n2C)cc(OC)c1]

The compound was synthesized in a manner that similar to compound 58 to finally obtain 8.2 mg (75.1%) as a white solid. $^1$H-NMR (400 MHz, CDCl$_3$): δ6.45 (s, 1H), 6.31 (s, 2H), 4.58 (s, 2H), 3.87 (s, 3H), 3.72 (s, 6H), 3.62 (s, 3H), 3.40 (s, 3H). Mass (m/z): 409.11 [M+H]+.

Compound 60: 8-(5-bromo-2-methoxybenzylsulfonyl)-1,3,7-trimethyl-1H-purine-2,6(3H,7H)-dione

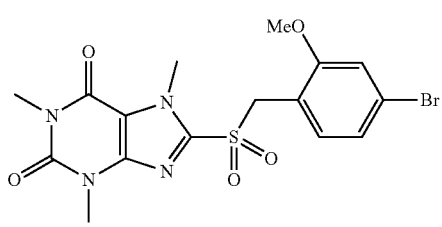 [SMILES: COc1cc(Br)ccc1CS(=O)(=O)c1nc2c(c(=O)n(C)c(=O)n2C)n1C]

(I) Synthesis of 4-bromo-1-(bromomethyl)-2-methoxybenzene

To a solution of (4-bromo-2-methoxyphenyl)methanol (100 mg) in DME was slowly added tribromophosphine (124.7 mg) at 0° C. Then the mixture was stirred at RT overnight. The solvent was removed and extracted with EA (3*10 mL) and concentrated to give a white solid (136.3 mg, 72%).

(II) Synthesis of 8-((4-bromo-2-methoxybenzyl)thio)-1,3,7-trimethyl-1H-purine-2,6(3H,7H)-dione To a solution of compound 1 (50.0 mg, 0.22 mmol) and K$_2$CO$_3$ (36.6 mg, 0.26 mmol) in anhydrous DMF (5 mL) was added 4-bromo-1-(bromomethyl)-2-methoxybenzene (75 mg, 0.26 mmol) and stirred under nitrogen at RT for overnight. Then the reaction mixture was poured into water and extracted with dichloromethane (3*10 mL) and the organic layer was separated, dried over Na$_2$SO$_4$, filtered, concentrated and purified by column chromatography (PE:EA 1:1) to give a white solid (35 mg, 37%).

(III) Synthesis of 8-((4-bromo-2-methoxybenzyl)sulfonyl)-1,3,7-trimethyl-1H-purine-2,6(3H,7H)-dione To a solution of 8-((4-bromo-2-methoxybenzyl)thio)-1,3,7-trimethyl-1H-purine-2,6(3H,7H)-dione (40 mg) in MeOH (5 mL) was added oxone (650 mg) in H$_2$O (5 mL). Then the mixture was stirred at RT for 5 h. Then the solvent was removed and extracted with EA (3*10 mL) and the organic layer was separated, dried over Na$_2$SO$_4$, filtered, concentrated and purified by silica gel column chromatography to afford 10 mg (31%) as a white solid. $^1$H-NMR (400 MHz, CDCl$_3$): δ7.107 (d, J=2.0 Hz, 1H), 7.09 (s, 1H), 7.009 (d, J=2.0 Hz, 1H), 4.73 (s, 2H), 3.95 (s, 3H), 3.68 (s, 3H), 3.60 (s, 3H), 3.42 (s, 3H). Mass (m/z): 458.3 [M+H]+.

Compound 61: 8-(2,3-dimethoxybenzylsulfonyl)-1,3,7-trimethyl-1H-purine-2,6(3H,7H)-dione

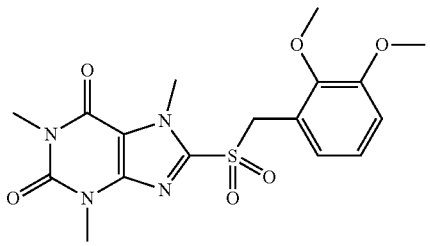

(I) Synthesis of 1-(bromomethyl)-2,3-dimethoxybenzene

To a solution of (2,3-dimethoxyphenyl)methanol (500 mg) in DME was slowly added tribromophosphine (805 mg) at 0° C. Then the mixture was stirred at RT overnight. The solvent was removed and extracted with EA (3*10 mL) and concentrated to give a white solid (176.8 mg, 26%).

(II) Synthesis of 8-((2,3-dimethoxybenzyl)thio)-1,3,7-trimethyl-1H-purine-2,6(3H,7H)-dione To a solution of compound 1 (50.0 mg, 0.22 mmol) and K$_2$CO$_3$ (62 mg, 0.44 mmol) in anhydrous DMF (5 mL) was added 1-(bromomethyl)-2,3-dimethoxybenzene (77 mg, 0.33 mmol) and stirred under nitrogen at RT for overnight. Then the reaction mixture was poured into water and extracted with dichloromethane (3*10 mL) and the organic layer was separated, dried over Na$_2$SO$_4$, filtered, concentrated and purified by column chromatography (PE:EA 1:1) to give a white solid (17 mg, 20.5%).

(III) Synthesis of 8-((2,3-dimethoxybenzyl)sulfonyl)-1,3,7-trimethyl-1H-purine-2,6(3H,7H)-dione To a solution of 8-((2,3-dimethoxybenzyl)thio)-1,3,7-trimethyl-1H-purine-2,6(3H,7H)-dione (17 mg, 0.045 mmol) in MeOH (1 mL) was added oxone (280 mg, 0.45 mmol) in H$_2$O (1 mL). Then the mixture was stirred at RT for 5 h. Then the solvent was removed and extracted with EA (3*10 mL) and the organic layer was separated, dried over Na$_2$SO$_4$, filtered, concentrated and purified by silica gel column chromatography (PE:EA 1:1) to afford 2 mg (10.9%) as a white solid. $^1$H-NMR (400 MHz, CDCl$_3$): δ7.73-7.71 (m, 1H), 7.55-7.52 (m, 1H), 6.69-6.67 (m, 1H), 4.79 (s, 2H), 3.88 (s, 3H), 3.86 (s, 3H), 3.85 (s, 3H), 3.63 (s, 3H), 3.43 (s, 3H). Mass (m/z): 409.4 [M+H]+.

119

Compound 62: 8-(2,6-dimethoxybenzylsulfonyl)-1,3,7-trimethyl-1H-purine-2,6(3H,7H)-dione

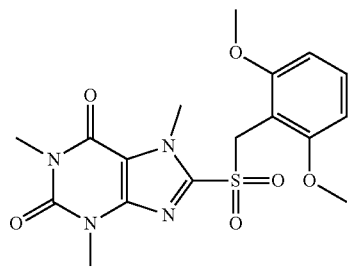

(I) Synthesis of 2-(bromomethyl)-1,3-dimethoxybenzene

To a solution of 1,3-dimethoxy-2-methylbenzene (500 mg, 3.29 mmol) in CCl₄ (10 ml) was slowly added NBS (585 mg, 3.29 mmol) and AIBN (150 mg). Then the mixture was heated to 80° C. for 20 minutes until a white solid was floating on the surface. The mixture was filtered and the filtrate was concentrated to produce a residue. The residue was diluted and extracted with EA (3*10 mL) and concentrated to give a crude product (purple solid).

(II) Synthesis of 8-((2,6-dimethoxybenzyl)thio)-1,3,7-trimethyl-1H-purine-2,6(3H,7H)-dione To a solution of compound 1 (50.0 mg, 0.22 mmol) and K₂CO₃ (62 mg, 0.44 mmol) in anhydrous DMF (5 mL) was added 2-(bromomethyl)-1,3-dimethoxybenzene (77 mg, 0.33 mmol) and stirred under nitrogen at RT for overnight. Then the reaction mixture was poured into water and extracted with dichloromethane (3*10 mL) and the organic layer was separated, dried over Na₂SO₄, filtered, concentrated and purified by column chromatography (PE:EA 1:1) to give a white solid (7 mg, 8%).

(III) Synthesis of 8-((2,6-dimethoxybenzyl)sulfonyl)-1,3,7-trimethyl-1H-purine-2,6(3H,7H)-dione To a solution of 8-((2,6-dimethoxybenzyl)thio)-1,3,7-trimethyl-1H-purine-2,6(3H,7H)-dione (7 mg, 0.019 mmol) in MeOH (1 mL) was added oxone (120 mg, 0.2 mmol) in H₂O (1 mL). Then the mixture was stirred at RT for 5 h. Then the solvent was removed and extracted with EA (3*10 mL) and the organic layer was separated, dried over Na₂SO₄, filtered, concentrated and purified by silica gel column chromatography (PE:EA 1:1) to afford 2 mg (26.3%) as a white solid. $^1$H-NMR (400 MHz, CDCl₃): δ7.308 (t, J=8.4 Hz, 1H), 6.514 (d, J=8.4 Hz, 2H), 4.82 (s, 2H), 3.81 (s, 3H), 3.64 (s, 6H), 3.62 (s, 3H), 3.42 (s, 3H). Mass (m/z): 409.4 [M+H]+.

120

Compound 63: 8-(3-chloro-2-methoxybenzylsulfonyl)-1,3,7-trimethyl-1H-purine-2,6(3H,7H)-dione

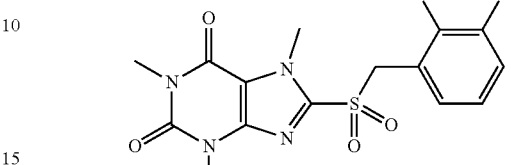

(I) Synthesis of 1-(bromomethyl)-3-chloro-2-methoxybenzene

To a solution of 1-chloro-2-methoxy-3-methylbenzene (300 mg, 1.92 mmol) in CCl₄ (10 ml) was slowly added NBS (350 mg, 1.92 mmol) and AIBN (150 mg). Then the mixture was heated to 90° C. for 5 hours until a white solid was floating on the surface. The mixture was filtered and the filtrate was concentrated to produce a residue. The residue was diluted and extracted with EA (3*10 mL) and concentrated to give a crude product (yellow solid).

(II) Synthesis of 8-((3-chloro-2-methoxybenzyl)thio)-1,3,7-trimethyl-1H-purine-2,6(3H,7H)-dione To a solution of compound 1 (50.0 mg, 0.22 mmol) and K₂CO₃ (62 mg, 0.44 mmol) in anhydrous DMF (5 mL) was added 1-(bromomethyl)-3-chloro-2-methoxybenzene (80 mg, 0.33 mmol) and stirred under nitrogen at RT for overnight. Then the reaction mixture was poured into water and extracted with dichloromethane (3*10 mL) and the organic layer was separated, dried over Na₂SO₄, filtered, concentrated and purified by column chromatography (PE:EA 1:1) to give a white solid (18 mg, 21.39%).

(III) Synthesis of 8-((3-chloro-2-methoxybenzyl)sulfonyl)-1,3,7-trimethyl-1H-purine-2,6(3H,7H)-dione To a solution of 8-((2,6-dimethoxybenzyl)thio)-1,3,7-trimethyl-1H-purine-2,6(3H,7H)-dione (18 mg, 0.048 mmol) in MeOH (1 mL) was added oxone (300 mg, 0.48 mmol) in H₂O (1 mL). Then the mixture was stirred at RT for 5 h. Then the solvent was removed and extracted with EA (3*10 mL) and the organic layer was separated, dried over Na₂SO₄, filtered, concentrated and purified by silica gel column chromatography (PE:EA 1:1) to afford 12 mg (61.5%) as a white solid. $^1$H-NMR (400 MHz, CDCl₃): δ7.432 (dd, J=1.6 Hz, J=8.0 Hz, 1H), 7.147 (dd, J=1.6 Hz, J=8.0 Hz, 1H), 7.06 (t, J=8.0 Hz, 1H), 4.81 (s, 2H), 4.00 (s, 3H), 3.90 (s, 3H), 3.60 (s, 3H), 3.43 (s, 3H). Mass (m/z): 413.8 [M+H]+.

121

Compound 64: 8-(4-bromo-3-chlorobenzylsulfonyl)-1,3,7-trimethyl-1H-purine-2,6(3H,7H)-dione cl

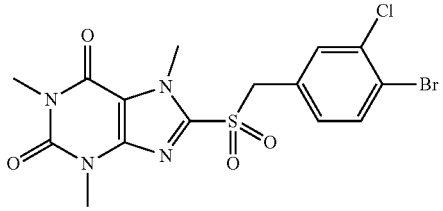 [SMILES: Cn1c(=O)c2c(nc(S(=O)(=O)Cc3ccc(Br)c(Cl)c3)n2C)n(C)c1=O]

(I) Synthesis of 1-bromo-4-(bromomethyl)-2-chlorobenzene

To a solution of 1-bromo-2-chloro-4-methylbenzene (500 mg, 2.43 mmol) in CCl$_4$ (10 ml) was slowly added NBS (433 mg, 2.43 mmol) and AIBN (200 mg). Then the mixture was heated to 90° C. for 5 hours until a white solid was floating on the surface. The mixture was filtered and the filtrate was concentrated to produce a residue. The residue was diluted and extracted with EA (3*10 mL) and concentrated to give a crude product (yellow solid) 930 mg.

(II) Synthesis of 8-((4-bromo-3-chlorobenzyl)thio)-1,3,7-trimethyl-1H-purine-2,6(3H,7H)-dione To a solution of compound 1 (50.0 mg, 0.22 mmol) and K$_2$CO$_3$ (62 mg, 0.44 mmol) in anhydrous DMF (5 mL) was added 1-bromo-4-(bromomethyl)-2-chlorobenzene (95 mg, 0.33 mmol) and stirred under nitrogen at RT for overnight. Then the reaction mixture was poured into water and extracted with dichloromethane (3*10 mL) and the organic layer was separated, dried over Na$_2$SO$_4$, filtered, concentrated and purified by column chromatography (PE:EA 1:1) to give a white solid (20.5 mg, 21.6%).

(III) Synthesis of 8-((4-bromo-3-chlorobenzyl)sulfonyl)-1,3,7-trimethyl-1H-purine-2,6(3H,7H)-dione To a solution of 8-((4-bromo-3-chlorobenzyl)thio)-1,3,7-trimethyl-1H-purine-2,6(3H,7H)-dione (20 mg, 0.048 mmol) in MeOH (1 mL) was added oxone (290 mg, 0.48 mmol) in H$_2$O (1 mL). Then the mixture was stirred at RT for 5 h. Then the solvent was removed and extracted with EA (3*10 mL) and the organic layer was separated, dried over Na$_2$SO$_4$, filtered, concentrated and purified by silica gel column chromatography (PE:EA 1:1) to afford 10 mg (46.5%) as a white solid. $^1$H-NMR (400 MHz, CDCl$_3$): δ7.62 (d, J=8.4 Hz, 1H), 7.45 (s, 1H), 7.07 (d, J=8.4 Hz, 1H), 4.68 (s, 2H), 4.07 (s, 3H), 3.62 (s, 3H), 3.41 (s, 3H). Mass (m/z): 462.7[M+H]+.

Compound 65: 8-(2-ethoxy-5-methoxybenzylsulfonyl)-1,3,7-trimethyl-1H-purine-2,6(3H,7H)-dione

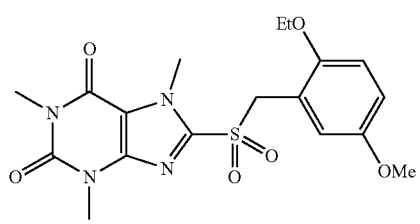 [SMILES: CCOc1ccc(OC)cc1CS(=O)(=O)c1nc2c(c(=O)n(C)c(=O)n2C)n1C]

122

(I) Synthesis of 2-ethoxy-5-methoxybenzaldehyde

To a solution of 2-hydroxy-5-methoxybenzaldehyde (200 mg, 1.31 mmol) and K$_2$CO$_3$ (220 mg, 1.6 mmol) in anhydrous DMF (5 mL) was added iodoethane (310 mg, 1.97 mmol) and stirred under nitrogen at RT for overnight. Then the reaction mixture was poured into water and extracted with EA (3*10 mL) and the organic layer was separated, dried over Na$_2$SO$_4$, filtered, and concentrated to give a yellow solid (325.1 mg).

(II) Synthesis of 2-ethoxy-5-methoxyphenyl)methanol

To a solution of 2-ethoxy-5-methoxybenzaldehyde (250 mg, 1.39 mmol) in MeOH (5 ml) was added NaBH$_4$ under N$_2$ protection at 0° C. Then the mixture was stirred at RT for 4 h. The solvent was removed and extracted with EA (3*10 mL) and concentrated to give a yellow solid (252.1 mg).

(III) Synthesis of 2-(bromomethyl)-1-ethoxy-4-methoxybenzene

To a solution of 2-ethoxy-5-methoxyphenyl)methanol (252 mg, 1.38 mmol) in DME was slowly added tribromophosphine (380 mg, 1.38 mmol) at 0° C. Then the mixture was stirred at RT overnight. The solvent was removed and extracted with EA (3*10 mL), the organic layer was separated, dried over Na$_2$SO$_4$, filtered, concentrated and purified by column chromatography (PE:EA 5:1) to give a white solid (336 mg, 99%).

(IV) Synthesis of 8-((2-ethoxy-5-methoxybenzyl)thio)-1,3,7-trimethyl-1H-purine-2,6(3H,7H)-dione To a solution of compound 1 (30.0 mg, 0.133 mmol) and K$_2$CO$_3$ (36 mg, 0.265 mmol) in anhydrous DMF (2 mL) was added 2-(bromomethyl)-1-ethoxy-4-methoxybenzene (48 mg, 0.2 mmol) and stirred under nitrogen at RT for overnight. Then the reaction mixture was poured into water and extracted with EA (3*10 mL) and the organic layer was separated, dried over Na$_2$SO$_4$, filtered, concentrated and purified by column chromatography (PE:EA 5:1) to give a white solid (5 mg, 9.8%).

(V) Synthesis of 8-((2-ethoxy-5-methoxybenzyl)sulfonyl)-1,3,7-trimethyl-1H-purine-2,6(3H,7H)-dione To a solution of 8-((2-ethoxy-5-methoxybenzyl)thio)-1,3,7-trimethyl-1H-purine-2,6(3H,7H)-dione (5 mg, 0.013 mmol) in MeOH (1 mL) was added oxone (80 mg, 0.13 mmol) in H$_2$O (1 mL). Then the mixture was stirred at RT for 5 h. Then the solvent was removed and extracted with EA (3*10 mL) and the organic layer was separated, dried over Na$_2$SO$_4$, filtered, concentrated and purified by silica gel column chromatography (PE:EA 1:1) to afford 2.3 mg (42.6%) as a white solid. $^1$H-NMR (400 MHz, CDCl$_3$): δ6.88 (d, J=8.8 Hz, 1H), 6.81 (s, 1H), 6.75 (d, J=8.8 Hz, 1H), 4.72 (s, 2H), 3.80-3.75 (m, J=7.2 Hz, 2H), 3.78 (s, 3H), 3.74 (s, 3H), 3.61 (s, 3H), 3.41 (s, 3H), 1.22 (t, J=7.2 Hz, 3H). Mass (m/z): 423.4[M+H]+.

Compound 66: 8-(5-methoxy-2-propoxybenzylsulfonyl)-1,3,7-trimethyl-1H-purine-2,6(3H,7H)-dione

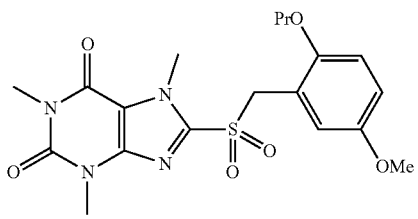

The compound was synthesized in a manner that similar to compound 65 to afford 2 mg (22.7%) as a white solid. $^1$H-NMR (400 MHz, CDCl$_3$): δ6.88 (dd, J=3.2 Hz, J=8.8 Hz, 1H), 6.80 (d, J=2.8 Hz, 1H), 6.77 (d, J=8.8 Hz, 1H), 4.72 (s, 2H), 3.78 (s, 3H), 3.74 (s, 3H), 3.68 (t, J=6.4 Hz, 2H), 3.61 (s, 3H), 3.41 (s, 3H), 1.63-1.58 (m, J=6.4 Hz, 2H), 0.94 (t, J=7.2 Hz, 3H). Mass (m/z): 437.4[M+H]+.

Compound 67: 8-(5-ethoxy-2-methoxybenzylsulfonyl)-1,3,7-trimethyl-1H-purine-2,6(3H,7H)-dione

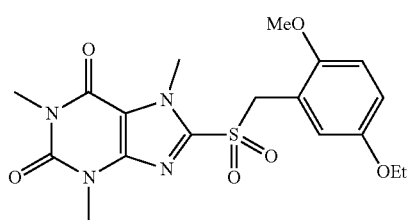 [SMILES: CCOc1ccc(OC)c(CS(=O)(=O)c2nc3c(c(=O)n(C)c(=O)n3C)n2C)c1]

(I) Synthesis of 4-ethoxy-1-methoxy-2-methylbenzene

To a solution of 4-methoxy-3-methylphenol (200 mg, 1.45 mmol) and K$_2$CO$_3$ (250 mg, 1.74 mmol) in anhydrous DMF (5 mL) was added iodoethane (340 mg, 2.17 mmol) and stirred under nitrogen at RT for 5 h. Then the reaction mixture was poured into water and extracted with EA (3*10 mL) and the organic layer was separated, dried over Na$_2$SO$_4$, filtered, concentrated and purified by silica gel column chromatography (PE:EA 5:1) to afford a yellow solid (86 mg, 35.8%).

(II) Synthesis of 2-(bromomethyl)-4-ethoxy-1-methoxybenzene

To a solution of 4-ethoxy-1-methoxy-2-methylbenzene (80 mg, 0.48 mmol) in CCl$_4$ (2 ml) was slowly added NBS (86 mg, 0.48 mmol) and AIBN (60 mg). Then the mixture was heated to 80° C. for 5 hours until a white solid was floating on the surface. The mixture was filtered and the filtrate was concentrated to produce a residue. The residue was diluted and extracted with EA (3*10 mL) and concentrated to give a crude product (yellow solid) 106 mg.

(III) Synthesis of 8-((5-ethoxy-2-methoxybenzyl)thio)-1,3,7-trimethyl-1H-purine-2,6(3H,7H)-dione To a solution of compound 1 (30.0 mg, 0.133 mmol) and K$_2$CO$_3$ (36 mg, 0.265 mmol) in anhydrous DMF (2 mL) was added 2-(bromomethyl)-4-ethoxy-1-methoxybenzene (48 mg, 0.2 mmol) and stirred under nitrogen at RT for overnight. Then the reaction mixture was poured into water and extracted with EA (3*10 mL) and the organic layer was separated, dried over Na$_2$SO$_4$, filtered, concentrated and purified by column chromatography (PE:EA 5:1) to give a white solid (60 mg).

(IV) Synthesis of 8-((5-ethoxy-2-methoxybenzyl)sulfonyl)-1,3,7-trimethyl-1H-purine-2,6(3H,7H)-dione To a solution of 8-((5-ethoxy-2-methoxybenzyl)thio)-1,3,7-trimethyl-1H-purine-2,6(3H,7H)-dione (30 mg, 0.077 mmol) in DCM (1 mL) was added m-CPBA (15 mg, 0.077 mmol). Then the mixture was stirred at RT for 5 h. Then the solvent was removed and extracted with EA (3*10 mL) and the organic layer was separated, dried over Na$_2$SO$_4$, filtered, concentrated and purified by silica gel column chromatography (PE:EA 1:1) to afford 29 mg (90.6%) as a white solid. $^1$H-NMR (400 MHz, CDCl$_3$): δ6.88 (dd, J=3.2 Hz, J=8.8 Hz, 1H), 6.79 (d, J=2.8 Hz, 1H), 6.74 (d, J=8.8 Hz, 1H), 4.70 (s, 2H), 3.94 (m, J=6.8 Hz, 2H), 3.82 (s, 3H), 3.62 (s, 3H), 3.55 (s, 3H), 3.41 (s, 3H), 1.37 (t, J=6.8 Hz, 3H). Mass (m/z): 423.4[M+H]+.

Compound 68: 8-(2-methoxy-5-propoxybenzylsulfonyl)-1,3,7-trimethyl-1H-purine-2,6(3H,7H)-dione

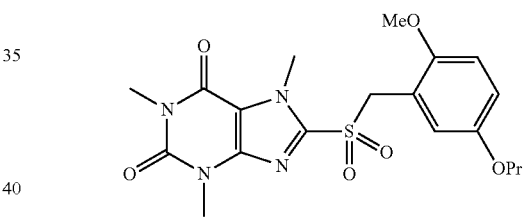

The compound was synthesized in a manner that similar to compound 67 to afford 23.1 mg (72.2%) as a white solid. $^1$H-NMR (400 MHz, CDCl$_3$): δ6.88 (dd, J=3.2 Hz, J=8.8 Hz, 1H), 6.77 (d, J=3.2 Hz, 1H), 6.74 (d, J=8.8 Hz, 1H), 4.70 (s, 2H), 3.83-3.80 (m, 2H), 3.82 (s, 3H), 3.62 (s, 3H), 3.56 (s, 3H), 3.41 (s, 3H), 1.80-1.73 (m, 2H), 1.00 (t, J=7.2 Hz, 3H). Mass (m/z): 437.4[M+H]+.

Compound 69: 8-(3-bromo-2,6-dimethoxybenzylsulfonyl)-1,3,7-trimethyl-1H-purine-2,6(3H,7H)-dione

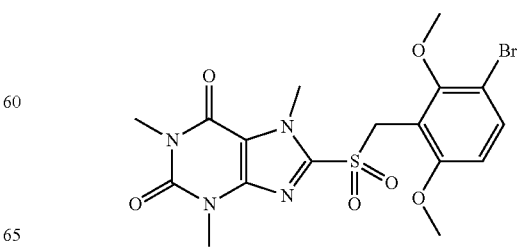

(I) Synthesis of 1-bromo-3-(bromomethyl)-2,4-dimethoxybenzene

To a solution of 1,3-dimethoxy-2-methylbenzene (500 mg, 3.29 mmol) in CCl$_4$ (10 ml) was slowly added NBS (585 mg, 3.29 mmol) and AIBN (150 mg). Then the mixture was heated to 90° C. for 5 h. The mixture was filtered and the filtrate was concentrated to produce a residue. The residue was diluted and extracted with EA (3*10 mL), concentrated and purified by column chromatography (PE:EA 5:1) to give a yellow solid (641 mg, 56%).

(II) Synthesis of 8-((3-bromo-2,6-dimethoxybenzyl)thio)-1,3,7-trimethyl-1H-purine-2,6(3H,7H)-dione To a solution of compound 1 (50.0 mg, 0.22 mmol) and K$_2$CO$_3$ (62 mg, 0.44 mmol) in anhydrous DMF (5 mL) was added 1-bromo-3-(bromomethyl)-2,4-dimethoxybenzene (80 mg, 0.33 mmol) and stirred under nitrogen at RT for overnight. Then the reaction mixture was poured into water and extracted with dichloromethane (3*10 mL) and the organic layer was separated, dried over Na$_2$SO$_4$, filtered, concentrated and purified by column chromatography (PE:EA 1:1) to give a white solid (67.5 mg, 81%).

(III) Synthesis of 8-((3-bromo-2,6-dimethoxybenzyl)sulfonyl)-1,3,7-trimethyl-1H-purine-2,6(3H,7H)-dione To a solution of 8-((3-bromo-2,6-dimethoxybenzyl)thio)-1,3,7-trimethyl-1H-purine-2,6(3H,7H)-dione (30 mg, 0.08 mmol) in MeOH (1 mL) was added oxone (655 mg, 0.8 mmol) in H$_2$O (1 mL). Then the mixture was stirred at RT for 5 h. Then the solvent was removed and extracted with EA (3*10 mL) and the organic layer was separated, dried over Na$_2$SO$_4$, filtered, concentrated and purified by silica gel column chromatography (PE:EA 1:1) to afford 15 mg (46.1%) as a white solid. $^1$H-NMR (400 MHz, CDCl$_3$): δ7.53 (d, J=9.2 Hz, 1H), 6.58 (d, J=8.8 Hz, 1H), 4.86 (s, 2H), 3.97 (s, 3H), 3.86 (s, 3H), 3.66 (s, 3H), 3.60 (s, 3H), 3.43 (s, 3H). Mass (m/z): 488.3 [M+H]+.

Compound 70: 8-(4-chloro-2,5-dimethoxybenzylsulfonyl)-1,3,7-trimethyl-1H-purine-2,6(3H,7H)-dione

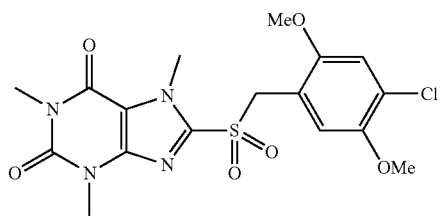 [SMILES: COc1cc(CS(=O)(=O)c2nc3c(c(=O)n(C)c(=O)n3C)n2C)c(OC)cc1Cl]

(I) Synthesis of 4-chloro-2,5-dimethoxybenzaldehyde

To a solution of 2-chloro-1,4-dimethoxybenzene (2.5 g, 14.48 mmol) and hexamethylenetetramine (2.05 g, 14.63 mmol) was carefully added TFA (25 mL). Then the mixture was heated to 95° C. for overnight. Then the mixture was poured into ice and adjusted PH=8 with NaHCO$_3$. Then the solvent was removed and extracted with dichloromethane (3*20 mL) and the organic layer was separated, dried over Na$_2$SO$_4$, filtered, concentrated and purified by chromatography on silica gel (EA:PE=1:10) to give a white solid (2.1 g, 72.7%). $^1$H-NMR (400 MHz, CDCl$_3$): δ 10.39 (s, 1H), 7.38 (s, 1H), 7.06 (s, 1H), 3.89 (s, 6H). Mass (m/z): 201.02 [M+H]+.

(II) Synthesis of (4-chloro-2,5-dimethoxyphenyl)methanol

To a solution of 4-chloro-2,5-dimethoxybenzaldehyde (1.5 g, 7.5 mmol) in MeOH (20 mL) was carefully added NaBH$_4$ (0.85 g, 22.48 mmol). Then the mixture was stirred at RT for 2 h.

Then the solvent was removed and extracted with dichloromethane (3*10 mL) and the organic layer was separated, dried over Na$_2$SO$_4$, filtered, concentrated and purified by chromatography on silica gel (EA:PE=1:4) to give a white solid (1.45 g, 96%). $^1$H-NMR (400 MHz, CDCl$_3$): δ 6.95 (s, 1H), 6.90 (s, 1H), 4.65 (s, 1H), 3.86 (s, 3H), 3.81 (s, 3H), 2.18 (br, 1H). Mass (m/z): 203.04 [M+H]+.

(III) Synthesis of 1-(bromomethyl)-4-chloro-2,5-dimethoxybenzene

To a solution of (4-chloro-2,5-dimethoxyphenyl)methanol (500 mg, 2.48 mmol) in DME (10 mL) was carefully added PBr$_3$ (0.99 g, 3.69 mmol) at 0° C. Then the mixture was stirred at RT for overnight. Then the solvent was removed and extracted with dichloromethane (3*10 mL) and the organic layer was separated, dried over Na$_2$SO$_4$, filtered, concentrated to give a yellow solid (438.2 mg). Mass (m/z): 264.96 [M+H]+.

(IV) Synthesis of 8-(4-chloro-2,5-dimethoxybenzylthio)-1,3,7-trimethyl-1H-purine-2,6(3H,7H)-dione To a solution of compound 1 (50.0 mg, 0.22 mmol) and K$_2$CO$_3$ (36.6 mg, 0.26 mmol) in anhydrous DMF (10 mL) was added 1-(bromomethyl)-4-chloro-2,5-dimethoxybenzene (71.2 mg, 0.26 mmol) and stirred under nitrogen at RT for overnight. Then the reaction mixture was poured into water and extracted with dichloromethane (3*10 mL) and the organic layer was separated, dried over Na$_2$SO$_4$, filtered, concentrated and purified by prep. TLC to give a white solid (23.4 mg, 25.8%). $^1$H-NMR (400 MHz, CDCl$_3$): δ 7.02 (s, 1H), 6.91 (s, 1H), 4.45 (s, 1H), 3.82 (s, 3H), 3.80 (s, 3H), 3.76 (s, 3H), 3.61 (s, 3H), 3.39 (s, 3H). Mass (m/z): 411.08 [M+H]+.

(V) Synthesis of 8-(4-chloro-2,5-dimethoxybenzylsulfonyl)-1,3,7-trimethyl-1H-purine-2,6(3H,7H)-dione To a solution of 8-(4-chloro-2,5-dimethoxybenzylthio)-1,3,7-trimethyl-1H-purine-2,6(3H,7H)-dione (10.0 mg, 0.02 mmol) in DCM (2 mL) was added m-CPBA (6.4 mg, 0.03 mmol). Then the mixture was stirred at RT for 2 h. Then the solvent was removed and extracted with dichloromethane (3*5 mL) and the organic layer was separated, dried over Na$_2$SO$_4$, filtered, concentrated and purified by prep. TLC to give a white solid (8.2 mg, 76.7%). $^1$H-NMR (400 MHz, CDCl$_3$): δ 6.93 (s, 1H), 6.89 (s, 1H), 4.73 (s, 1H), 4.00 (s, 3H), 3.84 (s, 3H), 3.60 (s, 6H), 3.42 (s, 3H). Mass (m/z): 443.07 [M+H]+.

Compound 71: 8-(4-fluoro-2,5-dimethoxyben-zylsulfonyl)-1,3,7-trimethyl-1H-purine-2,6(3H,7H)-dione

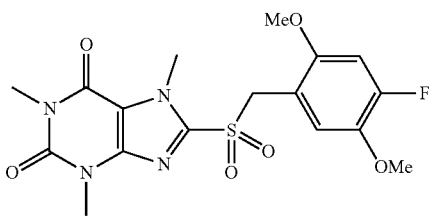 [SMILES: COc1cc(CS(=O)(=O)c2nc3c(c(=O)n(C)c(=O)n3C)n2C)c(OC)cc1F]

(I) Synthesis of 4-fluoro-2,5-dimethoxybenzaldehyde

A solution of 2-fluoro-1,4-dimethoxybenzene (2.07 g, 13.26 mmol) in DCM (15 mL) was cooled in a ice bath to 5-6° C. Under vigorous stirring, 6.75 g (25.99 mmol) of SnCl$_4$ was added, followed by the dropwise addition of dichloro(methoxy) methane (1.3 g, 11.41 mmol) at a rate which maintained the internal temperature below 10° C. Then the mixture was stirred at RT for 30 min and poured into a mixture of 50 g of ice and 15 mL HCl (com). Then the reaction mixture was extracted with dichloromethane (3*20 mL) and the organic layer was separated, dried over Na$_2$SO$_4$, filtered, concentrated and purified by chromatography on silica gel (EA:PE=1:10) to give a green solid (1.9 g, 77.86%). $^1$H-NMR (400 MHz, CDCl$_3$): δ 10.34 (s, 1H), 7.43 (d, J=9.6 Hz, 1H), 6.77 (d, J=12.4 Hz, 1H), 3.87 (s, 3H), 3.86 (s, 3H). Mass (m/z): 185.05 [M+H]+.

(II) Synthesis of (4-fluoro-2,5-dimethoxyphenyl)methanol

To a solution of 4-fluoro-2,5-dimethoxybenzaldehyde (500.0 mg, 2.71 mmol) in dry THF (10 mL) was carefully added NaBH$_4$ (410.8 mg, 10.86 mmol). Then the mixture was stirred at RT for overnight. Then the solvent was removed and extracted with dichloromethane (3*15 mL) and the organic layer was separated, dried over Na$_2$SO$_4$, filtered, concentrated and purified by prep.

TLC to give a white solid (238.1 mg, 47.2%). $^1$H-NMR (400 MHz, CDCl$_3$): δ 6.96 (d, J=9.6 Hz, 1H), 6.68 (d, J=12.8 Hz, 1H), 4.62 (s, 2H), 3.84 (s, 3H), 3.79 (s, 3H). Mass (m/z): 187.07 [M+H]+.

(III) Synthesis of 1-(bromomethyl)-4-fluoro-2,5-dimethoxybenzene

To a solution of (4-fluoro-2,5-dimethoxyphenyl)methanol (200 mg, 1.07 mmol) in DME (5 mL) was carefully added PBr$_3$ (431.2 mg, 1.67 mmol) at 0° C. Then the mixture was stirred at RT for overnight. Then the solvent was removed and extracted with dichloromethane (3*10 mL) and the organic layer was separated, dried over Na$_2$SO$_4$, filtered, concentrated to give a white solid (203.4 mg). Mass (m/z): 248.98 [M+H]+.

(IV) Synthesis of 8-(4-fluoro-2,5-dimethoxybenzyl-thio)-1,3,7-trimethyl-1H-purine-2,6(3H,7H)-dione To a solution of compound 1 (50.0 mg, 0.22 mmol) and K$_2$CO$_3$ (36.6 mg, 0.26 mmol) in anhydrous DMF (10 mL) was added 1-(bromomethyl)-4-fluoro-2,5-dimethoxyben-zene (65.8 mg, 0.26 mmol) and stirred under nitrogen at RT for overnight. Then the reaction mixture was poured into water and extracted with dichloromethane (3*10 mL) and the organic layer was separated, dried over Na$_2$SO$_4$, filtered, concentrated and purified by prep. TLC to give a white solid (30.1 mg). Mass (m/z): 395.11 [M+H]+.

(V) Synthesis of 8-(4-fluoro-2,5-dimethoxyben-zylsulfonyl)-1,3,7-trimethyl-1H-purine-2,6(3H,7H)-dione To a solution of 8-(4-fluoro-2,5-dimethoxybenzylthio)-1,3,7-trimethyl-1H-purine-2,6(3H,7H)-dione (20.0 mg, 0.05 mmol) in DCM (5 mL) was added m-CPBA (13.1 mg, 0.075 mmol). Then the mixture was stirred at RT for 2 h. Then the solvent was removed and extracted with dichloromethane (3*5 mL) and the organic layer was separated, dried over Na$_2$SO$_4$, filtered, concentrated and purified by prep. TLC to give a white solid (13.4 mg, 62.1%). $^1$H-NMR (400 MHz, CDCl$_3$): δ 6.96 (d, J=9.2 Hz, 1H), 6.66 (d, J=12.4 Hz, 1H), 4.71 (s, 1H), 3.99 (s, 3H), 3.82 (s, 3H), 3.60 (s, 3H), 3.58 (s, 3H), 3.42 (s, 3H). Mass (m/z): 427.10 [M+H]+.

Compound 72: 1,3-dimethyl-8-(methylsulfonyl)-1H-purine-2,6(3H,7H)-dione

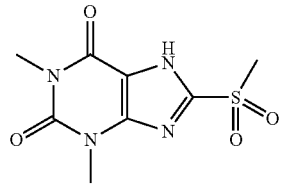 [SMILES: Cn1c(=O)c2[nH]c(S(C)(=O)=O)nc2n(C)c1=O]

(I) Synthesis of 1,3-dimethyl-8-(methylthio)-1H-purine-2,6(3H,7H)-dione

To a solution of 8-chloro-1,3-dimethyl-1H-purine-2,6 (3H,7H)-dione (100 mg, 0.46 mmol) in anhydrous NMP (2 mL) was added sodium methanethiolate (98.2 mg, 1.40 mmol) and reacted in the microwave on a Biotage Smith Synthesis at 180° C. for 3 h. Then the mixture was cooled to RT and acidified to PH=3. Then the reaction mixture was poured into water and extracted with dichloromethane (3*10 mL) and the organic layer was separated, dried over Na$_2$SO$_4$, filtered, concentrated to give a yellow oil (64.7 mg). Mass (m/z): 227.05 [M+H]+.

(II) Synthesis of 1,3-dimethyl-8-(methylsulfonyl)-1H-purine-2,6(3H,7H)-dione

To a solution of 1,3-dimethyl-8-(methylthio)-1H-purine-2,6(3H,7H)-dione (30.0 mg, 0.13 mmol) in MeOH (1 mL) was added oxone (409.9 mg, 0.67 mmol) in H$_2$O (2 mL). Then the mixture was stirred at RT for 5 h. Then the solvent was removed and extracted with dichloromethane (3*10 mL) and the organic layer was separated, dried over Na$_2$SO$_4$, filtered, concentrated and purified by prep. TLC to give a white solid (4.7 mg, 10.9%). $^1$H-NMR (400 MHz, CDCl$_3$): δ 5.56 (br, 1H), 3.68 (s, 3H), 3.43 (s, 3H), 3.19 (s, 3H). Mass (m/z): 259.04 [M+H]+.

129

Compound 73: 7-ethyl-1,3-dimethyl-8-(methylthio)-1H-purine-2,6(3H,7H)-dione

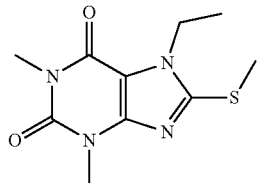

(I) Synthesis of 8-chloro-7-ethyl-1,3-dimethyl-1H-purine-2,6(3H,7H)-dione

To a solution of 8-chloro-1,3-dimethyl-1H-purine-2,6(3H,7H)-dione (200.0 mg, 0.93 mmol) and $K_2CO_3$ (154.8 mg, 1.12 mmol) in anhydrous DMF (2 mL) was added iodoethane (174.8 mg, 1.12 mmol) and stirred under nitrogen at RT for 4 h. Then the reaction mixture was poured into water and extracted with dichloromethane (3*10 mL) and the organic layer was separated, dried over $Na_2SO_4$, filtered, concentrated and purified by chromatography on silica gel (PE:EA=2:1) to give a white solid (203.0 mg). Mass (m/z): 243.06 [M+H]+.

(II) Synthesis of 7-ethyl-1,3-dimethyl-8-(methylthio)-1H-purine-2,6(3H,7H)-dione To a solution of 8-chloro-7-ethyl-1,3-dimethyl-1H-purine-2,6(3H,7H)-dione (213 mg, 0.87 mmol) in anhydrous DMF (2 mL) was added sodium methanethiolate (1.5 mL) and heated to 105° C. for 8 h. Then the mixture was cooled to RT and extracted with dichloromethane (3*10 mL) and the organic layer was separated, dried over $Na_2SO_4$, filtered, concentrated and purified by chromatography on silica gel (PE:EA=2:1) to give a white solid. (31.2 mg, 19.2%). $^1$H-NMR (400 MHz, $CDCl_3$): δ 4.29 (q, J=7.2 Hz, 2H), 3.57 (s, 3H), 3.39 (s, 3H), 2.72 (s, 3H), 1.39 (t, J=7.2 Hz, 3H). Mass (m/z): 255.08 [M+H]+.

Compound 74: 7-ethyl-1,3-dimethyl-8-(methylsulfonyl)-1H-purine-2,6(3H,7H)-dione

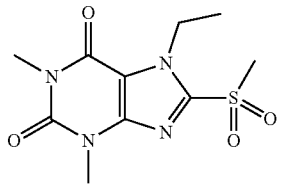 [SMILES: CCn1c(S(C)(=O)=O)nc2c1c(=O)n(C)c(=O)n2C]

To a solution of compound 74 (24.7 mg, 0.09 mmol) in MeOH (2 mL) was added oxone (237.3 mg, 0.38 mmol) in $H_2O$ (2 mL). Then the mixture was stirred at RT for 5 h. Then the solvent was removed and extracted with dichloromethane (3*10 mL) and the organic layer was separated, dried over $Na_2SO_4$, filtered, concentrated and purified by prep. TLC to give a white solid (20.3 mg, 73.1%). $^1$H-NMR (400 MHz, $CDCl_3$): δ 4.79 (q, J=7.2 Hz, 2H), 3.57 (s, 3H), 3.45 (s, 3H), 3.43 (s, 3H), 1.54 (t, J=7.2 Hz, 3H). Mass (m/z): 287.07 [M+H]+.

130

Compound 75: 7-ethyl-8-(ethylthio)-1,3-dimethyl-1H-purine-2,6(3H,7H)-dione

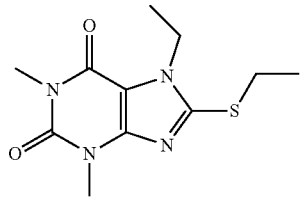 [SMILES: CCSc1nc2c(c(=O)n(C)c(=O)n2C)n1CC]

(I) Synthesis of 8-chloro-7-ethyl-1,3-dimethyl-1H-purine-2,6(3H,7H)-dione

To a solution of 8-chloro-1,3-dimethyl-1H-purine-2,6(3H,7H)-dione (200.0 mg, 0.93 mmol) and $K_2CO_3$ (154.8 mg, 1.12 mmol) in anhydrous DMF (2 mL) was added iodoethane (174.8 mg, 1.12 mmol) and stirred under nitrogen at RT for 4 h. Then the reaction mixture was poured into water and extracted with dichloromethane (3*10 mL) and the organic layer was separated, dried over $Na_2SO_4$, filtered, concentrated and purified by chromatography on silica gel (PE:EA=2:1) to give a white solid (203.0 mg). Mass (m/z): 243.06 [M+H]+.

(II) Synthesis of 7-ethyl-8-mercapto-1,3-dimethyl-1H-purine-2,6(3H,7H)-dione

To a solution of 8-chloro-7-ethyl-1,3-dimethyl-1H-purine-2,6(3H,7H)-dione (140.0 mg, 0.57 mmol) in anhydrous DMF (2 mL) was added NaHS (97.2 mg, 1.73 mmol) and heated to 105° C. for 7 h. Then the mixture was cooled to RT and acidified to PH=3. Then the reaction mixture was poured into water and extracted with dichloromethane (3*10 mL) and the organic layer was separated, dried over $Na_2SO_4$, filtered, concentrated and purified by chromatography on silica gel (PE:EA=1:2) to give a white solid (82.3 mg, 59.3%). $^1$H-NMR (400 MHz, $CDCl_3$): δ 13.18 (s, 1H), 4.79 (q, J=7.2 Hz, 2H), 3.58 (s, 3H), 3.39 (s, 3H), 1.40 (t, J=7.2 Hz, 3H). Mass (m/z): 241.07 [M+H]+.

(III) Synthesis of 7-ethyl-8-(ethylthio)-1,3-dimethyl-1H-purine-2,6(3H,7H)-dione To a solution of 7-ethyl-8-mercapto-1,3-dimethyl-1H-purine-2,6(3H,7H)-dione (30.0 mg, 0.12 mmol) and $K_2CO_3$ (20.7 mg, 0.15 mmol) in anhydrous DMF (2 mL) was added iodoethane (23.4 mg, 0.15 mmol) and stirred under nitrogen at RT for 3 h. The reaction mixture was poured into water and extracted with dichloromethane (3*10 mL) and the organic layer was separated, dried over $Na_2SO_4$, filtered, concentrated and purified by prep. TLC to give a white solid (32.3 mg, 99.38%). $^1$H-NMR (400 MHz, $CDCl_3$): δ 4.30 (q, J=6.8 Hz, 2H), 3.56 (s, 3H), 3.39 (s, 3H), 3.29 (q, J=6.8 Hz, 2H), 1.42 (t, J=6.8 Hz, 3H), 1.38 (t, J=6.8 Hz, 3H). Mass (m/z): 269.10 [M+H]+.

Compound 76: 7-ethyl-8-(ethylsulfinyl)-1,3-dimethyl-1H-purine-2,6(3H,7H)-dione

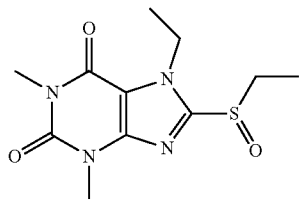 [SMILES: CCn1c(S(=O)CC)nc2c1c(=O)n(C)c(=O)n2C]

Compound 77: 7-ethyl-8-(ethylsulfonyl)-1,3-dimethyl-1H-purine-2,6(3H,7H)-dione

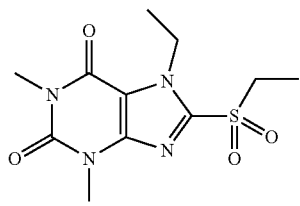 [SMILES: CCn1c(S(=O)(=O)CC)nc2c1c(=O)n(C)c(=O)n2C]

To a solution of compound 75 (25 mg) in MeOH (2 mL) was added oxone (86.3 mg) in H₂O (2 mL). Then the mixture was stirred at RT for 5 h. Then the solvent was removed and extracted with dichloromethane (3*10 mL) and the organic layer was separated, dried over Na₂SO₄, filtered, concentrated and purified by prep. TLC (PE:EA 1:1) to obtain compound 76 3.8 mg (20.4%) as a white solid. ¹H-NMR (400 MHz, CDCl₃): δ 4.71 (q, J=6.8 Hz, 2H), 3.57 (s, 3H), 3.44 (s, 3H), 3.40 (q, J=7.6 Hz, 2H), 1.53 (t, J=6.8 Hz, 3H), 1.38 (t, J=7.6 Hz, 3H). Mass (m/z): 285.09 [M+H]+.

To obtain compound 7718.2 mg (69.7%) as a white solid. ¹H-NMR (400 MHz, CDCl₃): δ 4.74 (q, J=7.2 Hz, 2H), 3.53 (q, J=7.2 Hz, 2H), 3.52 (s, 3H), 3.36 (s, 3H), 1.47 (t, J=7.2 Hz, 3H), 1.39 (t, J=7.2 Hz, 3H). Mass (m/z): 301.09 [M+H]+.

Compound 78: 7-ethyl-1,3-dimethyl-8-(propylthio)-1H-purine-2,6(3H,7H)-dione

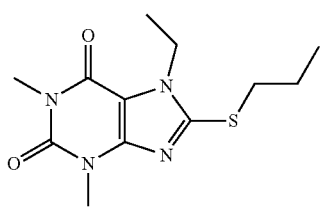 [SMILES: CCCSc1nc2c(c(=O)n(C)c(=O)n2C)n1CC]

(I) Synthesis of 8-chloro-7-ethyl-1,3-dimethyl-1H-purine-2,6(3H,7H)-dione

To a solution of 8-chloro-1,3-dimethyl-1H-purine-2,6(3H,7H)-dione (200.0 mg, 0.93 mmol) and K₂CO₃ (154.8 mg, 1.12 mmol) in anhydrous DMF (2 mL) was added iodoethane (174.8 mg, 1.12 mmol) and stirred under nitrogen at RT for 4 h. Then the reaction mixture was poured into water and extracted with dichloromethane (3*10 mL) and the organic layer was separated, dried over Na₂SO₄, filtered, concentrated and purified by chromatography on silica gel (PE:EA=2:1) to give a white solid (203.0 mg). Mass (m/z): 243.06 [M+H]+.

(II) Synthesis of 7-ethyl-8-mercapto-1,3-dimethyl-1H-purine-2,6(3H,7H)-dione

To a solution of 8-chloro-7-ethyl-1,3-dimethyl-1H-purine-2,6(3H,7H)-dione (140.0 mg, 0.57 mmol) in anhydrous DMF (2 mL) was added NaHS (97.2 mg, 1.73 mmol) and heated to 105° C. for 7 h. Then the mixture was cooled to RT and acidified to PH=3. Then the reaction mixture was poured into water and extracted with dichloromethane (3*10 mL) and the organic layer was separated, dried over Na₂SO₄, filtered, concentrated and purified by chromatography on silica gel (PE:EA=1:2) to give a white solid (82.3 mg, 59.3%). 1H-NMR (400 MHz, CDCl3): δ 13.18 (s, 1H), 4.79 (q, J=7.2 Hz, 2H), 3.58 (s, 3H), 3.39 (s, 3H), 1.40 (t, J=7.2 Hz, 3H). Mass (m/z): 241.07 [M+H]+.

(III) Synthesis of 7-ethyl-1,3-dimethyl-8-(propylthio)-1H-purine-2,6(3H,7H)-dione To a solution of 7-ethyl-8-mercapto-1,3-dimethyl-1H-purine-2,6(3H,7H)-dione (30.0 mg, 0.12 mmol) and K2CO3 (20.7 mg, 0.15 mmol) in anhydrous DMF (2 mL) was added 1-iodopropane (25.5 mg, 0.15 mmol) and stirred under nitrogen at RT for 3 h. The reaction mixture was poured into water and extracted with EA (3*10 mL) and the organic layer was separated, dried over Na₂SO₄, filtered, concentrated and purified by prep. TLC to obtain 31.5 mg (89.3%) as a white solid. ¹H-NMR (400 MHz, CDCl₃): δ 4.30 (q, J=6.8 Hz, 2H), 3.56 (s, 3H), 3.39 (s, 3H), 3.25 (t, J=6.8 Hz, 2H), 1.79 (m, 2H), 1.38 (t, J=6.8 Hz, 3H), 1.04 (t, J=7.6 Hz, 3H). Mass (m/z): 283.12 [M+H]+.

Compound 79: 7-ethyl-1,3-dimethyl-8-(propylsulfinyl)-1H-purine-2,6(3H,7H)-dione

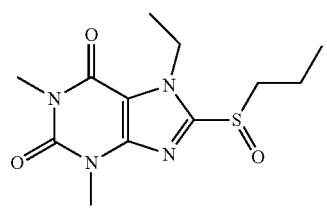 [SMILES: CCCS(=O)c1nc2c(c(=O)n(C)c(=O)n2C)n1CC]

Compound 80: 7-ethyl-1,3-dimethyl-8-(propylsulfonyl)-1H-purine-2,6(3H,7H)-dione

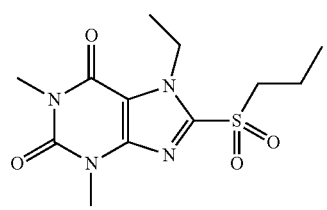 [SMILES: CCCS(=O)(=O)c1nc2c(c(=O)n(C)c(=O)n2C)n1CC]

To a solution of compound 78 (30 mg) in MeOH (2 mL) was added oxone (97.98 mg) in H₂O (2 mL). Then the mixture was stirred at RT for 5 h. Then the solvent was removed and extracted with dichloromethane (3*10 mL) and the organic layer was separated, dried over Na₂SO₄, filtered, concentrated and purified by prep. TLC to obtain compound 792.9 mg (22.3%) as a white solid. ¹H-NMR (400 MHz, CDCl₃): δ 4.74-4.67 (m, 2H), 3.57 (s, 3H), 3.46 (s, 3H), 3.51-3.25 (m, 2H), 1.85 (t, J=7.6 Hz, 2H), 1.53 (t, J=7.2 Hz, 3H), 1.14 (t, J=7.2 Hz, 3H). Mass (m/z): 299.11 [M+H]+.

To obtain compound 8019.2 mg (70.3%) as a white solid. ¹H-NMR (400 MHz, CDCl₃): δ 4.81 (q, J=7.2 Hz, 2H), 3.54 (s, 3H), 3.52 (q, J=7.6 Hz, 2H), 3.42 (s, 3H), 1.94 (t, J=7.6 Hz, 2H), 1.53 (t, J=7.2 Hz, 3H), 1.11 (t, J=7.6 Hz, 3H). Mass (m/z): 315.10 [M+H]+.

Compound 81: 8-(cyclopropylmethylthio)-7-ethyl-1,3-dimethyl-1H-purine-2,6(3H,7H)-dione

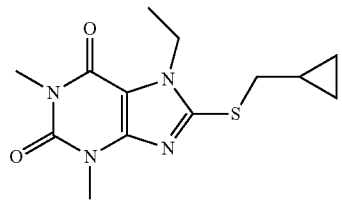 [SMILES: CCn1c(SCC2CC2)nc2c1c(=O)n(C)c(=O)n2C]

(I) Synthesis of 8-chloro-7-ethyl-1,3-dimethyl-1H-purine-2,6(3H,7H)-dione

To a solution of 8-chloro-1,3-dimethyl-1H-purine-2,6(3H,7H)-dione (200.0 mg, 0.93 mmol) and K₂CO₃ (154.8 mg, 1.12 mmol) in anhydrous DMF (2 mL) was added iodoethane (174.8 mg, 1.12 mmol) and stirred under nitrogen at RT for 4 h. Then the reaction mixture was poured into water and extracted with dichloromethane (3*10 mL) and the organic layer was separated, dried over Na₂SO₄, filtered, concentrated and purified by chromatography on silica gel (PE:EA=2:1) to give a white solid (203.0 mg). Mass (m/z): 243.06 [M+H]+.

(II) Synthesis of 7-ethyl-8-mercapto-1,3-dimethyl-1H-purine-2,6(3H,7H)-dione

To a solution of 8-chloro-7-ethyl-1,3-dimethyl-1H-purine-2,6(3H,7H)-dione (140.0 mg, 0.57 mmol) in anhydrous DMF (2 mL) was added NaHS (97.2 mg, 1.73 mmol) and heated to 105° C. for 7 h. Then the mixture was cooled to RT and acidified to PH=3. Then the reaction mixture was poured into water and extracted with dichloromethane (3*10 mL) and the organic layer was separated, dried over Na₂SO₄, filtered, concentrated and purified by chromatography on silica gel (PE:EA=1:2) to give a white solid (82.3 mg, 59.3%). ¹H-NMR (400 MHz, CDCl₃): δ 13.18 (s, 1H), 4.79 (q, J=7.2 Hz, 2H), 3.58 (s, 3H), 3.39 (s, 3H), 1.40 (t, J=7.2 Hz, 3H). Mass (m/z): 241.07 [M+H]+.

(III) Synthesis of 7-ethyl-1,3-dimethyl-8-(propyl-thio)-1H-purine-2,6(3H,7H)-dione To a solution of 7-ethyl-8-mercapto-1,3-dimethyl-1H-purine-2,6(3H,7H)-dione (30.0 mg, 0.12 mmol) and K₂CO₃ (20.7 mg, 0.15 mmol) in anhydrous DMF (2 mL) was added (bromomethyl)cyclopropane (20.25 mg, 0.15 mmol) and stirred under nitrogen at RT for 3 h. The reaction mixture was poured into water and extracted with EA (3*10 mL) and the organic layer was separated, dried over Na₂SO₄, filtered, concentrated and purified by prep. TLC (PE:EA 1:1) to obtain 25.6 mg (69.75%) as a white solid. ¹H-NMR (400 MHz, CDCl₃): δ 4.33 (q, J=7.2 Hz, 2H), 3.57 (s, 3H), 3.39 (s, 3H), 3.21 (d, J=7.6 Hz, 2H), 1.40 (q, J=7.2 Hz, 3H), 1.24-1.14 (m, 1H), 0.65-0.61 (m, 2H), 0.35-0.33 (m, 2H). Mass (m/z): 295.12 [M+H]+.

Compound 82: 8-(cyclopropylmethylsulfonyl)-7-ethyl-1,3-dimethyl-1H-purine-2,6(3H,7H)-dione

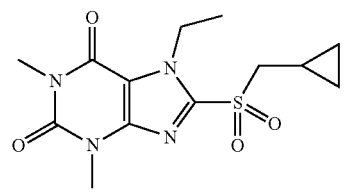 [SMILES: CCn1c(S(=O)(=O)CC2CC2)nc2c1c(=O)n(C)c(=O)n2C]

To a solution of compound 81 (23 mg) in MeOH (1 mL) was added oxone (240 mg) in H₂O (1 mL). Then the mixture was stirred at RT for 5 h. Then the solvent was removed and extracted with dichloromethane (3*10 mL) and the organic layer was separated, dried over Na₂SO₄, filtered, concentrated and purified by prep. TLC to obtain 11.5 mg (66.9%) as a white solid. ¹H-NMR (400 MHz, CDCl₃): δ 4.84 (q, J=6.8 Hz, 2H), 3.56 (s, 3H), 3.45 (s, 3H), 3.42 (d, J=5.2 Hz, 2H), 1.54 (t, J=6.8 Hz, 2H), 1.20-1.15 (m, 1H), 0.69-0.66 (m, 2H), 0.36-0.32 (m, 2H). Mass (m/z): 327.10 [M+H]+.

Compound 83: 1,3-dimethyl-8-(methylsulfonyl)-7-propyl-1H-purine-2,6(3H,7H)-dione

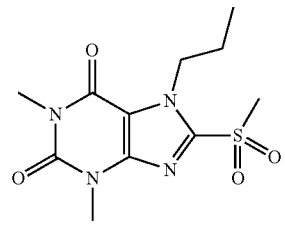 [SMILES: CCCn1c(S(C)(=O)=O)nc2c1c(=O)n(C)c(=O)n2C]

(I) Synthesis of 8-chloro-1,3-dimethyl-7-propyl-1H-purine-2,6(3H,7H)-dione

To a solution of 8-chloro-1,3-dimethyl-1H-purine-2,6(3H,7H)-dione (500.0 mg, 2.33 mmol) and K₂CO₃ (386.9 mg, 2.80 mmol) in anhydrous DMF (5 mL) was added 1-iodopropane (476.5 mg, 2.80 mmol) and stirred under nitrogen at RT for 4 h. Then the reaction mixture was poured into water and extracted with dichloromethane (3*10 mL) and the organic layer was separated, dried over Na₂SO₄, filtered, concentrated and purified by chromatography on silica gel (PE:EA=2:1) to give a white solid (467.3 mg). Mass (m/z): 257.07 [M+H]+.

(II) Synthesis of 8-mercapto-1,3-dimethyl-7-propyl-1H-purine-2,6(3H,7H)-dione

To a solution of 8-chloro-1,3-dimethyl-7-propyl-1H-purine-2,6(3H,7H)-dione (350.0 mg, 1.36 mmol) in anhydrous DMF (5 mL) was added NaHS (229.7 mg, 4.10 mmol) and heated to 120° C. for overnight. Then the mixture was cooled to RT and acidified to PH=3. Then the reaction mixture was poured into water and extracted with dichloromethane (3*10 mL) and the organic layer was separated, dried over Na$_2$SO$_4$, filtered, concentrated and purified by chromatography on silica gel (DCM:MeOH=20:1) to give a white solid (235.2 mg). Mass (m/z): 255.08 [M+H]+.

(III) Synthesis of 1,3-dimethyl-8-(methylthio)-7-propyl-1H-purine-2,6(3H,7H)-dione To a solution of 8-mercapto-1,3-dimethyl-7-propyl-1H-purine-2,6(3H,7H)-dione (50.0 mg, 0.19 mmol) and K$_2$CO$_3$ (32.5 mg, 0.23 mmol) in anhydrous DMF (5 mL) was added iodomethane (35.3 mg, 0.23 mmol) and stirred under nitrogen at RT for 2 h. Then the reaction mixture was poured into water and extracted with dichloromethane (3*10 mL) and the organic layer was separated, dried over Na$_2$SO$_4$, filtered, concentrated and purified by prep. TLC to give a white solid (47.8 mg, 90.62%). $^1$H-NMR (400 MHz, CDCl$_3$): δ 4.17 (t, J=7.2 Hz, 2H), 3.57 (s, 3H), 3.39 (s, 3H), 2.71 (s, 3H), 1.87-1.78 (m, 2H), 0.94 (t, J=7.2 Hz, 3H). Mass (m/z): 269.10 [M+H]+.

(IV) Synthesis of 1,3-dimethyl-8-(methylsulfonyl)-7-propyl-1H-purine-2,6(3H,7H)-dione To a solution of 1,3-dimethyl-8-(methylthio)-7-propyl-1H-purine-2,6(3H,7H)-dione (40.0 mg, 0.15 mmol) in MeOH (5 mL) was added oxone (366.9 mg, 0.59 mmol) in H$_2$O (5 mL). Then the mixture was stirred at RT for 5 h. Then the solvent was removed and extracted with dichloromethane (3*10 mL) and the organic layer was separated, dried over Na$_2$SO$_4$, filtered, concentrated and purified by prep. TLC to give a white solid (41.9 mg, 93.58%). $^1$H-NMR (400 MHz, CDCl$_3$): δ 4.67 (t, J=6.0 Hz, 2H), 3.57 (s, 3H), 3.44 (s, 3H), 3.42 (s, 3H), 2.03-1.90 (m, 2H), 1.00 (t, J=7.6 Hz, 3H). Mass (m/z): 301.09 [M+H]+.

Compound 84: 2-(1,3-dimethyl-8-(methylsulfonyl)-2,6-dioxo-2,3-dihydro-1H-purin-7(6H)-yl)acetonitrile

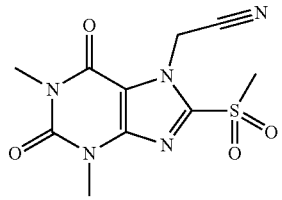 [SMILES: Cn1c(=O)c2c(nc(S(C)(=O)=O)n2CC#N)n(C)c1=O]

(I) Synthesis of 2-(8-chloro-1,3-dimethyl-2,6-dioxo-2,3-dihydro-1H-purin-7(6H)-yl)acetonitrile To a solution of 8-chloro-1,3-dimethyl-1H-purine-2,6 (3H,7H)-dione (3 g) and K$_2$CO$_3$ (2.32 g) in anhydrous DMF (30 mL) was added 2-bromoacetonitrile (2 g) and stirred under nitrogen at RT for 3 h. Then the reaction mixture was poured into water and extracted with EA (3*50 mL) and the organic layer was separated, dried over Na$_2$SO$_4$, filtered, concentrated and purified by chromatography on silica gel (PE:EA=1:1) to give a white solid (2.3 g 64.78%).

(II) Synthesis of 2-(8-mercapto-1,3-dimethyl-2,6-dioxo-2,3-dihydro-1H-purin-7(6H)-yl)acetonitrile To a solution of 2-(8-chloro-1,3-dimethyl-2,6-dioxo-2,3-dihydro-1H-purin-7(6H)-yl)acetonitrile (100 mg) in anhydrous DMF (3 mL) was added NaHS (44.3 mg) and heated to 135° C. for 3 h. Then the mixture was cooled to RT and acidified to PH=3. Then the reaction mixture was poured into water and extracted with dichloromethane (3*10 mL) and the organic layer was separated, dried over Na$_2$SO$_4$, filtered, concentrated and purified by chromatography on silica gel (PE:EA=1:1) to give a white solid (45.6 mg, 45.96%).

(III) Synthesis of 2-(1,3-dimethyl-8-(methylthio)-2,6-dioxo-2,3-dihydro-1H-purin-7(6H)-yl)acetonitrile To a solution of 2-(8-mercapto-1,3-dimethyl-2,6-dioxo-2,3-dihydro-1H-purin-7(6H)-yl)acetonitrile (20 mg) and K$_2$CO$_3$ (13.2 mg) in anhydrous DMF (5 mL) was added iodomethane (13.5 mg) and stirred under nitrogen at RT for 2 h. Then the reaction mixture was poured into water and extracted with EA (3*10 mL) and the organic layer was separated, dried over Na$_2$SO$_4$, filtered, concentrated and purified by prep. TLC (PE:EA 1:1) to give a white solid.

(IV) Synthesis of 2-(1,3-dimethyl-8-(methylsulfonyl)-2,6-dioxo-2,3-dihydro-1H-purin-7(6H)-yl)acetonitrile To a solution of 2-(1,3-dimethyl-8-(methylthio)-2,6-dioxo-2,3-dihydro-1H-purin-7(6H)-yl)acetonitrile (15 mg) in MeOH (2 mL) was added oxone (115.99 mg) in H$_2$O (2 mL). Then the mixture was stirred at RT for 6 h. Then the solvent was removed and extracted with dichloromethane (3*5 mL) and the organic layer was separated, dried over Na$_2$SO$_4$, filtered, concentrated and purified by prep. TLC to obtain 8.2 mg (46.86%) as a white solid. $^1$H-NMR (400 MHz, CDCl$_3$): δ 5.81 (s, 2H), 3.60 (s, 3H), 3.45 (s, 3H), 3.44 (s, 3H). Mass (m/z): 298.05 [M+H]+.

Compound 85: 2-(1,3-dimethyl-8-(methylthio)-2,6-dioxo-2,3-dihydro-1H-purin-7(6H)-yl)acetamide

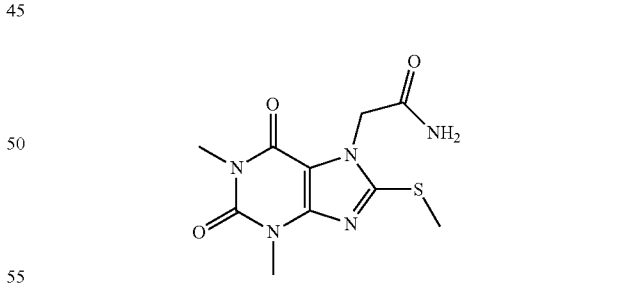

2-(1,3-dimethyl-8-(methylthio)-2,6-dioxo-2,3-dihydro-1H-purin-7(6H)-yl)acetonitrile was synthesized in a manner described in compound 84

To a solution of 2-(1,3-dimethyl-8-(methylthio)-2,6-dioxo-2,3-dihydro-1H-purin-7(6H)-yl)acetonitrile which (100 mg, 0.39 mmol) in EtOH (2 mL) was added sodium methanethiolate (33.2 mg, 0.47 mmol) and refluxed for 5 h. Then the mixture was cooled to RT and extracted with dichloromethane (3*5 mL) and the organic layer was separated, dried over Na$_2$SO$_4$, filtered, concentrated and purified by prep. TLC to give a white solid. (21.2 mg, 19.1%). $^1$H-NMR (400 MHz, DMSO-d$_6$): δ 7.67 (br, 1H), 7.33 (br, 1H), 4.83 (s, 2H), 3.44 (s, 3H), 3.20 (s, 3H), 2.65 (s, 3H). Mass (m/z): 284.07 [M+H]+.

Compound 86: 2-(1,3-dimethyl-8-(methylsulfonyl)-2,6-dioxo-2,3-dihydro-1H-purin-7(6H)-yl)acetamide

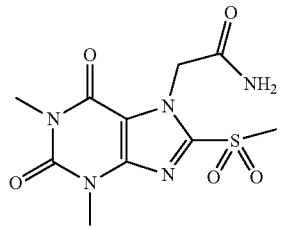

To a solution of compound 85 (20.0 mg, 0.07 mmol) in MeOH (2 mL) was added oxone (217.3 mg, 0.35 mmol) in H$_2$O (2 mL). Then the mixture was stirred at RT for 8 h. Then the solvent was removed and extracted with dichloromethane (3*5 mL) and the organic layer was separated, dried over Na$_2$SO$_4$, filtered, concentrated and purified by prep. TLC to give a white solid (15.4 mg, 73.65%). $^1$H-NMR (400 MHz, DMSO-d$_6$): δ 7.81 (br, 1H), 7.42 (br, 1H), 5.37 (s, 2H), 3.45 (s, 3H), 3.43 (s, 3H), 3.23 (s, 3H). Mass (m/z): 316.06 [M+H]+.

Compound 87: 3,7-dimethyl-8-(methylthio)-1H-purine-2,6(3H,7H)-dione

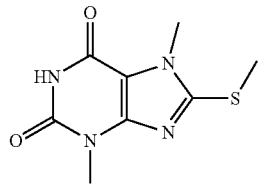

(I) Synthesis of 8-chloro-3,7-dimethyl-1H-purine-2,6(3H,7H)-dione

To a solution of 3,7-dimethyl-1H-purine-2,6(3H,7H)-dione (4.0 g, 22.19 mmol) in anhydrous THF (20 mL) was added NCS (4.5 g, 33.71 mmol) and stirred under nitrogen at RT for overnight. Then the solvent was removed and extracted with dichloromethane (3*10 mL) and the organic layer was separated, dried over Na$_2$SO$_4$, filtered, concentrated and recrystallized from EtOH:MeOH=2:1 to give a white solid (2.5 g, 52.3%).

(II) Synthesis of 3,7-dimethyl-8-(methylthio)-1H-purine-2,6(3H,7H)-dione

To a solution of 8-chloro-3,7-dimethyl-1H-purine-2,6(3H,7H)-dione (150 mg, 0.70 mmol) in anhydrous DMF (2 mL) was added sodium methanethiolate (195.9 mg, 2.79 mmol) and reacted in the microwave on a Biotage Smith Synthesis at 130° C. for 1 h. Then the mixture was cooled to RT and acidified to PH=3. Then the solid was precipitate out after 1 h stirred. The crude product was recrystallized from DCM:PE=1:10 and filtered to give a white solid. (89.5 mg, 62.3%). $^1$H-NMR (400 MHz, DMSO-d$_6$): δ11.08 (br, 1H), 7.33 (br, 1H), 3.72 (s, 3H), 3.36 (s, 3H), 2.67 (s, 3H). Mass (m/z): 227.05 [M+H]+.

Compound 88: 3,7-dimethyl-8-(methylsulfonyl)-1H-purine-2,6(3H,7H)-dione

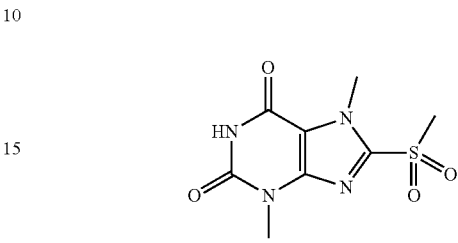

To a solution of compound 88 (20 mg, 0.08 mmol) in MeOH (1 mL) was added oxone (326.3 mg, 0.53 mmol) in H$_2$O (1 mL). Then the mixture was stirred at RT for 5 h. Then the solvent was removed and extracted with dichloromethane (3*5 mL) and the organic layer was separated, dried over Na$_2$SO$_4$, filtered, concentrated and purified by prep. TLC to give a white solid (4.5 mg, 39.4%). $^1$H-NMR (400 MHz, CDCl$_3$): δ 4.29 (s, 3H), 3.52 (s, 3H), 3.44 (s, 3H). Mass (m/z): 259.04 [M+H]+.

Compound 89: ethyl-3,7-dimethyl-8-(methylsulfonyl)-1H-purine-2,6(3H,7H)-dione

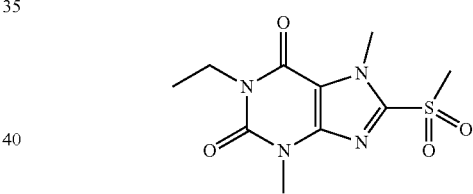

(I) Synthesis of 8-chloro-3,7-dimethyl-1H-purine-2,6(3H,7H)-dione

To a solution of 3,7-dimethyl-1H-purine-2,6(3H,7H)-dione (4.0 g, 22.19 mmol) in anhydrous THF (20 mL) was added NCS (4.5 g, 33.71 mmol) and stirred under nitrogen at RT for overnight. Then the solvent was removed and extracted with dichloromethane (3*10 mL) and the organic layer was separated, dried over Na$_2$SO$_4$, filtered, concentrated and recrystallized from EtOH:MeOH=2:1 to give a white solid (2.5 g). Mass (m/z): 215.03 [M+H]+.

(II) Synthesis of 8-chloro-1-ethyl-3,7-dimethyl-1H-purine-2,6(3H,7H)-dione

To a solution of 8-chloro-3,7-dimethyl-1H-purine-2,6(3H,7H)-dione (500 mg, 2.33 mmol) and K$_2$CO$_3$ (460.3 mg, 2.79 mmol) in anhydrous DMF (5 mL) was added iodoethane (519.6 mg, 2.79 mmol) and stirred under nitrogen at RT for 4 h. Then the reaction mixture was poured into water and extracted with dichloromethane (3*10 mL) and the organic layer was separated, dried over Na$_2$SO$_4$, filtered, concentrated and purified by chromatography on silica gel (PE:

EA=2:1) to give a white solid (141.2 mg, 16.3%). $^1$H-NMR (400 MHz, CDCl$_3$): δ 4.08 (q, J=7.2 Hz, 2H), 3.95 (s, 3H), 3.54 (s, 3H), 1.24 (t, J=7.2 Hz, 3H). Mass (m/z): 243.06 [M+H]+.

(III) Synthesis of 1-ethyl-8-mercapto-3,7-dimethyl-1H-purine-2,6(3H,7H)-dione

To a solution of 8-chloro-1-ethyl-3,7-dimethyl-1H-purine-2,6(3H,7H)-dione (40.0 mg, 0.16 mmol) in anhydrous DMF (2 mL) was added NaHS (26.9 mg, 0.48 mmol) and heated to 100° C. for 3 h. Then the mixture was cooled to RT and acidified to PH=3. Then the reaction mixture was poured into water and extracted with dichloromethane (3*5 mL) and the organic layer was separated, dried over Na$_2$SO$_4$, filtered, concentrated to give a white solid (35.9 mg). Mass (m/z): 241.07 [M+H]+.

(IV) Synthesis of 1-ethyl-3,7-dimethyl-8-(methylthio)-1H-purine-2,6(3H,7H)-dione To a solution of 1-ethyl-8-mercapto-3,7-dimethyl-1H-purine-2,6(3H,7H)-dione (25.0 mg, 0.10 mmol) and K$_2$CO$_3$ (17.3 mg, 0.12 mmol) in anhydrous DMF (1 mL) was added iodomethane (17.8 mg, 0.12 mmol) and stirred under nitrogen at RT for 2 h. Then the reaction mixture was poured into water and extracted with dichloromethane (3*10 mL) and the organic layer was separated, dried over Na$_2$SO$_4$, filtered, concentrated and purified by prep. TLC to give a white solid (12.0 mg, 43.5%). $^1$H-NMR (400 MHz, CDCl$_3$): δ 4.07 (t, J=6.8 Hz, 2H), 3.84 (s, 3H), 3.56 (s, 3H), 2.71 (s, 3H), 1.24 (t, J=6.8 Hz, 3H). Mass (m/z): 255.08 [M+1].

(V) Synthesis of 1-ethyl-3,7-dimethyl-8-(methylsulfonyl)-1H-purine-2,6(3H,7H)-dione To a solution of 1-ethyl-3,7-dimethyl-8-(methylthio)-1H-purine-2,6(3H,7H)-dione (10 mg, 0.03 mmol) in MeOH (1 mL) was added oxone (120.8 mg, 0.19 mmol) in H$_2$O (1 mL). Then the mixture was stirred at RT for 5 h. Then the solvent was removed and extracted with dichloromethane (3*5 mL) and the organic layer was separated, dried over Na$_2$SO$_4$, filtered, concentrated and purified by prep. TLC to give a white solid (8.2 mg, 77.4%). $^1$H-NMR (400 MHz, CDCl$_3$): δ 4.32 (s, 3H), 4.08 (q, J=6.0 Hz, 2H), 3.56 (s, 3H), 3.43 (s, 3H), 1.25 (t, J=6.0 Hz, 3H). Mass (m/z): 287.07 [M+H]+.

Compound 90: 3,7-dimethyl-8-(methylsulfonyl)-1-propyl-1H-purine-2,6(3H,7H)-dione

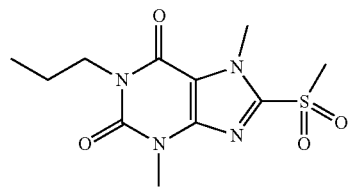 [SMILES: CCCn1c(=O)c2c(nc(S(C)(=O)=O)n2C)n(C)c1=O]

(I) Synthesis of 8-chloro-3,7-dimethyl-1H-purine-2,6(3H,7H)-dione

To a solution of 3,7-dimethyl-1H-purine-2,6(3H,7H)-dione (4.0 g, 22.19 mmol) in anhydrous THF (20 mL) was added NCS (4.5 g, 33.71 mmol) and stirred under nitrogen at RT for overnight. Then the solvent was removed and extracted with dichloromethane (3*10 mL) and the organic layer was separated, dried over Na$_2$SO$_4$, filtered, concentrated and recrystallized from EtOH:MeOH=2:1 to give a white solid (2.5 g, 52.3%).

(II) Synthesis of 3,7-dimethyl-8-(methylthio)-1H-purine-2,6(3H,7H)-dione

A mixture of 8-chloro-3,7-dimethyl-1H-purine-2,6(3H,7H)-dione (100 mg) and Sodium thiomethoxide (130.5 mg) in anhydrous DMF (4 mL) was reacted in the microwave on a Biotage Smith Synthesis at 100° C. for 1 h. Then the mixture was cooled to RT and acidified to pH=5. The reaction mixture was poured into water and extracted with dichloromethane (3*10 mL) and the organic layer was separated, dried over Na$_2$SO$_4$, filtered, concentrated to give a white solid (67.8 mg, 64.3%).

(III) Synthesis of 3,7-dimethyl-8-(methylthio)-1-propyl-1H-purine-2,6(3H,7H)-dione To a solution of 3,7-dimethyl-8-(methylthio)-1H-purine-2,6(3H,7H)-dione (30.0 mg, 0.13 mmol) and K$_2$CO$_3$ (21.9 mg, 0.15 mmol) in anhydrous DMF (2 mL) was added 1-iodopropane (27.1 mg, 0.15 mmol) and stirred under nitrogen at RT for 2 h. Then the reaction mixture was poured into water and extracted with dichloromethane (3*5 mL) and the organic layer was separated, dried over Na$_2$SO$_4$, filtered, concentrated and purified by prep. TLC to give a white solid (18.7 mg, 43.7%). $^1$H-NMR (400 MHz, CDCl$_3$): δ 3.94 (t, J=7.6 Hz, 2H), 3.83 (s, 3H), 3.55 (s, 3H), 2.70 (s, 3H), 1.69-1.63 (m, 2H), 0.95 (t, J=7.6 Hz, 3H). Mass (m/z): 269.10[M+H]+.

(IV) Synthesis of 3,7-dimethyl-8-(methylsulfonyl)-1-propyl-1H-purine-2,6(3H,7H)-dione To a solution of 3,7-dimethyl-8-(methylthio)-1-propyl-1H-purine-2,6(3H,7H)-dione (15.0 mg, 0.05 mmol) in MeOH (1 mL) was added oxone (171.8 mg, 0.27 mmol) in H$_2$O (1 mL). Then the mixture was stirred at RT for 5 h. Then the solvent was removed and extracted with dichloromethane (3*5 mL) and the organic layer was separated, dried over Na$_2$SO$_4$, filtered, concentrated and purified by prep. TLC to give a white solid (8.7 mg, 61.4%). $^1$H-NMR (400 MHz, CDCl$_3$): δ 4.31 (s, 3H), 3.96 (t, J=5.6 Hz, 2H), 3.55 (s, 3H), 3.42 (s, 3H), 1.69-1.63 (m, 2H), 0.95 (t, J=7.2 Hz, 3H). Mass (m/z): 301.09 [M+H]+.

Compound 91: 1-(cyclopropylmethyl)-3,7-dimethyl-8-(methylsulfonyl)-1H-purine-2,6(3H,7H)-dione

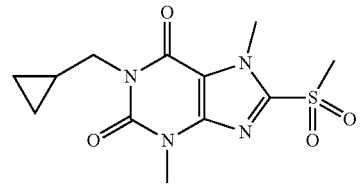 [SMILES: Cn1c(S(C)(=O)=O)nc2c1c(=O)n(CC1CC1)c(=O)n2C]

(I) Synthesis of 8-chloro-3,7-dimethyl-1H-purine-2,6(3H,7H)-dione

To a solution of 3,7-dimethyl-1H-purine-2,6(3H,7H)-dione (4.0 g, 22.19 mmol) in anhydrous THF (20 mL) was added NCS (4.5 g, 33.71 mmol) and stirred under nitrogen at RT for overnight. Then the solvent was removed and extracted with dichloromethane (3*10 mL) and the organic layer was separated, dried over Na₂SO₄, filtered, concentrated and recrystallized from EtOH:MeOH=2:1 to give a white solid.

(II) Synthesis of 8-chloro-1-(cyclopropylmethyl)-3,7-dimethyl-1H-purine-2,6(3H,7H)-dione To a solution of 8-chloro-3,7-dimethyl-1H-purine-2,6(3H,7H)-dione (500 mg, 2.33 mmol) and K₂CO₃ (385.8 mg) in anhydrous DMF (5 mL) was added (bromomethyl)cyclopropane (374.3 mg) and stirred under nitrogen at RT for 4 h. Then the reaction mixture was poured into water and extracted with EA (3*10 mL) and the organic layer was separated, dried over Na₂SO₄, filtered, concentrated and purified by chromatography on silica gel (PE:EA=2:1) to give a white solid (325 mg, 51.9%).

(III) Synthesis of 1-(cyclopropylmethyl)-8-mercapto-3,7-dimethyl-1H-purine-2,6(3H,7H)-dione To a solution of 8-chloro-1-(cyclopropylmethyl)-3,7-dimethyl-1H-purine-2,6(3H,7H)-dione (300 mg) in anhydrous DMF (2 mL) was added NaHS (187.6 mg) and heated to 130° C. for 1.5 h. Then the mixture was cooled to RT and acidified to PH=3. Then the reaction mixture was poured into water and extracted with dichloromethane (3*5 mL) and the organic layer was separated, dried over Na₂SO₄, filtered, concentrated to give a white solid.

(IV) Synthesis of 1-(cyclopropylmethyl)-3,7-dimethyl-8-(methylthio)-1H-purine-2,6(3H,7H)-dione To a solution of 1-(cyclopropylmethyl)-8-mercapto-3,7-dimethyl-1H-purine-2,6(3H,7H)-dione (289.1 mg) and K₂CO₃ (179.9 mg) in anhydrous DMF (5 mL) was added iodomethane (184.8 mg) and stirred under nitrogen at RT for 2 h. Then the reaction mixture was poured into water and extracted with dichloromethane (3*15 mL) and the organic layer was separated, dried over Na₂SO₄, filtered, concentrated and purified on silica gel (PE:EA 4:1) to give a white solid (280 mg, 92.1%).

(V) Synthesis of 1-(cyclopropylmethyl)-3,7-dimethyl-8-(methylsulfonyl)-1H-purine-2,6(3H,7H)-dione To a solution of 1-(cyclopropylmethyl)-3,7-dimethyl-8-(methylthio)-1H-purine-2,6(3H,7H)-dione (250 mg) in MeOH (5 mL) was added oxone (2.74 g) in H₂O (5 mL). Then the mixture was stirred at RT overnight. Then the solvent was removed and extracted with dichloromethane (3*15 mL) and the organic layer was separated, dried over Na₂SO₄, filtered, concentrated and purified on silica gel (PE:EA 1:1) to obtain 150 mg (53.8%) as a white solid. ¹H-NMR (400 MHz, CDCl₃): δ 4.31 (s, 3H), 3.90 (d, J=6.0 Hz, 2H), 3.56 (s, 3H), 3.43 (s, 3H), 1.27-1.24 (m, 1H), 0.48-0.41 (m, 4H). Mass (m/z): 313.09 [M+H]+.

Compound 92: 3,7-dimethyl-8-(methylsulfonyl)-1-phenyl-1H-purine-2,6(3H,7H)-dione

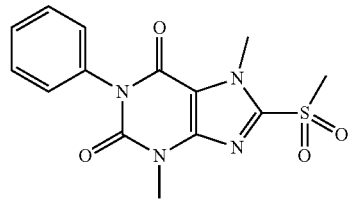 [SMILES: Cn1c(S(C)(=O)=O)nc2c1c(=O)n(-c1ccccc1)c(=O)n2C]

(I) Synthesis of 8-chloro-3,7-dimethyl-1H-purine-2,6(3H,7H)-dione

To a solution of 3,7-dimethyl-1H-purine-2,6(3H,7H)-dione (4.0 g, 22.19 mmol) in anhydrous THF (20 mL) was added NCS (4.5 g, 33.71 mmol) and stirred under nitrogen at RT for overnight. Then the solvent was removed and extracted with dichloromethane (3*10 mL) and the organic layer was separated, dried over Na₂SO₄, filtered, concentrated and recrystallized from EtOH:MeOH=2:1 to give a white solid (2.5 g, 52.3%).

(II) Synthesis of 3,7-dimethyl-8-(methylthio)-1H-purine-2,6(3H,7H)-dione

A mixture of 8-chloro-3,7-dimethyl-1H-purine-2,6(3H,7H)-dione (100 mg) and Sodium thiomethoxide (130.5 mg) in anhydrous DMF (4 mL) was reacted in the microwave on a Biotage Smith Synthesis at 100° C. for 1 h. Then the mixture was cooled to RT and acidified to pH=5. The reaction mixture was poured into water and extracted with dichloromethane (3*10 mL) and the organic layer was separated, dried over Na₂SO₄, filtered, concentrated to give a white solid.

(III) Synthesis of 3,7-dimethyl-8-(methylthio)-1-phenyl-1H-purine-2,6(3H,7H)-dione To a solution of 3,7-dimethyl-8-(methylthio)-1H-purine-2,6(3H,7H)-dione (50.0 mg, 0.22 mmol) and phenylboronic acid (26.9 mg, 0.22 mmol) in anhydrous DCM (2 mL) was added TEA (90.5 mg, 0.88 mmol) and Cu(OAc)₂ (60.1 mg, 0.33 mmol). Then the mixture was stirred at RT for overnight. Then the reaction mixture was poured into water and extracted with dichloromethane (3*10 mL) and the organic layer was separated, dried over Na₂SO₄, filtered, concentrated and purified by chromatography on silica gel (PE:EA=2:1) to give a white solid (15.0 mg, 18.4%). ¹H-NMR (400 MHz, CDCl₃): δ 7.51-7.22 (m, 5H), 3.82 (s, 3H), 3.60 (s, 3H), 2.75 (s, 3H). Mass (m/z): 303.08 [M+H]+.

(IV) Synthesis of 3,7-dimethyl-8-(methylsulfonyl)-1-phenyl-1H-purine-2,6(3H,7H)-dione To a solution of 3,7-dimethyl-8-(methylthio)-1-phenyl-1H-purine-2,6(3H,7H)-dione (20.0 mg, 0.06 mmol) in MeOH (2 mL) was added oxone (162.8 mg, 0.26 mmol) in H₂O (2 mL). Then the mixture was stirred at RT for 5 h. Then the solvent was removed and extracted with dichloromethane (3*5 mL) and the organic layer was separated, dried over Na₂SO₄, filtered, concentrated and purified by prep. TLC to give a white solid (14.3 mg, 64.2%). ¹H-NMR (400 MHz, CDCl$_3$): δ 7.54-7.21 (m, 5H), 4.30 (s, 3H), 3.60 (s, 3H), 3.46 (s, 3H). Mass (m/z): 335.07 [M+H]+.

Compound 93: 1-benzyl-3,7-dimethyl-8-(methylsulfonyl)-1H-purine-2,6(3H,7H)-dione

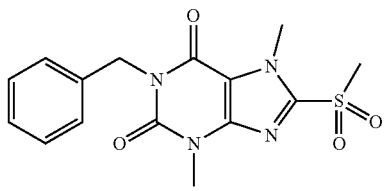 [SMILES: Cn1c(S(C)(=O)=O)nc2c1c(=O)n(Cc1ccccc1)c(=O)n2C]

(I) Synthesis of 8-chloro-3,7-dimethyl-1H-purine-2,6(3H,7H)-dione

To a solution of 3,7-dimethyl-1H-purine-2,6(3H,7H)-dione (4.0 g, 22.19 mmol) in anhydrous THF (20 mL) was added NCS (4.5 g, 33.71 mmol) and stirred under nitrogen at RT for overnight. Then the solvent was removed and extracted with dichloromethane (3*10 mL) and the organic layer was separated, dried over Na$_2$SO$_4$, filtered, concentrated and recrystallized from EtOH:MeOH=2:1 to give a white solid.

(II) Synthesis of 1-benzyl-8-chloro-3,7-dimethyl-1H-purine-2,6(3H,7H)-dione

To a solution of 8-chloro-3,7-dimethyl-1H-purine-2,6(3H,7H)-dione (500 mg, 2.33 mmol) and K$_2$CO$_3$ (385.8 mg) in anhydrous DMF (5 mL) was added (bromomethyl)benzene (478.6 mg) and stirred under nitrogen at RT for 4 h. Then the reaction mixture was poured into water and extracted with EA (3*10 mL) and the organic layer was separated, dried over Na$_2$SO$_4$, filtered, concentrated and purified by chromatography on silica gel (PE:EA=1:1) to give a white solid (423.5 mg, 58.5%).

(III) Synthesis of 1-benzyl-8-mercapto-3,7-dimethyl-1H-purine-2,6(3H,7H)-dione

To a solution of 1-benzyl-8-chloro-3,7-dimethyl-1H-purine-2,6(3H,7H)-dione (150 mg) in anhydrous DMF (5 mL) was added NaHS (39.5 mg) and heated to 130° C. for 1.5 h. Then the mixture was cooled to RT and acidified to PH=3. Then the reaction mixture was poured into water and extracted with dichloromethane (3*5 mL) and the organic layer was separated, dried over Na$_2$SO$_4$, filtered, concentrated to give a white solid.

(IV) Synthesis of 1-benzyl-3,7-dimethyl-8-(methylthio)-1H-purine-2,6(3H,7H)-dione To a solution of 1-benzyl-8-mercapto-3,7-dimethyl-1H-purine-2,6(3H,7H)-dione (128 mg) and K$_2$CO$_3$ (66.99 mg) in anhydrous DMF (5 mL) was added iodomethane (68.89 mg) and stirred under nitrogen at RT for 2 h. Then the reaction mixture was poured into water and extracted with dichloromethane (3*15 mL) and the organic layer was separated, dried over Na$_2$SO$_4$, filtered, concentrated and purified on silica gel (PE:EA 1:1) to give a white solid (108.3 mg, 81.12%).

(V) Synthesis of 1-benzyl-3,7-dimethyl-8-(methylsulfonyl)-1H-purine-2,6(3H,7H)-dione To a solution of 1-benzyl-3,7-dimethyl-8-(methylthio)-1H-purine-2,6(3H,7H)-dione (250 mg) in MeOH (5 mL) was added oxone (2.43 g) in H$_2$O (5 mL). Then the mixture was stirred at RT overnight. Then the solvent was removed and extracted with dichloromethane (3*15 mL) and the organic layer was separated, dried over Na$_2$SO$_4$, filtered, concentrated and purified on silica gel (PE:EA 1:1) to obtain 138.2 mg (50.1%) as a white solid. $^1$H-NMR (400 MHz, CDCl$_3$): δ 7.48-7.27 (m, 5H), 5.19 (s, 2H), 4.32 (s, 3H), 3.54 (s, 3H), 3.43 (s, 3H). Mass (m/z): 349.09 [M+H]+.

Compound 94: 3,7-dimethyl-8-(methylsulfonyl)-1-phenethyl-1H-purine-2,6(3H,7H)-dione

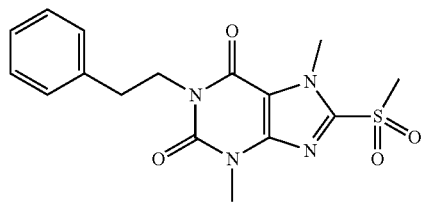 [SMILES: Cn1c(S(C)(=O)=O)nc2c1c(=O)n(CCc1ccccc1)c(=O)n2C]

(I) Synthesis of 8-chloro-3,7-dimethyl-1H-purine-2,6(3H,7H)-dione

To a solution of 3,7-dimethyl-1H-purine-2,6(3H,7H)-dione (4.0 g, 22.19 mmol) in anhydrous THF (20 mL) was added NCS (4.5 g, 33.71 mmol) and stirred under nitrogen at RT for overnight. Then the solvent was removed and extracted with dichloromethane (3*10 mL) and the organic layer was separated, dried over Na$_2$SO$_4$, filtered, concentrated and recrystallized from EtOH:MeOH=2:1 to give a white solid.

(II) Synthesis of 8-chloro-3,7-dimethyl-1-phenethyl-1H-purine-2,6(3H,7H)-dione

To a solution of 8-chloro-3,7-dimethyl-1H-purine-2,6(3H,7H)-dione (500 mg, 2.33 mmol) and K$_2$CO$_3$ (385.8 mg) in anhydrous DMF (5 mL) was added (2-bromoethyl)benzene (518.2 mg) and stirred under nitrogen at RT for 4 h. Then the reaction mixture was poured into water and extracted with EA (3*10 mL) and the organic layer was separated, dried over Na$_2$SO$_4$, filtered, concentrated and purified by chromatography on silica gel (PE:EA=1:1) to give a white solid (336.7 mg, 47.6%).

(III) Synthesis of 8-mercapto-3,7-dimethyl-1-phenethyl-1H-purine-2,6(3H,7H)-dione To a solution of 8-chloro-3,7-dimethyl-1-phenethyl-1H-purine-2,6(3H,7H)-dione (150 mg) in anhydrous DMF (5 mL) was added NaHS (39.5 mg) and heated to 130° C. for 1.5 h. Then the mixture was cooled to RT and acidified to PH=3. Then the reaction mixture was poured into water and extracted with dichloromethane (3*5 mL) and the organic layer was separated, dried over Na$_2$SO$_4$, filtered, concentrated to give a white solid.

(IV) Synthesis of 3,7-dimethyl-8-(methylthio)-1-phenethyl-1H-purine-2,6(3H,7H)-dione To a solution of 8-mercapto-3,7-dimethyl-1-phenethyl-1H-purine-2,6(3H,7H)-dione (128 mg) and K₂CO₃ (66.99 mg) in anhydrous DMF (5 mL) was added iodomethane (68.89 mg) and stirred under nitrogen at RT for 2 h. Then the reaction mixture was poured into water and extracted with dichloromethane (3*15 mL) and the organic layer was separated, dried over Na₂SO₄, filtered, concentrated and purified on silica gel (PE:EA 1:1) to give a white solid.

(V) Synthesis of 3,7-dimethyl-8-(methylsulfonyl)-1-phenethyl-1H-purine-2,6(3H,7H)-dione To a solution of 3,7-dimethyl-8-(methylthio)-1-phenethyl-1H-purine-2,6(3H,7H)-dione (100 mg) in MeOH (5 mL) was added oxone (931.5 mg) in H₂O (5 mL). Then the mixture was stirred at RT overnight. Then the solvent was removed and extracted with dichloromethane (3*15 mL) and the organic layer was separated, dried over Na₂SO₄, filtered, concentrated and purified on silica gel (PE:EA 1:1) to obtain 48.9 mg (45.7%) as a white solid. ¹H-NMR (400 MHz, CDCl₃): δ 7.32-7.25 (m, 5H), 4.32 (s, 3H), 4.22 (t, J=8.0 Hz, 2H), 3.57 (s, 3H), 3.44 (s, 3H), 2.92 (t, J=8.0 Hz, 2H). Mass (m/z): 363.10 [M+H]+.

Compound 95: 3,7-dimethyl-8-(methylsulfonyl)-1-(prop-2-ynyl)-1H-purine-2,6(3H,7H)-dione

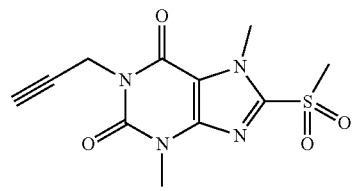 [SMILES: C#CCn1c(=O)c2c(nc(S(C)(=O)=O)n2C)n(C)c1=O]

(I) Synthesis of 8-chloro-3,7-dimethyl-1H-purine-2,6(3H,7H)-dione

To a solution of 3,7-dimethyl-1H-purine-2,6(3H,7H)-dione (4.0 g, 22.19 mmol) in anhydrous THF (20 mL) was added NCS (4.5 g, 33.71 mmol) and stirred under nitrogen at RT for overnight. Then the solvent was removed and extracted with dichloromethane (3*10 mL) and the organic layer was separated, dried over Na₂SO₄, filtered, concentrated and recrystallized from EtOH:MeOH=2:1 to give a white solid (2.5 g, 52.3%).

(II) Synthesis of 3,7-dimethyl-8-(methylthio)-1H-purine-2,6(3H,7H)-dione

A mixture of 8-chloro-3,7-dimethyl-1H-purine-2,6(3H,7H)-dione (100 mg) and Sodium thiomethoxide (130.5 mg) in anhydrous DMF (4 mL) was reacted in the microwave on a Biotage Smith Synthesis at 100° C. for 1 h. Then the mixture was cooled to RT and acidified to pH=5. The reaction mixture was poured into water and extracted with dichloromethane (3*10 mL) and the organic layer was separated, dried over Na₂SO₄, filtered, concentrated to give a white solid (67.8 mg, 64.3%).

(III) Synthesis of 3,7-dimethyl-8-(methylthio)-1-(prop-2-yn-1-yl)-1H-purine-2,6(3H,7H)-dione To a solution of 3,7-dimethyl-8-(methylthio)-1H-purine-2,6(3H,7H)-dione (30.0 mg, 0.13 mmol) and K₂CO₃ (21.9 mg, 0.15 mmol) in anhydrous DMF (2 mL) was added 3-bromoprop-1-yne (18.9 mg, 0.15 mmol) and stirred under nitrogen at RT for 2 h. Then the reaction mixture was poured into water and extracted with dichloromethane (3*5 mL) and the organic layer was separated, dried over Na₂SO₄, filtered, concentrated and purified by prep. TLC (PE:EA 1:1) to give a white solid (10.2 mg, 34.7%).

(IV) Synthesis of 3,7-dimethyl-8-(methylsulfonyl)-1-(prop-2-yn-1-yl)-1H-purine-2,6(3H,7H)-dione To a solution of 3,7-dimethyl-8-(methylthio)-1-(prop-2-yn-1-yl)-1H-purine-2,6(3H,7H)-dione (10 mg) in MeOH (1 mL) was added oxone (116.3 mg) in H₂O (1 mL). Then the mixture was stirred at RT for 5 h. Then the solvent was removed and extracted with dichloromethane (3*5 mL) and the organic layer was separated, dried over Na₂SO₄, filtered, concentrated and purified by prep. TLC (PE:EA 1:2) to obtain 4.8 mg (45.7%) as a white solid. ¹H-NMR (400 MHz, CDCl₃): δ 4.79 (d, J=2.0 Hz, 3H), 4.32 (s, 3H), 3.59 (s, 3H), 3.44 (s, 3H), 2.19 (t, J=2.0 Hz, 1H). Mass (m/z): 297.06 [M+H]+.

Compound 96: 2-(3,7-dimethyl-8-(methylsulfonyl)-2,6-dioxo-2,3,6,7-tetrahydro-1H-purin-1-yl)-N,N-dimethylacetamide

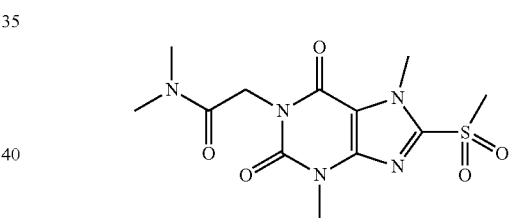

(I) Synthesis of 8-chloro-3,7-dimethyl-1H-purine-2,6(3H,7H)-dione

To a solution of 3,7-dimethyl-1H-purine-2,6(3H,7H)-dione (4.0 g, 22.19 mmol) in anhydrous THF (20 mL) was added NCS (4.5 g, 33.71 mmol) and stirred under nitrogen at RT for overnight. Then the solvent was removed and extracted with dichloromethane (3*10 mL) and the organic layer was separated, dried over Na₂SO₄, filtered, concentrated and recrystallized from EtOH:MeOH=2:1 to give a white solid (2.5 g, 52.3%).

(II) Synthesis of 3,7-dimethyl-8-(methylthio)-1H-purine-2,6(3H,7H)-dione

A mixture of 8-chloro-3,7-dimethyl-1H-purine-2,6(3H,7H)-dione (100 mg) and Sodium thiomethoxide (130.5 mg) in anhydrous DMF (4 mL) was reacted in the microwave on a Biotage Smith Synthesis at 100° C. for 1 h. Then the mixture was cooled to RT and acidified to pH=5. The reaction mixture was poured into water and extracted with dichloromethane (3*10 mL) and the organic layer was separated, dried over Na$_2$SO$_4$, filtered, concentrated to give a white solid (67.8 mg, 64.3%).

(III) Synthesis of 2-(3,7-dimethyl-8-(methylthio)-2,6-dioxo-2,3,6,7-tetrahydro-1H-purin-1-yl)-N,N-dimethylacetamide To a solution of 3,7-dimethyl-8-(methylthio)-1H-purine-2,6(3H,7H)-dione (50.0 mg) and K$_2$CO$_3$ (36.6 mg) in anhydrous DMF (2 mL) was added 2-chloro-N,N-dimethylacetamide (32.1 mg) and stirred under nitrogen at RT for 2 h. Then the reaction mixture was poured into water and extracted with dichloromethane (3*5 mL) and the organic layer was separated, dried over Na$_2$SO$_4$, filtered, concentrated and purified by prep. TLC (PE:EA 1:1) to give a white solid (43.4 mg, 63.9%).

(IV) Synthesis of 2-(3,7-dimethyl-8-(methylsulfonyl)-2,6-dioxo-2,3,6,7-tetrahydro-1H-purin-1-yl)-N,N-dimethylacetamide To a solution of 2-(3,7-dimethyl-8-(methylthio)-2,6-dioxo-2,3,6,7-tetrahydro-1H-purin-1-yl)-N,N-dimethylacetamide (10 mg) in MeOH (1 mL) was added oxone (78.9 mg) in H$_2$O (1 mL). Then the mixture was stirred overnight. Then the solvent was removed and extracted with dichloromethane (3*5 mL) and the organic layer was separated, dried over Na$_2$SO$_4$, filtered, concentrated and purified by prep. TLC (PE:EA 1:1) to obtain 6.8 mg (63.1%) as a white solid. $^1$H-NMR (400 MHz, CDCl$_3$): δ 4.82 (s, 2H), 4.28 (s, 3H), 3.55 (s, 3H), 3.41 (s, 3H), 3.11 (s, 3H), 2.97 (s, 3H). Mass (m/z): 344.10 [M+H]+.

Compound 97: 4-(2-(3,7-dimethyl-8-(methylsulfonyl)-2,6-dioxo-2,3,6,7-tetrahydro-1H-purin-1-yl)ethyl)morpholine 4-oxide

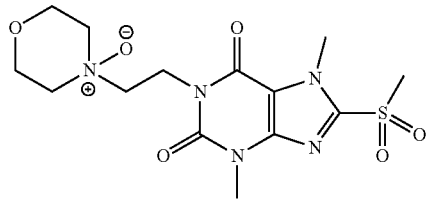 [SMILES: Cn1c(S(C)(=O)=O)nc2c1c(=O)n(CC[N+]1([O-])CCOCC1)c(=O)n2C]

(I) Synthesis of 8-chloro-3,7-dimethyl-1H-purine-2,6(3H,7H)-dione

To a solution of 3,7-dimethyl-1H-purine-2,6(3H,7H)-dione (4.0 g, 22.19 mmol) in anhydrous THF (20 mL) was added NCS (4.5 g, 33.71 mmol) and stirred under nitrogen at RT for overnight. Then the solvent was removed and extracted with dichloromethane (3*10 mL) and the organic layer was separated, dried over Na$_2$SO$_4$, filtered, concentrated and recrystallized from EtOH:MeOH=2:1 to give a white solid (2.5 g, 52.3%).

(II) Synthesis of 3,7-dimethyl-8-(methylthio)-1H-purine-2,6(3H,7H)-dione

A mixture of 8-chloro-3,7-dimethyl-1H-purine-2,6(3H,7H)-dione (100 mg) and Sodium thiomethoxide (130.5 mg) in anhydrous DMF (4 mL) was reacted in the microwave on a Biotage Smith Synthesis at 100° C. for 1 h. Then the mixture was cooled to RT and acidified to pH=5. The reaction mixture was poured into water and extracted with dichloromethane (3*10 mL) and the organic layer was separated, dried over Na$_2$SO$_4$, filtered, concentrated to give a white solid (67.8 mg, 64.3%).

(III) Synthesis of 3,7-dimethyl-8-(methylthio)-1-(2-morpholinoethyl)-1H-purine-2,6(3H,7H)-dione To a solution of 3,7-dimethyl-8-(methylthio)-1H-purine-2,6(3H,7H)-dione (15 mg) and Cs$_2$CO$_3$ (25.94 mg) in anhydrous DMF (2 mL) was added 4-(2-chloroethyl)morpholine hydrochloride (14.8 mg) and reacted in the microwave on a Biotage smith synthesis at 110° C. for 1 h. Then the reaction mixture was cooled to RT and extracted with dichloromethane (3*10 mL) and the organic layer was separated, dried over Na$_2$SO$_4$, filtered, concentrated and give a yellow oil (20.1 mg, 89.3%).

(IV) Synthesis of 4-(2-(3,7-dimethyl-8-(methylsulfonyl)-2,6-dioxo-2,3,6,7-tetrahydro-1H-purin-1-yl)ethyl)morpholine 4-oxide To a solution of 3,7-dimethyl-8-(methylthio)-1-(2-morpholinoethyl)-1H-purine-2,6(3H,7H)-dione (10 mg, 0.03 mmol) in DCM (2 mL) was added m-CPBA (12.73 mg, 0.07 mmol). Then the mixture was stirred at RT for 2 h. Then the solvent was removed and extracted with dichloromethane (3*5 mL) and the organic layer was separated, dried over Na$_2$SO$_4$, filtered, concentrated and purified by pre-HPLC to give a white solid (4.1 mg, 39.7%). $^1$H-NMR (400 MHz, CDCl$_3$): δ 4.60 (m, 2H), 4.30-4.15 (m, 7H), 4.15-3.97 (m, 2H), 3.97-3.55 (m, 2H), 3.41 (s, 3H) 3.39-3.37 (m, 5H). Mass (m/z): 388.12 [M+H]+.

Compound 98: 1-(furan-2-yl)-3,7-dimethyl-8-(methylsulfonyl)-1H-purine-2,6(3H,7H)-dione

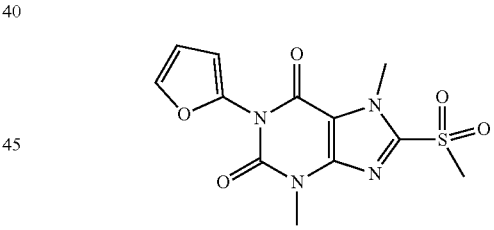

(I) Synthesis of 8-chloro-3,7-dimethyl-1H-purine-2,6(3H,7H)-dione

To a solution of 3,7-dimethyl-1H-purine-2,6(3H,7H)-dione (4.0 g, 22.19 mmol) in anhydrous THF (20 mL) was added NCS (4.5 g, 33.71 mmol) and stirred under nitrogen at RT for overnight. Then the solvent was removed and extracted with dichloromethane (3*10 mL) and the organic layer was separated, dried over Na$_2$SO$_4$, filtered, concentrated and recrystallized from EtOH:MeOH=2:1 to give a white solid (2.5 g, 52.3%).

(II) Synthesis of 3,7-dimethyl-8-(methylthio)-1H-purine-2,6(3H,7H)-dione

A mixture of 8-chloro-3,7-dimethyl-1H-purine-2,6(3H,7H)-dione (100 mg) and Sodium thiomethoxide (130.5 mg)

in anhydrous DMF (4 mL) was reacted in the microwave on a Biotage Smith Synthesis at 100° C. for 1 h. Then the mixture was cooled to RT and acidified to pH=5. The reaction mixture was poured into water and extracted with dichloromethane (3*10 mL) and the organic layer was separated, dried over $Na_2SO_4$, filtered, concentrated to give a white solid.

(III) Synthesis of 1-(furan-2-yl)-3,7-dimethyl-8-(methylthio)-1H-purine-2,6(3H,7H)-dione A solution of CuCl (3.0 mg, 0.03 mol), 2-furanboronic acid (59 mg, 0.53 mmol) and 3 Å molecular sieves (100 mg, freshly activated) in 1,2-dichloroethane (4 mL) was cooled to 0° C. under nitrogen atmosphere. Dry pyridine (0.3 mL) was added, followed by a solution of 3,7-dimethyl-8-(methylthio)-1H-purine-2,6(3H,7H)-dione (60 mg, 0.265 mmol) in 1,2-dichloroethane (1 mL). The reaction mixture was allowed to warm to room temperature. A balloon filled with dry $O_2$ was attached to the flask and the mixture stirred for 48 h. The reaction mixture was filtered and the filtrate was condensed, purified by Pre-TLC (PE/EA=2:3) to give a white solid (34 mg, 44%): $^1$H NMR (400 MHz, $CDCl_3$) δ 7.56-7.51 (m, 1H), 7.54-7.52 (m, 1H), 6.39-6.37 (m, 1H), 3.80 (s, 3H), 3.58 (s, 3H), 2.74 (s, 3H); LC-MS 293.3 $[MH]^+$.

(IV) Synthesis of 1-(furan-2-yl)-3,7-dimethyl-8-(methylsulfonyl)-1H-purine-2,6(3H,7H)-dione To a solution of 1-(furan-2-yl)-3,7-dimethyl-8-(methylthio)-1H-purine-2,6(3H,7H)-dione (34 mg, 0.12 mmol) in MeOH (2.5 mL) was added a mixture of oxone (359 mg, 0.60 mmol) in $H_2O$ (2 mL). The reaction mixture was stirred at RT for 16 h. The reaction mixture was partitioned between DCM (30 mL) and $H_2O$ (5 mL). The organic layer was dried ($Na_2SO_4$), concentrated and purified by Pre-TLC (PE:EA=2:3) to give a white solid (16 mg, 42%): $^1$H NMR (400 MHz, $CDCl_3$) δ 7.48-7.46 (m, 1H), 6.57-6.55 (m, 1H), 6.42-6.40 (m, 1H), 4.29 (s, 3H), 3.58 (s, 3H), 3.45 (s, 3H); LC-MS 325.2 $[MH]^+$.

Compound 99: 1,7-dimethyl-8-(methylsulfonyl)-1H-purine-2,6(3H,7H)-dione

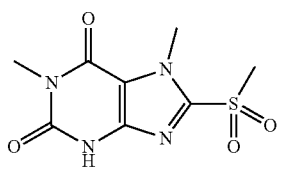 [SMILES: Cn1c(=O)[nH]c2nc(S(C)(=O)=O)n(C)c2c1=O]

(I) Synthesis of 1,7-dimethyl-1H-purine-2,6(3H,7H)-dione

To a solution of ethyl 4-amino-1-methyl-1H-imidazole-5-carboxylate (2.0 g, 11.83 mmol) and ethyl methylcarbamate (2.92 g, 28.32 mmol) in anhydrous THF (2 mL) was reacted at 75° C. under nitrogen for 30 min. Then to the mixture was added potassium 2-methylpropan-2-olate (1.98 g, 17.64 mmol) and reacted at 75° C. for overnight. Then the solvent was removed and extracted with dichloromethane (3*50 mL) and the organic layer was separated, dried over $Na_2SO_4$, filtered, concentrated and purified by chromatography on silica gel (DCM:MeOH=20:1) to give a white solid (1.2 g, 56.33%). $^1$H-NMR (400 MHz, DMSO-$d_6$): δ 11.82 (s, 1H), 7.90 (s, 1H), 3.84 (s, 3H), 3.16 (s, 3H). Mass (m/z): 181.06[M+H]+.

(II) Synthesis of 8-chloro-1,7-dimethyl-1H-purine-2,6(3H,7H)-dione

To a solution of 1,7-dimethyl-1H-purine-2,6(3H,7H)-dione (0.53 g, 2.94 mmol) in anhydrous THF (10 mL) was added NCS (0.59 g, 4.36 mmol) and stirred under nitrogen at RT for overnight. Then the solvent was removed and extracted with dichloromethane (3*20 mL) and the organic layer was separated, dried over $Na_2SO_4$, filtered, concentrated to give a white solid (0.45 g). Mass (m/z): 215.03 [M+H]+.

(III) Synthesis of 1,7-dimethyl-8-(methylthio)-1H-purine-2,6(3H,7H)-dione

To a solution of 8-chloro-1,7-dimethyl-1H-purine-2,6(3H,7H)-dione (100 mg, 0.46 mmol) in DMF (10 mL) and $H_2O$ (1 mL) was added sodium methanethiolate (130.8 mg, 1.86 mmol) and reacted in the microwave on a Biotage Smith Synthesis at 120° C. for 1 h. Then the mixture was cooled to RT and acidified to PH=3. The reaction mixture was poured into water and extracted with dichloromethane (3*10 mL) and the organic layer was separated, dried over $Na_2SO_4$, filtered, concentrated to give a white solid (38.3 mg). Mass (m/z): 227.05 [M+H]+.

(IV) Synthesis of 1,7-dimethyl-8-(methylsulfonyl)-1H-purine-2,6(3H,7H)-dione

To a solution of 1,7-dimethyl-8-(methylthio)-1H-purine-2,6(3H,7H)-dione (15.0 mg, 0.06 mmol) in MeOH (3 mL) was added oxone (163.2 mg, 0.26 mmol) in $H_2O$ (5 mL). Then the mixture was stirred at RT for 5 h. Then the solvent was removed and extracted with dichloromethane (3*10 mL) and the organic layer was separated, dried over $Na_2SO_4$, filtered, concentrated and purified by prep. TLC to give a white solid (12.8 mg, 74.85%). $^1$H-NMR (400 MHz, DMSO-$d_6$): δ 12.18 (s, 1H), 4.16 (s, 3H), 3.48 (s, 3H), 3.19 (s, 3H). Mass (m/z): 259.04 [M+H]+.

Compound 100: 3-ethyl-1,7-dimethyl-8-(methylsulfonyl)-1H-purine-2,6(3H,7H)-dione

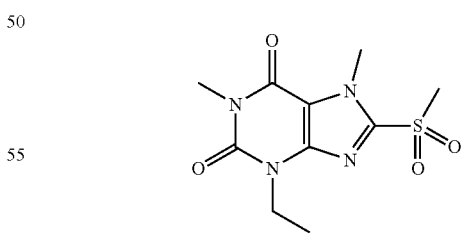

(I) Synthesis of 3-ethyl-1,7-dimethyl-8-(methylthio)-1H-purine-2,6(3H,7H)-dione

The compound 1,7-dimethyl-8-(methylthio)-1H-purine-2,6(3H,7H)-dione was synthesized from ethyl 4-amino-1-methyl-1H-imidazole-5-carboxylate in a manner that described for compound 99.

To a solution of 1,7-dimethyl-8-(methylthio)-1H-purine-2,6(3H,7H)-dione (15.0 mg, 0.06 mmol) and $K_2CO_3$ (11.1 mg, 0.08 mmol) in anhydrous DMF (2 mL) was added iodoethane (12.4 mg, 0.08 mmol) and stirred under nitrogen at RT for 2 h. Then the reaction mixture was poured into water and extracted with dichloromethane (3*5 mL) and the organic layer was separated, dried over $Na_2SO_4$, filtered, concentrated and purified by prep. TLC to give a white solid (11.0 mg, 65.48%). $^1$H-NMR (400 MHz, CDCl$_3$): δ 4.15 (q, J=6.0 Hz, 2H), 3.83 (s, 3H), 3.38 (s, 3H), 2.70 (s, 3H), 1.32 (t, J=6.0 Hz, 3H). Mass (m/z): 255.08[M+H]+.

(II) Synthesis of 3-ethyl-1,7-dimethyl-8-(methylsulfonyl)-1H-purine-2,6(3H,7H)-dione To a solution of 3-ethyl-1,7-dimethyl-8-(methylthio)-1H-purine-2,6(3H,7H)-dione (10.0 mg, 0.04 mmol) in MeOH (1 mL) was added oxone (96.8 mg) in $H_2O$ (1 mL). Then the mixture was stirred at RT for 5 h. Then the solvent was removed and extracted with dichloromethane (3*10 mL) and the organic layer was separated, dried over $Na_2SO_4$, filtered, concentrated and purified by prep. TLC to give a white solid (10.5 mg, 92.9%). $^1$H-NMR (400 MHz, CDCl3): δ 4.31 (s, 3H), 4.15 (q, J=6.4 Hz, 2H), 3.44 (s, 3H), 3.41 (s, 3H), 1.33 (t, J=6.4 Hz, 3H). Mass (m/z): 287.07[M+H]+.

Compound 101: 1,7-dimethyl-8-(methylsulfonyl)-3-propyl-1H-purine-2,6(3H,7H)-dione

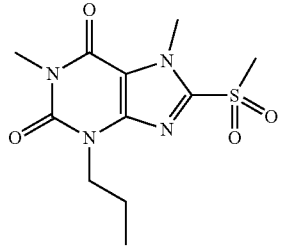 [SMILES: CCCn1c(=O)n(C)c(=O)c2c1nc(S(C)(=O)=O)n2C]

(I) Synthesis of 1,7-dimethyl-8-(methylthio)-3-propyl-1H-purine-2,6(3H,7H)-dione The compound 1,7-dimethyl-8-(methylthio)-1H-purine-2,6(3H,7H)-dione was synthesized from ethyl 4-amino-1-methyl-1H-imidazole-5-carboxylate in a manner that described for compound 99.

To a solution of 1,7-dimethyl-8-(methylthio)-1H-purine-2,6(3H,7H)-dione (30 mg) and $K_2CO_3$ (29.97 mg) in anhydrous DMF (5 mL) was added 1-iodopropane (27.1 mg) and stirred under nitrogen at RT for 2 h. Then the reaction mixture was poured into water and extracted with dichloromethane (3*5 mL) and the organic layer was separated, dried over $Na_2SO_4$, filtered, concentrated and purified by prep. TLC (PE:EA 1:1) to give a white solid (31.1 mg, 87.36%).

(II) Synthesis of 1,7-dimethyl-8-(methylsulfonyl)-3-propyl-1H-purine-2,6(3H,7H)-dione To a solution of 1,7-dimethyl-8-(methylthio)-3-propyl-1H-purine-2,6(3H,7H)-dione (30 mg) in MeOH (2 mL) was added oxone (275.3 mg) in $H_2O$ (2 mL). Then the mixture was stirred at RT for 5 h. Then the solvent was removed and extracted with dichloromethane (3*10 mL) and the organic layer was separated, dried over $Na_2SO_4$, filtered, concentrated and purified by prep. TLC (PE:EA 1:1) to obtain 28.3 mg (84.3%) as a white solid. $^1$H-NMR (400 MHz, CDCl$_3$): δ 4.31 (s, 3H), 4.05 (t, J=7.6 Hz, 2H), 3.44 (s, 3H), 3.41 (s, 3H), 1.80-1.74 (m, 2H), 0.96 (t, J=7.6 Hz, 3H). Mass (m/z): 301.09 [M+H]+.

Compound 102: 3-(cyclopropylmethyl)-1,7-dimethyl-8-(methylsulfonyl)-1H-purine-2,6(3H,7H)-dione

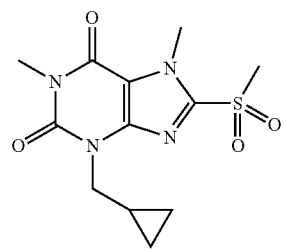 [SMILES: Cn1c(=O)c2c(nc(S(C)(=O)=O)n2C)n(CC2CC2)c1=O]

(I) Synthesis of 3-(cyclopropylmethyl)-1,7-dimethyl-8-(methylthio)-1H-purine-2,6(3H,7H)-dione The compound 1,7-dimethyl-8-(methylthio)-1H-purine-2,6(3H,7H)-dione was synthesized from ethyl 4-amino-1-methyl-1H-imidazole-5-carboxylate in a manner that described for compound 99.

To a solution of 1,7-dimethyl-8-(methylthio)-1H-purine-2,6(3H,7H)-dione (30 mg) and $K_2CO_3$ (21.97 mg) in anhydrous DMF (5 mL) was added (bromomethyl)cyclopropane (21.3 mg) and stirred under nitrogen at RT for 2 h. Then the reaction mixture was poured into water and extracted with dichloromethane (3*5 mL) and the organic layer was separated, dried over $Na_2SO_4$, filtered, concentrated and purified by prep. TLC (PE:EA 1:1) to give a white solid (31.9 mg, 85.98%).

(II) Synthesis of 3-(cyclopropylmethyl)-1,7-dimethyl-8-(methylsulfonyl)-1H-purine-2,6(3H,7H)-dione To a solution of 3-(cyclopropylmethyl)-1,7-dimethyl-8-(methylthio)-1H-purine-2,6(3H,7H)-dione (30 mg) in MeOH (2 mL) was added oxone (263.5 mg) in $H_2O$ (2 mL). Then the mixture was stirred at RT for 5 h. Then the solvent was removed and extracted with dichloromethane (3*10 mL) and the organic layer was separated, dried over $Na_2SO_4$, filtered, concentrated and purified by prep. TLC (PE:EA 1:1) to obtain 31.4 mg (94.1%) as a white solid. $^1$H-NMR (400 MHz, CDCl$_3$): δ 4.32 (s, 3H), 3.95 (d, J=7.2 Hz, 2H), 3.43 (s, 3H), 3.42 (s, 3H), 1.33-1.30 (m, 1H), 0.52-0.49 (m, 2H), 0.46-0.44 (m, 2H). Mass (m/z): 313.09 [M+H]+.

Compound 103: 3-benzyl-1,7-dimethyl-8-(methyl-sulfonyl)-1H-purine-2,6(3H,7H)-dione

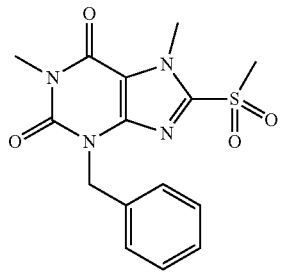 [SMILES: Cn1c(=O)c2c(nc(S(C)(=O)=O)n2C)n(Cc2ccccc2)c1=O]

(I) Synthesis of 3-benzyl-1,7-dimethyl-8-(methyl-thio)-1H-purine-2,6(3H,7H)-dione The compound 1,7-dimethyl-8-(methylthio)-1H-purine-2,6(3H,7H)-dione was synthesized from ethyl 4-amino-1-methyl-1H-imidazole-5-carboxylate in a manner that described for compound 99.

To a solution of 1,7-dimethyl-8-(methylthio)-1H-purine-2,6(3H,7H)-dione (30 mg) and $K_2CO_3$ (21.97 mg) in anhydrous DMF (5 mL) was added (bromomethyl)benzene (27.3 mg) and stirred under nitrogen at RT for 2 h. Then the reaction mixture was poured into water and extracted with dichloromethane (3*5 mL) and the organic layer was separated, dried over $Na_2SO_4$, filtered, concentrated and purified by prep. TLC (PE:EA 1:1) to give a white solid (32.1 mg, 76.6%).

(II) Synthesis of 3-benzyl-1,7-dimethyl-8-(methyl-sulfonyl)-1H-purine-2,6(3H,7H)-dione To a solution of 3-benzyl-1,7-dimethyl-8-(methylthio)-1H-purine-2,6(3H,7H)-dione (30 mg) in MeOH (2 mL) was added oxone (233.1 mg) in $H_2O$ (2 mL). Then the mixture was stirred at RT for 5 h. Then the solvent was removed and extracted with dichloromethane (3*10 mL) and the organic layer was separated, dried over $Na_2SO_4$, filtered, concentrated and purified by prep. TLC (PE:EA 1:1) to obtain 30.9 mg (93.6%) as a white solid. $^1$H-NMR (400 MHz, CDCl$_3$): δ 7.47-7.28 (m, 5H), 5.23 (s, 2H), 4.30 (s, 3H), 3.45 (s, 3H), 3.40 (s, 3H). Mass (m/z): 349.09 [M+H]+.

Compound 104: N-(3-(1,7-dimethyl-8-(methylsulfo-nyl)-2,6-dioxo-1H-purin-3(2H,6H,7H)-yl)propyl)-5-((4R)-2-oxohexahydro-1H-thieno[3,4-d]imidazol-4-yl)pentanamide

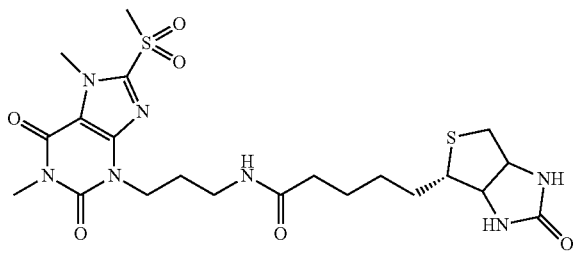 [SMILES: Cn1c(=O)c2c(nc(S(C)(=O)=O)n2C)n(CCCNC(=O)CCCC[C@@H]2SCC3NC(=O)NC32)c1=O]

(I) Synthesis of N-(3-chloropropyl)-5-((4R)-2-oxo-hexahydro-1H-thieno[3,4-d]imidazol-4-yl)pentana-mide To a solution A of 5-((4R)-2-oxohexahydro-1H-thieno[3,4-d]imidazol-4-yl) pentanoicacid (2.0 g, 8.18 mmol) and CDI (2.0 g, 12.33 mmol) in dry DMF/THF (20 mL/5 mL) was added DIEA (1.6 g, 12.37 mmol). The mixture was stirred at 0° C. for 0.5 h. To another solution B of 3-chloropropan-1-amine hydrochloride (1.4 g, 10.76 mmol) in dry DMF (10 mL) was added DIEA (1.6 g, 12.37 mmol) and stirred at RT for 0.5 h. Then the solution B was added to the solution A and stirred at RT for overnight. The solvent was removed and adjusted PH=5. Then the mixture was extracted with DCM (3*50 mL), and the organic layer was washed with NaHCO$_3$ (3*50 mL) and recrystallization from DCM:PE=7:3 to give a white solid (1.82 g, 37.2%). $^1$H-NMR (400 MHz, DMSO-d$_6$): δ7.87-7.83 (m, 1H), 6.42 (s, 1H), 6.35 (s, 1H), 4.31-4.28 (m, 1H), 4.14-4.10 (m, 1H), 3.60 (t, J=6.0 Hz, 2H), 3.16-3.07 (m, 3H), 2.84-2.79 (m, 1H), 2.58-2.55 (m, 1H), 2.05 (t, J=7.6 Hz, 2H), 1.86-1.79 (m, 2H), 1.61-1.57 (m, 1H), 1.51-1.43 (m, 3H), 1.33-1.26 (m, 2H). Mass (m/z): 320.11 [M+H]+.

(II) Synthesis of N-(3-(1,7-dimethyl-8-(methylsulfo-nyl)-2,6-dioxo-1H-purin-3(2H,6H,7H)-yl)propyl)-5-((4R)-2-oxohexahydro-1H-thieno[3,4-d]imidazol-4-yl)pentanamide To a solution of compound 99 (50.0 mg, 0.19 mmol) and $K_2CO_3$ (32.1 mg, 0.23 mmol) in anhydrous DMF (10 mL) was added N-(3-chloropropyl)-5-((4R)-2-oxohexahydro-1H-thieno[3,4-d]imidazol-4-yl)pentanamide (74.2 mg, 0.23 mmol) and stirred under nitrogen at RT for 2 h. Then the reaction mixture was poured into water and extracted with dichloromethane (3*10 mL) and the organic layer was separated, dried over $Na_2SO_4$, filtered, concentrated and purified by pre-HPLC to give a white solid (8.2 mg, 7.8%). $^1$H-NMR (400 MHz, CDCl$_3$): δ 6.71-6.68 (m, 1H), 6.28-6.23 (m, 1H), 5.83-5.79 (m, 1H), 4.59-4.56 (m, 1H), 4.41-4.38 (m, 1H), 4.33 (s, 3H), 4.16 (t, J=6.0 Hz, 2H), 3.41 (s, 6H), 3.22-3.18 (m, 5H), 2.96-2.92 (m, 1H), 2.78-2.74 (m, 1H), 2.30-2.22 (m, 2H), 1.97-1.94 (m, 2H), 1.74-1.69 (m, 2H), 1.51-1.47 (m, 2H). Mass (m/z): 542.18 [M+H]+.

Compound 105: N-(2-(2-(2-(1,7-dimethyl-8-(meth-ylsulfonyl)-2,6-dioxo-1H-purin-3(2H,6H,7H)-yl)ethoxy)ethoxy)ethyl)-5-((4R)-2-oxohexahydro-1H-thieno[3,4-d]imidazol-4-yl)pentanamide

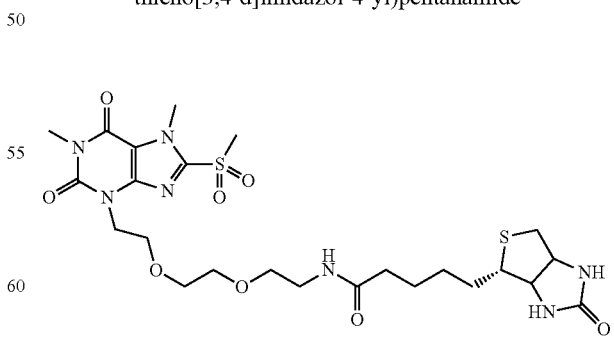

To a solution of compound 99 (50.0 mg, 0.19 mmol) and $K_2CO_3$ (32.1 mg, 0.23 mmol) in anhydrous DMF (10 mL) was added 2-(2-(2-(5-((4R)-2-oxohexahydro-1H-thieno[3,4-d]imidazol-4-yl)pentanamido)ethoxy)ethoxy)ethyl 4-methylbenzenesulfonate (123.1 mg, 0.23 mmol) and stirred under nitrogen at RT overnight. Then the reaction mixture was poured into water and extracted with dichloromethane (3*5 mL) and the organic layer was separated, dried over Na₂SO₄, filtered, concentrated and purified by pre-HPLC to give 15.2 mg (12.77%) as a white solid. ¹H-NMR (400 MHz, CDCl₃): δ 6.45-6.32 (m, 2H), 5.81-5.77 (m, 1H), 4.59-4.55 (m, 1H), 4.40-4.35 (m, 1H), 4.31-4.29 (m, 5H), 3.87-3.82 (m, 2H), 3.63-3.65 (m, 2H), 3.56-3.50 (m, 4H), 3.41-3.40 (m, 8H), 3.21-3.11 (m, 1H), 2.96-2.89 (m, 1H), 2.77-2.73 (m, 1H), 2.28-2.19 (m, 2H), 1.75-1.64 (m, 4H), 1.50-1.40 (m, 2H). Mass (m/z): 616.21 [M+H]+.

Compound 106: 1,7-dimethyl-8-(methylsulfonyl)-3-(prop-2-ynyl)-1H-purine-2,6(3H,7H)-dione

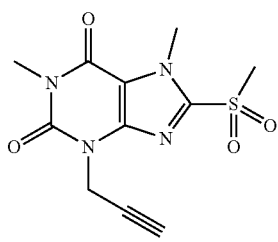 [SMILES: C#CCn1c(=O)n(C)c(=O)c2c1nc(S(C)(=O)=O)n2C]

To a solution of compound 99 (20 mg) and K₂CO₃ (12.8 mg) in anhydrous DMF (5 mL) was added 3-bromoprop-1-yne (10.96 mg) and stirred under nitrogen at RT for 2 h. Then the reaction mixture was poured into water and extracted with dichloromethane (3*5 mL) and the organic layer was separated, dried over Na₂SO₄, filtered, concentrated and purified by prep. TLC (PE:EA 1:1) to obtain 10.3 mg (44.89%) as a white solid. ¹H-NMR (400 MHz, CDCl₃): δ 4.82 (d, J=2.4 Hz, 2H), 4.31 (s, 3H), 3.46 (s, 3H), 3.42 (s, 3H), 2.25 (t, J=2.4 Hz, 1H). Mass (m/z): 297.06 [M+H]+.

Compound 107: 2-(1,7-dimethyl-8-(methylsulfonyl)-2,6-dioxo-1H-purin-3(2H,6H,7H)-yl)acetonitrile

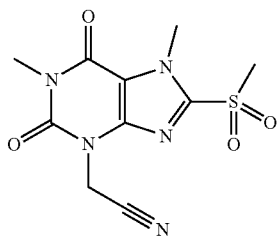 [SMILES: Cn1c(=O)c2c(nc(S(C)(=O)=O)n2C)n(CC#N)c1=O]

To a solution of compound 99 (10 mg) and K₂CO₃ (6.4 mg) in anhydrous DMF (5 mL) was added 2-bromoacetonitrile (5.6 mg) and stirred under nitrogen at RT for 2 h. Then the reaction mixture was poured into water and extracted with dichloromethane (3*5 mL) and the organic layer was separated, dried over Na₂SO₄, filtered, concentrated and purified by prep. TLC (PE:EA 1:1) to obtain 4.7 mg (40.9%) as a white solid. ¹H-NMR (400 MHz, CDCl₃): δ 4.97 (s, 2H), 4.33 (s, 3H), 3.46 (s, 3H), 3.43 (s, 3H). Mass (m/z): 298.05 [M+H]+.

Compound 108: 1,7-dimethyl-8-(methylsulfonyl)-3-(3-phenylprop-2-ynyl)-1H-purine-2,6(3H,7H)-dione

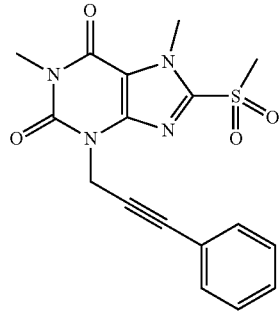 [SMILES: Cn1c(=O)c2c(nc(S(C)(=O)=O)n2C)n(CC#Cc2ccccc2)c1=O]

(I) Synthesis of (3-bromoprop-1-yn-1-yl)benzene

To a solution of 3-phenylprop-2-yn-1-ol (300 mg) in DME was slowly added tribromophosphine (912.7 mg). Then the mixture was stirred under nitrogen at RT for 2 h. Then the reaction mixture was poured into ice and extracted with dichloromethane (3*10 mL) and the organic layer was separated, dried over Na₂SO₄, filtered, concentrated to obtain 323.4 mg (73.2%) as a red oil.

(II) Synthesis of 1,7-dimethyl-8-(methylsulfonyl)-3-(3-phenylprop-2-yn-1-yl)-1H-purine-2,6(3H,7H)-dione To a solution of compound 99 (10 mg) and K₂CO₃ (6.4 mg) in anhydrous DMF (5 mL) was added (3-bromoprop-1-yn-1-yl)benzene (9.1 mg) and stirred under nitrogen at RT for 2 h. Then the reaction mixture was poured into water and extracted with EA (3*5 mL) and the organic layer was separated, dried over Na₂SO₄, filtered, concentrated and purified by prep. TLC (PE:EA 1:1) to obtain 8.3 mg (57.7%) as a white solid. ¹H-NMR (400 MHz, CDCl₃): δ 7.35-7.26 (m, 5H), 5.04 (s, 2H), 4.30 (s, 3H), 3.44 (s, 3H), 3.41 (s, 3H). Mass (m/z): 373.09 [M+H]+.

Compound 109: 3-(3-(3-hydroxyphenyl)prop-2-yn-1-yl)-1,7-dimethyl-8-(methylsulfonyl)-1H-purine-2,6(3H,7H)-dione

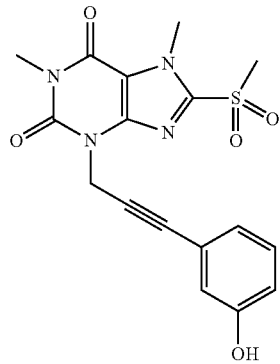

(I) Synthesis of 3-(3-((tetrahydro-2H-pyran-2-yl)oxy)prop-1-yn-1-yl)phenol

To the solution of 2-(prop-2-yn-1-yloxy)tetrahydro-2H-pyran (2.6 g, 18 mmol) in DMF (10 ml) was added 3-iodophenol (1 g, 5 mmol), copper(I) iodide (catalytic), (Ph₃P)₄Pd (catalytic) and TEA (1 g, 9 mmol). Then the mixture was heated to 90° C. under nitrogen protection for 2 hours. The resulting reaction was cooled to room temperature, filtrated and extracted with EA (3*5 ml) and the organic layer was separated, dried over $Na_2SO_4$, filtered, concentrated and purified by column chromatography (PE:EA 10:1) to obtain a yellow oil (1.3 g, 93%). Mass (m/z): 233.3 [M+H]+.

(II) Synthesis of 3-(3-hydroxyprop-1-yn-1-yl)phenol

To a solution of 3-(3-((tetrahydro-2H-pyran-2-yl)oxy)prop-1-yn-1-yl)phenol (1.3 g, 5.6 mmol) in MeOH (15 mL) was added 4-methylbenzenesulfonic acid (193 mg, 1.12 mmol) and stirred at RT for 2 h. Then the reaction mixture was concentrated and extracted with EA (3*5 mL) and the organic layer was separated, dried over $Na_2SO_4$, filtered, concentrated and purified by column chromatography (PE:EA 1:1) to obtain a yellow oil (600 mg, 75%). Mass (m/z): 149.2 [M+H]+.

(III) Synthesis of 3-(3-bromoprop-1-yn-1-yl)phenol

To a solution of 3-(3-hydroxyprop-1-yn-1-yl)phenol (430 mg, 2.8 mmol) in DCM (8 ml) was slowly added triphenylphosphine (1.29 g, 3.2 mmol) and perbromomethane (2.15 g, 5.6 mmol) at 0° C. Then the mixture was stirred at RT for 2 h. Then the reaction mixture was poured into water and extracted with dichloromethane (3*10 mL) and the organic layer was separated, dried over $Na_2SO_4$, filtered, concentrated and purified by column chromatography (PE:EA 5:1) to obtain a yellow oil 600 mg (95%) as a yellow oil. Mass (m/z): 212.06 [M+H]+.

(IV) Synthesis of 3-(3-(3-hydroxyphenyl)prop-2-yn-1-yl)-1,7-dimethyl-8-(methylsulfonyl)-1H-purine-2,6(3H,7H)-dione To a solution of compound 99 (75 mg, 0.3 mmol) and $K_2CO_3$ (70 mg, 0.48 mmol) in anhydrous DMF (3 mL) was added 3-(3-bromoprop-1-yn-1-yl)phenol (60 mg, 0.3 mmol) and stirred under nitrogen at RT for 0.5 h. Then the reaction mixture was poured into water and extracted with EA (3*5 mL) and the organic layer was separated, dried over $Na_2SO_4$, filtered, concentrated and purified by column chromatography (PE:EA 1:1) to obtain 80 mg (87%) as a white solid. ¹H-NMR (400 MHz, DMSO): δ 9.64 (s, 1H), 7.14 (s, 1H), 6.83-6.75 (m, 3H), 4.98 (s, 2H), 4.21 (s, 3H), 3.54 (s, 3H), 3.28 (s, 3H). Mass (m/z): 389.1 [M+H]+.

Compound 110: 3-(3-(3-methoxyphenyl)prop-2-yn-1-yl)-1,7-dimethyl-8-(methylsulfonyl)-1H-purine-2,6(3H,7H)-dione

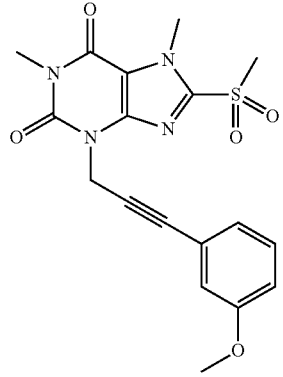 [SMILES: COc1cccc(C#CCn2c(=O)n(C)c(=O)c3c2nc(S(C)(=O)=O)n3C)c1]

To a solution of compound 109 (30 mg, 0.08 mmol) and $K_2CO_3$ (22 mg, 0.16 mmol) in anhydrous DMF (2 mL) was added iodomethane (17 mg, 0.12 mmol) and stirred at RT for 0.5 h.

Then the reaction mixture was poured into water and extracted with EA (3*5 mL) and the organic layer was separated, dried over $Na_2SO_4$, filtered, concentrated and purified by column chromatography (PE:EA 1:1) to obtain 26 mg (83.66%) as a white solid. ¹H-NMR (400 MHz, CDCL3): δ 7.18 (t, J=8.0 Hz, 1H), 7.01-6.98 (m, 1H), 6.93-6.92 (m, 1H), 6.88-6.85 (m, 1H), 5.07 (s, 2H), 4.33 (s, 3H), 3.78 (s, 3H), 3.48 (s, 3H), 3.45 (s, 3H). Mass (m/z): 403.4 [M+H]+.

Compound 111: 1,7-dimethyl-8-(methylsulfonyl)-3-(3-(3-propoxyphenyl)prop-2-yn-1-yl)-1H-purine-2,6(3H,7H)-dione

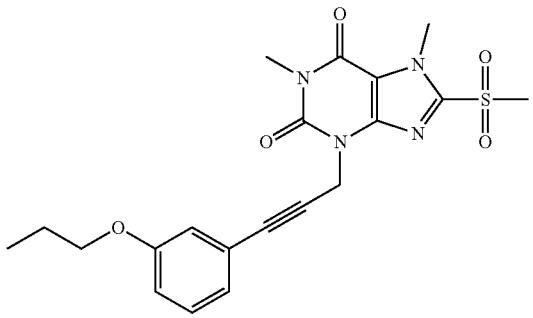 [SMILES: CCCOc1cccc(C#CCn2c(=O)n(C)c(=O)c3c2nc(S(C)(=O)=O)n3C)c1]

To a solution of compound 109 (30 mg, 0.08 mmol) and K2CO3 (22 mg, 0.16 mmol) in anhydrous DMF (2 mL) was added 1-iodopropane (20 mg, 0.12 mmol) and stirred at RT for 0.5 h.

Then the reaction mixture was poured into water and extracted with EA (3*5 mL) and the organic layer was separated, dried over $Na_2SO_4$, filtered, concentrated and purified by column chromatography (PE:EA 5:1) to obtain 25 mg (80.7%) as a white solid. ¹H-NMR (400 MHz, CDCL3): δ 7.16 (t, J=8.0 Hz, 1H), 6.98-6.96 (m, 1H), 6.93-6.92 (m, 1H), 6.87-6.84 (m, 1H), 5.06 (s, 2H), 4.33 (s, 3H), 3.88 (t, J=6.4 Hz, 2H), 3.48 (s, 3H), 3.45 (s, 3H), 1.82-1.73 (m, 2H), 1.01 (t, J=7.2 Hz, 3H). Mass (m/z): 431.4 [M+H]+.

Compound 112: 3-(3-(4-fluorophenyl)prop-2-yn-1-yl)-1,7-dimethyl-8-(methylsulfonyl)-3,7-dihydro-1H-purine-2,6-dione

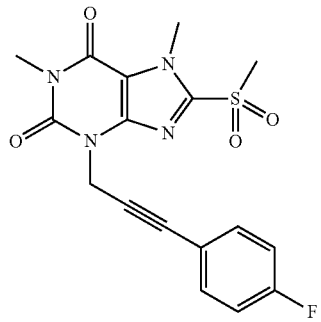 [SMILES: Cn1c(=O)c2c(nc(S(C)(=O)=O)n2C)n(CC#Cc2ccc(F)cc2)c1=O]

The compound was synthesized in a manner that similar to compound 109. ¹H NMR (400 MHz, cdcl₃) δ 7.41-7.36 (m, 2H), 7.01-6.94 (m, 2H), 5.05 (s, 2H), 4.33 (s, 3H), 3.47 (s, 3H), 3.45 (s, 3H). Mass (m/z): 431.4 [M+H]+.

Compound 113: 3-(3-(3-aminophenyl)prop-2-yn-1-yl)-1,7-dimethyl-8-(methylsulfonyl)-3,7-dihydro-1H-purine-2,6-dione

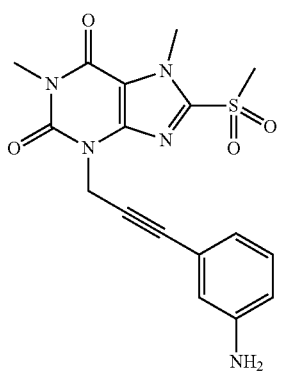 [SMILES: Cn1c(=O)c2c(nc(S(C)(=O)=O)n2C)n(CC#Cc2cccc(N)c2)c1=O]

Compound 113 was prepared from 1,7-dimethyl-8-(methylthio)-1H-purine-2,6 (3H,7H)-dione according to the similar procedure outlined for compound 109 (yellow solid, 8 mg, yield 70%). ¹H NMR (400 MHz, cdcl₃) δ 7.07 (t, J=8.0 Hz, 1H), 6.82 (d, J=8.0 Hz, 1H), 6.76 (s, 1H), 6.67 (d, J=8.0 Hz, 1H), 5.04 (s, 2H), 4.32 (s, 3H), 3.47 (s, 3H), 3.44 (s, 3H). ¹³C NMR (101 MHz, cdcl₃) δ 155.25 (s), 150.38 (s), 146.16 (s), 145.93 (s), 144.89 (s), 129.16 (s), 122.76 (s), 122.32 (s), 118.20 (s), 115.72 (s), 109.89 (s), 83.90 (s), 81.84 (s), 42.74 (s), 33.58 (s), 29.67 (s), 28.35 (s). HRMS-ESI+: [M+H]+ calcd for C17H17N5O4S, 388.1074; found, 388.1074.

Compound 114: 1,7-dimethyl-3-(3-(3-(methylamino)phenyl)prop-2-yn-1-yl)-8-(methylsulfonyl)-3,7-dihydro-1H-purine-2,6-dione

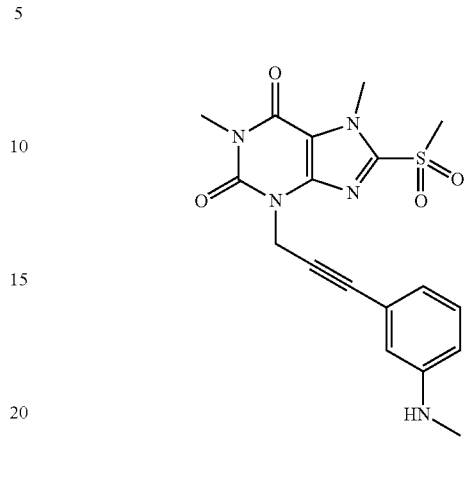

Compound 114 was prepared from 1,7-dimethyl-8-(methylthio)-1H-purine-2,6 (3H,7H)-dione according to the similar procedure outlined for compound 109 (yellow solid, 10 mg, yield 72%). ¹H NMR (400 MHz, dmso) δ 7.04 (t, J=8.0 Hz, 1H), 6.55-6.49 (m, 3H), 5.79 (d, J=5.2 Hz, 1H), 4.97 (s, 2H), 4.21 (s, 3H), 3.55 (s, 3H), 3.28 (s, 3H), 2.62 (d, J=5.2 Hz, 3H). ¹³C NMR (101 MHz, dmso) δ 155.29 (s), 150.42 (s), 150.20 (s), 145.68 (s), 144.85 (s), 129.51 (s), 122.30 (s), 119.08 (s), 114.19 (s), 113.09 (s), 110.06 (s), 84.09 (s), 83.03 (s), 43.65 (s), 34.50 (s), 33.63 (s), 29.88 (s), 28.44 (s). HRMS-ESI+: [M+H]⁺ calcd for C18H19N5O4S, 402.1231; found, 402.1231.

Compound 115: 8-((cyclopropylmethyl)sulfonyl)-1,7-dimethyl-3-(3-phenylprop-2-yn-1-yl)-3,7-dihydro-1H-purine-2,6-dione

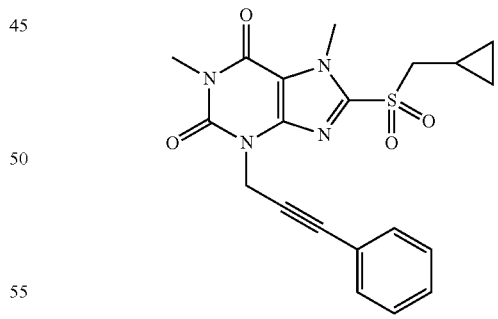

Compound 115 was prepared from 8-((cyclopropylmethyl)thio)-1,7-dimethyl-3,7-dihydro-1H-purine-2,6-dione according to the similar procedure outlined for compound 109 (yellow solid, 6 mg, yield 70%). ¹H-NMR (400 MHz, CDCl₃) δ 7.38-7.36 (m, 2H), 7.30-7.25 (m, 3H), 5.08 (s, 2H), 4.36 (s, 3H), 3.46 (d, J=4.0 Hz, 2H), 3.45 (s, 3H), 1.21-1.15 (m, 1H), 0.62 (q, J=4.0 Hz, 2H), 0.31 (q, J=4.0 Hz, 2H). Mass (m/z): 413.46 [M+H]+.

Compound 116: 8-((cyclopropylmethyl)sulfonyl)-3-(3-(3-hydroxyphenyl)prop-2-yn-1-yl)-1,7-dimethyl-3,7-dihydro-1H-purine-2,6-dione

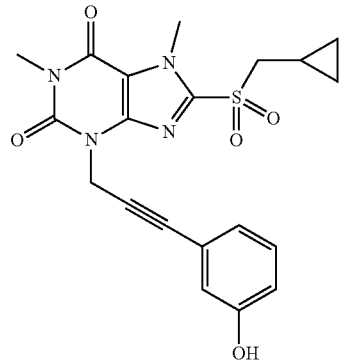

Compound 16 was prepared from 8-((cyclopropylmethyl)thio)-1,7-dimethyl-3,7-dihydro-1H-purine-2,6-dione according to the similar procedure outlined for compound 109 (yellow solid, 22 mg, yield 80%). $^1$H-NMR (400 MHz, CDCl$_3$) δ 7.13 (t, J=8.0 Hz, 1H), 6.94 (d, J=8.0 Hz, 1H), 6.85 (s, 1H), 6.79 (d, J=8.0 Hz, 1H), 5.06 (s, 2H), 4.36 (s, 3H), 3.45 (d, J=4.0 Hz, 2H), 3.44 (s, 3H), 1.19-1.17 (m, 1H), 0.63 (q, J=4.0 Hz, 2H), 0.31 (q, J=4.0 Hz, 2H). Mass (m/z): 429.46 [M+H]+.

Compound 117: 8-((cyclopropylmethyl)sulfonyl)-3-(3-(3-methoxyphenyl)prop-2-yn-1-yl)-1,7-dimethyl-3,7-dihydro-1H-purine-2,6-dione

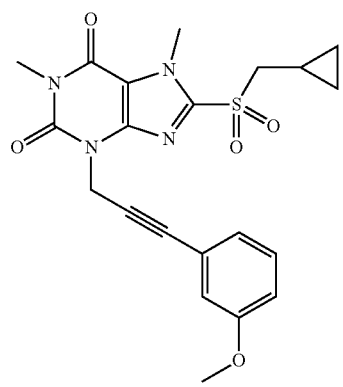 [SMILES: COc1cccc(C#CCn2c(=O)n(C)c(=O)c3c2nc(S(=O)(=O)CC2CC2)n3C)c1]

Compound 117 was prepared from 8-((cyclopropylmethyl)thio)-1,7-dimethyl-3,7-dihydro-1H-purine-2,6-dione according to the similar procedure outlined for compound 109 (white solid, 8 mg, yield 73%). Mass (m/z): 443.49 [M+H]+.

Compound 118: 8-((cyclopropylmethyl)sulfonyl)-3-(3-(3-fluorophenyl)prop-2-yn-1-yl)-1,7-dimethyl-3,7-dihydro-1H-purine-2,6-dione

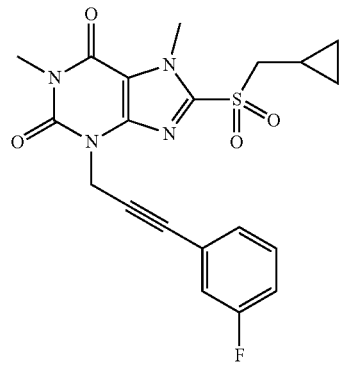

Compound 118 was prepared from 8-((cyclopropylmethyl)thio)-1,7-dimethyl-3,7-dihydro-1H-purine-2,6-dione according to the similar procedure outlined for compound 109 (white solid, 10 mg). Mass (m/z): 431.45 [M+H]+.

Compound 119: 3-(3-(3-chlorophenyl)prop-2-yn-1-yl)-8-((cyclopropylmethyl)sulfonyl)-1,7-dimethyl-3,7-dihydro-1H-purine-2,6-dione

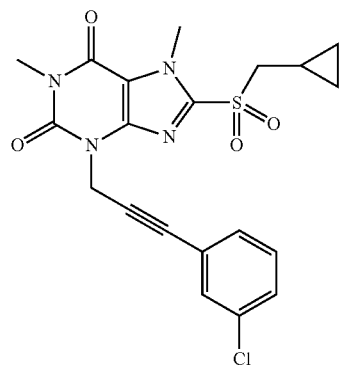

Compound 119 was prepared from 8-((cyclopropylmethyl)thio)-1,7-dimethyl-3,7-dihydro-1H-purine-2,6-dione according to the similar procedure outlined for compound 109 (white solid, 16 mg). Mass (m/z): 447.91 [M+H]+.

Compound 120: 8-((cyclopropylmethyl)sulfonyl)-3-(3-(4-fluorophenyl)prop-2-yn-1-yl)-1,7-dimethyl-3,7-dihydro-1H-purine-2,6-dione

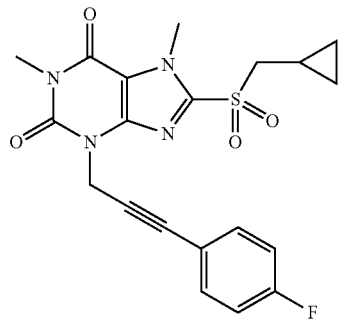

Compound 120 was prepared from 8-((cyclopropylmethyl)thio)-1,7-dimethyl-3,7-dihydro-1H-purine-2,6-dione according to the similar procedure outlined for compound 109 (white solid, 22 mg, yield 85%). $^1$H-NMR (400 MHz, CDCl$_3$) δ 7.39-7.32 (m, 2H), 7.00-6.92 (m, 2H), 5.06 (s, 2H), 4.36 (s, 3H), 3.45 (d, J=6.4 Hz, 2H), 3.44 (s, 3H), 1.21-1.4 (m, 1H), 0.62 (q, J=6.4 Hz, 2H), 0.30 (q, J=6.4 Hz, 2H). Mass (m/z): 431.45 [M+H]+.

Compound 121: 3-(3-(4-chlorophenyl)prop-2-yn-1-yl)-8-((cyclopropylmethyl)sulfonyl)-1,7-dimethyl-3,7-dihydro-1H-purine-2,6-dione

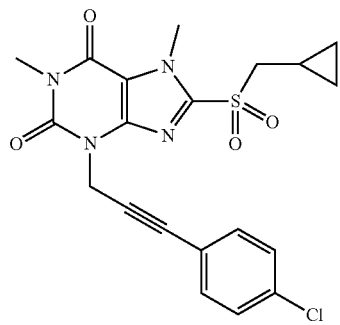

Compound 121 was prepared from 8-((cyclopropylmethyl)thio)-1,7-dimethyl-3,7-dihydro-1H-purine-2,6-dione according to the similar procedure outlined for compound 109 (white solid, 16 mg). $^1$H-NMR (400 MHz, CDCl$_3$) δ 7.32-7.29 (m, 2H), 7.25-7.23 (m, 2H), 5.06 (s, 2H), 4.36 (s, 3H), 3.45 (d, J=6.8 Hz, 2H), 3.44 (s, 3H), 1.21-1.14 (m, 1H), 0.62 (q, J=6.4 Hz, 2H), 0.30 (q, J=6.4 Hz, 2H). Mass (m/z): 447.91 [M+H]+.

Compound 122: 3-(3-(4-bromophenyl)prop-2-yn-1-yl)-8-((cyclopropylmethyl)sulfonyl)-1,7-dimethyl-3,7-dihydro-1H-purine-2,6-dione

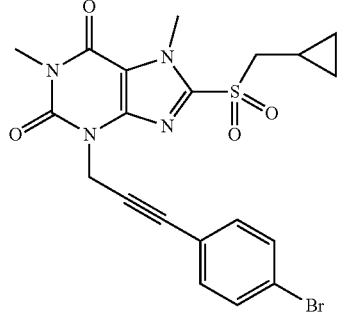 [SMILES: Cn1c(=O)c2c(nc(S(=O)(=O)CC3CC3)n2C)n(CC#Cc2ccc(Cl)cc2)c1=O]

Compound 122 was prepared from 8-((cyclopropylmethyl)thio)-1,7-dimethyl-3,7-dihydro-1H-purine-2,6-dione according to the similar procedure outlined for TC013172 (white solid, 22 mg). $^1$H-NMR (400 MHz, CDCl$_3$) δ 7.41-7.39 (m, 2H), 7.24-7.22 (m, 2H), 5.05 (s, 2H), 4.35 (s, 3H), 3.45 (d, J=5.6 Hz, 2H), 3.44 (s, 3H), 1.21-1.13 (m, 1H), 0.62 (q, J=5.6 Hz, 2H), 0.30 (q, J=5.6 Hz, 2H). Mass (m/z): 492.36 [M+H]+.

Compound 123: tert-butyl(3-(3-(8-((cyclopropylmethyl)sulfonyl)-1,7-dimethyl-2,6-dioxo-1,2,6,7-tetrahydro-3H-purin-3-yl)prop-1-yn-1-yl)phenyl)carbamate

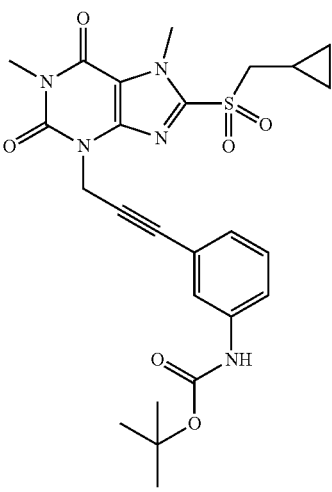 [SMILES: Cn1c(=O)c2c(nc(S(=O)(=O)CC3CC3)n2C)n(CC#Cc2cccc(NC(=O)OC(C)(C)C)c2)c1=O]

Compound 123 was prepared from 8-((cyclopropylmethyl)thio)-1,7-dimethyl-3,7-dihydro-1H-purine-2,6-dione according to the similar procedure outlined for compound 109 (yellow solid, 10 mg). Mass (m/z): 528.59 [M+H]+.

Compound 124: 3-(3-(3-aminophenyl)prop-2-yn-1-yl)-8-((cyclopropylmethyl)sulfonyl)-1,7-dimethyl-3,7-dihydro-1H-purine-2,6-dione Compound 126: 8-((cyclopropylmethyl)sulfonyl)-1,7-dimethyl-3-(3-(2-(methylamino)pyridin-4-yl)prop-2-yn-1-yl)-3,7-dihydro-1H-purine-2,6-dione

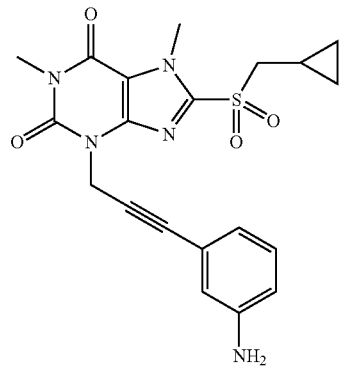

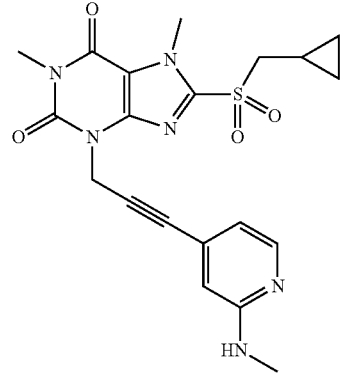 [SMILES: CNc1cc(C#CCn2c(=O)n(C)c(=O)c3c2nc(S(=O)(=O)CC2CC2)n3C)ccn1]

Compound 124 was prepared from 8-((cyclopropylmethyl)thio)-1,7-dimethyl-3,7-dihydro-1H-purine-2,6-dione according to the similar procedure outlined for compound 109 (yellow solid, 13 mg). $^1$H-NMR (400 MHz, CDCl$_3$) δ 7.72-7.26 (m, 1H), 7.03 (t, J=8.0 Hz, 1H), 6.76-6.60 (m, 2H), 5.05 (s, 2H), 4.33 (s, 3H), 3.45 (d, J=8.4 Hz, 2H), 3.44 (s, 3H), 1.21-1.13 (m, 1H), 0.62 (q, J=5.6 Hz, 2H), 0.30 (q, J=5.6 Hz, 2H). Mass (m/z): 428.48 [M+H]+.

Compound 126 was prepared from 8-((cyclopropylmethyl)thio)-1,7-dimethyl-3,7-dihydro-1H-purine-2,6-dione according to the similar procedure outlined for compound 109 (white solid, 12 mg). $^1$H-NMR (400 MHz, CDCl$_3$) δ 7.91 (d, J=5.2 Hz, 1H), 6.53 (d, J=5.2 Hz, 1H), 6.43 (s, 1H), 5.08 (s, 2H), 4.37 (s, 3H), 3.45 (d, J=7.2 Hz, 2H), 3.44 (s, 3H), 2.88 (d, J=3.6 Hz, 3H), 1.20-1.15 (m, 1H), 0.62 (q, J=5.6 Hz, 2H), 0.30 (q, J=5.6 Hz, 2H). Mass (m/z): 443.49 [M+H]+.

Compound 125: 8-((cyclopropylmethyl)sulfonyl)-1,7-dimethyl-3-(3-(3-nitrophenyl)prop-2-yn-1-yl)-3,7-dihydro-1H-purine-2,6-dione Compound 127: 8-((2,5-dimethoxybenzyl)sulfonyl)-1,7-dimethyl-3-(3-(2-(methylamino)pyridin-4-yl)prop-2-yn-1-yl)-3,7-dihydro-1H-purine-2,6-dione

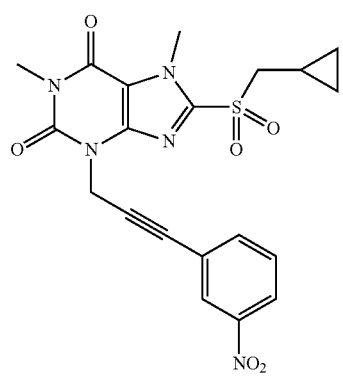

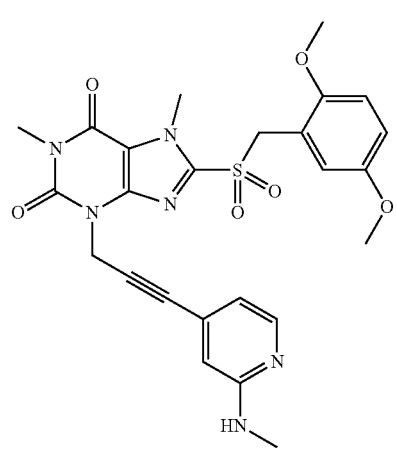 [SMILES: CNc1cc(C#CCn2c(=O)n(C)c(=O)c3c2nc(S(=O)(=O)Cc2cc(OC)ccc2OC)n3C)ccn1]

Compound 125 was prepared from 8-((cyclopropylmethyl)thio)-1,7-dimethyl-3,7-dihydro-1H-purine-2,6-dione according to the similar procedure outlined for compound 109 (yellow solid, 11 mg). $^1$H-NMR (400 MHz, CDCl$_3$) δ 8.21 (s, 1H), 8.16-8.14 (m, 1H), 7.7-7.68 (m, 1H), 7.47 (t, J=8.0 Hz, 1H), 5.10 (s, 2H), 4.37 (s, 3H), 3.46 (d, J=8.0 Hz, 2H), 3.45 (s, 3H), 1.21-1.13 (m, 1H), 0.62 (q, J=5.6 Hz, 2H), 0.30 (q, J=5.6 Hz, 2H). Mass (m/z): 458.46 [M+H]+.

Compound 127 was prepared from 8-((cyclopropylmethyl)thio)-1,7-dimethyl-3,7-dihydro-1H-purine-2,6-dione according to the similar procedure outlined for compound 109 (white solid, 5 mg). Mass (m/z): 539.58 [M+H]+.

Compound 128: 8-((2,5-dimethoxybenzyl)sulfinyl)-1,7-dimethyl-3-(3-(2-(methylamino)pyridin-4-yl)prop-2-yn-1-yl)-3,7-dihydro-1H-purine-2,6-dione

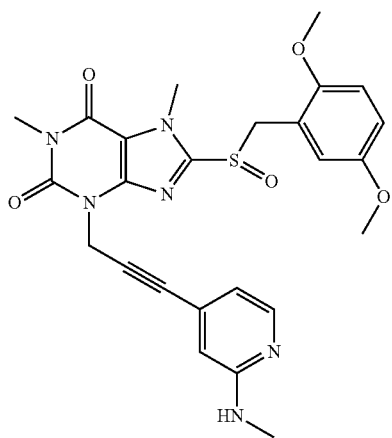 [SMILES: CNc1cc(C#CCn2c(=O)n(C)c(=O)c3c2nc(S(=O)Cc2cc(OC)ccc2OC)n3C)ccn1]

Compound 128 was prepared from 8-((cyclopropylmethyl)thio)-1,7-dimethyl-3,7-dihydro-1H-purine-2,6-dione according to the similar procedure outlined for compound 109 (white solid, 3 mg). Mass (m/z): 523.58 [M+H]+.

Compound 129: 3-(2,5-dimethoxybenzyl)-8-(2,5-dimethoxybenzylsulfonyl)-1,7-dimethyl-1H-purine-2,6(3H,7H)-dione

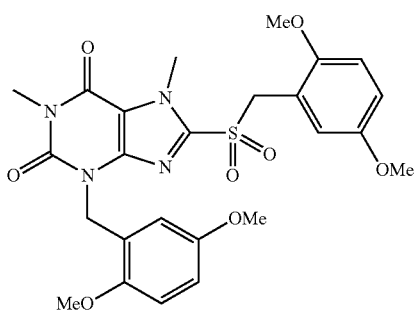 [SMILES: COc1ccc(OC)c(Cn2c(=O)n(C)c(=O)c3c2nc(S(=O)(=O)Cc2cc(OC)ccc2OC)n3C)c1]

(I) Synthesis of 2-(bromomethyl)-1,4-dimethoxybenzene

To a solution of 1,4-dimethoxy-2-methylbenzene (500 mg, 3.29 mmol) in CCl$_4$ (10 ml) was slowly added NBS (585 mg, 3.29 mmol) and AIBN (150 mg). Then the mixture was heated to 80° C. for 1 h. The mixture was filtered and the filtrate was concentrated to produce a residue. The residue was diluted and extracted with EA (3*10 mL) and concentrated to afford a yellow solid.

(II) Synthesis of 3-(2,5-dimethoxybenzyl)-8-((2,5-dimethoxybenzyl)thio)-1,7-dimethyl-1H-purine-2,6(3H,7H)-dione To a solution of 8-mercapto-1,3,7-trimethyl-1H-purine-2,6(3H,7H)-dione (30.0 mg, 0.14 mmol) and K$_2$CO$_3$ (16 mg) in anhydrous DMF (5 mL) was added 2-(bromomethyl)-1,4-dimethoxybenzene (40 mg, 0.18 mmol) and stirred under nitrogen at RT for overnight. Then the reaction mixture was poured into water and extracted with dichloromethane (3*10 mL) and the organic layer was separated, dried over Na$_2$SO$_4$, filtered, concentrated and purified by column chromatography (PE:EA 1:1) to give a white solid (83 mg).

(III) Synthesis of 3-(2,5-dimethoxybenzyl)-8-((2,5-dimethoxybenzyl)sulfonyl)-1,7-dimethyl-1H-purine-2,6(3H,7H)-dione To a solution of 3-(2,5-dimethoxybenzyl)-8-((2,5-dimethoxybenzyl)thio)-1,7-dimethyl-1H-purine-2,6(3H,7H)-dione (30 mg, 0.06 mmol) in DCM (2 mL) was added m-CPBA (30 mg, 0.18 mmol). Then the mixture was stirred at RT for 2 h. Then the solvent was removed and extracted with EA (3*10 mL) and the organic layer was separated, dried over Na$_2$SO$_4$, filtered, concentrated and purified by silica gel column chromatography (PE:EA 5:1) to afford 25 mg (81%) as a white solid. $^1$H-NMR (400 MHz, CDCl$_3$): δ6.96 (d, J=8.8 Hz, 1H), 6.94-6.91 (m, 1H), 6.86 (d, J=3.6 Hz, 2H), 6.84-6.81 (m, 1H), 6.42 (d, J=3.2 Hz, 1H), 5.06 (s, 2H), 4.78 (s, 2H), 3.80 (d, J=2.0 Hz, 6H), 3.66 (s, 3H), 3.63 (s, 3H), 3.41 (s, 3H), 3.28 (s, 3H). Mass (m/z): 545.5 [M+H]+.

Compound 130: 1,7-dimethyl-8-(methylsulfonyl)-3-((1-phenyl-1H-1,2,3-triazol-5-yl)methyl)-3,7-dihydro-1H-purine-2,6-dione

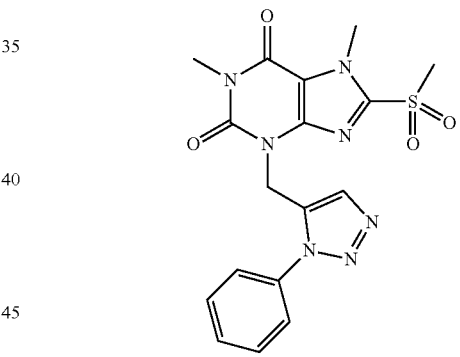

To the solution of 1,7-dimethyl-8-(methylthio)-3-(prop-2-yn-1-yl)-3,7-dihydro-1H-purine-2,6-dione (20 mg, 0.08 mmol) in DMF (1 ml) was added azidobenzene (15 mg), copper(I) iodide (catalytic) and TEA (catalytic). Then the mixture was stirred at room temperature under nitrogen protection for 2 hours. The resulting reaction was extracted with DCM (3*5 ml) and the organic layer was separated, dried over Na$_2$SO$_4$, filtered, concentrated and purified by column chromatography (DCM:Methanol 10:1) to obtain white solid. The intermediate (15 mg) was dissolved in the mixture of THF (1 ml) and H$_2$O (1 ml) with oxone (50 mg). Then the mixture was stirred at room temperature overnight. The resulting reaction was extracted with DCM (3*5 ml) and the organic layer was separated, dried over Na$_2$SO$_4$, filtered, concentrated and purified by prep. TLC (DCM:Methanol 10:1) to obtain white solid (5 mg). $^1$H-NMR (400 MHz, CDCl$_3$) δ 8.13 (s, 1H), 7.70-7.68 (m, 2H), 7.53-7.48 (m, 2H), 7.44-7.42 (m, 1H), 5.44 (s, 2H), 4.29 (s, 3H), 3.48 (s, 3H), 3.40 (s, 3H). Mass (m/z): 416.43[M+H]+.

Compound 131: 1,7-dimethyl-8-(methylsulfonyl)-3-(thiophen-2-ylmethyl)-1H-purine-2,6(3H,7H)-dione

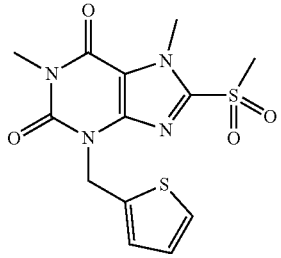 [SMILES: Cn1c(=O)c2c(nc(S(C)(=O)=O)n2C)n(Cc2cccs2)c1=O]

(I) Synthesis of 2-(bromomethyl)thiophene

To a solution of thiophen-2-ylmethanol (1 g) in DME was slowly added tribromophosphine (3.5 g). Then the mixture was stirred under nitrogen at RT for 2 h. Then the reaction mixture was poured into ice and extracted with dichloromethane (3*10 mL) and the organic layer was separated, dried over $Na_2SO_4$, filtered, concentrated to obtain 1.04 g (67.1%) as a red oil.

(II) Synthesis of 1,7-dimethyl-8-(methylsulfonyl)-3-(thiophen-2-ylmethyl)-1H-purine-2,6(3H,7H)-dione To a solution of compound 99 (10 mg) and $K_2CO_3$ (6.5 mg) in anhydrous DMF (5 mL) was added 2-(bromomethyl)thiophene (8.3 mg) and stirred under nitrogen at RT for 2 h. Then the reaction mixture was poured into water and extracted with EA (3*5 mL) and the organic layer was separated, dried over $Na_2SO_4$, filtered, concentrated and purified by prep. TLC (PE:EA 1:1) to obtain 5.4 mg (39.5%) as a white solid. $^1$H-NMR (400 MHz, $CDCl_3$): δ 7.26-7.21 (m, 2H), 6.95-6.92 (m, 1H), 5.40 (s, 2H), 4.29 (s, 3H), 3.49 (s, 3H), 3.40 (s, 3H). Mass (m/z): 355.05 [M+H]+.

Compound 132: 4-(1,7-dimethyl-8-(methylsulfonyl)-2,6-dioxo-1H-purin-3(2H,6H,7H)-yl)-N-ethyl-but-2-ynamide

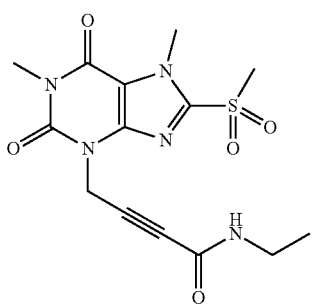 [SMILES: CCNC(=O)C#CCn1c(=O)n(C)c(=O)c2c1nc(S(C)(=O)=O)n2C]

To a solution of compound 99 (10 mg) and $K_2CO_3$ (6.5 mg) in anhydrous DMF (5 mL) was added 4-bromo-N-ethylbut-2-ynamide (8.8 mg) and stirred under nitrogen at RT for 2 h. Then the reaction mixture was poured into water and extracted with EA (3*5 mL) and the organic layer was separated, dried over $Na_2SO_4$, filtered, concentrated and purified by prep. TLC (PE:EA 1:1) to obtain 5.2 mg (36.6%) as a white solid. $^1$H-NMR (400 MHz, $CDCl_3$): δ 5.83 (s, 1H), 4.94 (s, 2H), 4.32 (s, 3H), 3.45 (s, 3H), 3.42 (s, 3H), 3.30 (q, J=7.6 Hz, 2H), 1.14 (t, J=7.6 Hz, 3H). Mass (m/z): 368.10 [M+H]+.

Compound 133: 8-((cyclopropylmethyl)sulfonyl)-3-(2-fluorobenzyl)-1,7-dimethyl-1H-purine-2,6(3H,7H)-dione

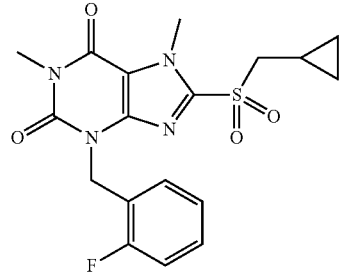

(I) Synthesis of 1,7-dimethyl-1H-purine-2,6(3H,7H)-dione

To a solution of ethyl 4-amino-1-methyl-1H-imidazole-5-carboxylate (2.0 g, 11.83 mmol) and ethyl methylcarbamate (2.92 g, 28.32 mmol) in anhydrous THF (2 mL) was reacted at 75° C. under nitrogen for 30 min. Then to the mixture was added potassium 2-methylpropan-2-olate (1.98 g, 17.64 mmol) and reacted at 75° C. for overnight. Then the solvent was removed and extracted with dichloromethane (3*50 mL) and the organic layer was separated, dried over $Na_2SO_4$, filtered, concentrated and purified by chromatography on silica gel (DCM:MeOH=20:1) to give a white solid (1.2 g, 56.33%). $^1$H-NMR (400 MHz, DMSO-$d_6$): δ 11.82 (s, 1H), 7.90 (s, 1H), 3.84 (s, 3H), 3.16 (s, 3H). Mass (m/z): 181.06[M+H]+.

(II) Synthesis of 8-chloro-1,7-dimethyl-1H-purine-2,6(3H,7H)-dione

To a solution of 1,7-dimethyl-1H-purine-2,6(3H,7H)-dione (0.53 g, 2.94 mmol) in anhydrous THF (10 mL) was added NCS (0.59 g, 4.36 mmol) and stirred under nitrogen at RT for overnight. Then the solvent was removed and extracted with dichloromethane (3*20 mL) and the organic layer was separated, dried over Na2SO4, filtered, concentrated to give a white solid (0.45 g). Mass (m/z): 215.03 [M+H]+.

(III) Synthesis of 8-mercapto-1,7-dimethyl-1H-purine-2,6(3H,7H)-dione

To a solution of 8-chloro-1,7-dimethyl-1H-purine-2,6(3H,7H)-dione (500 mg, 2.2 mmol) in anhydrous DMF was added sodium hydrosulfide (370 mg, 6.5 mmol) and heated to 100° C. for 12 hours. The reaction mixture changed pH to 5 and poured slowly into water (10 ml), a yellow precipitate was obtained and filtrated to finally got the crude product. $^1$H-NMR (400 MHz, DMSO-$d_6$): δ 3.68 (s, 3H), 3.38 (s, 3H), 3.20 (s, 3H). Mass (m/z): 227.2[M+H]+.

(IV) Synthesis of 8-((cyclopropylmethyl)thio)-1,7-dimethyl-1H-purine-2,6(3H,7H)-dione To a solution of 8-mercapto-1,7-dimethyl-1H-purine-2,6 (3H,7H)-dione (1 g, 4.7 mmol) and K₂CO₃ (1.32 g, 9.4 mmol) in anhydrous DMF (15 mL) was added (bromomethyl)cyclopropane (580 mg, 4.24 mmol) and stirred under nitrogen at RT for 2 h. Then the reaction mixture was poured into water and extracted with EA (3*10 mL) and the organic layer was separated, dried over Na₂SO₄, filtered, concentrated and purified by column chromatography (PE:EA 1:1) to obtain 1.06 g (88.8%) as a white solid. Mass (m/z): 267.3 [M+H]+.

(V) Synthesis of 8-((cyclopropylmethyl)sulfonyl)-1,7-dimethyl-1H-purine-2,6(3H,7H)-dione To a solution of 8-((cyclopropylmethyl)thio)-1,7-dimethyl-1H-purine-2,6(3H,7H)-dione (1 g, 3.76 mmol) in DCM (10 mL) was added m-CPBA (1.95 g, 11.3 mmol). Then the mixture was stirred at RT for 2 h. Then the solvent was removed and extracted with dichloromethane (3*10 mL) and the organic layer was separated, dried over Na₂SO₄, filtered, concentrated and purified by column chromatography (PE:EA 1:1) to give a white solid (800 mg, 71.4%). Mass (m/z): 299.32 [M+H]+.

(VI) Synthesis of 3-(2-chlorobenzyl)-8-((cyclopropylmethyl)sulfonyl)-1,7-dimethyl-1H-purine-2,6(3H,7H)-dione To a solution of 8-((cyclopropylmethyl)sulfonyl)-1,7-dimethyl-1H-purine-2,6(3H,7H)-dione (20 mg, 0.068 mmol) and K₂CO₃ (19 mg, 0.134 mmol) in anhydrous DMF (2 mL) was added 1-(bromomethyl)-2-fluorobenzene (21 mg, 0.101 mmol) and stirred under nitrogen at RT for 0.5 h. Then the reaction mixture was poured into water and extracted with EA (3*5 mL) and the organic layer was separated, dried over Na₂SO₄, filtered, concentrated and purified by column chromatography (PE:EA 5:1) to finally get 16 mg (60%) as a white solid. ¹H-NMR (400 MHz, CDCl₃): δ 7.35-7.30 (m, 2H), 7.08-7.00 (m, 2H), 5.34 (s, 2H), 4.34 (s, 3H), 3.41 (d, J=7.2 Hz, 5H), 1.11-1.06 (m, 1H), 0.64-0.59 (m, 2H), 0.25-0.21 (m, 2H). Mass (m/z): 407.43 [M+H]+.

Compound 134: 8-((cyclopropylmethyl)sulfonyl)-3-(3-fluorobenzyl)-1,7-dimethyl-1H-purine-2,6(3H,7H)-dione

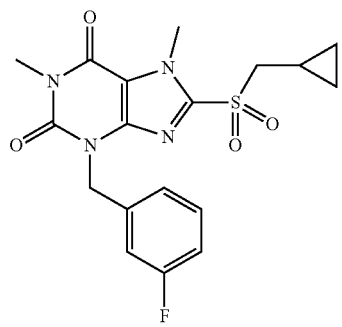

The compound was synthesized in a manner similar to that described for compound 133 to finally get 18 mg (66.7%) as a white solid. ¹H-NMR (400 MHz, CDCl₃): δ 7.30-7.28 (m, 1H), 7.25 (s, 1H), 7.18-7.15 (m, 1H), 6.71-6.93 (m, 1H), 5.24 (s, 2H), 4.34 (s, 3H), 3.43-3.40 (m, 5H), 1.15-1.10 (m, 1H), 0.66-0.62 (m, 2H), 0.25-0.21 (m, 2H). Mass (m/z): 407.43 [M+H]+.

Compound 135: 8-((cyclopropylmethyl)sulfonyl)-3-(4-fluorobenzyl)-1,7-dimethyl-1H-purine-2,6(3H,7H)-dione

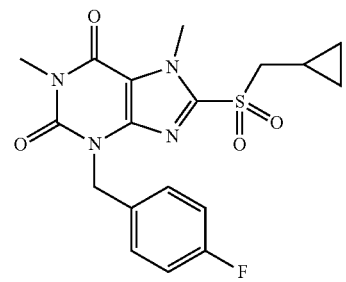 [SMILES: Cn1c(=O)c2c(nc(S(=O)(=O)CC3CC3)n2C)n(Cc2ccc(F)cc2)c1=O]

The compound was synthesized in a manner similar to that described for compound 133 to finally get 16 mg (59.3%) as a white solid. ¹H-NMR (400 MHz, CDCl₃): δ 7.49-7.45 (m, 2H), 7.00-6.96 (m, 2H), 5.21 (s, 2H), 4.34 (s, 3H), 3.42 (d, J=7.2 Hz, 5H), 1.17-1.07 (m, 1H), 0.67-0.62 (m, 2H), 0.27-0.23 (m, 2H). Mass (m/z): 407.43 [M+H]+.

Compound 136: 3-(2-chlorobenzyl)-8-((cyclopropylmethyl)sulfonyl)-1,7-dimethyl-1H-purine-2,6(3H,7H)-dione

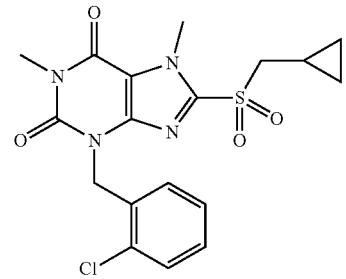 [SMILES: Cn1c(=O)c2c(nc(S(=O)(=O)CC3CC3)n2C)n(Cc2ccccc2Cl)c1=O]

The compound was synthesized in a manner similar to that described for compound 133 to finally obtain 27 mg (96.4%) as a white solid. ¹H-NMR (400 MHz, CDCl₃): δ 7.38 (dd, J=1.6 Hz, J=7.6 Hz, 1H), 7.23-7.14 (m, 2H), 7.05 (dd, J=1.6 Hz, J=7.6 Hz, 1H), 5.39 (s, 2H), 4.35 (s, 3H), 3.45 (s, 3H), 3.37 (d, J=7.2 Hz, 2H), 1.11-1.03 (m, 1H), 0.61-0.56 (m, 2H), 0.22-0.19 (m, 2H). Mass (m/z): 423.89 [M+H]+.

Compound 137: 3-(3-chlorobenzyl)-8-((cyclopropylmethyl)sulfonyl)-1,7-dimethyl-1H-purine-2,6(3H,7H)-dione

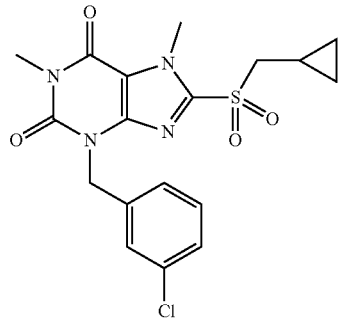

The compound was synthesized in a manner similar to that described for compound 133 to finally get 20 mg (71.4%) as a white solid. $^1$H-NMR (400 MHz, CDCl$_3$): δ 7.46 (s, 1H), 7.37-7.35 (m, 1H), 7.25-7.23 (m, 2H), 5.22 (s, 2H), 4.34 (s, 3H), 3.42 (t, J=4.0 Hz, J=3.2 Hz, 5H), 1.16-1.08 (m, 1H), 0.65-0.61 (m, 2H), 0.25-0.21 (m, 2H). Mass (m/z): 423.89 [M+H]+.

Compound 138: 3-(4-chlorobenzyl)-8-((cyclopropylmethyl)sulfonyl)-1,7-dimethyl-1H-purine-2,6(3H,7H)-dione

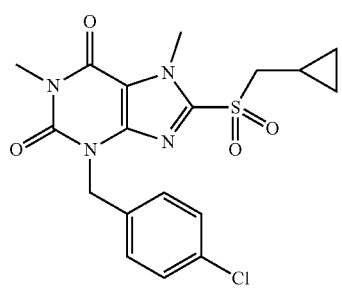 [SMILES: Cn1c(=O)c2c(nc(S(=O)(=O)CC3CC3)n2C)n(Cc2ccc(Cl)cc2)c1=O]

The compound was synthesized in a manner similar to that described for compound 133 to finally get 16 mg (58%) as a white solid. $^1$H-NMR (400 MHz, CDCl$_3$): δ 7.42-7.39 (m, 2H), 7.28-7.27 (m, 1H), 7.25 (d, J=2.4 Hz, 1H), 5.21 (s, 2H), 4.34 (s, 3H), 3.41 (s, 3H), 3.40 (d, J=7.6 Hz, 2H) 1.15-1.07 (m, 1H), 0.67-0.62 (m, 2H), 0.26-0.22 (m, 2H). Mass (m/z): 423.89 [M+H]+.

Compound 139: 3-(2-bromobenzyl)-8-((cyclopropylmethyl)sulfonyl)-1,7-dimethyl-1H-purine-2,6(3H,7H)-dione

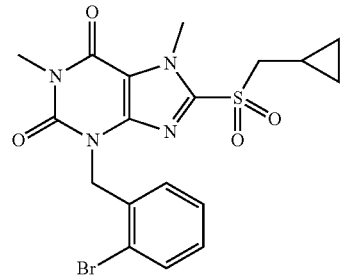

The compound was synthesized in a manner similar to that described for compound 133 to finally get 25 mg (80.6%) as a white solid. $^1$H-NMR (400 MHz, CDCl$_3$): δ 7.57 (dd, J=1.2 Hz, J=8.0 Hz, 1H), 7.22-7.18 (m, 1H), 7.15-7.10 (m, 1H), 6.98 (dd, J=1.6 Hz, J=7.6 Hz, 1H), 5.37 (s, 2H), 4.35 (s, 3H), 3.45 (s, 3H), 3.38 (d, J=7.2 Hz, 2H), 1.10-1.03 (m, 1H), 0.60-0.54 (m, 2H), 0.22-0.12 (m, 2H). Mass (m/z): 468.34 [M+H]+.

Compound 140: 3-(3-bromobenzyl)-8-((cyclopropylmethyl)sulfonyl)-1,7-dimethyl-1H-purine-2,6(3H,7H)-dione

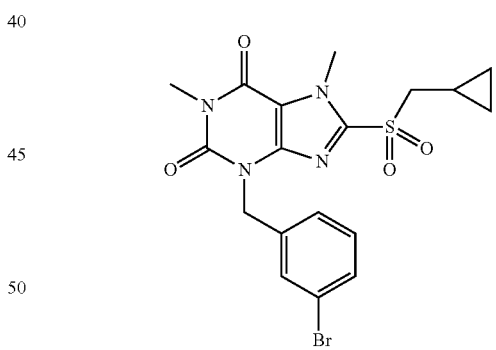

The compound was synthesized in a manner similar to that described for compound 133 to finally get 22 mg (71%) as a white solid. $^1$H-NMR (400 MHz, CDCl$_3$): δ 7.63 (s, 1H), 7.42-7.39 (m, 2H), 7.20-7.16 (m, 1H), 5.21 (s, 2H), 4.34 (s, 3H), 3.42 (d, J=6.0 Hz, 5H), 1.17-1.07 (m, 1H), 0.66-0.61 (m, 2H), 0.26-0.22 (m, 2H). Mass (m/z): 468.34 [M+H]+.

Compound 141: 3-(4-bromobenzyl)-8-((cyclopropylmethyl)sulfonyl)-1,7-dimethyl-1H-purine-2,6(3H,7H)-dione

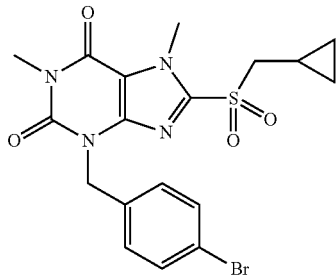

The compound was synthesized in a manner similar to that described for compound 133 to finally get 25 mg (80.6%) as a white solid. $^1$H-NMR (400 MHz, CDCl$_3$): δ 7.43-7.41 (m, 2H), 7.35-7.33 (m, 2H), 5.19 (s, 2H), 4.34 (s, 3H), 3.40 (d, J=6.0 Hz, 5H), 1.16-1.06 (m, 1H), 0.67-0.62 (m, 2H), 0.26-0.22 (m, 2H). Mass (m/z): 468.34 [M+H]+.

Compound 142: 8-((cyclopropylmethyl)sulfonyl)-1,7-dimethyl-3-(pyridin-2-ylmethyl)-1H-purine-2,6(3H,7H)-dione

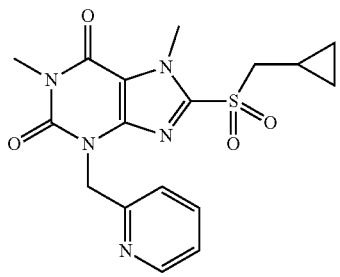

The compound was synthesized in a manner similar to that described for compound 133 to finally get 16 mg (61.5%) as a white solid. $^1$H-NMR (400 MHz, CDCl$_3$): δ 8.45 (d, J=4.8 Hz, 1H), 7.66-7.62 (m, 1H), 7.26-7.24 (m, 1H), 7.17-7.14 (1H), 5.40 (s, 2H), 4.35 (s, 3H), 3.43 (s, 3H), 3.32 (d, J=7.2 Hz, 2H), 1.13-1.00 (m, 1H), 0.59-0.54 (m, 2H), 0.19-0.15 (m, 2H). Mass (m/z): 390.43 [M+H]+.

Compound 143: 8-((cyclopropylmethyl)sulfonyl)-1,7-dimethyl-3-(pyridin-3-ylmethyl)-1H-purine-2,6(3H,7H)-dione

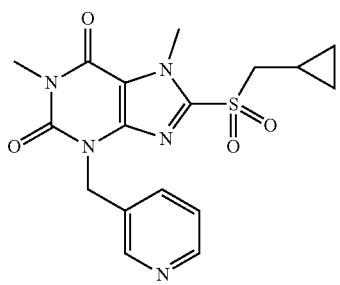 [SMILES: Cn1c(=O)c2c(nc(S(=O)(=O)CC3CC3)n2C)n(Cc2cccnc2)c1=O]

The compound was synthesized in a manner similar to that described for compound 133 to finally get 16 mg (61.5%) as a white solid. $^1$H-NMR (400 MHz, CDCl$_3$): δ8.80-8.55 (m, 2H), 7.86 (d, J=8.0 Hz, 1H), 7.29 (s, 1H), 5.27 (s, 2H), 4.34 (s, 3H), 3.42 (d, J=7.2 Hz, 2H), 3.41 (s, 3H), 1.18-1.07 (m, 1H), 0.68-0.63 (m, 2H), 0.28-0.24 (m, 2H). Mass (m/z): 390.43 [M+H]+.

Compound 144: 8-((cyclopropylmethyl)sulfonyl)-1,7-dimethyl-3-(pyridin-4-ylmethyl)-1H-purine-2,6(3H,7H)-dione

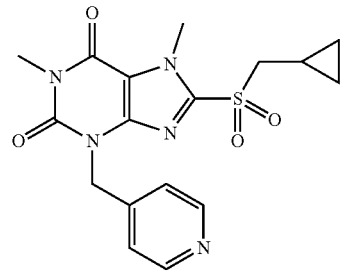

The compound was synthesized in a manner similar to that described for compound 133 to finally get 18 mg (69.2%) as a white solid. $^1$H-NMR (400 MHz, CDCl$_3$): δ8.57 (brs, 2H), 7.30 (d, J=4.8 Hz, 2H), 5.25 (s, 2H), 4.35 (s, 3H), 3.43 (s, 3H), 3.37 (d, J=7.2 Hz, 2H), 1.13-1.04 (m, 1H), 0.66-0.61 (m, 2H), 0.24-0.20 (m, 2H). Mass (m/z): 390.43 [M+H]+.

Compound 145: 3,5,7-trimethyl-2-(methylsulfonyl)-2H-pyrazolo[3,4-d]pyrimidine-4,6(5H,7H)-dione

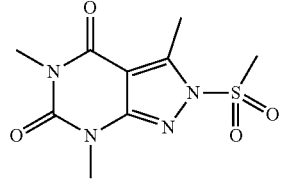 [SMILES: Cc1c2c(=O)n(C)c(=O)n(C)c2nn1S(C)(=O)=O]

(I) Synthesis of 6-hydrazinyl-1,3-dimethylpyrimidine-2,4(1H,3H)-dione

To a solution of 6-chloro-1,3-dimethylpyrimidine-2,4(1H,3H)-dione (2.0 g, 11.45 mmol) in isopropanol (6 mL) was added hydrazine hydrate (6 mL) and stirred at RT for overnight. Then the precipitated white solid was filtered off and washed with water (3*15 mL), dried well to give TM (1.67 g, 85.6%) as a white solid. $^1$H-NMR (400 MHz, DMSO-d$_6$): δ 8.06 (s, 1H), 5.09 (s, 1H), 4.37 (s, 2H), 3.21 (s, 3H), 3.08 (s, 3H). Mass (m/z): 171.08 [M+H]+.

(II) Synthesis of 3,5,7-trimethyl-2H-pyrazolo[3,4-d]pyrimidine-4,6(5H,7H)-dione

A mixture of 6-hydrazinyl-1,3-dimethylpyrimidine-2,4(1H,3H)-dione (1.6 g, 9.40 mmol) and acetic anhydride (10 mL) in dry pyride (12 mL) were refluxed for 3 h. Then the reaction was cooled to 0° C. and acidified with 1N HCl (30 mL). The solid obtained was collected by filtration, washed with 1N HCl (2*5 mL), water (2*10 mL) and dried to give TM (1.1 g, 60.5%) as a white solid. $^1$H-NMR (400 MHz, DMSO-d$_6$): δ 3.64 (br, 1H), 3.19 (s, 3H), 2.84 (s, 3H), 2.65 (s, 3H). Mass (m/z): 195.08 [M+H]+.

(III) Synthesis of 3,5,7-trimethyl-2-(methylsulfonyl)-2H-pyrazolo[3,4-d]pyrimidine-4,6(5H,7H)-dione To a solution of 3,5,7-trimethyl-2H-pyrazolo[3,4-d]pyrimidine-4,6(5H,7H)-dione (50.0 mg, 0.26 mmol) in NaOH (aq) (10 mL) was added methanesulfonyl chloride (44.2 mg, 0.38 mmol). Then the mixture was stirred at RT for overnight. The solid was precipitate out. The crude product was purified by prep. TLC to give TM (31.2 mg, 44.6%) as a white solid. $^1$H-NMR (400 MHz, CDCl3): δ 3.51 (s, 3H), 3.42 (s, 3H), 3.37 (s, 3H), 2.92 (s, 3H). Mass (m/z): 273.06[M+H]+.

Compound 146: 1,3,9-trimethyl-8-(methylsulfonyl)-3,9-dihydro-1H-purine-2,6-dione

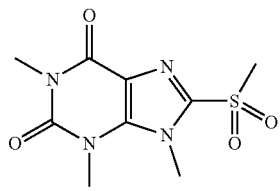 [SMILES: Cn1c(=O)c2nc(S(C)(=O)=O)n(C)c2n(C)c1=O]

To a solution of 5,6-diamino-1,3-dimethylpyrimidine-2,4 (1H,3H)-dione (500 mg, 3 mmol) in 95% ethanol (3 mL) was added isothiocyanatomethane (215 mg) and stirred at 100° C. for 6 h. Then the precipitated white solid was filtered off and washed with water (3*15 mL), dried well to give 1-(6-amino-1,3-dimethyl-2,4-dioxo-1,2,3,4-tetrahydropyrimidin-5-yl)-3-methylthiourea 250 mg as a yellow solid.

The yellow solid (0.04 mole) was dissolved in concentrated hydrochloric acid and was refluxed vigorously for 6 hours. The precipitate was filtered from the hot mixture and was washed with concentrated hydrochloric acid to get 80 mg 8-mercapto-1,3,9-trimethyl-3,9-dihydro-1H-purine-2,6-dione as yellow solid.

The residue (20 mg) was dissolved in anhydrous DMF (2 mL), K$_2$CO$_3$ (50 mg) and iodomethane (25 mg) were added and stirred under nitrogen at RT for 2 h. The reaction mixture was poured into water and extracted with dichloromethane (3*5 mL) and the organic layer was separated, dried over Na$_2$SO$_4$, filtered, concentrated and purified by prep. TLC to give 1,3,9-trimethyl-8-(methylthio)-3,9-dihydro-1H-purine-2,6-dione as a yellow solid (15 mg).

To a solution of 1,3,9-trimethyl-8-(methylthio)-3,9-dihydro-1H-purine-2,6-dione (12 mg) in MeOH (3 mL) was added oxone (92 mg) in H$_2$O (3 mL). Then the mixture was stirred at RT for 5 h. Then the solvent was removed and extracted with dichloromethane (3*10 mL) and the organic layer was separated, dried over Na$_2$SO$_4$, filtered, concentrated and purified by prep. TLC to obtain 1,3,9-trimethyl-8-(methylsulfonyl)-3,9-dihydro-1H-purine-2,6-dione as a white solid (6 mg). Mass (m/z): 273.06 [M+H]+.

Compound 147 is prepared according to the procedure outlined in scheme:

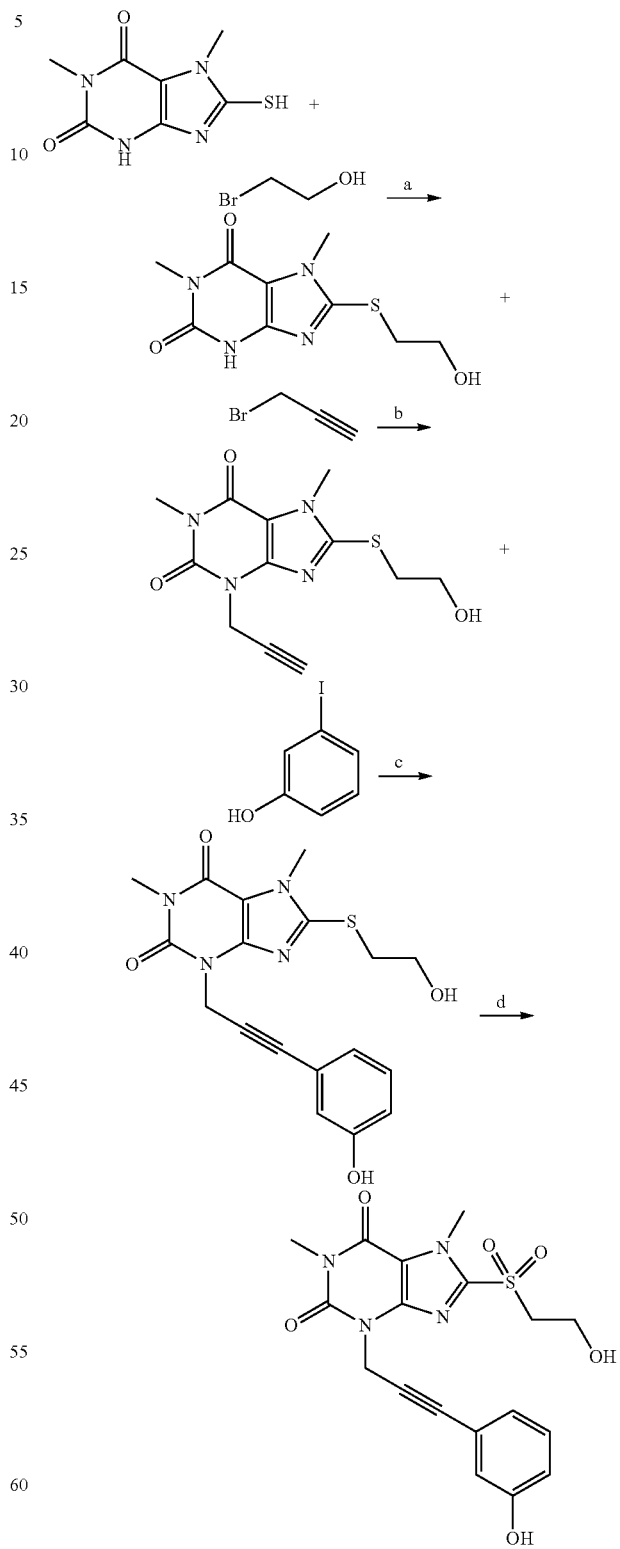

(a) K$_2$CO$_3$, DMF, rt, 1 h; (b) K$_2$CO$_3$, DMF, rt, 1 h; (c) Pd(PPh$_3$)$_4$, CuI, TEA, anhydrous DMF, 60° C., 6 h; (d) Oxone, MeOH:H2O 1:1, rt, 4 h.

Compound 148 is prepared according to the procedure outlined in scheme:

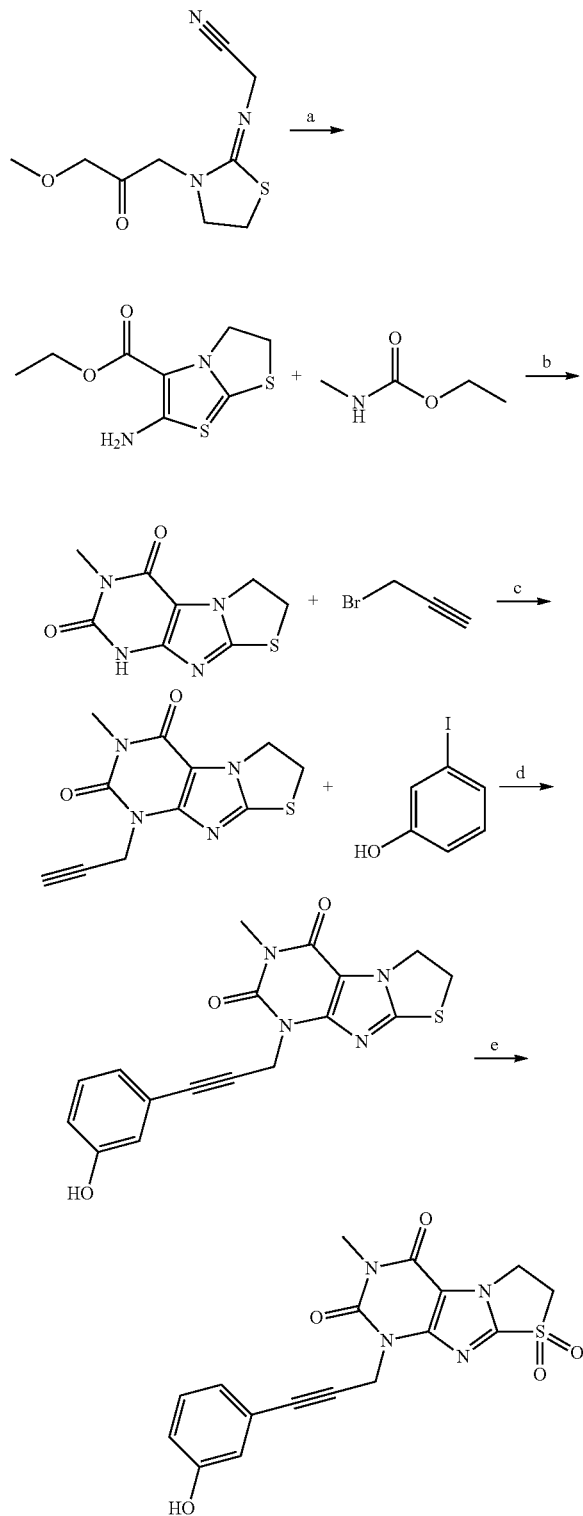

(a) Sodium ethanolate, ethanol, reflux; (b) Potassium tert-butanolate, anhydrous THF, 75° C., overnight; (c) K2CO3, DMF, rt, 1 h; (d) Pd(PPh₃)₄, CuI, TEA, anhydrous DMF, 60° C., 6 h; (e) Oxone, MeOH:H2O 1:1, rt, 4 h.

Compound 149 is prepared according to the procedure outlined in scheme

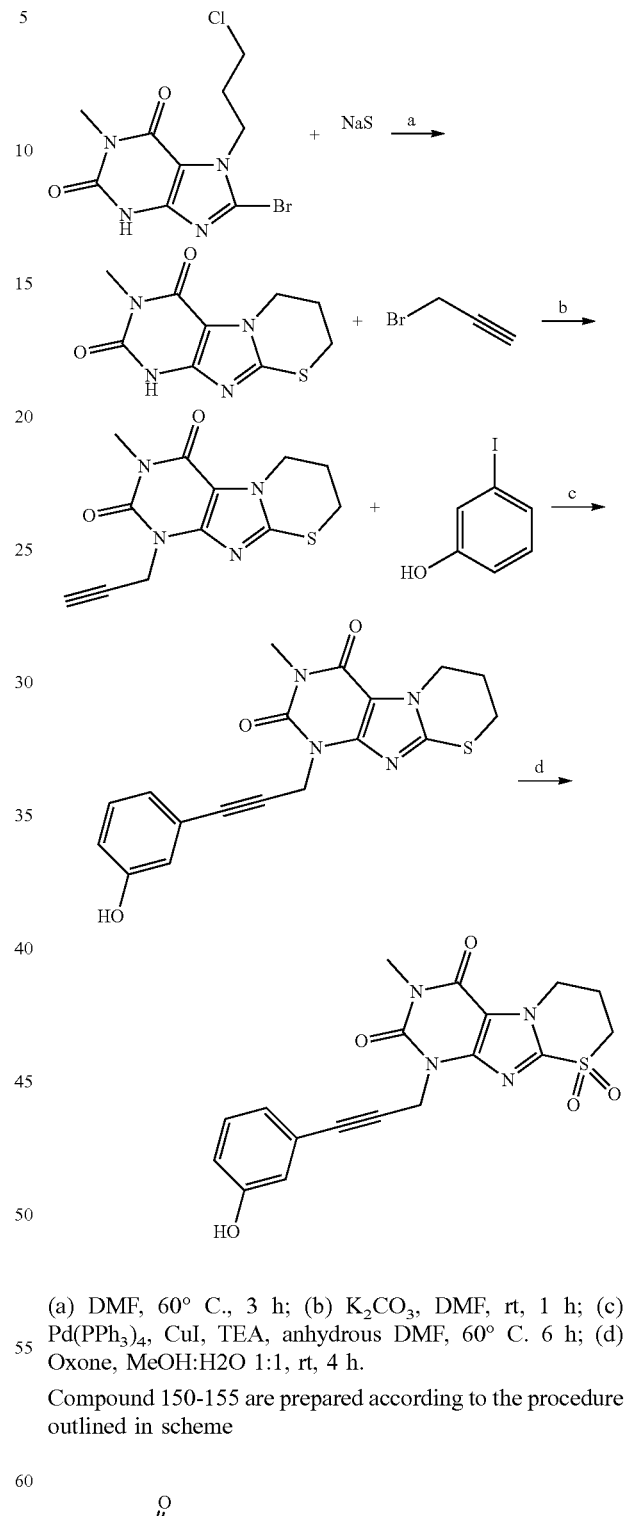

(a) DMF, 60° C., 3 h; (b) K₂CO₃, DMF, rt, 1 h; (c) Pd(PPh₃)₄, CuI, TEA, anhydrous DMF, 60° C. 6 h; (d) Oxone, MeOH:H2O 1:1, rt, 4 h.

Compound 150-155 are prepared according to the procedure outlined in scheme

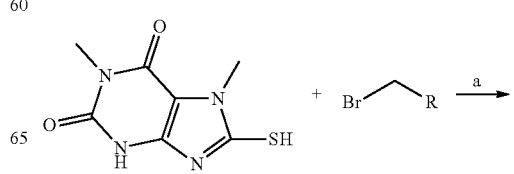

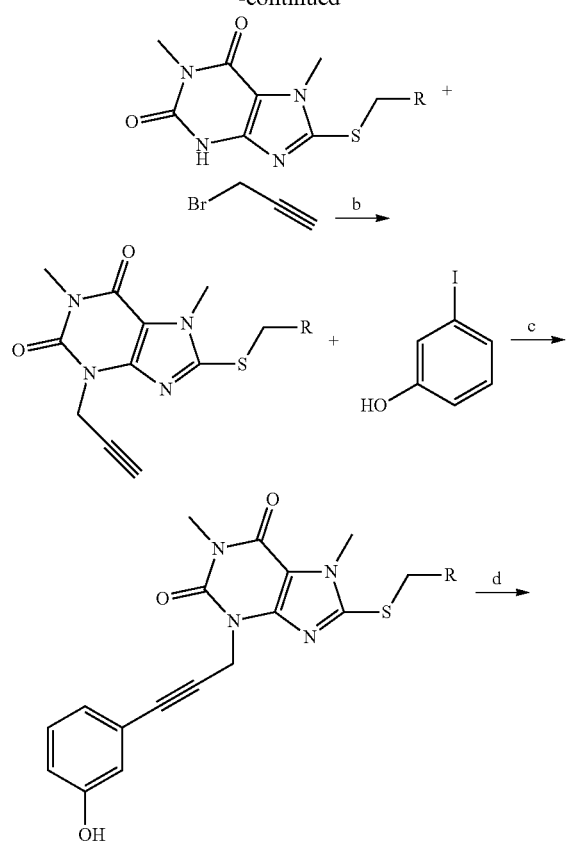
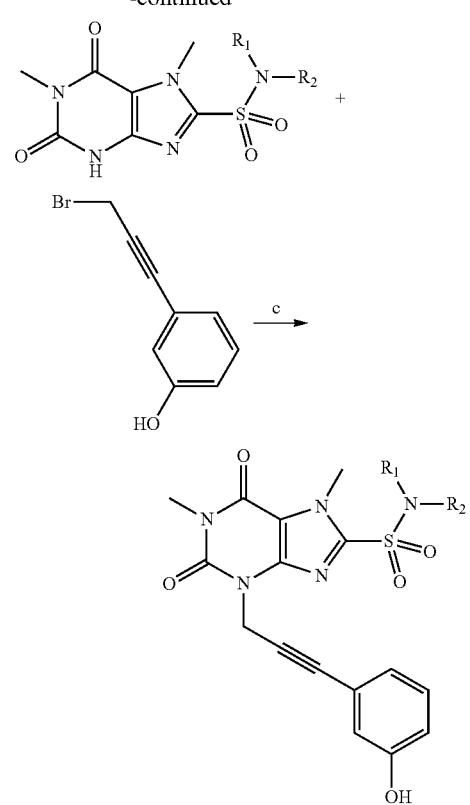
(a) K$_2$CO$_3$, DMF, rt, 1 h; (b) K$_2$CO$_3$, DMF, rt, 1 h; (c) Pd(PPh$_3$)$_4$, CuI, TEA, anhydrous DMF, 60° C., 6 h; (d) Oxone, MeOH:H2O 1:1, rt, 4 h.
Compound 156-158 are prepared according to the procedure outlined in scheme
(a) Anhydrous DMF, 120° C., 6 h; (b) NaOCl (aq), HCl, −25° C.; (c) K$_2$CO$_3$, DMF, rt, 1 h.
Compound 159-175 are prepared according to the procedure outlined in scheme:
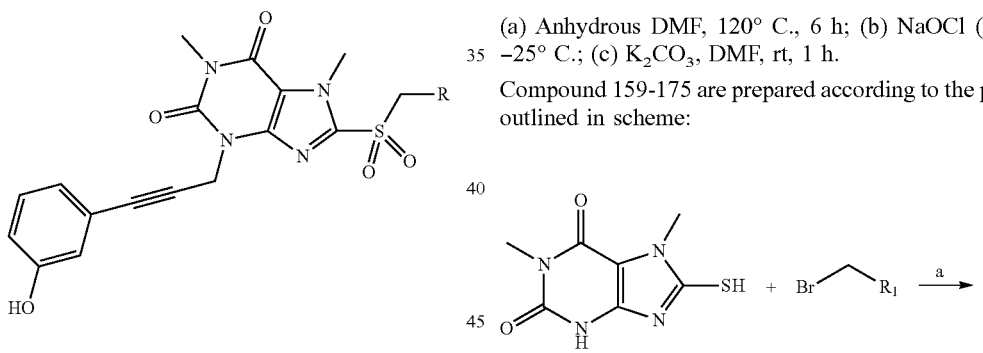
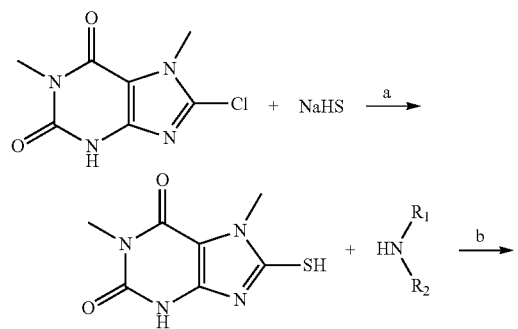
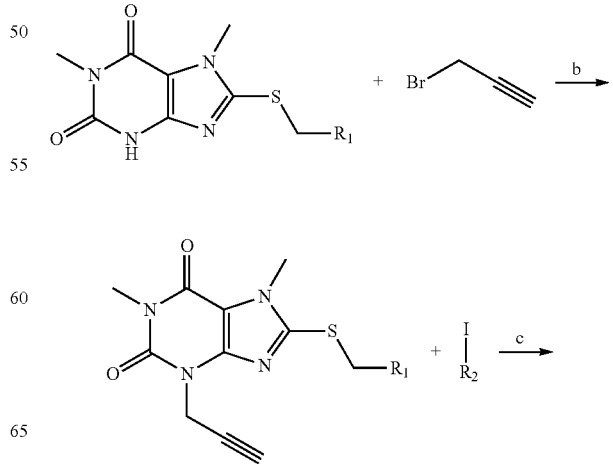

183

-continued

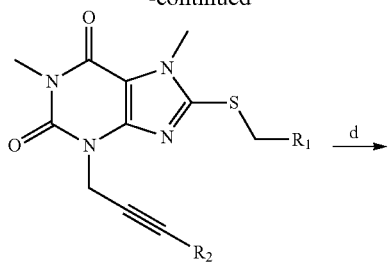

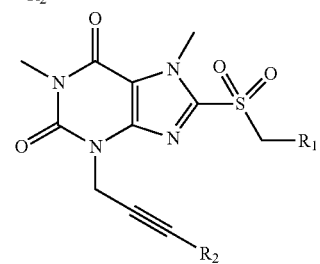

(a) $K_2CO_3$, DMF, rt, 1 h; (b) $K_2CO_3$, DMF, rt, 1 h; (c) Pd(PPh$_3$)$_4$, CuI, TEA, anhydrous DMF, 60° C., 6 h; (d) Oxone, MeOH:H$_2$O 1:1, rt, 4 h.

Compound 176 is prepared according to the procedure outlined in scheme

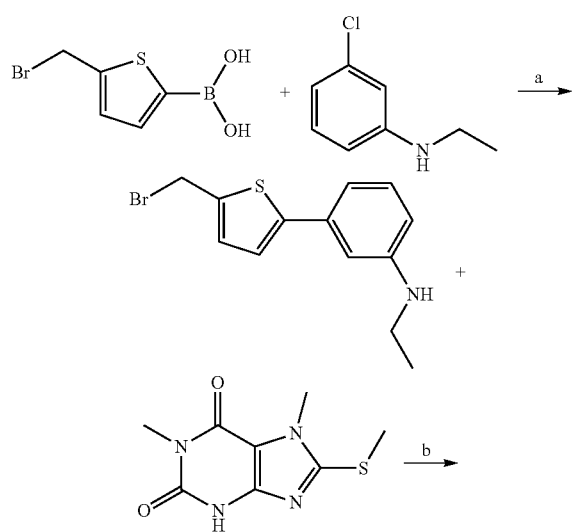

184

-continued

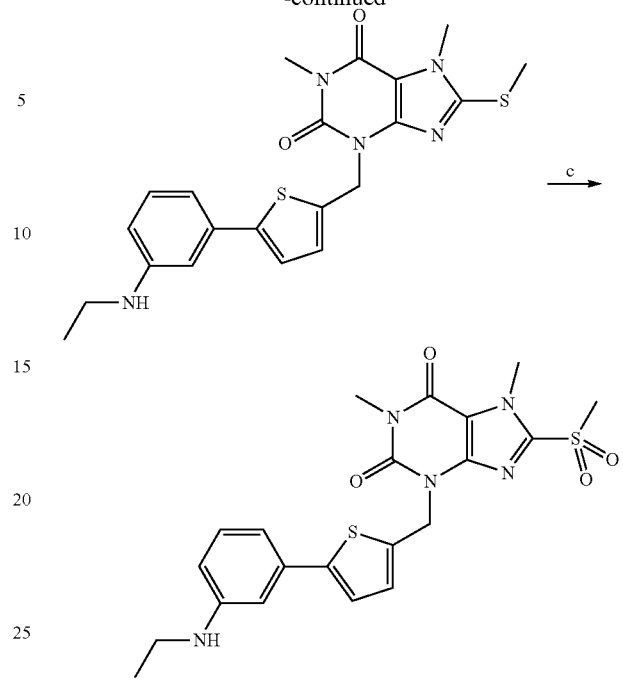

(a) Pd(PPh$_3$)$_4$, CuI, TEA, anhydrous DMF, 60° C., 6 h; (b) $K_2CO_3$, DMF, rt, 1 h; (c) Oxone, MeOH:H2O 1:1, rt, 4 h.

Necroptosis Assay

Methods: HT-29 cells were cultured in McCoy's 5 A culture medium (Invitrogen). On day one, HT-29 cells were plated in 96-well assay plates at density of 2,500-3,500 cells per well. On day two, necrosis were induced by adding 20 ng/ml TNF-α (T), 100 nM Smac mimetic (S), and 20 mM z-VAD (Z). At the same time, 10 mM compound from a chemical library of ~200,000 compounds was delivered into each well. After 24 hrs treatment, cell viability was determined by measuring ATP level using the Cell Titer-Glo Luminescent Cell Viability Assay kit. A CellTiter-Glo Assay (Promega) was performed according to the manufacturer's instructions. Luminescence was recorded with a PerkinElmer EnSpire Multimode Plate Reader. Survived cells were normalized to those cells treated with DMSO. RIPA-56 was used as a positive control for screening necroptosis inhibitors. Data are represented as mean±standard deviation of duplicates.

Series 1 compound necroptosis activity; activity for 147-176 are extrapolated.

| # |  | # |  | # |  | # |  |
|---|---|---|---|---|---|---|---|
| 1 | 1-1000 µM | 2 | 1-1000 µM | 3 | 1-1000 µM | 4 | 1-10 µM |
| 5 | 1-1000 µM | 6 | 1-1000 µM | 7 | 1-100 µM | 8 | 1-1000 µM |
| 9 | 1-1000 µM | 10 | 1-100 µM | 11 | 1-1000 µM | 12 | 1-1000 µM |
| 13 | 1-100 µM | 14 | 1-1000 µM | 15 | 1-1000 µM | 16 | 1-1000 µM |
| 17 | 1-1000 µM | 18 | 1-100 µM | 19 | 1-1000 µM | 20 | 1-1000 µM |
| 21 | 1-100 µM | 22 | 1-1000 µM | 23 | 1-1000 µM | 24 | 1-1000 µM |
| 25 | 1-1000 µM | 26 | 1-1000 µM | 27 | 1-1000 µM | 28 | 1-1000 µM |
| 29 | 1-1000 µM | 30 | 1-1000 µM | 31 | 1-1000 µM | 32 | 1-1000 µM |
| 33 | 1-1000 µM | 34 | 1-1000 µM | 35 | 1-1000 µM | 36 | 1-1000 µM |
| 37 | 1-1000 µM | 38 | 1-1000 µM | 39 | 1-1000 µM | 40 | 1-1000 µM |
| 41 | 1-1000 µM | 42 | 1-1000 µM | 43 | 1-1000 µM | 44 | 1-1000 µM |
| 45 | 1-1000 µM | 46 | 1-1000 µM | 47 | 1-1000 µM | 48 | 1-1000 µM |
| 49 | 1-1000 µM | 50 | 1-1000 µM | 51 | 1-1000 µM | 52 | 1-1000 µM |
| 53 | 1-1000 µM | 54 | 1-1000 µM | 55 | 1-100 µM | 56 | 1-100 µM |
| 57 | 1-1000 µM | 58 | 1-10 µM | 59 | 1-1000 µM | 60 | 1-1000 µM |
| 61 | 1-1000 µM | 62 | 1-1000 µM | 63 | 1-1000 µM | 64 | 1-1000 µM |

-continued

| # | | # | | # | | # | |
|---|---|---|---|---|---|---|---|
| 65 | 1-1000 μM | 66 | 1-1000 μM | 67 | 1-1000 μM | 68 | 1-1000 μM |
| 69 | 1-1000 μM | 70 | 1-1000 μM | 71 | 1-1000 μM | 72 | 1-1000 μM |
| 73 | 1-1000 μM | 74 | 1-10 μM | 75 | 1-1000 μM | 76 | 1-1000 μM |
| 77 | 1-1000 μM | 78 | 1-1000 μM | 79 | 1-1000 μM | 80 | 1-1000 μM |
| 81 | 1-1000 μM | 82 | 1-100 μM | 83 | 1-1000 μM | 84 | 1-1000 μM |
| 85 | 1-1000 μM | 86 | 1-1000 μM | 87 | 1-1000 μM | 88 | 1-1000 μM |
| 89 | 1-1000 μM | 90 | 1-1000 μM | 91 | 1-1000 μM | 92 | 1-1000 μM |
| 93 | 1-1000 μM | 94 | 1-1000 μM | 95 | 1-1000 μM | 96 | 1-1000 μM |
| 97 | 1-1000 μM | 98 | 1-1000 μM | 99 | 1-100 μM | 100 | 1-100 μM |
| 101 | 1-100 μM | 102 | 1-100 μM | 103 | 1-100 μM | 104 | 1-1000 μM |
| 105 | 1-1000 μM | 106 | 1-10 μM | 107 | 1-100 μM | 108 | 1-1000 nM |
| 109 | 1-1000 nM | 110 | 1-1000 nM | 111 | 1-1000 nM | 112 | 1-1000 nM |
| 113 | 1-1000 nM | 114 | 1-1000 nM | 115 | 1-1000 nM | 116 | 1-1000 nM |
| 117 | 1-1000 nM | 118 | 1-1000 nM | 119 | 1-10 μM | 120 | 1-1000 nM |
| 121 | 1-1000 nM | 122 | 1-1000 nM | 123 | 1-1000 nM | 124 | 1-1000 nM |
| 125 | 1-1000 nM | 126 | 1-1000 nM | 127 | 1-10 μM | 128 | 1-100 μM |
| 129 | 1-100 μM | 130 | 1-1000 μM | 131 | 1-1000 nM | 132 | 1-1000 μM |
| 133 | 1-100 μM | 134 | 1-100 μM | 135 | 1-100 μM | 136 | 1-100 μM |
| 137 | 1-100 μM | 138 | 1-100 μM | 139 | 1-100 μM | 140 | 1-100 μM |
| 141 | 1-100 μM | 142 | 1-100 μM | 143 | 1-1000 μM | 144 | 1-1000 μM |
| 145 | 1-1000 μM | 146 | 1-1000 μM | 147 | 1-1000 μM | 148 | 1-1000 μM |
| 149 | 1-1000 μM | 150 | 1-1000 μM | 151 | 1-1000 μM | 152 | 1-1000 μM |
| 153 | 1-1000 μM | 154 | 1-1000 μM | 155 | 1-1000 μM | 156 | 1-1000 μM |
| 157 | 1-1000 μM | 158 | 1-1000 μM | 159 | 1-1000 μM | 160 | 1-1000 μM |
| 161 | 1-1000 μM | 162 | 1-1000 μM | 163 | 1-1000 μM | 164 | 1-1000 μM |
| 165 | 1-1000 μM | 166 | 1-1000 μM | 167 | 1-1000 μM | 168 | 1-1000 μM |
| 169 | 1-1000 μM | 170 | 1-1000 μM | 171 | 1-1000 μM | 172 | 1-1000 μM |
| 173 | 1-1000 μM | 174 | 1-1000 μM | 175 | 1-1000 μM | 176 | 1-1000 μM |

Exemplary Compounds

In embodiments the compounds are selected from Table 2.

TABLE 2

Series 2 Compounds

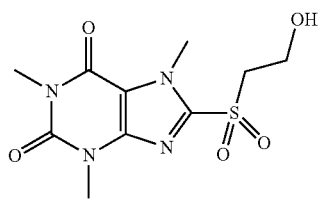 [SMILES: Cn1c(=O)c2c(nc(S(=O)(=O)CCO)n2C)n(C)c1=O]

1

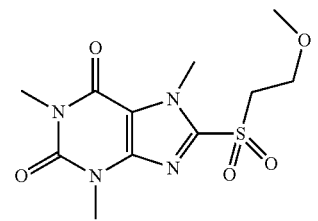 [SMILES: COCCS(=O)(=O)c1nc2c(c(=O)n(C)c(=O)n2C)n1C]

2

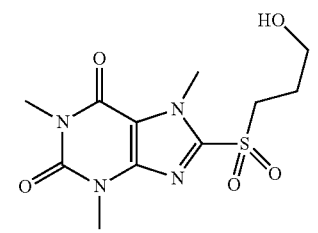 [SMILES: Cn1c(=O)c2c(nc(S(=O)(=O)CCCO)n2C)n(C)c1=O]

3

TABLE 2-continued

Series 2 Compounds

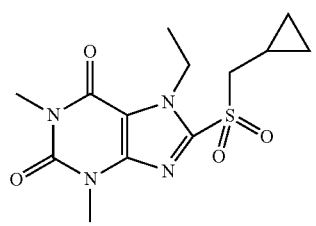 [SMILES: CCn1c(S(=O)(=O)CC2CC2)nc2c1c(=O)n(C)c(=O)n2C]

4

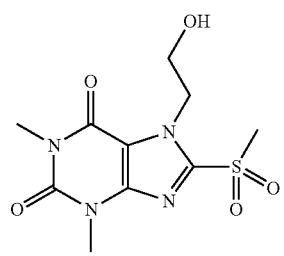 [SMILES: Cn1c(=O)c2c(nc(S(C)(=O)=O)n2CCO)n(C)c1=O]

5

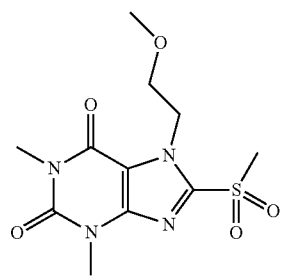 [SMILES: COCCn1c(S(C)(=O)=O)nc2c1c(=O)n(C)c(=O)n2C]

6

TABLE 2-continued
Series 2 Compounds
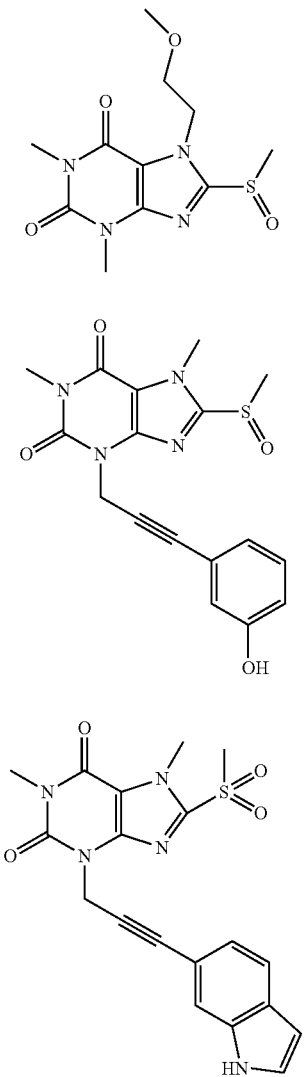
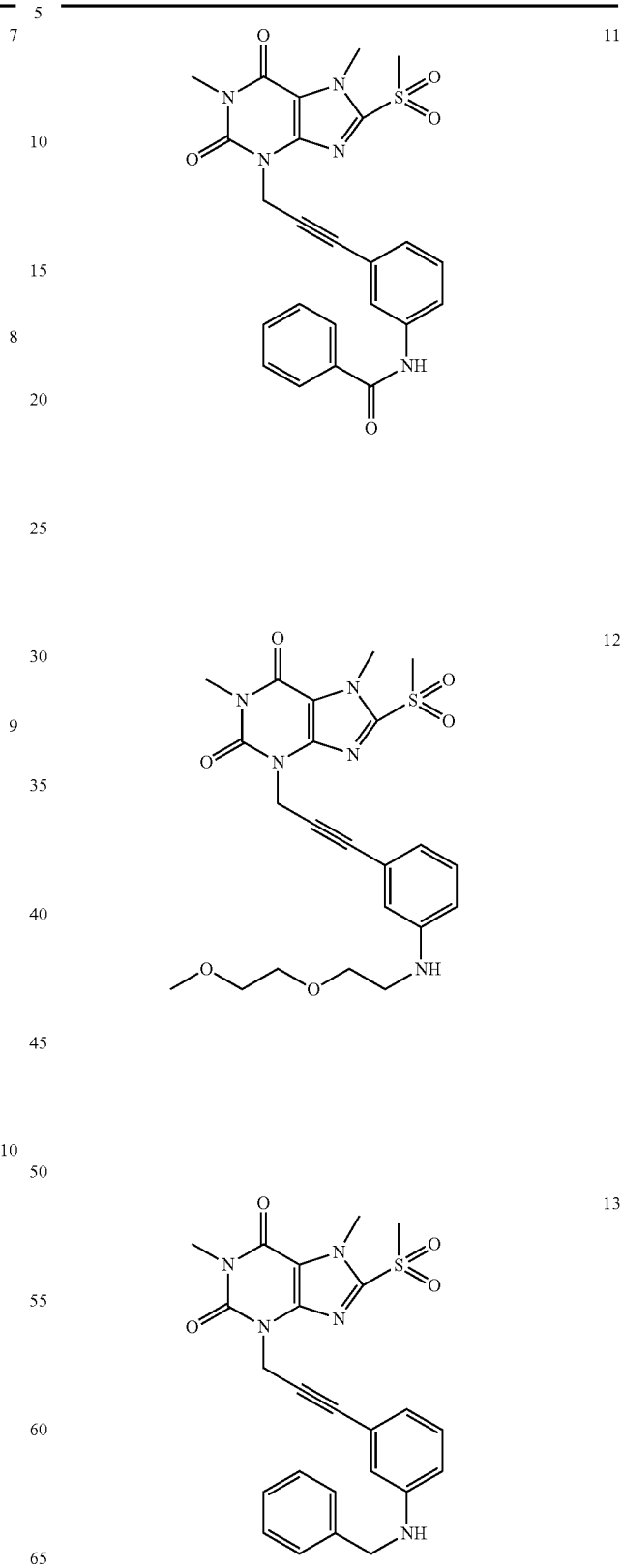

TABLE 2-continued
Series 2 Compounds
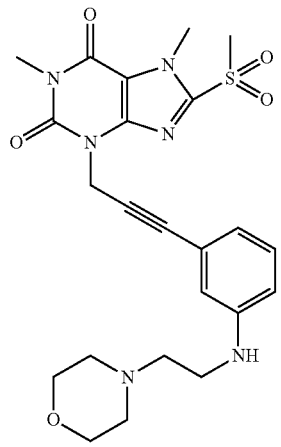 [SMILES: Cn1c(=O)c2c(nc(S(C)(=O)=O)n2C)n(CC#Cc2cccc(NCCN3CCOCC3)c2)c1=O]
14
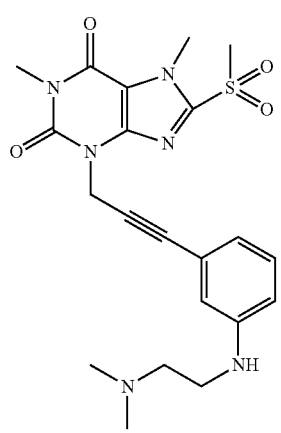 [SMILES: CN(C)CCNc1cccc(C#CCn2c(=O)n(C)c(=O)c3c2nc(S(C)(=O)=O)n3C)c1]
15
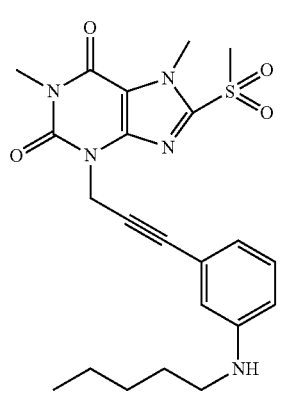 [SMILES: CCCCCNc1cccc(C#CCn2c(=O)n(C)c(=O)c3c2nc(S(C)(=O)=O)n3C)c1]
16
TABLE 2-continued
Series 2 Compounds
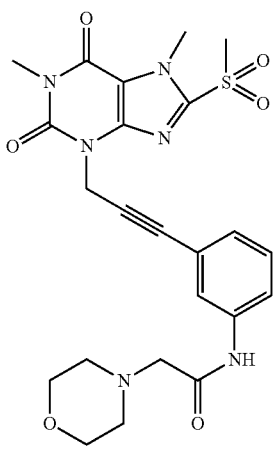 [SMILES: Cn1c(=O)c2c(nc(S(C)(=O)=O)n2C)n(CC#Cc2cccc(NC(=O)CN3CCOCC3)c2)c1=O]
17
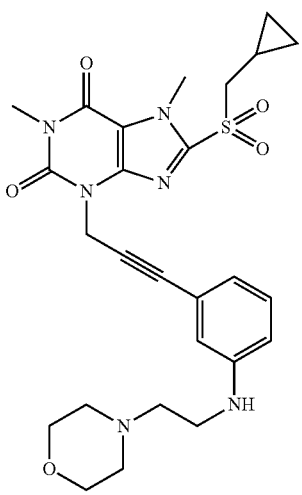 [SMILES: Cn1c(=O)c2c(nc(S(=O)(=O)CC3CC3)n2C)n(CC#Cc2cccc(NCCN3CCOCC3)c2)c1=O]
18
19

TABLE 2-continued
Series 2 Compounds
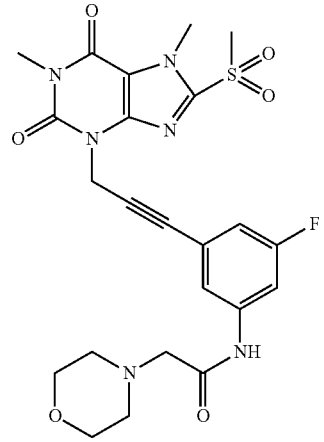 [SMILES: Cn1c(=O)c2c(nc(S(C)(=O)=O)n2C)n(CC#Cc2cc(F)cc(NC(=O)CN3CCOCC3)c2)c1=O]
20
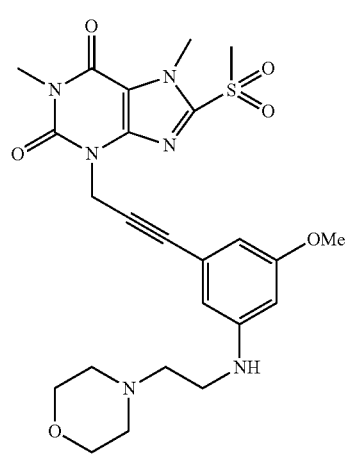 [SMILES: COc1cc(C#CCn2c(=O)n(C)c(=O)c3c2nc(S(C)(=O)=O)n3C)cc(NCCN2CCOCC2)c1]
21
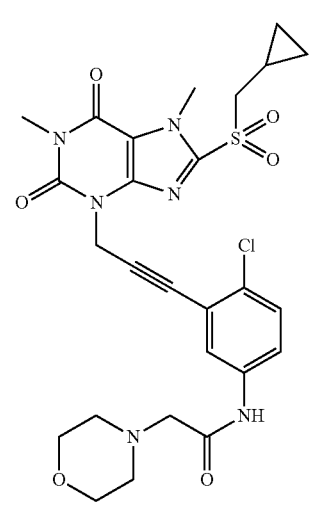 [SMILES: Cn1c(=O)c2c(nc(S(=O)(=O)CC3CC3)n2C)n(CC#Cc2cc(NC(=O)CN3CCOCC3)ccc2Cl)c1=O]
22
TABLE 2-continued
Series 2 Compounds
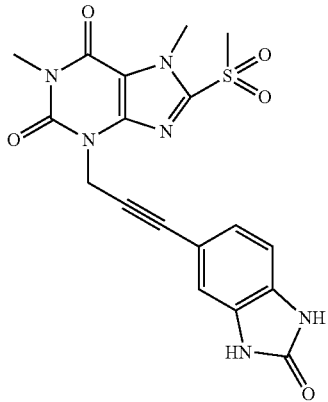 [SMILES: Cn1c(=O)c2c(nc(S(C)(=O)=O)n2C)n(CC#Cc2ccc3[nH]c(=O)[nH]c3c2)c1=O]
23
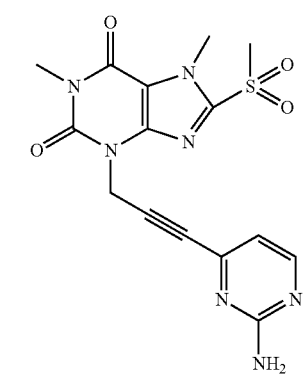 [SMILES: Cn1c(=O)c2c(nc(S(C)(=O)=O)n2C)n(CC#Cc2ccnc(N)n2)c1=O]
24
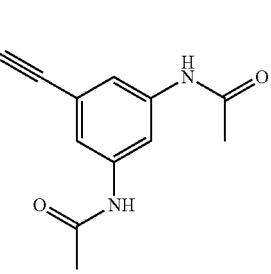
25

TABLE 2-continued
Series 2 Compounds
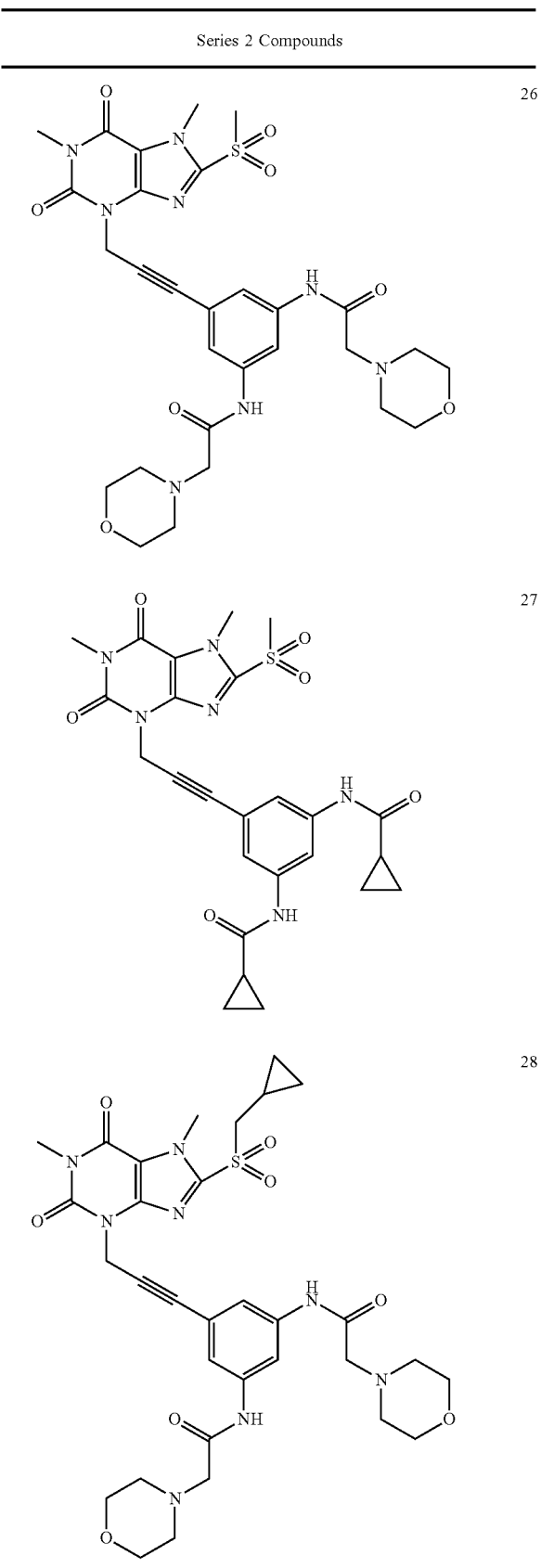
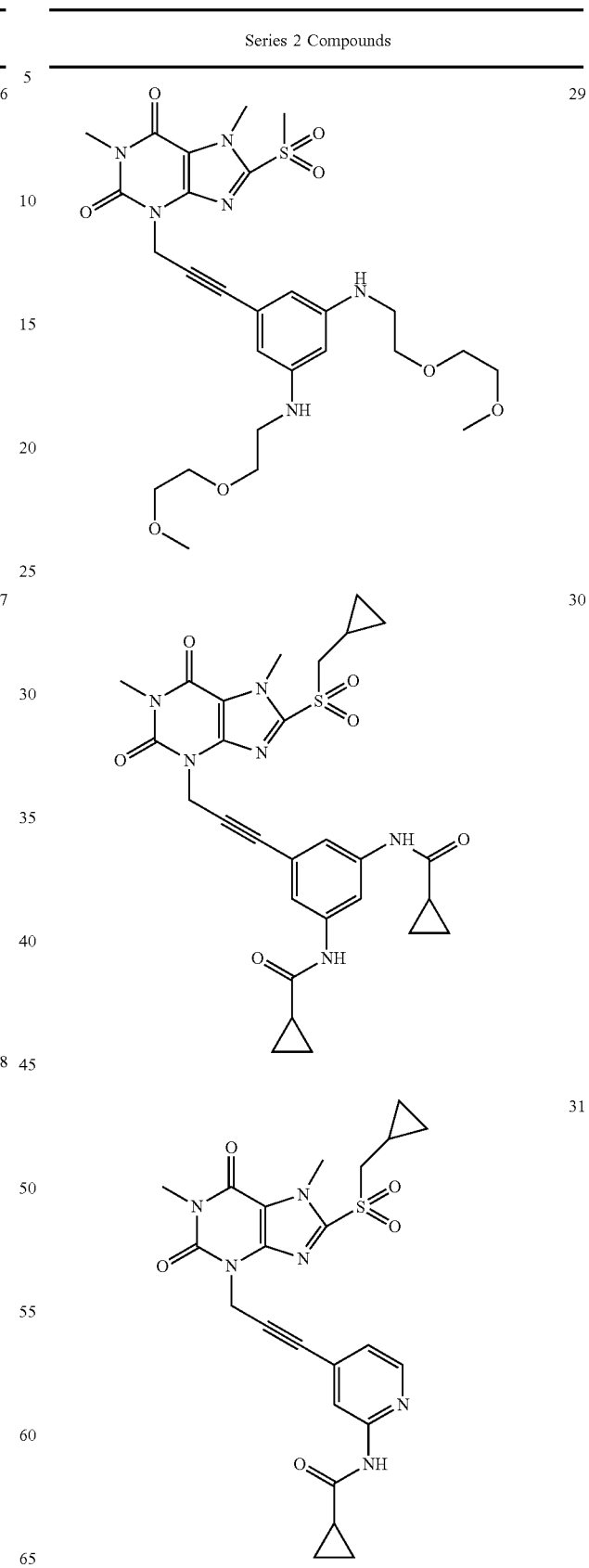

TABLE 2-continued
Series 2 Compounds
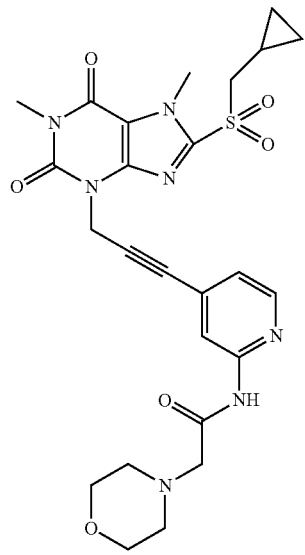 [SMILES: Cn1c(=O)c2c(nc(S(=O)(=O)CC3CC3)n2C)n(CC#Cc2ccnc(NC(=O)CN3CCOCC3)c2)c1=O]
32
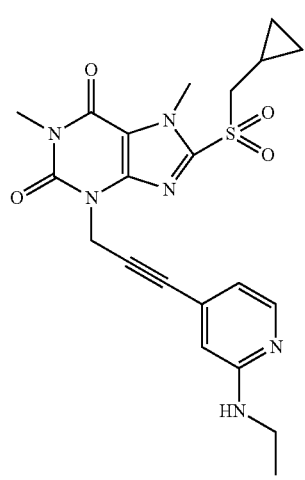 [SMILES: CCNc1cc(C#CCn2c(=O)n(C)c(=O)c3c2nc(S(=O)(=O)CC2CC2)n3C)ccn1]
33
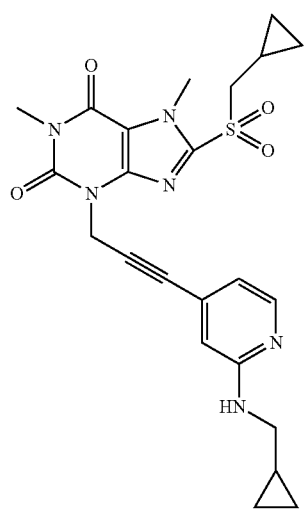 [SMILES: Cn1c(=O)c2c(nc(S(=O)(=O)CC3CC3)n2C)n(CC#Cc2ccnc(NCC3CC3)c2)c1=O]
34
TABLE 2-continued
Series 2 Compounds
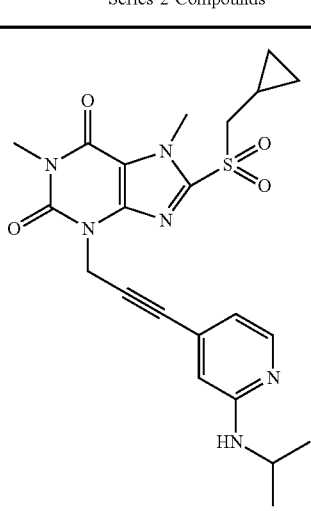
35
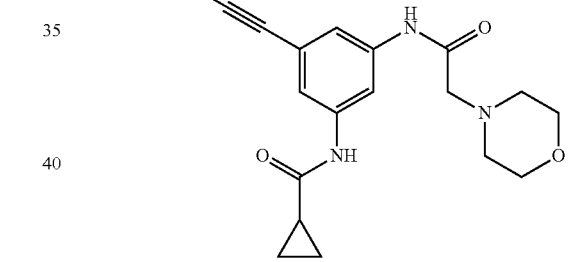
36
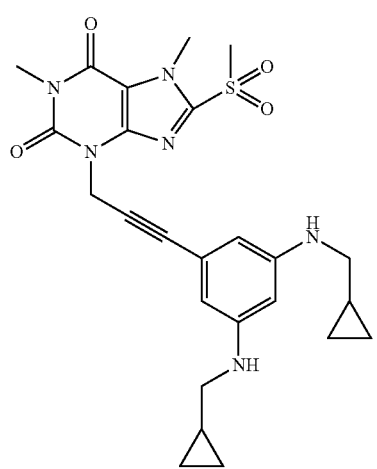 [SMILES: Cn1c(=O)c2c(nc(S(C)(=O)=O)n2C)n(CC#Cc2cc(NCC3CC3)cc(NCC3CC3)c2)c1=O]
37

TABLE 2-continued
Series 2 Compounds
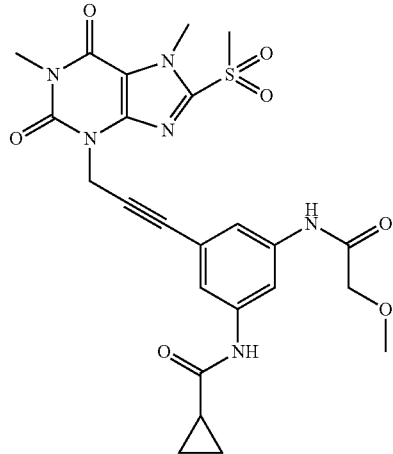
38
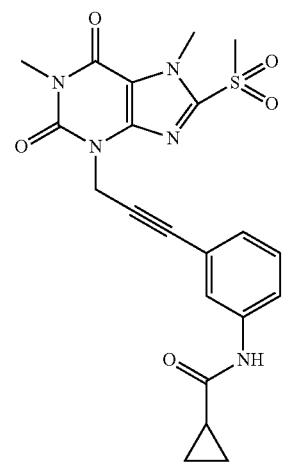 [SMILES: Cn1c(=O)c2c(nc(S(C)(=O)=O)n2C)n(CC#Cc2cccc(NC(=O)C3CC3)c2)c1=O]
39
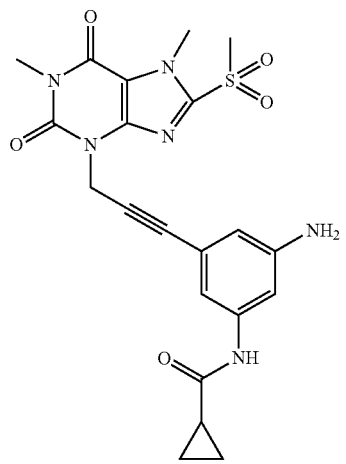 [SMILES: Cn1c(=O)c2c(nc(S(C)(=O)=O)n2C)n(CC#Cc2cc(N)cc(NC(=O)C3CC3)c2)c1=O]
40
TABLE 2-continued
Series 2 Compounds
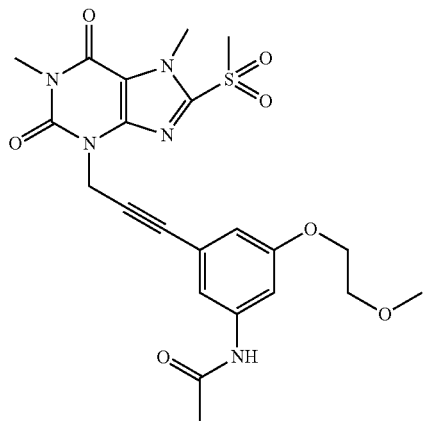
41
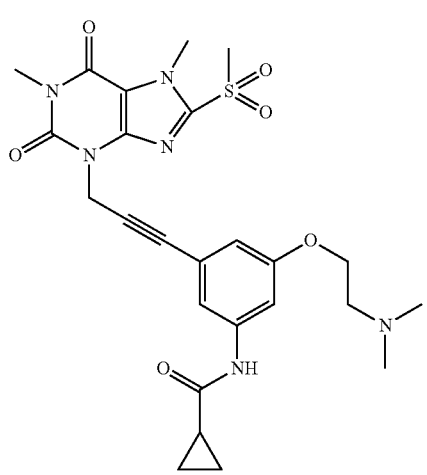
42
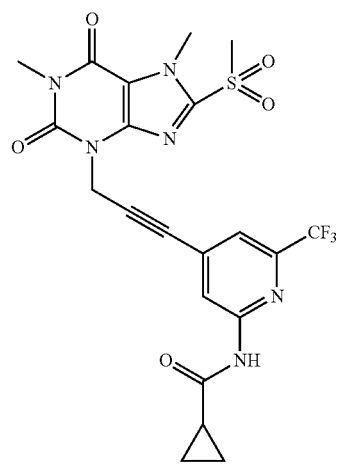 [SMILES: Cn1c(=O)c2c(nc(S(C)(=O)=O)n2C)n(CC#Cc2cc(NC(=O)C3CC3)nc(C(F)(F)F)c2)c1=O]
43

TABLE 2-continued
Series 2 Compounds
44
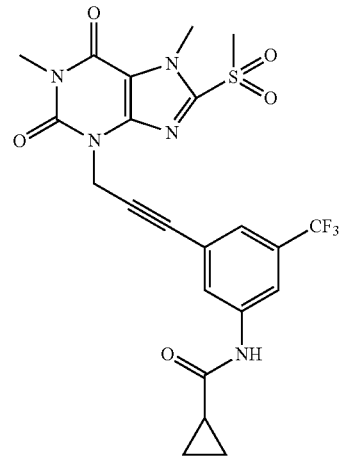 [SMILES: Cn1c(=O)c2c(nc(S(C)(=O)=O)n2C)n(CC#Cc2cc(NC(=O)C3CC3)cc(C(F)(F)F)c2)c1=O]
45
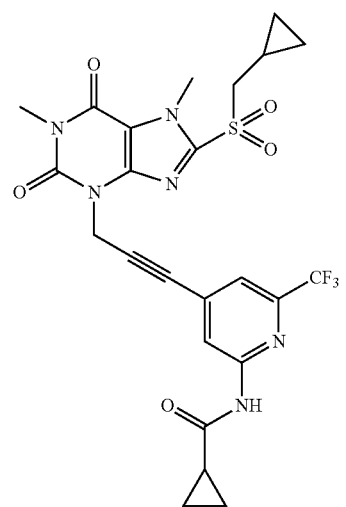 [SMILES: Cn1c(=O)c2c(nc(S(=O)(=O)CC3CC3)n2C)n(CC#Cc2cc(NC(=O)C3CC3)nc(C(F)(F)F)c2)c1=O]
46
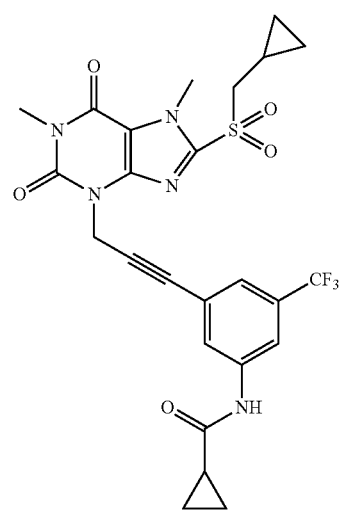 [SMILES: Cn1c(=O)c2c(nc(S(=O)(=O)CC3CC3)n2C)n(CC#Cc2cc(NC(=O)C3CC3)cc(C(F)(F)F)c2)c1=O]
TABLE 2-continued
Series 2 Compounds
47
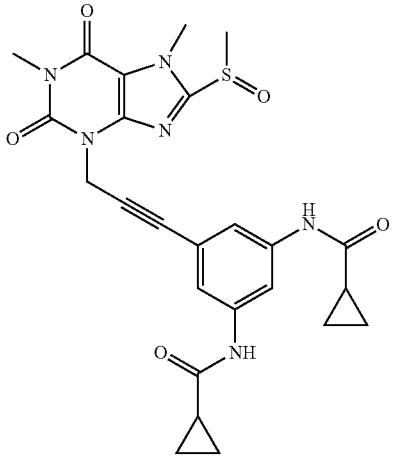 [SMILES: Cn1c(=O)c2c(nc(S(C)=O)n2C)n(CC#Cc2cc(NC(=O)C3CC3)cc(NC(=O)C3CC3)c2)c1=O]
48
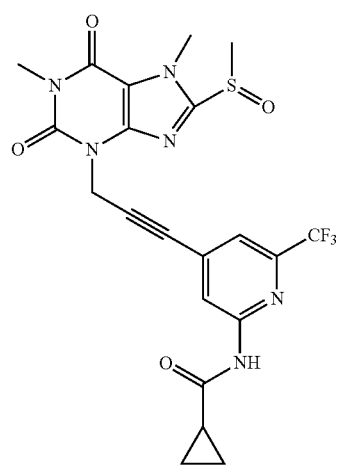 [SMILES: Cn1c(=O)c2c(nc(S(C)=O)n2C)n(CC#Cc2cc(NC(=O)C3CC3)nc(C(F)(F)F)c2)c1=O]
49
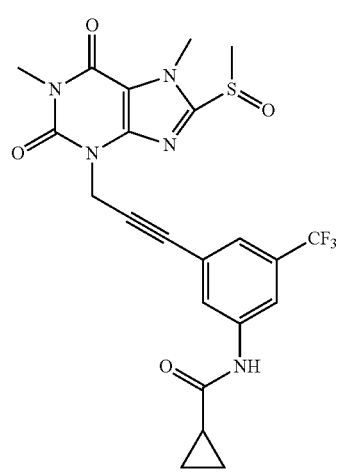 [SMILES: Cn1c(=O)c2c(nc(S(C)=O)n2C)n(CC#Cc2cc(NC(=O)C3CC3)cc(C(F)(F)F)c2)c1=O]

TABLE 2-continued
Series 2 Compounds
50 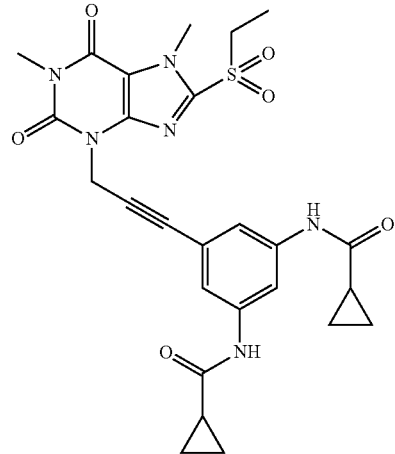 [SMILES: CCS(=O)(=O)c1nc2c(c(=O)n(C)c(=O)n2CC#Cc2cc(NC(=O)C3CC3)cc(NC(=O)C3CC3)c2)n1C]
51 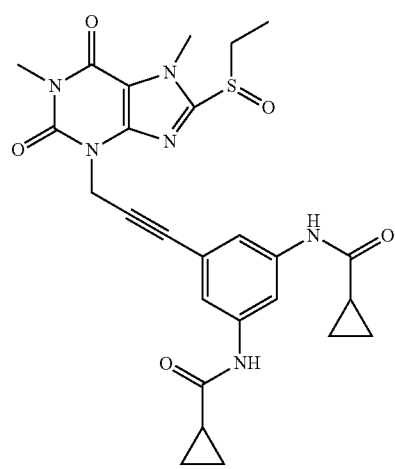 [SMILES: CCS(=O)c1nc2c(c(=O)n(C)c(=O)n2CC#Cc2cc(NC(=O)C3CC3)cc(NC(=O)C3CC3)c2)n1C]
52 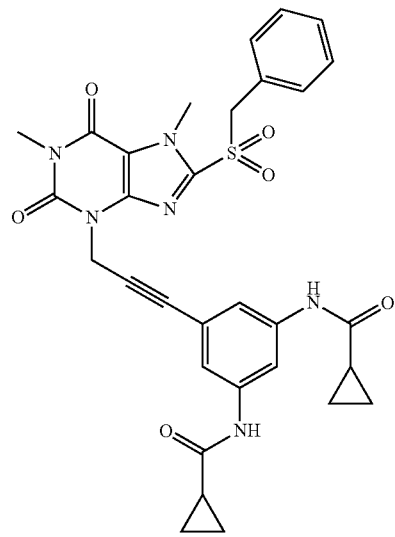 [SMILES: Cn1c(=O)c2c(nc(S(=O)(=O)Cc3ccccc3)n2C)n(CC#Cc2cc(NC(=O)C3CC3)cc(NC(=O)C3CC3)c2)c1=O]
TABLE 2-continued
Series 2 Compounds
53 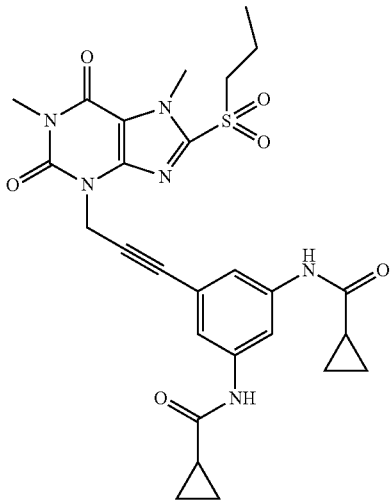 [SMILES: CCCS(=O)(=O)c1nc2c(c(=O)n(C)c(=O)n2CC#Cc2cc(NC(=O)C3CC3)cc(NC(=O)C3CC3)c2)n1C]
54 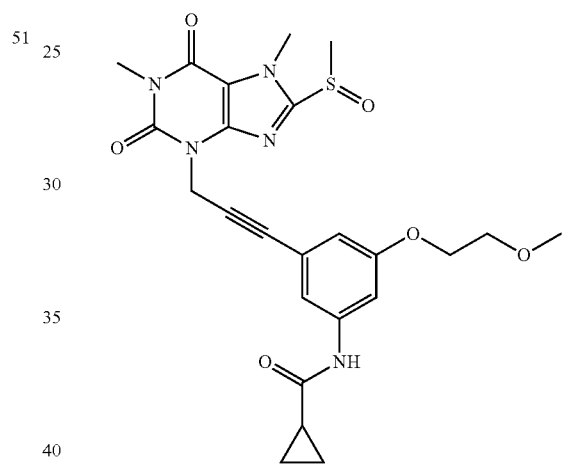
55 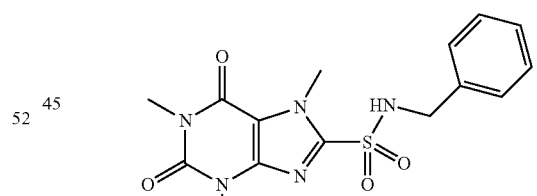
56 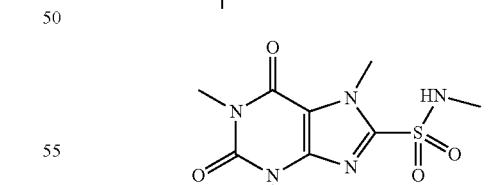
57 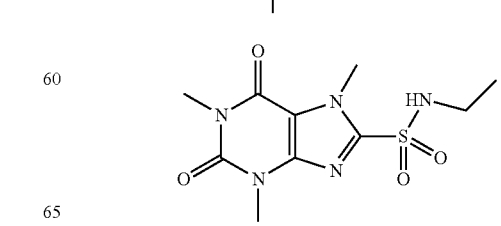

TABLE 2-continued
Series 2 Compounds
58 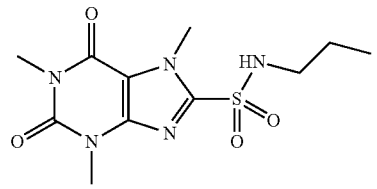 [SMILES: CCCNS(=O)(=O)c1nc2c(c(=O)n(C)c(=O)n2C)n1C]
59 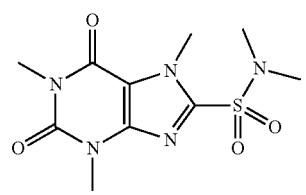
60 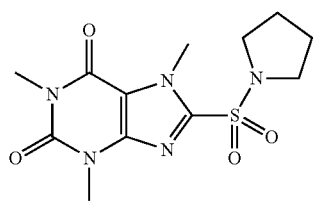 [SMILES: Cn1c(=O)c2c(nc(S(=O)(=O)N3CCCC3)n2C)n(C)c1=O]
61 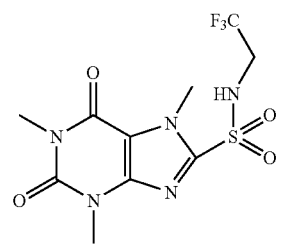 [SMILES: Cn1c(=O)c2c(nc(S(=O)(=O)NCC(F)(F)F)n2C)n(C)c1=O]
62 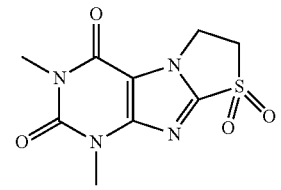 [SMILES: Cn1c(=O)c2c(nc3n2CCS3(=O)=O)n(C)c1=O]
63 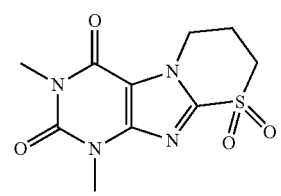 [SMILES: Cn1c(=O)c2c(nc3n2CCCS3(=O)=O)n(C)c1=O]
TABLE 2-continued
Series 2 Compounds
64 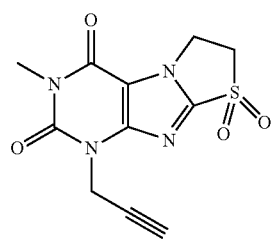 [SMILES: C#CCn1c(=O)n(C)c(=O)c2c1nc1n2CCS1(=O)=O]
65 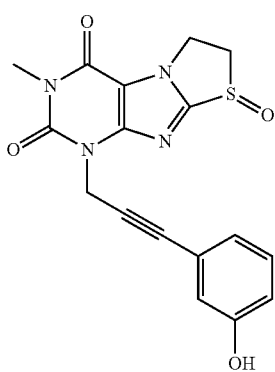 [SMILES: Cn1c(=O)c2c(nc3n2CCS3=O)n(CC#Cc2cccc(O)c2)c1=O]
66 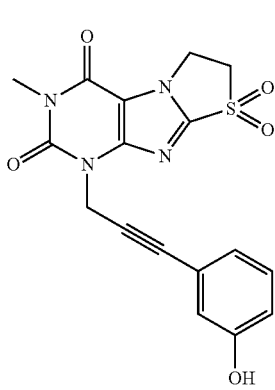 [SMILES: Cn1c(=O)c2c(nc3n2CCS3(=O)=O)n(CC#Cc2cccc(O)c2)c1=O]
67 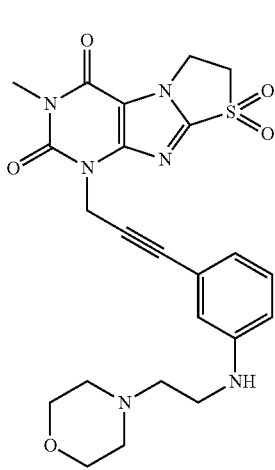 [SMILES: Cn1c(=O)c2c(nc3n2CCS3(=O)=O)n(CC#Cc2cccc(NCCN3CCOCC3)c2)c1=O]

TABLE 2-continued
Series 2 Compounds
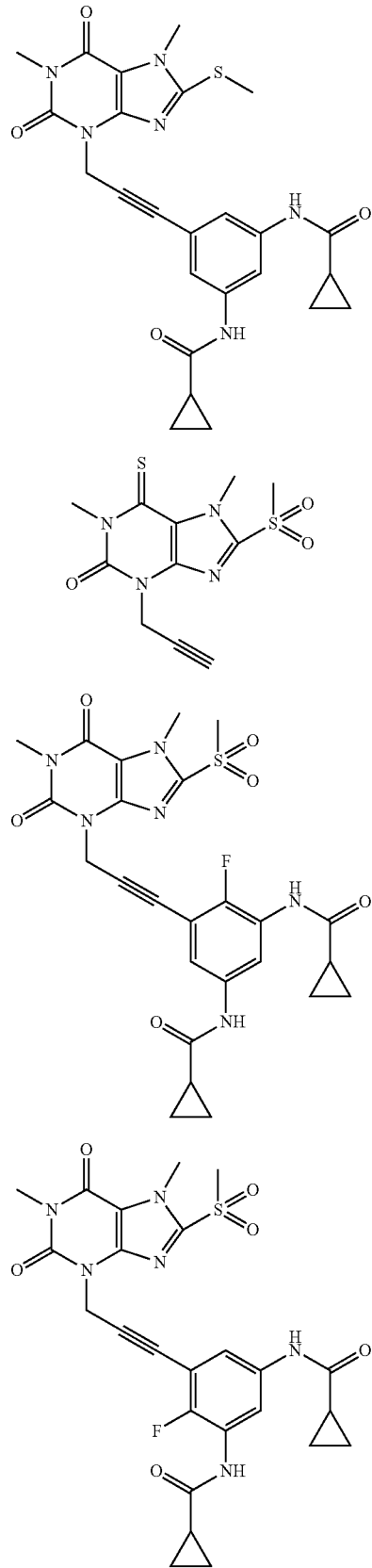
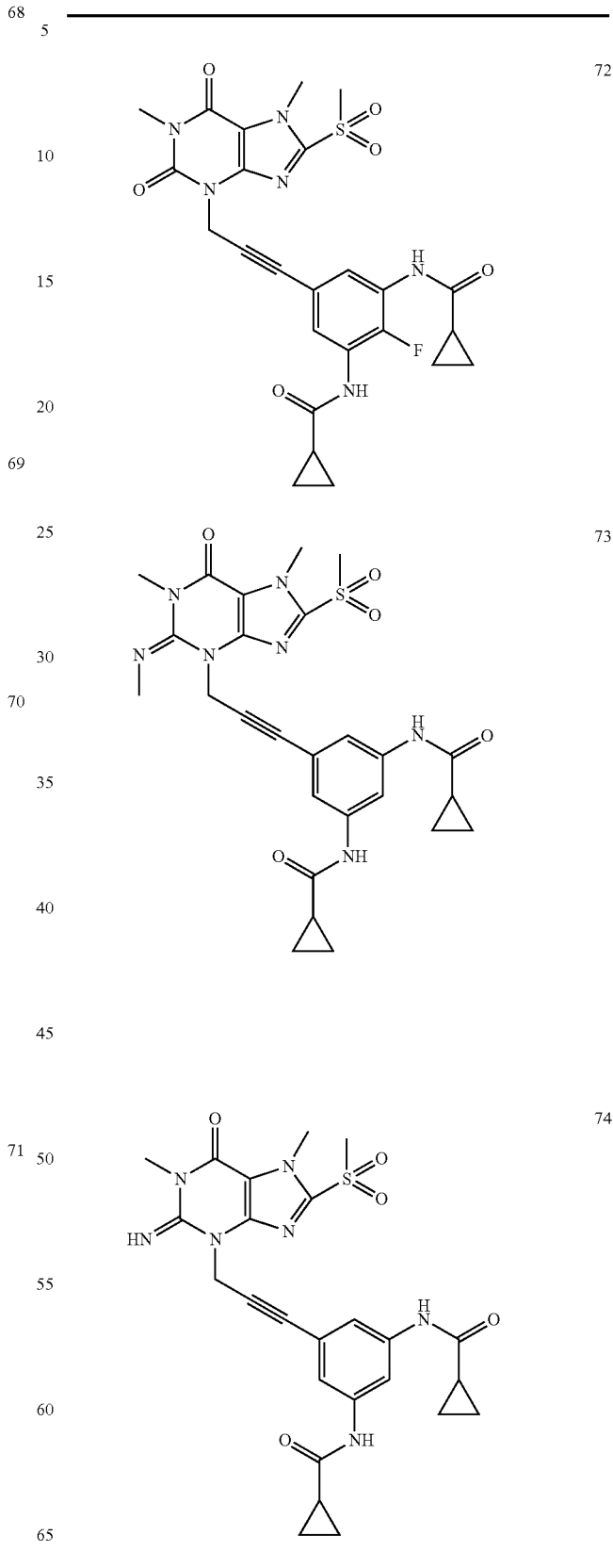

TABLE 2-continued
Series 2 Compounds
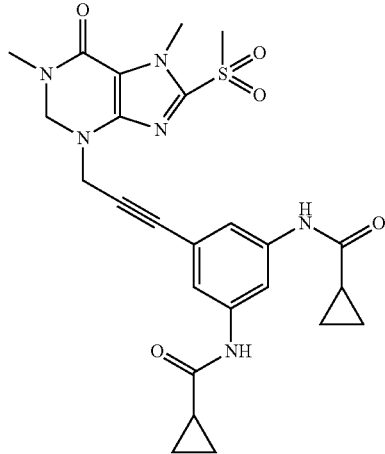 [SMILES: CN1CN(CC#Cc2cc(NC(=O)C3CC3)cc(NC(=O)C3CC3)c2)c2nc(S(C)(=O)=O)n(C)c2C1=O]
75
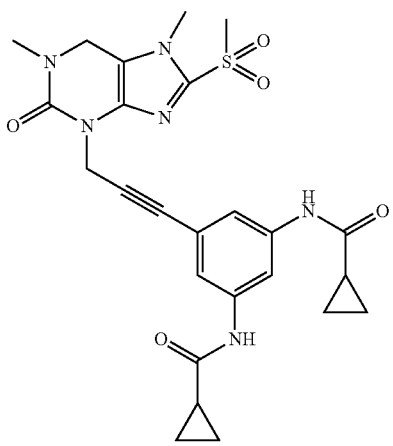 [SMILES: CN1Cc2c(nc(S(C)(=O)=O)n2C)N(CC#Cc2cc(NC(=O)C3CC3)cc(NC(=O)C3CC3)c2)C1=O]
76
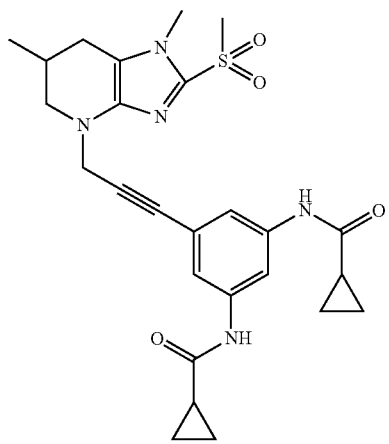 [SMILES: CC1Cc2c(nc(S(C)(=O)=O)n2C)N(CC#Cc2cc(NC(=O)C3CC3)cc(NC(=O)C3CC3)c2)C1]
77
TABLE 2-continued
Series 2 Compounds
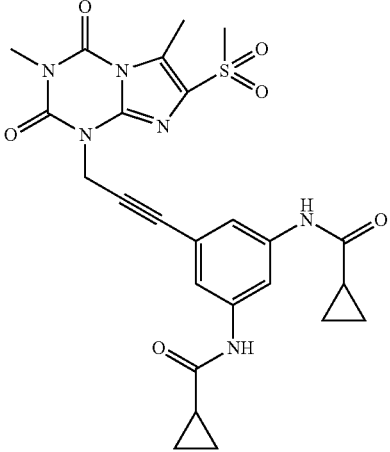 [SMILES: Cc1c(S(C)(=O)=O)nc2n(CC#Cc3cc(NC(=O)C4CC4)cc(NC(=O)C4CC4)c3)c(=O)n(C)c(=O)n12]
78
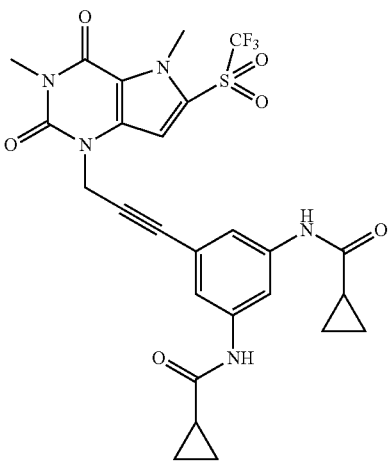 [SMILES: Cn1c(=O)c2c(cc(S(=O)(=O)C(F)(F)F)n2C)n(CC#Cc2cc(NC(=O)C3CC3)cc(NC(=O)C3CC3)c2)c1=O]
79
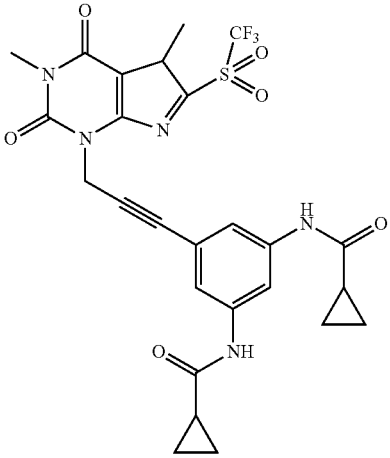 [SMILES: CC1C(S(=O)(=O)C(F)(F)F)=Nc2c1c(=O)n(C)c(=O)n2CC#Cc1cc(NC(=O)C2CC2)cc(NC(=O)C2CC2)c1]
80

TABLE 2-continued
Series 2 Compounds
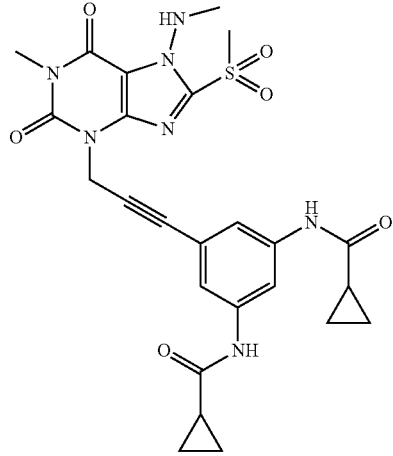 [SMILES: CNn1c(S(C)(=O)=O)nc2c1c(=O)n(C)c(=O)n2CC#Cc1cc(NC(=O)C2CC2)cc(NC(=O)C2CC2)c1]
81
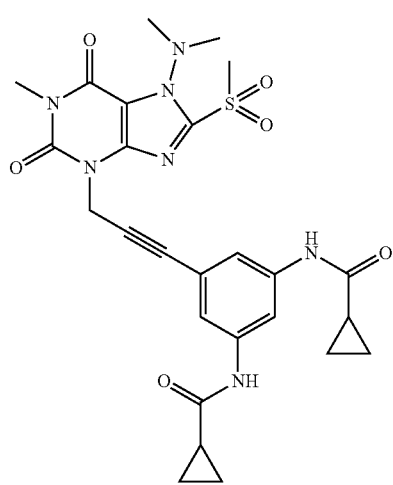 [SMILES: CN(C)n1c(S(C)(=O)=O)nc2c1c(=O)n(C)c(=O)n2CC#Cc1cc(NC(=O)C2CC2)cc(NC(=O)C2CC2)c1]
82
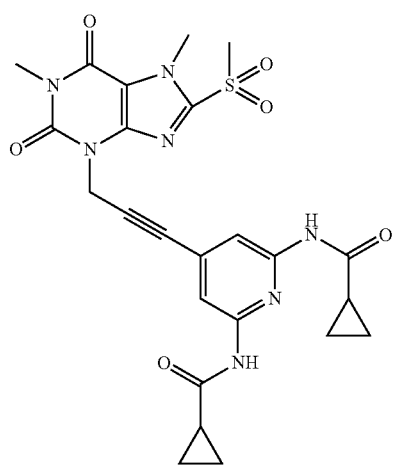 [SMILES: Cn1c(=O)c2c(nc(S(C)(=O)=O)n2C)n(CC#Cc2cc(NC(=O)C3CC3)nc(NC(=O)C3CC3)c2)c1=O]
83
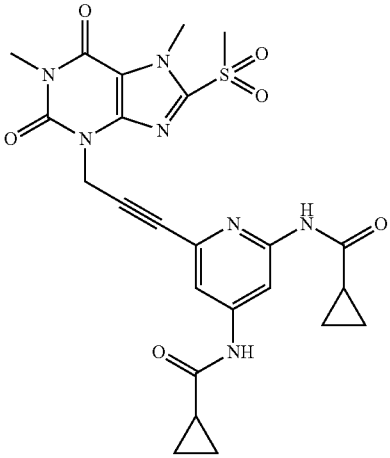 [SMILES: Cn1c(=O)c2c(nc(S(C)(=O)=O)n2C)n(CC#Cc2cc(NC(=O)C3CC3)cc(NC(=O)C3CC3)n2)c1=O]
84
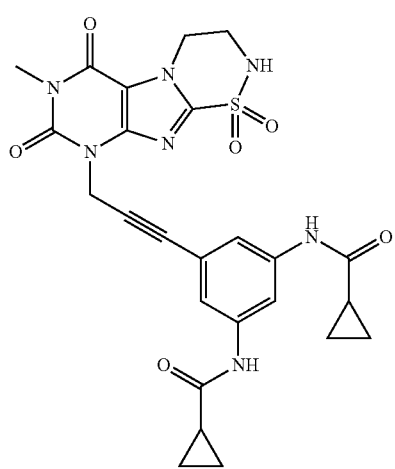 [SMILES: Cn1c(=O)c2c(nc3n2CCNS3(=O)=O)n(CC#Cc2cc(NC(=O)C3CC3)cc(NC(=O)C3CC3)c2)c1=O]
86

TABLE 2-continued
Series 2 Compounds
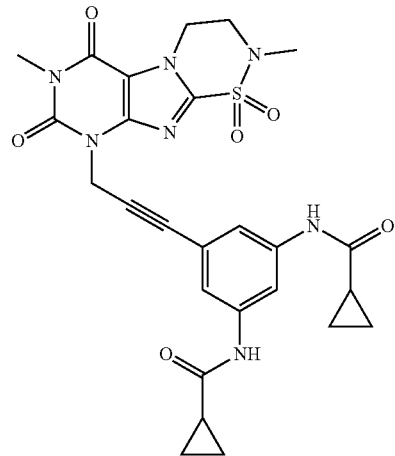 [SMILES: CN1CCn2c(nc3c2c(=O)n(C)c(=O)n3CC#Cc2cc(NC(=O)C3CC3)cc(NC(=O)C3CC3)c2)S1(=O)=O]
87
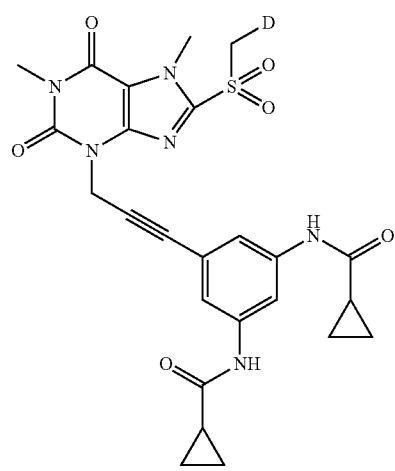 [SMILES: [2H]CS(=O)(=O)c1nc2c(c(=O)n(C)c(=O)n2CC#Cc2cc(NC(=O)C3CC3)cc(NC(=O)C3CC3)c2)n1C]
88
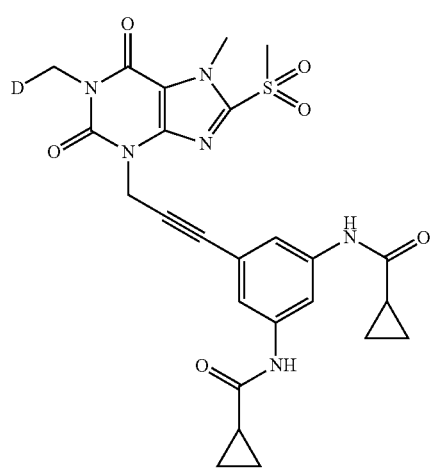 [SMILES: [2H]Cn1c(=O)c2c(nc(S(C)(=O)=O)n2C)n(CC#Cc2cc(NC(=O)C3CC3)cc(NC(=O)C3CC3)c2)c1=O]
89
TABLE 2-continued
Series 2 Compounds
90
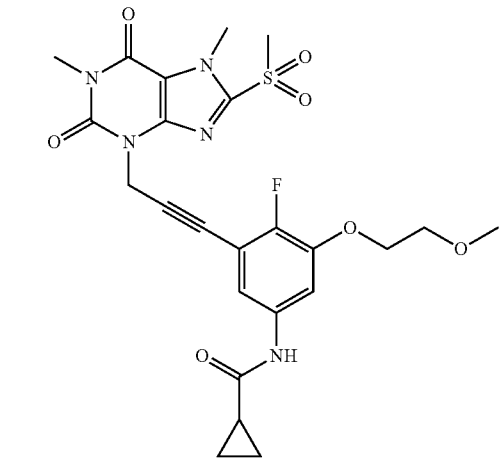
91
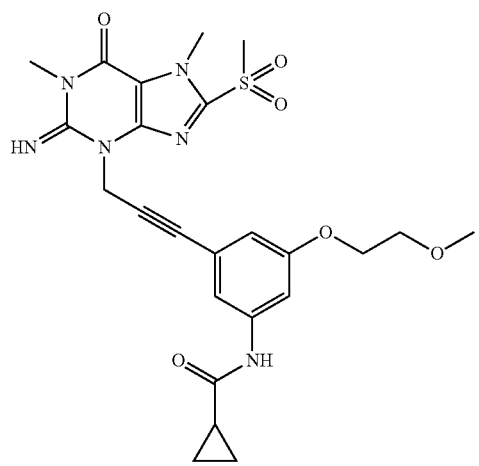
92

TABLE 2-continued
Series 2 Compounds
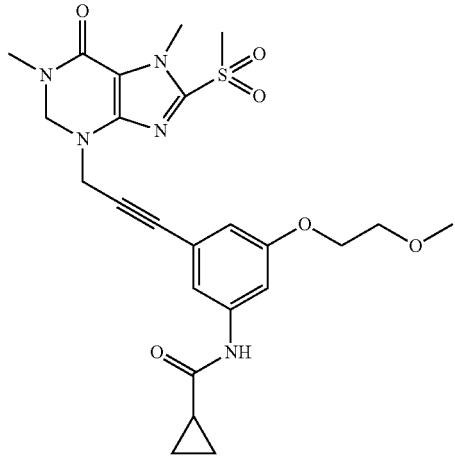
93
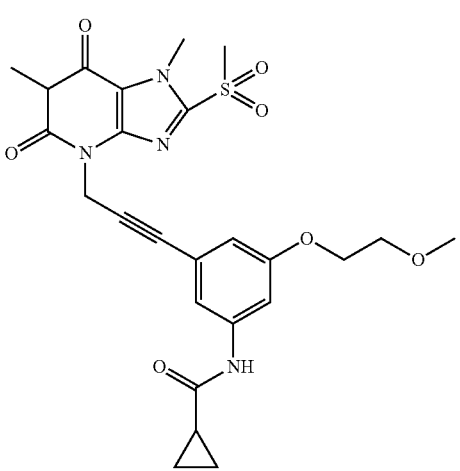
94
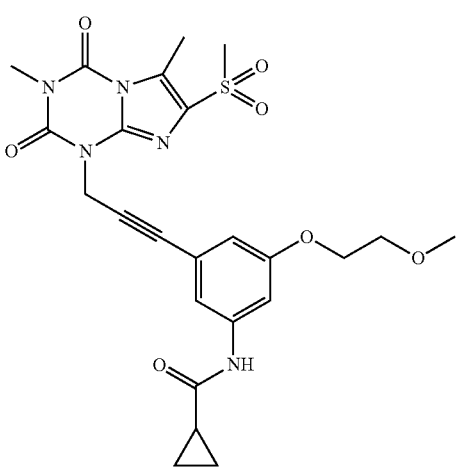
95
TABLE 2-continued
Series 2 Compounds
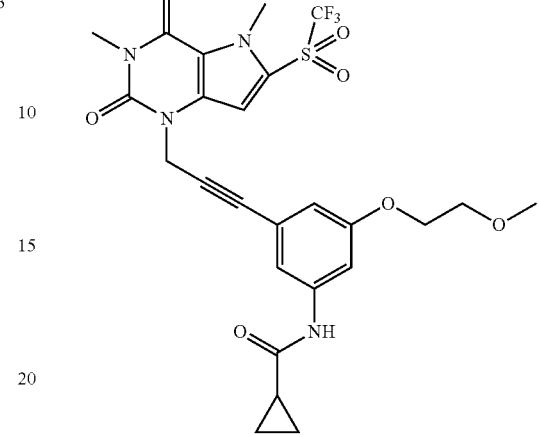
96
97
98
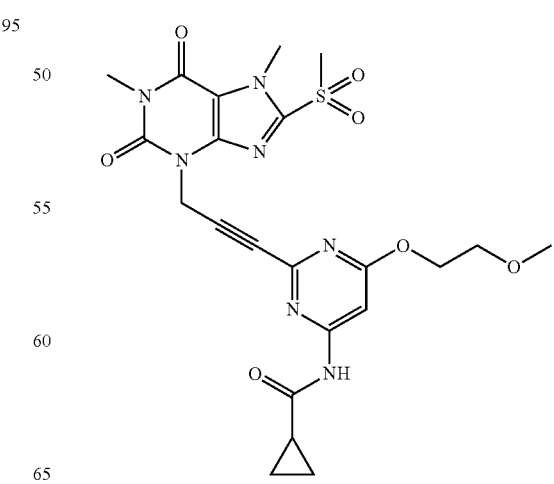

TABLE 2-continued
Series 2 Compounds
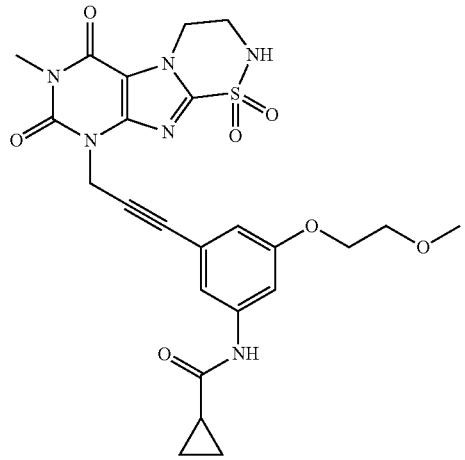
99
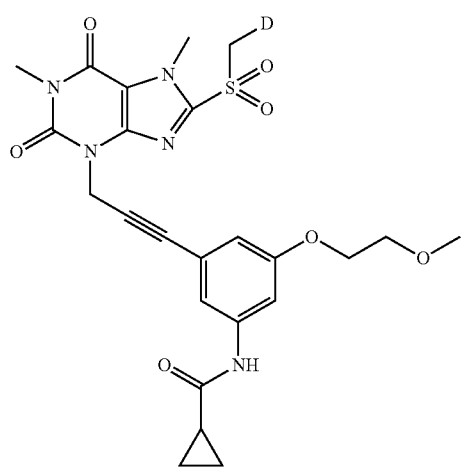
100
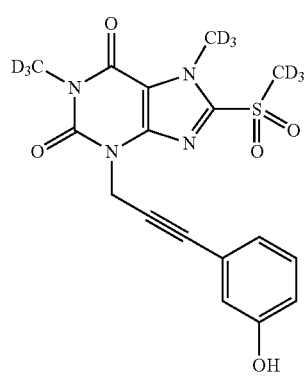 [SMILES: [2H]C([2H])([2H])n1c(=O)c2c(nc(S(=O)(=O)C([2H])([2H])[2H])n2C([2H])([2H])[2H])n(CC#Cc2cccc(O)c2)c1=O]
101
TABLE 2-continued
Series 2 Compounds
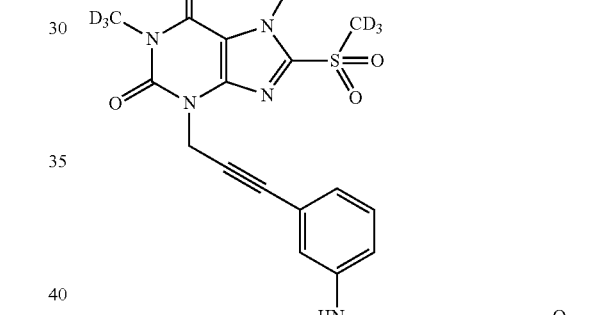
102
103
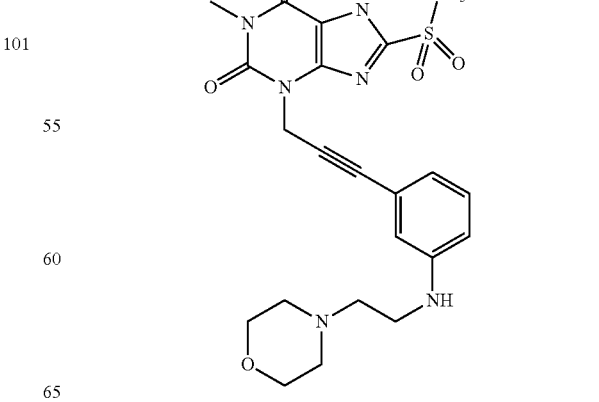
104

TABLE 2-continued
Series 2 Compounds
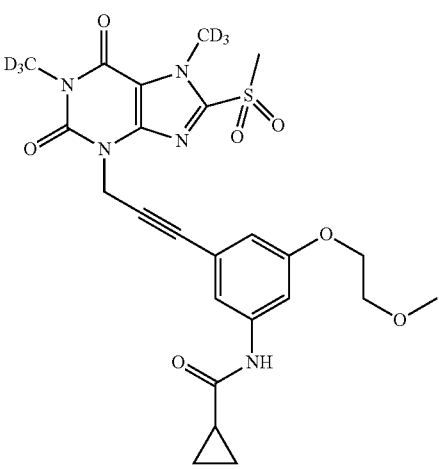 [SMILES: [2H]C([2H])([2H])n1c(=O)c2c(nc(S(C)(=O)=O)n2C([2H])([2H])[2H])n(CC#Cc2cc(NC(=O)C3CC3)cc(OCCOC)c2)c1=O]
105
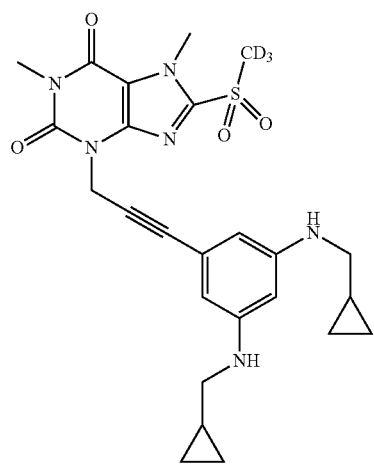 [SMILES: [2H]C([2H])([2H])S(=O)(=O)c1nc2c(c(=O)n(C)c(=O)n2CC#Cc2cc(NCC3CC3)cc(NCC3CC3)c2)n1C]
107
TABLE 2-continued
Series 2 Compounds
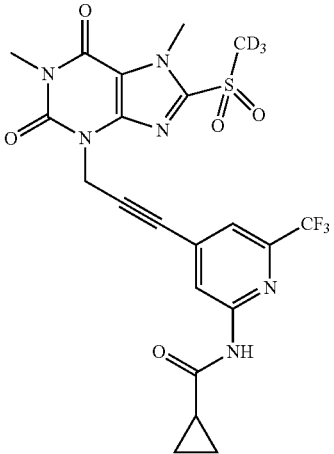 [SMILES: [2H]C([2H])([2H])S(=O)(=O)c1nc2c(c(=O)n(C)c(=O)n2CC#Cc2cc(NC(=O)C3CC3)nc(C(F)(F)F)c2)n1C]
108
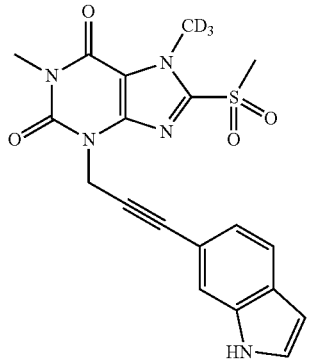 [SMILES: [2H]C([2H])([2H])n1c(S(C)(=O)=O)nc2c1c(=O)n(C)c(=O)n2CC#Cc1ccc2cc[nH]c2c1]
109
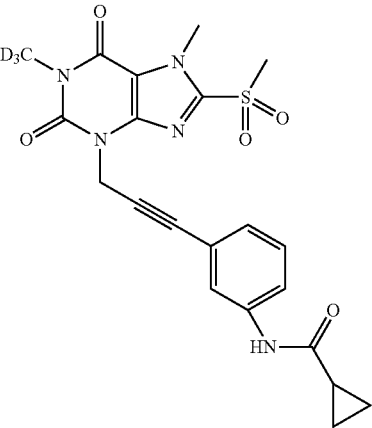 [SMILES: [2H]C([2H])([2H])n1c(=O)c2c(nc(S(C)(=O)=O)n2C)n(CC#Cc2cccc(NC(=O)C3CC3)c2)c1=O]
110

TABLE 2-continued
Series 2 Compounds
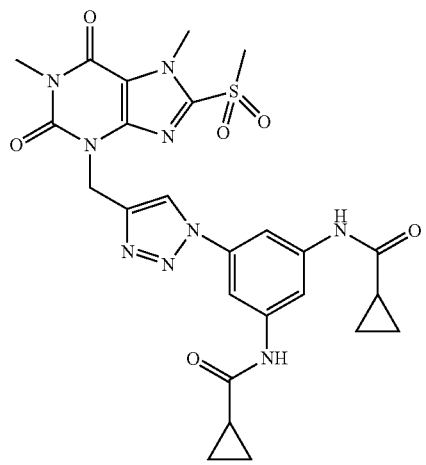
111
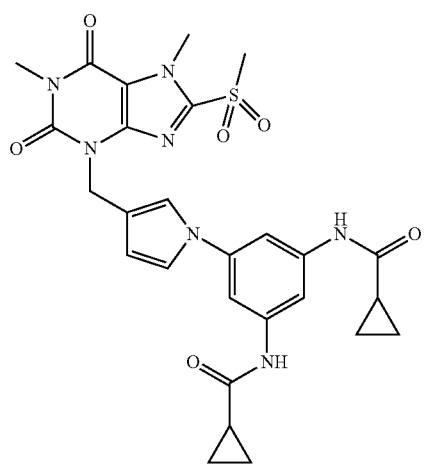 [SMILES: Cn1c(=O)c2c(nc(S(C)(=O)=O)n2C)n(Cc2ccn(-c3cc(NC(=O)C4CC4)cc(NC(=O)C4CC4)c3)c2)c1=O]
112
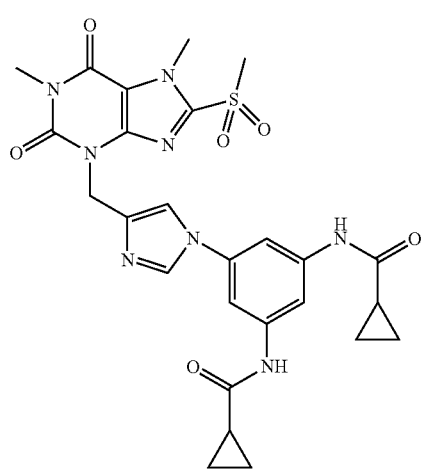 [SMILES: Cn1c(=O)c2c(nc(S(C)(=O)=O)n2C)n(Cc2cn(-c3cc(NC(=O)C4CC4)cc(NC(=O)C4CC4)c3)cn2)c1=O]
113
TABLE 2-continued
Series 2 Compounds
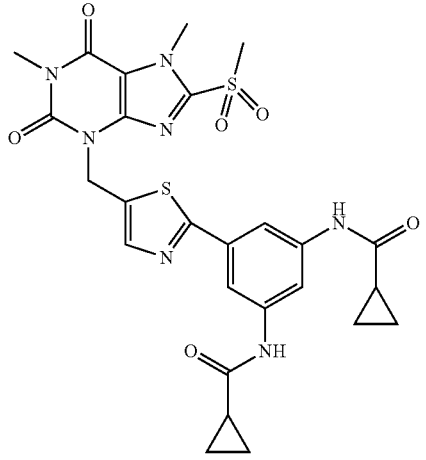 [SMILES: Cn1c(=O)c2c(nc(S(C)(=O)=O)n2C)n(Cc2cnc(-c3cc(NC(=O)C4CC4)cc(NC(=O)C4CC4)c3)s2)c1=O]
114
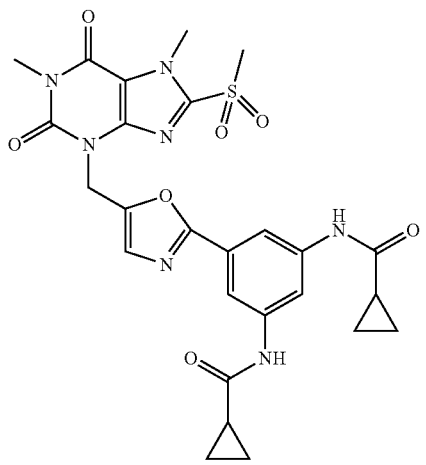
115
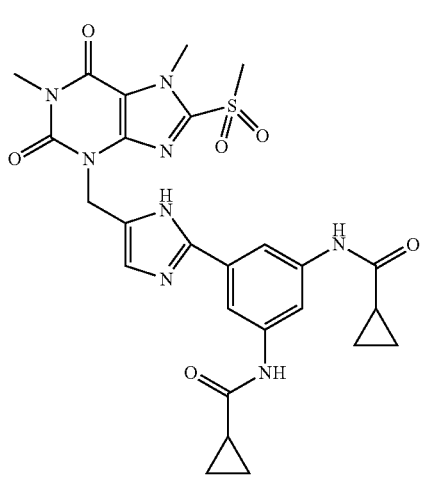
116

TABLE 2-continued
Series 2 Compounds
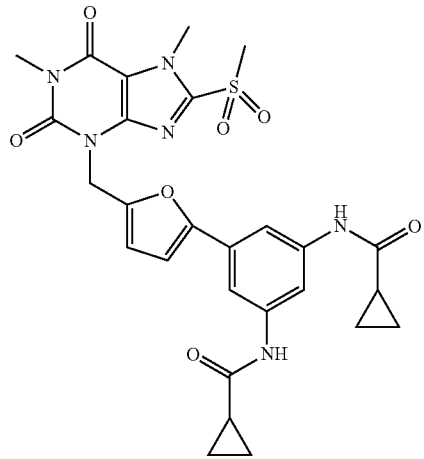 [SMILES: Cn1c(=O)c2c(nc(S(C)(=O)=O)n2C)n(Cc2ccc(-c3cc(NC(=O)C4CC4)cc(NC(=O)C4CC4)c3)o2)c1=O]
117
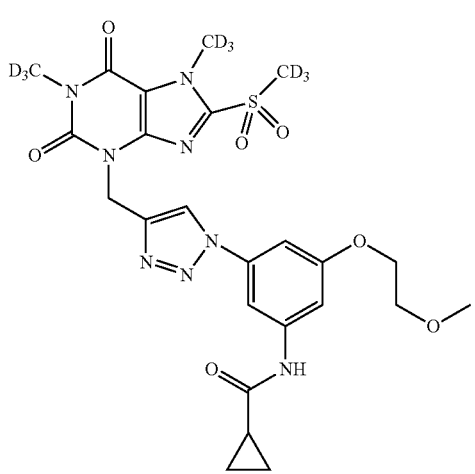
120
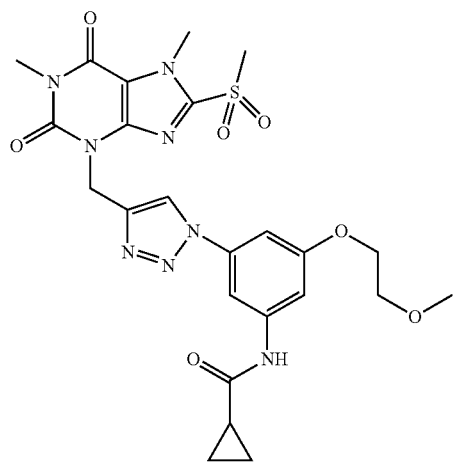
118
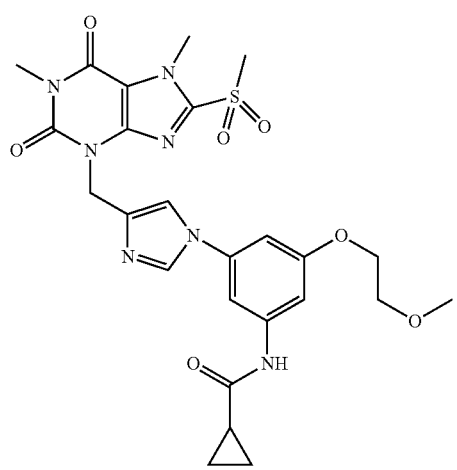
119
Series 2; Compound 1
8-((2-hydroxyethyl)sulfonyl)-1,3,7-trimethyl-3,7-dihydro-1H-purine-2,6-dione
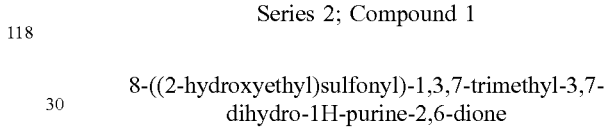
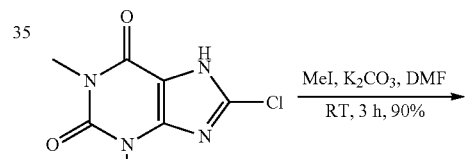
1-1
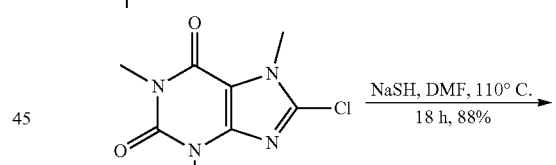
1-2
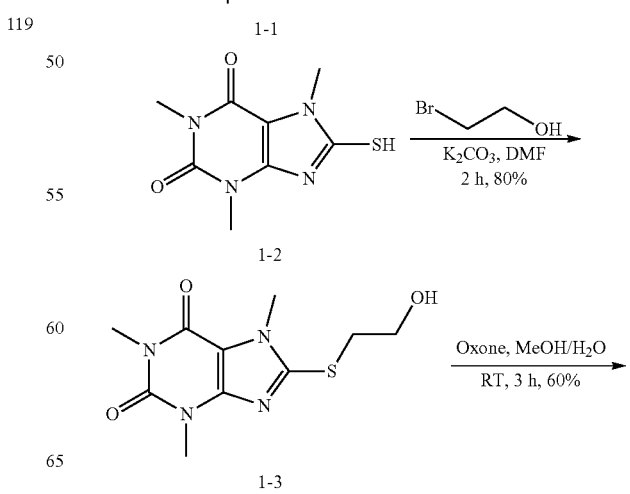
1-3

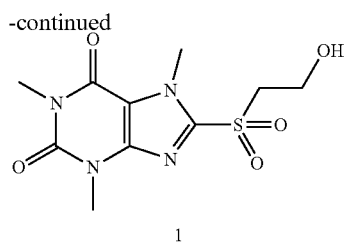

1

Step 1.

To a solution of 8-chloro-1,3-dimethyl-3,7-dihydro-1H-purine-2,6-dione (428 mg, 2.0 mmol) in DMF (6 mL) were added MeI (188 µL, 3.0 mmol) and K₂CO₃ (414 mg, 3.0 mmol). Then the mixture was stirred at RT for 3 hours. The reaction mixture was extracted by EtOAc and H₂O 3 times. The organic layer was combined, washed with brine, dried over Na₂SO₄, concentrated and further purified by silica gel column chromatography (DCM/MeOH=200/1) to give 409 mg 1-1 as a yellow solid (90%). LC-MS (ESI) m/z: calcd for [M+H]⁺, 229.04, found 229.06.

Step 2.

NaSCH₃ (170 mg, 3.0 mmol) was added to a solution of 1-1 (456 mg, 2.0 mmol) in DMF (6 mL). The reaction mixture was stirred at 110° C. for 18 hours. The solvent was evaporated under reduced pressure and further purified by silica gel column chromatography (DCM/MeOH=100/1) to give 93 mg of 1-2 (88%). LC-MS (ESI) m/z: calcd for [M+H]⁺, 227.05, found 227.03.

Step 3.

To a solution of 1-2 (40 mg, 0.18 mmol) and K₂CO₃ (61 mg, 0.44 mmol) in anhydrous DMF (2 mL) was added 2-Bromoethanol (23 µL, 0.33 mmol)) and stirred under nitrogen at RT for 3 hours. The reaction mixture was poured into water and extracted with ethyl acetate (3×5 mL) and the organic layer was separated, dried over Na₂SO₄, filtered, concentrated and further purified by silica gel column chromatography (EA/PE=30/70) to give 47 mg of 1-3 (80%). LC-MS (ESI) m/z: calcd for [M+H]⁺, 271.08, found 271.06.

Step 4.

To a solution of 1-3 (47 mg, 0.18 mmol) in MeOH (2 mL) was added Oxone (214 mg, 0.35 mmol) in H₂O (2 mL). Then the mixture was stirred at RT for 3 hours. Then the solvent was removed and extracted with dichloromethane (3×5 mL) and the organic layer was separated, dried over Na₂SO₄, filtered, concentrated and purified by Prep. TLC to obtain compound 1 31.7 mg (60%) as a white solid. ¹H NMR (400 Hz, CDCl3) δ 4.34 (s, 3H), 4.20 (t, J=5.6 Hz, 2H), 3.77 (t, J=5.6 Hz, 2H), 3.56 (s, 3H), 3.42 (s, 3H). LC-MS (ESI) m/z: calcd for [M+H]⁺, 303.07, found 303.16.

Compound 2

8-((2-methoxyethyl)sulfonyl)-1,3,7-trimethyl-3,7-dihydro-1H-purine-2,6-dione

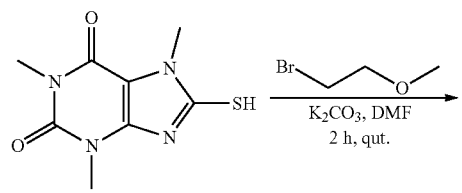

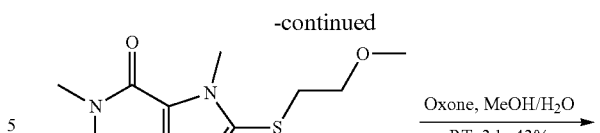

2-1

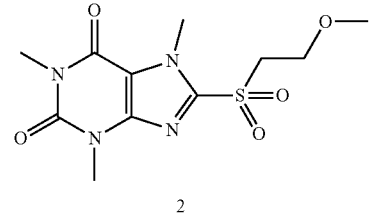

2

Step 1.

2-1 was prepared in a yield of 100% (50 mg) from 1-2 (40 mg, 0.175 mmol) and 1-bromo-2-methoxyethane (31 µL, 0.33 mmol) according to the procedure for 1. LC-MS (ESI) m/z: calcd for [M+H]⁺, 285.09, found 285.13.

Step 2.

2 was prepared in a yield of 43% (24 mg) from 2-1 (50 mg, 0.18 mmol) and Oxone (214 mg, 0.35 mmol) as a yellow solid according to the procedure for 1. ¹H NMR (400 Hz, CDCl3) δ 4.29 (s, 3H), 3.87 (t, J=5.6 Hz, 2H), 3.73 (t, J=5.6 Hz, 2H), 3.57 (s, 3H), 3.41 (s, 3H), 3.25 (s, 3H). LC-MS (ESI) m/z: calcd for [M+H]⁺, 317.08, found 317.20.

Compound 3:

8-((3-hydroxypropyl)sulfonyl)-1,3,7-trimethyl-3,7-dihydro-1H-purine-2,6-dione

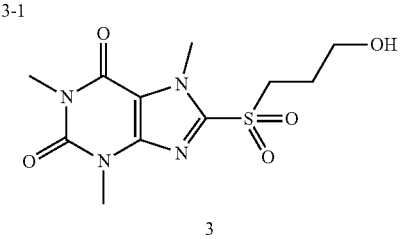

3-1

3

Step 1.

3-1 was prepared in a yield of 100% (49 mg) from 1-2 (40 mg, 0.175 mmol) and 3-bromopropan-1-ol (25 µL, 0.26 mmol) according to the procedure for compound 1. LC-MS (ESI) m/z: calcd for [M+H]⁺, 285.09, found 285.13.

Step 2.

3 was prepared in a yield of 32% (17.8 mg) from 3-1 (49 mg, 0.18 mmol) and Oxone (214 mg, 0.35 mmol) as a yellow solid according to the procedure for 1. $^1$H NMR (400 Hz, CDCl3) δ 4.32 (s, 3H), 3.80 (m, 2H), 9.71 (m, 3H), 3.56 (s, 2H), 3.41 (s, 3H), 2.15 (m, 3H). LC-MS (ESI) m/z: calcd for [M+H]$^+$, 317.08, found 317.20.

Compound 4

8-((cyclopropylmethyl)sulfonyl)-7-ethyl-1,3-dimethyl-1H-purine-2,6(3H,7H)-dione

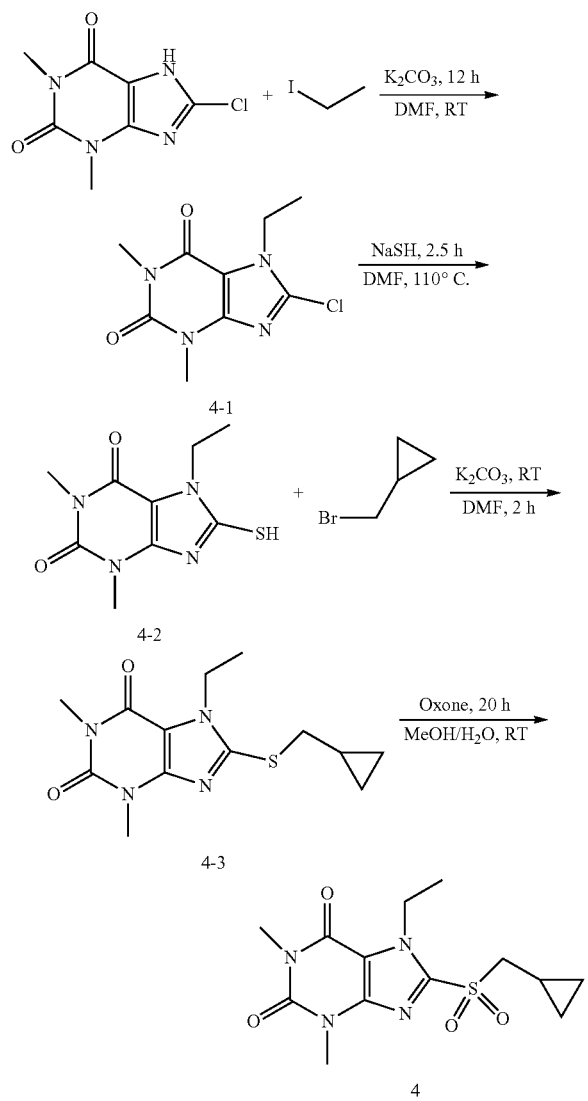

Step 1.

To a solution of 8-chloro-1,3-dimethyl-3,7-dihydro-1H-purine-2,6-dione (500 mg, 2.3 mmol) in DMF (10 mL) was added iodoethane (437 mg, 2.8 mmol) and K$_2$CO$_3$ (483 mg, 3.5 mmol) at rt, then the mixture was stirred at rt overnight. UPLC-MS monitored the completion of the reaction. Then the solvent was evaporated to get crude 566 mg 4-1 as a yellow solid and without any further purification. LC-MS (ESI) m/z: calcd for [M+H]$^+$, 243.06, found 243.12.

Step 2.

To a solution of 4-1 (566 mg, 2.3 mmol) in DMF (10 mL) was added NaSH (170 mg, 3.03 mmol) at r.t. Then the mixture was stirred at 110° C. for 2 hours. UPLC-MS monitored the completion of the reaction. Then the solvent was evaporated to get crude 500 mg 4-2 as a yellow solid and without any further purification. LC-MS (ESI) m/z: calcd for [M+H]$^+$, 241.07, found 241.01.

Step 3.

To a solution of 4-2 (200 mg, 0.83 mmol) in DMF (3 mL) was added (bromomethyl)cyclopropane (135 mg, 1.0 mmol) and K$_2$CO$_3$ (173 mg, 1.25 mmol) at r.t., then the mixture was stirred at r.t. for 2 hours. UPLC-MS monitored the completion of the reaction. The reaction mixture was poured into water and extracted with DCM. The organic layer was separated, and the aqueous layer was repeatedly extracted with DCM (2×20 mL). The combined extracts were dried with Na$_2$SO$_4$ and concentrated. The resulting residue was purified by silica gel chromatography (PE:EA=1:1) to give 234 mg of 4-3 as a yellow solid, yield: 95%. LC-MS (ESI) m/z: calcd for [M+H]$^+$, 295.12, found 295.20.

Step 4.

To a solution of 4-3 (100 mg, 0.34 mmol) in methanol (3 mL) and H$_2$O (1 mL) was added Oxone (626 mg, 1.2 mmol). Then the mixture was stirred at r.t. for 20 hours. UPLC-MS monitored the completion of the reaction. The reaction mixture was poured into water and extracted with DCM. The organic layer was separated, and the aqueous layer was repeatedly extracted with DCM (2×20 mL). The combined extracts were dried with Na$_2$SO$_4$ and concentrated. The resulting residue was purified by silica gel chromatography (PE:EA=5:1) to give 72 mg of 4 as a yellow solid, yield: 64.9%. 1H NMR (400 MHz, CDCl$_3$) δ 4.67 (q, J=8 Hz, 2H), 3.98-3.93 (m, 2H), 3.41 (s, 3H), 3.32-3.29 (m, 3H), 1.38 (t, J=8 Hz, 3H), 1.04-0.96 (m, 1H), 0.53 (q, J=4 Hz, 2H), 0.18 (q, J=4 Hz, 2H). LC-MS (ESI) m/z: calcd for [M+H]$^+$, 327.10, found 327.37.

Compound 5:

7-(2-hydroxyethyl)-1,3-dimethyl-8-(methylsulfonyl)-3,7-dihydro-1H-purine-2,6-dione

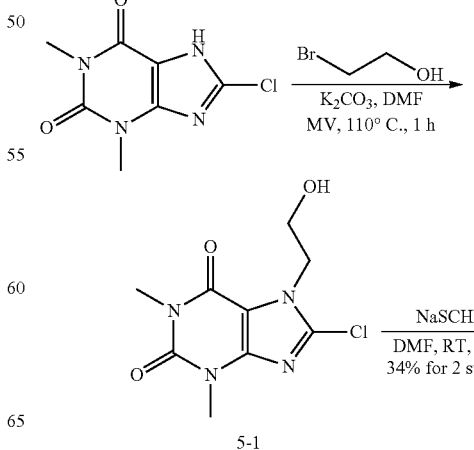

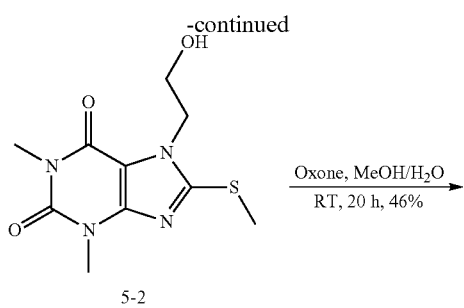

5-2

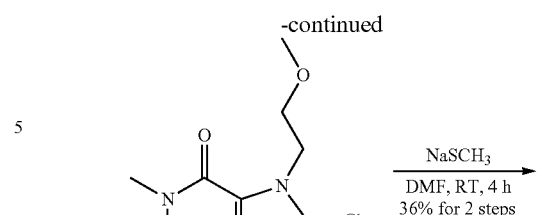

6-1

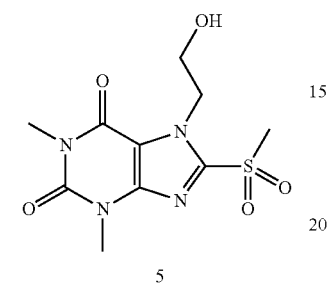

5

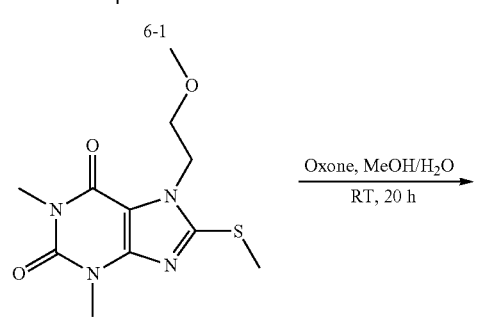

6-2

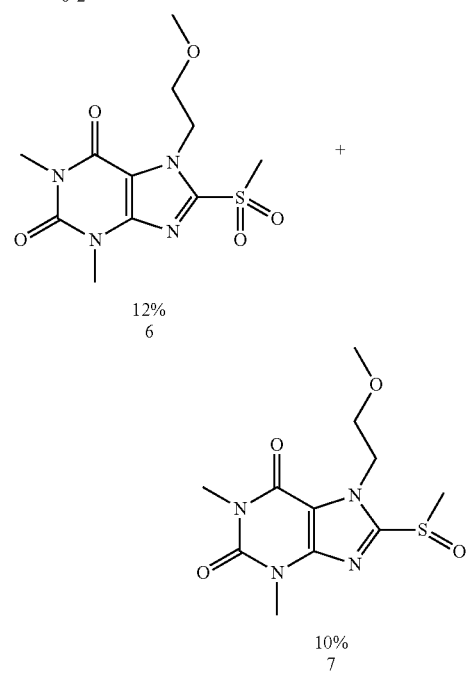

Step 1.

To a solution of 8-chloro-1,3-dimethyl-3,7-dihydro-1H-purine-2,6-dione (214 mg, 1.0 mmol) in DMF (5 mL), 2-Bromoethanol (106 μL, 1.5 mmol) and $K_2CO_3$ (276 mg, 2.0 mmol) were added. The mixture was heated to 110° C. for 1 hours by microwave irradiation. The solvent was evaporated under reduced pressure to provide crude product 5-1 which was used in the next reaction step without any further purification. For 5-1, LC-MS (ESI) m/z: calcd for $[M+H]^+$, 259.05, found 259.11.

Step 2.

$NaSCH_3$ (105 mg, 1.5 mmol) was added to a solution of 5-1 in DMF (4 mL). The reaction mixture was stirred at room temperature for 4 hours. The solvent was evaporated under reduced pressure to provide crude product 5-2 and further purified by silica gel column chromatography (DCM/MeOH=100/1) to give 5-2 as a white solid (34% for two steps). LC-MS (ESI) m/z: calcd for $[M+H]^+$, 271.08, found 271.01.

Step 3.

5 was prepared in a yield of 46% (21.0 mg) from 5-2 (40 mg, 0.15 mmol) and Oxone (272 mg, 0.44 mmol) as a white solid according to the procedure for 1. $^1$H NMR (400 Hz, CDCl3) δ 4.94 (t, J=5.2 Hz, 2H), 4.05 (t, J=5.2 Hz, 2H), 3.58 (s, 3H), 3.45 (s, 3H), 3.42 (s, 3H). LC-MS (ESI) m/z: calcd for $[M+H]^+$, 303.27, found 303.34.

Compound 6: 7-(2-methoxyethyl)-1,3-dimethyl-8-(methylsulfonyl)-3,7-dihydro-1H-purine-2,6-dione and Compound 7: 7-(2-methoxyethyl)-1,3-dimethyl-8-(methylsulfinyl)-3,7-dihydro-1H-purine-2,6-dione

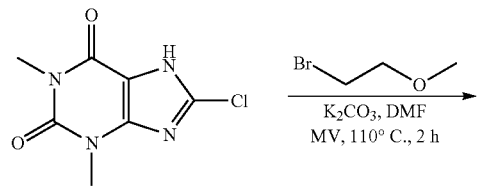

Step 1.

6-1 was prepared from 8-chloro-1,3-dimethyl-1H-purine-2,6(3H,7H)-dione (214 mg, 1.0 mmol) and 1-bromo-2-methoxyethane according to the procedure for compound 1. 6-1 was used in the next reaction step without any further purification LC-MS (ESI) m/z: calcd for $[M+H]^+$, 273.07, found 273.13.

Step 2.

6-2 was prepared in a yield of 36% (2 steps) from 6-1 (2724 mg, 1.0 mmol) and $NaSCH_3$ (105 mg, 1.5 mmol) according to the procedure for 1. LC-MS (ESI) m/z: calcd for $[M+H]^+$, 285.09, found 285.13.

Step 3.

6 was prepared in a yield of 12% (10.0 mg) from 6-2 (80 mg, 0.28 mmol) and oxone (522 mg, 0.85 mmol) as a white solid according to the procedure for 1. ¹H NMR: (400 Mz, CDCl3): δ 4.49 (t, J=5.2 Hz, 2H), 3.74 (t, J=5.2 Hz, 2H), 3.54 (s, 3H), 3.37 (s, 3H), 3.32 (s, 3H) 3.31 (s, 3H). LC-MS (ESI) m/z: calcd for [M+H]⁺, 317.18, found 317.24.

7 was prepared in a yield of 10% (9.2 mg) from 6-2 (80 mg, 0.28 mmol) and Oxone (522 mg, 0.85 mmol) as a white solid according to the procedure for 1. ¹H NMR: (400 Mz, CDCl3): δ 4.93-4.88 (m, 1H), 4.69-4.63 (m, 1H), 3.71-3.65 (m, 2H), 3.59 (s, 3H), 3.39 (s, 3H), 3.27 (s, 3H), 3.21 (s, 3H). LC-MS (ESI) m/z: calcd for [M+H]⁺, 301.20, found 301.21.

Compound 8: 3-(3-(3-hydroxyphenyl)prop-2-yn-1-yl)-1,7-dimethyl-8-(methylsulfinyl)-3,7-dihydro-1H-purine-2,6-dione

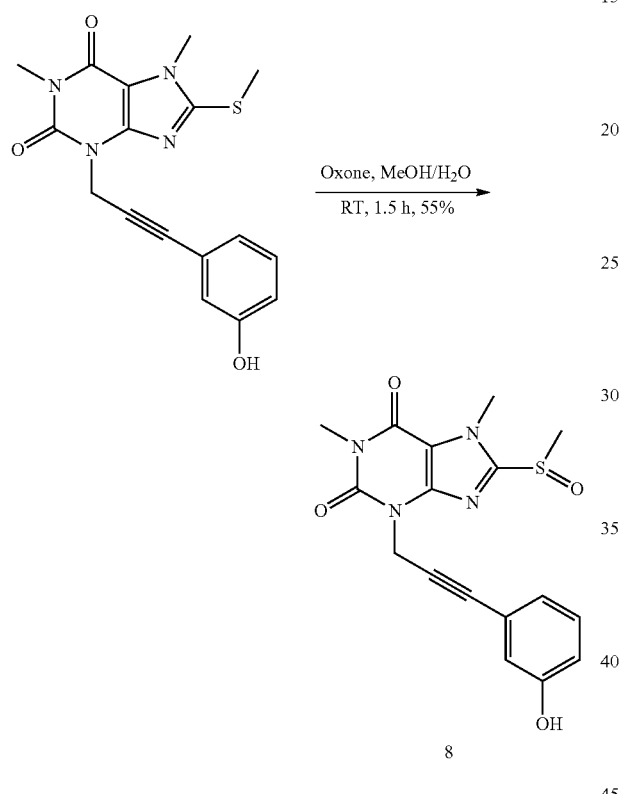

8 was prepared in a yield of 55% (9.8 mg) from 3-(3-(3-hydroxyphenyl)prop-2-yn-1-yl)-1,7-dimethyl-8-(methylthio)-3,7-dihydro-1H-purine-2,6-dione (17 mg, 0.048 mmol) and Oxone (73 mg, 0.12 mmol) as a yellow solid according to the procedure for compound 1. ¹H NMR (400 Hz, CDCl3) δ 7.08 (m, 1H), 6.90 (m, 1H), 8.84 (m, 1H), 6.75 (m, 1H), 5.04 (s, 2H), 4.24 (s, 3H), 3.43 (s, 3H), 3.23 (s, 3H). LC-MS (ESI) m/z: calcd for [M+H]⁺, 373.09, found 373.13.

Compound 9: 3-(3-(1H-indol-6-yl)prop-2-yn-1-yl)-1,7-dimethyl-8(methylsulfonyl)-1H-purine-2,6(3H,7H)-dione

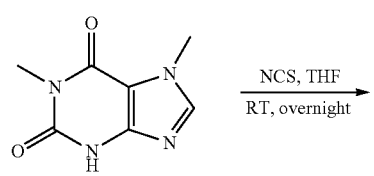

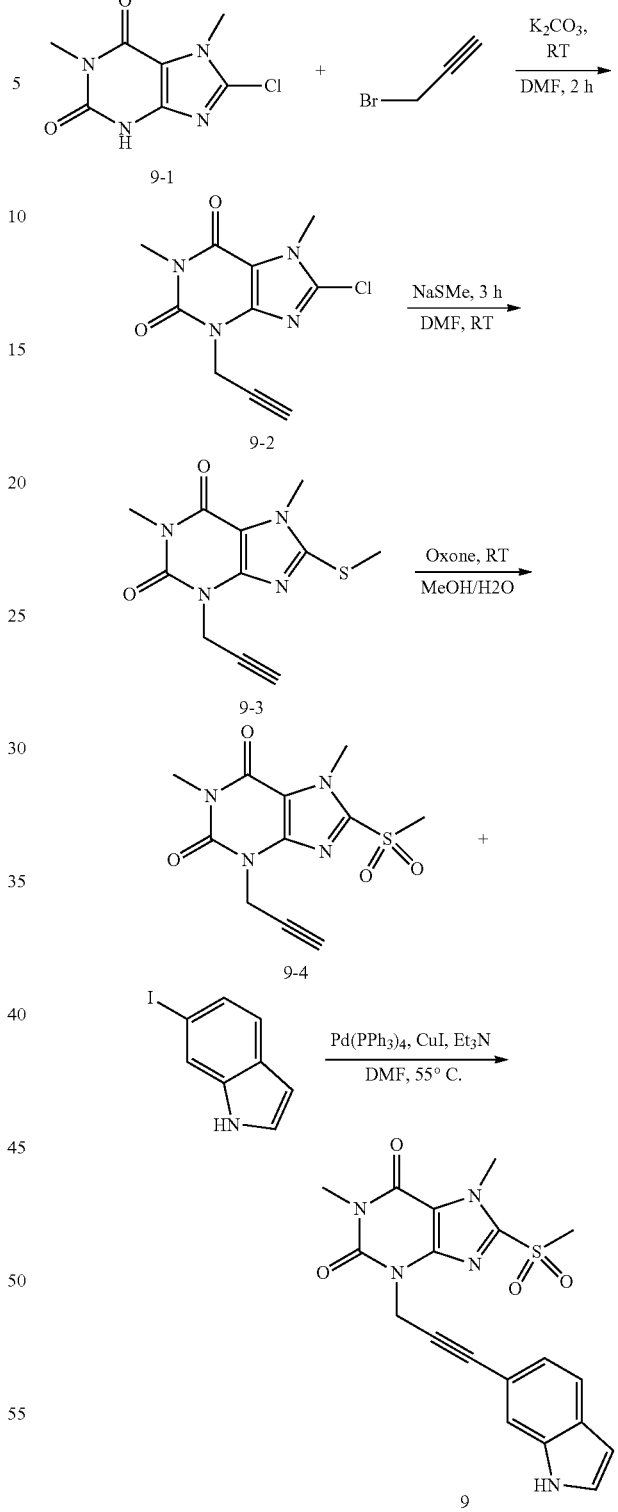

Step 1.

To a solution of 1,7-dimethyl-1H-purine-2,6(3H,7H)-dione (748 mg, 4.2 mmol) in THF (20 mL) was added NCS (832 mg, 6.3 mmol) under N₂ atmosphere. Then the mixture was stirred at r.t. overnight. UPLC-MS monitored the completion of the reaction. The reaction mixture was poured into water and extracted with DCM. The organic layer was separated, and the aqueous layer was repeatedly extracted with DCM (2×20 mL). The combined extracts were dried with Na$_2$SO$_4$ and concentrated. The resulting residue was purified by silica gel chromatography (PE:EA=5:1) to give 908 mg of 9-1 as a yellow solid, yield: 100%. LC-MS (ESI) m/z: calcd for [M+H]$^+$, 215.03, found 215.09.

Step 2.

To a solution of 9-1 (1.33 g, 6.2 mmol) in DMF (20 mL) was added 3-bromoprop-1-yne (1.47 g, 12.4 mmol) and K$_2$CO$_3$ (1.71 g, 12.4 mmol) at r.t., then the mixture was stirred at r.t. for 2 hours. UPLC-MS monitored the completion of the reaction. The reaction mixture was poured into water and extracted with DCM. The organic layer was separated, and the aqueous layer was repeatedly extracted with DCM (2×20 mL). The combined extracts were dried with Na$_2$SO$_4$ and concentrated. The resulting residue was purified by silica gel chromatography (PE:EA=3:1) to give 2.01 g of 9-2 as a yellow solid, yield: 93.5%. LC-MS (ESI) m/z: calcd for [M+H]$^+$, 253.03, found 253.05.

Step 3.

To a solution of 9-2 (200 mg, 0.80 mmol) in DMF (5 mL) was added NaSMe (67 mg, 0.95 mmol) at r.t. Then the mixture was stirred at r.t. for 2 hours. UPLC-MS monitored the completion of the reaction. The reaction mixture was poured into water and extracted with DCM. The organic layer was separated, and the aqueous layer was repeatedly extracted with DCM (2×20 mL). The combined extracts were dried with Na$_2$SO$_4$ and concentrated. The resulting residue was purified by silica gel chromatography (PE: EA=3:1) to give 271 mg of 9-3 as a yellow solid, yield: 90%. LC-MS (ESI) m/z: calcd for [M+H]$^+$, 264.07, found 264.12.

Step 4.

To a solution of 9-3 (271 mg, 0.79 mmol) in methanol (9 mL) and H$_2$O (3 mL) was added Oxone (1.46 g, 2.38 mmol). Then the mixture was stirred at r.t. for 20 hours. UPLC-MS monitored the completion of the reaction. The reaction mixture was poured into water and extracted with DCM. The organic layer was separated, and the aqueous layer was repeatedly extracted with DCM (2×20 mL). The combined extracts were dried with Na$_2$SO$_4$ and concentrated. The resulting residue was purified by silica gel chromatography (PE:EA=5:1) to give 205 mg of 9-4 as a yellow solid, yield: 87.2%. LC-MS (ESI) m/z: calcd for [M+H]$^+$, 297.06, found 297.12.

Step 5.

To a solution of 9-4 (40 mg, 0.14 mmol) in DMF (2 mL) was added 6-iodo-1H-indole (40 mg, 0.16 mmol), TEA (33 mg, 0.32 mmol), Pd(PPh$_3$)$_4$ (8 mg, 0.007 mmol) and CuI (3 mg, 0.014 mmol) under N$_2$ atmosphere. Then the mixture was degassed for 15 min. Then the mixture was stirred at 55° C. for 4 hours. UPLC-MS monitored the completion of the reaction. The reaction mixture was poured into water and extracted with DCM. The organic layer was separated, and the aqueous layer was repeatedly extracted with DCM (2×20 mL). The combined extracts were dried with Na$_2$SO$_4$ and concentrated. The resulting residue was purified by silica gel chromatography (PE:EA=1:1) to give 20 mg of 9 as a yellow solid, yield: 36.4%. 1H NMR (400 MHz, DMSO) δ 11.23 (s, 1H), 7.50 (d, J=8 Hz, 1H), 7.44-7.42 (m, 2H), 6.99 (d, J=8 Hz, 1H), 6.43 (s, 1H), 5.01 (s, 2H), 4.22 (s, 3H), 3.56 (s, 3H), 3.29 (s, 3H). LC-MS (ESI) m/z: calcd for [M+H]$^+$, 412.40, found 412.43.

Compound 10: N-(3-(3-(1,7-dimethyl-8-(methyl-sulfonyl)-2,6-dioxo-1H-purin-3(2H,6H,7H)-yl)prop-1-yn-1-yl)phenyl)acetamide

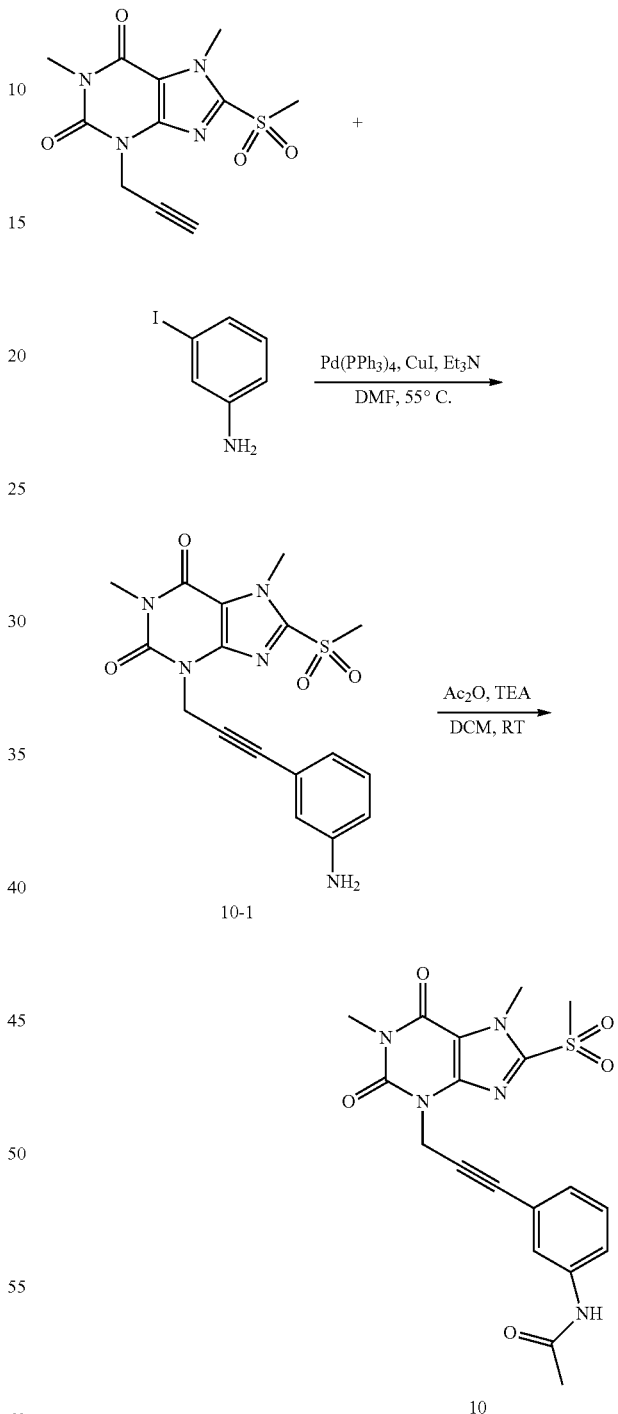

Step 1.

10-1 was prepared n a yield of 74% (48 mg) from 9-4 (50 mg, 0.17 mmol) and 3-iodoaniline (45 mg, 0.20 mmol) according to the procedure for compound 9. LC-MS (ESI) m/z: calcd for [M+H]$^+$, 388.10, found 388.19.

Step 2.

To a solution of 10-1 (20 mg, 0.052 mmol) in DCM (2 mL) was added TEA (12 mg, 0.11 mmol) and Ac$_2$O (7 mg, 0.062 mmol) at 0° C. Then the mixture was stirred at r.t. for 3 hours. UPLC-MS monitored the completion of the reaction. The reaction mixture was poured into water and extracted with DCM. The organic layer was separated, and the aqueous layer was repeatedly extracted with DCM (2×20 mL). The combined extracts were dried with Na$_2$SO$_4$ and concentrated. The resulting residue was purified by silica gel chromatography (PE:EA=1:1) to give 14 mg of 10 as a yellow solid, yield: 63.6%. 1H NMR (400 MHz, DMSO) δ 10.00 (s, 1H), 7.74 (t, J=4 Hz, 1H), 7.48-7.45 (m, 1H), 7.27 (t, J=8 Hz, 1H), 7.08-7.05 (m, 1H), 5.00 (s, 2H), 4.21 (s, 3H), 3.54 (s, 3H), 3.28 (s, 3H), 2.03 (s, 3H). LC-MS (ESI) m/z: calcd for [M+H]$^+$, 430.41, found 430.45.

Compound 11: N-(3-(3-(1,7-dimethyl-8-(methylsulfonyl)-2,6-dioxo-1H-purin-3(2H,6H,7H)-yl)prop-1-yn-1-yl)phenyl)benzamide

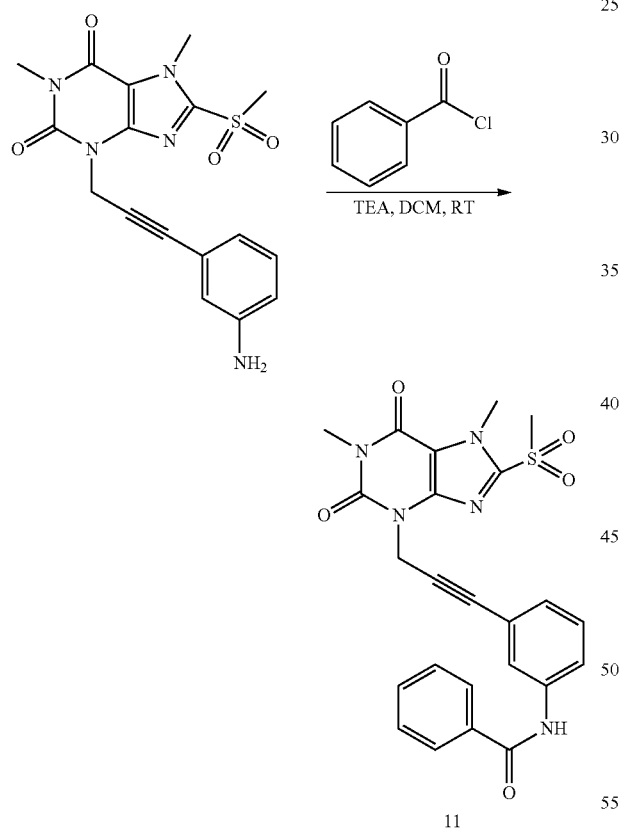

11 was prepared in a yield of 55% (16 mg) from 10-1 (24 mg, 0.062 mmol), TEA (14 mg, 0.14 mmol) and benzoyl chloride (11 mg, 0.074 mmol) according to the procedure for compound 10. $^1$H NMR (400 MHz, DMSO) δ 10.30 (s, 1H), 7.94 (s, 1H), 7.93-7.92 (m, 2H), 7.77-7.74 (m, 1H), 7.60-7.58 (m, 1H), 7.55-7.51 (m, 2H), 7.35 (t, J=8 Hz, 1H), 7.16-7.14 (m, 1H), 5.02 (s, 2H), 4.21 (s, 3H), 3.56 (s, 3H), 3.29 (s, 3H). 492.52. LC-MS (ESI) m/z: calcd for [M+H]$^+$, 492.13, found 492.20.

Compound 12: 3-(3-(3-((2-(2-methoxyethoxy)ethyl)amino)phenyl)prop-2-yn-1-yl)-1,7-dimethyl-8-(methylsulfonyl)-1H-purine-2,6(3H,7H)-dione

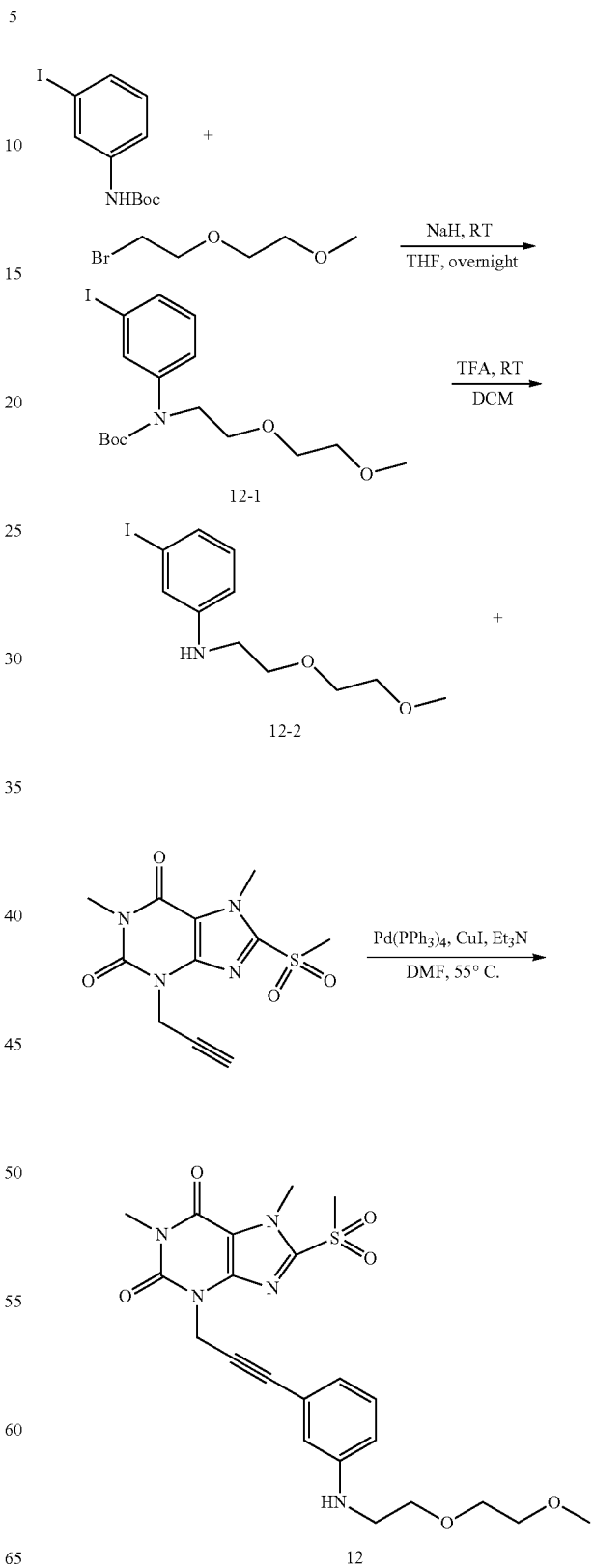

235

Step 1.

To a solution of tert-butyl (3-iodophenyl)carbamate (1 e.q.) in THF was added NaH (1.2 e.q.) at 0° C. and stirred for 30 min at RT. Then 1-bromo-2-(2-methoxyethoxy)ethane (1.2 e.q.) was added to the reaction mixture and stirred overnight. UPLC-MS monitored the completion of the reaction. The reaction mixture was poured into water and extracted with DCM. The organic layer was separated, and the aqueous layer was repeatedly extracted with DCM (2×20 mL). The combined extracts were dried with Na$_2$SO$_4$ and concentrated. The resulting residue was purified by silica gel chromatography (PE:EA=5:1) to give 12-1 as a yellow solid.

Step 2.

To a solution of 12-1 (1 e.q.) in DCM was added TFA (5 e.q.) at 0° C. Then the mixture was stirred at r.t. for 4 hours. UPLC-MS monitored the completion of the reaction. The reaction mixture was poured into water and extracted with DCM. The organic layer was separated, and the aqueous layer was repeatedly extracted with DCM (2×20 mL). The combined extracts were dried with Na$_2$SO$_4$ and concentrated. The resulting residue was purified by silica gel chromatography (PE:EA=1:1) to give 12-2 as a yellow solid.

Step 3.

To a solution of 12-2 (1 e.q.) in DMF was added 9-4 (1.2 e.q.), TEA (2.4 e.q.), Pd(PPh$_3$)$_4$ (0.05 e.q.) and CuI (0.1 e.q.) under N$_2$ atmosphere. Then the mixture was stirred at 55° C. for 4 hours. UPLC-MS monitored the completion of the reaction. The reaction mixture was poured into water and extracted with DCM. The organic layer was separated, and the aqueous layer was repeatedly extracted with DCM (2×20 mL). The combined extracts were dried with Na$_2$SO$_4$ and concentrated. The resulting residue was purified by silica gel chromatography (PE:EA=1:1) to give 12 as a yellow solid. $^1$H NMR (400 MHz, CDCl$_3$) δ 7.12 (t, J=8 Hz, 1H), 6.87 (d, J=8 Hz, 1H), 6.83 (s, 1H), 6.74 (d, J=8 Hz, 1H), 5.05 (s, 2H), 4.33 (s, 3H), 3.72 (t, J=4 Hz, 2H), 3.66-3.64 (m, 2H), 3.57-3.55 (m, 2H), 3.48 (s, 3H), 3.45 (s, 3H), 3.40 (s, 3H), 3.30 (t, J=4 Hz, 2H). LC-MS (ESI) m/z: calcd for [M+H]$^+$, 490.47, found 490.54.

Compound 13: 3-(3-(3-(benzylamino)phenyl)prop-2-yn-1-yl)-1,7-dimethyl-8-(methylsulfonyl)-1H-purine-2,6(3H,7H)-dione

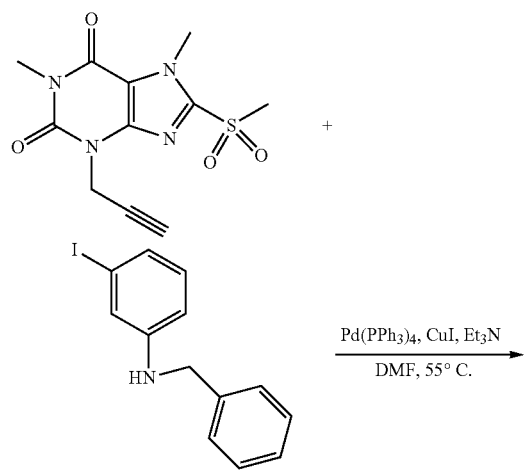

236

-continued

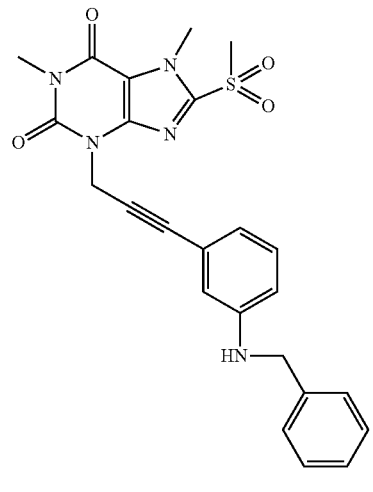

13

13 was prepared according to the procedure for 12. 1H NMR (400 MHz, DMSO) δ 7.31 (s, 2H), 7.30 (d, J=4 Hz, 2H), 7.00 (t, J=8 Hz, 1H), 6.60-6.52 (m, 3H), 6.70 (t, J=4 Hz, 1H), 4.94 (s, 2H), 4.23 (d, J=8 Hz, 2H), 4.19 (s, 3H), 3.52 (s, 3H), 3.26 (s, 3H). LC-MS (ESI) m/z: LC-MS (ESI) m/z: calcd for [M+H]+ 478.46, found 478.54.

Compound 14: 1,7-dimethyl-8-(methylsulfonyl)-3-(3-(3-((2-morpholinoethyl)amino)phenyl)prop-2-yn-1-yl)-1H-purine-2,6(3H,7H)-dione

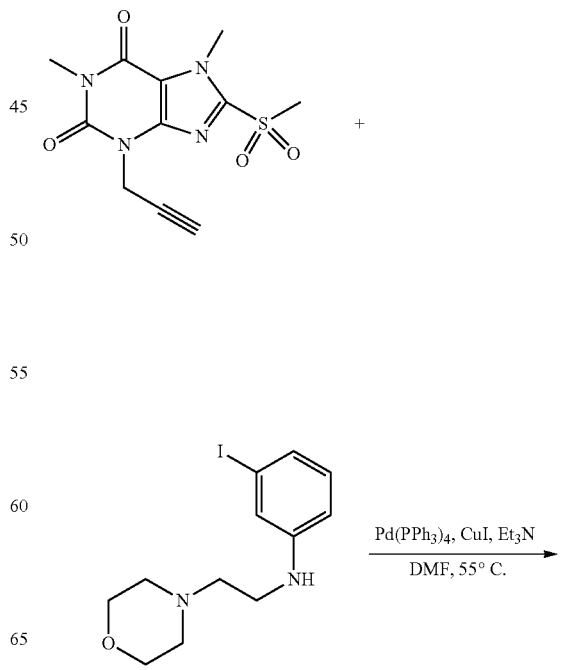

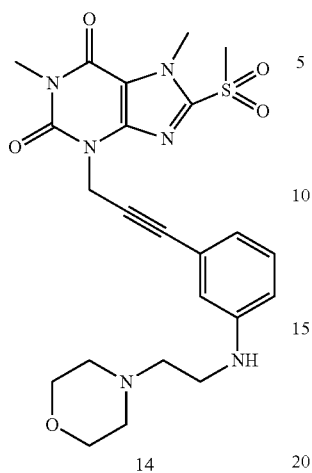

14

14 was prepared according to the procedure for 12. ¹H NMR (400 Hz, CDCl3) δ 7.05 (t, J=8.0 Hz, 1H), 6.72 (d, J=7.2 Hz, 1H), 6.64 (s, 1H), 6.56 (d, J=8.0 Hz, 1H), 5.04 (s, 2H), 4.30 (s, 3H), 3.73 (m, 4H), 3.43 (s, 3H), 3.46 (s, 3H), 3.15 (m, 2H), 2.66 (m, 2H), 2.52 (m, 4H). LC-MS (ESI) m/z: calcd for [M+H]+, 501.18, found 501.27.

Compound 15: 3-(3-(3-((2-(dimethylamino)ethyl)amino)phenyl)prop-2-yn-1-yl)-1,7-dimethyl-8-(methylsulfonyl)-1H-purine-2,6(3H,7H)-dione

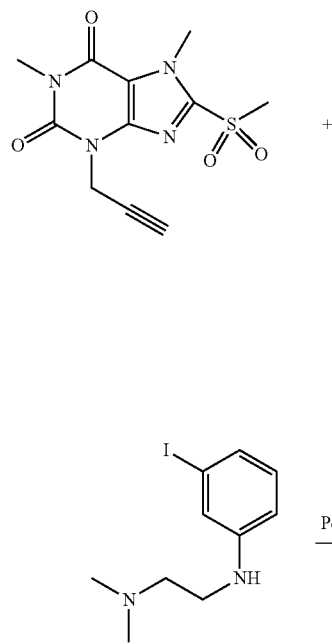

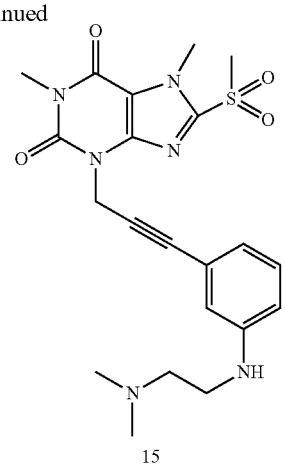

15

15 was prepared according to the procedure for 12. ¹H NMR (400 MHz, CDCl3) δ 7.07 (t, J=8 Hz, 1H), 6.75 (d, J=8 Hz, 1H), 6.66 (s, 1H), 6.60 (d, J=8 Hz, 1H), 5.30 (s, 4H), 5.05 (s, 2H), 4.33 (s, 3H), 3.48 (s, 3H), 3.44 (s, 3H), 3.20 (s, 3H), 2.71 (s, 3H). LC-MS (ESI) m/z: calcd for [M+H]+, 459.17, found 459.25.

Compound 16: 1,7-dimethyl-8-(methylsulfonyl)-3-(3-(3-(pentylamino)phenyl)prop-2-yn-1-yl)-1H-purine-2,6(3H,7H)-dione

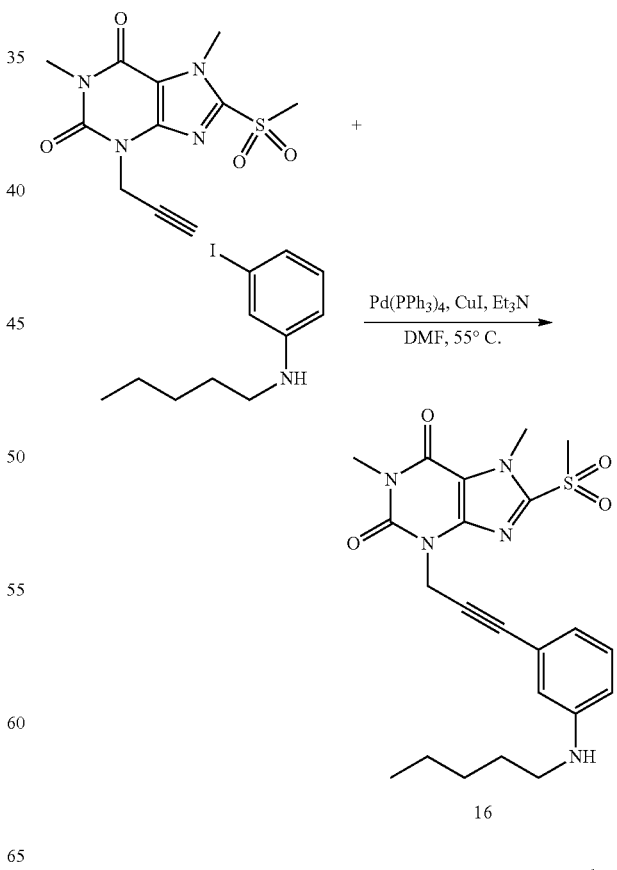

16

16 was prepared according to the procedure for 12. ¹H NMR (400 MHz, CDCl3) δ 7.09 (t, J=8 Hz, 1H), 6.81 (d, J=8

Hz, 1H), 6.74 (s, 1H), 6.66 (s, 1H), 5.05 (s, 2H), 4.33 (s, 3H), 3.48 (s, 3H), 3.45 (s, 3H), 3.07 (t, J=8 Hz, 2H), 1.36-1.32 (m, 6H), 0.90 (t, J=4 Hz, 3H). LC-MS (ESI) m/z: calcd for [M+H]$^+$, 459.47, found 458.55.

Compound 17: N-(3-(3-(1,7-dimethyl-8-(methylsulfonyl)-2,6-dioxo-1H-purin-3(2H,6H,7H)-yl)prop-1-yn-1-yl)phenyl)-2-morpholinoacetamide

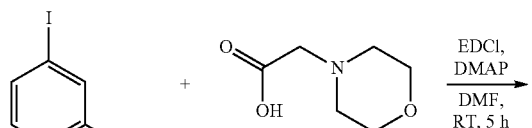

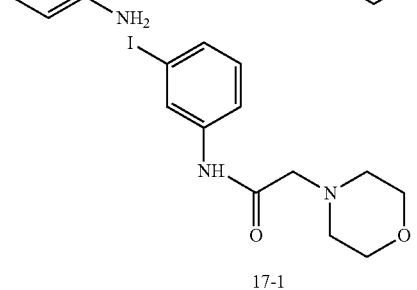

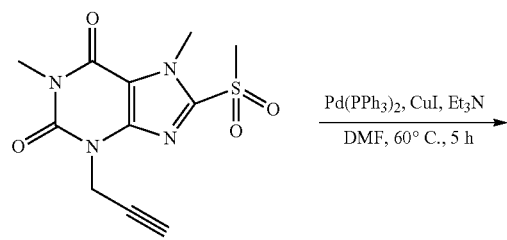

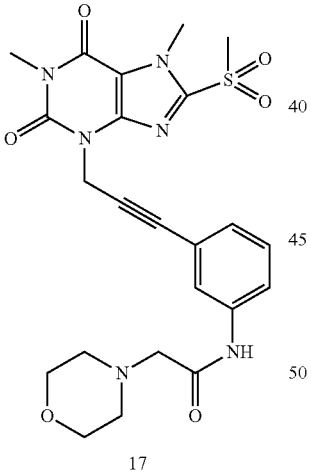

Step 1.

To a solution of 2-morpholinoacetic acid (100 mg, 0.69 mmol) in DMF (2 mL) was added 3-iodoaniline (151 mg, 0.69 mmol), EDCI (199 mg, 1.03 mmol) and DMAP (127 mg, 1.03 mmol) at RT under N$_2$ atmosphere. Then the mixture was stirred at 55° C. for 4 hours. UPLC-MS monitored the completion of the reaction. The reaction mixture was poured into water and extracted with DCM. The organic layer was separated, and the aqueous layer was repeatedly extracted with DCM (2×20 mL). The combined extracts were dried with Na$_2$SO$_4$ and concentrated. The resulting residue was purified by silica gel chromatography (PE:EA=1:1) to give 214 mg 17-1 as a yellow solid, yield: 89.9%. LC-MS (ESI) m/z: calcd for [M+H]+, 347.02, found 347.14.

Step 2. Sonogashira Coupling 17 was prepared in a yield of 31% (16 mg) according to the procedure for 12. $^1$H NMR (400 MHz, CDCl$_3$) δ 7.68 (s, 1H), 7.55 (d, J=8 Hz, 1H), 7.24 (s, 1H), 7.16 (d, J=8 Hz, 1H), 5.06 (s, 2H), 4.34 (s, 3H), 3.84 (s, 4H), 3.49 (s, 3H), 3.45 (s, 3H), 2.10 (s, 2H), 1.25 (s, 4H). LC-MS (ESI) m/z: calcd for [M+H]$^+$, 515.48, found 515.55.

Compound 18: 1,7-dimethyl-8-(methylsulfonyl)-3-(3-(3-((2-(piperidin-1-yl)ethyl)amino)phenyl)prop-2-yn-1-yl)-1H-purine-2,6(3H,7H)-dione

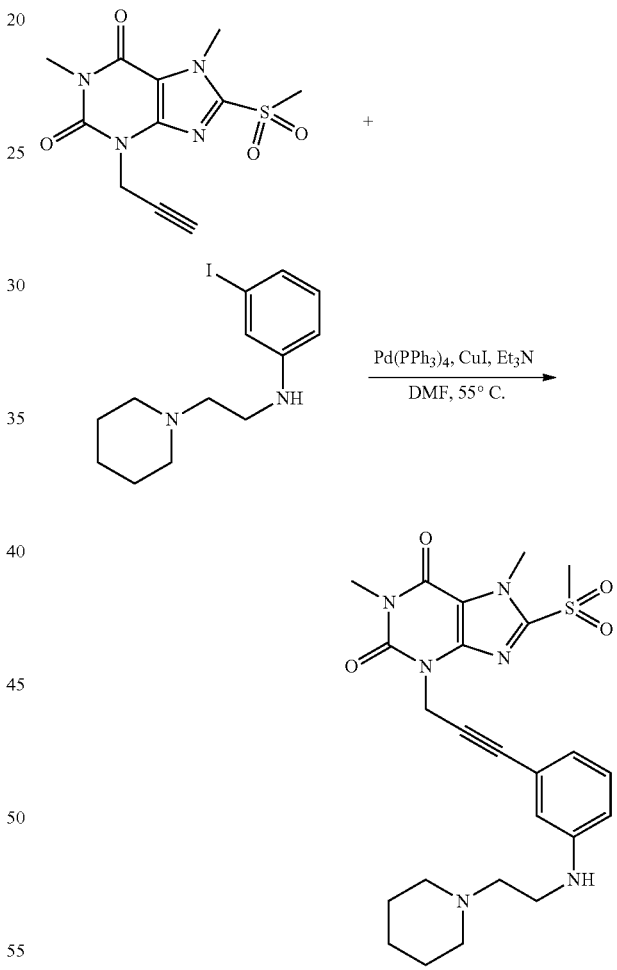

18 was prepared in a yield of 17% (12 mg) from 3-iodo-N-(2-(piperidin-1-yl)ethyl) aniline (37 mg, 0.11 mmol) as a yellow solid according to the procedure for 12. $^1$H NMR (400 Hz, CDCl3) δ 7.70 (s, 1H), 7.53 (d, J=3.2 Hz, 1H), 7.48 (m, 1H), 7.28 (m, 1H), 5.09 (s, 2H), 4.29 (s, 3H), 3.62 (m, 4H), 3.51 (s, 3H), 3.44 (s, 3H), 2.62 (m, 4H), 1.72 (m, 3H), 1.42 (m, 3H). LC-MS (ESI) m/z: calcd for [M+H]+, 499.38, found 499.42.

Compound 19: 8-((cyclopropylmethyl)sulfonyl)-1,7-dimethyl-3-(3-(3-((2-morpholinoethyl)amino)phenyl)prop-2-yn-1-yl)-3,7-dihydro-1H-purine-2,6-dione

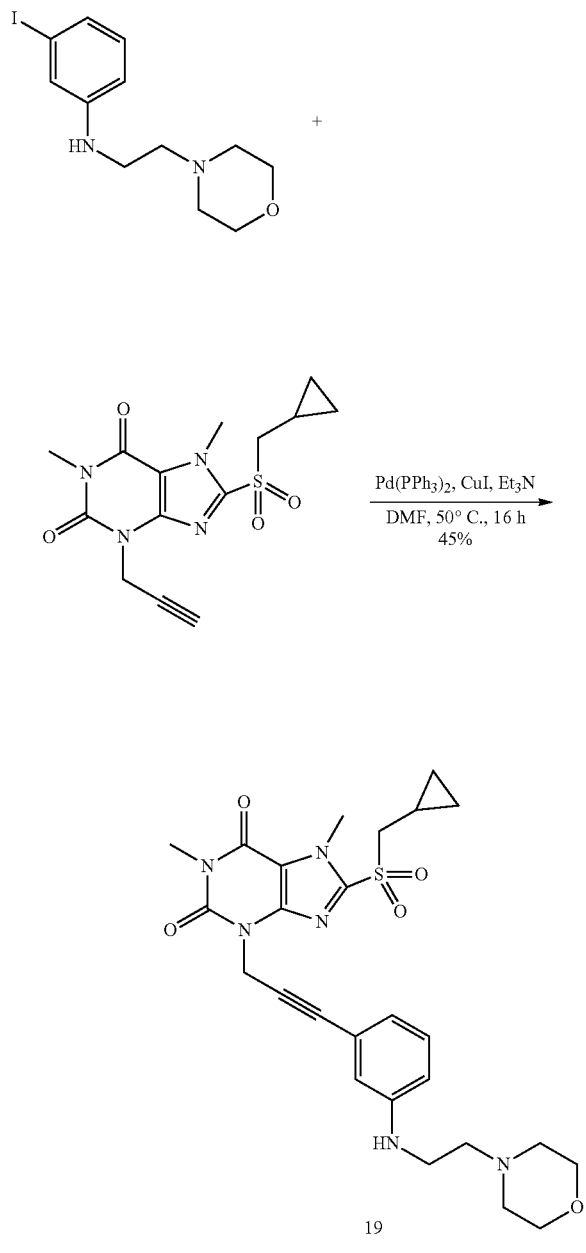

19 was prepared in a yield of 45% (18 mg) from 3-iodo-N-(2-morpholinoethyl) aniline (30 mg, 0.09 mmol) as a yellow solid according to the procedure for 12. $^1$H NMR (400 Hz, CDCl3) δ 7.05 (m, 1H), 6.72 (d, J=7.2 Hz, 1H), 6.64-6.58 (m, 2H), 5.05 (s, 2H), 4.32 (s, 3H), 3.83-3.70 (m, 4H), 3.43 (s, 3H), 3.40 (m, 2H), 3.19 (m, 1H), 2.73 (m, 1H), 2.59 (m, 2H), 0.94 (m, 1H), 0.62 (m, 2H), 0.32 (m, 2H). LC-MS (ESI) m/z: calcd for [M+H]$^+$, 541.22, found 541.30.

Compound 20: N-(3-(3-(1,7-dimethyl-8-(methylsulfonyl)-2,6-dioxo-1H-purin-3(2H,6H,7H)-yl)prop-1-yn-1-yl)-5-fluorophenyl)-2-morpholinoacetamide

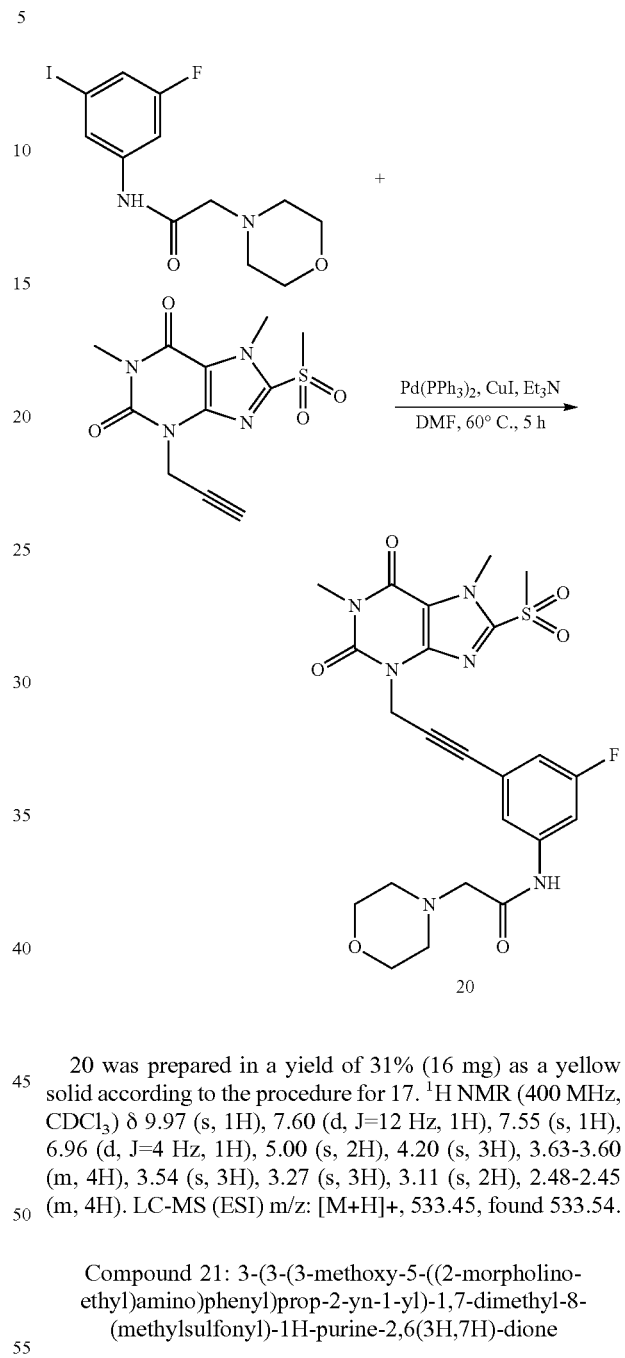

20 was prepared in a yield of 31% (16 mg) as a yellow solid according to the procedure for 17. $^1$H NMR (400 MHz, CDCl$_3$) δ 9.97 (s, 1H), 7.60 (d, J=12 Hz, 1H), 7.55 (s, 1H), 6.96 (d, J=4 Hz, 1H), 5.00 (s, 2H), 4.20 (s, 3H), 3.63-3.60 (m, 4H), 3.54 (s, 3H), 3.27 (s, 3H), 3.11 (s, 2H), 2.48-2.45 (m, 4H). LC-MS (ESI) m/z: [M+H]+, 533.45, found 533.54.

Compound 21: 3-(3-(3-methoxy-5-((2-morpholinoethyl)amino)phenyl)prop-2-yn-1-yl)-1,7-dimethyl-8-(methylsulfonyl)-1H-purine-2,6(3H,7H)-dione

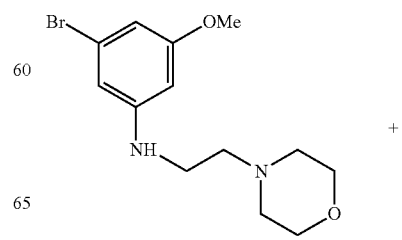

243
-continued

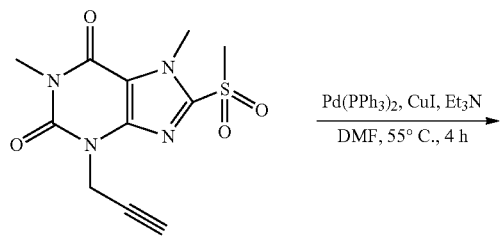

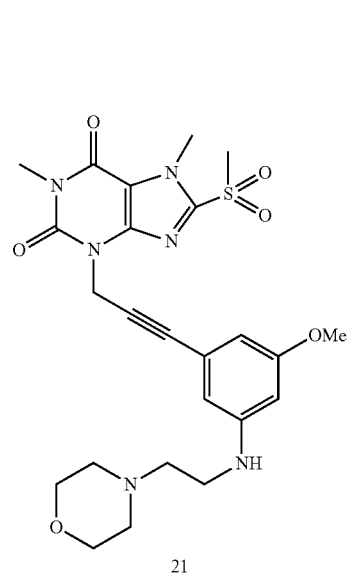

21

21 was prepared in a yield of 9.4% (6 mg) from 3-bromo-5-methoxy-N-(2-morpholinoethyl) aniline and 1,7-dimethyl-8-(methylsulfonyl)-3-(prop-2-yn-1-yl)-1H-purine-2,6 (3H,7H)-dione as a yellow solid according to the procedure for 12. 1H NMR (400 MHz, CDCl$_3$) δ 6.44 (s, 1H) 6.39 (s, 1H), 6.28 (s, 1H), 5.04 (s, 2H), 4.34 (s, 3H), 3.97 (s, 4H), 3.74 (s, 3H), 3.49 (s, 3H), 3.44 (s, 3H), 2.22 (t, J=8 Hz, 2H) 2.10 (s, 2H), 1.25 (s, 4H). LC-MS (ESI) m/z: [M+H]$^+$, 531.51, found 531.60.

Compound 22: N-(4-chloro-3-(3-(8-((cyclopropylmethyl)sulfonyl)-1,7-dimethyl-2,6-dioxo-1H-purin-3 (2H,6H,7H)-yl)prop-1-yn-1-yl)phenyl-2-morpholinoacetamide

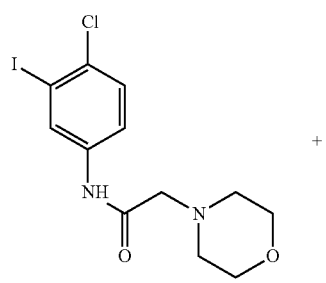

+

244
-continued

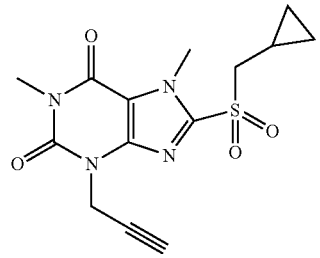

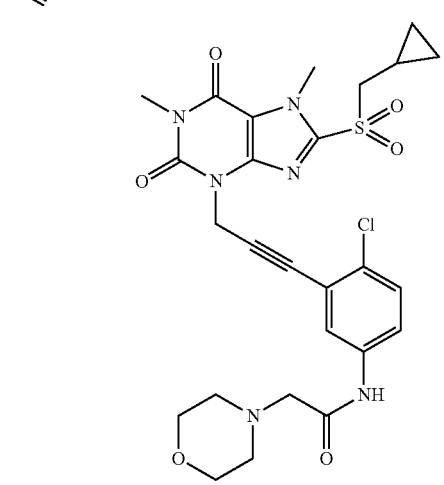

22

22 was prepared in a yield of 16% (12 mg) from N-(4-chloro-3-iodophenyl)-2-morpholinoacetamide and 8-((cyclopropylmethyl)sulfonyl)-1,7-dimethyl-3-(prop-2-yn-1-yl)-1H-purine-2,6(3H,7H)-dione as a yellow solid according to the procedure for 12. $^1$H NMR (400 MHz, DMSO) δ 9.92 (s, 1H), 7.88 (d, J=4 Hz, 1H), 7.63 (dd, J=4, 8 Hz, 1H), 7.45 (d, J=8 Hz, 1H), 5.06 (s, 2H), 4.34 (s, 3H), 3.84 (s, 4H), 3.49 (s, 3H), 3.38 (m, 2H), 2.10 (s, 2H), 1.25 (s, 4H), 1.04-0.96 (m, 1H), 0.53 (q, J=4 Hz, 2H), 0.18 (q, J=4 Hz, 2H). LC-MS (ESI) m/z: [M+H]$^+$, 589.09, found 589.16.

Compound 23: 1,7-dimethyl-8-(methylsulfonyl)-3-(3-(2-oxo-2,3-dihydro-1H-benzo[d]imidazol-5-yl)prop-2-yn-1-yl)-3,7-dihydro-1H-purine-2,6-dione (244)

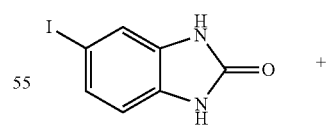

+

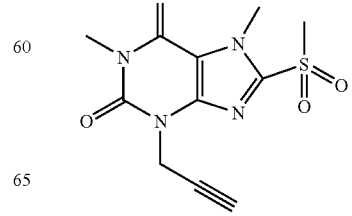

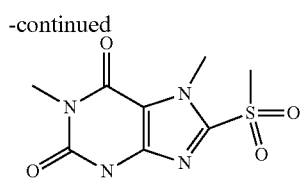

23

23 was prepared in a yield of 2% (7 mg) from 5-iodo-1,3-dihydro-2H-benzo[d]imidazol-2-one (22 mg, 0.09 mmol) as a yellow solid according to the procedure for 12. $^1$H NMR (400 Hz, CDCl3) δ 7.87 (s, 1H), 7.71 (m, 1H), 7.62 (m, 1H), 5.34 (m, 2H), 3.20 (s, 3H), 3.76 (s, 6H). LC-MS (ESI) m/z: calcd for [M+H]+, 429.09, found 429.17.

Compound 24: 3-(3-(2-aminopyrimidin-4-yl)prop-2-yn-1-yl)-1,7-dimethyl-8-(methylsulfonyl)-3,7-dihydro-1H-purine-2,6-dione (245)

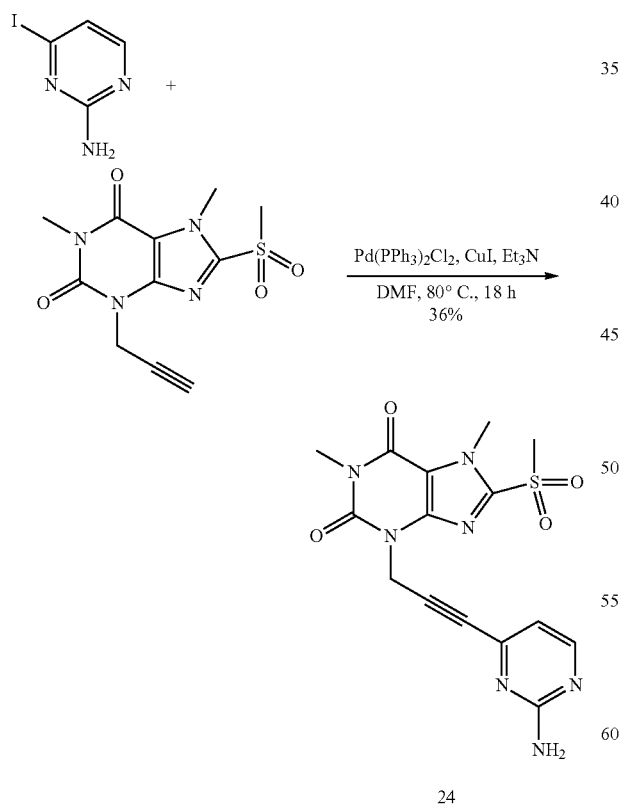

24

24 was prepared in a yield of 36% (16 mg) from 4-iodopyrimidin-2-amine as a yellow solid according to the procedure for 232. $^1$H NMR (400 Hz, DMSO) δ 8.22 (d, J=4.8 Hz, 1H), 6.76 (s, 2H), 6.1 (d, J=4.2 Hz, 1H), 5.01 (s, 2H), 4.21 (s, 3H), 3.54 (s, 3H), 3.28 (s, 3H). LC-MS (ESI) m/z: calcd for [M+H]+, 390.21, found 390.29.

Compound 25

N,N'-(5-(3-(1,7-dimethyl-8-(methylsulfonyl)-2,6-dioxo-1H-purin-3(2H,6H,7H)-yl)prop-1-yn-1-yl)-1,3-phenylene)diacetamide

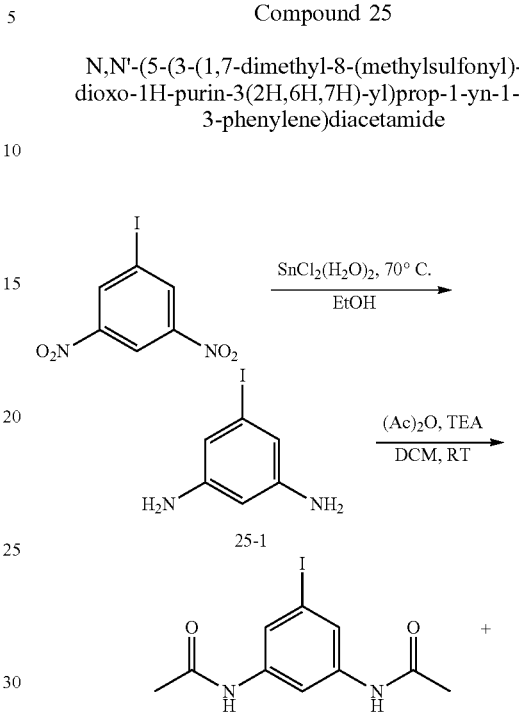

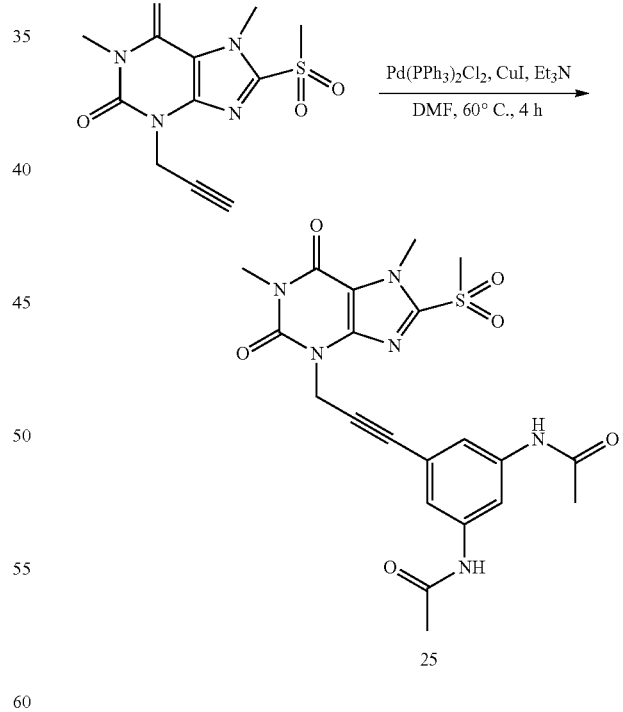

25

Step 1.

To a solution of 1-iodo-3,5-dinitrobenzene (400 mg, 1.36 mmol) in ethanol (10 mL) was added SnCl₂.(H₂O)₂ (1.84 g, 8.16 mmol) at r.t. Then the mixture was stirred at 70° C. for 2 hours. UPLC-MS monitored the completion of the reaction. The reaction mixture was poured into water and extracted with DCM. The organic layer was separated, and the aqueous layer was repeatedly extracted with DCM (2×20 mL). The combined extracts were dried with Na₂SO₄ and concentrated. The resulting residue was purified by silica gel chromatography (DCM:MeOH=10:1) to give 160 mg of 25-1 as a yellow solid, yield: 50.3%. LC-MS (ESI) m/z: calcd for [M+H]⁺, 234.97, found 235.02.

Step 2.

To a solution of 25-1 (50 mg, 0.21 mmol) in DCM (3 mL) was added acetic anhydride (66 mg, 0.64 mmol) and TEA (87 mg, 0.86 mmol) at 0° C. Then the mixture was stirred at RT for 1 hour. UPLC-MS monitored the completion of the reaction. The reaction mixture was poured into water and extracted with DCM. The organic layer was separated, and the aqueous layer was repeatedly extracted with DCM (2×20 mL). The combined extracts were dried with Na₂SO₄ and concentrated. The resulting residue was purified by silica gel chromatography (DCM:MeOH=40:1) to give 50 mg of 25-2 as a yellow solid, yield: 73.5%. LC-MS (ESI) m/z: calcd for [M+H]⁺, 318.99, found 319.03.

Step 3.

To a solution of 1,7-dimethyl-8-(methylsulfonyl)-3-(prop-2-yn-1-yl)-1H-purine-2,6(3H,7H)-dione (25 mg, 0.084 mmol) in DMF (2 mL) was added 25-2 (27 mg, 0.084 mmol), TEA (21 mg, 0.202 mmol), Pd(PPh₃)₄ (4.9 mg, 0.004 mmol) and CuI (1.6 mg, 0.008 mmol) under N₂ atmosphere. Then the mixture was stirred at 60° C. for 4 hours. UPLC-MS monitored the completion of the reaction. The reaction mixture was poured into water and extracted with DCM. The organic layer was separated, and the aqueous layer was repeatedly extracted with DCM (2×20 mL). The combined extracts were dried with Na₂SO₄ and concentrated. The resulting residue was purified by silica gel chromatography (PE:EA=1:1) to give 8.5 mg of 25 as a yellow solid, yield: 20.7%. 1H NMR (400 MHz, DMSO) δ 10.00 (s, 2H), 7.76 (s, 1H), 7.38 (d, J=4 Hz, 2H), 4.98 (s, 2H), 4.20 (s, 3H), 3.53 (s, 3H), 3.27 (s, 3H), 2.01 (s, 6H). LC-MS (ESI) m/z: calcd for [M+H]⁺, 487.42, found 487.50.

Compound 26: N,N'-(5-(3-(1,7-dimethyl-8-(methylsulfonyl)-2,6-dioxo-1H-purin-3(2H,6H,7H)-yl)prop-1-yn-1-yl)-1,3-phenylene)bis(2-morpholinoacetamide)

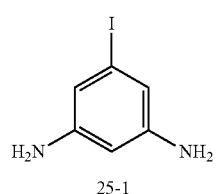

25-1

+

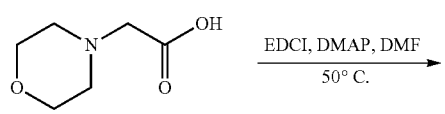

EDCI, DMAP, DMF
50° C.

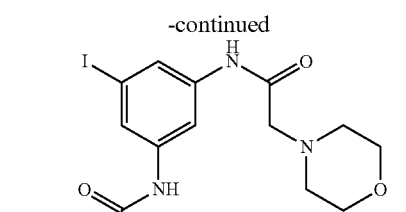

26-1

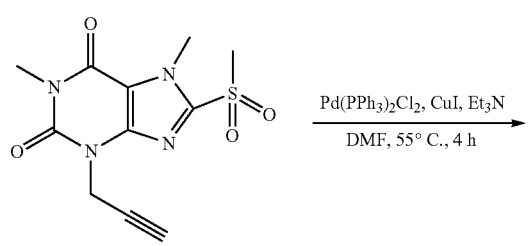

Pd(PPh₃)₂Cl₂, CuI, Et₃N
DMF, 55° C., 4 h

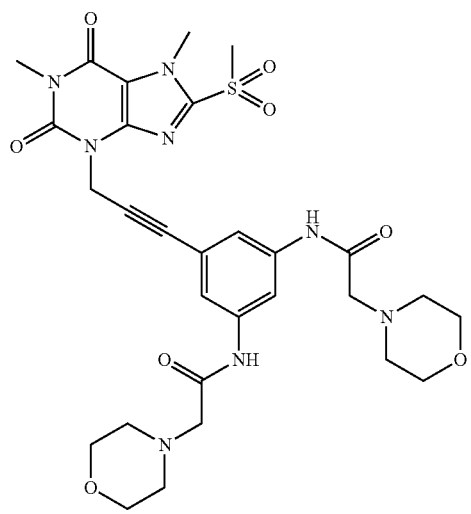

26

Step 1.

To a solution of 2-morpholinoacetic acid (62 mg, 0.43 mmol) in DMF (2 mL) was added 25-1 (50 mg, 0.21 mmol), EDCI (124 mg, 0.64 mmol) and DMAP (79 mg, 0.64 mmol) at r.t. under N₂ atmosphere. Then the mixture was stirred at 55° C. for 4 hours. UPLC-MS monitored the completion of the reaction. The reaction mixture was poured into water and extracted with DCM. The organic layer was separated, and the aqueous layer was repeatedly extracted with DCM (2×20 mL). The combined extracts were dried with Na₂SO₄ and concentrated. The resulting residue was purified by silica gel chromatography (PE:EA=3:1) to give 21 mg 26-1 as a yellow solid, yield: 20.2%. LC-MS (ESI) m/z: calcd for [M+H]+, 489.09, found 489.41.

Step 2.

To a solution of 1,7-dimethyl-8-(methylsulfonyl)-3-(prop-2-yn-1-yl)-1H-purine-2,6(3H,7H)-dione (16 mg, 0.053 mmol) in DMF (2 mL) was added 26-1 (21 mg, 0.043 mmol), TEA (11 mg, 0.10 mmol), Pd(PPh$_3$)$_4$ (2.5 mg, 0.002 mmol) and CuI (0.82 mg, 0.004 mmol) under N$_2$ atmosphere. Then the mixture was stirred at 55° C. for 4 hours. UPLC-MS monitored the completion of the reaction. The reaction mixture was poured into water and extracted with DCM. The organic layer was separated, and the aqueous layer was repeatedly extracted with DCM (2×20 mL). The combined extracts were dried with Na$_2$SO$_4$ and concentrated. The resulting residue was purified by silica gel chromatography (PE:EA=1:1) to give 2.6 mg of 26 as a yellow solid, yield: 9.2%. 1H NMR (400 MHz, CDCl$_3$) δ 9.07 (s, 2H), 7.87 (t, J=4 Hz, 1H), 7.43 (d, J=4 Hz, 2H), 5.05 (s, 2H), 4.34 (s, 3H), 3.79 (t, J=4 Hz, 8H), 3.49 (s, 3H), 3.45 (s, 3H), 3.13 (s, 4H), 2.61 (m. 8H). LC-MS (ESI) m/z: calcd for [M+H]$^+$, 657.61, found 657.71.

Compound 27: N,N'-(5-(3-(1,7-dimethyl-8-(methylsulfonyl)-2,6-dioxo-1,2,6,7-tetrahydro-3H-purin-3-yl)prop-1-yn-1-yl)-1,3-phenylene)dicyclopropanecarboxamide

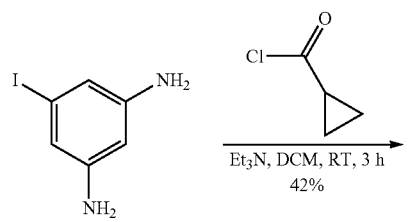

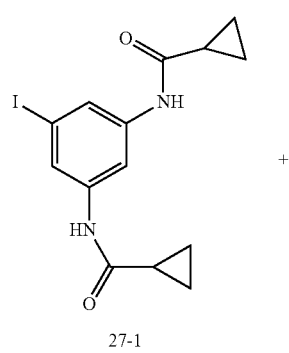

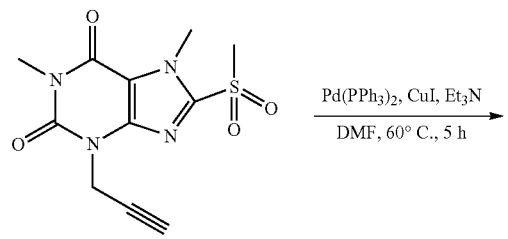

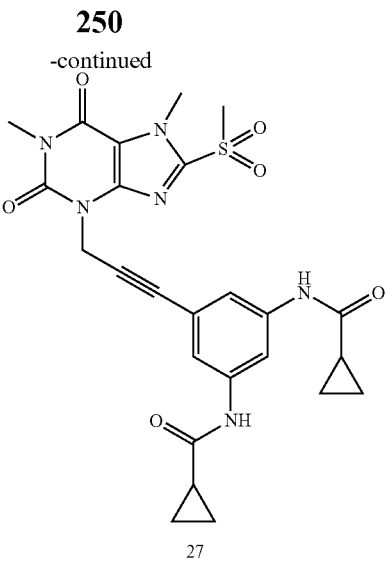

27

Step 1.

To a solution of 5-iodobenzene-1,3-diamine (60 mg, 0.26 mmol) in DCM (5 ml) were added cyclopropanecarbonyl chloride (116 μL, 0.64 mmol), Et$_3$N (98 μL, 0.64 mmol), then the mixture was stirred at RT for 3 hours. UPLC-MS monitored the completion of the reaction. The solvent was evaporated under reduced pressure and further purified by silica gel column chromatography (PE/EA=60/40) to give 40 mg 27-1 as a yellow solid (42%). LC-MS (ESI) m/z: calcd for [M+H]+, 371.01, found 371.18.

Step 2. Sonogashira Coupling 27 was prepared in a yield of 18% (10 mg) from 27-1 (56 mg, 0.15 mmol) as a yellow solid according to the procedure for 12. $^1$H NMR (400 Hz, CDCl3) δ 7.91 (s, 1H), 7.79 (s, 1H), 7.29 (s, 1H), 5.01 (s, 2H), 4.33 (s, 3H), 3.48 (s, 3H), 3.41 (s, 3H), 1.51 (m, 2H), 1.03 (m, 4H), 0.83 (m, 4H). LC-MS (ESI) m/z: calcd for [M+H]+, 459.16, found 459.23.

Compound 28: N,N'-(5-(3-(8-((cyclopropylmethyl)sulfonyl)-1,7-dimethyl-2,6-dioxo-1,2,6,7-tetrahydro-3H-purin-3-yl)prop-1-yn-1-yl)-1,3-phenylene)bis(2-morpholinoacetamide)

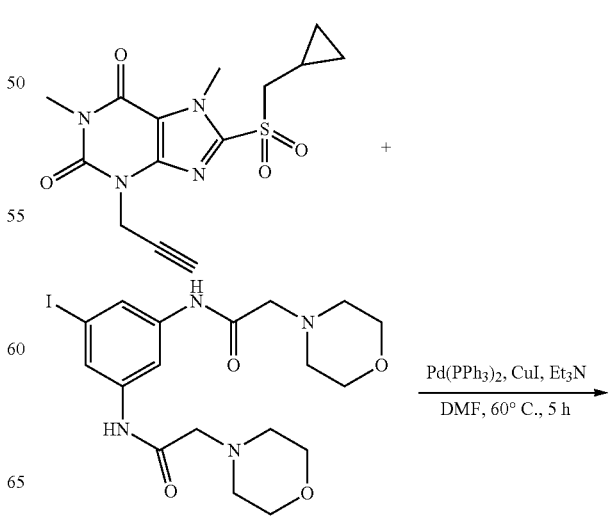

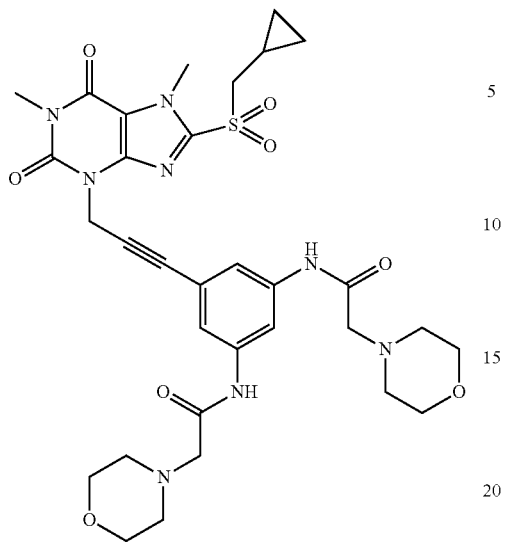

28

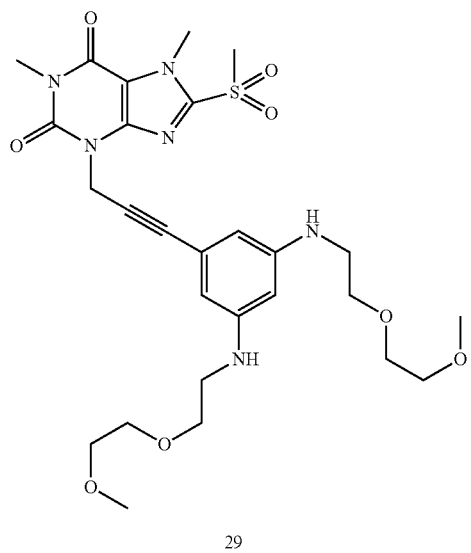

29

28 was prepared in a yield of 10% (6.2 mg) from N,N'-(5-iodo-1,3-phenylene)bis(2-morpholinoacetamide) (48 mg, 0.11 mmol) as a yellow solid according to the procedure for 22. $^1$H NMR (400 Hz, CDCl3) δ 7.89 (s, 1H), 7.21 (s, 1H), 5.06 (s, 2H), 4.34 (s, 3H), 3.81 (m, 8H), 3.40 (s, 3H), 3.21 (s, 4H), 2.73 (m, 8H), 3.41 (m, 2H), 0.63 (m, 4H), 0.35 (m, 4H). LC-MS (ESI) m/z: calcd for [M+H]+, 697.27, found 697.35.

Compound 29: 3-(3-(3,5-bis((2-morpholinoethyl) amino)phenyl)prop-2-yn-1-yl)-1,7-dimethyl-8-(methylsulfonyl)-3,7-dihydro-1H-purine-2,6-dione 29 was prepared in a yield of 10% (6.1 mg) from 5-iodo-N1,N3-bis(2-morpholinoethyl)benzene-1,3-diamine (66 mg, 0.15 mmol) as a yellow solid according to the procedure for 12. $^1$H NMR (400 Hz, CDCl3) δ 6.25 (s, 2H), 6.17 (s, 1H), 5.03 (s, 2H), 4.33 (s, 3H), 3.63 (s, 3H), 3.48 (s, 3H), 3.45 (s, 3H), 3.40 (s, 3H), 3.70-3.67 (m, 4H), 3.63-3.62 (m, 4H), 3.56-3.54 (m, 8H). LC-MS (ESI) m/z: calcd for [M+H]$^+$, 607.25, found 607.34.

Compound 30: N,N'-(5-(3-(8-((cyclopropylmethyl) sulfonyl)-1,7-dimethyl-2,6-dioxo-1,2,6,7-tetrahydro-3H-purin-3-yl)prop-1-yn-1-yl)-1,3 phenylene)dicyclopropanecarboxamide

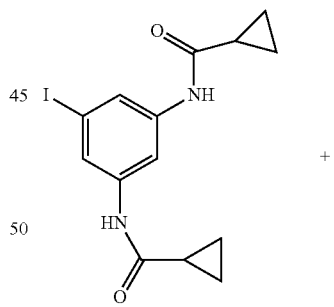

+

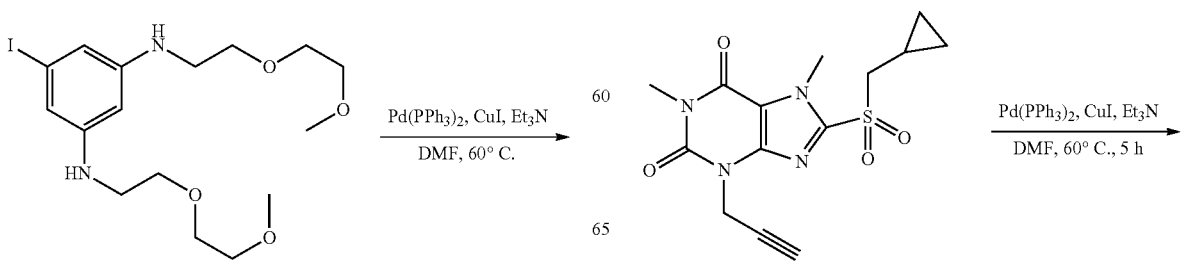

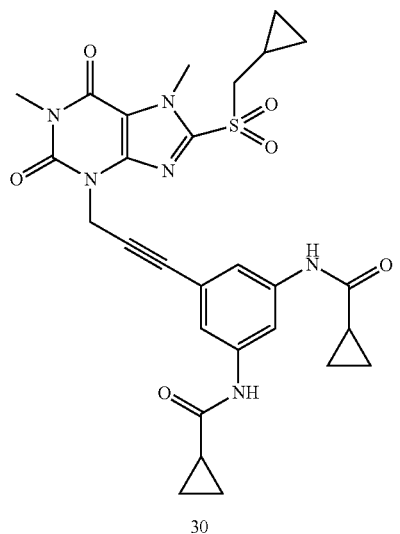

30

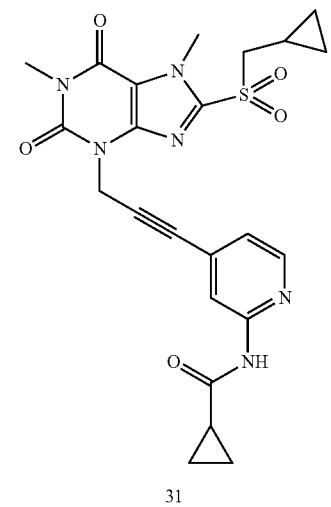

31

30 was prepared in a yield of 10% (5.0 mg) from as a yellow solid according to the procedure for 12. $^1$H NMR (400 Hz, CDCl3) δ 7.82 (s, 1H), 7.61 (s, 1H), 7.28 (s, 1H), 5.03 (s, 2H), 4.34 (s, 3H), 3.41 (s, 3H), 3.48-3.37 (m, 2H), 1.21 (m, 2H), 1.01 (m, 3H), 0.82 (m, 2H), 0.63 (m, 4H), 0.34 (m, 4H). LC-MS (ESI) m/z: calcd for [M+H]$^+$, 579.19, found 579.24.

Compound 31: N-(4-(3-(8-((cyclopropylmethyl)sulfonyl)-1,7-dimethyl-2,6-dioxo-1,2,6,7-tetrahydro-3H-purin-3-yl)prop-1-yn-1-yl)pyridin-2-yl)cyclopropanecarboxamide 31 was prepared in a yield of 27% (10 mg) from as a yellow solid according to the procedure for 12. $^1$H NMR (400 Hz, CDCl3) δ 8.25 (s, 1H), 8.12 (s, 1H), 7.0 (d, d, J=4.8 Hz, 1H), 5.08 (s, 2H), 4.37 (s, 3H), 3.45 (s, 3H), 3.46-3.38 (m, 2H), 1.7 (m, 1H), 1.42 (m, 1H), 1.08 (m, 2H), 0.92 (m, 2H), 0.65 (m, 2H), 0.35 (m, 2H). LC-MS (ESI) m/z: calcd for [M+H]$^+$, 497.15, found 497.23.

Compound 32: N-(4-(3-(8-((cyclopropylmethyl)sulfonyl)-1,7-dimethyl-2,6-dioxo-1,2,6,7-tetrahydro-3H-purin-3-yl)prop-1-yn-1-yl)pyridin-2-yl)-2-morpholinoacetamide

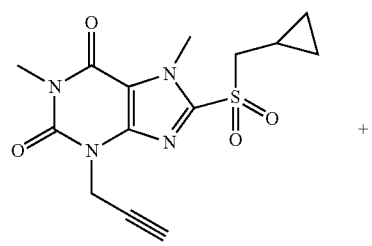 +

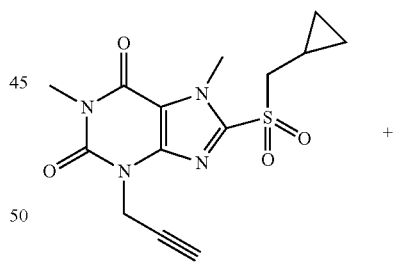 +

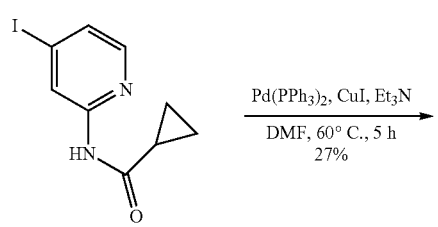

Pd(PPh3)2, CuI, Et3N
DMF, 60° C., 5 h
27%

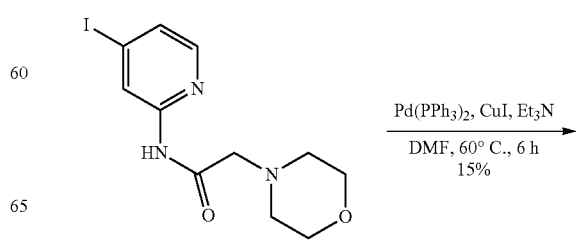

Pd(PPh3)2, CuI, Et3N
DMF, 60° C., 6 h
15%

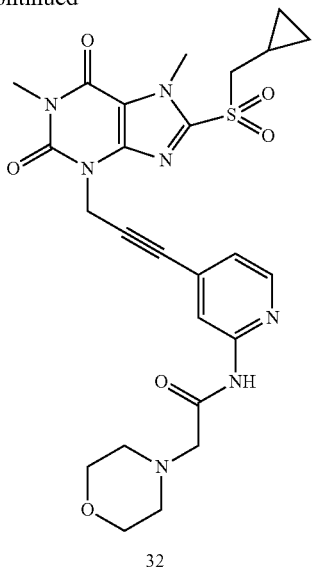

32

32 was prepared in a yield of 15% (6 mg) from as a yellow solid according to the procedure for 12. $^1$H NMR (400 Hz, CDCl3) δ 8.22 (m, 2H), 7.02 (d, J=4.8 Hz, 1H), 5.09 (s, 2H), 4.37 (s, 3H), 3.83 (m, 4H), 3.41 (m, 5H), 3.38 (m, 2H) 2.69 (m, 4H), 0.83 (m, 1H), 0.63 (m, 2H), 0.34 (m, 2H). LC-MS (ESI) m/z: calcd for [M+H]$^+$, 556.19, found 556.26.

Compound 33: 8-((cyclopropylmethyl)sulfonyl)-3-(3-(2-(ethylamino)pyridin-4-yl)prop-2-yn-1-yl)-1,7-dimethyl-1H-purine-2,6(3H,7H)-dione

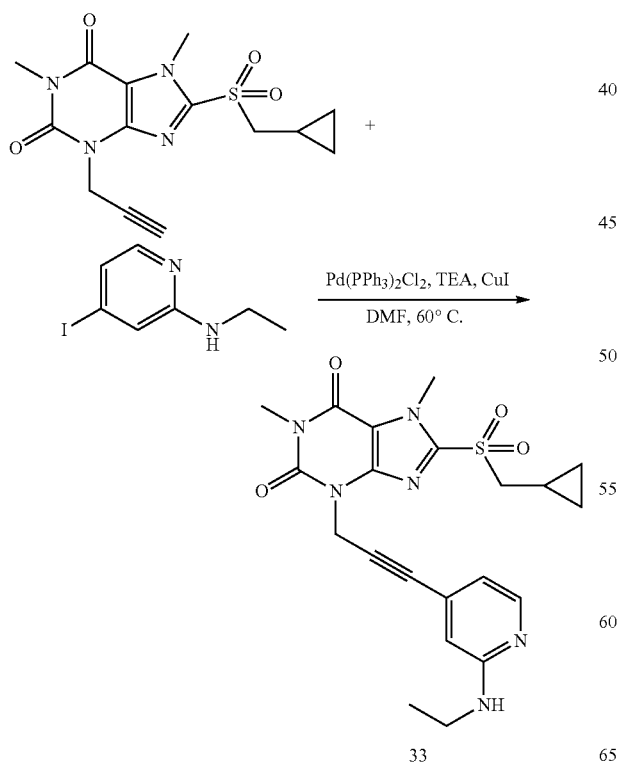

33

A mixture of 8-((cyclopropylmethyl)sulfonyl)-1,7-dimethyl-3-(prop-2-yn-1-yl)-1H-purine-2,6(3H,7H)-dione (25 mg, 75 nmol), N-ethyl-4-iodopyridin-2-amine (28 mg, 0.11 mmol), PdCl$_2$(PPh$_3$)$_2$ (5.3 mg, 7.5 nmol), copper(I) iodide (0.7 mg, 3.75 nmol) in DMF (3 ml) was stirred for 5 mins under an atmosphere of Argon at room temperature. Triethylamine (0.25 ml, 0.75 mmol) was added and the reaction was sealed and stirred overnight. The reaction mixture was filtered and the filtrate was washed with water and extracted with DCM (3*5 ml). The combined organic layers was washed with brine and dried over MgSO4, filtered and concentrated in vacuo. The residue was purified by silica gel chromatography using 100:1 DCM/MeOH to afford 33 in 66% yield as a light yellow solid. $^1$H NMR (400 Mz, CDCl3): δ 7.89 (d, J=5.6 Hz, 1H), 6.51 (d, J=5.6 Hz, 1H), 6.42 (s, 1H), 5.08 (s, 2H), 4.36 (s, 3H), 3.45 (d, J=7.2 Hz, 2H), 3.45 (s, 3H), 3.23 (q, J=7.2 Hz, 2H), 1.26 (t, J=7.2 Hz, 3H), 0.88 (m, 1H), 0.65 (m, 2H), 0.31 (m, 2H). LC-MS (ESI) m/z: calcd for [M+H]$^+$, 457.16, found 457.25.

Compound 34: 3-(3-(2-((cyclopropylmethyl)amino)pyridin-4-yl)prop-2-yn-1-yl)-8-((cyclopropylmethyl)sulfonyl)-1,7-dimethyl-1H-purine-2,6(3H,7H)-dione

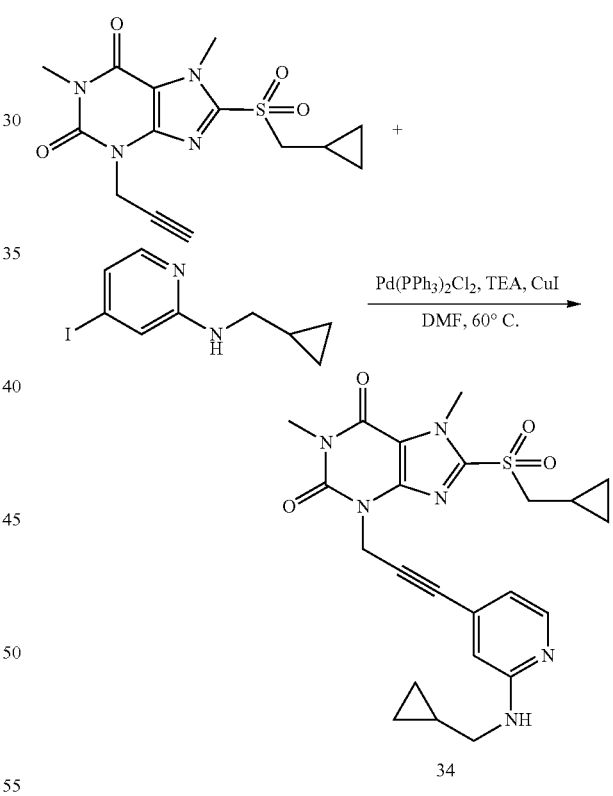

34

34 was prepared in a yield of 63% (36 mg) as a light yellow solid from 8-((cyclopropylmethyl)sulfonyl)-1,7-dimethyl-3-(prop-2-yn-1-yl)-1H-purine-2,6(3H,7H)-dione (25 mg, 75 nmol) and N-(cyclopropylmethyl)-4-iodopyridin-2-amine (30 mg, 0.11 mmol) according to the procedure for 12. $^1$H NMR (400 Mz, CDCl3): δ 7.87 (d, J=5.6 Hz, 1H), 6.51 (d, J=5.6 Hz, 1H), 6.46 (s, 1H), 5.08 (s, 2H), 4.36 (s, 3H), 3.45 (d, J=7.2 Hz, 2H), 3.45 (s, 3H), 3.06 (d, J=6.8 Hz, 2H), 0.90 (m, 2H), 0.64 (m, 2H), 0.57 (m, 2H), 0.30 (m, 2H), 0.26 (m, 2H). LC-MS (ESI) m/z: calcd for [M+H]$^+$, 483.17, found 483.25.

Compound 35: 8-((cyclopropylmethyl)sulfonyl)-3-(3-(2-(isopropylamino)pyridin-4-yl)prop-2-yn-1-yl)-1,7-dimethyl-1H-purine-2,6(3H,7H)-dione

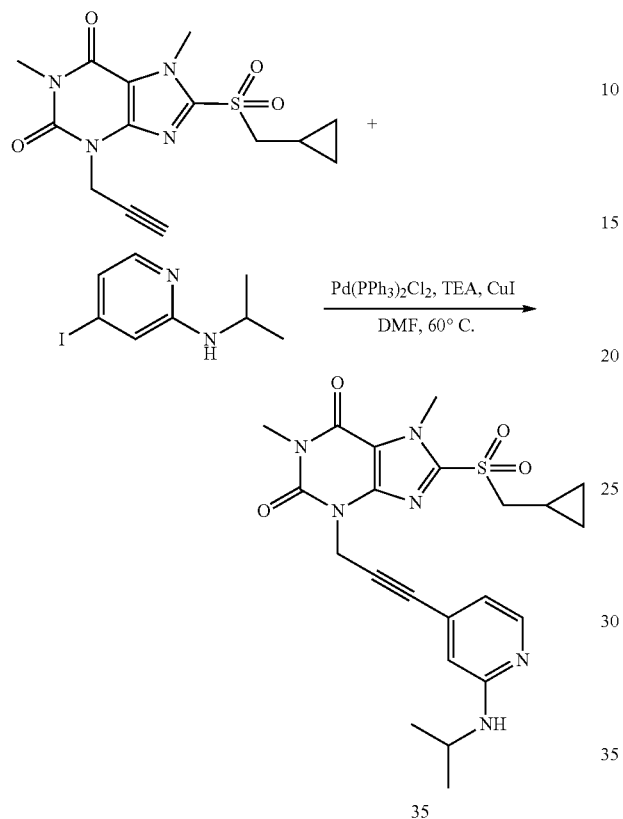

35 was prepared in a yield of 30% (10.5 mg) as a light yellow solid from 8-((cyclopropylmethyl)sulfonyl)-1,7-dimethyl-3-(prop-2-yn-1-yl)-1H-purine-2,6(3H,7H)-dione (25 mg, 75 nmol) and 4-iodo-N-isopropylpyridin-2-amine (29 mg, 0.11 mmol) according to the procedure for 12. $^1$H NMR (400 Mz, CDCl3): δ 7.90 (d, J=5.6 Hz, 1H), 6.50 (d, J=5.6 Hz, 1H), 6.41 (s, 1H), 5.08 (s, 2H), 4.37 (s, 3H), 3.84-3.67 (m, 1H), 3.45 (d, J=7.2 Hz, 2H), 3.45 (s, 3H), 1.24 (s, 3H), 1.22 (s, 3H), 0.87 (m, 1H), 0.64 (m, 2H), 0.31 (m, 2H). LC-MS (ESI) m/z: calcd for [M+H]$^+$, 471.17, found 471.24.

Compound 36: N-(3-(3-(1,7-dimethyl-8-(methylsulfonyl)-2,6-dioxo-1,2,6,7-tetrahydro-3H-purin-3-yl)prop-1-yn-1-yl)-5-(2-morpholinoacetamido)phenyl)cyclopropanecarboxamide

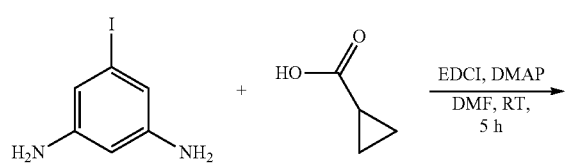

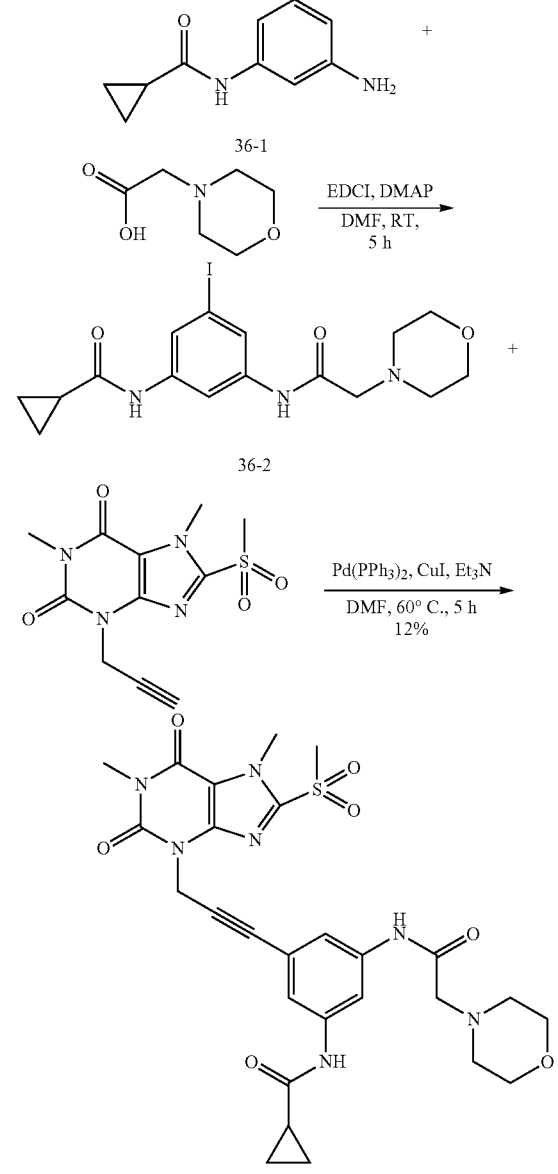

Step 1.

To a solution of cyclopropanecarboxylic acid (85 mg, 1.0 mmol) in DMF (8 mL) was added 5-iodobenzene-1,3-diamine (234 mg, 1.0 mmol), EDCI (192 mg, 1.0 mmol) and DMAP (122 mg, 1.0 mmol) at r.t. under N$_2$ atmosphere. Then the mixture was stirred at RT for 5 hours. UPLC-MS monitored the completion of the reaction. The reaction mixture was poured into water and extracted with DCM. The organic layer was separated, and the aqueous layer was repeatedly extracted with DCM (2×20 mL). The combined extracts were dried with Na$_2$SO$_4$ and concentrated. The crude product 36-1 was used in the next reaction step without any further purification.

Step 2.

36-2 was prepared in a yield of 11% (47 mg, 2 steps) from as a yellow solid according to the procedure for 36-1.

Step 3.

36 was prepared in a yield of 12% (6 mg) from as a yellow solid according to the procedure for 12. $^1$H NMR (400 Hz, CDCl3) δ 7.7 (s, 1H), 7.40 (s, 1H), 7.36 (s, 1H), 5.03 (s, 2H), 4.33 (s, 3H), 3.81 (s, 3H), 3.43 (s, 3H), 3.41 (s, 2H), 3.17 (m, 4H), 2.6 (m, 4H), 1.52 (m, 1H) 1.03 (m, 2H), 0.85 (m, 2H). LC-MS (ESI) m/z: calcd for [M+H]$^+$, 598.20, found 598.27.

Compound 37: 3-(3-(3,5-bis((cyclopropylmethyl)amino)phenyl)prop-2-yn-1-yl)-1,7-dimethyl-8-(methylsulfonyl)-3,7-dihydro-1H-purine-2,6-dione

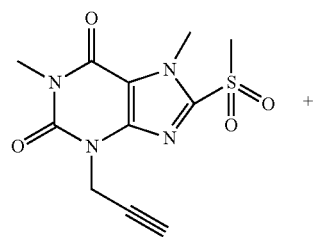

+

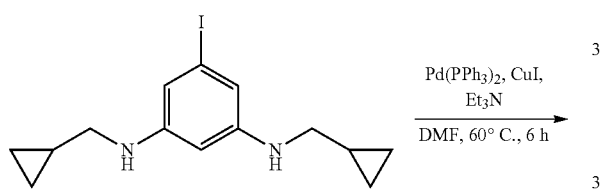

37 was prepared in a yield of 12% (6.2 mg) from as a yellow solid according to the procedure for 12. $^1$H NMR (400 Hz, CDCl3) δ 6.14 (s, 2H), 5.94 (s, 1H), 5.03 (s, 2H), 4.32 (s, 3H), 3.47 (s, 3H), 3.43 (s, 3H), 2.90 (d, J=7.2 Hz, 4H), 1.03 (m, 2H), 0.52 (m, 4H), 0.23 (m, 4H). LC-MS (ESI) m/z: calcd for [M+H]$^+$, 511.20, found 511.27.

Compound 38: N-(3-(3-(1,7-dimethyl-8-(methylsulfonyl)-2,6-dioxo-1,2,6,7-tetrahydro-3H-purin-3-yl)prop-1-yn-1-yl)-5-(2-methoxyacetamido)phenyl)cyclopropanecarboxamide

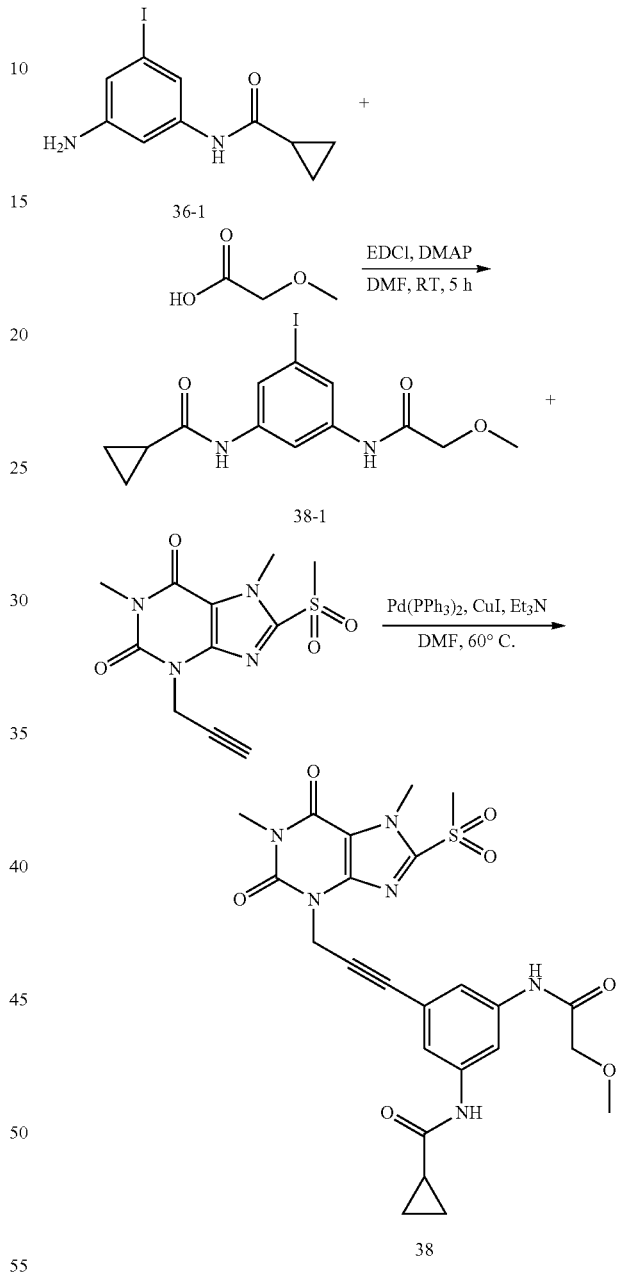

Step 1.
38-1 was prepared in a yield of 38% (38 mg) from 36-1 (80 mg, 0.27) as a yellow solid according to the procedure for 36.
Step 2.
38 was prepared in a yield of 30% (13 mg) from as a yellow solid according to the procedure for 12. $^1$H NMR (400 Hz, CDCl3) δ 7.83 (s, 1H), 7.40 (s, 1H), 7.37 (s, 1H), 5.03 (s, 2H), 4.33 (s, 3H), 3.96 (s, 2H), 3.49 (s, 3H), 3.47 (s, 3H), 3.41 (s, 3H), 1.21 (m, 1H), 1.04 (m, 2H), 0.85 (m, 2H). LC-MS (ESI) m/z: calcd for [M+H]$^+$, 543.16, found 543.25.

Compound 39: N-(3-(3-(1,7-dimethyl-8-(methyl-sulfonyl)-2,6-dioxo-1,2,6,7-tetrahydro-3H-purin-3-yl)prop-1-yn-1-yl)-5-(2-(dimethylamino)acetamido)phenyl)cyclopropanecarboxamide Compound 40: N-(3-amino-5-(3-(1,7-dimethyl-8-(methylsulfonyl)-2,6-dioxo-1H-purin-3(2H,6H,7H)-yl)prop-1-yn-1-yl)phenyl)cyclopropanecarboxamide

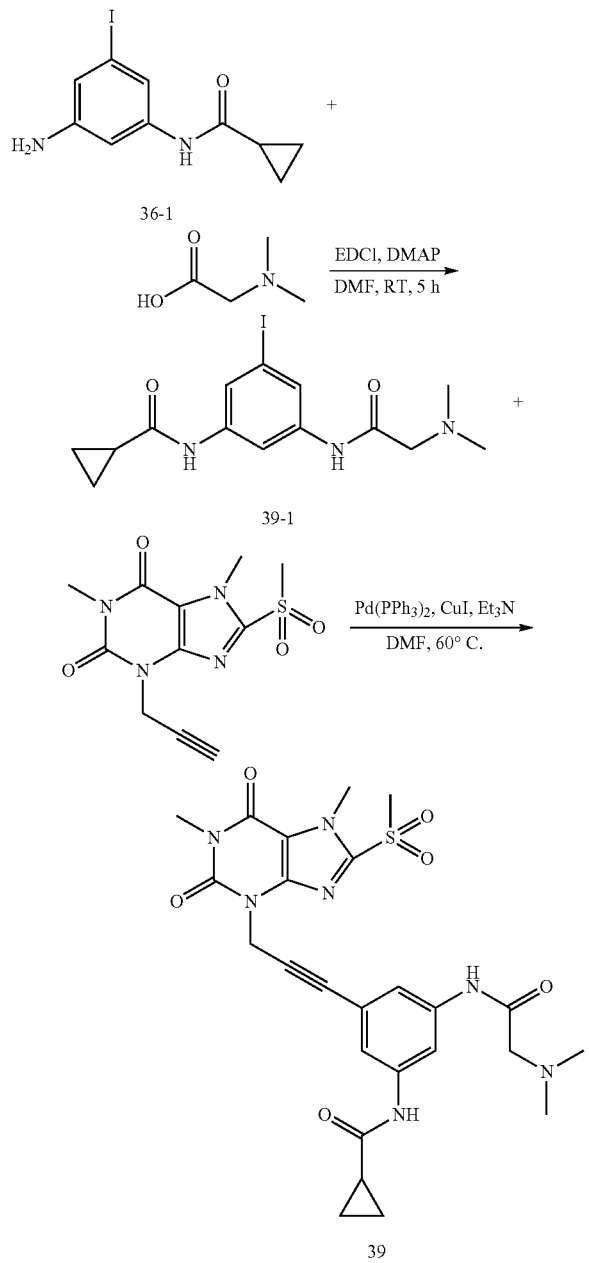

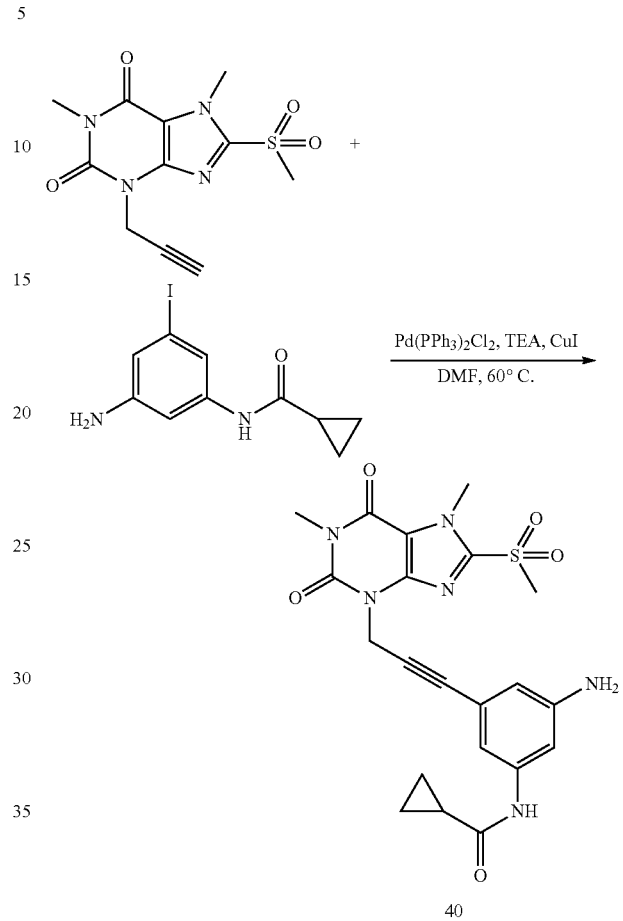

40 was prepared in a yield of 46% (28.6 mg) as a white solid from 1,7-dimethyl-8-(methylsulfonyl)-3-(prop-2-yn-1-yl)-1H-purine-2,6(3H,7H)-dione (39.5 mg, 0.13 mmol) and N-(3-amino-5-iodophenyl)cyclopropanecarboxamide (60.4 mg, 0.2 mmol) according to the procedure for 12. $^1$H NMR (400 Mz, CDCl3): 7.08 (s, 1H), 6.79 (s, 1H), 6.45 (s, 1H), 5.03 (s, 2H), 4.33 (s, 3H), 3.48 (s, 3H), 3.44 (s, 3H), 1.04 (m, 1H), 0.86 (m, 4H). LC-MS (ESI) m/z: calcd for [M+H]$^+$, 471.14, found 471.23.

Compound 41: N-(3-(3-(1,7-dimethyl-8-(methyl-sulfonyl)-2,6-dioxo-1,2,6,7-tetrahydro-3H-purin-3-yl)prop-1-yn-1-yl)-5-(2-methoxyethoxy)phenyl)cyclopropanecarboxamide

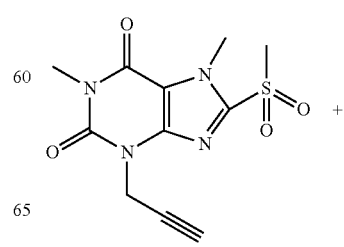

Step 1.
39-1 was prepared in a yield of 39% (40 mg) from 36-1 (80 mg, 0.27) as a yellow solid according to the procedure for 36.

Step 2.
39 was prepared in a yield of 9% (5 mg) from as a yellow solid according to the procedure for 12. $^1$H NMR (400 Hz, CDCl3) δ 7.83 (s, 1H), 7.43 (s, 1H), 7.37 (s, 1H), 5.03 (s, 2H), 4.34 (s, 3H), 3.49 (s, 3H), 3.47 (s, 3H), 3.11 (s, 2H), 2.38 (s, 6H). LC-MS (ESI) m/z: calcd for [M+H]$^+$, 556.19, found 556.28.

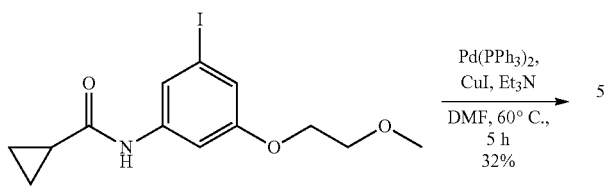

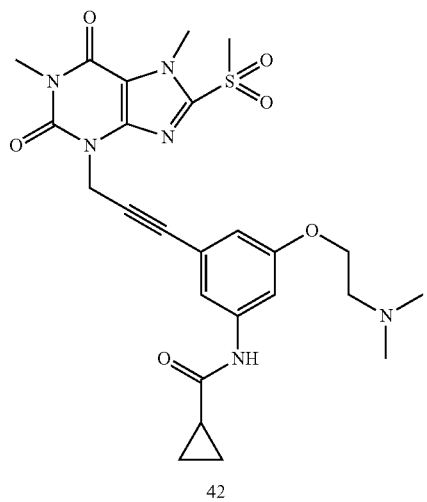

42 was prepared in a yield of 12% (5.5 mg) according to the procedure for 12. ¹H NMR (400 Hz, CDCl3) δ 7.32 (s, 1H), 7.23 (s, 1H), 6.45 (s, 1H), 5.30 (s, 2H), 4.33 (s, 3H), 4.31-4.28 (m, 2H), 3.46 (s, 3H), 3.45 (s, 3H), 2.84 (s, 6H), 1.1 (m, 1H), 0.98 (m, 2H), 0.81 (m, 2H). LC-MS (ESI) m/z: calcd for [M+H]⁺, 543.19, found 543.25.

Compound 43: N-(4-(3-(1,7-dimethyl-8-(methyl-sulfonyl)-2,6-dioxo-1,2,6,7-tetrahydro-3H-purin-3-yl)prop-1-yn-1-yl)-6-(trifluoromethyl)pyridin-2-yl)cyclopropanecarboxamide 41 was prepared in a yield of 13% (5.8 mg) according to the procedure for 12. ¹H NMR (400 Hz, CDCl3) δ 7.20 (s, 1H), 7.15 (s, 1H), 6.64 (s, 1H), 5.01 (s, 2H), 4.31 (s, 3H), 4.03 (m, 2H), 3.67 (m, 2H), 3.46 (s, 3H), 3.42 (s, 3H), 3.40 (s, 3H), 1.51 (m, 1H), 1.00 (m, 2H), 0.79 (m, 2H). LC-MS (ESI) m/z: calcd for [M+H]⁺, 530.16, found 530.22.

Compound 42: N-(3-(3-(1,7-dimethyl-8-(methyl-sulfonyl)-2,6-dioxo-1,2,6,7-tetrahydro-3H-purin-3-yl)prop-1-yn-1-yl)-5-(2-methoxyethoxy)phenyl)cyclopropanecarboxamide

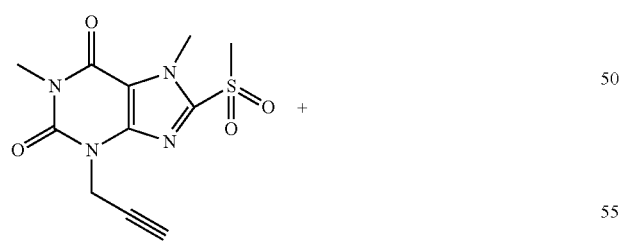

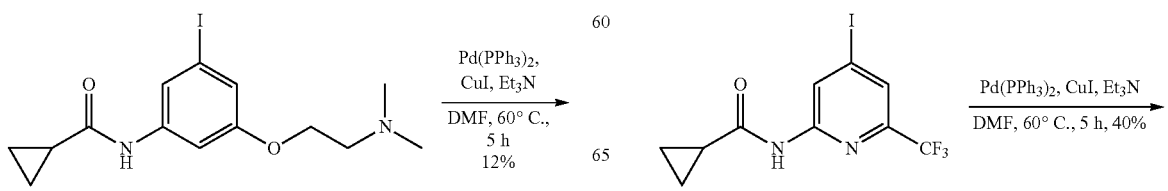

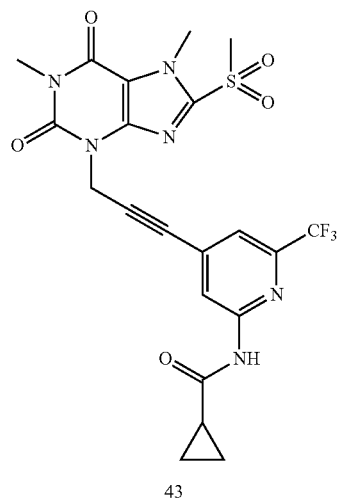

43

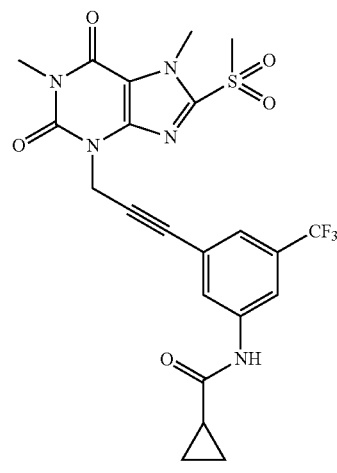

44

43 was prepared in a yield of 40% (16 mg) according to the procedure for 12. $^1$H NMR (400 Hz, DMSO) δ 8.68 (s, 1H), 8.24 (s, 1H), 5.09 (s, 2H), 4.21 (s, 3H), 3.52 (s, 3H), 3.28 (s, 3H), 1.41 (m, 1H), 0.85 (m, 4H). LC-MS (ESI) m/z: calcd for [M+H]+, 525.11, found 525.19.

Compound 44: N-(3-(3-(1,7-dimethyl-8-(methyl-sulfonyl)-2,6-dioxo-1,2,6,7-tetrahydro-3H-purin-3-yl)prop-1-yn-1-yl)-5-(trifluoromethyl)phenyl)cyclopropanecarboxamide 44 was prepared in a yield of 36% (15.9 mg) according to the procedure for 12. $^1$H NMR (400 Hz, DMSO) δ 7.99 (s, 1H), 7.89 (s, 1H), 7.39 (s, 1H), 5.03 (s, 2H), 4.21 (s, 3H), 3.32 (s, 6H), 3.43 (s, 3H), 3.23 (s, 3H), 1.2 (m, 1H), 0.82 (m, 4H). LC-MS (ESI) m/z: calcd for [M+H]$^+$, 524.11, found 524.19.

Compound 45: N-(4-(3-(8-((cyclopropylmethyl)sulfonyl)-1,7-dimethyl-2,6-dioxo-1,2,6,7-tetrahydro-3H-purin-3-yl)prop-1-yn-1-yl)-6-(trifluoromethyl)pyridin-2-yl)cyclopropanecarboxamide

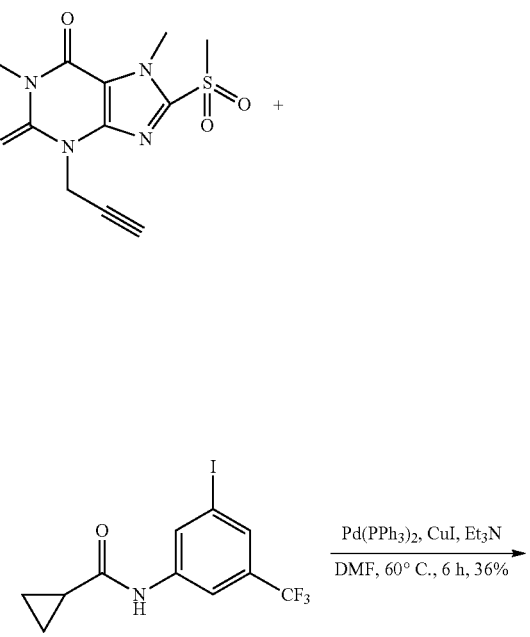

+

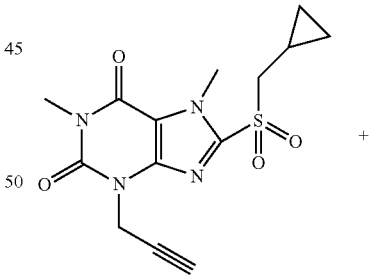

+

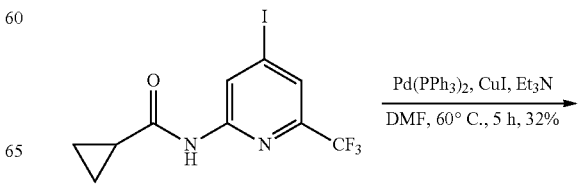

Pd(PPh$_3$)$_2$, CuI, Et$_3$N
DMF, 60° C., 6 h, 36%

Pd(PPh$_3$)$_2$, CuI, Et$_3$N
DMF, 60° C., 5 h, 32%

45

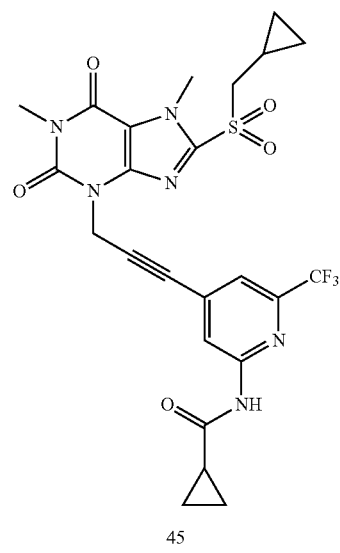

45 was prepared in a yield of 32% (18 mg) according to the procedure for 12. $^1$H NMR (400 Hz, CDCl3) δ 8.68 (s, 1H), 8.23 (s, 1H), 7.39 (s, 1H), 5.09 (s, 2H), 4.23 (s, 3H), 3.55 (d, J=7.2 Hz, 2H), 3.28 (s, 3H), 1.2 (m, 2H), 0.83 (m, 4H), 0.49 (m, 4H), LC-MS (ESI) m/z: calcd for [M+H]$^+$, 565.14, found 565.21.

Compound 46: N-(3-(3-(8-((cyclopropylmethyl)sulfonyl)-1,7-dimethyl-2,6-dioxo-1,2,6,7-tetrahydro-3H-purin-3-yl)prop-1-yn-1-yl)-5-(trifluoromethyl)phenyl)cyclopropanecarboxamide

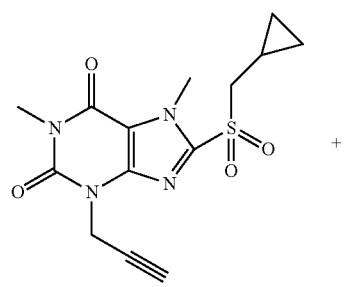
+
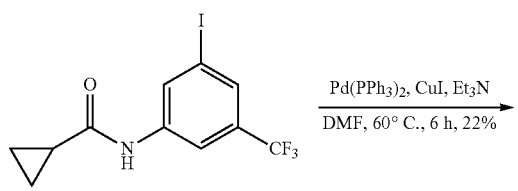

46

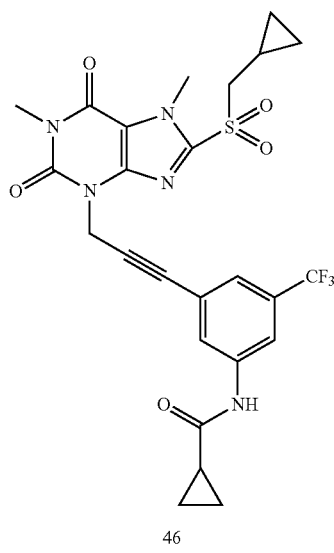

46 was prepared in a yield of 22% (12.5 mg) according to the procedure for 12. $^1$H NMR (400 Hz, CDCl3) δ 7.79 (s, 1H), 7.76 (s, 1H), 7.32 (s, 1H), 5.06 (s, 2H), 4.37 (s, 3H), 3.46 (s, 3H), 3.45 (m, 2H), 1.27 (m, 2H), 1.08 (m, 2H), 0.88 (m, 2H), 0.65 (m, 2H), 0.33 (m, 2H). LC-MS (ESI) m/z: calcd for [M+H]$^+$, 564.14, found 564.23.

Compound 47: N,N'-(5-(3-(1,7-dimethyl-8-(methylsulfinyl)-2,6-dioxo-1,2,6,7-tetrahydro-3H-purin-3-yl)prop-1-yn-1-yl)-1,3-phenylene)dicyclopropanecarboxamide

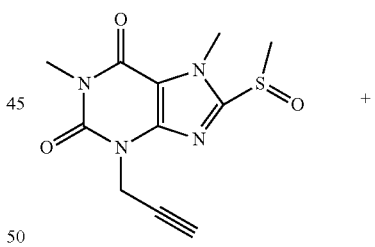
+
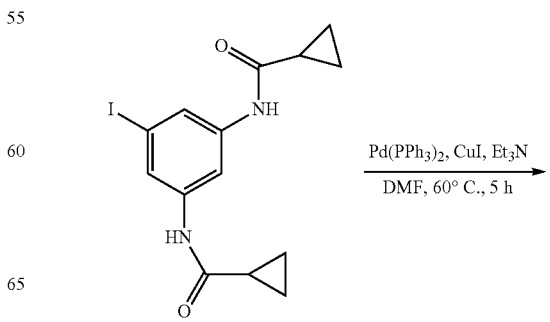

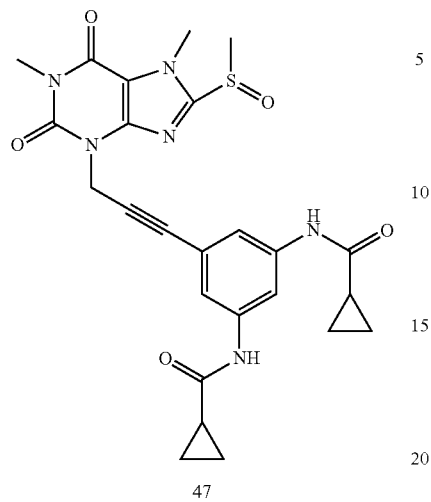

47

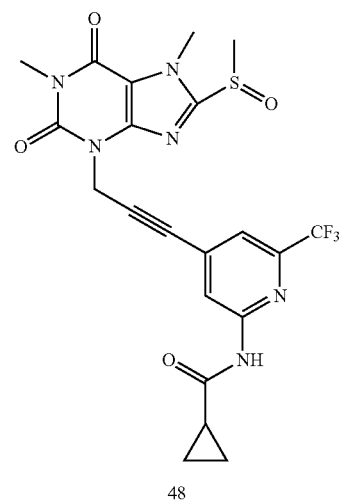

48

47 was prepared in a yield of 11% (5.3 mg) according to the procedure for 12. ¹H NMR (400 Hz, CDCl3) δ 7.83 (s, 1H), 7.37 (s, 2H), 5.00 (s, 2H), 4.12 (s, 3H), 3.27 (s, 3H), 3.14 (s, 3H), 1.73 (m, 2H), 0.78 (m, 8H). LC-MS (ESI) m/z: calcd for [M+H]⁺, 523.17, found 523.22.

Compound 48: N-(4-(3-(1,7-dimethyl-8-(methylsulfinyl)-2,6-dioxo-1,2,6,7-tetrahydro-3H-purin-3-yl)prop-1-yn-1-yl)-6-(trifluoromethyl)pyridin-2-yl)cyclopropanecarboxamide 48 was prepared in a yield of 34% (17 mg) according to the procedure for 12. ¹H NMR (400 Hz, DMSO) δ 8.68 (s, 1H), 8.23 (s, 1H), 5.11 (s, 2H), 4.12 (s, 3H), 3.26 (s, 3H), 3.11 (s, 3H), 1.23 (m, 1H), 1.12 (m, 2H), 0.85 (m, 2H). LC-MS (ESI) m/z: calcd for [M+H]⁺, 509.11, found 509.20.

Compound 49

N-(3-(3-(1,7-dimethyl-8-(methylsulfinyl)-2,6-dioxo-1,2,6,7-tetrahydro-3H-purin-3-yl)prop-1-yn-1-yl)-5-(trifluoromethyl)phenyl)cyclopropanecarboxamide (272)

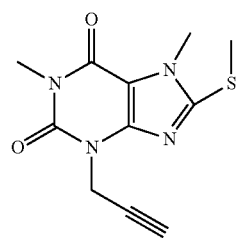 +

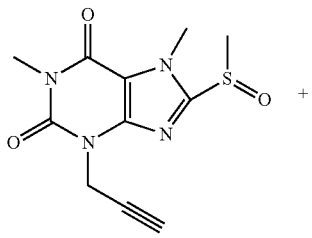 +

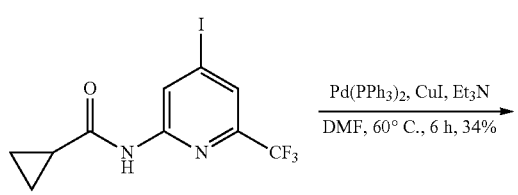 Pd(PPh₃)₂, CuI, Et₃N / DMF, 60° C., 6 h, 34% →

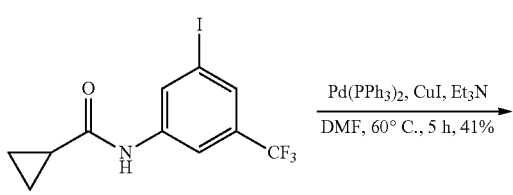 Pd(PPh₃)₂, CuI, Et₃N / DMF, 60° C., 5 h, 41% →

271
-continued

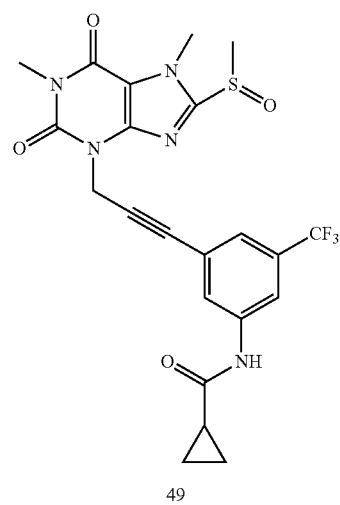

49

49 was prepared in a yield of 41% (21 mg) according to the procedure for 12. ¹H NMR (400 Hz, CDCl3) δ 7.99 (s, 1H), 7.88 (s, 1H), 7.38 (s, 1H), 5.04 (s, 2H), 4.12 (s, 3H), 3.28 (s, 3H), 3.10 (s, 3H), 1.77 (m, 1H), 1.17 (m, 2H), 0.84 (m, 2H). LC-MS (ESI) m/z: calcd for [M+H]⁺, 508.12, found 508.21.

Compound 50 and Compound 51

N,N'-(5-(3-(8-(ethylsulfonyl)-1,7-dimethyl-2,6-di-oxo-1H-purin-3(2H,6H,7H)-yl)prop-1-yn-1-yl)-1,3-phenylene)dicyclopropanecarboxamide and N,N'-(5-(3-(8-(ethylsulfinyl)-1,7-dimethyl-2,6-dioxo-1H-purin-3(2H,6H,7H)-yl)prop-1-yn-1-yl)-1,3-phenylene)dicyclopropanecarboxamide

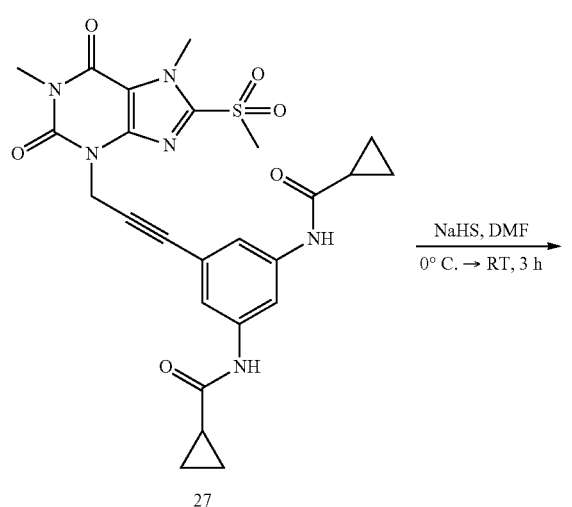

27

272
-continued

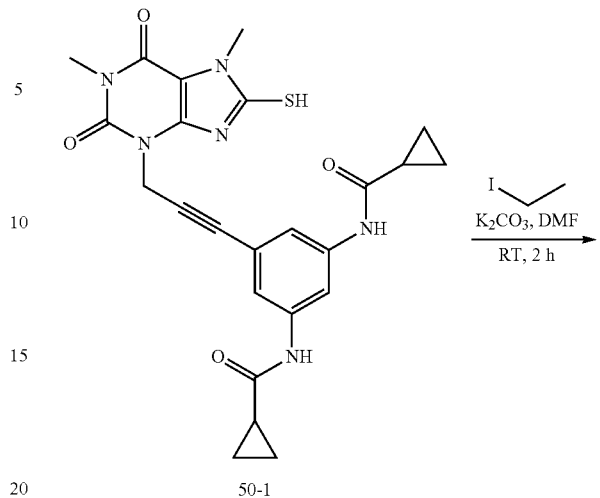

50-1

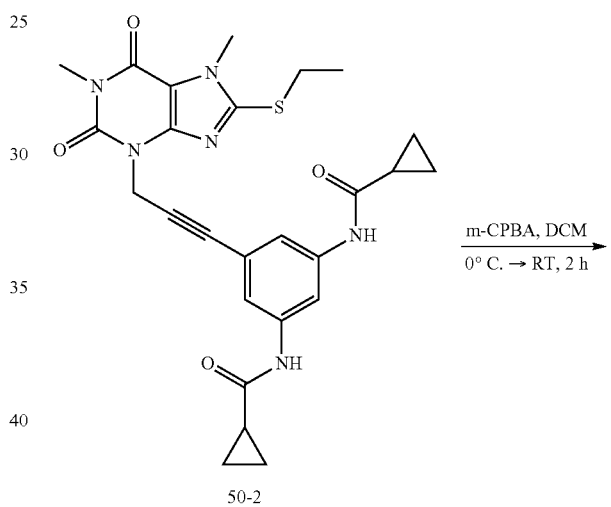

50-2

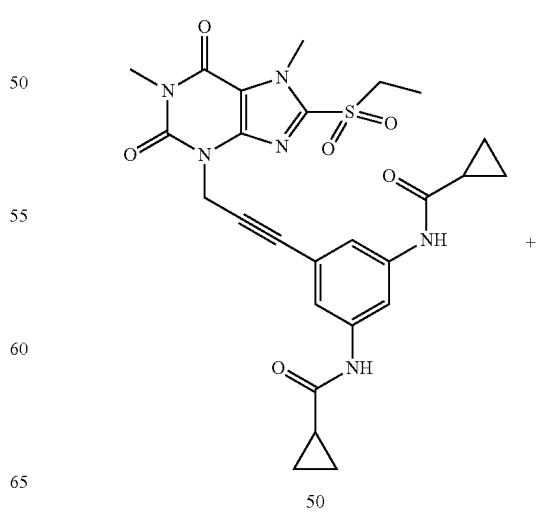

50

273
-continued

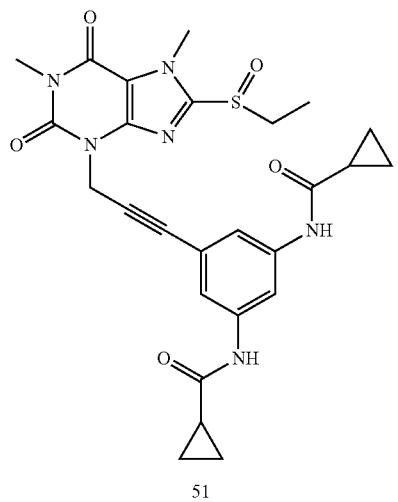

51

Step 1.

To a solution of 27 in anhydrous DMF (0.5 mL) at 0° C. was added NaHS (6.7 mg, 0.12 mmol) and the temperature was allowed to rise to r.t. The mixture was stirred at r.t. for 3 hours. Then the mixture was acidified to pH=3 and extracted with dichloromethane (3*10 mL) and the organic layer was separated, washed by brine, dried over Na$_2$SO$_4$, filtered, concentrated and purified by chromatography on silica gel (PE:EA=1:4) to give 77 mg of 50-1 as a white solid (67%). LC-MS (ESI) m/z: calcd for [M+H]$^+$, 493.16, found 493.23.

Step 2.

To a solution of 50-1 (20.0 mg, 0.04 mmol) and K$_2$CO$_3$ (16.8 mg, 0.12 mmol) in anhydrous DMF (1 mL) was added iodoethane (0.01 ml, 0.12 mmol) and stirred under nitrogen at RT for 2 hours. Then the reaction mixture was poured into water and extracted with dichloromethane (3*5 mL) and the organic layer was separated, washed by brine, dried over Na$_2$SO$_4$, filtered and concentrated to give cruel product 50-2. The cruel product was used directly without further purification. LC-MS (ESI) m/z: calcd for [M+H]$^+$, 521.19, found 521.25.

Step 3.

To a solution of the product of 50-2 in DCM (1 mL) at 0° C. was added m-CPBA (13.8 mg, 0.06 mmol). Then the mixture was stirred at r.t. for 2 hours. Then the solvent was removed and extracted with dichloromethane (3*5 mL) and the organic layer was separated, dried over Na$_2$SO$_4$, filtered, concentrated and purified by Prep. TLC to give 50 (4.6 mg) as a white solid (21% in two steps). $^1$H NMR (400 Mz, CDCl3): δ 7.82 (s, 1H), 7.33 (s, 2H), 5.03 (s, 2H), 4.35 (s, 3H), 3.61 (q, J=7.2 Hz, 2H), 3.44 (s, 3H), 1.47 (t, J=7.2 Hz, 3H), 1.04 (m, 2H), 0.86 (m, 8H). LC-MS (ESI) m/z: calcd for [M+H]$^+$, 553.18, found 553.24.

Compound 51 as a white solid (13% in two steps). $^1$H NMR (400 Mz, CDCl3): δ 7.82 (s, 1H), 7.33 (s, 2H), 5.03 (s, 2H), 4.30 (s, 3H), 3.61 (q, J=7.2 Hz, 2H), 3.44 (s, 3H), 1.47 (t, J=7.2 Hz, 3H), 1.04 (m, 2H), 0.88 (m, 8H). LC-MS (ESI) m/z: calcd for [M+H]$^+$, 537.18, found 537.25.

274

Compound 52: N,N'-(5-(3-(1,7-dimethyl-2,6-dioxo-8-(phenylsulfonyl)-1H-purin-3(2H,6H,7H)-yl)prop-1-yn-1-yl)-1,3-phenylene)dicyclopropanecarboxamide

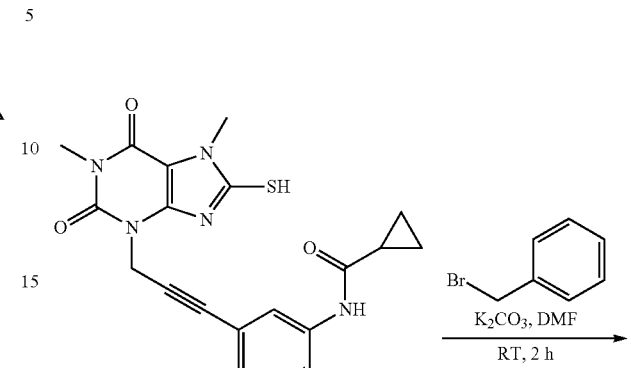

50-1

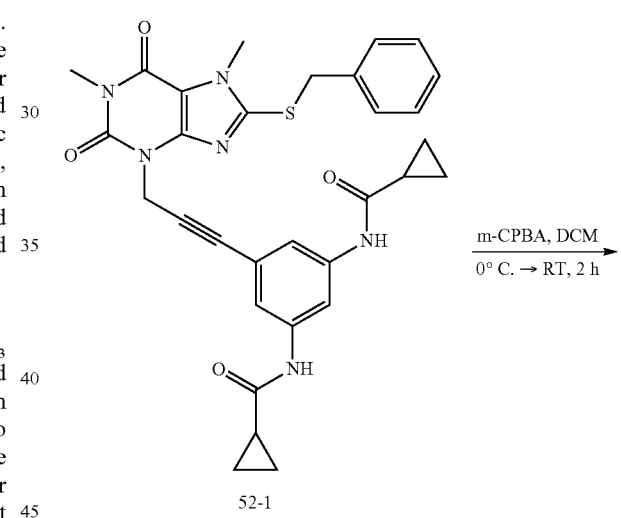

52-1

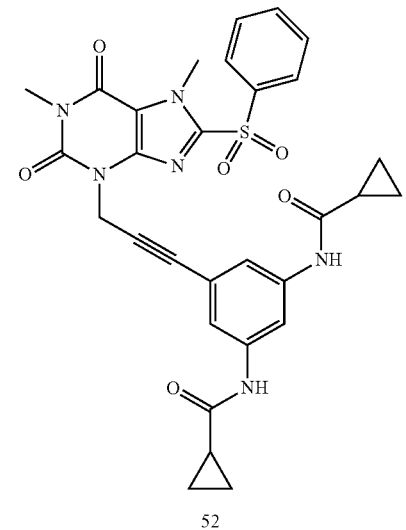

52

52 was prepared from N,N'-(5-(3-(8-mercapto-1,7-dimethyl-2,6-dioxo-1H-purin-3 (2H,6H,7H)-yl)prop-1-yn-1-yl)-1,3-phenylene)dicyclopropanecarboxamide according to the similar procedure outlined for 50 (white solid, 5.7 mg, yield 23% in two steps). ¹H NMR (400 Mz, CDCl3): δ 8.02 (s, 2H), 7.81 (s, 1H), 7.27-7.41 (m, 5H), 5.03 (s, 2H), 4.35 (s, 3H), 3.44 (s, 3H), 1.04 (m, 2H), 0.86 (m, 8H). LC-MS (ESI) m/z: calcd for [M+H]⁺, 601.18, found 601.25.

Compound 53: N,N'-(5-(3-(1,7-dimethyl-2,6-dioxo-8-(propylsulfonyl)-1H-purin-3(2H,6H,7H)-yl)prop-1-yn-1-yl)-1,3-phenylene)dicyclopropanecarboxamide

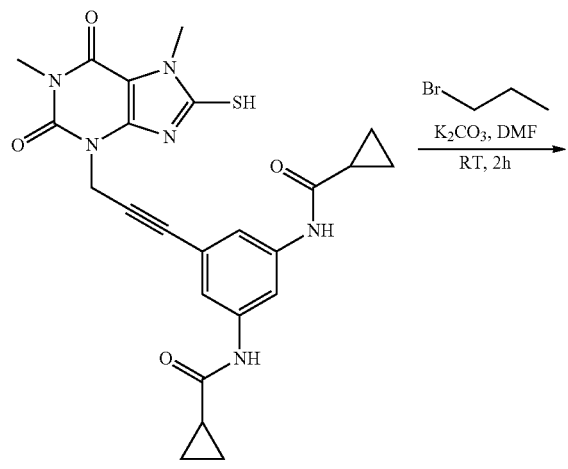

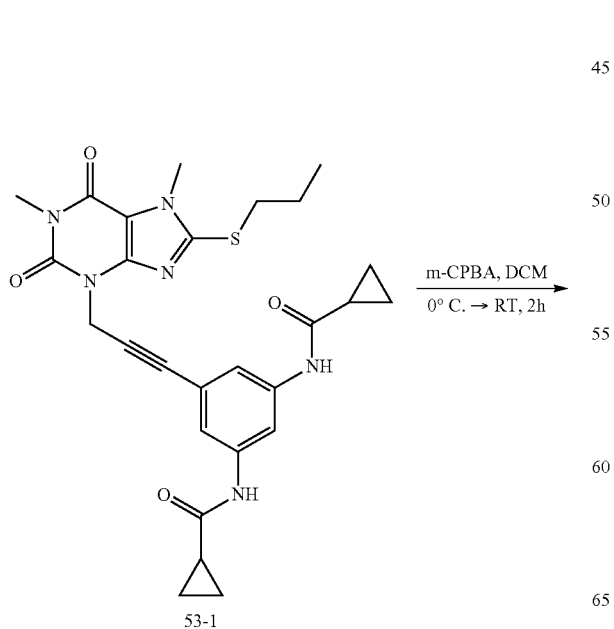

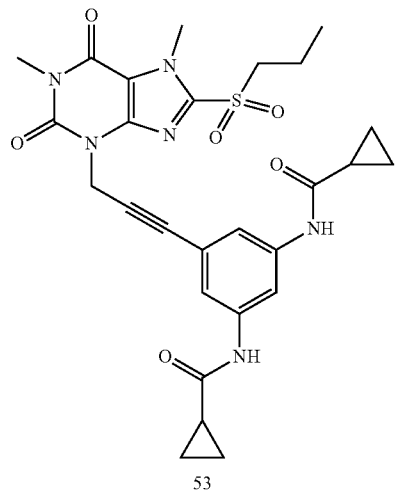

53 was prepared from 50-1 according to the similar procedure outlined for 50 (white solid, 4.7 mg, yield 21% in two steps). ¹H NMR (400 Mz, CDCl3): δ7.84 (s, 1H), 7.33 (s, 2H), 5.04 (s, 2H), 4.35 (s, 3H), 3.55 (m, 2H), 3.44 (s, 3H), 1.64 (m, 2H), 1.04 (m, 2H), 0.86 (m, 11H). LC-MS (ESI) m/z: calcd for [M+H]⁺, 567.19, found 567.25.

Compound 54

N-(3-(3-(1,7-dimethyl-8-(methylsulfinyl)-2,6-dioxo-1,2,6,7-tetrahydro-3H-purin-3-yl)prop-1-yn-1-yl)-5-(2-methoxyethoxy)phenyl)cyclopropanecarboxamide

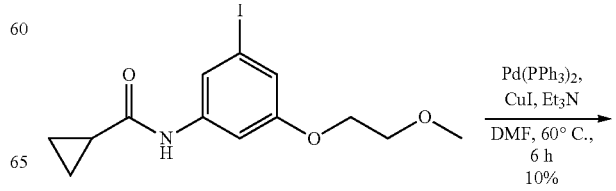

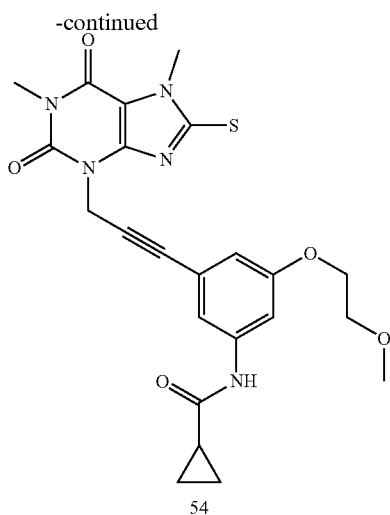

54

54 was prepared in a yield of 10% (3.0 mg) according to the procedure for 12. $^1$H NMR (400 Hz, CDCl3) δ 7.26 (s, 1H), 7.21 (s, 1H), 6.23 (s, 1H), 5.01 (s, 2H), 4.12 (s, 3H), 4.03 (t, J=4.8 Hz, 2H), 3.60 (t, J=4.8 Hz, 2H), 3.30 (s, 3H), 3.27 (s, 3H), 3.14 (s, 3H), 1.77 (m, 1H), 1.15 (m, 2H), 0.86 (m, 2H). LC-MS (ESI) m/z: calcd for [M+H]+, 514.17, found 514.24.

Compound 55: N-benzyl-1,3,7-trimethyl-2,6-dioxo-2,3,6,7-tetrahydro-1H-purine-8-sulfonamide

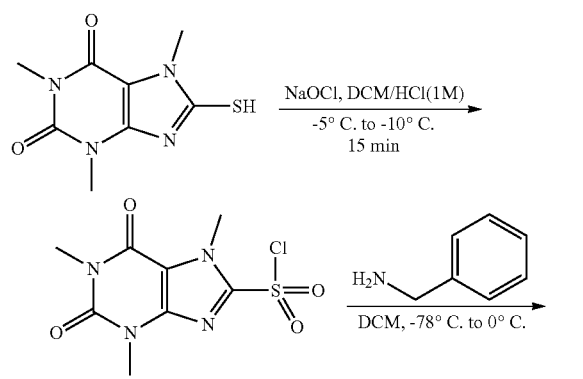

55

8-mercapto-1,3,7-trimethyl-1H-purine-2,6(3H,7H)-dione (50 mg, 0.22 mmol) was stirred in a mixture of 2 mL of DCM and 2 mL of 1 M HCl in a flask for 10 min at −10 to −5° C. Cold (5° C.) sodium hypochlorite (6% solution, 0.68 M, 1 mL, 0.72 mmol) was added dropwise with very rapid stirring, maintaining the temperature at −10 to −5° C. The mixture was stirred for 15 min at −10 to −5° C. after the addition was completed. The mixture was transferred to a separatory funnel (pre-cooled with ice water) and the CH$_2$Cl$_2$ layer was rapidly separated and collected in a clean flask cooled in a dry ice-acetone bath. Benzylamine (1.4 mL, 12.5 mmol) was added with stirring, whereupon the CH$_2$Cl$_2$ layer became a white suspension. The flask was removed to an ice-water bath and the suspension was stirred for 30 min at 0° C. The suspension was then washed with 1 M phosphoric acid (all solids dissolved at once), then with water and brine. Drying (Na$_2$SO$_4$) and further purified by silica gel column chromatography (DCM/MeOH=200/1) to give 7.9 mg 55 as a yellow solid (10%). $^1$H NMR (400 Hz, DMSO-d$_6$) δ 7.26-7.17 (m, 5H), 5.76 (s, 2H), 4.05 (s, 3H), 3.40 (s, 3H), 3.23 (s, 3H). LC-MS (ESI) m/z: calcd for [M+H]+, 364.10, found 364.19.

Compound 56: N, 1,3,7-tetramethyl-2,6-dioxo-2,3,6,7-tetrahydro-1H-purine-8-sulfonamide

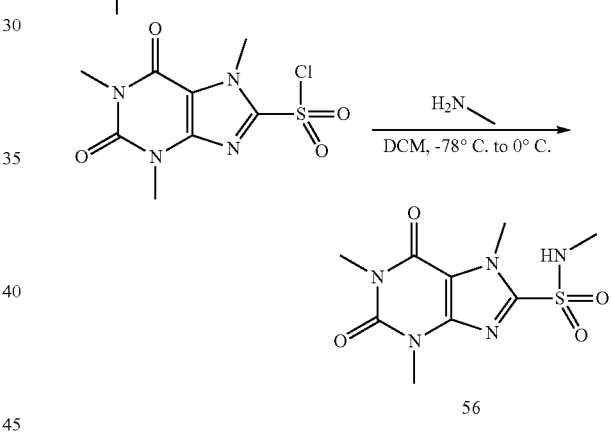

56

56 was prepared as a yellow solid according to the procedure for 55. $^1$H NMR (400 Hz, CDCl3) δ 4.26 (s, 3H), 3.56 (s, 3H), 3.41 (s, 3H), 2.98 (s, 3H). LC-MS (ESI) m/z: calcd for [M+H]+, 288.07, found 288.12.

Compound 57

N-ethyl-1,3,7-trimethyl-2,6-dioxo-2,3,6,7-tetrahydro-1H-purine-8-sulfonamide

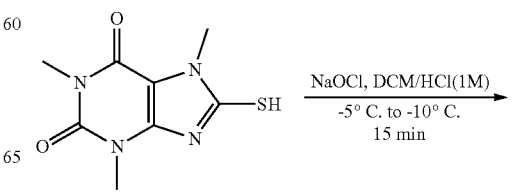

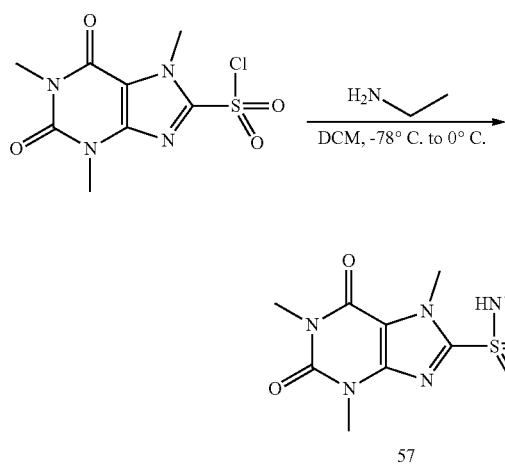

57 was prepared as a yellow solid according to the procedure for 55. $^1$H NMR (400 Hz, CDCl3) δ 4.25 (s, 3H), 3.56 (s, 3H), 3.40 (s, 3H), 3.33 (m, 2H), 1.27 (m, 3H). LC-MS (ESI) m/z: calcd for [M+H]$^+$, 302.07, found 302.14.

Compound 58: 1,3,7-trimethyl-2,6-dioxo-N-propyl-2,3,6,7-tetrahydro-1H-purine-8-sulfonamide

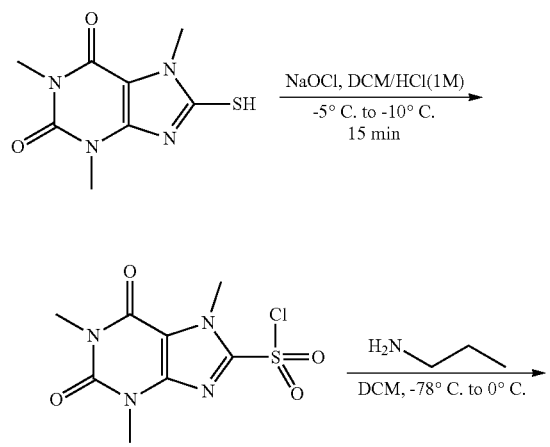

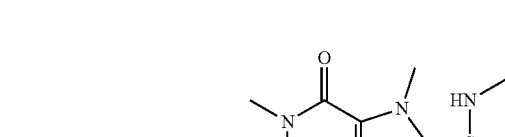

58 was prepared as a yellow solid according to the procedure for 55. $^1$H NMR (400 Hz, CDCl3) δ 4.21 (s, 3H), 3.53 (s, 3H), 3.31 (s, 3H), 3.14 (t, J=6.8 Hz, 2H), 1.57 (m, 2H), 0.94 (t, J=6.4 Hz, 3H). LC-MS (ESI) m/z: calcd for [M+H]$^+$, 316.10, found 316.17.

Compound 59: N,N,1,3,7-pentamethyl-2,6-dioxo-2,3,6,7-tetrahydro-1H-purine-8-sulfonamide

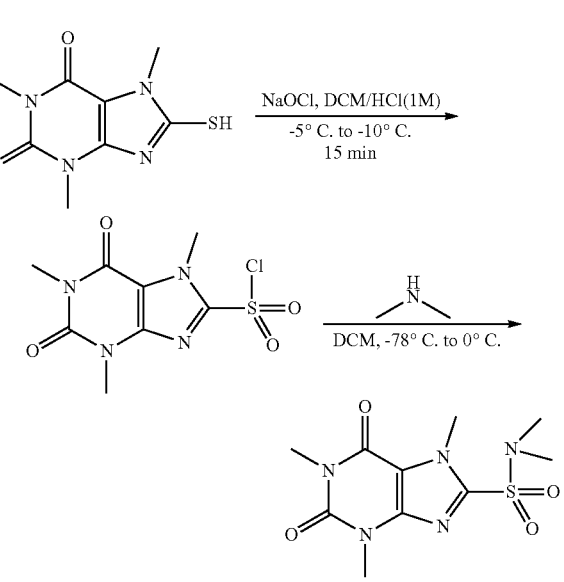

59 was prepared as a yellow solid according to the procedure for 55. $^1$H NMR (400 Hz, CDCl3) δ 4.24 (s, 3H), 3.56 (s, 3H), 3.42 (s, 3H), 3.23 (s, 3H), 2.92 (s, 3H). LC-MS (ESI) m/z: calcd for [M+H]$^+$, 302.08, found 302.14.

Compound 60: 1,3,7-trimethyl-8-(pyrrolidin-1-ylsulfonyl)-3,7-dihydro-1H-purine-2,6-dione

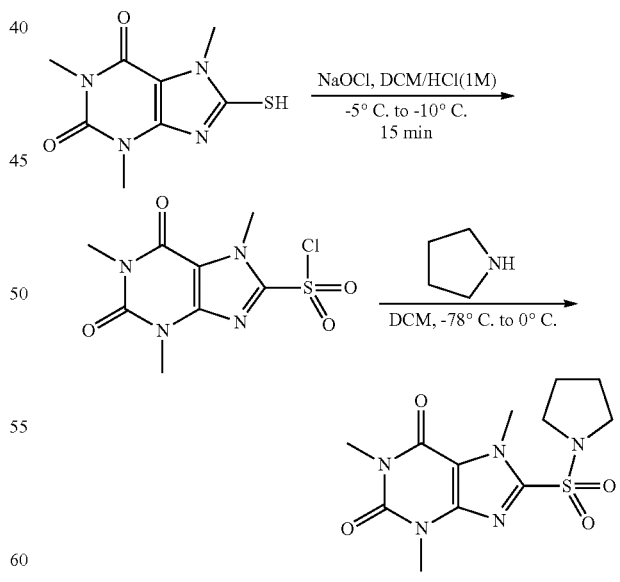

60 was prepared as a yellow solid according to the procedure for 55. $^1$H NMR (400 Hz, CDCl3) δ 4.24 (s, 3H), 3.59 (m, 2H), 3.54 (s, 3H), 3.42 (s, 3H), 2.05 (m, 2H). LC-MS (ESI) m/z: calcd for [M+H]+, 328.10, found 328.18.

Compound 61: 1,3,7-trimethyl-2,6-dioxo-N-(2,2,2-trifluoroethyl)-2,3,6,7-tetrahydro-1H-purine-8-sulfonamide

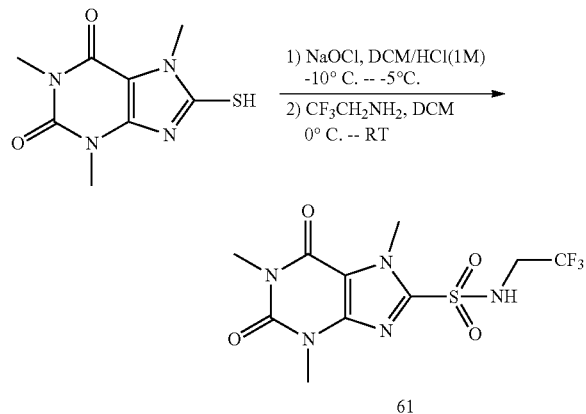

61 was prepared as a yellow solid according to the procedure for 55. $^1$H NMR (400 Hz, CDCl3) δ 4.31 (s, 3H), 3.49 (s, 3H), 3.40 (s, 3H), 3.3 (m, 2H). LC-MS (ESI) m/z: calcd for [M+H]$^+$, 356.06, found 356.12.

Compound 62

1,3-dimethyl-6,7-dihydrothiazolo[2,3-f]purine-2,4(1H,3H)-dione 8,8-dioxide

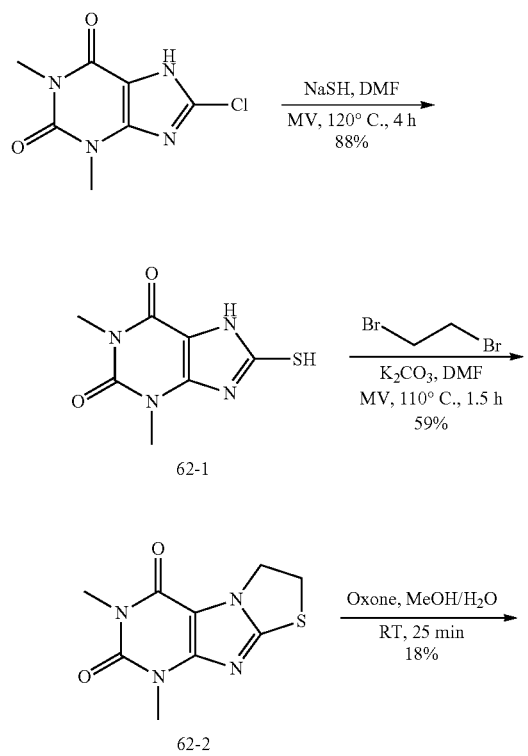

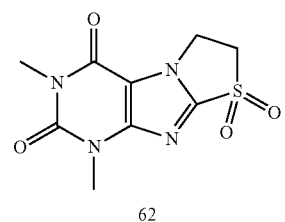

Step 1.
To a solution of 8-chloro-1,3-dimethyl-3,7-dihydro-1H-purine-2,6-dione (456 mg, 2.0 mmol) in DMF (6 mL) was added NaSH (170 mg, 3.0 mmol). Then the mixture was stirred at 110° C. for 2 hours by microwave irradiation. UPLC-MS monitored the completion of the reaction. The solvent was evaporated under reduced pressure and further purified by silica gel column chromatography (DCM/MeOH=100/1) to give 404 mg 62-1 as a yellow solid (88%). LC-MS (ESI) m/z: calcd for [M+H]$^+$, 213.04, found 213.12.

Step 2.
To a solution of 62-1 (80 mg, 0.38 mmol) in DMF (2 mL), 1,2-Dibromoethane (204 μL, 2.4 mmol) and K$_2$CO$_3$ (130 mg, 0.95 mmol) were added. The mixture was heated to 110° C. for 1.5 h by microwave irradiation. The solvent was evaporated under reduced pressure and further purified by silica gel column chromatography (DCM/MeOH=200/1) to give 53 mg 62-2 as a yellow solid (59%), LC-MS (ESI) m/z: calcd for [M+H]$^+$, 239.05, found 239.14.

Step 3.
62 was prepared in a yield of 18% (10.0 mg) from 62-2 (50 mg, 0.21 mmol) and Oxone (193 mg, 0.32 mmol) as a white solid according to the procedure for 1. $^1$H NMR: (400 Hz, DMSO-d$_6$) δ 4.79 (t, J=6.4 Hz, 2H), 4.28 (t, J=6.4 Hz, 2H), 3.44 (s, 3H), 3.24 (s, 3H). LC-MS (ESI) m/z: calcd for [M+H]+, 271.04, found 271.13.

Compound 63: 1,3-dimethyl-7,8-dihydro-6H-[1,3]thiazino[2,3-f]purine-2,4(1H,3H)-dione 9,9-dioxide

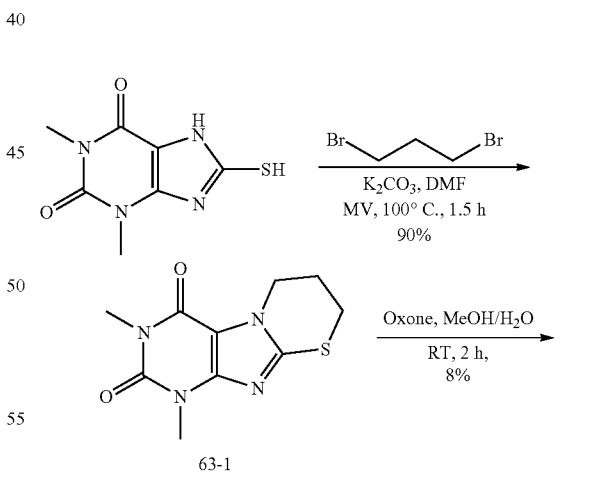

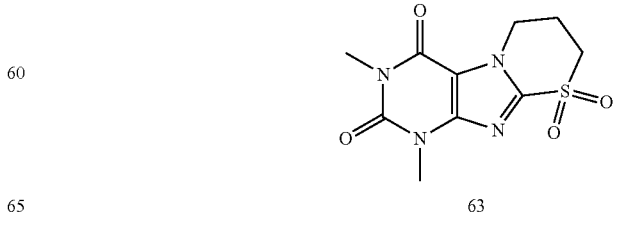

Step 1.

63-1 was prepared in a yield of 90% (10.0 mg) from 8-mercapto-1,3-dimethyl-1H-purine-2,6(3H,7H)-dione (60 mg, 0.28 mmol) and 1,3-Dibromopropane (142 μL, 1.4 mmol) according to the procedure for 62. LC-MS (ESI) m/z: calcd for [M+H]+, 253.07, found 253.13.

Step 2.

63 was prepared in a yield of 8% (6.0 mg) from 63-1 (65 mg, 0.26 mmol) and Oxone (475 mg, 0.77 mmol) as a yellow solid according to the procedure for 1. $^1$H NMR: (400 Hz, CDCl3) δ 4.60 (t, J=5.6 Hz, 2H), 3.45 (m, 2H), 3.61 (s, 3H), 3.19 (s, 3H), 2.81 (m, 2H). LC-MS (ESI) m/z: calcd for [M+H]+, 285.06, found 285.13.

Compound 64: 3-methyl-1-(prop-2-yn-1-yl)-6,7-dihydrothiazolo[2,3-f]purine-2,4(1H,3H)-dione 8,8-dioxide

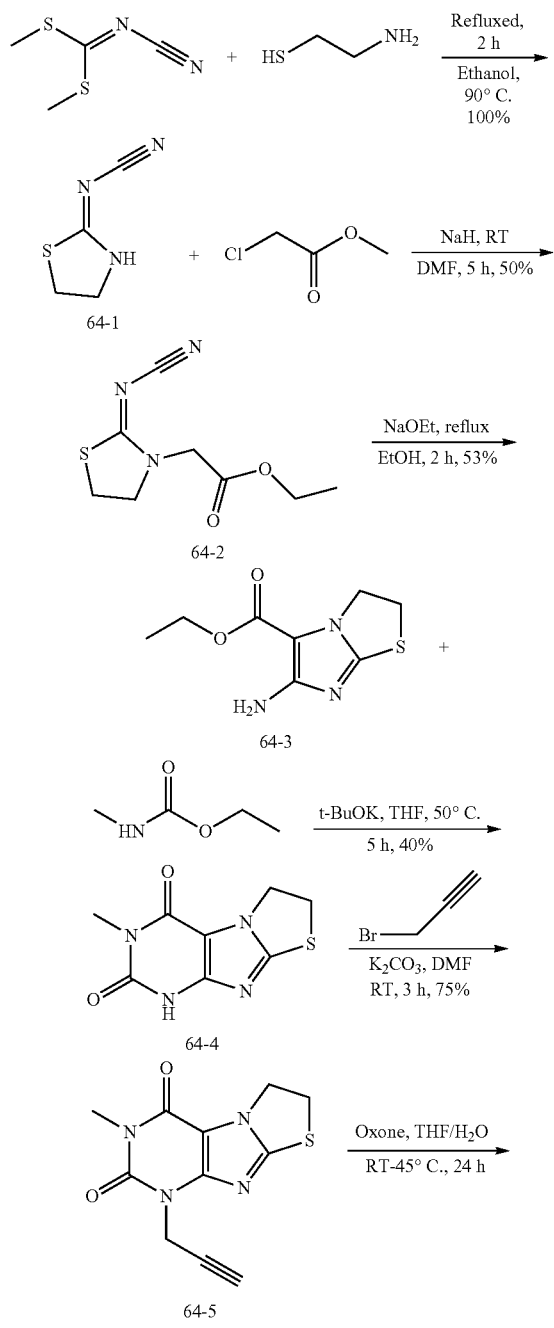

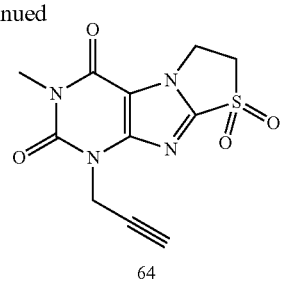

64

Step 1.

To a solution of dimethyl cyanocarbonimidodithioate (2.0 g) in EtOH (60 ml) were added 2-aminoethane-1-thiol (1.06 g). Then the mixture was stirred at 90° C. for 2 hours. UPLC-MS monitored the completion of the reaction. The solvent was evaporated under reduced pressure and further purified by silica gel column chromatography (DCM/MeOH=100/1) to give 1.7 g 64-1 as a yellow solid (100%). LC-MS (ESI) m/z: calcd for [M+H]+, 128.02, found 128.11.

Step 2.

To a solution of 64-1 (500 mg) in DMF (8 mL), ethyl 2-chloroacetate (517 mg) and NaH were added. The mixture was stirred at RT for 5 hours. The solvent was evaporated under reduced pressure and further purified by silica gel column chromatography (DCM/MeOH=200/1) to give 392 mg 64-2 as a yellow solid (50%), LC-MS (ESI) m/z: calcd for [M+H]$^+$, 214.06, found 214.12.

Step 3.

To a solution of 64-2 (200 mg) in EtOH (6 ml) were added EtONa. Then the mixture was stirred at 90° C. for 2 hours. UPLC-MS monitored the completion of the reaction. The solvent was evaporated under reduced pressure and further purified by silica gel column chromatography (DCM/MeOH=100/1) to give 108 mg 64-3 as a yellow solid (53%). LC-MS (ESI) m/z: calcd for [M+H]$^+$, 214.06, found 214.12.

Step 4.

To a solution of 64-3 (1.49 g) in THF (60 ml) were added ethyl methylcarbamate (1.73 g) and t-BuOK (2.35 g). Then the mixture was stirred at 50° C. for 5 hours. UPLC-MS monitored the completion of the reaction. The solvent was evaporated under reduced pressure and further purified by silica gel column chromatography (DCM/MeOH=100/1) to give 625 mg 64-4 as a yellow solid (40%). LC-MS (ESI) m/z: calcd for [M+H]$^+$, 225.04, found 225.13.

Step 5.

To a solution of 64-4 (500 mg) in DMF (5 mL), Propargyl bromide (336 mg) and K$_2$CO$_3$ (615 mg) were added. The mixture was stirred at RT for 3 h. The solvent was evaporated under reduced pressure and further purified by silica gel column chromatography (DCM/MeOH=200/1) to give 3438 mg 64-5 as a yellow solid (75%), LC-MS (ESI) m/z: calcd for [M+H]$^+$, 263.05, found 263.12.

Step 6.

64 was prepared in a yield of 30% (3.3 mg) from 64-5 (10 mg, 0.038 mmol) and Oxone (95 mg, 0.15 mmol) as a yellow solid according to the procedure for 1. $^1$H NMR (400 Hz, CDCl3) δ 4.89 (d, J=0.8 Hz, 2H), 4.85 (m, 2H), 4.03 (m, 2H), 3.48 (s, 3H), 2.28 (t, J=1.6 Hz, 1H). LC-MS (ESI) m/z: calcd for [M+H]$^+$, 295.04, found 295.11.

Compound 65: 1-(3-(3-hydroxyphenyl)prop-2-yn-1-yl)-3-methyl-6,7-dihydrothiazolo[2,3-f]purine-2,4(1H,3H)-dione 8-oxide and Compound 66 1-(3-(3-hydroxyphenyl)prop-2-yn-1-yl)-3-methyl-6,7-dihydrothiazolo[2,3-f]purine-2,4(1H,3H)-dione 8,8-dioxide

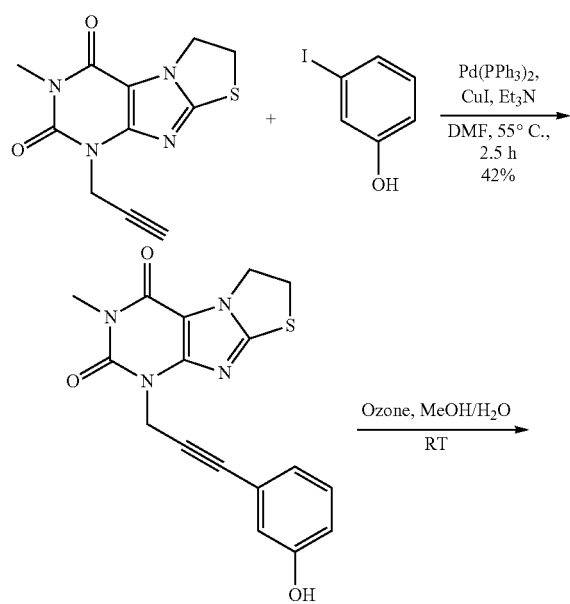

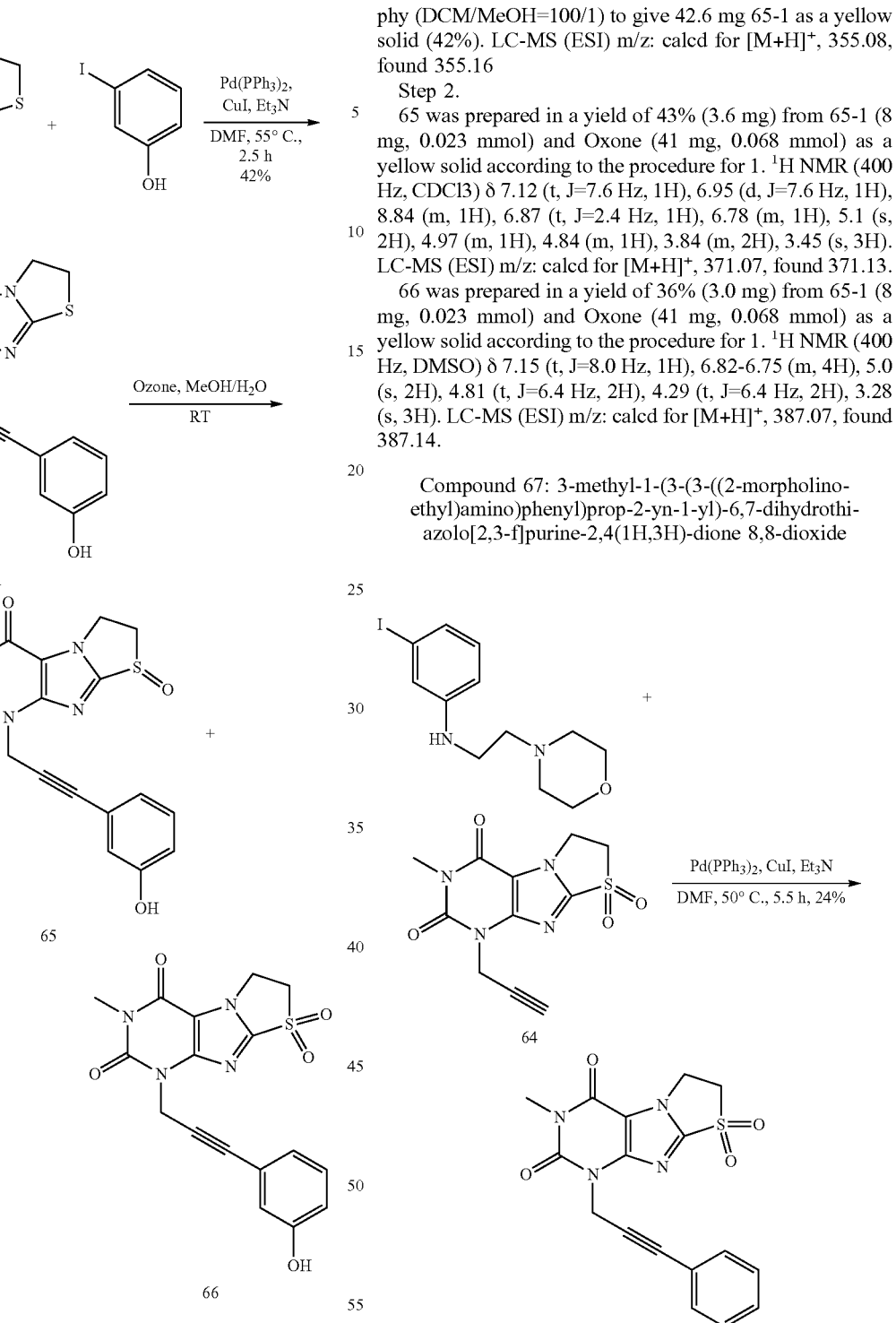

Step 1. Sonogashira Coupling

To a solution of 3-methyl-1-(prop-2-yn-1-yl)-6,7-dihydrothiazolo[2,3-f]purine-2,4(1H,3H)-dione (75 mg, 0.29 mmol) in DMF (5 ml) were added 3-iodophenol (143 mg, 0.43 mmol), Pd(PPh$_3$)$_2$ (20 mg, 0.028 mmol), CuI (5.3 mg, 0.028 mmol), Et$_3$N (60 µL, 0.43 mmol). Then the mixture was degassed for 15 min, then the mixture was stirred at 55° C. for 2.5 hours. UPLC-MS monitored the completion of the reaction. The solvent was evaporated under reduced pressure and further purified by silica gel column chromatography (DCM/MeOH=100/1) to give 42.6 mg 65-1 as a yellow solid (42%). LC-MS (ESI) m/z: calcd for [M+H]$^+$, 355.08, found 355.16

Step 2.

65 was prepared in a yield of 43% (3.6 mg) from 65-1 (8 mg, 0.023 mmol) and Oxone (41 mg, 0.068 mmol) as a yellow solid according to the procedure for 1. $^1$H NMR (400 Hz, CDCl3) δ 7.12 (t, J=7.6 Hz, 1H), 6.95 (d, J=7.6 Hz, 1H), 8.84 (m, 1H), 6.87 (t, J=2.4 Hz, 1H), 6.78 (m, 1H), 5.1 (s, 2H), 4.97 (m, 1H), 4.84 (m, 1H), 3.84 (m, 2H), 3.45 (s, 3H). LC-MS (ESI) m/z: calcd for [M+H]$^+$, 371.07, found 371.13.

66 was prepared in a yield of 36% (3.0 mg) from 65-1 (8 mg, 0.023 mmol) and Oxone (41 mg, 0.068 mmol) as a yellow solid according to the procedure for 1. $^1$H NMR (400 Hz, DMSO) δ 7.15 (t, J=8.0 Hz, 1H), 6.82-6.75 (m, 4H), 5.0 (s, 2H), 4.81 (t, J=6.4 Hz, 2H), 4.29 (t, J=6.4 Hz, 2H), 3.28 (s, 3H). LC-MS (ESI) m/z: calcd for [M+H]$^+$, 387.07, found 387.14.

Compound 67: 3-methyl-1-(3-(3-((2-morpholinoethyl)amino)phenyl)prop-2-yn-1-yl)-6,7-dihydrothiazolo[2,3-f]purine-2,4(1H,3H)-dione 8,8-dioxide 67 was prepared in a yield of 24% (11 mg) from 3-iodo-N-(2-morpholinoethyl) aniline (41 mg, 0.12 mmol) as a yellow solid according to the procedure for 12. $^1$H NMR (400 Hz, CDCl3) δ 7.05 (m, 1H), 6.75 (d, J=7.6 Hz, 1H), 6.65 (s, 1H), 6.55 (m, 1H), 5.08 (s, 2H), 4.84 (t, J=6.0 Hz, 2H), 4.01 (t, J=6.0 Hz, 2H), 3.75 (t, J=7.6 Hz, 4H) 3.43 (s, 3H), 3.17 (t, J=6.0 Hz, 2H), 2.67 (t, J=6.0 Hz, 2H), 2.54 (m, 4H). LC-MS (ESI) m/z: calcd for [M+H]$^+$, 499.17, found 499.23.

Compound 68

N,N'-(5-(3-(1,7-dimethyl-8-(methylthio)-2,6-dioxo-1H-purin-3(2H,6H,7H)-yl)prop-1-yn-1-yl)-1,3-phenylene)dicyclopropanecarboxamide

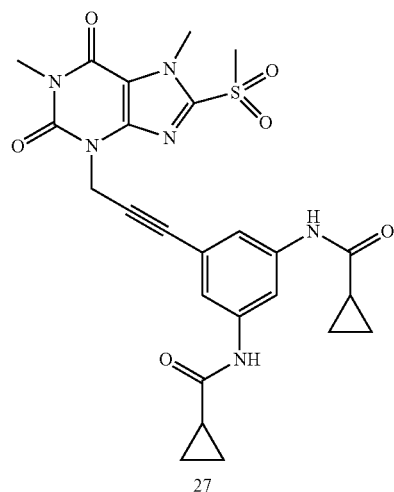

To a solution of 27 (7.0 mg, 0.013 mmol) in DMF (2 mL) was added MeSNa (1.4 mg, 0.02 mmol). Then the mixture was stirred at RT for 4 hours. Then the solvent was removed and extracted with dichloromethane (3×5 mL) and the organic layer was separated, dried over Na$_2$SO$_4$, filtered, concentrated and purified by Prep. TLC to obtain 68 3.3 mg (50%) as a white solid. LC-MS (ESI) m/z: calcd for [M+H]$^+$, 507.17, found 507.23.

Compound 69

1,7-dimethyl-8-(methylsulfonyl)-3-(prop-2-yn-1-yl)-6-thioxo-6,7-dihydro-1H-purin-2(3H)-one

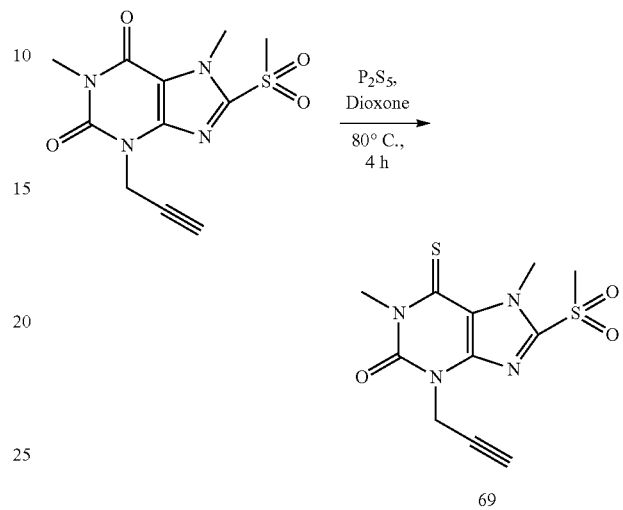

To a solution of compound 1,7-dimethyl-8-(methylsulfonyl)-3-(prop-2-yn-1-yl)-1H-purine-2,6(3H,7H)-dione (60 mg, 0.2 mmol) in dioxone (3 mL) was added P$_2$S$_5$ (108 mg, 0.24 mmol). Then the mixture was stirred at 80° C. for 4 hours. Then the solvent was removed and extracted with dichloromethane (3×5 mL) and the organic layer was separated, ried over Na$_2$SO$_4$, filtered, concentrated and purified by Prep. TLC to obtain compound 69 19 mg (30%) as a white solid. LC-MS (ESI) m/z: calcd for [M+H]+, 313.04, found 313.13.

Compound 70-72 are prepared according to the procedure outlined in scheme

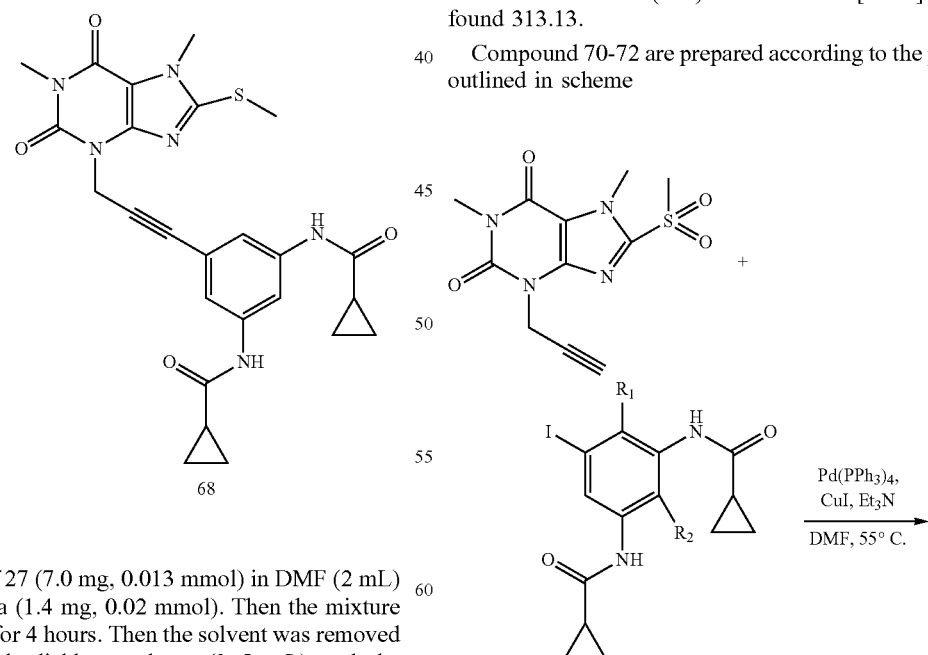

70: R$_1$ = F, R$_2$ = H
71: R$_1$ = F, R$_2$ = F
71: R$_1$ = H, R$_2$ = F

289
-continued
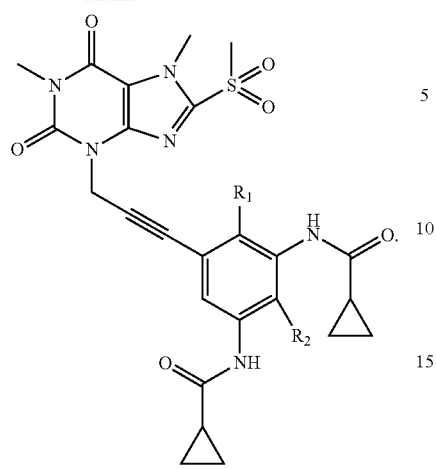
75-77 are prepared according to the procedure outlined in scheme
290
-continued
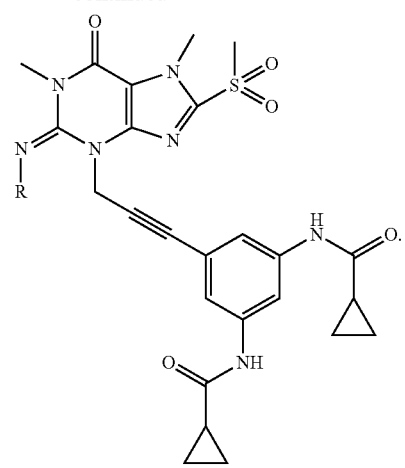 [SMILES: Cc1c(S(C)(=O)=O)nc2n(CC#Cc3cc(NC(=O)C4CC4)cc(NC(=O)C4CC4)c3)c(=O)n(C)c(=O)n12]
78 is prepared according to the procedure outlined in scheme
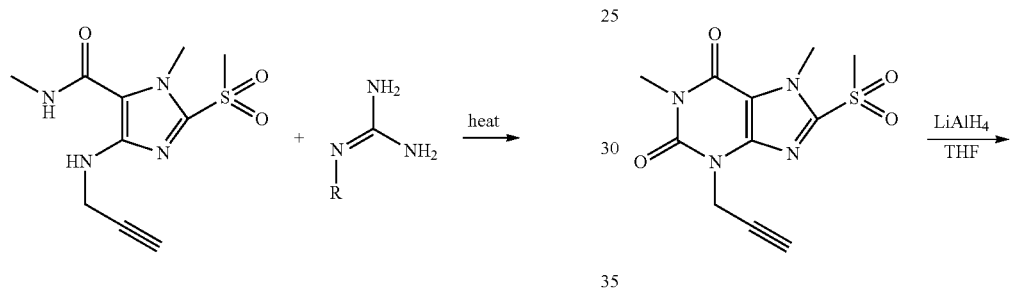
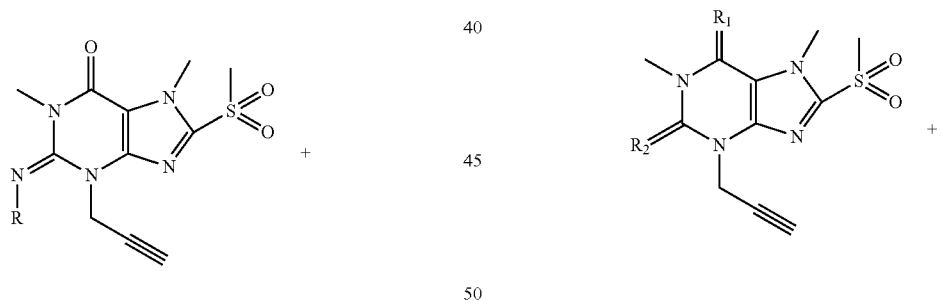
73: R = Me
74: R = H
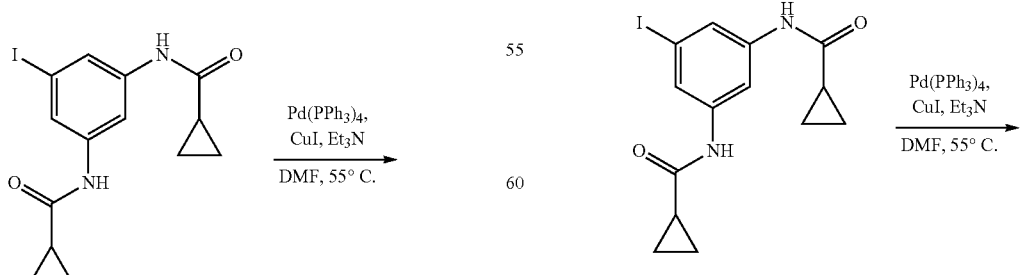
75: $R_1$ = O, $R_2$ = H
76: $R_1$ = H, $R_2$ = O
77: $R_1$ = H, $R_2$ = H 291
-continued
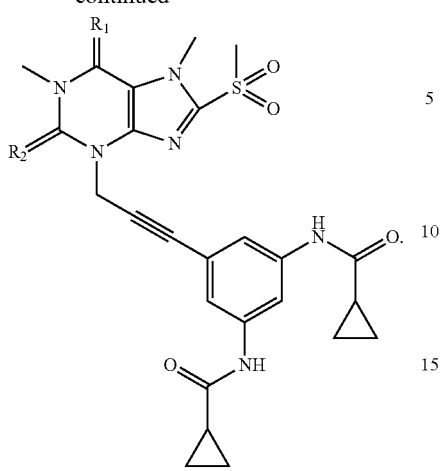
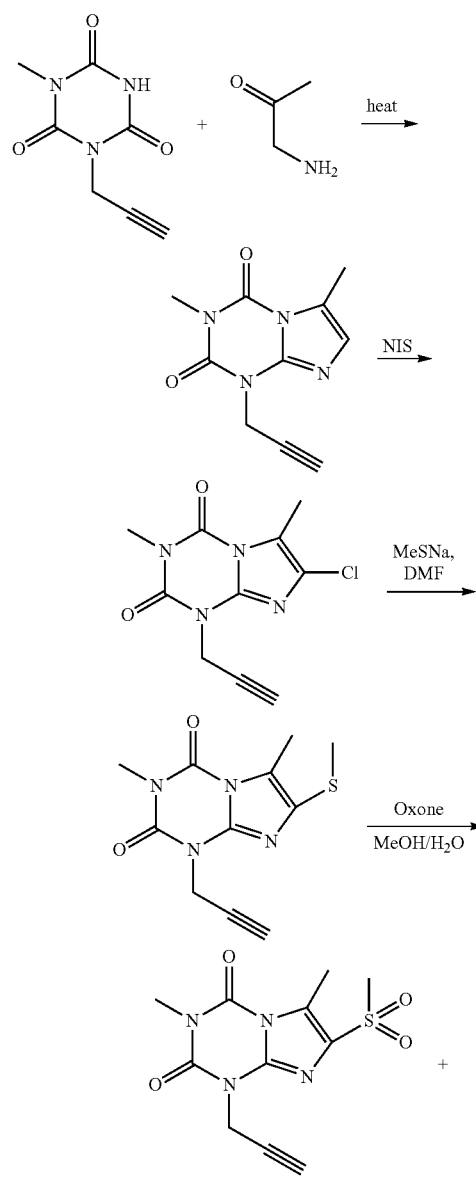
292
-continued
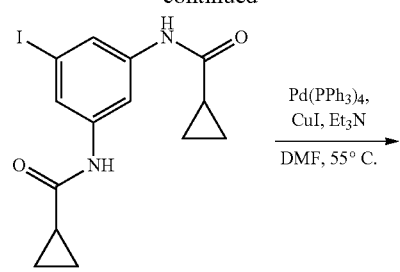
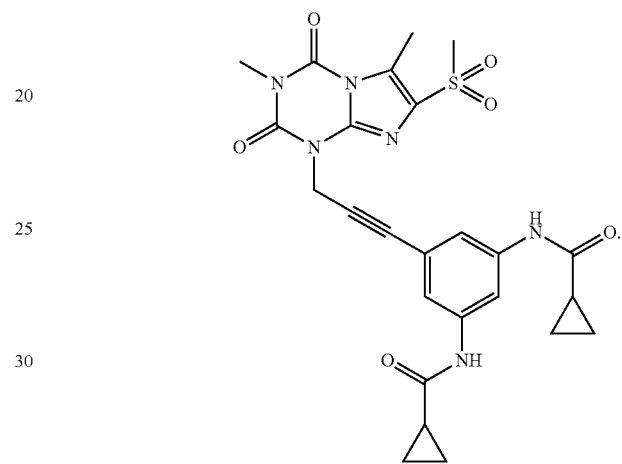
79-80 are prepared according to the procedure outlined in scheme
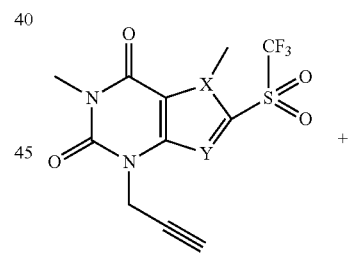
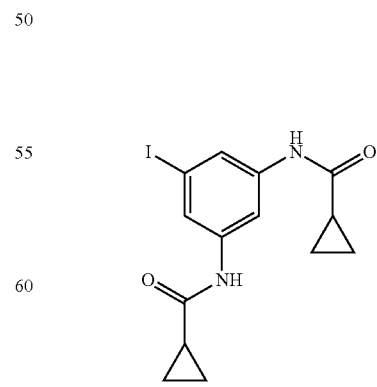
79: X = N, Y = C
80: X = C, Y = N

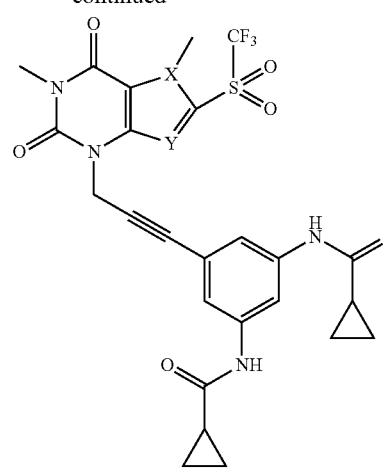
81-82 are prepared according to the procedure outlined in scheme
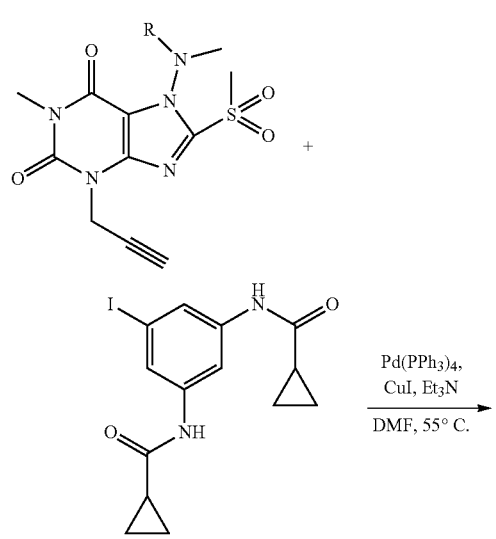
81: R = H
82: R = Me
83-85 are prepared according to the procedure outlined in scheme
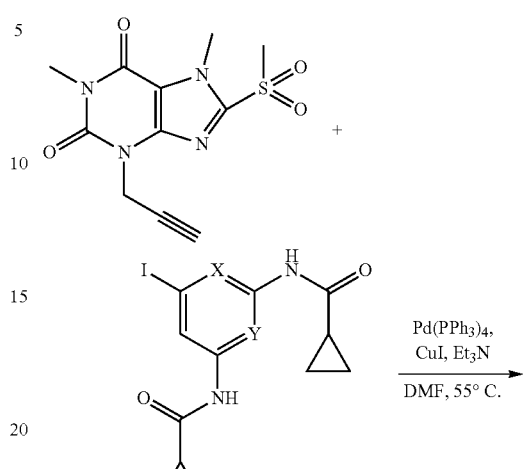
83: X = H, Y = N
84: X = N, Y = H
85: X = N, Y = N
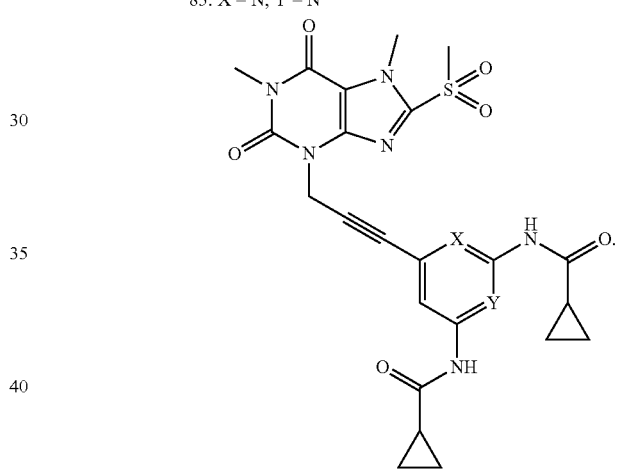
86-87 are prepared according to the procedure outlined in scheme
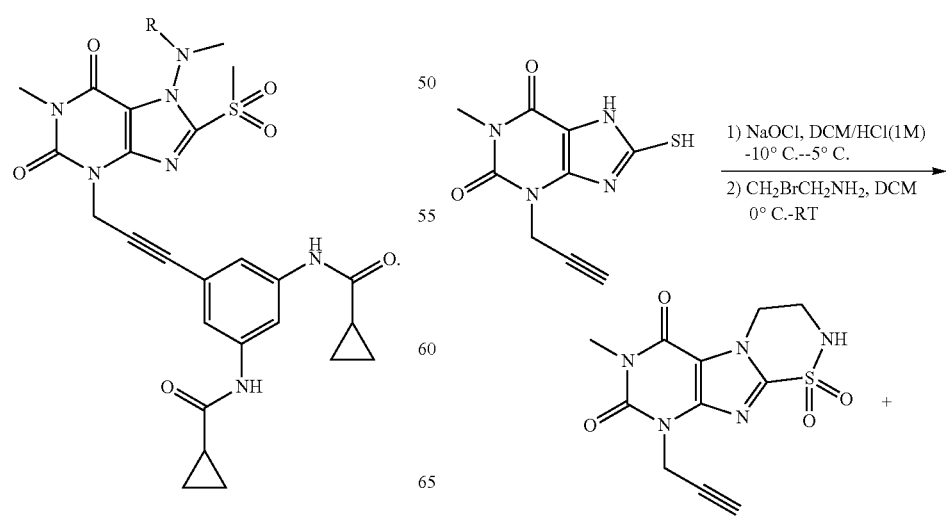

295
-continued

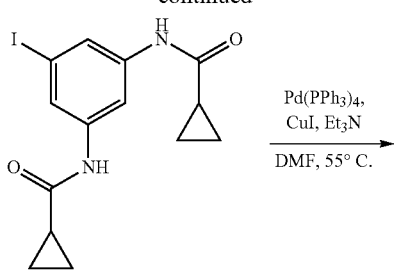

86: R₁ = H
87: R₂ = Me

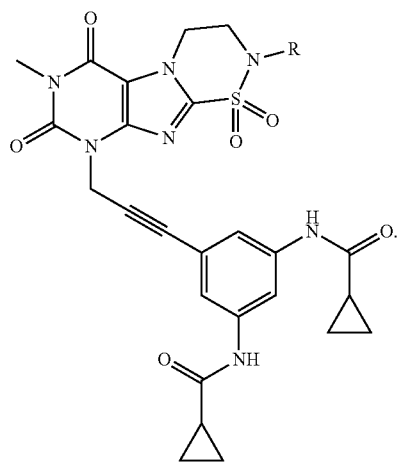

88-90 are prepared according to the procedure outlined in scheme

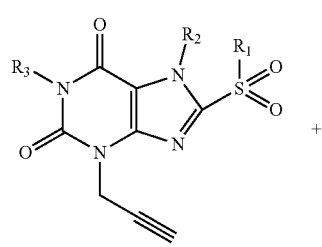

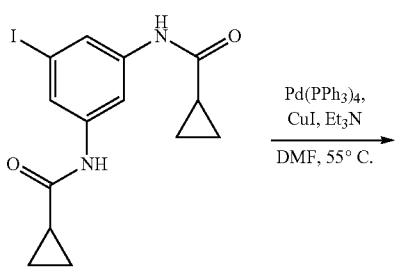

88: R₁ = CD₃, R₂ = H, R₃ = H
89: R₁ = H, R₂ = H, R₃ = CD₃
90: R₁ = H, R₂ = CD₃, R₃ = H

296
-continued

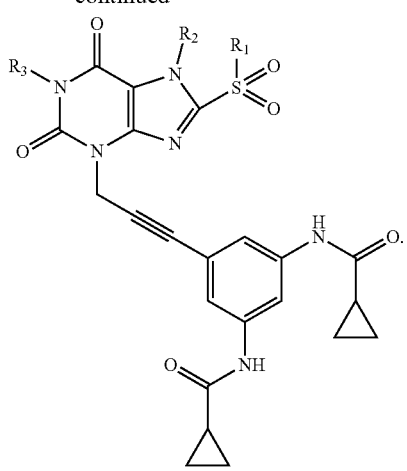

91-100 are prepared according to the procedure of Compound 70-90.

101-110 are prepared according to the procedure outlined in scheme

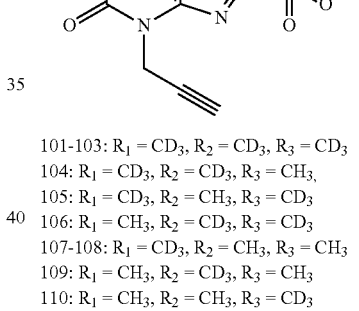

101-103: R₁ = CD₃, R₂ = CD₃, R₃ = CD₃
104: R₁ = CD₃, R₂ = CD₃, R₃ = CH₃
105: R₁ = CD₃, R₂ = CH₃, R₃ = CD₃
106: R₁ = CH₃, R₂ = CD₃, R₃ = CD₃
107-108: R₁ = CD₃, R₂ = CH₃, R₃ = CH₃
109: R₁ = CH₃, R₂ = CD₃, R₃ = CH₃
110: R₁ = CH₃, R₂ = CH₃, R₃ = CD₃

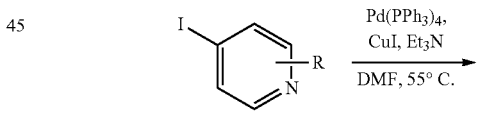

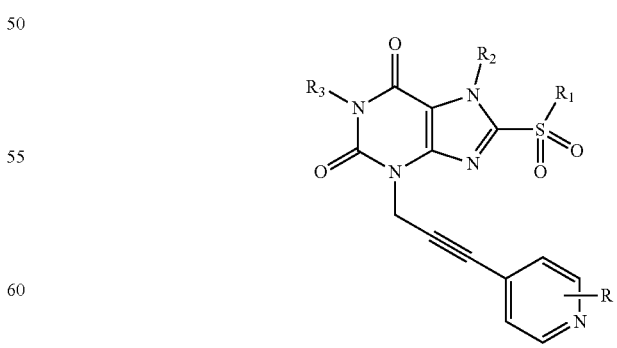

X = C or N    R = OH, 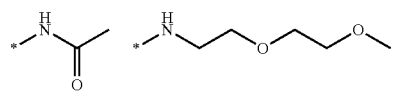

297
-continued
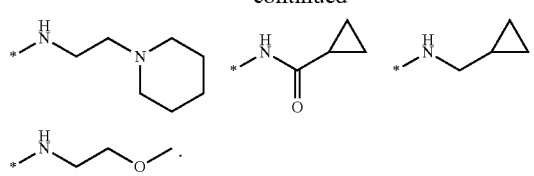
111 are prepared according to the procedure outlined in scheme
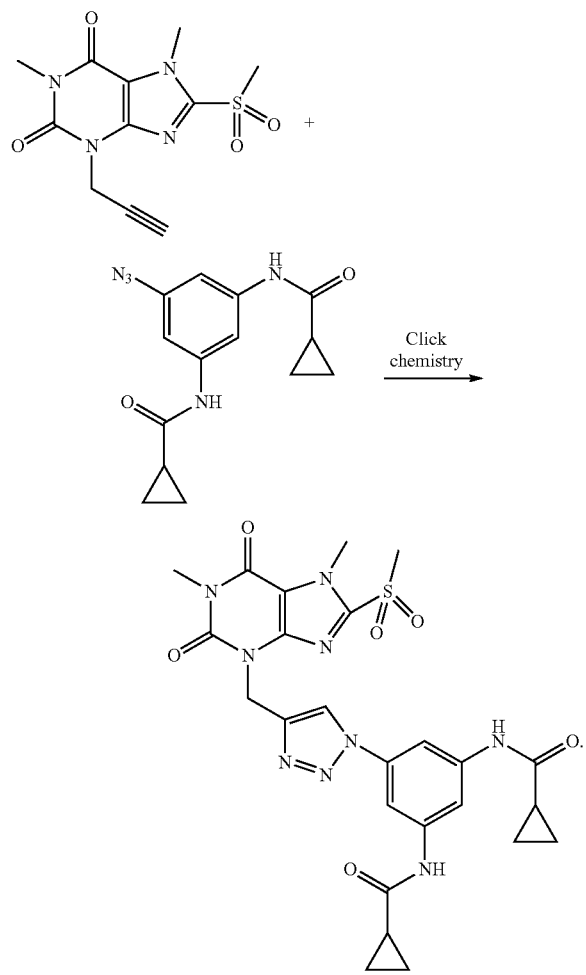
112-113 are prepared according to the procedure outlined in scheme
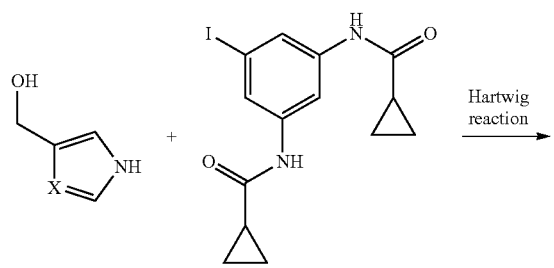
298
-continued
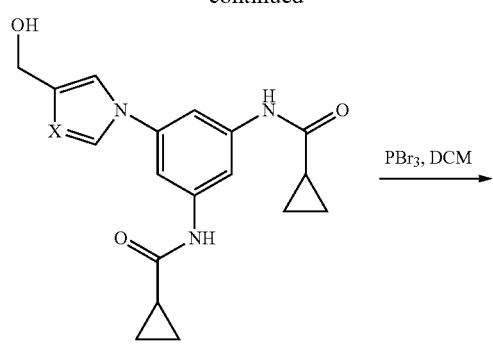
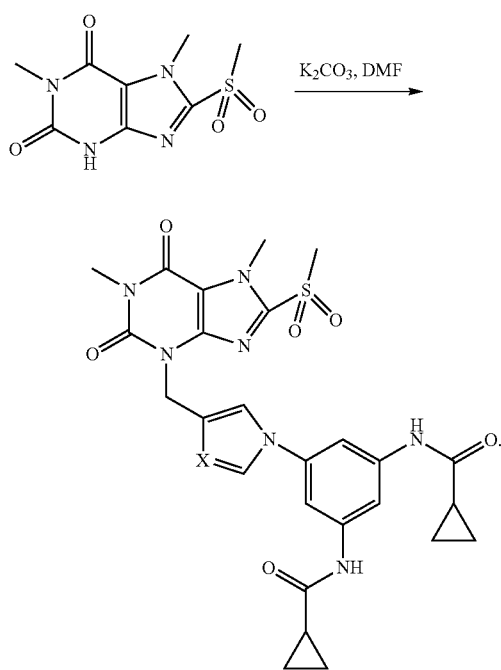
112: X = N
113: X = C
114-117 are prepared according to the procedure outlined in scheme
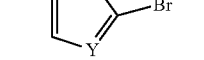

299
-continued

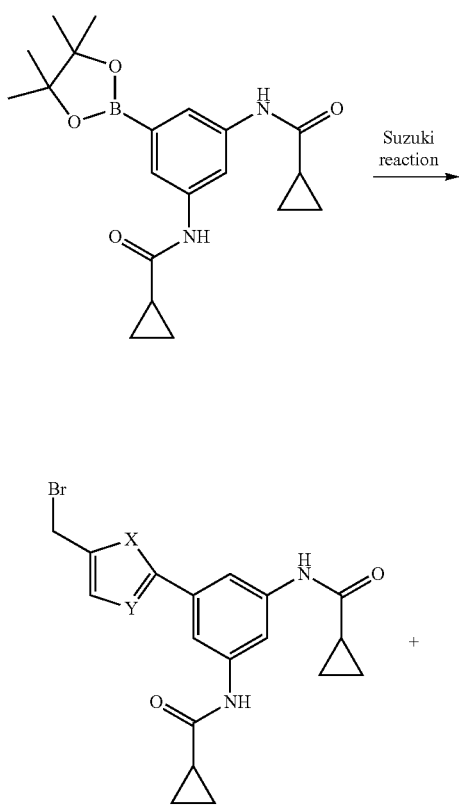

300
-continued

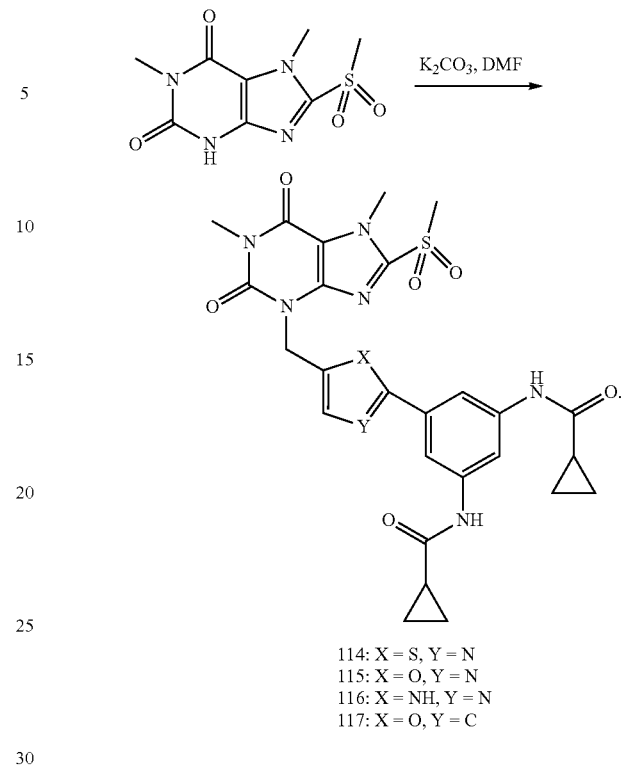

114: X = S, Y = N
115: X = O, Y = N
116: X = NH, Y = N
117: X = O, Y = C 118-120 are prepared according to the procedure of Compound 110-117.

Series 2 compound necroptosis activity;

| # |  | # |  | # |  | # |  |
|---|---|---|---|---|---|---|---|
| 1 | 0.1-10 µM | 2 | 0.1-10 µM | 3 | 0.1-10 µM | 4 | 0.1-10 µM |
| 5 | 0.1-10 µM | 6 | 10-100 µM | 7 | 10-100 µM | 8 | 1-100 nM |
| 9 | 1-100 nM | 10 | 1-100 nM | 11 | 1-100 nM | 12 | 1-100 nM |
| 13 | 1-100 nM | 14 | 1-100 nM | 15 | 1-100 nM | 16 | 0.1-10 µM |
| 17 | 1-100 nM | 18 | 0.1-10 µM | 19 | 1-100 nM | 20 | 1-100 nM |
| 21 | 1-100 nM | 22 | 1-100 nM | 23 | 0.1-10 µM | 24 | 1-100 nM |
| 25 | 1-100 nM | 26 | 1-100 nM | 27 | 1-100 nM | 28 | 1-100 nM |
| 29 | 1-100 nM | 30 | 1-100 nM | 31 | 1-100 nM | 32 | 1-100 nM |
| 33 | 1-100 nM | 34 | 1-100 nM | 35 | 1-100 nM | 36 | 1-100 nM |
| 37 | 1-100 nM | 38 | 1-100 nM | 39 | 1-100 nM | 40 | 1-100 nM |
| 41 | 1-100 nM | 42 | 1-100 nM | 43 | 1-100 nM | 44 | 1-100 nM |
| 45 | 1-100 nM | 46 | 0.1-10 µM | 47 | 0.1-10 µM | 48 | 0.1-10 µM |
| 49 | >10 µM | 50 | 1-100 nM | 51 | 0.1-10 µM | 52 | 0.1-10 µM |
| 53 | 0.1-10 µM | 54 | 1-100 nM | 55 | 10-100 µM | 56 | 10-100 µM |
| 57 | 10-100 µM | 58 | 10-100 µM | 59 | 10-100 µM | 60 | 10-100 µM |
| 61 | 10-100 µM | 62 | 0.1-10 µM | 63 | 0.1-10 µM | 64 | 0.1-10 µM |
| 65 | 1-100 nM | 66 | 1-100 nM | 67 | 1-100 nM | 68 | 10-100 µM |
| 69 | 0.1-10 µM | 70 | 1-1000 nM | 71 | 1-1000 nM | 72 | 1-1000 nM |
| 73 | 1-1000 nM | 74 | 1-1000 nM | 75 | 1-1000 nM | 76 | 1-1000 nM |
| 77 | 1-1000 nM | 78 | 1-1000 nM | 79 | 1-1000 nM | 80 | 1-1000 nM |
| 81 | 1-1000 nM | 82 | 1-1000 nM | 83 | 1-1000 nM | 84 | 1-1000 nM |
| 85 | 1-1000 nM | 86 | 1-1000 nM | 87 | 1-1000 nM | 88 | 1-1000 nM |
| 89 | 1-1000 nM | 90 | 1-1000 nM | 91 | 1-1000 nM | 92 | 1-1000 nM |
| 93 | 1-1000 nM | 94 | 1-1000 nM | 95 | 1-1000 nM | 96 | 1-1000 nM |
| 97 | 1-1000 nM | 98 | 1-1000 nM | 99 | 1-1000 nM | 100 | 1-1000 nM |
| 101 | 1-1000 nM | 102 | 1-1000 nM | 103 | 1-1000 nM | 104 | 1-1000 nM |
| 105 | 1-1000 nM | 106 | 1-1000 nM | 107 | 1-1000 nM | 108 | 1-1000 nM |
| 109 | 1-1000 nM | 110 | 1-1000 nM | 111 | 1-1000 nM | 112 | 1-1000 nM |
| 113 | 1-1000 nM | 114 | 1-1000 nM | 115 | 1-1000 nM | 116 | 1-1000 nM |
| 117 | 1-1000 nM | 118 | 1-1000 nM | 119 | 1-1000 nM | 120 | 1-1000 nM |

Experimental

Discovery of a New Class of Highly Potent Necroptosis Inhibitors Targeting the Mixed Lineage Kinase Domain-Like Protein In previous work, we performed a cell-based high-throughput screen to identify necroptosis inhibitors using a chemical library of ~200,000 compounds and identified multiple compounds that protected human colorectal adenocarcinoma (HT-29) cells from TNF-α/Smac mimetic/Z-VAD-fmk (TSZ)-induced necroptosis.[4] Among these hits, one was developed into the first MLKL inhibitor NSA which revealed the biological function of MLKL in necroptosis.[4] Another hit was identified as a RIP1 inhibitor and was further developed into the highly potent and selective anti-inflammation reagent RIPA-56.[10] We investigated another hit from this high-throughput screen, compound 1 (compound 4, supra), which has good anti-necroptosis potency ($EC_{50}=390\pm8$ nM).

In order to determine if compound 1 interacts with an unknown target or interacts with one of the three proteins known to be directly involved in TSZ-induced necroptosis (RIP1, RIP3, and MLKL), we performed several experiments to determine the effect of compound 1 on the functions of RIP1, RIP3, and MLKL. First, we tested whether compound 1 alters RIP1 and RIP3 kinase activities in enzymatic assays, as their kinase activities are required for the progression of necroptosis. We found that compound 1 did not inhibit the kinase activities of RIP1 or RIP3 at concentrations up to 10 μM, which excluded the possibility of RIPK1 or RIPK3 being the target. Based on western-blot analysis with antibodies against phosphorylated MLKL (pMLKL), compound 1 did not block the phosphorylation of MLKL. However, compound 1 did block the binding of MLKL to NSA according to the binding competition experiment testing the ability of compound 1 to compete with NSA for MLKL binding. This suggests that MLKL may be a target of compound 1.

In order to obtain direct evidence that compound 1 targets MLKL, we employed a chemical genetic method. Specifically, an affinity probe was used to fish out the targets of compound 1. We synthesized a series of derivatives based on compound 1 with the aims of increasing its anti-necroptosis potency and obtaining a high affinity probe for target identification. We first conducted SAR studies on the 8-/1-/7-position of compound 1 by substituting the original methyl group with various functional groups. Necroptosis assay results indicated that all of the tested substitutions at the 8-/1-/7-position deleteriously affected potency, revealing that the methyl group is the best of the tested structures at these positions. We then switched our efforts to the 3-position of compound 1. The related derivative compounds 7-12 and 14-18 were synthesized by the routes showed in Table A.

A

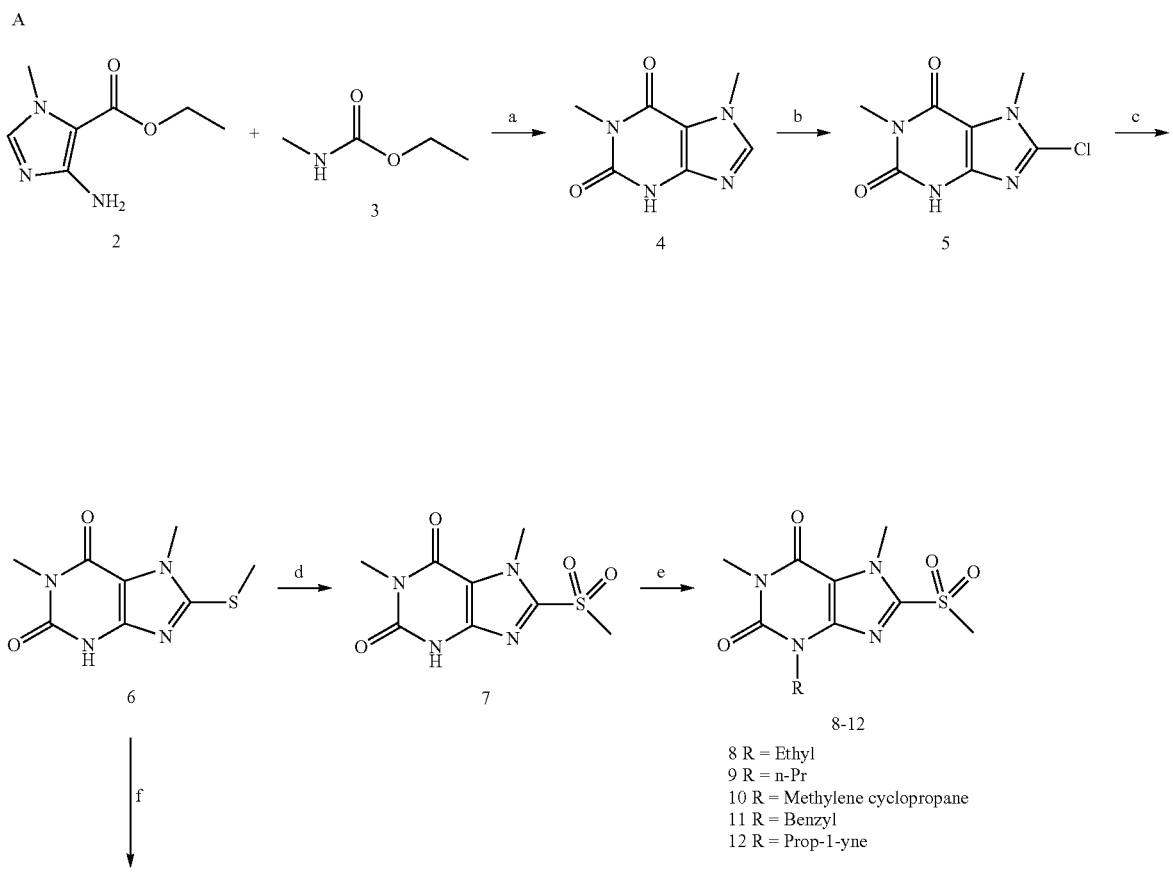

8-12
8 R = Ethyl
9 R = n-Pr
10 R = Methylene cyclopropane
11 R = Benzyl
12 R = Prop-1-yne

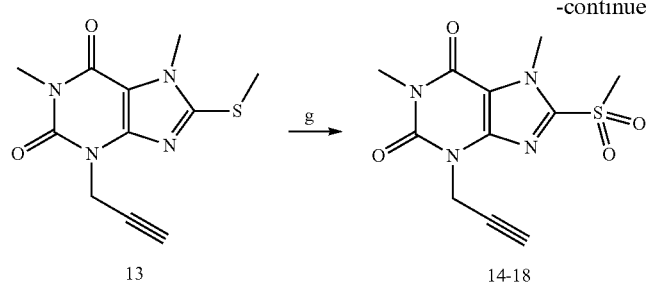

13 → 14-18

14 R = Phenyl
15 R = 3-hydroxyphenyl
16 R = 3-methoxyphenyl
17 R = 3-aminophenyl
18 R = 3(methylamino)phenyl

B

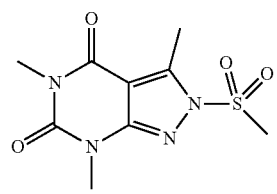

19

Table A. (A) Synthesis of compounds 7-12 and 14-18. (a) Potassium tert-butanolate, anhydrous THF, 75° C., overnight; (b) NCS, THF, rt, overnight; (c) NaSMe, DMF, 100° C., 3 h; (d) Oxone, MeOH:H2O 1:1, rt, 4 h; (e) K2CO3, DMF, rt, 1 h; (f) 3-bromoprop-1-yne, K2CO3, DMF, rt, 1 h; (g) Pd(PPh3)4, CuI, TEA, anhydrous DMF, 60° C., 6 h; Oxone, MeOH:H2O 1:1, rt, 4 h. (B) The structure of compound 19.

The imidazole derivative 2 was cyclized with ethyl methylcarbamate (3), yielding 1,7-dimethylxanthine (4). Subsequent chlorine and mercapto substitution yielded purine derivative 6, which was oxidized with oxone to yield 7. The substitution of 7 with different bromo derivatives generated the target compounds 8-12. Compounds 14-18 were synthesized using intermediate 6 as the starting material. Intermediate 6 was substituted by 3-bromoprop-1-yne, yielding intermediate 13; subsequent Suzuki coupling with different iodobenzene derivatives and oxidation with oxone yielded target compounds 14-18.

The anti-necroptosis potency of compounds 7-12 and 14-18 was evaluated in the HT-29 cell line; the $EC_{50}$ values are shown in Table B.

TABLE B

Potency ($EC_{50}$) of compounds 7-12 and 14-18 in TSZ-induced necroptosis assays in HT-29 cells.

| Compound | $EC_{50}$ (nM) |
| --- | --- |
| 1 | 390 ± 8 |
| 7 | 5983 ± 926 |
| 8 | 2510 ± 130 |
| 9 | 925 ± 28 |
| 10 | 651 ± 103 |
| 11 | 700 ± 21 |
| 12 | 152 ± 23 |
| 14 | 25 ± 3.4 |
| 15 | 2 ± 0.6 |
| 16 | 35 ± 8.5 |
| 17 | 7 ± 1.0 |
| 18 | 7 ± 0.2 |

TABLE B-continued

Potency ($EC_{50}$) of compounds 7-12 and 14-18 in TSZ-induced necroptosis assays in HT-29 cells.

| Compound | $EC_{50}$ (nM) |
| --- | --- |
| NSA | 447 ± 32 |
| GW806742X | 589 ± 12 |

[a] Necroptosis was induced in HT-29 cells for 24 h; the $EC_{50}$ values given here are the mean values of at least three independent analyses.

Lacking the methyl group, compound 7 had a more than 10-fold reduction in potency relative to compound 1. The ethyl analogue 8 had a 5-fold reduction in potency compared with compound 1. Further extending the length of the alkyl chain recovered some potency (see compounds 9 and 10). Interestingly, compound 12, which has a propyne group, was 3-fold more potent than compound 1 (methyl group); however, the benzyl analogue 11 had a 4-fold reduction in potency relative to compound 12, suggesting the presence of a relatively-narrow hydrophobic space in the target. To probe the putative binding pocket beyond the region defined by the propyne group, we synthesized 14 by adding a phenyl group at the end of the propyne group of 12. Surprisingly, compound 14 showed a 6-fold improvement in potency over compound 12 suggesting the presence of an 'open space' in this area for generating additional interactions between target and the inhibitors. To look into the possibility of generating an extra hydrogen bond interaction around the phenyl group, we designed and synthesized compounds 15-18. To our surprise, compounds 15 (3-OH), 17 (3-$NH_2$), and 18 (3-NHMe) had inhibition potency of 2 nM, 7 nM, and 7 nM respectively against cell necroptosis. Conversely, methylating the 3-OH of compound 15 (compound 16) resulted in a 15-fold reduction in potency. The potency enhancement with compounds 15, 17, and 18 suggested possible hydrogen bond formation between the hydrogen-bond donor, 3-OH of compound 15 (or 3-NHR of compound 17-18), and an acceptor residue on the target. The methoxy group of compound 16 (3-OMe) lacks the hydrogen-bond donating property, which abolished hydrogen bond formation and led to the loss of potency. Our SAR study successfully improved the potency of the initial hit, compound 1, from an $EC_{50}$ value of 390 nM, all the way down to an $EC_{50}$ value of 2 nM (compound 15). This important achievement demonstrates that MLKL is a druggable target and provides useful chemical tools to study the function of MLKL.

Considering that certain hetero aromatic sulfonyl groups can be replaced by various nucleophiles, we speculated that the methylsulfonyl group in compound 1 may act as a leaving group for covalent binding in its interaction with MLKL.[11] To test this hypothesis, we synthesized compound 19, a close structural analogue of compound 1, but in which the methylsulfonyl group has no leaving ability. Compound 19 showed no potency in a necroptosis assay, indicating that covalent binding appears to be crucial for the potency of these inhibitors.

We further confirmed the irreversible covalent binding behavior of compounds 12 and 15 by comparing their potency in wash/no-wash cell assays. For both compounds, the $EC_{50}$ values recorded for the washed samples were comparable with those of the non-washed samples, indicating that these compounds are covalent inhibitors.

Similar to compound 1, compounds 12 and 14-16 (10 µM) did not inhibit the kinase activities of RIP1 or RIP3 in in vitro assays. To determine whether the direct target of this series of compounds is MLKL, we performed activity based protein profiling (ABPP). Compound 12, an affinity probe, was incubated with MLKL-flag-HT-29 cell lysates for 2 hours, followed by a click reaction to conjugate the probe to a biotin-tag. The biotin-labeled compound-protein complexes were pulled down and analysed via SDS-PAGE. We observed that compound 12 could indeed covalently bind to MLKL in cell lysates and observed that compound 15 efficiently outcompeted 12 in binding to MLKL.

The BTC-ABPP method, which was developed recently in our lab, greatly facilitates the identification of probe-modified sites of target proteins in living cells.[12] Here, we used BTC-ABPP with HT-29 cells to identify the binding sites of compound 12 and MLKL. The b/y ion spectra from MS/MS analysis revealed that the covalent binding site of compound 12 was Cys-86 in the SNICR peptide of human MLKL; this is the same residue proposed to be the site of NSA modification.[4] To further verify the relationship between probe binding at this site and the function of compound 12 in necroptosis, MLKL-knockout RIP3-HeLa cells were transfected with wild-type or the C86S (Cysteine 86 is mutated to Serine) mutated form of MLKL. TSZ stimulation of both types of cells resulted in necroptosis, indicating that the C86S mutated form of MLKL functioned normally in transducing the necroptosis signal. Cells transfected with wild-type MLKL, but not cells transfected with C86S-MLKL, were protected from necroptosis by compound 12, further confirming that compound 12 inhibits MLKL by directly binding to Cys-86. Cys-86 in human MLKL structurally corresponds to a tryptophan residue in mouse and rat MLKL. Helix H4 at the N-terminal domain of the human MLKL structure, which contains Cys-86, is not present in mouse MLKL.[13] Given this, we speculated that compound 12 and 15 may show poor inhibition against the function of mouse or rat MLKL in necroptosis. We performed necroptosis assays in mouse MEF and L929 cell lines and in the rat L6 cell line, and found that neither compound 12 nor compound 15 showed inhibition activity, even at concentrations excesses of their previously-determined $EC_{50}$ values. These results establish that Cys-86 of the target MLKL is required for the covalent binding and potency of this series of MLKL inhibitors.

Previous studies showed that MLKL forms homo-oligomers when it is phosphorylated by RIP3. This is a crucial step in the translocation of MLKL from the cytoplasm to the cell membrane, where it mediates ion influx and/or causes the disruption of cell structures.[5] To evaluate the mechanism of this series of compounds on MLKL, we detected the status (state of oligomerization and phosphorylation) of MLKL under TSZ stimulation in the presence of compound 12 or 15. We first showed that compound 12 and 15 can both block the formation of MLKL homo-oligomers. Next, we evaluated the effects of MLKL inhibitors on the translocation of MLKL from the cytoplasm to the cell membrane. HT-29 cells were treated with TSZ in the presence of RIPA-56, NSA, compound 12, or compound 15 for 6 h. The proteins from cell lysates were separated and the soluble phase and membrane phase were analyzed separately with anti-MLKL and anti-pMLKL antibodies. As expected, compounds 12 and 15 did not disrupt the phosphorylation of MLKL, but did decrease the level of MLKL in the membrane phase, demonstrating that these MLKL inhibitors block the translocation of MLKL to the cell membrane, thereby protecting cells from necroptosis. We also performed immunofluorescence staining in HT-29 cells using a monoclonal anti-pMLKL antibody. After TSZ stimulation, large, bright-green fluorescent dots (pMLKL) were present in the plasma membrane. RIPA-56 and GW806742X blocked the phosphorylation of MLKL completely, and no pMLKL dots were observed in cells treated with these compounds. In contrast, small pMLKL dots were dispersed in the cytoplasm of cells treated with the MLKL inhibitors NSA and compounds 12 and 15, indicating that, NSA and compounds 12 and 15 share similar modes of action and block the translocation of MLKL to the cell membrane. These results are consistent with earlier studies.[5]

1. aL. Sun, X. Wang, Trends Biochem. Sci 2014, 39, 587-593; bM. Pasparakis, P. Vandenabeele, Nature 2015, 517, 311-320.
2. N. Holler, R. Zaru, O. Micheau, M. Thome, A. Attinger, S. Valitutti, J.-L. Bodmer, P. Schneider, B. Seed, J. Tschopp, Nat. Immunol. 2000, 1, 489-495.
3. aS. He, L. Wang, L. Miao, T. Wang, F. Du, L. Zhao, X. Wang, Cell 2009, 137, 1100-1111; bD.-W. Zhang, J. Shao, J. Lin, N. Zhang, B.-J. Lu, S.-C. Lin, M.-Q. Dong, J. Han, Science 2009, 325, 332-336.
4. L. Sun, H. et al. Cell 2012, 148, 213-227.
5. aH. Wang, L. Sun, L. Su, J. Rizo, L. Liu, L.-F. Wang, F.-S. Wang, X. Wang, Mol. Cell 2014, 54, 133-146; bZ. Cai, S. Jitkaew, J. Zhao, H.-C. Chiang, S. Choksi, J. Liu, Y. Ward, L.-g. Wu, Z.-G. Liu, Nat. Cell Biol. 2014, 16, 55-65.
6. aJ. Wu, et al., Cell Res. 2013, 23, 994-1006; bD. Ofengeim, Y. Ito, A. Najafov, Y. Zhang, B. Shan, J. P. DeWitt, J. Ye, X. Zhang, A. Chang, H. Vakifahmetoglu-Norberg, Cell reports 2015, 10, 1836-1849; cM. Pierdomenico, A. Negroni, L. Stronati, R. Vitali, E. Prete, J. Bertin, P. J. Gough, M. Aloi, S. Cucchiara, Am J. Gastroenterol. 2014, 109, 279-287.
7. J. M. Hildebrand, et al, Proc. Natl. Acad. Sci. U.S.A. 2014, 111, 15072-15077.
8. D. Liao, L. Sun, W. Liu, S. He, X. Wang, X. Lei, Medchemcomm 2014, 5, 333-337.
9. D. M. Sammond, et al., Bioorg. Med. Chem. Lett. 2005, 15, 3519-3523.
10. Y. Ren, et al., J. Med. Chem. (http://dx.doi.org/10.1021/acs.jmedchem. 6b01196, in Press)

11. P. Lan, et al. Tetrahedron Lett. 2008, 49, 1910-1914.
12. H. Sun, Y. Ren, W. Hou, L. Li, F. Zeng, S. Li, Y. Ma, X. Liu, S. Chen, Z. Zhang, Chem. Commun. 2016, 52, 10225-10228.
13. L. Su, B. Quade, H. Wang, L. Sun, X. Wang, J. Rizo, Structure 2014, 22, 1489-1500.

What is claimed is:
1. An MLKL-inhibitor compound of formula I:

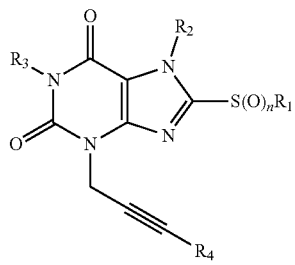

wherein:
R1 is H, or optionally substituted, optionally cyclic C1-C18 hydrocarbyl, or optionally substituted, optionally cyclic C1-C18 heterohydrocarbyl, or optionally substituted heteroatom selected from O, P, S and N, and R1 and R2 are optionally joined to form a ring;
R2 and R3 are methyl;
R4 is optionally substituted, C5-C18 aryl, or optionally substituted C5-C18 heteroaryl; and
n is 1 or 2;
or a pharmaceutically acceptable salt, hydrate or stereoisomer the compound.

2. The compound of claim 1 wherein:
R1 is optionally substituted C1-C18 hydrocarbyl, or optionally substituted C1-C18 heterohydrocarbyl, or optionally substituted heteroatom.

3. The compound of claim 1 wherein:
R1 is optionally substituted C1-C18 alkyl, optionally substituted C1-C18 heteroalkyl, or optionally substituted N.

4. The compound of claim 1 wherein:
R1 is optionally substituted methyl.

5. The compound of claim 1 wherein:
R1 is methyl, cyclopropylmethyl, hydroxymethyl or trifluoromethyl.

6. The compound of claim 1 wherein:
R4 is optionally substituted C6 aryl or optionally substituted C6 heteroaryl.

7. The compound of claim 1 wherein:
R4 is substituted phenyl.

8. The compound of claim 1 wherein:
R1 is optionally substituted methyl;
R4 is substituted phenyl; and
R4 has from one to three substituents.

9. The compound of claim 1 wherein:
R1 is optionally substituted methyl;
R4 is substituted phenyl;
R4 has from one to three substituents; and
the substituents of R1 and R4 are independently selected from: halogen, —OR', —OC(O)R', —NR'R", —SR', —R', —CN, —NO$_2$, —CONR'R", —C(O)R', —OC(O)NR'R", —NR"C(O)R', —NR"CO2R', —NR'—C(O)NR"R''', —NR'—SO$_2$NR"R''', —NH—C(NH2)=NH, —NR'C(NH$_2$)=NH, —NH—C(NH$_2$)=NR', —S(O)R', —SO$_2$NR'R", —NR"SO$_2$R, —N$_3$, —CH(Ph)$_2$, perfluoro(C1-C4)alkoxy and perfluoro(C1-C4)alkyl, where R', R" and R''' are independently selected from hydrogen, (C1-C8)alkyl and heteroalkyl, unsubstituted aryl and heteroaryl, (unsubstituted aryl)-(C1-C4)alkyl and (unsubstituted aryl)oxy-(C1-C4)alkyl.

10. The compound of claim 1 wherein:
R1 is optionally substituted methyl;
R4 is substituted phenyl;
R4 has from one to three substituents; and
the substituents of R1 and R4 are independently selected from halogen, —OR', —OC(O)R', —SR', —R', —CN, —NO$_2$, —CONR'R", —C(O)R', —OC(O)NR'R", —NR"C(O)R', —S(O)R', —SO$_2$NR'R", —NR"SO$_2$R, —N$_3$, —CH(Ph)$_2$, perfluoro(C1-C4)alkoxy and perfluoro(C1-C4)alkyl, where R', R" and R''' are independently selected from hydrogen, (C1-C8)alkyl and heteroalkyl, unsubstituted aryl and heteroaryl, (unsubstituted aryl)-(C1-C4)alkyl and (unsubstituted aryl)oxy-(C1-C4)alkyl.

11. The compound of claim 1 wherein:
R1 is optionally substituted methyl;
R4 is substituted phenyl;
R4 has from one to three substituents; and
the substituents of R1 and R4 are independently selected from halogen, —OR', —OC(O)R', —NR'R", —R', —CN, —NO$_2$, —CO$_2$R', —CONR'R", —NR"C(O)R', —SO$_2$R', —SO$_2$NR'R", —NR"SO$_2$R, perfluoro(C1-C4)alkoxy and perfluoro(C1-C4)alkyl, where R', R" and R''' are independently selected from hydrogen, (C1-C8)alkyl and heteroalkyl, unsubstituted aryl and heteroaryl, (unsubstituted aryl)-(C1-C4)alkyl and (unsubstituted aryl)oxy-(C1-C4)alkyl.

12. The compound of claim 1 wherein:
R1 is methyl, cyclopropylmethyl, hydroxymethyl or trifluoromethyl;
R4 is substituted phenyl;
R4 has from one to three substituents; and
the substituents are independently selected from: halogen, —OR', —OC(O)R', —NR'R", —SR', —R', —CN, —NO$_2$, —CO$_2$R', —CONR'R", —C(O)R', —OC(O)NR'R", —NR"C(O)R', —NR"CO2R', —NR—C(O)NR"R''', —NR'—SO$_2$NR"R''', —NH—C(NH2)=NH, —NR'C(NH$_2$)=NH, —NH—C(NH$_2$)=NR', —S(O)R', —SO$_2$R', —SO$_2$NR'R", —NR"SO$_2$R, —N$_3$, —CH(Ph)$_2$, perfluoro(C1-C4)alkoxy and perfluoro(C1-C4)alkyl, where R', R" and R''' are independently selected from hydrogen, (C1-C8)alkyl and heteroalkyl, unsubstituted aryl and heteroaryl, (unsubstituted aryl)-(C1-C4)alkyl and (unsubstituted aryl)oxy-(C1-C4)alkyl.

13. The compound of claim 1 wherein one or more hydrogens are in the form of deuterium, such as —CD$_3$, CD$_2$H or CDH$_2$ in place of methyl.

14. The compound of claim 1 having a Series 1 structure selected from:

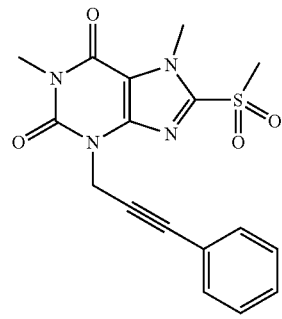

108

-continued
109
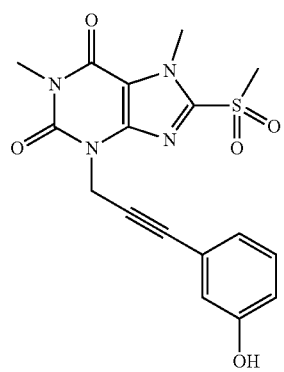
110
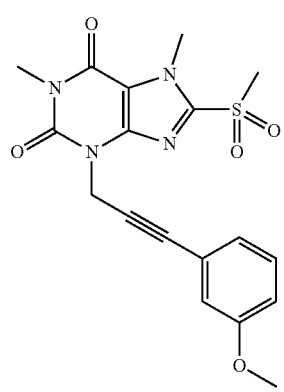
111
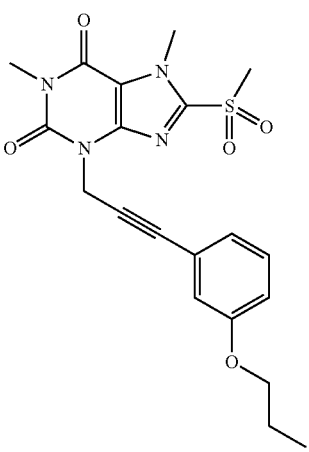
112
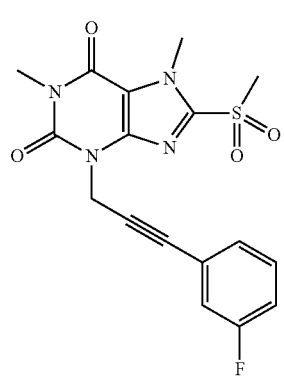
-continued
113
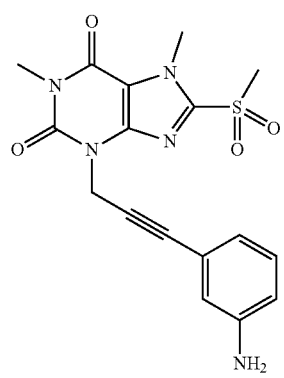
114
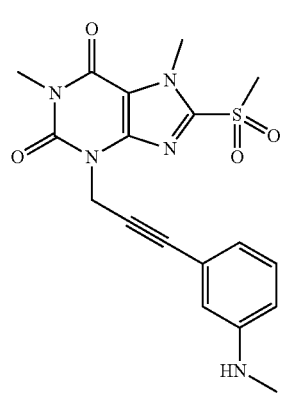
115
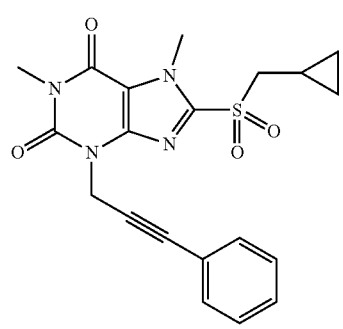
116
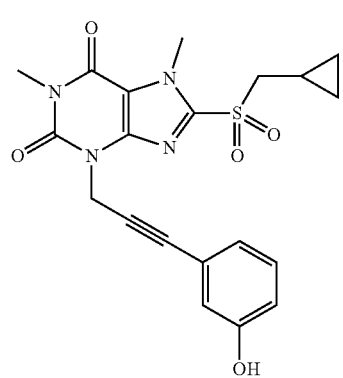

117
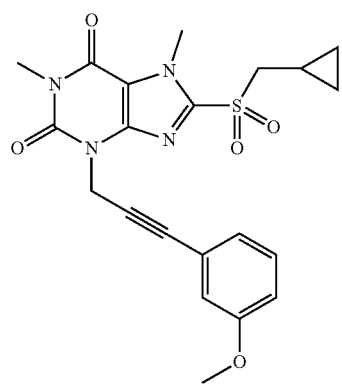
118
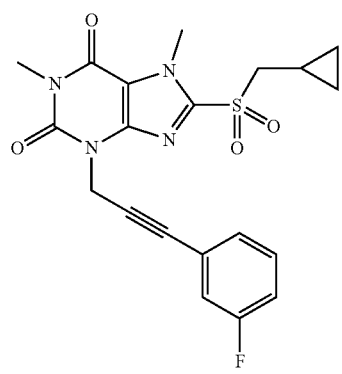
119
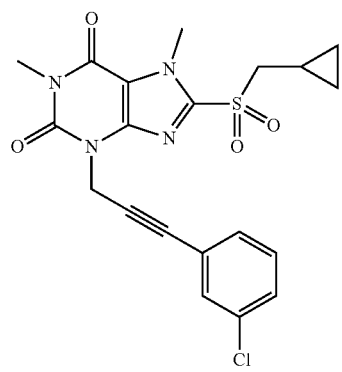
120
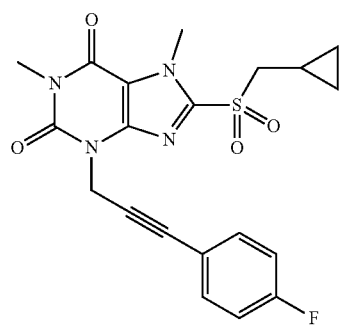
121
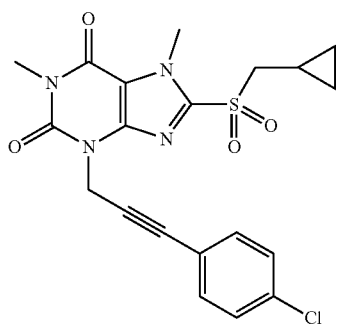
122
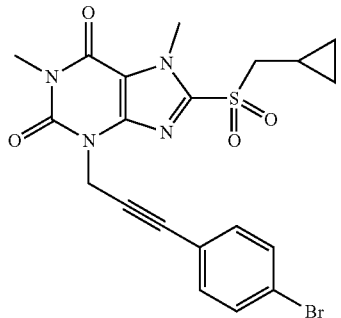
123
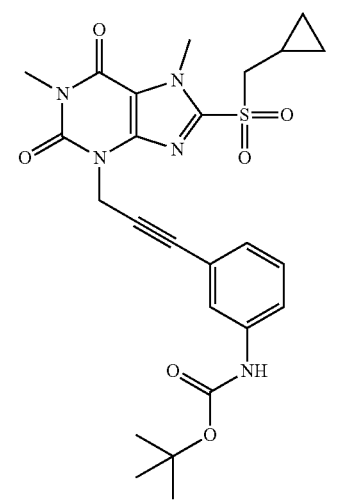
124
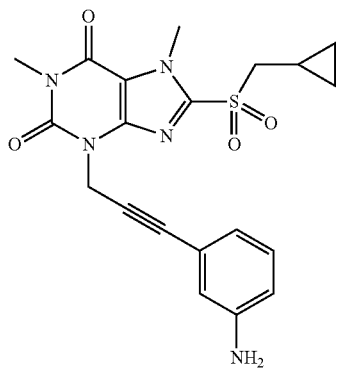

| 125 | 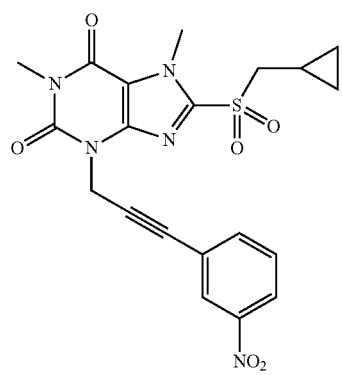 | 147 | 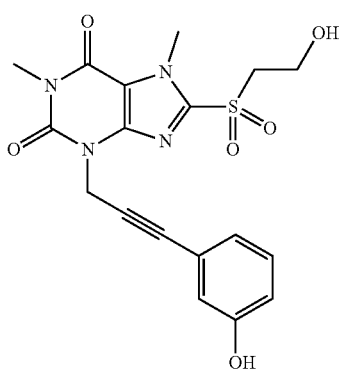 |
| 126 | 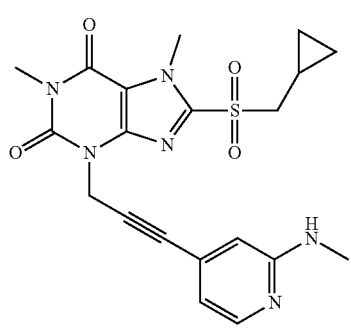 | 150 | 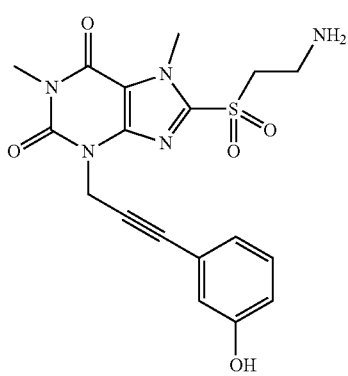 |
| 127 | 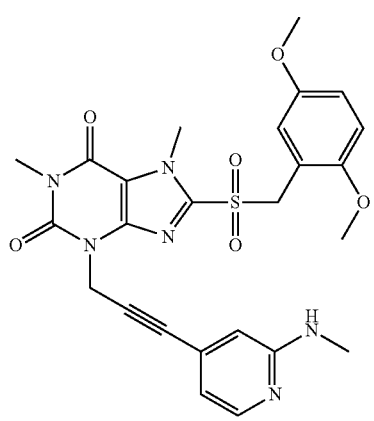 | 151 | 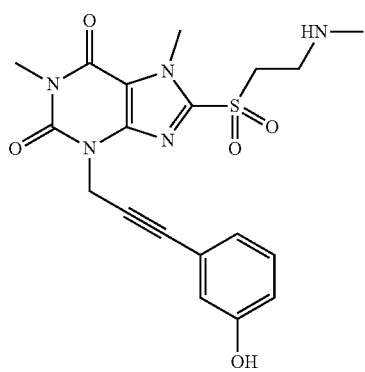 |
| 128 | 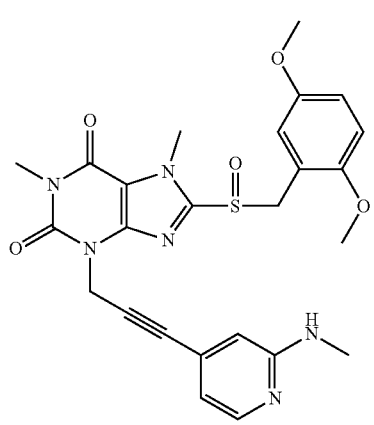 | 152 | 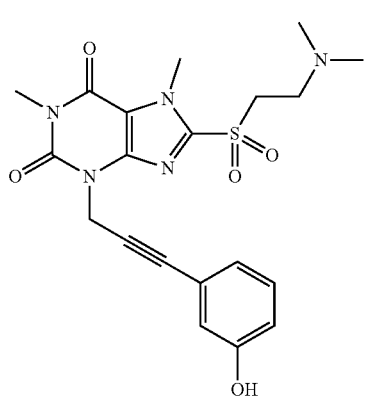 |

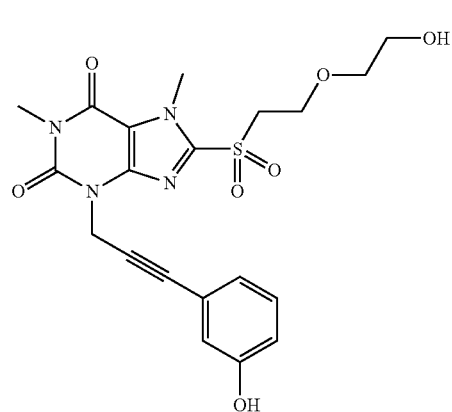
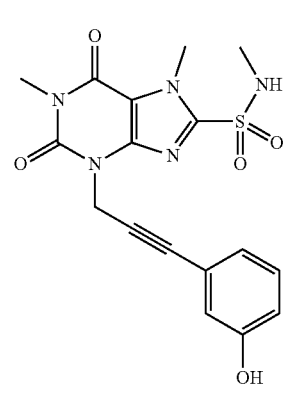

317
-continued
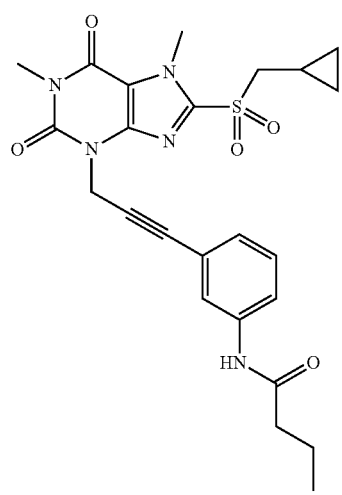
161
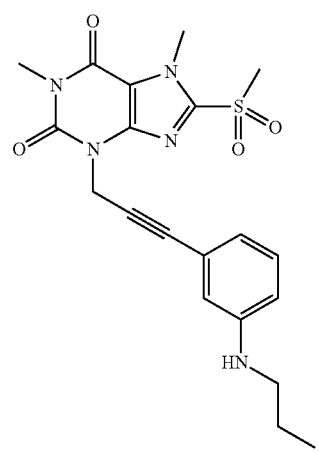
162
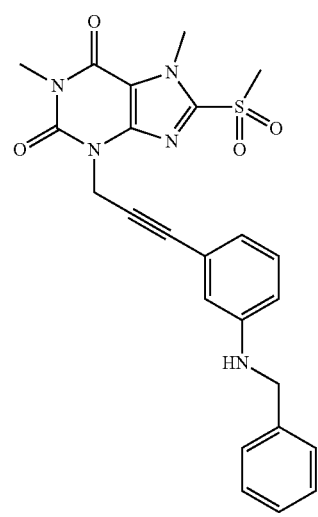
163
318
-continued
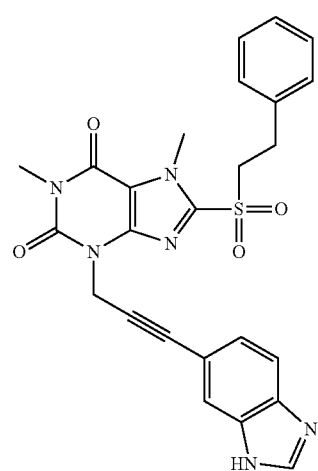
164
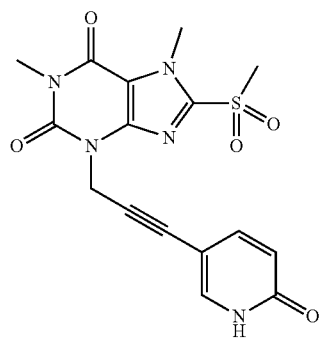
165
166

319
-continued
168
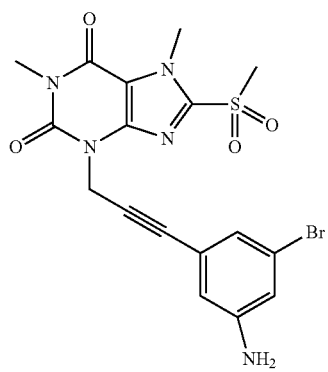
169
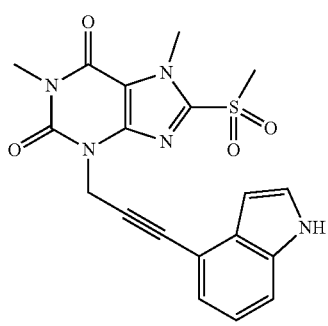
170
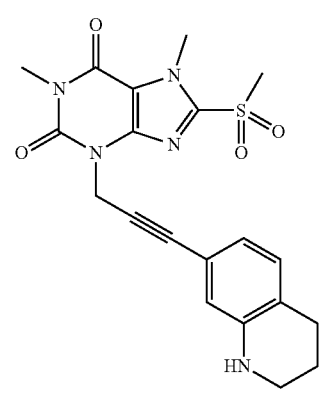
171
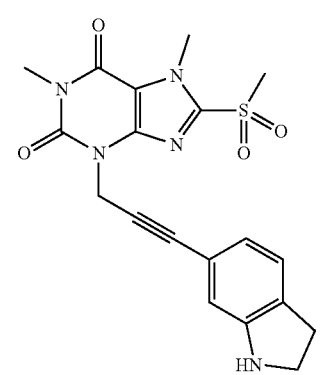
320
-continued
174
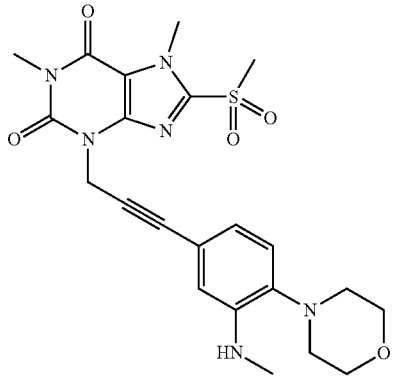
175
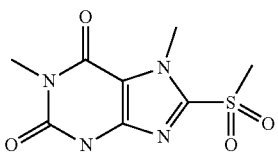
15. The compound of claim 1 having a Series 2 structure selected from:
8
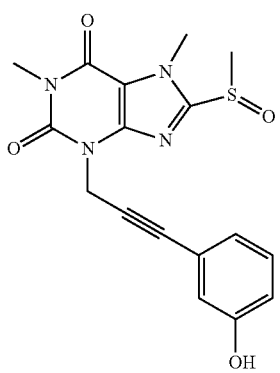
9
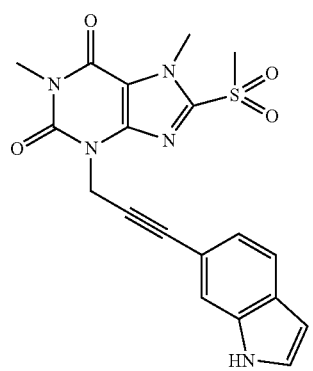

321
-continued
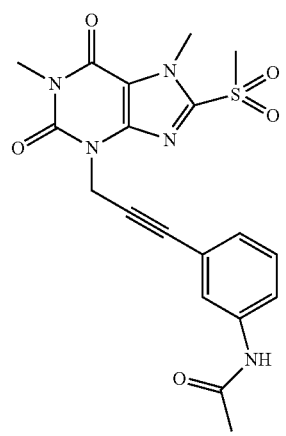
10
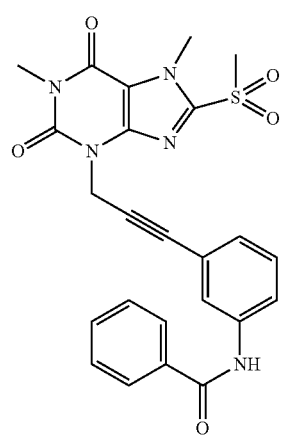
11
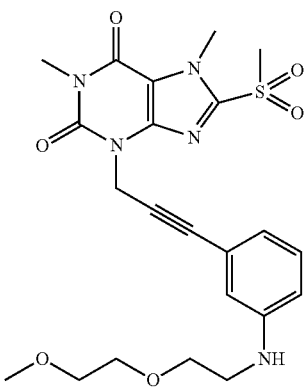
12
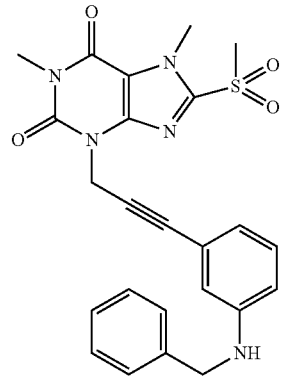
13
322
-continued
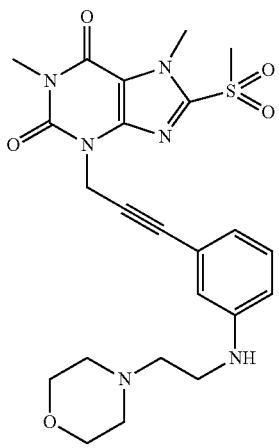
14
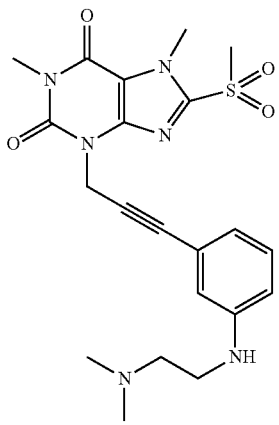
15
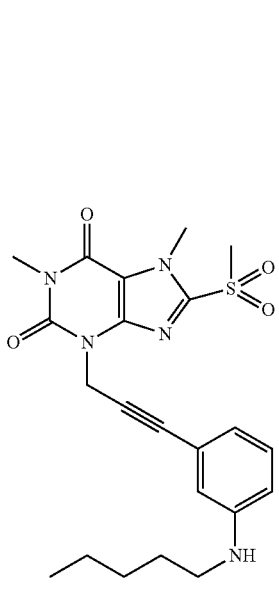
16

17
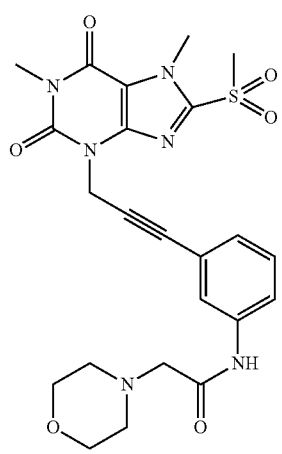
20
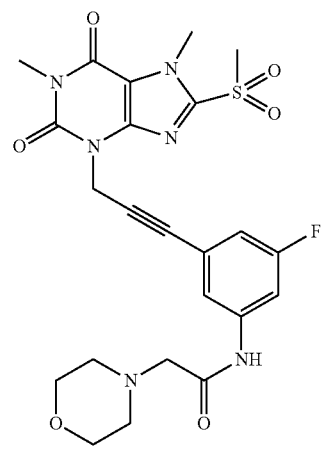
18
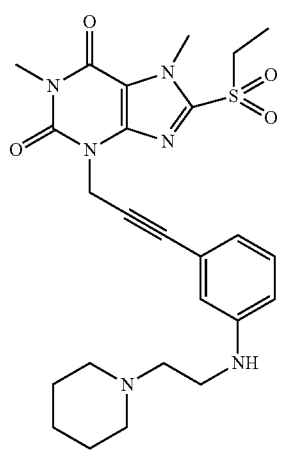
21
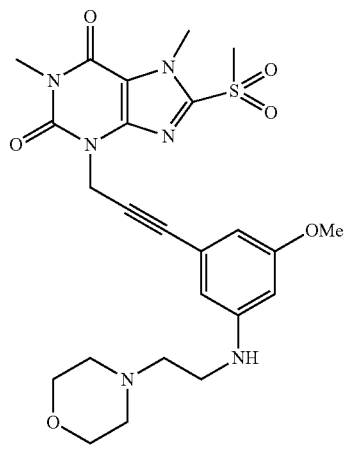
19
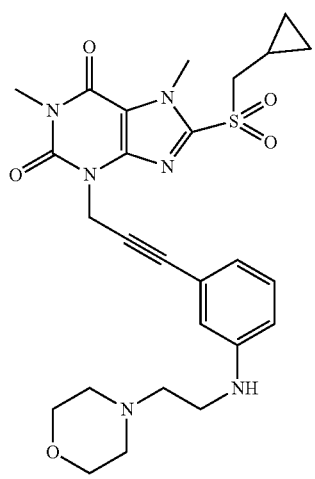
22
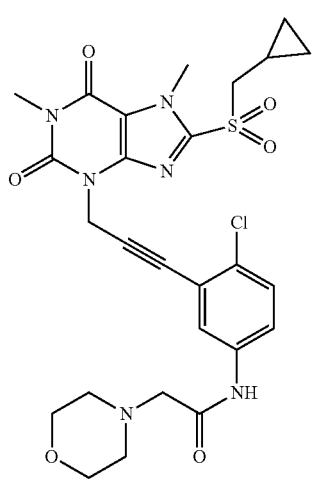

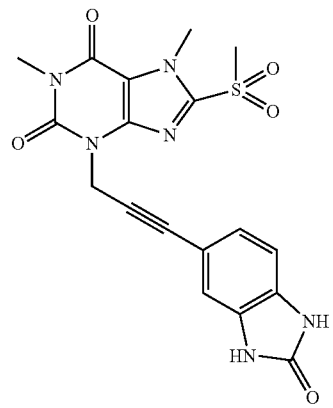
23
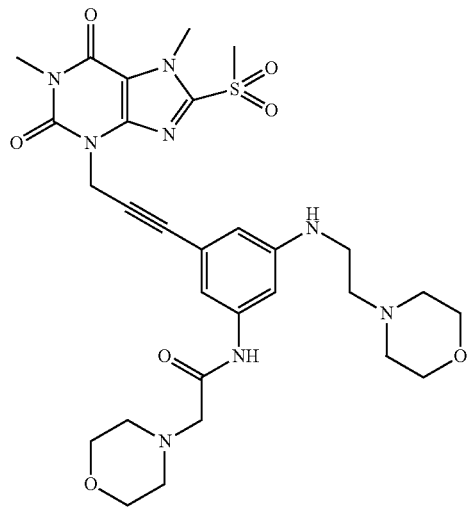
26
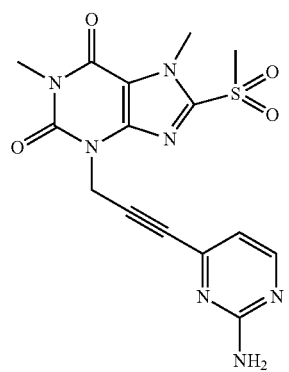
24
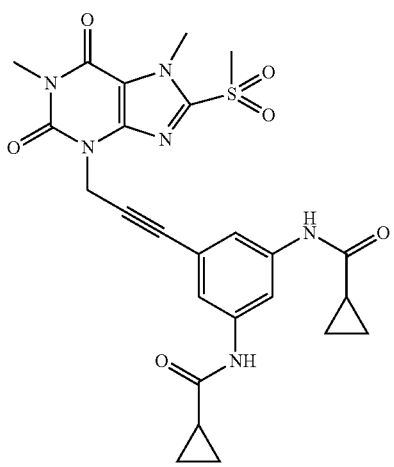
27
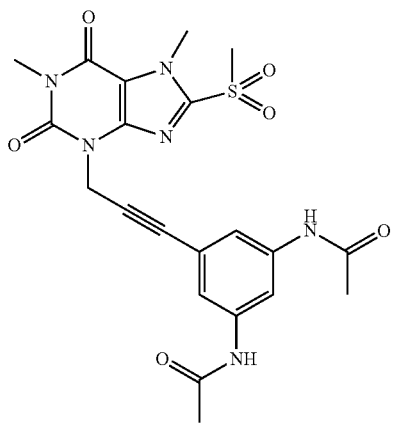
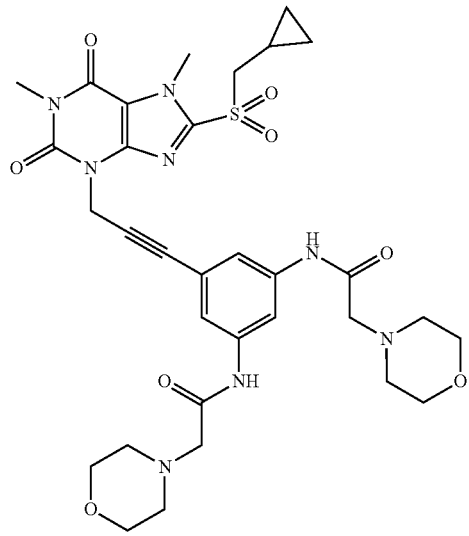
28

29
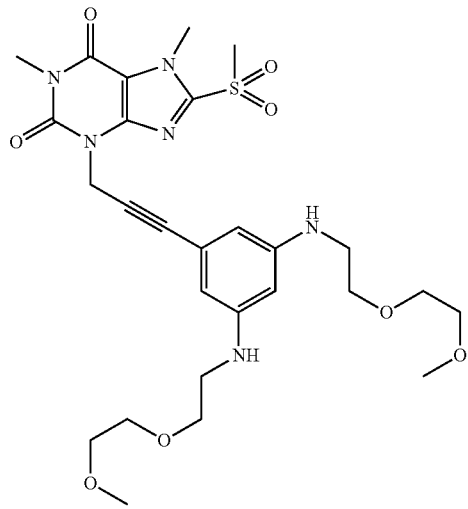
30
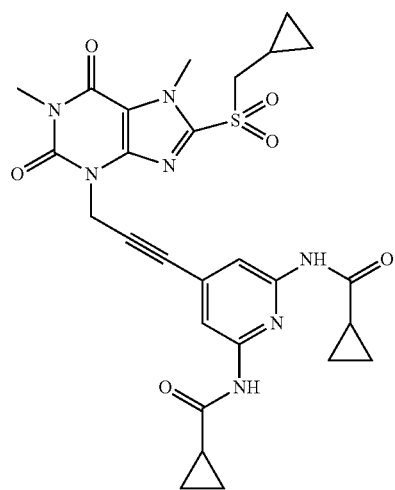
31
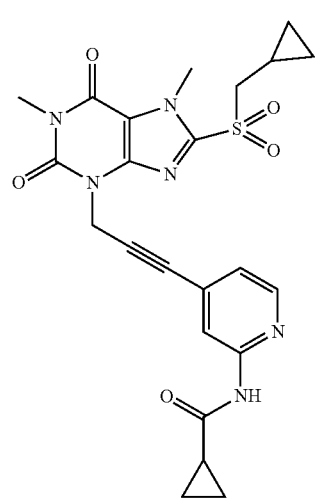
32
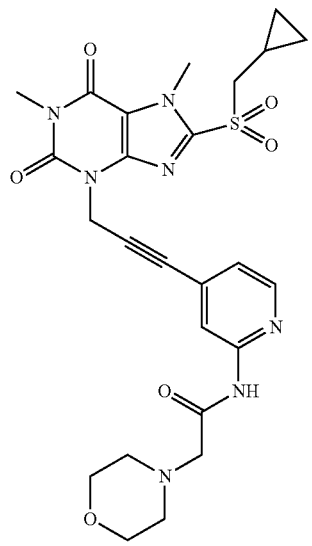
33
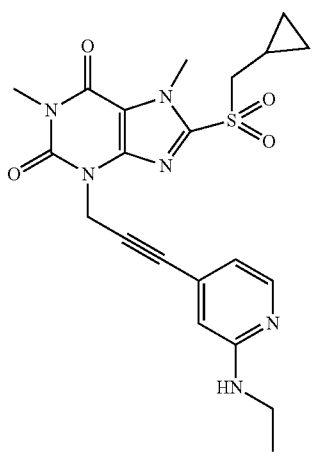
34
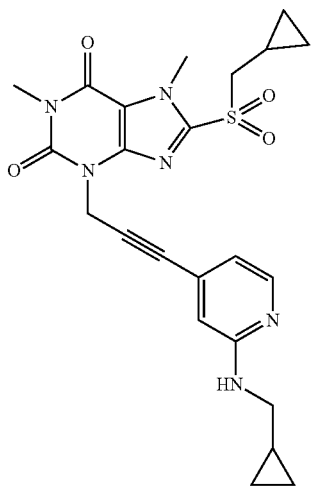

329
-continued
35
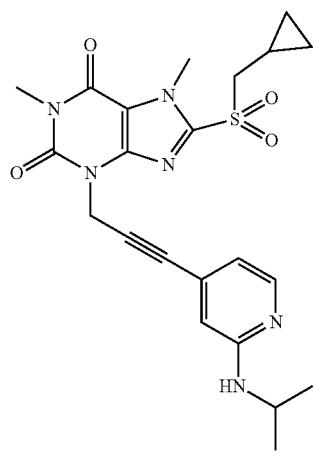
36
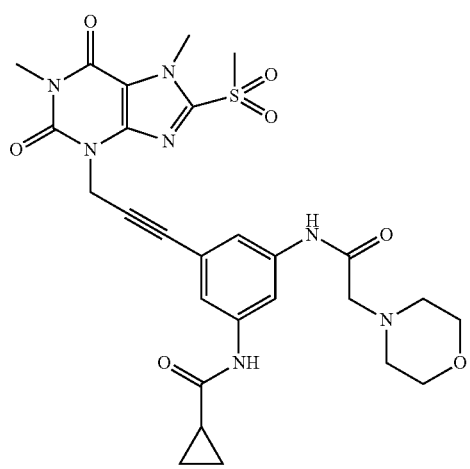
37
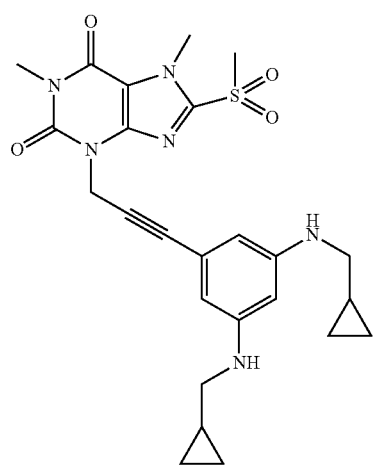
330
-continued
38
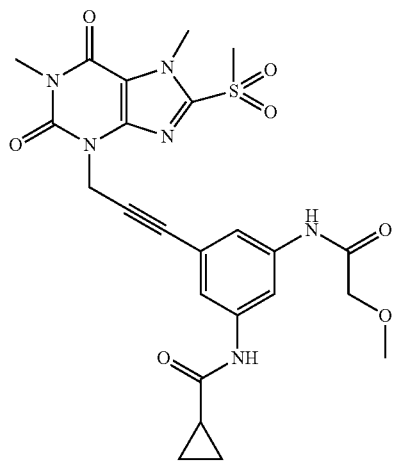
39
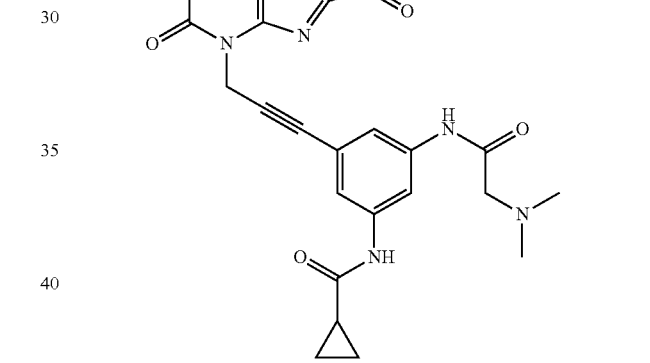
40
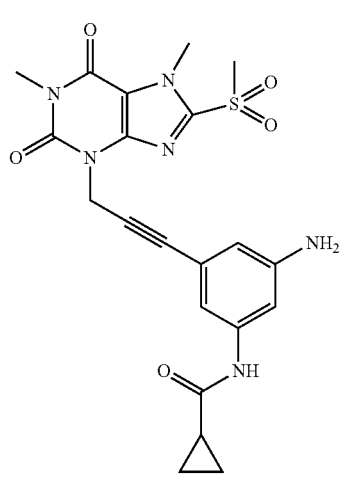

-continued
41
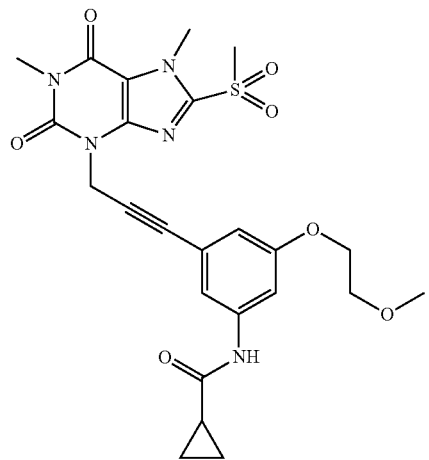
42
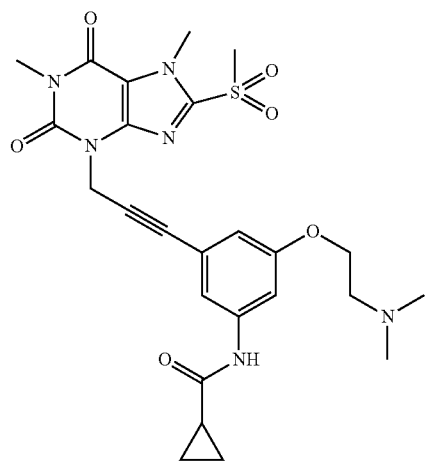
43
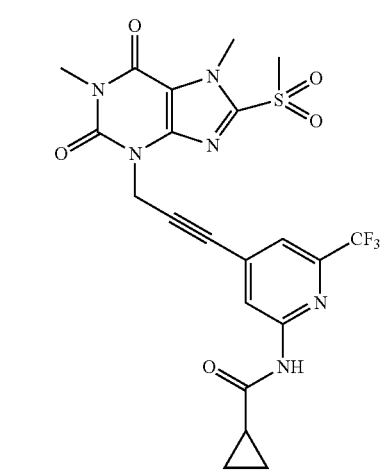
-continued
44
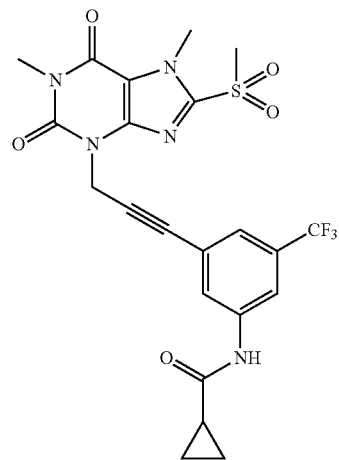
45
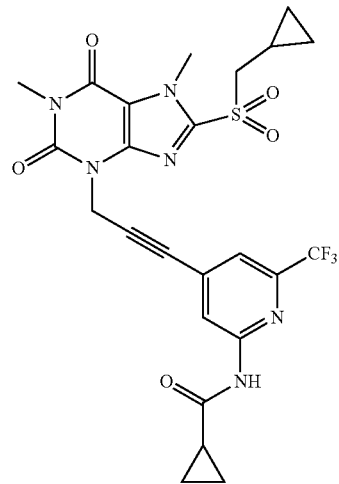
46
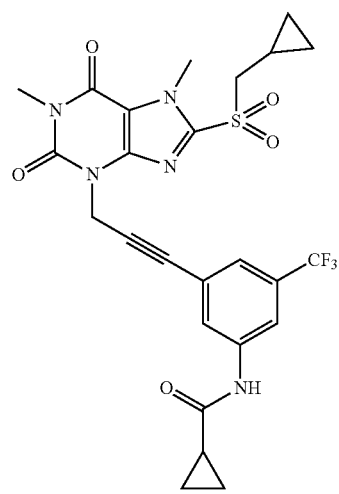

| 47 | 50 |
|---|---|
| 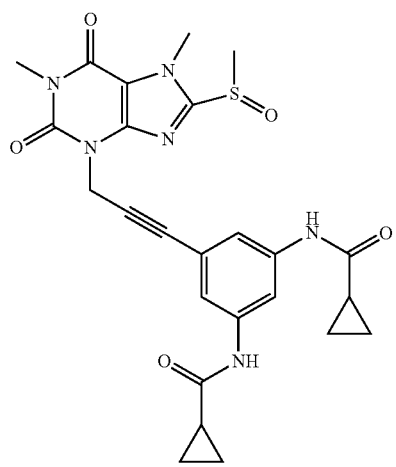 | 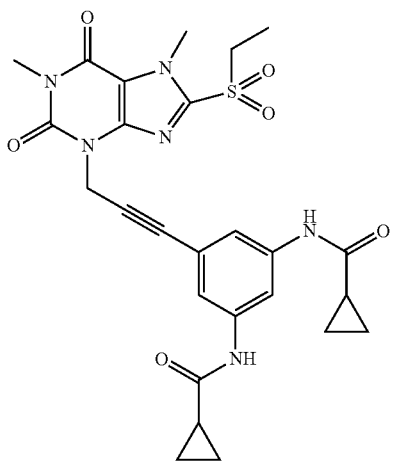 |
| 48 | 51 |
| 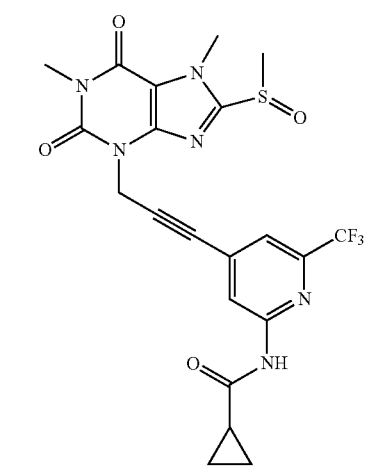 | 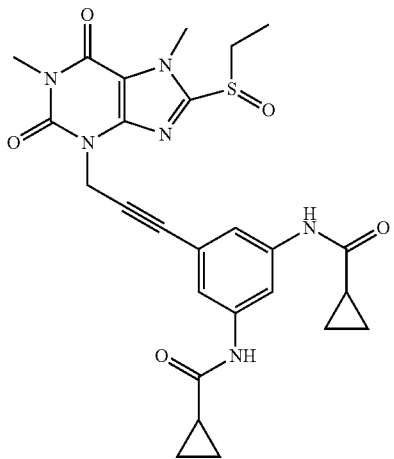 |
| 49 | 52 |
| 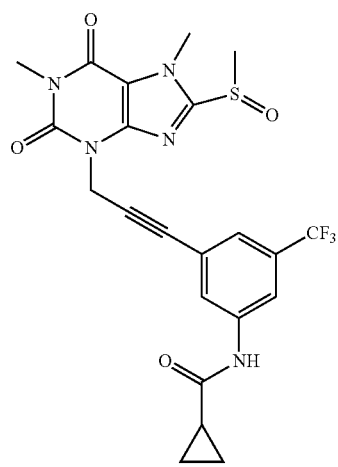 | 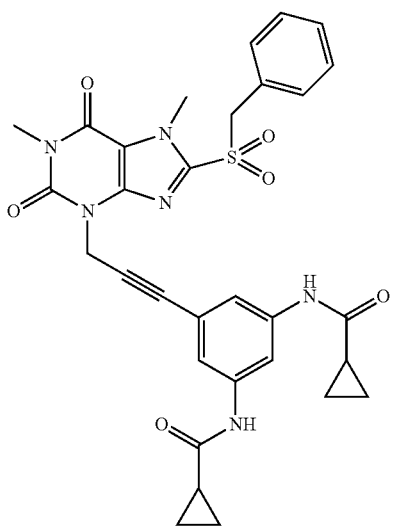 |

53
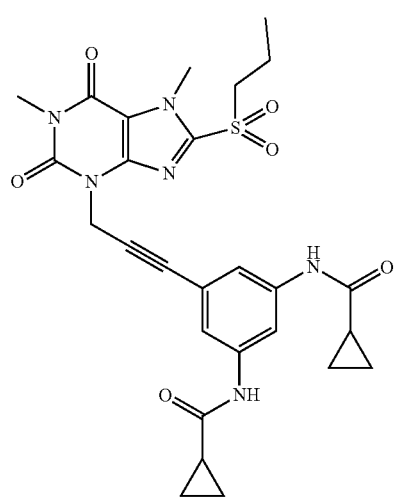
71
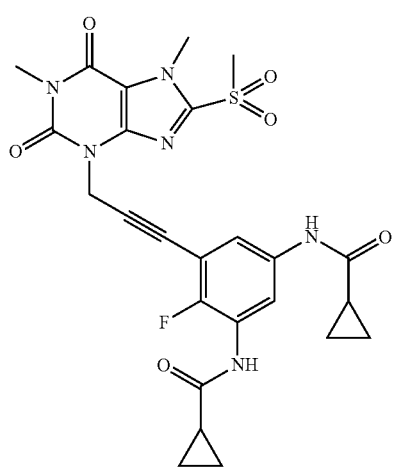
54
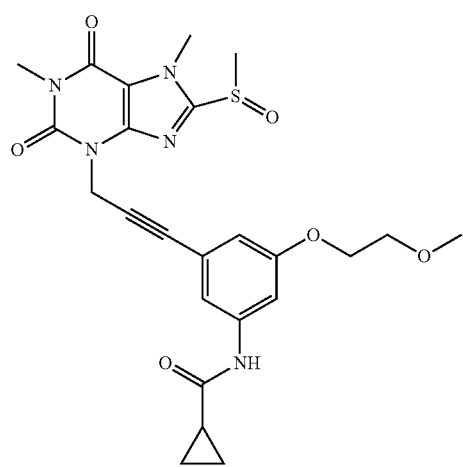
72
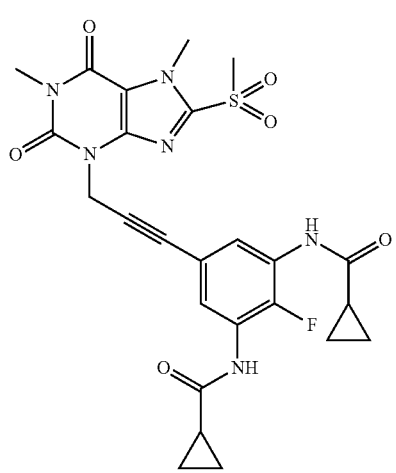
70
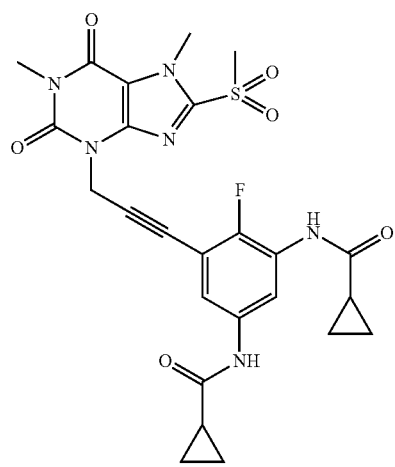
83
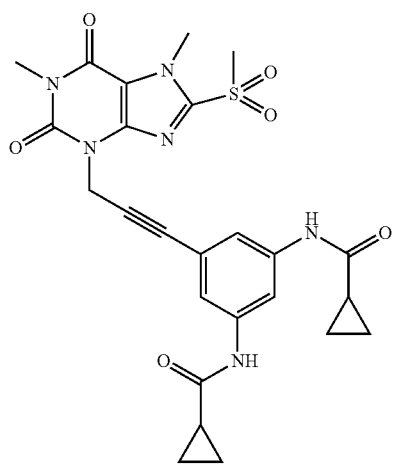

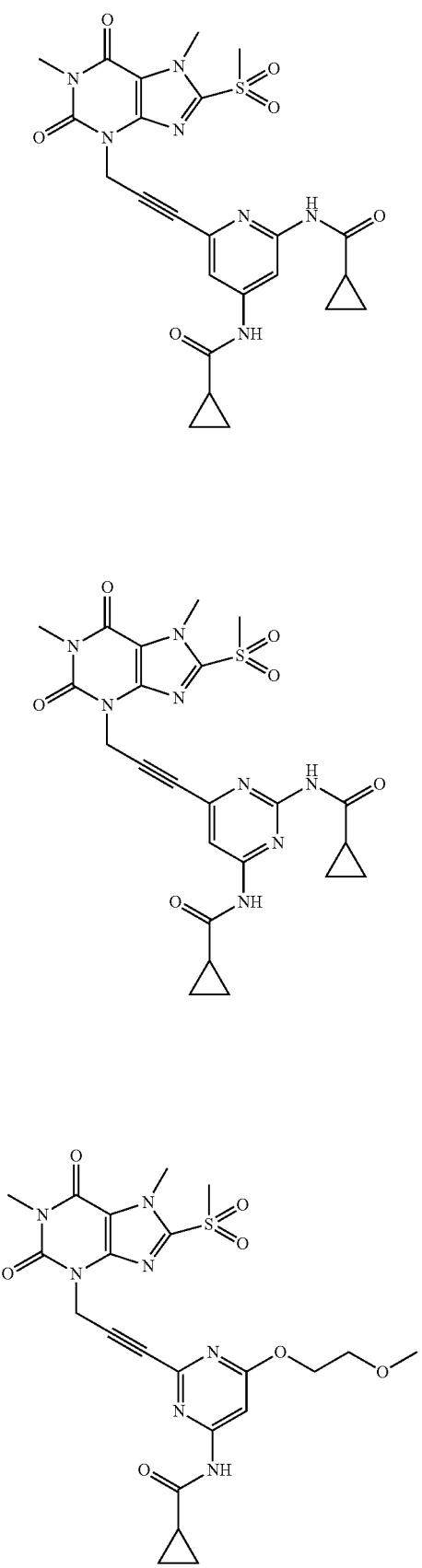
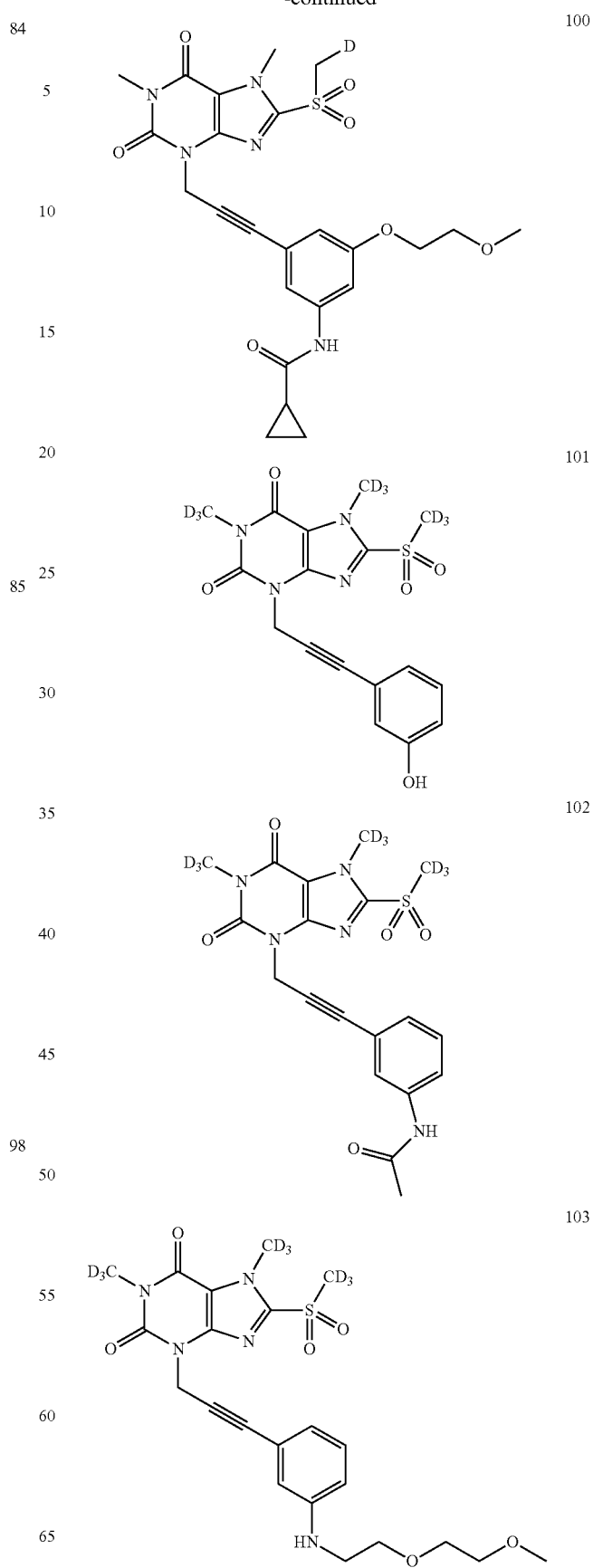

| 339 -continued | 340 -continued |
|---|---|
| 104 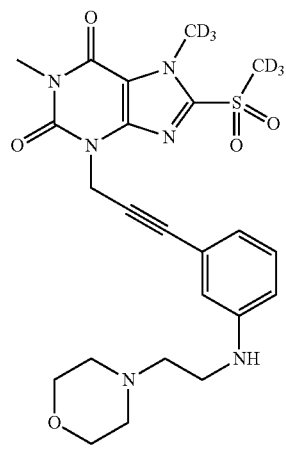 | 107 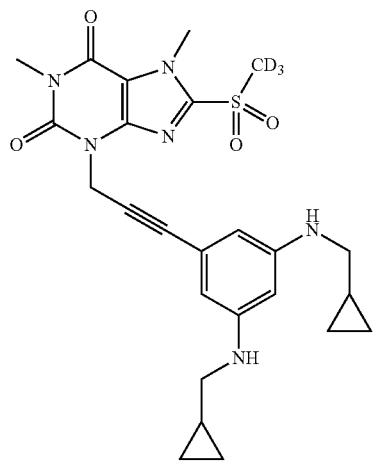 |
| 105 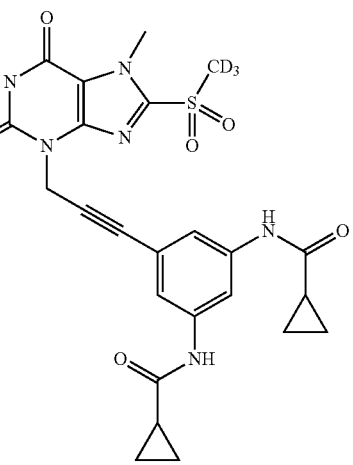 | 108 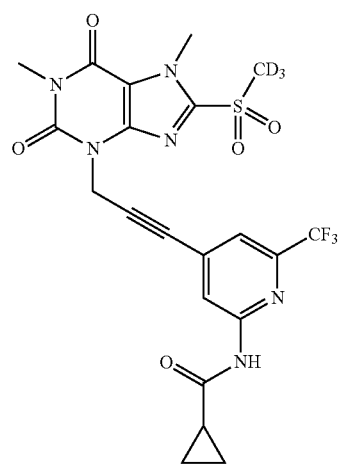 |
| 106 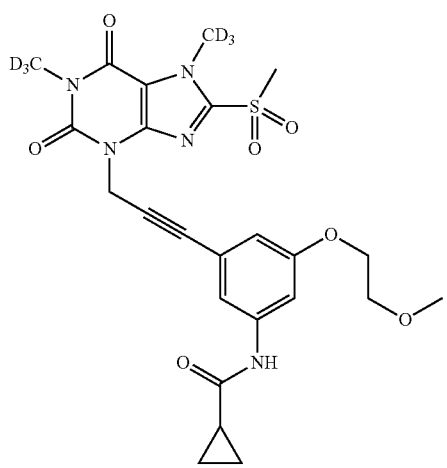 | 109 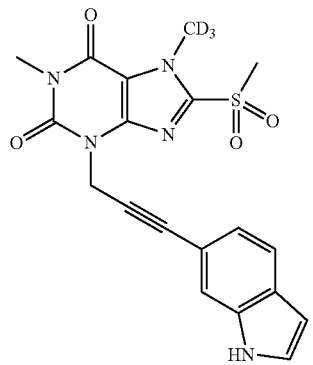 |

-continued

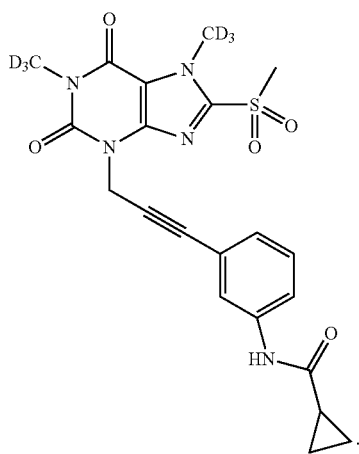

16. A pharmaceutical composition comprising a compound of claim 1 and a pharmaceutically acceptable excipient, in predetermined, unit dosage form selected from a pill, tablet or capsule.

17. A pharmaceutical composition comprising a compound of claim 8 and a pharmaceutically acceptable excipient, in predetermined, unit dosage form selected from a pill, tablet or capsule.

18. A pharmaceutical composition comprising a compound of claim 14 and a pharmaceutically acceptable excipient, in predetermined, unit dosage form selected from a pill, tablet or capsule.

19. A pharmaceutical composition comprising a compound of claim 15 and a pharmaceutically acceptable excipient, in predetermined, unit dosage form selected from a pill, tablet or capsule.

20. A method of treating an MLKL-mediated disorder selected from ischemia-reperfusion damage, neurodegeneration, and inflammation, comprising treating a person in need thereof with an MLKL-inhibitor compound of claim 1.

* * * * *